United States Patent
Berghausen et al.

(10) Patent No.: US 9,051,279 B2
(45) Date of Patent: Jun. 9, 2015

(54) SUBSTITUTED ISOQUINOLINONES AND QUINAZOLINONES

(71) Applicant: Novartis AG, Basel (CH)

(72) Inventors: Joerg Berghausen, Lorrach (DE); Nicole Buschmann, Basel (CH); Pascal Furet, Thann (FR); Francois Gessier, Altkirch (FR); Joanna Hergovich Lisztwan, Walton-on-Thames (GB); Philipp Holzer, Sissach (CH); Edgar Jacoby, Basel (CH); Joerg Kallen, Basel (CH); Keiichi Masuya, Basel (CH); Carole Pissot Soldermann, Village Neuf (FR); Haixia Ren, Shanghai (CN); Stefan Stutz, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/778,910

(22) Filed: Feb. 27, 2013

(65) Prior Publication Data

US 2013/0281473 A1 Oct. 24, 2013

Related U.S. Application Data

(62) Division of application No. 12/973,474, filed on Dec. 20, 2010, now Pat. No. 8,440,693.

(60) Provisional application No. 61/288,992, filed on Dec. 22, 2009.

(30) Foreign Application Priority Data

Nov. 19, 2010 (WO) ............... PCT/CN2010/078927

(51) Int. Cl.

| C07D 239/82 | (2006.01) |
| A01N 43/54 | (2006.01) |
| A61K 31/517 | (2006.01) |
| C07D 217/24 | (2006.01) |
| C07D 401/04 | (2006.01) |
| C07D 401/10 | (2006.01) |
| C07D 401/12 | (2006.01) |
| C07D 401/14 | (2006.01) |
| C07D 405/04 | (2006.01) |
| C07D 405/12 | (2006.01) |
| C07D 405/14 | (2006.01) |
| C07D 409/12 | (2006.01) |
| C07D 413/10 | (2006.01) |
| C07D 413/12 | (2006.01) |
| C07D 413/14 | (2006.01) |
| C07D 417/12 | (2006.01) |

(52) U.S. Cl.
CPC ............ *C07D 239/82* (2013.01); *C07D 217/24* (2013.01); *C07D 401/04* (2013.01); *C07D 401/10* (2013.01); *C07D 401/12* (2013.01); *C07D 401/14* (2013.01); *C07D 405/04* (2013.01); *C07D 405/12* (2013.01); *C07D 405/14* (2013.01); *C07D 409/12* (2013.01); *C07D 413/10* (2013.01); *C07D 413/12* (2013.01); *C07D 413/14* (2013.01); *C07D 417/12* (2013.01)

(58) Field of Classification Search
USPC .................................... 514/266.31; 544/286
See application file for complete search history.

(56) References Cited

U.S. PATENT DOCUMENTS

| 3,829,420 A | 8/1974 | Inaba et al. |
| 3,865,827 A | 2/1975 | Yamamoto et al. |

(Continued)

FOREIGN PATENT DOCUMENTS

| EP | 1 657 238 A1 | 5/2006 |
| EP | 2 143 713 A1 | 1/2010 |

(Continued)

OTHER PUBLICATIONS

Ivanov et al., Polyphosphoric acid-induced construction of quinazolinone skeleton from 1-(3,4-dimethoxyphenyl)-3-phenylurea and carboxylic acids Heterocycles (2006), 68(7), 1443-1449 CODEN: HTCYAM; ISSN: 0385-5414; English.*

De Luca, Laura et al., "3D Pharmacophore Models for 1,2,3,4-Tetrahydroisoquinoline Derivatives Acting as Anticonvulsant Agents" Arch. Pharm. Chem. Life Sci., 2006, 339, 388-400.

Shangary, Sanjeev et al., "Targeting the MDM2-p53 Interaction for Cancer Therapy", Clin. Cancer Res., 2008, 14, 5318-5324.

Acharya, B.P. et al., "Friedel-Crafts Acylation with 2-Isocyanatobenzoyl Chlorides: The Structure of the Intermediate Complex," Journal of Chemical Research, Synopses, (4):96-7 (1987)[Abstract only].

(Continued)

*Primary Examiner* — Paul V. Ward
(74) *Attorney, Agent, or Firm* — Scott W. Reid

(57) ABSTRACT

The invention relates to substituted nitrogen containing bicyclic heterocycles of the formula (I)

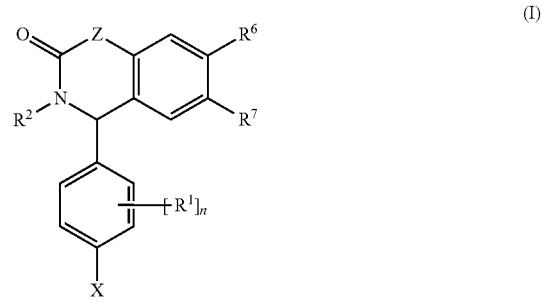

wherein Z is $CH_2$ or $N-R^4$ and X, $R^1$, $R^2$, $R^4$, $R^6$, $R^7$ and n are as defined in the description. Such compounds are suitable for the treatment of a disorder or disease which is mediated by the activity of MDM2 and/or MDM4, or variants thereof.

14 Claims, 2 Drawing Sheets

(56) References Cited

U.S. PATENT DOCUMENTS

| | | | |
|---|---|---|---|
| 3,923,710 A | 12/1975 | Ishizumi et al. | |
| 4,099,002 A | 7/1978 | Inaba et al. | |
| 4,258,187 A | 3/1981 | Middleton | |
| 4,335,127 A | 6/1982 | Vandenberk et al. | |
| 4,695,633 A | 9/1987 | Berneth et al. | |
| 6,479,499 B1 | 11/2002 | Kuo et al. | |
| 6,734,302 B2 | 5/2004 | Kong et al. | |
| 7,541,354 B2 | 6/2009 | Fancelli et al. | |
| 8,101,644 B2 | 1/2012 | Kai et al. | |
| 8,222,288 B2 | 7/2012 | Wang et al. | |
| 8,440,693 B2 * | 5/2013 | Berghausen et al. | 514/312 |
| 2003/0153580 A1 | 8/2003 | Kong et al. | |
| 2006/0069085 A1 | 3/2006 | Zhao et al. | |
| 2008/0153791 A1 | 6/2008 | Wilckens | |
| 2009/0163545 A1 | 6/2009 | Goldfarb | |
| 2010/0160356 A1 | 6/2010 | Heinrich et al. | |
| 2010/0210632 A1 | 8/2010 | Kai et al. | |
| 2011/0183939 A1 | 7/2011 | Kai et al. | |
| 2011/0230457 A1 | 9/2011 | Berghausen et al. | |
| 2011/0301133 A1 | 12/2011 | Wu et al. | |
| 2012/0065210 A1 | 3/2012 | Chu et al. | |
| 2013/0245036 A1 | 9/2013 | Berghausen et al. | |
| 2013/0317024 A1 | 11/2013 | Cotesta et al. | |
| 2014/0011798 A1 | 1/2014 | Furet et al. | |
| 2014/0135306 A1 | 5/2014 | Buschmann et al. | |

FOREIGN PATENT DOCUMENTS

| | | |
|---|---|---|
| JP | 2001-302515 | 10/2001 |
| WO | WO 93/04047 A1 | 3/1993 |
| WO | 95/19362 A1 | 7/1995 |
| WO | 98/19362 A1 | 7/1995 |
| WO | 98/01467 A2 | 1/1998 |
| WO | 98/45276 A2 | 10/1998 |
| WO | WO 00/66560 A1 | 11/2000 |
| WO | 02/12242 A2 | 2/2002 |
| WO | 03/051359 A1 | 6/2003 |
| WO | WO 03/062392 A2 | 7/2003 |
| WO | 03/095625 A2 | 11/2003 |
| WO | WO 03/095625 A2 | 11/2003 |
| WO | WO 03/101985 A1 | 12/2003 |
| WO | WO 2004/096134 A2 | 11/2004 |
| WO | WO 2005/027882 A1 | 3/2005 |
| WO | 2005/051922 A1 | 6/2005 |
| WO | 2005/110996 A1 | 11/2005 |
| WO | 2005/117876 A1 | 12/2005 |
| WO | WO 2006/024837 A1 | 3/2006 |
| WO | 2006/074262 A1 | 7/2006 |
| WO | WO 2006/097337 A2 | 9/2006 |
| WO | WO 2006/136606 A2 | 12/2006 |
| WO | 2007/068637 A1 | 6/2007 |
| WO | 2007/096334 A1 | 8/2007 |
| WO | WO 2008/034039 A2 | 3/2008 |
| WO | 2008/120725 A1 | 10/2008 |
| WO | 2008/130614 A2 | 10/2008 |
| WO | 2010/007116 A2 | 1/2010 |
| WO | 2010/035727 A1 | 4/2010 |
| WO | 2010/141738 A2 | 12/2010 |
| WO | 2011/076786 A1 | 6/2011 |
| WO | 2011/161031 A1 | 12/2011 |
| WO | 2012/046030 A2 | 4/2012 |
| WO | 2012/065022 A2 | 5/2012 |
| WO | 2012/151512 A2 | 11/2012 |
| WO | 2012/174487 A2 | 12/2012 |
| WO | 2012/175487 A2 | 12/2012 |
| WO | 2012/175520 A1 | 12/2012 |
| WO | 2013/033268 A2 | 3/2013 |
| WO | 2013/080141 A1 | 6/2013 |
| WO | 2013/111105 A1 | 8/2013 |

OTHER PUBLICATIONS

Bahloul, A. et al., "1,3-Dipolar Cycloaddition of Diarylnitrilimines with 4-Arylidene-1,2-Diphenyl-1,4-Dihydro-3(2H)-Isoquinolin-3-Ones," Journal de la Societe Marocaine de Chimie, 2(1):12-17 (French)(1993)[Abstract only].

Chen, R. et al., "Ytterbium(III) Triflate-Catalyzed Stereoselective Synthesis of Beta-lactams via [2 + 2] Cyclocondensation in Ionic Liquid," Synthetic Communications, 36(21):3167-3174, Taylor & Francis Group, LLC (English)(2006).

Dietz, G. et al.; "Synthesis and Conversion of 3,4-Dihydroquinazolin-4-ols. Part 2: Conversion of 3,4-Dihydroquinazolin-4-ols;" Direktionsber. Forsch. Entwickl., VEB Pharm. Komb. Germed Dresden, Dresden, Ger. Dem. Rep.; Pharmazie; 35(12):751-5 (German)(1980)[Abstract only].

Ishiwaka, N. et al., "o-Aminobenzophenone Derivatives. V. Reactions of 2-Amino-5-Chloro-Benzophenone with Isocyanates and Isothiocyanates," Kagaku Zasshi, 90(9):917-20 (Japanese)(1969)[Abstract only].

Ishiwaka, N. et al., "Reaction of 2-Amino-5-Chlorobenzophenone with P-Substituted Phenyl Isocyanates," Kagaku Zasshi, 91(10):994-7 (Japanese)(1970)[Abstract only].

Ivanov, I. et al., "Polyphosphoric Acid-Induced Construction of Quinazolinone Skeleton from 1-(3,4-Dimethoxyphenyl)-3-Phenylurea and Carboxylic Acids," Heterocycles, 68(7):1443-1449, The Japan Institute of Heterocyclic Chemistry (English)(2006).

Ivanov, I., "Synthesis of 6,7-Dimethoxy-3,4-Diphenyl-2(1H)-Quinazolinone from 1-(3,4-Dimethoxyphenyl)Urea and Benzoic Acid in Polyphosphoric Acid," Molbank M492/1-M492/2 (English)(2006)[Abstract only].

Mollov, N.M. et al., "Internal Alpha-Amidoalkylation Leading to 1,4-Dihydro-3(2H)-Isoquinolinones," Acta Chimica Academiae Scientiarum Hungaricae, 98(3):315-19 (English)(1978).

Mollov, N.M. et al., "Reactivity of Adducts Obtained from Arylacetyl Chloride and Aromatic Schiff Bases," Izvestiya po Khimiya, 10(4):616-20 (English)(1977).

Mollov, N.M. et al., "Synthesis of 3(2H)-isoquinolinones by Means of Inner Alpha-Amidoalkylation," Doklady Bolgarskoi Akademii Nauk, 28(8):1055-7 (English)(1975)[Abstract only].

Mumm, O. et al., "Diacylamides," Berichte der Deutschen Chemischen Gesellschaft, 48:379-91 (1915)[Abstract only].

Pfeiffer, P. et al., "Autoxidation Phenomena in the Anils of the Indandione Series. II," Journal fuer Praktische Chemie (Leipzig), 159:13-35 (1941)[Abstract and Article].

Pfeiffer, P. et al., "Autoxidation Phenomena. VI," Justus Liebigs Annalen der Chemie, 563:73-85 (1949)[Abstract and Article].

Pfeiffer, P. et al., "Autoxidation Reactions. VII," Justus Liebigs Annalen der Chemie, 581:149-59 (1953)[Abstract and Article].

Richter, D., "Anthraquinone Coloring Matters: Ruberythric Acid," Journal of the Chemical Society, 1701-3 (1936).

Richter, P. et al., "Synthesis of Derivatives of 2-Hydrazino-1,4- or 3,4-Dihydroquinazolines," Pharmazie, 45 (10)721-4 (German)(1990)[Abstract only].

Schonberg, A. et al., "Autoxidation Effects in the Indone Series," Naturwissenschaften, 24:620 (1936)[Abstract only].

Schonberg, A. et al., "Autoxidation Phenomena and Valency Tautomerism in the Indone Series," Journal of the Chemical Society, 109-12 (1937).

Venkov, A. et al., "An Improved Synthesis of N-Substituted 1-Aryl-3-Oxo-1,2,3,4-Tetrahydroisoquinolines," Synthesis, 216-17, Stuttgart, New York (English)(1982).

Ventsov, A. et al., "Synthesis of N-Substituted 1,4-Dihydro-3(2H)-Isoquinolinones from 3,4,5-Trimethoxyphenylacetyl chloride and Schiff Bases," Bolgarskoi Akademii Nauk, 34(10):1405-7 (English)(1981)[Abstract only].

Yamamoto, M. et al., "Synthetic Studies on Quinazoline Derivatives. II. The Reactions of 2-Trichloro- and 2-Trifluoroacetamidobenzophenones with Primary Amines," Chemical & Pharmaceutical Bulletin, 29(8):2135-56 (English)(1981).

Zhang, Y. et al., "Superacid-Promoted Reactions of N-Acyliminium Ions: An Effective Route to Substituted 3-Oxo-1,2,3,4-Tetrahydroisoquinolines and Related Products," Synthesis (11):1775-1780 (English)(2006).

(56) References Cited

OTHER PUBLICATIONS

Zin'Kovskaya, V.R. et al., "Ring-chain transformations involving the carbonyl group. XVI. Amides of 2-benzoylphenyl-Alpha,Alpha-dimethylacetic acid," Latvijas PSR Zinatnu, Akademijas Vestis, Kimijas Serija, (1)65-8 (Russian)(1976)[Abstract only].

Dudkina, Anna S. et al. "Small Molecule Protein-Protein Inhibitors for the p53-MDM2 Interaction", Current Topics in Medicinal Chemistry, 2007, 7, pp. 952-960.

Zhang et al., Superacid-promoted reactions of N-acyliminium ions: An effective route to substituted 3-oxo-1,2,3,4-tetrahydroisoquinolines and related products. Synthesis (2006), (11), 1775-1780 CODEN: SYNTBF; ISSN: 0039-7881; English.

Mollov et al., Internal _-amidoalkylation leading to 1,4-dihydro-3(2H)-isoquinolinones. Acta Chimica Academiae Scientiarum Hungaricae (1978), 98(3), 315-19 CODEN: ACASA2; ISSN: 0001-5407; English.

Mollov et al., Reactivity of adducts obtained from arylacetyl chloride and aromatic schiff bases. Izvestiya po Khimiya (1977), 10(4), 616-21 CODEN: IZKHDX; ISSN: 0324-0401; English.

Andreichikov et al., Chemistry of Oxalyl Derivatives of Methyl Ketones XLIV. Synthesis of 4-Aroyl-1,5-Diphenyltetrahydropyrrole-2,3-Diones and their Reaction with Amines and Hydrazine. Journal of Organic Chemistry 1986;22(8):1572-7.

Dohrn et al., Berichte der Deutschen Chemischen Gesellschaft [Abteilung] B: Abhandlungen. 1931;64B:2863-5.

Gein et al., 5-Membered 2,3-Dioxoheterocyclic Compounds. Journal of General Chemistry. 1993;63(10):2324-8.

Gein et al., Reactions of 4-Acyl-1-alkoxyaryl-5-aryl-3-hydroxy-2,5-dihydro-1 H-pyrrol-2-ones with Nucleophilic Reagents. Russian Journal of Organic Chemistry. 2011;47(1):95-9.

Hackam et al., Translation of research evidence from animals to humans. JAMA. Oct. 11, 2006;296(14):1731-2.

Jordan, Tamoxifen: a most unlikely pioneering medicine. Nat Rev Drug Discov. Mar. 2003;2(3):205-13.

Lee et al., Novel Pyrrolopyrimidine-Based alpha-Helix Mimetics: Cell Permeable Inhibitors of Protein-Protein Interactions. Journal of the American Chemical Society. 2010;133:676-9.

Miyazaki et al., Lead optimization of novel p53-MDM2 interaction inhibitors possessing dihydroimidazothiazole scaffold. Bioorganic and Medicinal Chemistry Letters. 2013;23:728-32.

Richter et al., An Optimised Small-Molecule Stabiliser of the 14-3-3-PMA2 Protein-Protein Interaction. Chem. Eur. J. 2012;18(21):6520-7.

Vanotti et al., Cdc7 Kinase Inhibitors: Pyrrolopyrimidinones as Potential Antitumor Agents. 1. Synthesis and Structure-Activity Relationships. Journal of Medicinal Chemistry. 2008;51:487-501.

Wang et al., Benzimidazole-2-one: A novel anchoring principle for antagonizing p53-Mdm2. Bioorganic & Medicinal Chemistry. 2013;21:3982-95.

Westphal The formation of pyrrolo[3,4-c]pyrazoles. Journal for Practical Chemistry. 1969;311:379-84.

Chung et al., Fragment-based discovery of bromodomain inhibitors part 1: inhibitor binding modes and implications for lead discovery. J Med Chem. Jan. 26, 2012; 55(2):576-86.

Filippakopoulos et al., Benzodiazepines and benzotriazepines as protein interaction inhibitors targeting bromodomains of the BET family. Bioorg Med Chem. Mar. 15, 2012; 20(6):1878-86.

Filippakopoulos et al., Selective inhibition of BET bromodomains. Nature. Dec. 23, 2010; 468(7327):1067-73.

No Auhtor Listed, WedMD "Leukemia." Available from: <http://www.webmd.com/cancer/tc/leukemia-prevention> @2010. 1 page.

No Author Listed, American Cancer Society. "Leukemia-Acute Myeloid (Myelogenous)." © 2013. Available from: <http://www.cancer.org/cancer/leukemia-acutemyeloidaml/detailedguide/leukemia-acute-myeloid-myelogenous-what-is-aml>. 59 pages.

No Author Listed, Mayo Clinic "Leukemia Medications." Available from: <http://www.drugs.com/condition/leukemia.html> @ 2013. 1 page.

No Author Listed, National Cancer Institute. "Drugs Approved for Leukemia." © 2013. Available from: http://www.cancer.gov/cancertopics/druginfo/leukemia/print>. 4 pages.

Sun et al., Single-Nucleotide Polymorphisms in p53 Pathway and Aggressiveness of Prostate Cancer in a Caucasian Population. Clin. Cancer Res. 2010; 16:5244-51.

Wade et al., Targeting Mdm2 and Mdmx in Cancer Therapy: Better Living through Medicinal Chemistry? Mol. Cancer Res. 2009; 7:1-11.

Wu et al., the double bromodomain-containing chromatin adaptor Brd4 and transcriptional regulation. J Biol Chem. May 4, 2007; 282(18):13141-5.

* cited by examiner

XRPD data for Example 106 sulphate salt crystalline form I (slurry method)

XRPD data for Example 106 sulphate salt crystalline form I (anti-solvent method)

SUBSTITUTED ISOQUINOLINONES AND QUINAZOLINONES

The present invention relates to substituted nitrogen containing bicyclic heterocycles, capable of inhibiting the interaction between p53, or variants thereof, and MDM2 and/or MDM4, or variants thereof, respectively, especially binding to MDM2 and/or MDM4, or variants thereof, a process for the preparation of such compounds, pharmaceutical preparations comprising such compounds, uses and methods of use for such compounds in the treatment (including therapy and/or prophylaxis), and/or related subject matter as specified below. p53 refers to all genes and/or proteins encoded thereof with the names TP53, p53, TP73, p73, TP63, TP73L, p63. MDM2 refers to all genes and/or proteins encoded thereof with the names MDM2, Mdm2, HDM2, Hdm2. MDM4 refers to all genes and/or proteins encoded thereof with the names MDM4, Mdm4, HDM4, Hdm4, MDMX, MdmX, HDMX, HdmX.

Protein p53 is known as a tumor suppressor protein which helps to control cellular integrity and prevents the proliferation of permanently damaged cells by initiating, among other responses, growth arrest or apoptosis (controlled cell death). p53 mediates its effects in that it is a transcription factor capable of regulating a number of genes that regulate e.g. cell cycle and apoptosis. Thus, p53 is an important cell cycle inhibitor. These activities are tightly controlled by MDM2, an important negative regulator of the p53 tumor supressor. "MDM2" (originally from the oncogene "murine double minute 2") refers both to the name of the gene as well as the protein encoded by that gene. MDM2 protein functions both as an E3 ubiquitin ligase that recognizes the N-terminal transactivation domain (TAD) of the p53 tumor suppressor and thus mediates the ubiquitin-dependent degradation of p53, and as an inhibitor of p53 transcriptional activation.

The original mouse oncogene, which codes for the MDM2 protein, was originally cloned from a transformed mouse cell line. The human homologue of this protein was later identified and is sometimes also called HDM2 (for "human double minute 2"). Further supporting the role of MDM2 as an oncogene, several human tumor and proliferative disease types have been shown to have increased levels of MDM2, including inter alia soft tissue sarcomas, bone cancer, e.g. osteosarcomas, breast tumors, bladder cancer, Li-Fraumeni syndrome, brain tumor, rhabdomyosarcoma and adrenocortical carcinoma and the like. Another protein belonging to the MDM2 family is MDM4, also known as MDMX.

Dysregulation of the MDM2/p53 ratio, e.g. due to mutations, polymorphisms or molecular defects in the affected cells, can thus be found in many proliferative diseases. MDM2, in view of its mentioned effects, is capable to inhibit the activity of the tumor suppressor protein p53, thus leading to loss of p53's tumor suppressor activity and inhibiting regulatory mechanisms that impede cells from uncontrolled proliferation. As a consequence, uncontrolled proliferation can take place, leading to tumors, leukemias or other proliferative diseases.

Thus there is a need for new drugs that are capable to interfere with the interaction between p53 and MDM2 or especially oncogenic variants thereof and that thus allow p53 to exert its beneficial effect against uncontrolled tumor growth, allowing it e.g. to accumulate, to arrest the cell cycle and/or to cause apoptosis of affected cells.

SUMMARY OF THE INVENTION

It has now been found that a novel class of substituted nitrogen containing bicyclic heterocycles shows potent inhibition of the MDM2/p53 interaction (this term including MDM2/p53 interaction and/or MDM4/p53 interaction herein, in particular Hdm2/p53 and/or Hdm4/p53 interaction) and the corresponding compounds thus represent a novel type of compounds that are useful in the treatment of a number of disorders, such as proliferative diseases. The invention relates therefore to these compounds as drugs as well as to the other inventive embodiments indicated above and below.

DETAILED DESCRIPTION OF THE INVENTION

The invention relates in a first aspect to a compound of formula (I), and/or a tautomer and/or N-oxide and/or a pharmaceutically acceptable salt and/or solvate thereof,

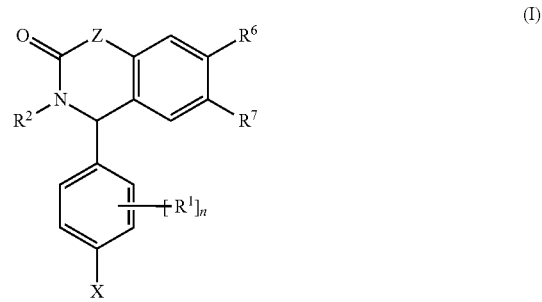

(I)

wherein
Z is $CH_2$ or N—$R^4$;
X is halogen;
$R^4$ is selected from the group consisting of
H—
$C_1$-$C_7$-alkyl-;
$R^6$ is independently selected from the group consisting of
H—
R'O—
(R')$_2$N—;
$R^7$ is independently selected from the group consisting of
R'O—
(R)$_2$N—;
each R' is independently selected from the group consisting of
H—
$C_1$-$C_7$-alkyl-
$C_1$-$C_7$-alkenyl-
halo-$C_1$-$C_7$-alkyl-
halo-$C_1$-$C_7$-alkenyl-
$C_3$-$C_{12}$-cycloalkyl-
heterocyclyl-
aryl-
hydroxy-$C_1$-$C_7$-alkyl-
$C_1$-$C_7$-alkoxy-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
$C_3$-$C_{12}$-cycloalkyl-$C_1$-$C_7$-alkyl-
heterocyclyl-$C_1$-$C_7$-alkyl-
aryl-$C_1$-$C_7$-alkyl-
$C_1$-$C_7$-alkyl-carbonyl-
halo-$C_1$-$C_7$-alkyl-carbonyl-
hydroxy-$C_1$-$C_7$-alkyl-carbonyl-
$C_1$-$C_7$-alkoxy-$C_1$-$C_7$-alkyl-carbonyl-
amino-$C_1$-$C_7$-alkyl-carbonyl-
N—$C_1$-$C_7$-alkyl-amino-$C_1$-$C_7$-alkyl-carbonyl-
N,N-di-$C_1$-$C_7$-alkyl-amino-$C_1$-$C_7$-alkyl-carbonyl-
$C_3$-$C_{12}$-cycloalkyl-carbonylheterocyclyl-$C_1$-$C_7$-alkyl-carbonyl-
aryl-$C_1$-$C_7$-alkyl-carbonyl-
$C_3$-$C_{12}$-cycloalkyl-$C_1$-$C_7$-alkyl-carbonyl-
heterocyclyl-carbonyl-
aryl-carbonyl-
$C_1$-$C_7$-alkyl-carbonyl-$C_1$-$C_7$-alkyl-
halo-$C_1$-$C_7$-alkyl-carbonyl-$C_1$-$C_7$-alkyl-
hydroxy-$C_1$-$C_7$-alkyl-carbonyl-$C_1$-$C_7$-alkyl-
$C_1$-$C_7$-alkoxy-$C_1$-$C_7$-alkyl-carbonyl-$C_1$-$C_7$-alkyl-
amino-$C_1$-$C_7$-alkyl-carbonyl-$C_1$-$C_7$-alkyl-
N—$C_1$-$C_7$-alkyl-amino-$C_1$-$C_7$-alkyl-carbonyl-$C_1$-$C_7$-alkyl-
N,N-di-$C_1$-$C_7$-alkyl-amino-$C_1$-$C_7$-alkyl-carbonyl-$C_1$-$C_7$-alkyl-
$C_3$-$C_{12}$-cycloalkyl-carbonyl-$C_1$-$C_7$-alkyl-
heterocyclyl-carbonyl-$C_1$-$C_7$-alkyl-
aryl-carbonyl-$C_1$-$C_7$-alkyl-
carbonyl-$C_1$-$C_7$-alkyl-
hydroxy-carbonyl-$C_1$-$C_7$-alkyl-
$C_1$-$C_7$-alkoxy-carbonyl-$C_1$-$C_7$-alkyl-
amino-carbonyl-$C_1$-$C_7$-alkyl-
N—$C_1$-$C_7$-alkyl-amino-carbonyl-$C_1$-$C_7$-alkyl-
N,N-di-$C_1$-$C_7$-alkyl-amino-carbonyl-$C_1$-$C_7$-alkyl-
$C_3$-$C_{12}$-cycloalkyl-carbonyl-$C_1$-$C_7$-alkyl-
heterocyclyl-carbonyl-$C_1$-$C_7$-alkyl-
aryl-carbonyl-$C_1$-$C_7$-alkyl-
$C_1$-$C_7$-alkyl-carbonyl-amino-$C_1$-$C_7$-alkyl-
$C_1$-$C_7$-alkyl-carbonyl-N—$C_1$-$C_7$-alkyl-amino-$C_1$-$C_7$-alkyl-
halo-$C_1$-$C_7$-alkyl-carbonyl-amino-$C_1$-$C_7$-alkyl-
halo-$C_1$-$C_7$-alkyl-carbonyl-N—$C_1$-$C_7$-alkyl-amino-$C_1$-$C_7$-alkyl-
  wherein aryl, heterocyclyl and $C_3$-$C_{12}$-cycloalkyl are unsubstituted or substituted by 1-4 substituents selected from $C_1$-$C_7$-alkyl, halo-$C_1$-$C_7$-alkyl, halogen, hydroxy, $C_1$-$C_7$-alkoxy, amino, nitro or cyano;
each $R^1$ is independently selected from the group consisting of
halogen-
cyano-
nitro-
$C_1$-$C_7$-alkyl-
$C_1$-$C_7$-alkenyl-
halo-$C_1$-$C_7$-alkyl-
hydroxy-
$C_1$-$C_7$-alkoxy-
amino-
N—$C_1$-$C_7$-alkyl-amino-
N,N-di-$C_1$-$C_7$-alkyl-amino-
amino-carbonyl-amino-
N—$C_1$-$C_7$-alkyl-amino-carbonyl-amino-
N,N-di-$C_1$-$C_7$-alkyl-amino-carbonyl-amino-
$C_1$-$C_7$-alkyl-carbonyl-amino-
amino-carbonyl-
N—$C_1$-$C_7$-alkyl-amino-carbonyl-
N,N-di-$C_1$-$C_7$-alkyl-amino-carbonyl-
hydroxy-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
$C_1$-$C_7$-alkyl-carbonyl-amino-$C_1$-$C_7$-alkyl-
$C_1$-$C_7$-alkyl-carbonyl-N—$C_1$-$C_7$-alkyl-amino-$C_1$-$C_7$-alkyl-;
n is 0, 1 or 2;
$R^2$ is selected from
  (A) phenyl, 2-pyridyl or 3-pyridyl
    said phenyl, 2-pyridyl or 3-pyridyl being substituted in para-position (relative to the isoquinolinone or quinazolinone), by
    $(R^3)_2$N—Y—
    wherein Y is absent (a bond) or
    $(R^3)_2$N—Y— is selected from

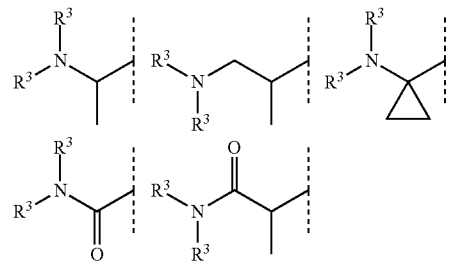

and said phenyl, 2-pyridyl or 3-pyridyl being optionally substituted by 1-2 additional substituents selected from
    halogen-
    cyano-
    $C_1$-$C_7$-alkyl-
    halo-$C_1$-$C_7$-alkyl-
    hydroxy-
    $C_1$-$C_7$-alkoxy-
    hydroxy-$C_1$-$C_7$-alkyl-;
or
  (B) phenyl, 2-pyridyl or 3-pyridyl
    said phenyl, 2-pyridyl or 3-pyridyl being substituted in para-position (relative to the isoquinolinone or quinazolinone), by a substituent selected from
    cyano-
    halogen-
    nitro-
    $C_1$-$C_7$-alkyl-
    halo-$C_1$-$C_7$-alkyl-
    hydroxy-$C_1$-$C_7$-alkyl-
    hydroxy-carbonyl-
    $C_1$-$C_7$-alkoxy-carbonyl-
    $C_1$-$C_7$-alkyl-carbonyl-
    $C_1$-$C_7$-alkoxy-
    (C-bound)-heterocyclyl-
      wherein (C-bound)-heterocyclyl is unsubstituted or substituted by 1-4 substituents selected from $C_1$-$C_7$-alkyl, halo-$C_1$-$C_7$-alkyl, halogen, hydroxy, $C_1$-$C_7$-alkoxy, amino, nitro or cyano;
    and wherein said phenyl, 2-pyridyl and 3-pyridyl are optionally substituted by 1-2 additional substituents independently selected from
    halogen-
    cyano-
    $C_1$-$C_7$-alkyl-
    halo-$C_1$-$C_7$-alkyl-
    hydroxy-
    $C_1$-$C_7$-alkoxy-
    (C-bound or N-bound)heterocyclyl-$C_1$-$C_4$-alkyl- and
    hydroxy-$C_1$-$C_7$-alkyl-;
or
  (C) phenyl,
    substituted in ortho-position (relative to the isoquinolinone or quinazolinone), by $R^3$O—
    and substituted in para- or meta-position by a substituent selected from methyl, chloro, $C_1$-$C_7$-alkyl-carbonyl- or $C_1$-$C_7$-alkoxy-carbonyl-;

(D) (C-bound)-heterocycle selected from

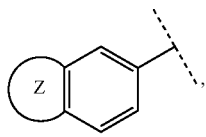

wherein Z is a 4-6 membered heterocyclic ring, annulated to phenyl in para and meta position, containing 1-3 heteroatoms selected from N, O or S, which is optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy-
hydroxy-$C_1$-$C_7$-alkyl-;

(E) pyrazin-2-yl (relative to the isoquinolinone or quinazolinone), substituted at the 5 position by:

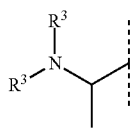

(F) pyridazin-3-yl (relative to the isoquinolinone or quinazolinone), substituted at the 6 position by:

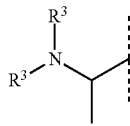

or (G) pyrimidin-2-yl (relative to the isoquinolinone or quinazolinone), substituted at the 5 position by:

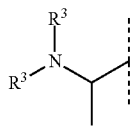

wherein each $R^3$ is independently selected from
H—
$C_1$-$C_7$-alkyl-
hydroxy-$C_1$-$C_7$-alkyl-
$C_3$-$C_{12}$-cycloalkyl-
$C_1$-$C_7$-alkoxy-$C_1$-$C_7$-alkyl-carbonyl-
amino-$C_1$-$C_7$-alkyl-carbonyl
N—$C_1$-$C_7$-alkyl-amino-$C_1$-$C_7$-alkyl-carbonyl
N,N-di $C_1$-$C_7$-alkyl-amino-$C_1$-$C_7$-alkyl-carbonyl
$(R^5)_2$N—$C_3$-$C_{12}$-cycloalkyl-
$(R^5)_2$N—$C_1$-$C_7$-alkyl-
$(R^5)_2$N—$C_3$-$C_{12}$-cycloalkyl-$C_1$-$C_7$-alkyl-
$(R^5)_2$N—$C_3$-$C_{12}$-cycloalkyl-carbonyl-
$R^5$O—$C_3$-$C_{12}$-cycloalkyl-
$R^5$O—$C_1$-$C_7$-alkyl-
$R^5$O—$C_3$-$C_{12}$-cycloalkyl-$C_1$-$C_7$-alkyl-
$R^5$O—($C_1$-$C_7$-alkyl)-$C_3$-$C_{12}$-cycloalkyl-$C_1$-$C_7$-alkyl-
$R^5$O-(hydroxy-$C_1$-$C_7$-alkyl)-$C_3$-$C_{12}$-cycloalkyl-$C_1$-$C_7$-alkyl-
$(R^5)_2$N—CO—$C_3$-$C_{12}$-cycloalkyl-$C_1$-$C_7$-alkyl-
$C_1$-$C_7$-alkoxycarbonyl-$C_3$-$C_{12}$-cycloalkyl-$C_1$-$C_7$-alkyl-
hydroxycarbonyl-$C_3$-$C_{12}$-cycloalkyl-$C_1$-$C_7$-alkyl-
amino-carbonyl-$C_3$-$C_{12}$-cycloalkyl-$C_1$-$C_7$-alkyl-
$R^5$O—$C_3$-$C_{12}$-cycloalkyl-carbonyl-
$(R^5)_2$N-carbonyl-$C_1$-$C_7$-alkyl-
$R^5$O-carbonyl-$C_1$-$C_7$-alkyl-
aryl-$C_1$-$C_7$-alkyl-
heterocyclyl-$C_1$-$C_7$-alkyl-
$C_1$-$C_7$-alkyl-carbonyl-
halo-$C_1$-$C_7$-alkyl-carbonyl-
heterocyclyl-carbonyl-
aryl-carbonyl-
$C_3$-$C_{12}$-cycloalkyl-carbonyl-
$C_3$-$C_{12}$-cycloalkyl-$C_1$-$C_7$-alkyl-
heterocyclyl-
aryl-
wherein aryl, heterocyclyl and $C_3$-$C_{12}$-cycloalkyl are unsubstituted or substituted by 1-4 substituents selected from
halogen-
$C_1$-$C_7$-alkyl-
halo-$C_1$-$C_7$-alkyl-
$C_1$-$C_7$-alkyl-carbonyl-
$C_3$-$C_{12}$-cycloalkyl-carbonyl-
$C_1$-$C_7$-alkyl-sulfonyl-
amino-sulfonyl-
N—$C_1$-$C_7$-alkyl-amino-sulfonyl-
N,N-di-$C_1$-$C_7$-alkyl-amino-sulfonyl-
amino-carbonyl-
N—$C_1$-$C_7$-alkyl-amino-carbonyl-
N,N-di-$C_1$-$C_7$-alkyl-amino-carbonyl-
oxo=
or
two $R^3$, together with the N to which they are attached my form a 3-9 membered heterocyclic ring, optionally containing 1-4 additional heteroatoms selected from N, O or S, said heterocyclic ring is unsubstituted or substituted by 1-3 substituents selected from:
halogen-
hydroxy-$C_1$-$C_7$-alkyl-
$C_1$-$C_7$-alkyl-
halo-$C_1$-$C_7$-alkyl-
oxo=
hydroxy-
$C_1$-$C_7$-alkoxy-
amino-
N—$C_1$-$C_7$-alkyl-amino-
N,N-di-$C_1$-$C_7$-alkyl-amino-
hydroxy-carbonyl-
$C_1$-$C_7$-alkoxy-carbonyl-
amino-carbonyl-
N—$C_1$-$C_7$-alkyl-amino-carbonyl-
N,N-di-$C_1$-$C_7$-alkyl-amino-carbonyl-
$C_1$-$C_7$-alkyl-carbonyl-
$C_1$-$C_7$-alkyl-sulphonyl-
heterocyclyl-
$C_1$-$C_7$-alkyl-carbonyl-amino-
$C_1$-$C_7$-alkyl-carbonyl-N—$C_1$-$C_7$-alkyl-amino-;
and
each $R^5$ is independently selected from:
H—
$C_1$-$C_7$-alkyl-
hydroxy-$C_1$-$C_7$-alkyl-
$C_1$-$C_7$-alkyl-carbonyl- $C_1$-$C_7$-alkoxy-carbonyl-$C_1$-$C_7$-alkyl-
amino-carbonyl-$C_1$-$C_7$-alkyl-
N—$C_1$-$C_7$-alkyl-amino-carbonyl-$C_1$-$C_7$-alkyl-
N,N-di-$C_1$-$C_7$-alkyl-amino-carbonyl-$C_1$-$C_7$-alkyl-
$C_1$-$C_7$-alkyl-sulfonyl-
amino-sulfonyl-
N—$C_1$-$C_7$-alkyl-amino-sulfonyl-
N,N-di-$C_1$-$C_7$-alkyl-amino-sulfonyl-
heterocyclyl-carbonyl-
amino-carbonyl-
N—$C_1$-$C_7$-alkyl-amino-carbonyl-
N,N-di-$C_1$-$C_7$-alkyl-amino-carbonyl-
$C_3$-$C_{12}$-cycloalkyl-carbonyl-
$C_1$-$C_7$-alkoxy-carbonyl-amino-$C_1$-$C_7$-alkyl-
$C_1$-$C_7$-alkoxy-carbonyl-N—$C_1$-$C_7$-alkyl-amino-$C_1$-$C_7$-alkyl-
$C_1$-$C_7$-alkoxy-carbonyl-
$C_3$-$C_{12}$-cycloalkyl-
hydroxy-$C_3$-$C_{12}$-cycloalkyl-
or
two $R^5$, together with the N to which they are attached may form a 3, 4, 5, 6, 7, 8 or 9 membered heterocyclic ring, optionally containing 1, 2, 3 or 4 additional heteroatoms selected from N, O or S, said heterocyclic ring is unsubstituted or substituted by from 1 to 3 substituents independently selected from $C_1$-$C_7$-alkyl-
oxo=,
$C_1$-$C_7$-alkyl-carbonyl,
$C_1$-$C_7$-alkyl-sulphonyl,
hydroxy-$C_1$-$C_7$-alkyl;
with the proviso that if Z is $CH_2$, n is 0 or 1, and when present, $R^1$ is ortho-chloro, and $R^2$ is selected from
para-$C_1$-$C_3$-alkyl-phenyl-
para-(halo-$C_1$-$C_3$-alkyl)-phenyl-
para-$C_1$-$C_3$-alkoxy-phenyl-
para-halo-phenyl-
para-nitro-phenyl-
para-($C_1$-$C_3$-alkoxy-carbonyl)-phenyl-
para-(hydroxy-carbonyl)-phenyl-
wherein the phenyl is optionally substituted by 1-2 additional substituents, said substituents being independently selected from halo and methyl, then $R^6$ and $R^7$ are not both ethoxy or methoxy.

Wherever a compound or compounds of the formula (I) are mentioned, this is further also intended to include N-oxides of such compounds, tautomers thereof, and/or a (preferably pharmaceutically acceptable) salt thereof.

For purposes of interpreting this specification, the following definitions will apply and whenever appropriate, terms used in the singular will also include the plural and vice versa.

As used herein, "formula (I)" also means "formula I". These terms are used interchangeably.

As used herein, the term "alkyl" refers to a fully saturated branched, including single or multiple branching, or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Typically, alkyl groups have 1-7, more preferably 1-4 carbons.

As used herein, the term "alkenyl" refers to a branched, including single or multiple branching, or unbranched hydrocarbon moiety having up to 20 carbon atoms containing at least one carbon carbon double bond. Unless otherwise provided, alkenyl refers to hydrocarbon moieties having 2 to 16 carbon atoms, 2 to 10 carbon atoms, 2 to 7 carbon atoms, or 2 to 4 carbon atoms. Representative examples of alkyl include, but are not limited to ethenyl, propenyl, propenylene, allyl, and 1,4-butadienyl.

As used herein, the term "halo-alkyl" refers to an alkyl as defined herein, that is substituted by one or more halogen groups as defined herein. The halo-alkyl can be mono-halo-alkyl, di-halo-alkyl or poly-halo-alkyl including per-halo-alkyl. A mono-halo-alkyl can have one iodo, bromo, chloro or fluoro within the alkyl group. Di-halo-alkyl and poly-halo-alkyl groups can have two or more of the same halo atoms or a combination of different halo groups within the alkyl. Typically the poly-halo-alkyl contains up to 12, or 10, or 8, or 6, or 4, or 3, or 2 halo groups. Non-limiting examples of halo-alkyl include fluoro-methyl, di-fluoro-methyl, tri-fluoro-methyl, chloro-methyl, di-chloro-methyl, tri-chloro-methyl, penta-fluoro-ethyl, hepta-fluoro-propyl, di-fluoro-chloro-methyl, di-chloro-fluoro-methyl, di-fluoro-ethyl, di-fluoro-propyl, di-chloro-ethyl and dichloro-propyl. A per-halo-alkyl refers to an alkyl having all hydrogen atoms replaced with halogen atoms.

As used herein, unless otherwise specified, the term "hydroxyalkyl", or "hydroxyethyl", "hydroxypropyl" etc, refers to an alkyl as defined, that is substituted by one or more, preferably one, hydroxy groups.

As used herein, the term "halogen" (or "halo") refers to iodo, bromo, chloro or fluoro. In the context of X, halogen is preferably chloro or bromo, more preferably chloro. In the context of (B), halogen as a substituent on phenyl, 2-pyridyl or 3-pyridyl is preferably iodo.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have 1-7, more preferably 1-4 carbons.

As used herein, the term "cycloalkyl" refers to a saturated or partially saturated, monocyclic, fused polycyclic, or spiro polycyclic, carbocycle having from 3 to 12 ring atoms per carbocycle. Unless otherwise provided, cycloalkyl refers to cyclic hydrocarbon groups having between 3 and 10 ring carbon atoms or between 3 and 7 ring carbon atoms. The term cycloalkyl excludes "aryl". Exemplary monocyclic hydrocarbon groups include, but are not limited to, cyclopropyl, cyclobutyl, cyclopentyl, cyclopentenyl, cyclohexyl and cyclohexenyl. Exemplary bicyclic hydrocarbon groups include octahydroindyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl. Exemplary tricyclic hydrocarbon groups include adamantyl. As used herein, the term "cycloalkyl" preferably refers to cyclopropyl, cyclopentyl or cyclohexyl.

The term "aryl" refers to an aromatic hydrocarbon group having 6-20 carbon atoms in the ring portion. Typically, aryl is monocyclic, bicyclic or tricyclic aryl having 6-20 carbon atoms. Furthermore, the term "aryl" as used herein, refers to an aromatic substituent which can be a single aromatic ring, or multiple aromatic rings that are fused together. Non-limiting examples include phenyl or naphthyl. As used herein, the term "aryl" preferably refers to phenyl.

As used herein, the term "heterocyclyl" or "heterocyclic" refers to a unsaturated (carrying the highest possible number of conjugated double bonds in the ring(s), then also called heteroaryl), saturated (then also called saturated heterocyclyl) or partially saturated ring or ring system, for example a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from N, O and S, where the N and S can also optionally be oxidized to various oxidation states. The heterocyclic group can be attached at a heteroatom or a carbon atom. The heterocyclyl can include fused or bridged rings as well as spirocyclic rings.

In one embodiment herein, heterocyclyl means an unsaturated, saturated, or partially saturated ring or ring system comprising 3, 4, 5, 6, 7, 8, 9, 10, 11 or 12 ring atoms, and containing at least one heteroatom selected from N, O and S, where the N and S can also optionally be oxidized, and wherein, unless otherwise stated, the heterocyclic group can be attached at a heteroatom or a carbon atom. In one embodiment, heterocyclyl may contain 1, 2, 3 or 4 N atoms, and/or 1 S atom and/or one O atom.

Examples of heterocycles include oxiranyl, azirinyl, aziridinyl, 1,2-oxathiolanyl, thienyl, furanyl, tetrahydrofuryl, pyranyl, thiopyranyl, thianthrenyl, isobenzofuranyl, benzofuranyl, benzoisoxazolyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, oxadiazolyl, isoxazolyl, pyridyl, pyrazinyl, pyrimidinyl, piperidinyl, piperazinyl, pyridazinyl, morpholinyl, thiomorpholinyl, indolizinyl, azepanyl, diazepanyl, especially 1,4-diazepanyl, isoindolyl, 3H-indolyl, indolyl, isoindolyl, indazolyl, benzimidazolyl, cumaryl, triazolyl, tetrazolyl, purinyl, 4H-quinolizinyl, isoquinolyl, isoquinolyl, tetrahydroquinolyl, tetrahydroisoquinolyl, decahydroquinolyl, octahydroisoquinolyl, dibenzofuranyl, benzothiophenyl, dibenzothiophenyl, phthalazinyl, naphthyridinyl, quinoxalyl (=quinoxalinyl), quinazolinyl, quinazolinyl, cinnolinyl, pteridinyl, carbazolyl, betacarbolinyl, phenanthridinyl, acridinyl, perimidinyl, phenanthrolinyl, furazanyl, phenazinyl, phenothiazinyl, phenoxazinyl, chromenyl, isochromenyl, chromanyl, benzo[1,3]dioxol-5-yl, 2,3-dihydro-benzo[1,4]dioxin-6-yl, thiochromenyl and isothiochromenyl.

In the context of R', the term "heterocyclyl-" refers preferably to 5 to 6-membered monocyclic unsaturated, partially saturated or saturated ring systems. Examples include, but are not limited to pyridyl, imidazolidinyl, pyrrolindiyl, pyrimindinyl, piperazinyl, piperidinyl, thiomorpholinyl and morpholinyl.

In the context of (B), the term "(C-bound)-heterocyclyl-" refers preferably to 5- to 6-membered monocyclic unsaturated or partially saturated ring systems. Examples include, but are not limited to pyrazolyl, imidazole, triazole and tetrazole.

In the context of (D), the term "(C-bound)-heterocyclyl-" refers preferably to 9- to 11-membered bicyclic unsaturated or partially saturated ring systems. Examples include, but are not limited to indazolyl, indolyl, benzoisoxazolyl, benzofuranyl and benzothiophenyl.

In the context of $R^3$, the term "heterocyclyl-" refers preferably to 5 to 6-membered monocyclic unsaturated, partially saturated or saturated ring systems. Examples include, but are not limited to pyridyl, pyrimindinyl, piperazinyl, piperidinyl, pyrrolindiyl, imidazolyl, imidazolidinyl, furanyl, tetrazolyl, tetrahydrofuranyl, thienyl, oxazolyl, thiomorpholinyl and morpholinyl.

In the context of $R^3$, where two $R^3$, together with the N to which they are attached may form a 3-9 membered heterocyclic ring, the term "heterocyclyl-" refers preferably to 4, 5 or 6-membered monocyclic unsaturated, partially saturated or saturated ring systems. Examples include, but are not limited to azetidinyl, pyrazolyl, piperazinyl, piperidinyl, pyrrolindiyl, imidazolidinyl, imidazolyl, furanyl, tetrahydrofuranyl, thienyl, oxazolyl, thiomorpholinyl and morpholinyl.

In the context of $R^5$, where two $R^5$, together with the N to which they are attached may form a 3-9 membered heterocyclic ring, the term "heterocyclyl-" refers preferably to 5, 6 or 7-membered monocyclic partially saturated or saturated ring systems. Examples include, but are not limited to, piperazinyl, piperidinyl, pyrrolindiyl, imidazolidinyl, thiomorpholinyl, morpholinyl and di-azepanyl.

As used herein, the term "oxy" refers to an —O— linking group.

As used herein, all substituents are written in a way to show the order of functional groups (groups) they are composed of. The functional groups are defined herein above. The point of their attachment is indicated with a hyphen (-), wherein said hyphen indicates a single bond, or an equal sign (=), wherein said equal sign indicates a double bond, as appropriate.

"C-bound" means attached via a carbon atom, for example in (C-bound)-heterocyclyl-.

"N-bound" means attached via a nitrogen atom, for example in (N-bound)-heterocyclyl-.

Unless otherwise indicated herein, * indicates a point of attachment

As used herein, the term "protected hydroxy" refers to a hydroxy functionality bearing a "protecting group". Within the scope of this text, only a readily removable group that is not a constituent of the particular desired end product of the compounds of the present invention is designated a "protecting group", unless the context indicates otherwise; e.g. a protecting group can be part of a compound of the formula (I), if specifically mentioned. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methodn der organischen Chemie" (Methods of Organic Chemistry), Houben Weyl, 4th edition, Volume 15/l, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

The term "and/or an N-oxide thereof, a tautomer thereof and/or a (preferably pharmaceutically acceptable) salt thereof" especially means that a compound of the formula (I) may be present as such or in mixture with its N-oxide, as tautomer (e.g. due to keto-enol, lactam-lactim, amide-imidic acid or enamine-imine tautomerism) or in (e.g. equivalency reaction caused) mixture with its tautomer, or as a salt of the compound of the formula (I) and/or any of these forms or mixtures of two or more of such forms.

Various embodiments of the invention are described herein. It will be recognized that features specified in each embodiment may be combined with other specified features to provide further embodiments.

In another embodiment there is provided a compound of formula (I) as described herein with the proviso that the compound of formula (I) is not:

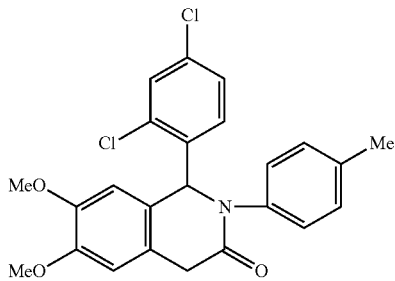 [SMILES: COc1cc2c(cc1OC)C(c1ccc(Cl)cc1Cl)N(c1ccc(C)cc1)C(=O)C2]

In another embodiment, there is provided a compound of formula (I), and/or a tautomer and/or N-oxide and/or a pharmaceutically acceptable salt and/or solvate thereof,

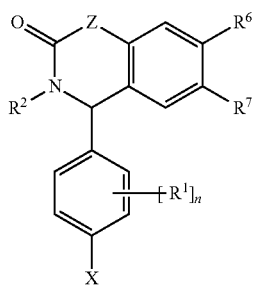

(I)

wherein
Z is $CH_2$ or $N-R^4$;
X is halogen;
$R^4$ is selected from the group consisting of
H—
$C_1$-$C_4$-alkyl-;
$R^6$ is independently selected from the group consisting of
H—
R'O—
$(R')_2N$—;
$R^7$ is independently selected from the group consisting of
R'O—
$(R')_2N$—;
each R' is independently selected from the group consisting of
H—
$C_1$-$C_6$-alkyl-
$C_1$-$C_6$-alkenyl-
halo-$C_1$-$C_4$-alkyl-
halo-$C_1$-$C_4$-alkenyl-
$C_3$-$C_7$-cycloalkyl-
heterocyclyl-
aryl-
hydroxy-$C_1$-$C_4$-alkyl-
$C_1$-$C_4$-alkoxy-$C_1$-$C_4$-alkyl-
amino-$C_1$-$C_4$-alkyl-
N—$C_1$-$C_4$-alkyl-amino-$C_1$-$C_4$-alkyl-
N,N-di-$C_1$-$C_4$-alkyl-amino-$C_1$-$C_4$-alkyl-
$C_3$-$C_7$-cycloalkyl-$C_1$-$C_4$-alkyl-
heterocyclyl-$C_1$-$C_4$-alkyl-
aryl-$C_1$-$C_4$-alkyl-
$C_1$-$C_4$-alkyl-carbonyl-
halo-$C_1$-$C_4$-alkyl-carbonyl-
hydroxy-$C_1$-$C_4$-alkyl-carbonyl-
$C_1$-$C_4$-alkoxy-$C_1$-$C_4$-alkyl-carbonyl-
amino-$C_1$-$C_4$-alkyl-carbonyl-
N—$C_1$-$C_4$-alkyl-amino-$C_1$-$C_4$-alkyl-carbonyl-
N,N-di-$C_1$-$C_4$-alkyl-amino-$C_1$-$C_4$-alkyl-carbonyl-
$C_3$-$C_7$-cycloalkyl-carbonyl-
heterocyclyl-$C_1$-$C_4$-alkyl-carbonyl-
aryl-$C_1$-$C_4$-alkyl-carbonyl-
$C_3$-$C_7$-cycloalkyl-$C_1$-$C_4$-alkyl-carbonyl-
heterocyclyl-carbonyl-
aryl-carbonyl-
$C_1$-$C_4$-alkyl-carbonyl-$C_1$-$C_4$-alkyl-
halo-$C_1$-$C_4$-alkyl-carbonyl-$C_1$-$C_4$-alkyl-
hydroxy-$C_1$-$C_4$-alkyl-carbonyl-$C_1$-$C_4$-alkyl-
$C_1$-$C_4$-alkoxy-$C_1$-$C_4$-alkyl-carbonyl-$C_1$-$C_4$-alkyl-
N—$C_1$-$C_4$-alkyl-amino-$C_1$-$C_4$-alkyl-carbonyl-$C_1$-$C_4$-alkyl-
N,N-di-$C_1$-$C_4$-alkyl-amino-$C_1$-$C_4$-alkyl-carbonyl-$C_1$-$C_4$-alkyl-
$C_3$-$C_7$-cycloalkyl-carbonyl-$C_1$-$C_4$-alkyl-
heterocyclyl-carbonyl-$C_1$-$C_4$-alkyl-
aryl-carbonyl-$C_1$-$C_4$-alkyl-
carbonyl-$C_1$-$C_4$-alkyl-
hydroxy-carbonyl-$C_1$-$C_4$-alkyl-
$C_1$-$C_4$-alkoxy-carbonyl-$C_1$-$C_4$-alkyl-
amino-carbonyl-$C_1$-$C_4$-alkyl-
N—$C_1$-$C_4$-alkyl-amino-carbonyl-$C_1$-$C_4$-alkyl-
N,N-di-$C_1$-$C_4$-alkyl-amino-carbonyl-$C_1$-$C_4$-alkyl-
$C_3$-$C_7$-cycloalkyl-carbonyl-$C_1$-$C_4$-alkyl-
heterocyclyl-carbonyl-$C_1$-$C_4$-alkyl-
aryl-carbonyl-$C_1$-$C_4$-alkyl-
$C_1$-$C_4$-alkyl-carbonyl-amino-$C_1$-$C_4$-alkyl-
$C_1$-$C_4$-alkyl-carbonyl-N—$C_1$-$C_4$-alkyl-amino-$C_1$-$C_4$-alkyl-
halo-$C_1$-$C_4$-alkyl-carbonyl-amino-$C_1$-$C_4$-alkyl-
halo-$C_1$-$C_4$-alkyl-carbonyl-N—$C_1$-$C_4$-alkyl-amino-$C_1$-$C_4$-alkyl-
wherein aryl, heterocyclyl and $C_3$-$C_7$-cycloalkyl are unsubstituted or substituted by 1-4 substituents selected from $C_1$-$C_4$-alkyl, halo-$C_1$-$C_4$-alkyl, halogen, hydroxy, $C_1$-$C_4$-alkoxy, amino, nitro or cyano;
each $R^1$ is independently selected from the group consisting of
halogen-
cyano-
nitro-
$C_1$-$C_4$-alkyl-
$C_1$-$C_4$-alkenyl-
halo-$C_1$-$C_4$-alkyl-
hydroxy-
$C_1$-$C_4$-alkoxy-
amino-
N—$C_1$-$C_4$-alkyl-amino-
N,N-di-$C_1$-$C_4$-alkyl-amino-
amino-carbonyl-amino-
N—$C_1$-$C_4$-alkyl-amino-carbonyl-amino-
N,N-di-$C_1$-$C_4$-alkyl-amino-carbonyl-amino-
$C_1$-$C_4$ alkyl-carbonyl-amino-
amino-carbonyl-
N—$C_1$-$C_4$-alkyl-amino-carbonyl-
N,N-di-$C_1$-$C_4$-alkyl-amino-carbonyl-
hydroxy-$C_1$-$C_4$-alkyl-
amino-$C_1$-$C_4$-alkyl-
N—$C_1$-$C_4$-alkyl-amino-$C_1$-$C_4$-alkyl-
N,N-di-$C_1$-$C_4$-alkyl-amino-$C_1$-$C_4$-alkyl-
$C_1$-$C_4$-alkyl-carbonyl-amino-$C_1$-$C_4$-alkyl-
$C_1$-$C_4$-alkyl-carbonyl-N—$C_1$-$C_4$-alkyl-amino-$C_1$-$C_4$-alkyl-;

n is 0, 1 or 2;
$R^2$ is selected from
(A) phenyl, 2-pyridyl or 3-pyridyl
substituted in para-position by
$(R^3)_2N—Y—$
wherein Y is absent (a bond) or
$(R^3)_2N—Y—$ is selected from

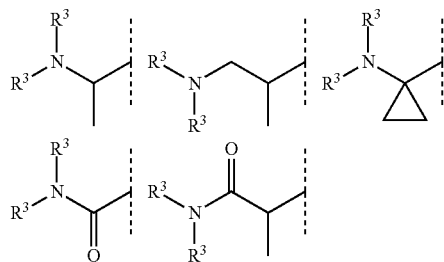

and optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
hydroxy-$C_1$-$C_4$-alkyl-;
or
(B) phenyl, 2-pyridyl or 3-pyridyl
substituted in para-position by a substituent selected from
cyano-
halogen-
nitro-
$C_1$-$C_4$-alkyl-
halo-$C_1$-$C_4$-alkyl-
hydroxy-$C_1$-$C_4$-alkyl-
hydroxy-carbonyl-
$C_1$-$C_4$-alkoxy-carbonyl-
$C_1$-$C_4$-alkyl-carbonyl-
$C_1$-$C_4$-alkoxy-
(C-bound)-heterocyclyl-
wherein (C-bound)-heterocyclyl is unsubstituted or substituted by 1-4 substituents selected from $C_1$-$C_4$-alkyl, halo-$C_1$-$C_4$-alkyl, halogen, hydroxy, $C_1$-$C_4$-alkoxy, amino, nitro or cyano;
and optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
(C-bound or N-bound)heterocyclyl-$C_1$-$C_4$-alkyl-
hydroxy-$C_1$-$C_4$-alkyl-;
or
(C) phenyl,
substituted in ortho-position by
$R^3$O—
and substituted in para- or meta-position by a substituent selected from methyl, chloro, $C_1$-$C_4$-alkyl-carbonyl- or $C_1$-$C_4$-alkoxy-carbonyl-;

(D) (C-bound)-heterocycle selected from

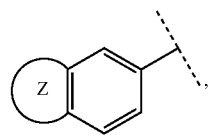

wherein Z is a 4-6 membered heterocyclic ring, annulated to phenyl in para and meta position, containing 1-3 heteroatoms selected from N, O or S,
which is optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
hydroxy-$C_1$-$C_4$-alkyl-;
(E) pyrazin-2-yl (relative to the isoquinolinone or quinazolinone), substituted at the 5 position by:

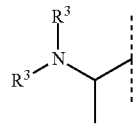

(F) pyridazin-3-yl (relative to the isoquinolinone or quinazolinone), substituted at the 6 position by:

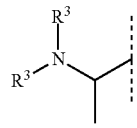

or
(G) pyrimidin-2-yl (relative to the isoquinolinone or quinazolinone), substituted at the 5 position by:

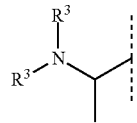

wherein each $R^3$ is independently selected from
H—
$C_1$-$C_4$-alkyl-
hydroxy-$C_1$-$C_4$-alkyl-
$C_3$-$C_7$-cycloalkyl-
$C_1$-$C_4$-alkoxy-$C_1$-$C_4$-alkyl-carbonyl-
amino-$C_1$-$C_4$-alkyl-carbonyl
N—$C_1$-$C_4$-alkyl-amino-$C_1$-$C_4$-alkyl-carbonyl
N,N-di $C_1$-$C_4$-alkyl-amino-$C_1$-$C_4$-alkyl-carbonyl
$(R^5)_2N$—$C_3$-$C_7$-cycloalkyl-
$(R^5)_2N$—$C_1$-$C_4$-alkyl-
$(R^5)_2N$—$C_3$-$C_7$-cycloalkyl-$C_1$-$C_4$-alkyl-
$(R^5)_2N$—$C_3$-$C_7$-cycloalkyl-carbonyl-
$R^5O$—$C_3$-$C_7$-cycloalkyl- R⁵O—C₁-C₄-alkyl-
R⁵O—C₃-C₇-cycloalkyl-C₁-C₄-alkyl-
R⁵O—(C₁-C₄-alkyl)-C₃-C₇-cycloalkyl-C₁-C₄-alkyl-
R⁵O—(hydroxy-C₁-C₄-alkyl)-C₃-C₇-cycloalkyl-C₁-C₄-alkyl-
(R⁵)₂N—CO—C₃-C₇-cycloalkyl-C₁-C₄-alkyl-
C₁-C₄-alkoxycarbonyl-C₃-C₇-cycloalkyl-C₁-C₄-alkyl-
hydroxycarbonyl-C₃-C₇-cycloalkyl-C₁-C₄-alkyl-
amino-carbonyl-C₃-C₇-cycloalkyl-C₁-C₄-alkyl-
R⁵O—C₃-C₇-cycloalkyl-carbonyl-
(R⁵)₂N-carbonyl-C₁-C₄-alkyl-
R⁵O-carbonyl-C₁-C₄-alkyl-
aryl-C₁-C₄-alkyl-
heterocyclyl-C₁-C₄-alkyl-
C₁-C₄-alkyl-carbonyl-
halo-C₁-C₄-alkyl-carbonyl-
heterocyclyl-carbonyl-
aryl-carbonyl-
C₃-C₇-cycloalkyl-carbonyl-
C₃-C₇-cycloalkyl-C₁-C₄-alkyl-
heterocyclyl-
aryl-
  wherein aryl, heterocyclyl and C₃-C₇-cycloalkyl are unsubstituted or substituted by 1-4 substituents selected from
halogen-
C₁-C₄-alkyl-
halo-C₁-C₄ alkyl-
C₁-C₄-alkyl-carbonyl-
C₃-C₇-cycloalkyl-carbonyl-
C₁-C₄-alkyl-sulfonyl-
amino-sulfonyl-
N—C₁-C₄-alkyl-amino-sulfonyl-
N,N-di-C₁-C₄-alkyl-amino-sulfonyl-
amino-carbonyl-
N—C₁-C₄-alkyl-amino-carbonyl-
N,N-di-C₁-C₄-alkyl-amino-carbonyl-
oxo=
or
two R³, together with the N to which they are attached my form a 3, 4, 5, 6 or 7 membered heterocyclic ring, optionally containing 1, 2, 3 or 4 additional N heteroatoms and optionally containing a O atom and for a S atom, said heterocyclic ring being unsubstituted or substituted by 1, 2 or 3 substituents selected from:
halogen-
hydroxy-C₁-C₄-alkyl-
C₁-C₄-alkyl-
halo-C₁-C₄-alkyl-
oxo=
hydroxy-
C₁-C₄-alkoxy-
amino-
N—C₁-C₄-alkyl-amino-
N,N-di-C₁-C₄-alkyl-amino-
hydroxy-carbonyl-
C₁-C₄-alkoxy-carbonyl-
amino-carbonyl-
N—C₁-C₄-alkyl-amino-carbonyl-
N,N-di-C₁-C₄-alkyl-amino-carbonyl-
C₁-C₄-alkyl-carbonyl-
C₁-C₄-alkyl-sulphonyl-
heterocyclyl-
C₁-C₄-alkyl-carbonyl-amino-
C₁-C₄-alkyl-carbonyl-N—C₁-C₄-alkyl-amino-;
and
each R⁵ is independently selected from:
H—
C₁-C₄-alkyl-
hydroxy-C₁-C₄-alkyl-
C₁-C₄-alkyl-carbonyl-
C₁-C₄-alkoxy-carbonyl-C₁-C₄-alkyl-
amino-carbonyl-C₁-C₄-alkyl-
N—C₁-C₄-alkyl-amino-carbonyl-C₁-C₄-alkyl-
N,N-di-C₁-C₄-alkyl-amino-carbonyl-C₁-C₄-alkyl-
C₁-C₄-alkyl-sulfonyl-
amino-sulfonyl-
N—C₁-C₄-alkyl-amino-sulfonyl-
N,N-di-C₁-C₄-alkyl-amino-sulfonyl-
heterocyclyl-carbonyl-
amino-carbonyl-
N—C₁-C₄-alkyl-amino-carbonyl-
N,N-di-C₁-C₄-alkyl-amino-carbonyl-
C₃-C₇-cycloalkyl-carbonyl-
C₁-C₄-alkoxy-carbonyl-amino-C₁-C₄-alkyl-
C₁-C₄-alkoxy-carbonyl-N—C₁-C₄-alkyl-amino-C₁-C₄-alkyl-
C₁-C₄-alkoxy-carbonyl-
C₃-C₇-cycloalkyl-
hydroxy-C₃-C₇-cycloalkyl-
or
two R⁵, together with the N to which they are attached may form a 3, 4, 5, 6 or 7 membered heterocyclic ring, optionally containing 1, 2, 3 or 4 additional N heteroatoms and/or optionally containing a O atom and/or a S atom, said heterocyclic ring being unsubstituted or substituted by from 1, 2 or 3 substituents independently selected from
C₁-C₄-alkyl-
oxo=,
C₁-C₄-alkyl-carbonyl,
C₁-C₄-alkyl-sulphonyl,
hydroxy-C₁-C₄-alkyl;
with the proviso that if Z is CH₂, n is 0 or 1, and when present, R¹ is ortho-chloro, and R² is selected from
para-C₁-C₃-alkyl-phenyl-
para-(halo-C₁-C₃-alkyl)-phenyl-
para-C₁-C₃-alkoxy-phenyl-
para-halo-phenyl-
para-nitro-phenyl-
para-(C₁-C₃-alkoxy-carbonyl)-phenyl-
para-(hydroxy-carbonyl)-phenyl-
wherein the phenyl is optionally substituted by 1-2 additional substituents, said substituents being independently selected from halo and methyl, then R⁶ and R⁷ are not both ethoxy or methoxy.

In another embodiment, the invention relates to a compound of formula (I), and/or a tautomer and/or N-oxide and/or a pharmaceutically acceptable salt and/or solvate thereof,

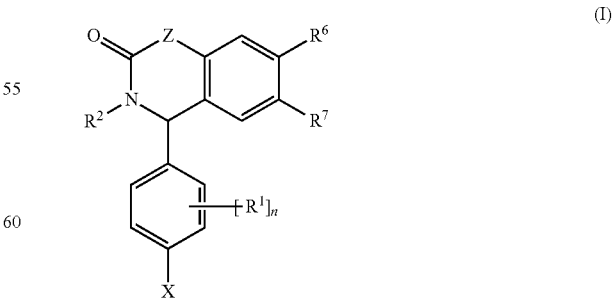

(I)

wherein
Z is CH₂ or N—R⁴;
X is halogen;

R⁴ is selected from the group consisting of
H—
$C_1$-$C_7$-alkyl-;
R⁶ is independently selected from the group consisting of
H—
—R'O—
(R')₂N—;
R⁷ is independently selected from the group consisting of
R'O—
(R')₂N—;
R' is selected from the group consisting of
H—
$C_1$-$C_7$-alkyl-
$C_1$-$C_7$-alkenyl-
halo-$C_1$-$C_7$-alkyl-
halo-$C_1$-$C_7$-alkenyl-
$C_3$-$C_{12}$-cycloalkyl-
heterocyclyl-
aryl-
hydroxy-$C_1$-$C_7$-alkyl-
$C_1$-$C_7$-alkoxy-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
$C_3$-$C_{12}$-cycloalkyl-$C_1$-$C_7$-alkyl-
heterocyclyl-$C_1$-$C_7$-alkyl-
$C_1$-$C_7$-alkyl-carbonyl-
halo-$C_1$-$C_7$-alkyl-carbonyl-
hydroxy-$C_1$-$C_7$-alkyl-carbonyl-
$C_1$-$C_7$-alkoxy-$C_1$-$C_7$-alkyl-carbonyl-
amino-$C_1$-$C_7$-alkyl-carbonyl-
N—$C_1$-$C_7$-alkyl-amino-$C_1$-$C_7$-alkyl-carbonyl-
N,N-di-$C_1$-$C_7$-alkyl-amino-$C_1$-$C_7$-alkyl-carbonyl-
$C_3$-$C_{12}$-cycloalkyl-carbonyl-
heterocyclyl-$C_1$-$C_7$-alkyl-carbonyl-
aryl-$C_1$-$C_7$-alkyl-carbonyl-
$C_3$-$C_{12}$-cycloalkyl-$C_1$-$C_7$-alkyl-carbonyl-
heterocyclyl-carbonyl-
aryl-carbonyl-
$C_1$-$C_7$-alkyl-carbonyl-$C_1$-$C_7$-alkyl-
halo-$C_1$-$C_7$-alkyl-carbonyl-$C_1$-$C_7$-alkyl-
hydroxy-$C_1$-$C_7$-alkyl-carbonyl-$C_1$-$C_7$-alkyl-
$C_1$-$C_7$-alkoxy-$C_1$-$C_7$-alkyl-carbonyl-$C_1$-$C_7$-alkyl-
amino-$C_1$-$C_7$-alkyl-carbonyl-$C_1$-$C_7$-alkyl-
N—$C_1$-$C_7$-alkyl-amino-$C_1$-$C_7$-alkyl-carbonyl-$C_1$-$C_7$-alkyl-
N,N-di-$C_1$-$C_7$-alkyl-amino-$C_1$-$C_7$-alkyl-carbonyl-$C_1$-$C_7$-alkyl-
$C_3$-$C_{12}$-cycloalkyl-carbonyl-$C_1$-$C_7$-alkyl-
heterocyclyl-carbonyl-$C_1$-$C_7$-alkyl-
aryl-carbonyl-$C_1$-$C_7$-alkyl-
carbonyl-$C_1$-$C_7$-alkyl-
hydroxy-carbonyl-$C_1$-$C_7$-alkyl-
$C_1$-$C_7$-alkoxy-carbonyl-$C_1$-$C_7$-alkyl-
amino-carbonyl-$C_1$-$C_7$-alkyl-
N—$C_1$-$C_7$-alkyl-amino-carbonyl-$C_1$-$C_7$-alkyl-
N,N-di-$C_1$-$C_7$-alkyl-amino-carbonyl-$C_1$-$C_7$-alkyl-
$C_3$-$C_{12}$-cycloalkyl-carbonyl-$C_1$-$C_7$-alkyl-
heterocyclyl-carbonyl-$C_1$-$C_7$-alkyl-
aryl-carbonyl-$C_1$-$C_7$-alkyl-
$C_1$-$C_7$-alkyl-carbonyl-amino-$C_1$-$C_7$-alkyl-
$C_1$-$C_7$-alkyl-carbonyl-N—$C_1$-$C_7$-alkyl-amino-$C_1$-$C_7$-alkyl-
halo-$C_1$-$C_7$-alkyl-carbonyl-amino-$C_1$-$C_7$-alkyl-
halo-$C_1$-$C_7$-alkyl-carbonyl-N—$C_1$-$C_7$-alkyl-amino-$C_1$-$C_7$-alkyl-
 wherein aryl, heterocyclyl and $C_3$-$C_{12}$-cycloalkyl are unsubstituted or substituted by 1-4 substituents selected from $C_1$-$C_7$-alkyl, halo-$C_1$-$C_7$-alkyl, halogen, hydroxy, $C_1$-$C_7$-alkoxy, amino, nitro or cyano;
R¹ is selected from the group consisting of
halogen-
cyano-
nitro-
$C_1$-$C_7$-alkyl-
$C_1$-$C_7$-alkenyl-
halo-$C_1$-$C_7$-alkyl-
hydroxy-
$C_1$-$C_7$-alkoxy-
amino-
N—$C_1$-$C_7$-alkyl-amino-
N,N-di-$C_1$-$C_7$-alkyl-amino-
hydroxy-$C_1$-$C_7$-alkyl-
amino-$C_1$-$C_7$-alkyl-
$C_1$-$C_7$-alkyl-carbonyl-amino-$C_1$-$C_7$-alkyl-
$C_1$-$C_7$-alkyl-carbonyl-N—$C_1$-$C_7$-alkyl-amino-$C_1$-$C_7$-alkyl-;
n is 0 to 2;
R² is selected from
 (A) phenyl, 2-pyridyl or 3-pyridyl
  substituted in para-position by
  (R³)₂N—Y—
   wherein Y is absent (a bond) or
   (R³)₂N—Y— is selected from and optionally substituted by 1-2 additional substituents selected from
halogen-
cyano-
halo-$C_1$-$C_7$-alkyl-
hydroxy-
$C_1$-$C_7$-alkoxy-
hydroxy-$C_1$-$C_7$-alkyl-;
or
 (B) phenyl, 2-pyridyl or 3-pyridyl
  substituted in para-position by a substituent selected from
  cyano-
  halogen-
  nitro-
  $C_1$-$C_7$-alkyl-
  halo-$C_1$-$C_7$-alkyl-
  hydroxy-$C_1$-$C_7$-alkyl-
  hydroxy-carbonyl-
  $C_1$-$C_7$-alkoxy-carbonyl-
  $C_1$-$C_7$-alkyl-carbonyl-
  $C_1$-$C_7$-alkoxy-
  (C-bound)-heterocyclyl-
   wherein (C-bound)-heterocyclyl is unsubstituted or substituted by 1-4 substituents selected from $C_1$-$C_7$-alkyl, halo-$C_1$-$C_7$-alkyl, halogen, hydroxy, $C_1$-$C_7$-alkoxy, amino, nitro or cyano;

and optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy-
hydroxy-$C_1$-$C_7$-alkyl-;
or
(C) phenyl,
substituted in ortho-position by
$R^3O$—
and substituted in para- or meta-position by a substituent selected from methyl or chloro;
or
(D) (C-bound)-heterocycle selected from

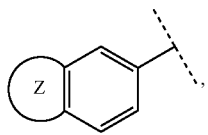

wherein Z is a 4-6 membered heterocyclic ring, annulated to phenyl in para and meta position, containing 1-3 heteroatoms selected from N, O or S,
which is optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy-
hydroxy-$C_1$-$C_7$-alkyl-;
wherein $R^3$ is independently selected from
H—
$C_1$-$C_7$-alkyl-
$C_3$-$C_{12}$-cycloalkyl-
$(R^5)_2N$—$C_3$-$C_{12}$-cycloalkyl-
$(R^5)_2N$—$C_1$-$C_7$-alkyl-
$(R^5)_2N$—$C_3$-$C_{12}$-cycloalkyl-$C_1$-$C_7$-alkyl-
$(R^5)_2N$—$C_3$-$C_{12}$-cycloalkyl-carbonyl-
$R^5O$—$C_3$-$C_{12}$-cycloalkyl-
$R^5O$—$C_1$-$C_7$-alkyl-
$R^5O$—$C_3$-$C_{12}$-cycloalkyl-$C_1$-$C_7$-alkyl-
$R^5O$—$C_3$-$C_{12}$-cycloalkyl-carbonyl-
$(R^5)_2N$-carbonyl-$C_1$-$C_7$-alkyl-
$R^5O$-carbonyl-$C_1$-$C_7$-alkyl-
aryl-$C_1$-$C_7$-alkyl-
heterocyclyl-$C_1$-$C_7$-alkyl-
$C_1$-$C_7$-alkyl-carbonyl-
heterocyclyl-carbonyl-
aryl-carbonyl-
$C_3$-$C_{12}$-cycloalkyl-carbonyl-
$C_3$-$C_{12}$-cycloalkyl-$C_1$-$C_7$-alkyl-
heterocyclyl-
aryl-
wherein aryl, heterocyclyl and $C_3$-$C_{12}$-cycloalkyl are unsubstituted or substituted by 1-4 substituents selected from
halogen-
$C_1$-$C_7$-alkyl-
halo-$C_1$-$C_7$-alkyl-
$C_1$-$C_7$-alkyl-carbonyl-
$C_3$-$C_{12}$-cycloalkyl-carbonyl-
$C_1$-$C_7$-alkyl-sulfonyl-
amino-sulfonyl-
N—$C_1$-$C_7$-alkyl-amino-sulfonyl-
N,N-di-$C_1$-$C_7$-alkyl-amino-sulfonyl-
amino-carbonyl-
N—$C_1$-$C_7$-alkyl-amino-carbonyl-
N,N-di-$C_1$-$C_7$-alkyl-amino-carbonyl-
oxo=
or
two $R^3$, together with the N to which they are attached my form a 3-9 membered heterocyclic ring, optionally containing 1-4 additional heteroatoms selected from N, O or S, said heterocyclic ring is unsubstituted or substituted by 1-3 substituents selected from:
halogen-
oxo=
hydroxy-
$C_1$-$C_7$-alkoxy-
amino-
N—$C_1$-$C_7$-alkyl-amino-
N,N-di-$C_1$-$C_7$-alkyl-amino-
hydroxy-carbonyl-
$C_1$-$C_7$-alkoxy-carbonyl-
amino-carbonyl-
N—$C_1$-$C_7$-alkyl-amino-carbonyl-
N,N-di-$C_1$-$C_7$-alkyl-amino-carbonyl-
$C_1$-$C_7$-alkyl-carbonyl-
$C_1$-$C_7$-alkyl-carbonyl-amino-
$C_1$-$C_7$-alkyl-carbonyl-N—$C_1$-$C_7$-alkyl-amino-;
and
$R^5$ is independently selected from:
H—
$C_1$-$C_7$-alkyl-
$C_1$-$C_7$-alkoxy-carbonyl-$C_1$-$C_7$-alkyl-
amino-carbonyl-$C_1$-$C_7$-alkyl-
N—$C_1$-$C_7$-alkyl-amino-carbonyl-$C_1$-$C_7$-alkyl-
N,N-di-$C_1$-$C_7$-alkyl-amino-carbonyl-$C_1$-$C_7$-alkyl-
$C_1$-$C_7$-alkyl-sulfonyl-
amino-sulfonyl-
N—$C_1$-$C_7$-alkyl-amino-sulfonyl-
N,N-di-$C_1$-$C_7$-alkyl-amino-sulfonyl-
amino-carbonyl-
N—$C_1$-$C_7$-alkyl-amino-carbonyl-
N,N-di-$C_1$-$C_7$-alkyl-amino-carbonyl-
$C_3$-$C_{12}$-cycloalkyl-carbonyl-
$C_1$-$C_7$-alkoxy-carbonyl-amino-$C_1$-$C_7$-alkyl-
$C_1$-$C_7$-alkoxy-carbonyl-N—$C_1$-$C_7$-alkyl-amino-$C_1$-$C_7$-alkyl-
$C_1$-$C_7$-alkoxy-carbonyl-
or
two $R^5$, together with the N to which they are attached my form a 3-9 membered heterocyclic ring, optionally containing 1-4 additional heteroatoms selected from N, O or S, said heterocyclic ring is unsubstituted or substituted by 1-3 substituent selected from
$C_1$-$C_7$-alkyl-
oxo=;
with the proviso that if Z is $CH_2$, n is 0 and $R^2$ is selected from
para-$C_1$-$C_3$-alkyl-phenyl-
para-(halo-$C_1$-$C_3$-alkyl)-phenyl-
para-$C_1$-$C_3$-alkoxy-phenyl-
para-halo-phenyl-
para-nitro-phenyl-
para-($C_1$-$C_3$-alkoxy-carbonyl)-phenylpara-(hydroxy-carbonyl)-phenyl-
  wherein the phenyl is optionally substituted by 1-2 additional substituents, then $R^6$ and $R^7$ are not both ethoxy or methoxy.
In another embodiment,
Z is $CH_2$.
In another embodiment
Z is N—$R^4$.
In another embodiment
Z is N—$R^4$; wherein
$R^4$ is selected from the group consisting of
H—,
$C_1$-$C_4$-alkyl-.
In another embodiment,
$R^6$ is selected from
R'O—
and
$R^7$ is selected from
R'O—.
In another embodiment,
$R^6$ is selected from
H—
and
$R^7$ is selected from
$(R')_2$N—.
In another embodiment,
R' is independently selected from the group consisting of
H—
$C_1$-$C_7$-alkyl-
$C_1$-$C_7$-alkenyl-
halo-$C_1$-$C_7$-alkyl-
$C_3$-$C_{12}$-cycloalkyl-
hydroxy-$C_1$-$C_7$-alkyl-
$C_1$-$C_7$-alkoxy-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
$C_3$-$C_{12}$-cycloalkyl-$C_1$-$C_7$-alkyl-
heterocyclyl-$C_1$-$C_7$-alkyl-
$C_1$-$C_7$-alkyl-carbonyl-
carbonyl-$C_1$-$C_7$-alkyl-
hydroxy-carbonyl-$C_1$-$C_7$-alkyl-
$C_1$-$C_7$-alkoxy-carbonyl-$C_1$-$C_7$-alkyl-
amino-carbonyl-$C_1$-$C_7$-alkyl-
N—$C_1$-$C_7$-alkyl-amino-carbonyl-$C_1$-$C_7$-alkyl-
N,N-di-$C_1$-$C_7$-alkyl-amino-carbonyl-$C_1$-$C_7$-alkyl-
heterocyclyl-carbonyl-$C_1$-$C_7$-alkyl-
$C_1$-$C_7$-alkyl-carbonyl-amino-$C_1$-$C_7$-alkyl-
  wherein aryl, heterocyclyl and $C_3$-$C_{12}$-cycloalkyl are unsubstituted or substituted by 1-4 substituents selected from $C_1$-$C_7$-alkyl, halo-$C_1$-$C_7$-alkyl, halogen, hydroxy, $C_1$-$C_7$-alkoxy, amino, nitro or cyano.
In another embodiment,
R' is independently selected from the group consisting of
H—
$C_1$-$C_4$-alkyl-
$C_1$-$C_4$-alkenyl-
halo-$C_1$-$C_4$-alkyl-
$C_3$-$C_{12}$-cycloalkyl-
$C_3$-$C_{12}$-cycloalkyl-$C_1$-$C_2$-alkyl-
  wherein aryl, heterocyclyl and $C_3$-$C_{12}$-cycloalkyl are unsubstituted or substituted by 1-2 substituents selected from $C_1$-$C_4$-alkyl, halo-$C_1$-$C_4$-alkyl, halogen, hydroxy, $C_1$-$C_4$-alkoxy, amino, nitro or cyano.
In another embodiment,
$R^1$ is independently selected from the group consisting of
halogen-
cyano-
nitro-
$C_1$-$C_7$-alkyl-
$C_1$-$C_7$-alkenyl-
halo-$C_1$-$C_7$-alkyl-
amino-
hydroxy-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl
$C_1$-$C_7$-alkyl-carbonyl-amino-$C_1$-$C_7$-alkyl-.
In another embodiment,
$R^1$ is independently selected from the group consisting of
halogen-
cyano-
nitro-
$C_1$-$C_4$-alkyl-
$C_1$-$C_4$-alkenyl-
halo-$C_1$-$C_4$-alkyl-
amino-
N—$C_1$-$C_4$-alkyl-amino-
N,N-di-$C_1$-$C_4$-alkyl-amino-
hydroxy-$C_1$-$C_2$-alkyl-
amino-$C_1$-$C_2$-alkyl-
N—$C_1$-$C_4$-alkyl-amino-$C_1$-$C_2$-alkyl-
N,N-di-$C_1$-$C_4$-alkyl-amino-$C_1$-$C_2$-alkyl-
$C_1$-$C_4$-alkyl-carbonyl-amino-$C_1$-$C_2$-alkyl-.
In another embodiment,
n is 0 to 1.
In another embodiment,
n is 0.
In another embodiment,
$R^2$ is selected from
phenyl, 2-pyridyl or 3-pyridyl
  substituted in para-position by
    $(R^3)_2$N—Y—
      wherein Y is absent (a bond) or
      $(R^3)_2$N—Y— is selected from

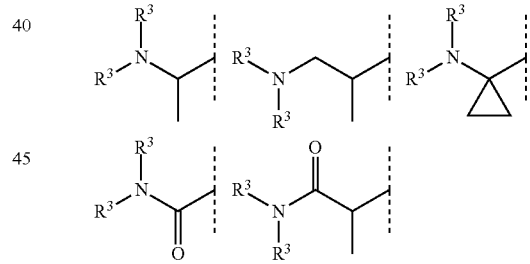

and optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy-
hydroxy-$C_1$-$C_7$-alkyl.
In another embodiment,
$R^2$ is selected from
phenyl, 2-pyridyl or 3-pyridyl
  substituted in para-position by
    $(R^3)_2$N—Y—
      wherein Y is absent (a bond) or
      $(R^3)_2$N—Y— is selected from

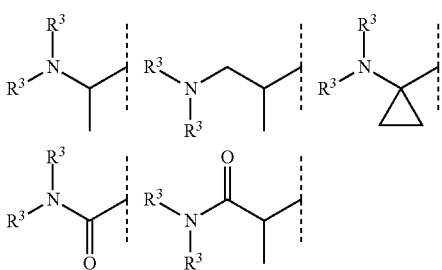

and optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
hydroxy-$C_1$-$C_4$-alkyl,
wherein
$R^3$ is independently selected from
H—
$C_1$-$C_7$-alkyl-
$C_3$-$C_{12}$-cycloalkyl-
$(R^5)_2$N—$C_3$-$C_{12}$-cycloalkyl-
$(R^5)_2$N—$C_1$-$C_7$-alkyl-
$(R^5)_2$N—$C_3$-$C_{12}$-cycloalkyl-$C_1$-$C_7$-alkyl-
$(R^5)_2$N—$C_3$-$C_{12}$-cycloalkyl-carbonyl-
$R^5$O—$C_1$-$C_7$-alkyl-
$(R^5)_2$N-carbonyl-$C_1$-$C_7$-alkyl-
$R^5$O-carbonyl-$C_1$-$C_7$-alkyl-
aryl-$C_1$-$C_7$-alkyl-
heterocyclyl-$C_1$-$C_7$-alkyl-
$C_1$-$C_7$-alkyl-carbonyl-
heterocyclyl-carbonyl-
$C_3$-$C_{12}$-cycloalkyl-$C_1$-$C_7$-alkyl-
heterocyclyl-
wherein aryl, heterocyclyl and $C_3$-$C_{12}$-cycloalkyl are unsubstituted or substituted by 1-4 substituents selected from
halo-
$C_1$-$C_7$-alkyl-
halo-$C_1$-$C_7$-alkyl-
$C_1$-$C_7$-alkyl-carbonyl-
$C_3$-$C_{12}$-cycloalkyl-carbonyl-
$C_1$-$C_7$-alkyl-sulfonyl-
N,N-di-$C_1$-$C_7$-alkyl-amino-carbonyl-
oxo=
or
two $R^3$, together with the N to which they are attached my form a 3-9 membered heterocyclic ring, optionally containing 1-4 additional heteroatoms selected from N, O or S, said heterocyclic ring is unsubstituted or substituted by 1-3 substituents selected from:
oxo=
hydroxy-
amino-
N,N-di-$C_1$-$C_7$-alkyl-amino-
hydroxy-carbonyl-
$C_1$-$C_7$-alkoxy-carbonyl-
amino-carbonyl-
N—$C_1$-$C_7$-alkyl-amino-carbonyl-
$C_1$-$C_7$-alkyl-carbonyl-
$C_1$-$C_7$-alkyl-carbonyl-amino-;
and
$R^5$ is independently selected from:
H—
$C_1$-$C_7$-alkyl-
$C_1$-$C_7$-alkoxy-carbonyl-$C_1$-$C_7$-alkyl-
amino-carbonyl-$C_1$-$C_7$-alkyl-
$C_1$-$C_7$-alkyl-sulfonyl-
N,N-di-$C_1$-$C_7$-alkyl-amino-carbonyl-
$C_1$-$C_7$-alkoxy-carbonyl-amino-$C_1$-$C_7$-alkyl-
$C_1$-$C_7$-alkoxy-carbonyl-
or
two $R^5$, together with the N to which they are attached my form a 3-9 membered heterocyclic ring, optionally containing 1-4 additional heteroatoms selected from N, O or S, said heterocyclic ring is unsubstituted or substituted by 1-3 substituent selected from oxo=.
In another embodiment,
$R^2$ is selected from
phenyl, 2-pyridyl or 3-pyridyl
substituted in para-position by
$(R^3)_2$N—Y—
wherein Y is absent (a bond) or
$(R^3)_2$N—Y— is selected from

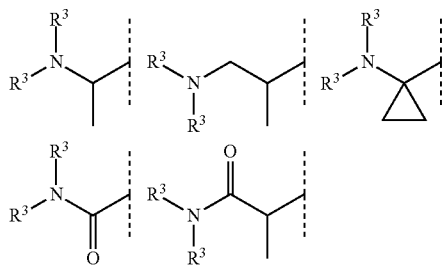

and optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy-
hydroxy-$C_1$-$C_7$-alkyl,
wherein
$R^3$ is independently selected from:
H—
$C_1$-$C_4$-alkyl-
$C_3$-$C_{12}$-cycloalkyl-
$(R^5)_2$N—$C_3$-$C_7$-cycloalkyl-
$(R^5)_2$N—$C_1$-$C_7$-alkyl-
$(R^5)_2$N—$C_3$-$C_7$-cycloalkyl-$C_1$-$C_2$-alkyl-
$(R^5)_2$N—$C_3$-$C_7$-cycloalkyl-carbonyl-
aryl-$C_1$-$C_2$-alkyl-
heterocyclyl-$C_1$-$C_2$-alkyl-
$C_1$-$C_4$-alkyl-carbonyl-
heterocyclyl-carbonyl-
$C_3$-$C_7$-cycloalkyl-$C_1$-$C_2$-alkyl-
heterocyclyl-
wherein aryl, heterocyclyl and $C_3$-$C_{12}$-cycloalkyl are unsubstituted or substituted by 1-2 substituents selected from
halo-
$C_1$-$C_4$-alkyl-
halo-$C_1$-$C_4$-alkyl-
$C_1$-$C_4$-alkyl-carbonyl-
$C_3$-$C_7$-cycloalkyl-carbonyl-
$C_1$-$C_4$-alkyl-sulfonyl-
N,N-di-$C_1$-$C_4$-alkyl-amino-carbonyl-
oxo= or
two $R^3$, together with the N to which they are attached my form a 4-7 membered heterocyclic ring, optionally containing 1-2 additional heteroatoms selected from N, O or S, said heterocyclic ring is unsubstituted or substituted by 1-2 substituents selected from:
$C_1$-$C_4$-alkyl-
oxo=
hydroxy-
amino-
N,N-di-$C_1$-$C_4$-alkyl-amino-
hydroxy-carbonyl-
$C_1$-$C_4$-alkoxy-carbonyl-
amino-carbonyl-
N—$C_1$-$C_4$-alkyl-amino-carbonyl-
$C_1$-$C_4$-alkyl-carbonyl-
$C_1$-$C_4$-alkyl-carbonyl-amino-;
and
$R^5$ is independently selected from:
H—
$C_1$-$C_4$-alkyl-
$C_1$-$C_4$-alkoxy-carbonyl-$C_1$-$C_2$-alkyl-
amino-carbonyl-$C_1$-$C_2$-alkyl-
$C_1$-$C_4$-alkyl-sulfonyl-
N,N-di-$C_1$-$C_4$-alkyl-amino-carbonyl-
$C_1$-$C_4$-alkoxy-carbonyl-amino-$C_1$-$C_2$-alkyl-
$C_1$-$C_4$-alkoxy-carbonyl-
or
two $R^5$, together with the N to which they are attached my form a 4-7 membered heterocyclic ring, optionally containing 1-4 additional heteroatoms selected from N, O or S, said heterocyclic ring is unsubstituted or substituted by 1-2 substituent selected from:
$C_1$-$C_4$-alkyl-
oxo=.
In another embodiment,
$R^2$ is selected from
phenyl, 2-pyridyl or 3-pyridyl
substituted in para-position by
$(R^3)_2$N—Y—
wherein Y is absent (a bond)
and optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy-
hydroxy-$C_1$-$C_7$-alkyl.
In another embodiment,
$R^2$ is selected from
phenyl, 2-pyridyl or 3-pyridyl
substituted in para-position by
$(R^3)_2$N—Y—
wherein
$(R^3)_2$N—Y— is selected from

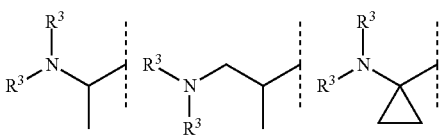

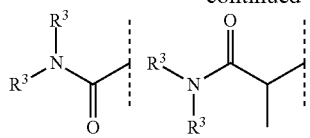

and optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
hydroxy-$C_1$-$C_4$-alkyl.
In another embodiment, Z is $CH_2$ or $NR^4$ wherein $R^4$ is H or $C_1$-$C_3$-alkyl. Preferably, Z is $CH_2$ or NH, more preferably $CH_2$.
In another embodiment, X is chloro or fluoro, preferably chloro.
In another embodiment, each R' is independently selected from
H—
$C_1$-$C_6$-alkyl-
heterocyclyl-$C_1$-$C_4$-alkyl-
amino-$C_1$-$C_4$-alkyl-
N—$C_1$-$C_4$-alkyl-amino-$C_1$-$C_4$-alkyl-
N,N-di-$C_1$-$C_4$-alkyl-amino-$C_1$-$C_4$-alkyl-
heterocyclyl-carbonyl-$C_1$-$C_4$-alkyl-
hydroxy-$C_1$-$C_4$-alkyl-
amino-carbonyl-$C_1$-$C_4$-alkyl-
N—$C_1$-$C_4$-alkyl-amino-carbonyl-$C_1$-$C_4$-alkyl-
N,N-di-$C_1$-$C_4$-alkyl-amino-carbonyl-$C_1$-$C_4$-alkyl-
$d_3$ methoxy,
$C_3$-$C_7$-cycloalkyl-$C_1$-$C_4$-alkyl-
$C_3$-$C_7$-cycloalkyl-
aryl-$C_1$-$C_4$-alkyl-
$C_1$-$C_4$-alkoxy-$C_1$-$C_4$-alkyl-
$C_1$-$C_6$-alkenyl-
halo-$C_1$-$C_4$-alkyl-
halo-$C_1$-$C_4$-alkenyl-
$C_1$-$C_4$-alkyl-carbonyl-
$C_1$-$C_4$-alkyl-carbonyl-amino-$C_1$-$C_4$-alkyl-
aryl-$C_1$-$C_4$-alkyl-
heterocyclyl- and
aryl-
wherein said $C_3$-$C_7$-cycloalkyl (including the $C_3$-$C_7$-cycloalkyl substituent within $C_3$-$C_7$-cycloalkyl-$C_1$-$C_4$-alkyl-), is optionally substituted by hydroxy or methyl, and wherein aryl (including within aryl-$C_1$-$C_4$-alkyl-), and heterocyclyl (including within heterocyclyl-$C_1$-$C_4$-alkyl- and heterocyclyl-carbonyl-$C_1$-$C_4$-alkyl-), is optionally substituted by 1 or 2 $C_1$-$C_4$-alkyl substituents.
In another embodiment, at least one R' is independently selected from
H—, and
$C_1$-$C_6$-alkyl-.
In another embodiment, $R^6$ is selected from the group consisting of
H—
R'O— and
$(R')_2$N—,
wherein R' is independently selected from
H—
$C_1$-$C_4$-alkylheterocyclyl-$C_1$-$C_4$-alkyl-
amino-$C_1$-$C_4$-alkyl-
heterocyclyl-carbonyl-$C_1$-$C_4$-alkyl-
N,N-di-$C_1$-$C_4$-alkyl-amino-$C_1$-$C_4$-alkyl-
hydroxy-$C_1$-$C_4$-alkyl-
N—$C_1$-$C_4$-alkyl-amino-carbonyl-$C_1$-$C_4$-alkyl-
N,N-di-$C_1$-$C_4$-alkyl-amino-carbonyl-$C_1$-$C_4$-alkyl-
and
d$_3$ methoxy,
wherein heterocyclyl within heterocyclyl-$C_1$-$C_4$-alkyl- and heterocyclyl-carbonyl-$C_1$-$C_4$-alkyl-, is optionally substituted by 1 or 2 $C_1$-$C_4$-alkyl substituents.

In another embodiment, $R^7$ is independently selected from R'O—, and
(R')$_2$N—,
wherein R' is independently selected from
$C_1$-$C_6$-alkyl-
$C_3$-$C_7$-cycloalkyl-$C_1$-$C_4$-alkyl-
heterocyclyl-$C_1$-$C_4$-alkyl-
$C_3$-$C_7$-cycloalkyl-
heterocyclyl-$C_1$-$C_4$-alkyl-
hydroxy-$C_1$-$C_4$-alkyl-
N,N-di-$C_1$-$C_4$-alkyl-amino-$C_1$-$C_4$-alkyl-
amino-$C_1$-$C_4$-alkyl-
aryl-$C_1$-$C_4$-alkyl-
$C_1$-$C_4$-alkoxy-$C_1$-$C_4$-alkyl-
$C_1$-$C_6$-alkenyl-
halo-$C_1$-$C_4$-alkyl-
$C_1$-$C_4$-alkyl-carbonyl-
$C_1$-$C_4$-alkyl-carbonyl-amino-$C_1$-$C_4$-alkyl-
aryl-$C_1$-$C_4$-alkyl-
wherein said $C_3$-$C_7$-cycloalkyl, or the $C_3$-$C_7$-cycloalkyl substituent within $C_3$-$C_7$-cycloalkyl-$C_1$-$C_4$-alkyl-, is optionally substituted by hydroxy.

Preferably, $R^6$ is R'O—.
Preferably, $R^7$ is R'O—.
In another embodiment, R' is $C_1$-$C_6$-alkyl-.
In another embodiment, $R^1$ is independently selected from halogen, nitro-, $C_1$-$C_4$-alkyl, $C_1$-$C_4$-alkoxy-, amino, N—$C_1$-$C_4$-alkyl-amino-, N,N-di-$C_1$-$C_4$-alkyl-amino, amino-carbonyl-amino-, N—$C_1$-$C_4$-alkyl-amino-carbonyl-amino-, N,N-di-$C_1$-$C_4$-alkyl-amino-carbonyl-amino-, amino-carbonyl-, N—$C_1$-$C_4$-alkyl-amino-carbonyl-, N,N-di-$C_1$-$C_4$-alkyl-amino-carbonyl-, $C_1$-$C_4$ alkyl-carbonyl-amino-, hydroxy-$C_1$-$C_4$-alkyl-, amino-$C_1$-$C_4$-alkyl-, $C_1$-$C_4$-alkyl-carbonyl-amino-$C_1$-$C_4$-alkyl- and N—$C_1$-$C_4$-alkyl-amino-$C_1$-$C_4$-alkyl-.

In another embodiment, $R^2$ is selected from:
(A) phenyl, 2-pyridyl or 3-pyridyl
substituted in para-position by
($R^3$)$_2$N—Y—
wherein Y is absent (a bond) or
($R^3$)$_2$N—Y— is selected from

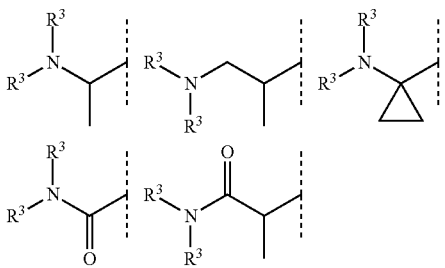

and optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
hydroxy-$C_1$-$C_4$-alkyl-;
(B) phenyl, 2-pyridyl or 3-pyridyl
substituted in para-position by a substituent selected from
cyano-
halogen-
nitro-
$C_1$-$C_4$-alkyl-
halo-$C_1$-$C_4$-alkyl-
hydroxy-$C_1$-$C_4$-alkyl-
hydroxy-carbonyl-
$C_1$-$C_4$-alkoxy-carbonyl-
$C_1$-$C_4$-alkyl-carbonyl-
$C_1$-$C_4$-alkoxy-
(C-bound)-heterocyclyl-
wherein (C-bound)-heterocyclyl is unsubstituted or substituted by 1-4 substituents selected from $C_1$-$C_4$-alkyl, halo-$C_1$-$C_4$-alkyl, halogen, hydroxy, $C_1$-$C_4$-alkoxy, amino, nitro or cyano;
and optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
(C-bound or N-bound)heterocyclyl-$C_1$-$C_4$-alkyl-
hydroxy-$C_1$-$C_4$-alkyl-;
or
(C) phenyl,
substituted in ortho-position by
$R^3$O—
and substituted in para- or meta-position by a substituent selected from methyl, chloro, $C_1$-$C_4$-alkyl-carbonyl- or $C_1$-$C_4$-alkoxy-carbonyl-.
In another embodiment, $R^2$ is selected from:
(A) phenyl, 2-pyridyl or 3-pyridyl
substituted in para-position by
($R^3$)$_2$N—Y—
wherein Y is absent (a bond) or
($R^3$)$_2$N—Y— is selected from

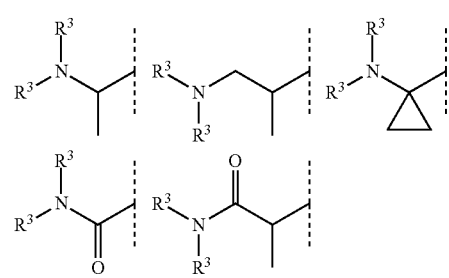

and optionally substituted by 1-2 additional substituents selected from
halogen-
cyano-
$C_1$-$C_4$-alkylhalo-$C_1$-$C_4$-alkyl-
hydroxy-
$C_1$-$C_4$-alkoxy-
hydroxy-$C_1$-$C_4$-alkyl-.

In another embodiment, $R^2$ is selected from:
(A) phenyl, 2-pyridyl or 3-pyridyl,
substituted in para-position by $(R^3)_2N$—Y—, wherein Y is absent (a bond) and optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
hydroxy-$C_1$-$C_4$-alkyl-.

In another embodiment, $R^2$ is selected from:
(A) phenyl, 2-pyridyl or 3-pyridyl,
substituted in para-position by $(R^3)_2N$—Y—, wherein Y is absent (a bond), and wherein the phenyl, 2-pyridyl or 3-pyridyl are not further substituted.

In another embodiment, each $R^3$ is independently selected from:
$C_1$-$C_4$-alkyl-
$C_3$-$C_7$-cycloalkyl-$C_1$-$C_4$-alkyl-
heterocyclyl-$C_1$-$C_4$-alkyl-
aryl-$C_1$-$C_4$-alkyl-
$(R^5)_2N$—$C_3$-$C_7$-cycloalkyl-
$(R^5)_2N$—$C_3$-$C_7$-cycloalkyl-$C_1$-$C_4$-alkyl-
$(R^5)_2N$—CO—$C_3$-$C_7$-cycloalkyl-$C_1$-$C_4$-alkyl-
aryl-
heterocyclyl-
$C_3$-$C_7$-cycloalkyl-
wherein aryl, heterocyclyl and $C_3$-$C_7$-cycloalkyl are unsubstituted or substituted by 1-4 substituents selected from
halogen-
$C_1$-$C_4$-alkyl-
halo-$C_1$-$C_4$-alkyl-
$C_1$-$C_4$-alkyl-carbonyl-
$C_3$-$C_7$-cycloalkyl-carbonyl-
$C_1$-$C_4$-alkyl-sulfonyl-
amino-sulfonyl-
N—$C_1$-$C_4$-alkyl-amino-sulfonyl-
N,N-di-$C_1$-$C_4$-alkyl-amino-sulfonyl-
amino-carbonyl-
N—$C_1$-$C_4$-alkyl-amino-carbonyl-
N,N-di-$C_1$-$C_4$-alkyl-amino-carbonyl- and
oxo=

In another embodiment, $R^2$ is selected from (A) phenyl, 2-pyridyl or 3-pyridyl, substituted in para-position by $(R^3)_2N$—Y—, wherein Y is absent (a bond), wherein one $R^3$ is $C_1$-$C_4$-alkyl-, preferably methyl, and the other $R^3$ is selected from:
$C_3$-$C_7$-cycloalkyl-$C_1$-$C_4$-alkyl-
heterocyclyl-$C_1$-$C_4$-alkyl-
aryl-$C_1$-$C_4$-alkyl-
$(R^5)_2N$—$C_3$-$C_7$-cycloalkyl-$C_1$-$C_4$-alkyl-
$(R^5)_2N$—CO—$C_3$-$C_7$-cycloalkyl-$C_1$-$C_4$-alkyl-
wherein aryl, heterocyclyl and $C_3$-$C_7$-cycloalkyl are unsubstituted or substituted by 1-4 substituents independently selected from:
halogen-, $C_1$-$C_4$-alkyl-, halo-$C_1$-$C_4$-alkyl-, $C_1$-$C_4$-alkyl-carbonyl-, $C_3$-$C_7$-cycloalkyl-carbonyl-, $C_1$-$C_4$-alkyl-sulfonyl-, amino-sulfonyl-, N—$C_1$-$C_4$-alkyl-amino-sulfonyl-, N,N-di-$C_1$-$C_4$-alkyl-amino-sulfonyl-, amino-carbonyl-, N—$C_1$-$C_4$-alkyl-amino-carbonyl-, N,N-di-$C_1$-$C_4$-alkyl-amino-carbonyl- and oxo=.

In another embodiment, $R^2$ is selected from (A) phenyl, 2-pyridyl or 3-pyridyl, substituted in para-position by $(R^3)_2N$—Y—, wherein Y is absent (a bond), wherein one $R^3$ is $C_1$-$C_4$-alkyl-, preferably methyl, and the other $R^3$ is selected from the group including $(R^5)_2N$—$C_3$-$C_7$-cycloalkyl-$C_1$-$C_4$-alkyl- and $(R^5)_2N$—CO—$C_3$-$C_7$-cycloalkyl-$C_1$-$C_4$-alkyl-, and the two $R^5$, together with the N to which they are attached form a 3, 4, 5, 6 or 7 membered heterocyclic ring, optionally containing 1, 2, 3 or 4 additional N heteroatoms and/or optionally containing a O atom and for a S atom, said heterocyclic ring being unsubstituted or substituted by from 1, 2 or 3 substituents independently selected from
$C_1$-$C_4$-alkyl-
oxo=,
$C_1$-$C_4$-alkyl-carbonyl,
$C_1$-$C_4$-alkyl-sulphonyl, and
hydroxy-$C_1$-$C_4$-alkyl.

In a preferred embodiment, $R^2$ is selected from (A) phenyl, 2-pyridyl or 3-pyridyl, substituted in para-position by $(R^3)_2N$—Y—, wherein Y is absent (a bond), and wherein one $R^3$ is $C_1$-$C_4$-alkyl-, preferably methyl, and the other $R^3$ is $(R^5)_2N$-cyclohexyl-$C_1$-$C_2$-alkyl-, and wherein the two $R^5$, together with the N to which they are attached form a 6 membered heterocyclic ring, optionally containing 1 additional N heteroatom and/or optionally containing a O atom and/or a S atom, said heterocyclic ring being unsubstituted or substituted by 1 or 2 substituents independently selected from
$C_1$-$C_4$-alkyl-, preferably methyl
oxo=,
$C_1$-$C_4$-alkyl-carbonyl,
$C_1$-$C_4$-alkyl-sulphonyl, and
hydroxy-$C_1$-$C_4$-alkyl.

In a more preferred embodiment, $R^2$ is selected from phenyl or 3-pyridyl, substituted in para-position by $(R^3)_2N$—Y—, wherein Y is absent (a bond), and wherein one $R^3$ is $C_1$-$C_4$-alkyl-, preferably methyl, and the other $R^3$ is $(R^5)_2N$-cyclohexyl-methyl-, and wherein the two $R^5$, together with the N to which they are attached, form a 6 membered heterocyclic ring containing 1 additional N heteroatom, said heterocyclic ring being substituted at a carbon atom by an oxo substituent and optionally N-substituted by methyl. Preferably said heterocyclic ring is piperazinyl. Preferably, the cyclohexyl ring is substituted at the 1 and 4 positions. Preferably, the stereochemistry of such substitution is trans.

In another embodiment, each $R^5$ is independently selected from:
H—
$C_1$-$C_4$-alkyl-
hydroxy-$C_1$-$C_4$-alkyl-
$C_1$-$C_4$-alkyl-carbonyl-
$C_1$-$C_4$-alkoxy-carbonyl-$C_1$-$C_4$-alkyl-
amino-carbonyl-$C_1$-$C_4$-alkyl-
N—$C_1$-$C_4$-alkyl-amino-carbonyl-$C_1$-$C_4$-alkyl-
N,N-di-$C_1$-$C_4$-alkyl-amino-carbonyl-$C_1$-$C_4$-alkyl-
$C_1$-$C_4$-alkyl-sulfonyl-
amino-sulfonyl-
N—$C_1$-$C_4$-alkyl-amino-sulfonyl-
N,N-di-$C_1$-$C_4$-alkyl-amino-sulfonyl-
heterocyclyl-carbonyl-
amino-carbonyl-
N—$C_1$-$C_4$-alkyl-amino-carbonyl-
N,N-di-$C_1$-$C_4$-alkyl-amino-carbonyl-
$C_3$-$C_7$-cycloalkyl-carbonyl-
$C_1$-$C_4$-alkoxy-carbonyl-amino-$C_1$-$C_4$-alkyl-
$C_1$-$C_4$-alkoxy-carbonyl-N—$C_1$-$C_4$-alkyl-amino-$C_1$-$C_4$-alkyl-
$C_1$-$C_4$-alkoxy-carbonyl-
$C_3$-$C_7$-cycloalkyl-
hydroxy-$C_3$-$C_7$-cycloalkyl-
or
two $R^5$, together with the N to which they are attached may form a 3, 4, 5, 6 or 7 membered heterocyclic ring, optionally containing 1, 2, 3 or 4 additional N heteroatoms and/or optionally containing a O atom and for a S atom, said heterocyclic ring being unsubstituted or substituted by from 1, 2 or 3 substituents independently selected from $C_1$-$C_4$-alkyl-
oxo=,
$C_1$-$C_4$-alkyl-carbonyl,
$C_1$-$C_4$-alkyl-sulphonyl,
hydroxy-$C_1$-$C_4$-alkyl;

In a further embodiment of the invention as described herein, when two $R^3$ substituents are present and they do not join to form a ring, at least one $R^3$ substituent is selected from hydrogen, $C_1$-$C_4$-alkyl, $C_1$-$C_4$-alkoxycarbonyl and $C_1$-$C_4$-alkylcarbonyl. Preferably at least one $R^3$ substituent is selected from H, methyl and ethyl, particularly methyl. In another embodiment, at least one $R^3$ is $C_1$-$C_7$-alkyl-, preferably $C_1$-$C_4$-alkyl-, preferably methyl.

In another embodiment, when $R^3$ includes a cyclohexylalkyl group which is further monosubstituted at a cyclohexyl ring atom, the cyclohexyl substitution is preferably at the 1 and 4 positions. Such substitution pattern is illustrated as an example below, and is not limited to the following specific example:

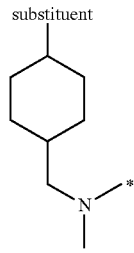

In another embodiment, the stereochemistry of such substitution is trans. An example of such stereochemistry is provided below, and is not limited to the following specific example:

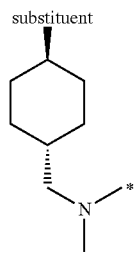

In another embodiment, the stereochemistry of the compound of formula I is shown below:

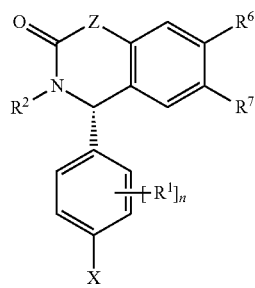

In another embodiment, $R^6$ is selected from H, hydroxy, methoxy, ethoxy, propoxy (isopropoxy or n-propoxy), butoxy (preferably isobutoxy), morpholin-4-ylethoxy, aminoethoxy, 4-methylpiperazin-1-ylcarbonylmethoxy, dimethylaminoethoxy, dimethylaminopropoxy, hydroxyethoxy, hydroxypropoxy, dimethylaminocarbonylmethoxy, methylaminocarbonylmethoxy and $d_3$ methoxy. Preferably $R^6$ is methoxy.

In another embodiment, $R^7$ is selected from methoxy, ethoxy, butoxy (including isobutoxy, sec-butoxy, (R)-sec-butoxy, (S)-sec-butoxy), propoxy (including isopropoxy, n-propoxy), cyclopropylmethoxy, cyclopentyloxy, morpholinyl-4-ylpropoxy, 3-hydroxypropoxy, 3-dimethylaminopropoxy, 1-ethylpropoxy, 3-aminopropoxy, cyclobutoxy, 1-methylbutoxy, 1,2-dimethylpropoxy, 3-amino-1-methyl-propoxy, cyclohexyloxy, benzyloxy, cyclohexylmethoxy, cyclobutylmethoxy, cyclopentylmethoxy, 2-methoxy-1-methyl-ethoxy (including in particular (R) 2-methoxy-1-methyl-ethoxy), 1,3-dimethyl-but-3-enyloxy, 1-methyl-but-3-enyloxy, pyridin-4-ylmethoxy, trifluoromethoxy, methoxyethoxy, (R) tetrahydrofuran-2-ylmethoxy, (S) tetrahydrofuran-2-ylmethoxy, (R)-2-methoxy-propoxy, 2-methoxy-1-methyl-ethoxy, 1-hydroxy-cyclopropylmethoxy, 3-methoxy-propoxy, oxetan-2-ylmethoxy, 2,2-difluoro-ethoxy, isopropylamino, ethylcarbonylamino, isopropyl-propyl-amino, (dimethylaminoethyl)-isopropyl-amino, (methylcarbonylaminoethyl)isopropylamino, isobutylamino, cyclopentylmethylamino, 1-ethyl-propyl-amino, cyclohexylamino, butylamino (including sec-butylamino), cyclobutylamino, cyclopentylamino, propylamino, ethylamino, benzylamino, cyclopropylmethylamino, cyclohexylmethylamino, methylcarbonylamino, isopropylcarbonylamino, (methylcarbonyl)isopropylamino, (ethylcarbonyl)isopropylamino, (isopropyl)methyl-amino and (isopropyl)ethyl-amino. Preferably $R^7$ is isopropoxy.

In a preferred embodiment, n is 0.

In another embodiment, $R^1$ is selected from hydrogen, fluoro, chloro, methyl, methoxy, bromo, nitro, amino, aminocarbonyl-amino-, methylaminocarbonylamino-, methylaminocarbonyl-, methylcarbonylamino-, ethylaminocarbonylamino-, ethylcarbonylamino-, (ethyl)methylamino-, dimethylamino-, aminocarbonyl-, hydroxymethyl-, aminomethyl-, methylcarbonylaminomethyl-, methylaminomethyl.

In a preferred embodiment, $R^2$ is selected from:
(A) i phenyl substituted by:
4-dimethylamino-, 4-methylamino-, 4-morpholin-4-yl-, 4-pyrrolidin-1-yl-, 4-dimethylamino-2-methoxy, 2-methoxy-4-methyl-, 2-methoxy-4-morpholin-4-yl-, 4-dimethylamino-2-methoxy-, 4-dimethylamino-2-methyl-, 4-(N-methyl-N-pyridin-4-ylmethyl-amino)-, 4-(2-oxo-pyrrolidin-1-yl)-, 4-pyrazol-1-yl-, 4-methylcarbonylamino-, 4-(2-oxo-azetidin-1-yl)-, 4-(N-methyl-N-ethyl-amino)carbonyl-, 4-(piperidine-1-carbonyl)-, 4-methylaminocarbonyl, 4-diethylaminocarbonyl-, 4-dimethylaminocarbonyl, 4-(pyrrolidine-1-carbonyl)-, 4-aminocarbonyl-, 4-(N-methyl-N-pyridin-4-yl-aminocarbonyl)-, 4-(N-pyridin-4-yl-aminocarbonyl)-, 4-(N-pyridin-3-yl-aminocarbonyl)-, 4-hydroxymethyl, 4-N-methylcarbonyl-N-methyl-amino-, 4-(N-methylcarbonyl-N-cyclopentylmethyl-amino)-, 4-(N-methyl-N-piperidin-3-yl-methyl-amino)-, 4-[methyl-(1-methyl-piperidin-3-ylmethyl)-amino]-, 4-(N-methyl-N-piperidin-4-ylmethyl-amino)-, 4-[(1-Acetyl-piperidin-4-ylmethyl)-methyl-amino]-, 4-[(1-methanesulfonyl-piperidin-4-ylmethyl)-methyl-amino]-, 4-[(4-Amino-cyclohexylmethyl)-methyl-amino]-, 4-[(4-ethylamino-cyclohexylmethyl)-methyl-amino]-, 4-{[4-(ethyl-methyl-amino)-cyclohexylmethyl]-methyl-amino}-, 4-diethylamino, 4-(N-cyclopentylmethyl-N-methyl-amino)-, 4-(N-isopropyl-N-methyl-amino)-, 4-(N-cyclopentyl-N-methyl-amino)-, 4-(N-cyclohexyl-N-methyl-amino)-, 4-(N-sec-butyl-N-methyl-amino)-, 4-(N-cyclopropylmethyl- N-methyl-amino)-, 4-(N-cyclohexylmethyl-N-methyl-amino)-, 4-(N-isobutyl-N-methyl-amino)-, 4-(N-Benzyl-N-methyl-amino)-, 4-(N-ethyl-N-methyl-amino)-, 4-ethylamino-, 4-dipropylamino-, 4-(N-cyclobutyl-N-methyl-amino)-, 4-[(2-fluoro-benzyl)-methyl-amino]-, 4-[(2,3-difluoro-benzyl)-methyl-amino]-, 4-[methyl-(3-trifluoromethyl-benzyl)-amino]-, 4-[methyl-(4-trifluoromethyl-benzyl)-amino]-, 4-[(3-fluoro-benzyl)-methyl-amino]-, 4-(N-methyl-N-pyridin-3-ylmethyl-amino)-, 4-[(4-fluoro-benzyl)-methyl-amino]-, 4-[(3,4-difluoro-benzyl)methyl-amino]-, 4-[(pyridin-4-ylmethyl)-amino]-, 4-(N-cyclopropylmethyl-N-pyridin-4-ylmethyl-amino)-, 4-(N-ethyl-N-pyridin-4-ylmethyl-amino)-, 4-[(2-morpholin-4-yl-ethyl)-pyridin-4-ylmethyl-amino]-, 4-(N-methyl-N-pyrimidin-4-ylmethyl-amino)-, 4-[(3-fluoro-pyridin-4-ylmethyl)-methyl-amino]-, 4-(N-methyl-N-thiophen-3-ylmethyl-amino)-, 4-[methyl-(3-methyl-3H-imidazol-4-ylmethyl)-amino]-, 4-(N-furan-3-ylmethyl-N-methyl-amino)-, 4-[methyl-(2-morpholin-4-yl-ethyl)-amino]-, 4-[methyl-(1-methyl-piperidin-4-ylmethyl)-amino]-, 4-[methyl-(4-propylamino-cyclohexylmethyl)-amino]-, 4-[(4-dimethylamino-cyclohexylmethyl)-methyl-amino]-, 4-[(4-amino-cyclohexylmethyl)-methyl-amino]-, 4-[(4-dimethylamino-cyclohexylmethyl)-ethyl-amino]-, 4-[methyl-(4-pyrrolidin-1-yl-cyclohexylmethyl)-amino]-, 4-[methyl-(4-piperidin-1-yl-cyclohexylmethyl)-amino]-, [4-(methyl-piperidin-4-ylmethyl-amino)-, 4-{methyl-[4-(3-methyl-4-oxo-imidazolidin-1-yl)-cyclohexylmethyl]-amino}-, 4-(3-amino-1H-pyrazol-4-yl)-, 4-(3-Amino-5-methyl-1H-pyrazol-4-yl)-, 4-(3,5-dimethyl-1H-pyrazol-4-yl)-, 4-(1-pyrrolidin-1-yl-ethyl)-, 4-(1-morpholin-4-yl-ethyl)-, 4-(1-hydroxy-ethyl)-, 4-[1-(piperidin-4-ylamino)-ethyl]-, 4-[1-(N-piperidin-4-yl-N-methylcarbonyl-amino)-ethyl]-, 4-[1-(N-methyl-N-piperidin-4-yl-amino)-ethyl]-, 4-{1-[(4-dimethylamino-cyclohexyl)-methyl-amino]-ethyl}-, 4-[1-(4-amino-cyclohexylamino)-ethyl]-, 4-[1-(4-dimethylamino-piperidin-1-yl)-ethyl]-, 4-{1-[4-(isopropyl-methyl-amino)-piperidin-1-yl]-ethyl}-, 4-(1-dimethylamino-ethyl)-, 4-[1-(4-hydroxy-piperidin-1-yl)-ethyl]-, 4-[1-(2-dimethylamino-ethylamino)-ethyl]-, 4-[1-((R)-3-hydroxy-pyrrolidin-1-yl)-ethyl]-, 4-[1-((S)-3-hydroxy-pyrrolidin-1-yl)-ethyl]-, 4-[1-((S)-3-hydroxy-piperidin-1-yl)-ethyl]-, 4-[1-((R)-3-hydroxy-piperidin-1-yl)-ethyl]-, 4-(1-thiomorpholin-4-yl-ethyl)-, 4-(1-N-isobutyl-N-methylcarbonyl-amino-ethyl)-, 4-(1-N-propyl-N-methylcarbonyl-amino-ethyl)-, 4-(1-N-isopropyl-N-methylcarbonyl-amino-ethyl)-, 4-(1-N-cyclopropyl-N-methylcarbonyl-amino-ethyl), 4-(1-N-cyclohexyl-methyl-N-methylcarbonyl-amino-ethyl)-, 4-(1-N-cyclopentyl-N-methylcarbonyl-amino-ethyl)-, 4-(1-N-cyclohexyl-N-methylcarbonyl-amino-ethyl)-, 4-(1-N-cyclopropylmethyl-N-methylcarbonyl-amino-ethyl)-, 4-(1-N-cyclopentylmethyl-N-methylcarbonyl-amino-ethyl)-, 4-(1-N-benzyl-N-methylcarbonyl-amino-ethyl)-, 4-(1-N-cyclobutyl-N-methylcarbonyl-amino-ethyl)-, 4-(1-N-pyrrolidine-3-carbonyl-N-ethyl-amino-ethyl)-, 4-(1-N-cis-4-amino-cyclohexanecarbonyl-N-ethyl-amino-ethyl)-, 4-(1-N-trans-4-amino-cyclohexanecarbonyl-N-ethyl-amino-ethyl)-, 4-(1-N-4-dimethylamino-cyclohexanecarbonyl-N-ethyl-amino-ethyl)-, 4-(1-N-4-dimethylamino-cyclopentanecarbonyl-N-ethyl-amino-ethyl)-, 4-(1-N-1-methyl-pyrrolidine-3-yl-carbonyl-N-ethyl-amino-ethyl)-, 4-(1-N-4-dimethylamino-cyclohexanecarbonyl-N-ethyl-amino-ethyl)-, 4-[1-(piperidin-3-ylamino)-ethyl]-, 4-(1-N-(2-aminoethyl)-N-methylcarbonyl-amino-ethyl)-, 4-(1-N-(2-dimethylaminoethyl)-N-methylcarbonyl-amino-ethyl)-, 4-(1-N-(3-aminopropyl)-N-methylcarbonyl-amino-ethyl)-, 4-(1-N-(3-dimethylaminopropyl)-N-methylcarbonyl-amino-ethyl)-, 4-[1-(N-ethyl-N-piperidin-4-yl-amino) ethyl]-, 4-[1-(3-Amino-piperidin-1-yl)ethyl]-, 4-[1-((R)-3-Amino-pyrrolidin-1-yl)-ethyl]-, 4-[1-((S)-3-Amino-pyrrolidin-1-yl)ethyl]-, 4-[1-(3-dimethylamino-pyrrolidin-1-yl)-ethyl]-, [1-(4-diethylamino-piperidin-1-yl)-ethyl]-, 4-[1-(3-oxo-morpholin-4-yl)-ethyl]-, 4-[(4-dimethylamino-cyclohexylmethyl)-methyl-amino]-, 4-(N-methyl-N-ethyl-amino-carbonyl)-, 4-(N-cyclopropylmethyl-N-methyl-amino)-, 4-(2-oxo-azetidin-1-yl)-, 4-(1-N-methylcarbonyl-N-ethyl-amino-ethyl), 4-(morpholin-4-yl-cyclohexylmethyl)-amino]-, 4-(morpholin-4-yl-cyclohexylmethyl)-methyl-amino]-, 4-[(4-dimethylamino-cyclohexylmethyl)-methyl-amino]-3-methyl-, 4-[(4-dimethylamino-cyclohexylmethyl)-methyl-amino]-3-fluoro-, 4-[(4-dimethylamino-cyclohexylmethyl)-methyl-amino]-2-methoxy-, 4-[1-(4-Acetyl-piperazin-1-yl)-ethyl]-, 4-[1-(4-dimethylamino-piperidin-1-yl)-ethyl]-, 4-[(-4-dimethylamino-cyclohexylmethyl)-methyl-amino]-, 4-[(-4-dimethylamino-cyclohexylmethyl)-ethyl-amino]-, 4-[2-(4-dimethylamino-piperidin-1-yl)-1-methyl-ethyl]-, 4-[2-(4-dimethylamino-piperidin-1-yl)-1-methyl-2-oxo-ethyl]-, 4-imidazol-1ylmethyl-, 4-(N-trifluoromethyl-carbonyl-N-methyl-amino)-, 4-[1-(2-oxo-piperazin-1-yl)-ethyl]-, 4-(2-hydroxy-ethyl)-2-oxo-piperazin-1-yl]-ethyl}-, 4-[1-(methyl-carbonylamino)-ethyl]-, 4-[1-(methoxymethylcarbonylamino)-ethyl]-, 4-[1-(dimethylamino-methyl-carbonylamino)-ethyl]-, 4-(2-oxo-pyrrolidin-1-yl), 4-(2-oxo-imidazolidin-1-yl)- or 4-(3-amino-5-ethyl-1H-pyrazol-4-yl)-, or $R^2$ is selected from phenyl substituted by:

2-fluoro or 3-fluoro and substituted in the para position (relative to the isoquinolinone or quinazolinone), by:

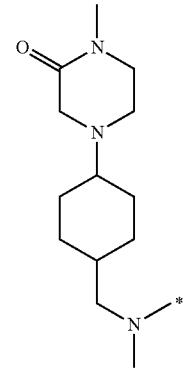

or $R^2$ is selected from phenyl substituted in the ortho position (relative to the isoquinolinone or quinazolinone), by methoxy and substituted in the para position (relative to the isoquinolinone or quinazolinone), by:

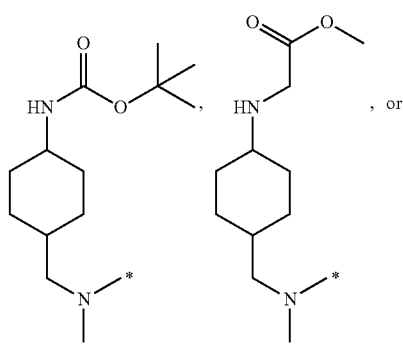

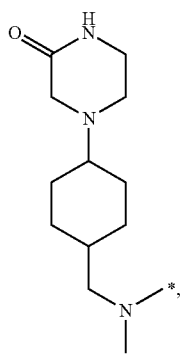
or R² is phenyl substituted in the para position (relative to the isoquinolinone or quinazolinone), by:
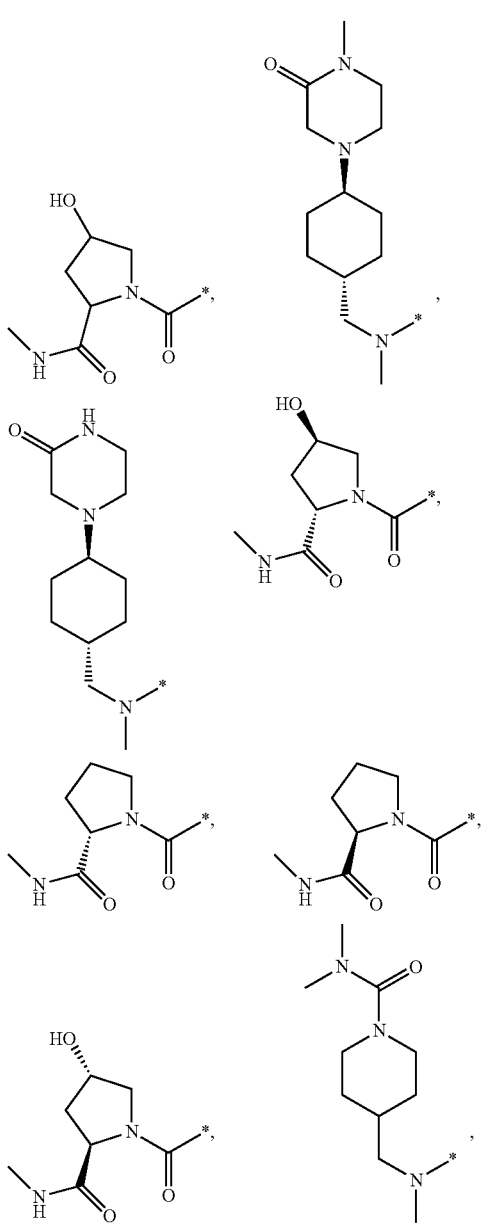
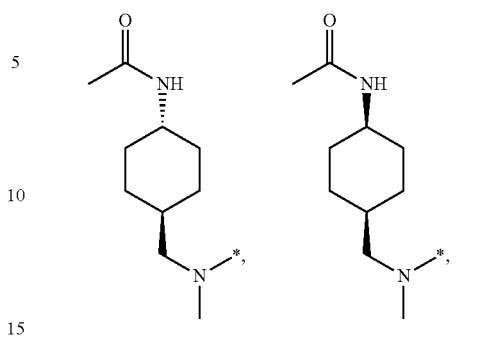
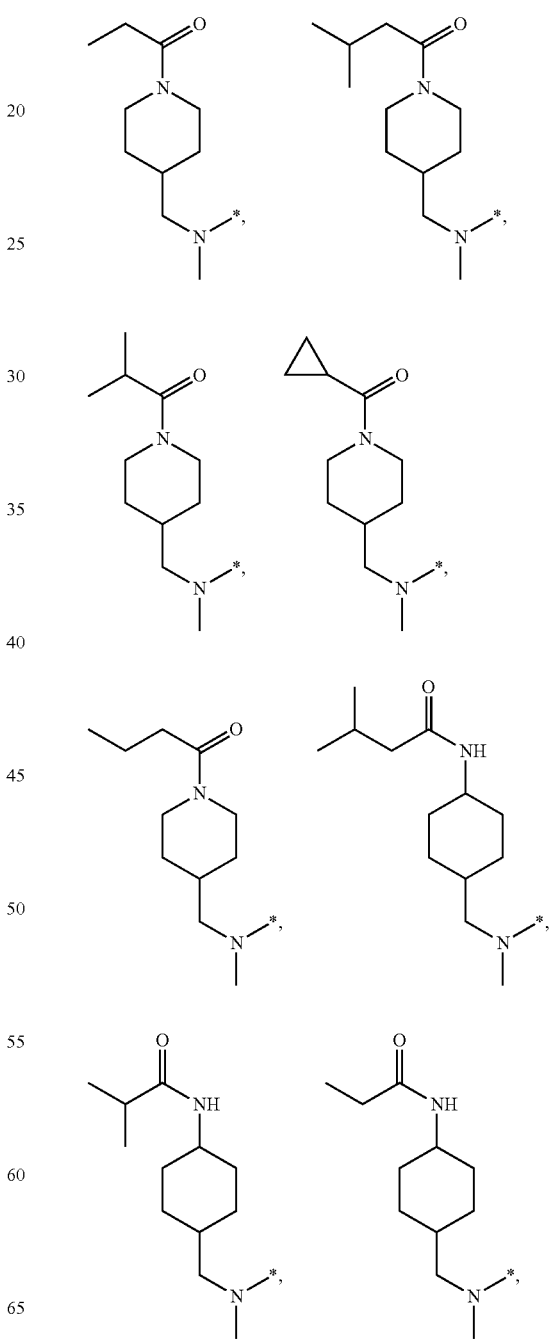

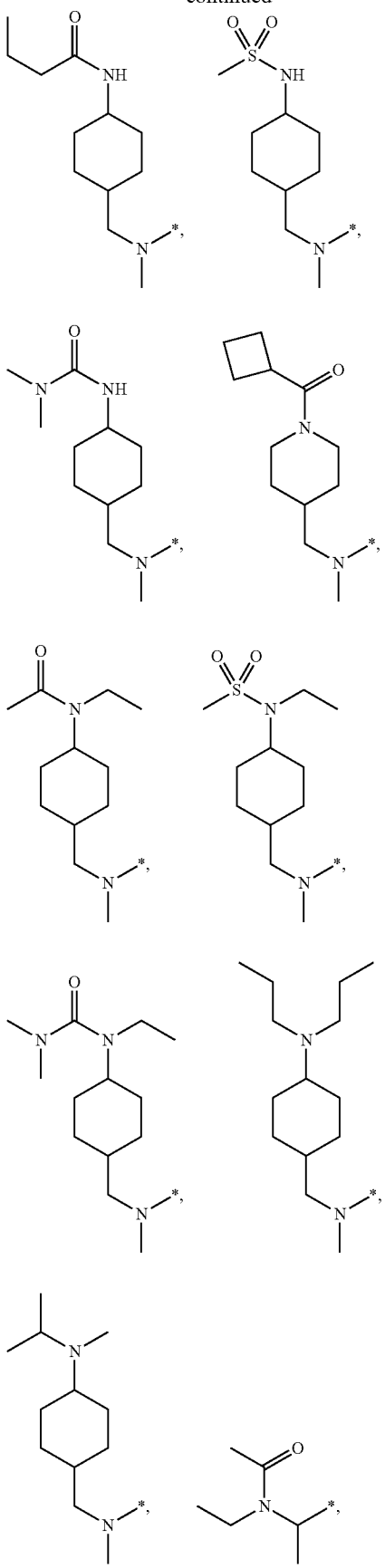
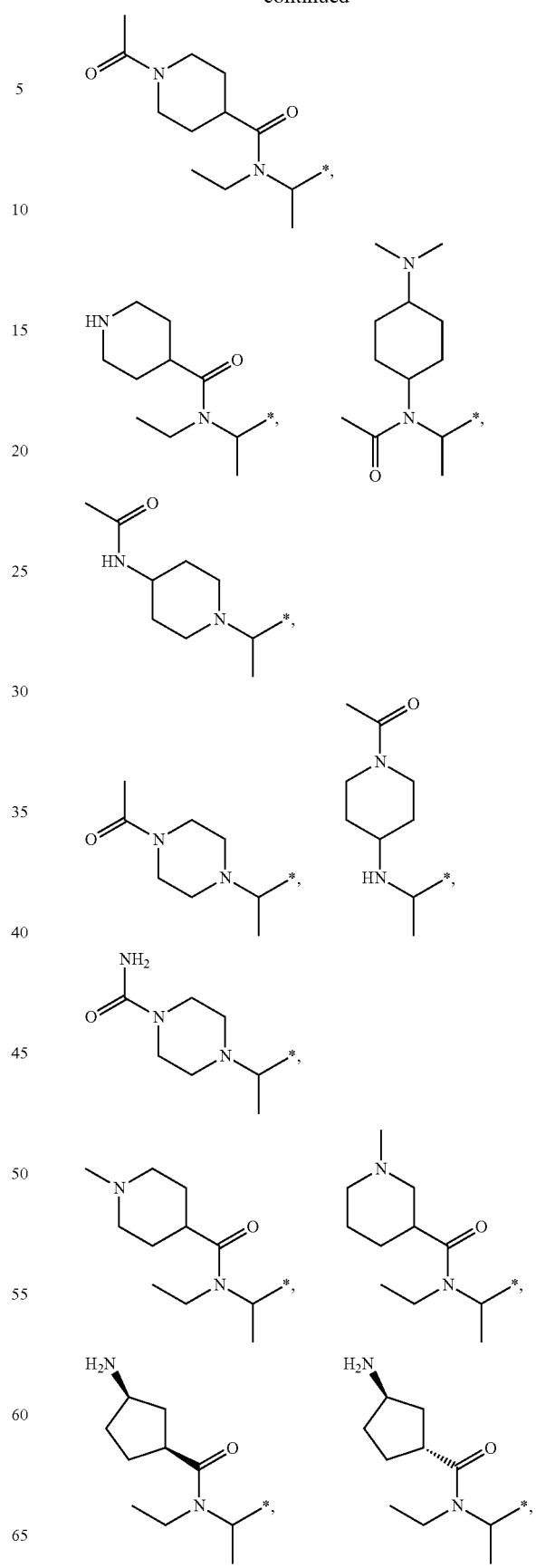

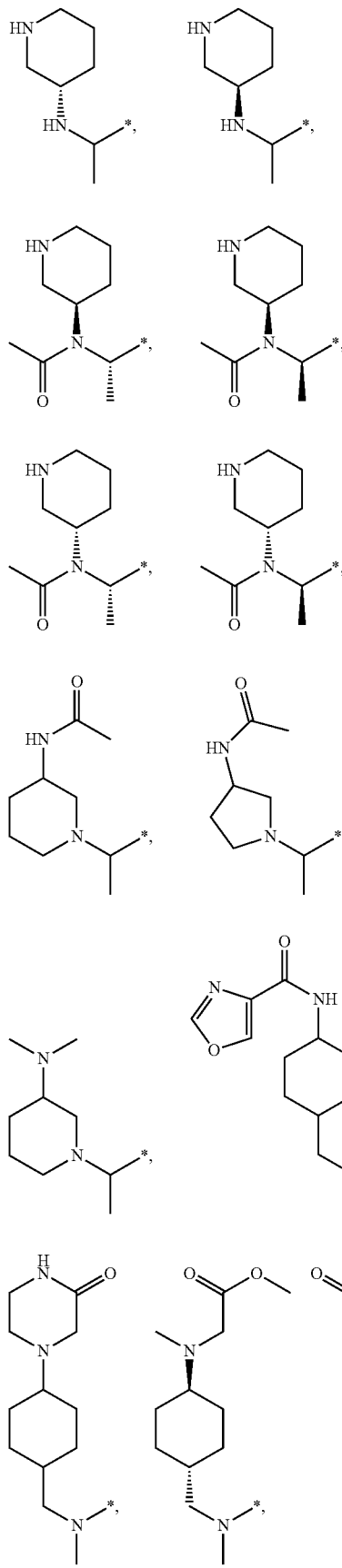
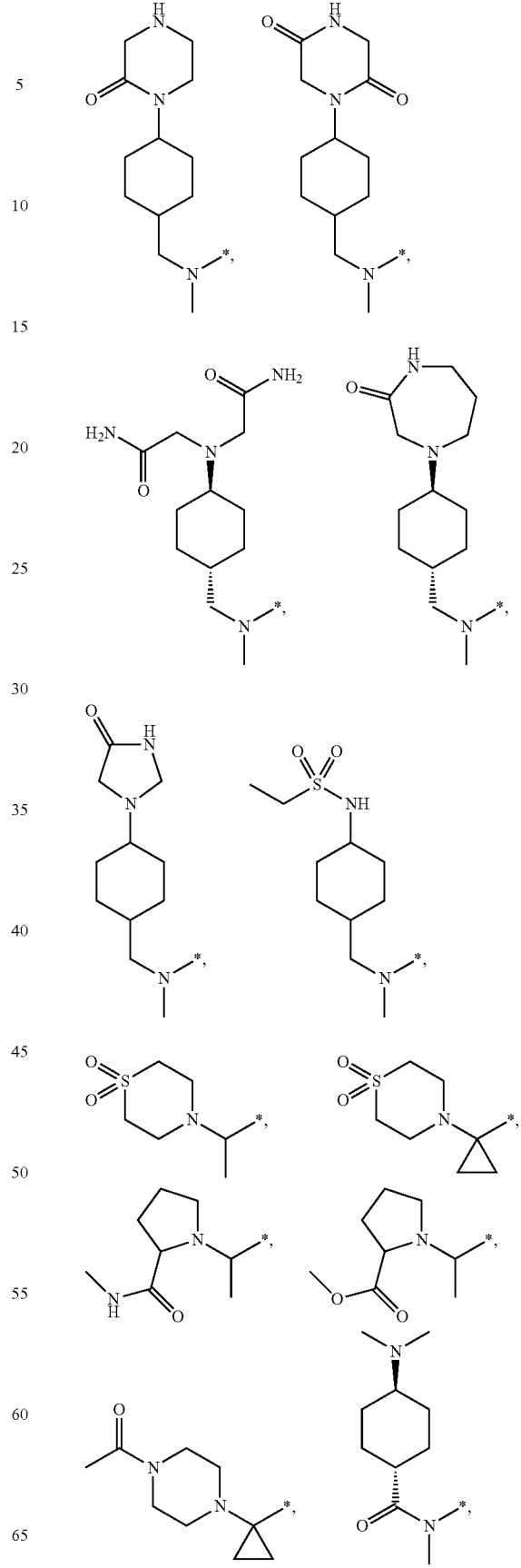

41
-continued
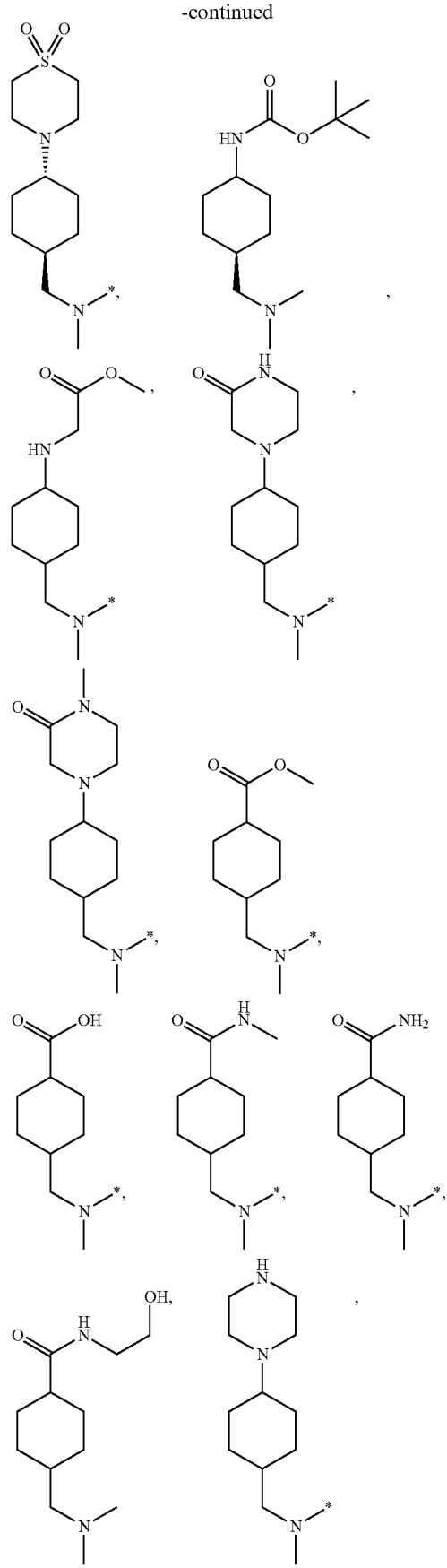
42
-continued
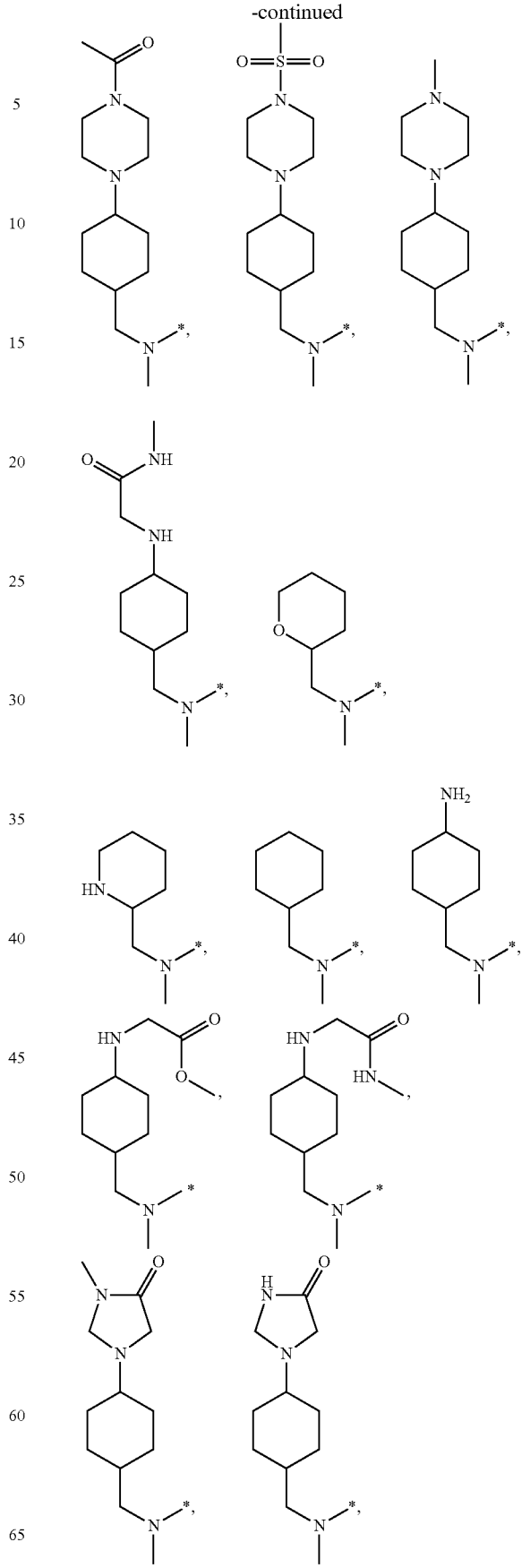

-continued
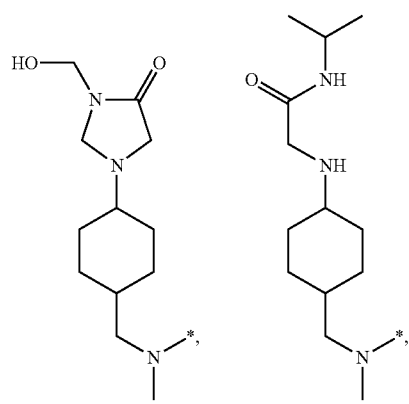
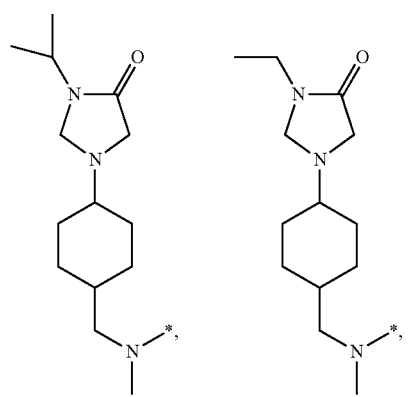
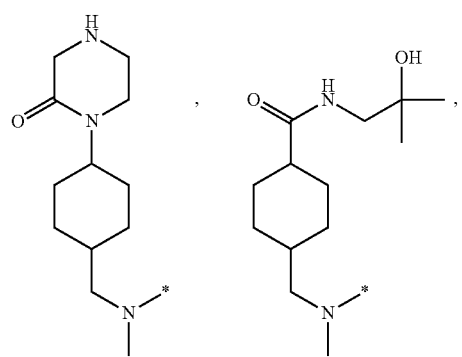
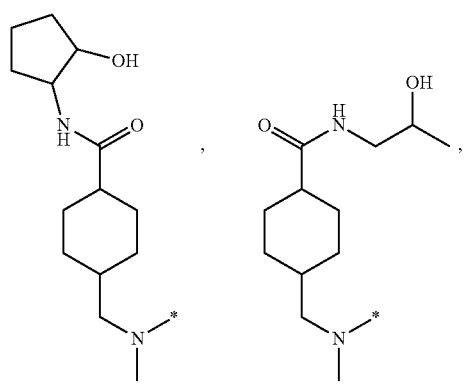
-continued
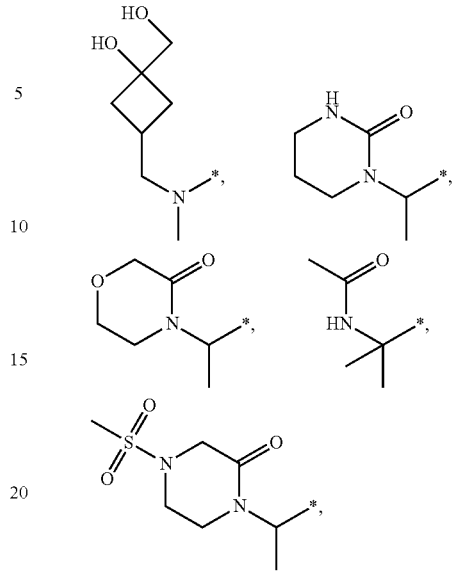
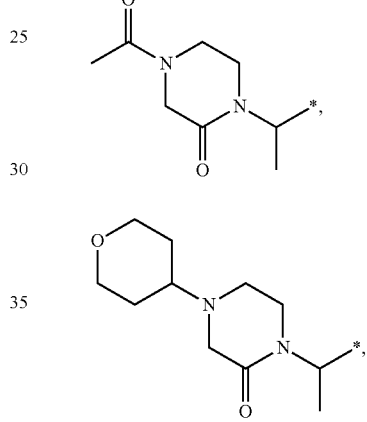
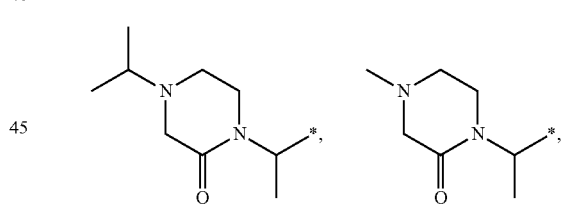
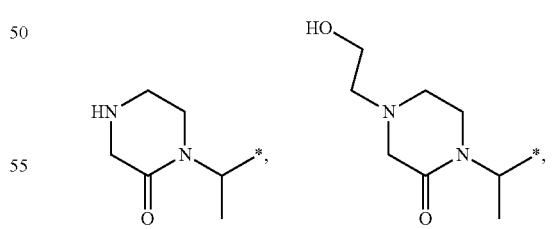
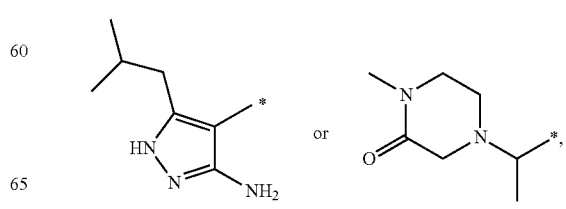

preferably
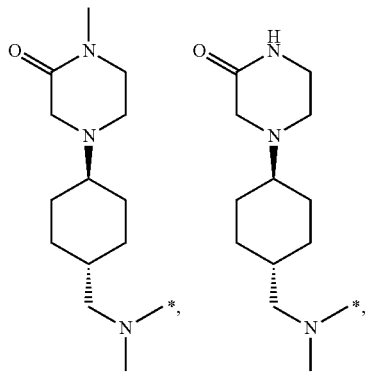
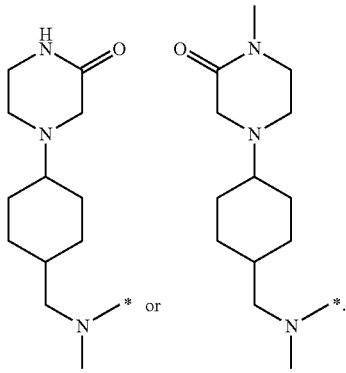
(A) ii or R[2] is 2-pyridyl (relative to the isoquinolinone or quinazolinone), substituted by: 5-[(4-dimethylamino-cyclohexylmethyl)-methyl-amino]-, 5-[(4-amino-cyclohexylmethyl)amino]-,
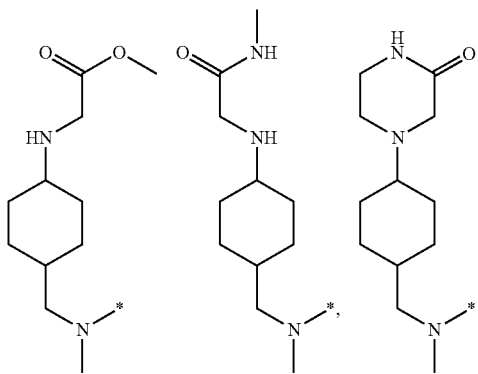
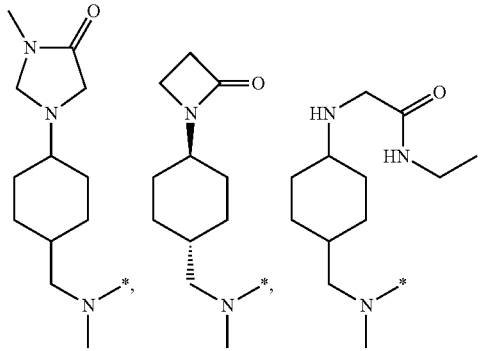
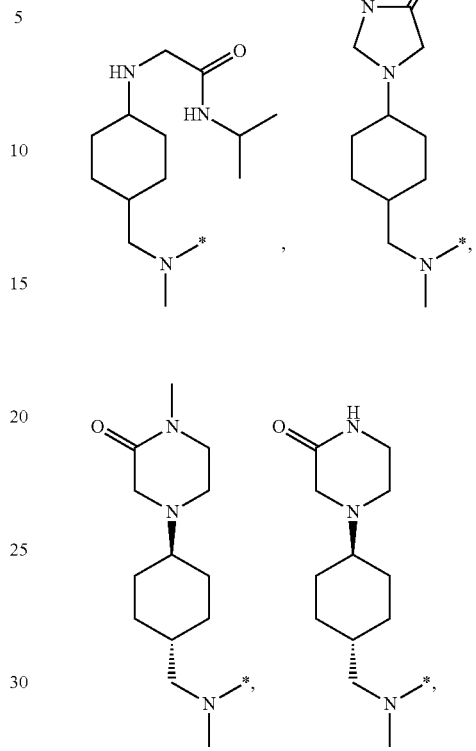
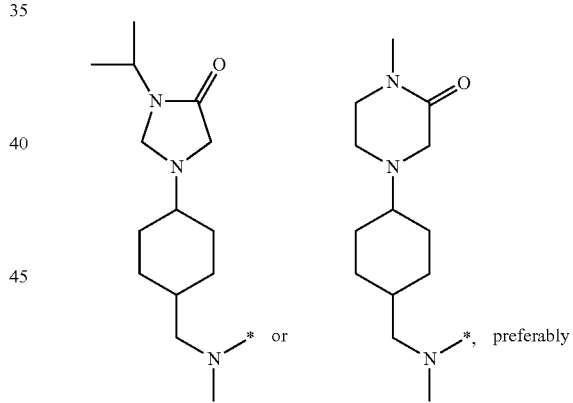

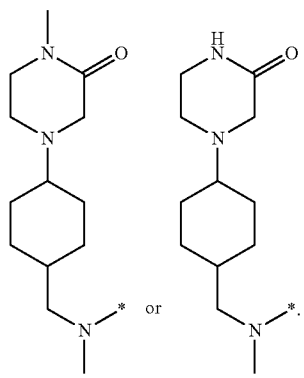

(A) iii or R² is 3-pyridyl (relative to the isoquinolinone or quinazolinone), substituted by: 6-[(4-dimethylamino-cyclohexylmethyl)-methyl-amino]- or 6-[(3-hydroxy-cyclobutylmethyl)-methyl-amino]-, or R² is 3-pyridyl (relative to the isoquinolinone or quinazolinone), substituted in the 6 position by: 6-{methyl-[4-(2-oxo-pyrrolidin-1-yl)cyclohexylmethyl]-amino}-, 6-{methyl-[4-(2-oxo-imidazolidin-1-yl)-cyclohexylmethyl]-amino}-,

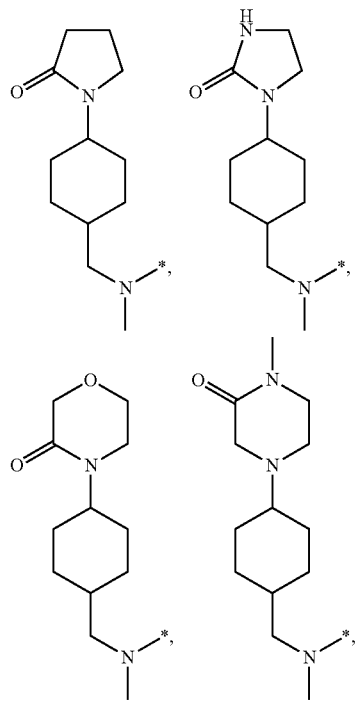

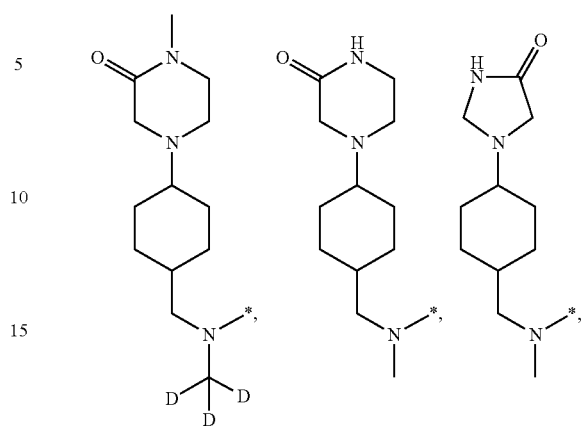

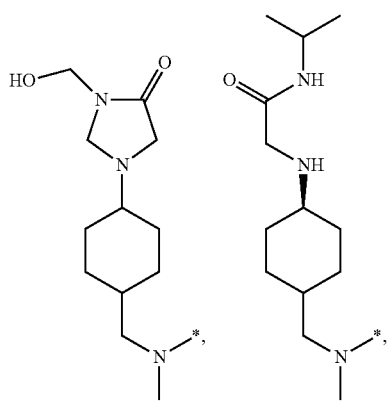

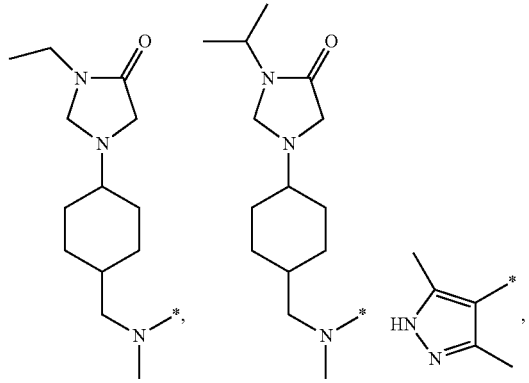

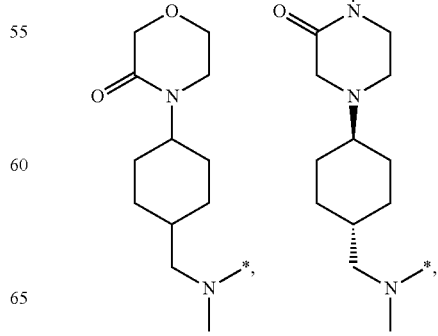

-continued

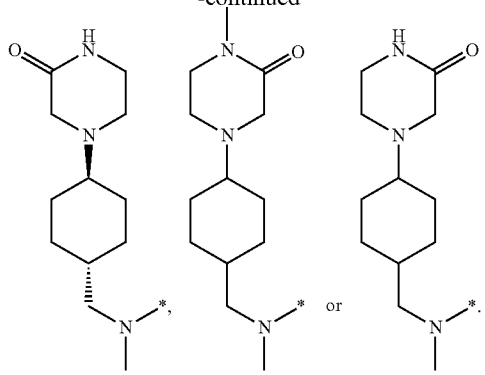

preferably

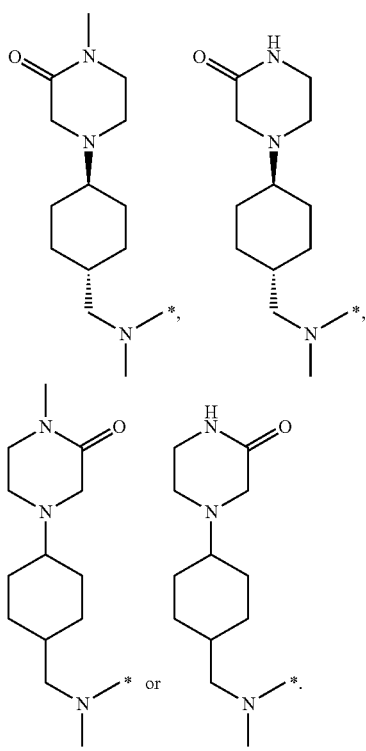

or R² is 3-pyridyl (relative to the isoquinolinone or quinazolinone), substituted by: 2 fluoro-6

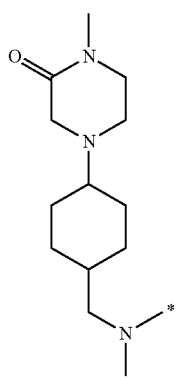

(B) i or R² is phenyl substituted by:
4-methoxy, 4-cyano, 3,4-dimethyl, 2,4-dimethyl, 4-methoxy-2-methyl-, 2-chloro-4-methyl-, 2,4-dimethoxy-, 3,4-dichloro-, 4-methyl-, 3,4-dimethoxy, 2-methoxy-4-methyl-, 4-(1H-pyrazol-4-yl)-, 4-(3,5-dimethyl-1H-pyrazol-4-yl)-,

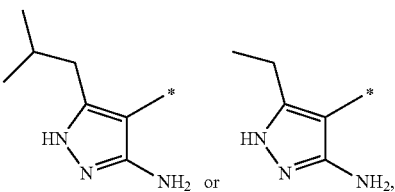

(B) ii or R² is 2-pyridyl (relative to the isoquinolinone or quinazolinone), substituted by 4-methyl, (B) iii or R² is 3-pyridyl (relative to the isoquinolinone or quinazolinone), substituted by 4-methyl, (C) or R² is phenyl substituted by:
4-methyl-2-(3-morpholin-4-yl-propoxy)-, 4-methyl-2-hydroxycarbonylmethoxy-, 2-methoxy-5-methyl-, 4-methyl-2-(2H-tetrazol-5-ylmethoxy)-, 4-methyl-2-(thiazol-5-ylmethoxy)-, 4-methoxycarbonyl-2-tetrazol-5-ylmethoxy, 4-methoxycarbonyl-2 methoxy, 4-methoxycarbonyl-2-thiazol-5-ylmethoxy)-, 4-methyl-2-(2-morpholin-4-yl-ethoxy), 2-(3-dimethylamino-propoxy)-4-methyl-, 4-methyl-2-[2-(4-methyl-piperazin-1-yl)-ethoxy]-, 4-methyl-2-[3-(4-methyl-piperazin-1-yl)-propoxy]-, 2-methoxycarbonylmethoxy-5-chloro-, 2-hydroxycarbonylmethoxy-5-chloro-, 5-chloro-2-(2-dimethylamino-ethoxy)-, 5-chloro-2-(3-morpholin-4-yl-propoxy)-, 5-chloro-2-(2-morpholin-4-yl-ethoxy)-, 5-chloro-2-(3-dimethylamino-propoxy)-, 5-chloro-2-(3-hydroxy-propoxy)- or 5-chloro-2-(2-hydroxy-ethoxy)-, (D) or R² is (C-bound)-heterocycle selected from benzofuran-5-yl and 1-methyl-1H-indazol-5-yl, (E) or R² is pyrazin-2-yl (relative to the isoquinolinone or quinazolinone), substituted at the 5 position by:

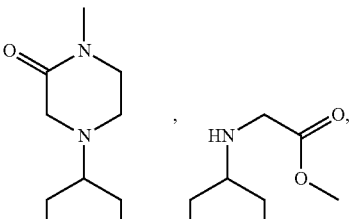

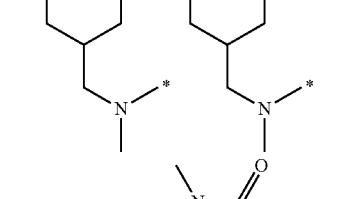

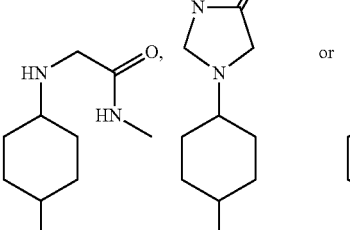

(F) or R² is pyridazin-3-yl (relative to the isoquinolinone or quinazolinone), substituted at the 6 position by:

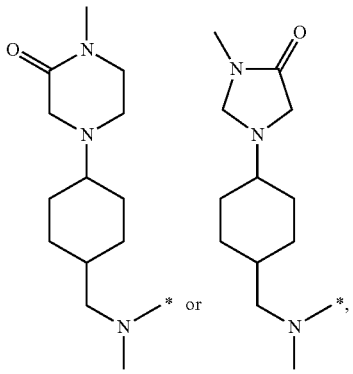

(G) or R² is pyrimidin-2-yl (relative to the isoquinolinone or quinazolinone), substituted at the 5 position by:

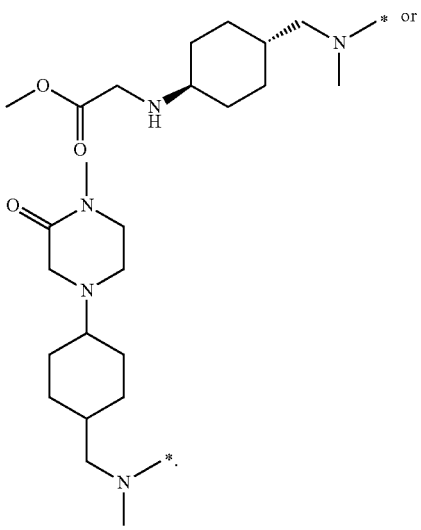

In another embodiment there is provided a compound of formula I or salt thereof as described herein, with the proviso that
if Z is $CH_2$, n is 0 or 1, so that when n is 1 then $R^1$ is ortho-chloro, and $R^2$ is selected from
para-$C_1$-$C_3$-alkyl-phenyl-
para-(halo-$C_1$-$C_3$-alkyl)-phenyl-
para-$C_1$-$C_3$-alkoxy-phenyl-
para-halo-phenyl-
para-nitro-phenyl-
para-($C_1$-$C_3$-alkoxy-carbonyl)-phenyl-
para-(hydroxy-carbonyl)-phenyl-
wherein the phenyl is optionally substituted by 1-2 additional substituents, said substituents being independently selected from halo and methyl, then $R^6$ and $R^7$ are not both ethoxy or methoxy.

As already indicated above, p53 refers to the human protein itself as described by Matlashewski et al. in EMBO J. 3, 3257-62 (1984) or related family members (e.g. p73 as described in Kaghad et al. in Cell 90, 809-19 (1997) and p63 as described in Yang et al in Mol Cell 2, 305-16 (1998)) (named also p53 wild type herein) or to any variant thereof (e.g. a splice variant, mutant, fragment or isoform due to deletion, insertion and/or exchange of one or more, e.g. one to 200, of the amino acids) that is still capable to retain preferably at least 1%, more preferably at least 5%, yet more preferably at least 10%, 20%, 30%, 40%, 50% or more than 50% of the p53 activity in growth suppression, e.g. in the growth suppression assay described in Pietenpol et al., Proc. Nat. Acad. Sci. USA 91, 1998-2002 (1994) and, if compared with the corresponding sequence of p53 wild type, shows at least 20%, more preferably at least 25% identity with the full sequence, e.g. at least 90% identity with a partial sequence thereof. Where not mentioned otherwise, p53 generally relates to TP53, p53, TP73, p73, TP63, TP73L, p63, or variants thereof, respectively, as just defined.

As already indicated above, MDM2 (especially when mentioned as MDM2 or variants thereof) generally refers to all genes and/or proteins encoded thereof with the names MDM2, Mdm2, HDM2, Hdm2, or a variant thereof. MDM4 (especially when mentioned as MDM4 or variants thereof) refers to all genes and/or proteins encoded thereof with the names MDM4, Mdm4, HDM4, Hdm4, MDMX, MdmX, HDMX, HdmX, or a variant thereof.

MDM2 specifically relates to MDM2 as described in EMBO J. 10, 1565-9, Fakharzadeh et al., 1991, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM2 to p53, and have at least 20%, more preferably at least 25%, sequence identity to MDM2 or to HDM2 as originally described or as mentioned below specifically. Where not mentioned otherwise, MDM2 generally relates to MDM2, Mdm2, HDM2 or Hdm2, or variants thereof, respectively, as just defined.

MDM4 specifically relates to MDM4 as described in Genomics 43, 34-42, Shvarts et al., 1997, a variant thereof refers to a variant thereof which still binds to p53 in the assay system described below (e.g. a splice variant, isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM4 to p53, and have at least 20%, more preferably at least 25%, sequence identity to MDM4, to MDMX, to HDM4 or to HDM2 as originally described or as mentioned below specifically. Where not mentioned otherwise, MDM4 generally relates to MDM4, Mdm4, HDM4, Hdm4, MDMX, MdmX, HDMX or HdmX, or variants thereof, respectively, as just defined.

The percentage of sequence identity, often also termed homology, between a protein and a variant thereof is preferably determined by a computer program commonly employed for this purpose, such as the Gap program (Wisconsin Sequence Analysis Package, Version 8 for Unix, Genetics Computer Group, University Research Park, Madison Wis., USA, which uses the algorithm of Smith and Waterman (Adv. Appl. Math. 2: 482-489 (1981), especially using an affine gap search with a gap open penalty of 12 and a gap extension penalty of 1.

"Variants thereof" where mentioned means one or more variant(s).

A proto-oncogene is a normal gene that can become an oncogene, either after mutation or increased expression.

Proto-oncogenes code for proteins that help to regulate cell growth and differentiation. Proto-oncogenes are often involved in signal transduction and execution of mitogenic signals, usually through their protein products. Upon activation, a proto-oncogene (or its product) becomes a tumor inducing agent, an oncogene.

Compounds of the formula (I) may have different isomeric forms. As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns 1 to 12 of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

For isolation or purification purposes it is also possible to use pharmaceutically unacceptable salts, for example picrates or perchlorates. For therapeutic use, only pharmaceutically acceptable salts or free compounds are employed.

In view of the close relationship between the novel compounds of the formula (I) in free form and those in the form of their salts, including those salts that can be used as intermediates, for example in the purification or identification of the novel compounds, any reference to the compounds or a compound of the formula (I) hereinbefore and hereinafter is to be understood as referring to the compound in free form and/or also to one or more salts thereof, as appropriate and expedient, as well as to one or more solvates, e.g. hydrates.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of the formula (I) that contain groups capable of acting as donors and/or acceptors for hydrogen bonds may be capable of forming co-crystals with suitable co-crystal formers. These co-crystals may be prepared from compounds of the formula (I) by known co-crystal forming procedures. Such procedures include grinding, heating, co-subliming, co-melting, or contacting in solution compounds of the formula (I) with the co-crystal former under crystallization conditions and isolating co-crystals thereby formed. Suitable co-crystal formers include those described in WO 2004/078163. Hence the invention further provides co-crystals comprising a compound of the formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

By "combination", there is meant either a fixed combination in one dosage unit form, or a kit of parts for the combined administration where a compound of the formula (I) and a combination partner may be administered independently at the same time or separately within time intervals that especially allow that the combination partners show a cooperative, e.g. synergistic effect.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by the dysregulation of the p53/MDM2 ratio, or (ii) associated with the dysregulation of the p53/MDM2 ratio, or (iii) characterized by the dysregulation of the MDM2/p53 ratio; or (2) reducing or inhibiting the activity of the p53/MDM2 interaction. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the p53/MDM2 interaction.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the omega-(amino, mono- or di-lower alkylamino, carboxy, lower alkoxycarbonyl)-lower alkyl esters, the alpha-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs, Elsevier* (1985)). Hydroxy groups have been masked as esters and ethers. EP 039,051 (Sloan and Little) discloses Mannich-base hydroxamic acid prodrugs, their preparation and use. Lower alkyl for the pro-drugs means $C_{1-6}$-alkyl.

Furthermore, the compounds of the present invention, including their salts, can also be obtained in the form of their hydrates, or include other solvents used for their crystallization.

The invention relates in a second aspect to pharmaceutical compositions comprising a compound of the present invention. The invention thus provides a pharmaceutical composition comprising (i.e. containing or consisting of) a compound as defined herein and one or more carriers/excipients;

a pharmaceutical composition comprising a therapeutically effective amount of a compound of formula (I) as defined herein, and one or more pharmaceutically acceptable carriers/excipients.

The present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/ or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The invention relates in a third aspect to the use of compounds of the present invention as pharmaceuticals. Particularly, the compounds of formula (I) have valuable pharmacological properties, as described hereinbefore and hereinafter. The invention thus provides:

a compound of the formula (I) as defined herein, as pharmaceutical/for use as pharmaceutical;
a compound of the formula (I) as defined herein, as medicament/for use as medicament;

a compound of the formula (I) as defined herein, for the treatment of/for use in the treatment of a disorder or a disease in a subject mediated by the activity of MDM2 and/or MDM4;

the use of a compound of formula (I) as defined herein, for the manufacture of a medicament for the treatment of a disorder or a disease in a subject mediated by the activity of MDM2 and/or MDM4;

the use of a compound of formula (I) as defined herein, for the treatment of a disorder or a disease in a subject mediated by the activity of MDM2 and/or MDM4;

the use of a compound of formula (I) as defined herein for the mediation of the activity of MDM2 and/or MDM4;

the use of a compound of formula (I) as defined herein, for the treatment of a disorder or disease selected from a proliferative disorder or disease;

the use of a compound of formula (I) as defined herein, for the treatment of a disorder or disease selected from a disorder or disease involving the immune system;

the use of a compound of formula (I) as defined herein, for the treatment of a proliferative disorder or disease selected from cancer or tumor diseases, such as benign or malignant tumors, a sarcoma, such as liposarcoma, rhabdomyosarcoma or bone cancer, e.g. osteosarcomas, a carcinoma, such as of the brain, kidney, liver, adrenal gland, bladder, breast, gastric, ovary, colon, rectum, prostate, pancreas, lung, vagina or thyroid, a glioblastoma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a leukemia or a lymphoma, such as of B- or T-cell origin, and metastases in other organs), viral infections (e.g. herpes, papilloma, HIV, Kaposi's, viral hepatitis);

the use of a compound of formula (I) as defined herein, for the treatment of a disorder or disease involving the immune system selected from autoimmune diseases or immune diseases resulting due to transplantation (such as rheumatoid arthritis, graft-versus-host disease, systemic lupus erythematosus, Sjögren's syndrome, multiple sclerosis, Hashimoto's thyreoiditis, polymyositis), chronic inflammatory conditions, such as asthma, osteoarthritis, atherosclerosis, Morbus Crohn or inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, pemphigus, epidermolysis bullosa acquisita, or other inflammatory or allergic conditions of the skin, hyperproliferative disorders, (e.g. Li-Fraumeni syndrome);

a method of modulating of MDM2 and/or MDM4 activity in a subject, comprising the step of administering to a subject a therapeutically effective amount of a compound of formula (I) as defined herein;

a method for the treatment of a disorder or a disease mediated by the activity of MDM2 and/or MDM4 comprising the step of administering to a subject a therapeutically effective amount of a compound of formula (I) as defined herein;

a method for modifying the activity of MDM2 and/or MDM4 in a cell, comprising contacting said cell with an effective amount of a compound of formula (I) as defined herein.

Quite unexpectedly, it has now been found that the compounds of the formula (I) have advantageous pharmacological properties and disturb the binding interaction (also referred to herein as p53/MDM2 and p53/MDM4 interaction or as p53/MDM2 interaction solely) between p53 on the one side and MDM2 and/or MDM4 or (especially oncogenic) variants thereof which still are capable of binding to p53, on the other side.

The efficacy of the compounds of the formula (I) and salts thereof as modulators affecting the interaction between can be demonstrated as shown in WO 98/01467 (which especially regarding the assays is included herein by reference) or preferably follows:

Time Resolved Fluorescence Energy Transfer (TR-FRET) Assay

The inhibition of p53-Hdm2 and p53-Hdm4 interactions is measured by time resolved fluorescence energy transfer (TR-FRET). Fluorescence energy transfer (or Foerster resonance energy transfer) describes an energy transfer between donor and acceptor fluorescent molecules. For this assay, MDM2 protein (amino acids 2-188) and MDM4 protein (amino acids 2-185), tagged with a C-terminal Biotin moiety, are used in combination with a Europium labeled streptavidin (Perkin Elmer, Inc., Waltham, Mass., USA) serving as the donor fluorophore. The p53 derived, Cy5 labeled peptide Cy5-TFS-DLWKLL (p53 aa 18-26) is the energy acceptor. Upon excitation of the donor molecule at 340 nm, binding interaction between MDM2 or MDM4 and the p53 peptide induces energy transfer and enhanced response at the acceptor emission wavelength at 665 nm. Disruption of the formation of the p53-MDM2 or p53-MDM4 complex due to an inhibitor molecule binding to the p53 binding site of MDM2 or MDM4 results in increased donor emission at 615 nm. The ratiometric FRET assay readout is calculated from the raw data of the two distinct fluorescence signals measured in time resolved mode (countrate 665 nm/countrate 615 nm×1000).

The test is performed in white 1536w microtiter plates (Greiner Bio-One GmbH, Frickenhausen, Germany) in a total volume of 3.1 µl by combining 100 nl of compounds diluted in 90% DMSO/10% $H_2O$ (3.2% final DMSO concentration) with 2 µl Europium labeled streptavidin (final concentration 2.5 nM) in reaction buffer (PBS, 125 mM NaCl, 0.001% Novexin (consists of carbohydrate polymers (Novexin polymers), designed to increase the solubility and stability of proteins; Novexin Ltd., Cambridgeshire, United Kingdom), Gelatin 0.01%, 0.2% Pluronic (block copolymer from ethylenoxide and propyleneoxide, BASF, Ludwigshafen, Germany), 1 mM DTT), followed by the addition of 0.5 µl MDM2-Bio or MDM4-Bio diluted in assay buffer (final concentration 10 nM). Allow the solution to pre-incubate for 15 minutes at room temperature, followed by addition of 0.5 µl Cy5-p53 peptide in assay buffer (final concentration 20 nM). Incubate at room temperature for 10 minutes prior to reading the plate. For measurement of samples, an Analyst GT multimode microplate reader (Molecular Devices) with the following settings is used: Dichroic mirror 380 nm, Excitation 330 nm, Emission Donor 615 nm and Emission Acceptor 665 nm. IC50 values are calculated by curve fitting using XLfit. If not specified, reagents are purchased from Sigma Chemical Co, St. Louis, Mo., USA.

The present invention also relates to novel aspects of the above described assays. Compounds described in the present invention preferably display inhibition of p53-Hdm2 interaction and p53-Hdm4 interaction at IC50s ranging from 0.0003 to 100 µM, preferably from 0.0003 to 25 µM.

Inhibitions of p53-Hdm2 and p53-Hdm4 by representative compounds in the present invention are displayed in Table 2 hereinbelow.

Having regard to their inhibitory effect on p53/MDM2 and/or p53/MDM4 interaction, compounds of the formula (I)

in free or pharmaceutically acceptable salt form, are useful in the treatment of conditions which are mediated by the activity (including normal activity or especially overactivity) of MDM2 and/or MDM4, or variants thereof, respectively, as described, such as proliferative and/or inflammatory conditions, e.g. by activation of the P53/MDM2 interaction, and/or that are responsive (meaning especially in a therapeutically beneficial way) to inhibition of the p53/MDM2 interaction, most especially a disease or disorder as mentioned hereinbelow.

Preferred is a compound of the formula (I) for use or the use thereof in the treatment of a disease or disorder that responds to treatment with a compound of the formula (I), especially selected from a disease that is based on dysregulation of cell cycle or especially apoptosis: e.g. diseases involving the immune system, e.g. autoimmune diseases or immune diseases resulting due to transplantation (such as rheumatoid arthritis, graft-versus-host disease, systemic lupus erythematosus, Sjögren's syndrome, multiple sclerosis, Hashimoto's thyreoiditis, polymyositis), chronic inflammatory conditions, such as asthma, osteoarthritis, atherosclerosis, Morbus Crohn or inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, pemphigus, epidermolysis bullosa acquisita, or other inflammatory or allergic conditions of the skin, hyperproliferative disorders, (e.g. Li-Fraumeni syndrome), cancer or tumor diseases, such as benign or malignant tumors, a sarcoma, such as liposarcoma, rhabdomyosarcoma or bone cancer, e.g. osteosarcomas, a carcinoma, such as of the brain, kidney, liver, adrenal gland, bladder, breast, gastric, ovary, colon, rectum, prostate, pancreas, lung, vagina or thyroid, a glioblastoma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a leukemia or a lymphoma, such as of B- or T-cell origin, and metastases in other organs), viral infections (e.g. herpes, papilloma, HIV, Kaposi's, viral hepatitis) or other diseases, for example those in which the p53/MDM2 and/or p53/MDM4 interaction is dysregulated and/or that are responsive to inhibition of the p53/MDM2 interaction and/or p53/MDM4 interaction.

The invention relates in a fourth aspect to combinations comprising a compound of formula (I) and one or more additional active ingredients. The invention thus provides
- a combination in particular a pharmaceutical combination, comprising a therapeutically effective amount of a compound of formula (I) and one or more therapeutically active agents, particularly antiproliferative agents;
- a combined pharmaceutical composition, adapted for simultaneous or sequential administration, comprising a therapeutically effective amount of a compound of formula (I) as defined herein; therapeutically effective amount(s) of one or more combination partners, particularly antiproliferative agents; one or more pharmaceutically acceptable excepients;
- a combined pharmaceutical composition as defined herein (i) as pharmaceutical, (ii) for use in the treatment of a disorder or a disease mediated by the activity of MDM2 and/or MDM4, (iii) in a method of treatment of a disorder or a disease mediated by the activity of MDM2 and/or MDM4.

The invention also relates to the use of a compound of the formula (I) (or a pharmaceutical formulation comprising a compound of the formula (I)) in the treatment of one or more of the diseases mentioned above and below where the disease(s) respond or responds (in a beneficial way, e.g. by partial or complete removal of one or more of its symptoms up to complete cure or remission) to an inhibition of the p53/MDM2 interaction, especially where the involved MDM2 or MDM4 and/or variant shows (e.g. in the context of other regulatory mechanisms, due to overexpression, to mutation or the like) inadequately high or more higher than normal activity.

The invention can also relate to the use of a compound of the formula (I) to induce cell cycle deceleration or preferably arrest and/or apoptosis in cells containing p53 or variants thereof that are still functional, for sensitizing cells to one or more additional pharmaceutically active agents, such as inducers of apoptosis and/or of cell cycle deceleration or arrest, and to chemoprotection of normal cells through the induction of cell cycle deceleration or arrest prior to treatment with one or more other chemotherapeutic agents, to the use in rendering normal cells resistant to chemotherapeutic agents and/or treatments, and/or the use in protecting cells from toxic side effects of chemotherapeutic agents or treatments, such as side effects resulting in mucositis, stomatitis, xerostomia, gastrointestinal disorders and/or alopecia.

All these aspects are preferred embodiments of the present invention.

There are also experiments that can demonstrate the anti-tumor activity of compounds of the formula (I) in vivo.

For example, female Harlan (Indianapolis, Ind., USA) athymic nu/nu mice with s.c. transplanted human osteosarcoma SJSA-1 tumors can be used to determine the anti-tumor activity of p53/MDM2 interaction inhibitors. On day 0, with the animals under peroral Forene® (1-chloro-2,2,2-trifluoro-ethyldifluormethylether, Abbot, Wiesbaden, Germany) narcosis, $3 \times 10^6$ cells are injected under the skin on the animals' left flank. When tumors reach a volume of 100 mm$^3$, the mice are divided at random into groups of 6-8 animals and treatment commences. The treatment is carried out for a 2-3 weeks period with peroral, intravenous or intra-peritoneal administration twice daily (or less frequently) of a compound of the formula (I) in a suitable vehicle at defined doses. The tumors are measured twice a week with a slide gauge and the volume of the tumors is calculated.

As an alternative to cell line SJSA-1, other cell lines may also be used in the same manner, for example,
- the HCT116 colon carcinoma cell line (ATCC No. CCL-247);
- the LNCaP clone FGC prostate carcinoma cell line (ATCC No. CRL-1740);
- the RKO colon carcinoma cell line (ATCC No. CRL-2577);
- the HT1080 fibrosarcoma cell line (ATCC No. CCL-121);
- the A375 malignant melanoma cell line (ATCC No. CRL-1619),
- the NCI-H460 large cell lung carcinoma cell line (ATCC No. HTB-177);
- the JEG-3 choriocarcinoma (ATCC No. HTB-36)
- the ZR-75-1 breast ductal carcinoma (ATCC No. CRL-1500)

A compound of the formula (I) may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibittors; mTOR inhibitors, such as RAD001; antineoplastic antimetabolites;

platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as fludarabine; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics and AUY922; temozolomide (TEMODALT™); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; MEK inhibitors such as ARRY142886 from Array PioPharma, AZD6244 from AstraZeneca, PD181461 from Pfizer, leucovorin, EDG binders, antileukemia compounds, ribonucleotide reductase inhibittors, S-adenosylmethionine decarboxylase inhibitors, regulators of apoptosis, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX™), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL™. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

m) compounds targeting, decreasing or inhibiting the activity of PI3K, such as BEZ235 or BKM120;

n) compounds targeting, decreasing or inhibiting the activity of the cyclin dependent kinase family, such as PD 0332991.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune™), everolimus (Certican™ or Afinitor™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetrazolyle derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors. An example HSP90 inhibitor is AUY922.

The term "regulators of apoptosis" as used herein includes, but is not limited to, compounds targeting, decreasing or inhibiting the activity of Bcl2 family members (such as ABT-263) and IAP family members (such as AEG40826); or inducing apoptosis by known or unknown mechanism(s) of action (e.g. TRAIL antibody, DR5 antibody).

The term "antiproliferative antibodies" as used herein includes, but is not limited to, trastuzumab (Herceptin™), Trastuzumab-DM1, erbitux, bevacizumab (Avastin™) rituximab (Rituxan™), PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the formula (I) can be used in combination with standard leukemia therapies, especially in combination with therapies used for the treatment of AML. In particular, compounds of the formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A, LDH589 disclosed in WO 02/22577 and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

Somatostatin receptor antagonists as used herein refer to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as e.g. VISUDYNE™ and porfimer sodium.

Angiostatic steroids as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

Pharmaceutical Formulations, Uses and Methods

The above-mentioned compounds, which can be used in combination with a compound of the formula (I), can be prepared and administered as described in the art, such as in the documents cited above.

The invention also provides a pharmaceutical preparation, comprising a compound of the formula (I) as defined herein, and/or an N-oxide or a tautomer thereof, and/or a pharmaceutically acceptable salt of such a compound, or a hydrate or solvate thereof (all referred to often as "a compound of the formula (I)" merely herein), and at least one pharmaceutically acceptable carrier.

A compound of the formula (I) can be administered alone or in combination with one or more other therapeutic compounds, possible combination therapy taking the form of fixed combinations or the administration of a compound of the invention and one or more other therapeutic (including prophylactic) compounds being staggered or given independently of one another, or the combined administration of fixed combinations and one or more other therapeutic compounds. A compound of the formula (I) can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

The dosage of the active ingredient depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy requires a regimen based on the kinetics of the drug's availability to target sites. This involves a consideration of the distribution, equilibrium, and elimination of a drug.

The dose of a compound of the formula (I) or a pharmaceutically acceptable salt thereof to be administered to warm-blooded animals, for example humans of approximately 70 kg body weight, is preferably from approximately 3 mg to approximately 15 g, more preferably from approximately 10 mg to approximately 3 g, yet more preferably from approximately 50 mg to 1.5 g per person per day, undivided in 1 dose or divided preferably into 2 to 4, e.g. 2 or 3, single doses which may, for example, be of the same size. Usually, children receive half of the adult dose.

The compounds of the formula (I) may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The invention relates also to pharmaceutical compositions comprising an effective amount, especially an amount effective in the treatment of one of the above-mentioned disorders, of a compound of the formula (I) and/or an N-oxide or a tautomer thereof, and/or a pharmaceutically acceptable salt thereof, together with one or more pharmaceutically acceptable carriers that are suitable for topical, enteral, for example oral or rectal, or parenteral administration and that may be inorganic or organic, solid or liquid. There can be used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting compounds and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectionning, dissolving or lyophilising processes, and comprise approximately from 1% to 99%, especially from approximately 1% to approximately 20%, active ingredient(s).

Additionally, the present invention provides a compound of the formula (I), and/or an N-oxide or a tautomer thereof, and/or a pharmaceutically acceptable salt thereof, for use in a method for the treatment of the human or animal body, especially for the treatment of a disease mentioned herein, most especially in a patient requiring such treatment.

The present invention also relates to the use of a compound of the formula (I) and/or an N-oxide or a tautomer thereof, and/or a pharmaceutically acceptable salt of such a compound, for the preparation of a medicament for the treatment especially of a proliferative disease, especially cancer.

Furthermore, the invention relates to a method for the treatment of a proliferative disease which responds to an inhibition of the p53/MDM2 interaction, which comprises administering a compound of the formula (I), and/or an N-oxide or a tautomer thereof, and/or a pharmaceutically acceptable salt thereof, wherein the radicals and symbols have the meanings as defined above, to a warm-blooded animal requiring such treatment, especially in a quantity effective against said disease and/or capable of inhibiting the p53/MDM2 interaction in said warm-blooded animal.

Furthermore, the invention relates to a pharmaceutical composition for treatment of solid or liquid tumors in warm-blooded animals, including humans, comprising an antiproliferatively effective dose of a compound of the formula (I) as described above or a pharmaceutically acceptable salt of such a compound together with a pharmaceutical carrier.

The invention relates in a fifth aspect to the manufacture of a compound of formula (I). The compounds of formula (I) or salts thereof are prepared in accordance with processes known per se (see references cited above), though not previously described for the manufacture of the compounds of the formula (I).

Synthesis of Compounds of the Formula (I)

Typically, the compounds of the formula (I) can be prepared according to the Schemes provided below.

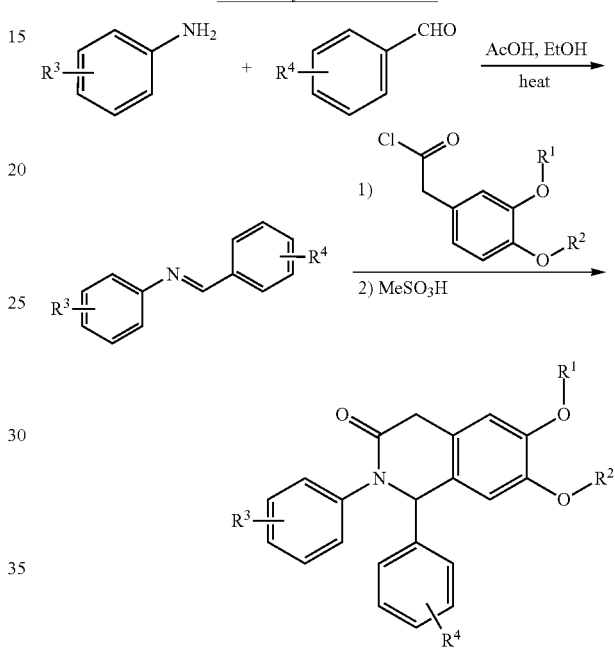

General Synthetic Scheme A.

Scheme A illustrates one method of preparing compounds of the invention mainly according to a modified published procedure (Venkov, A. and Molloy, N. *Synthesis* 1982, 3, 216-217).

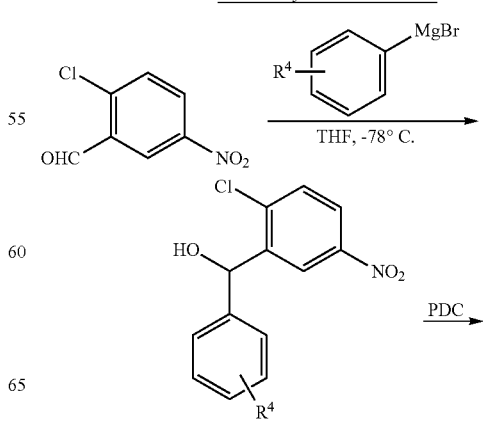

General Synthetic Scheme B.

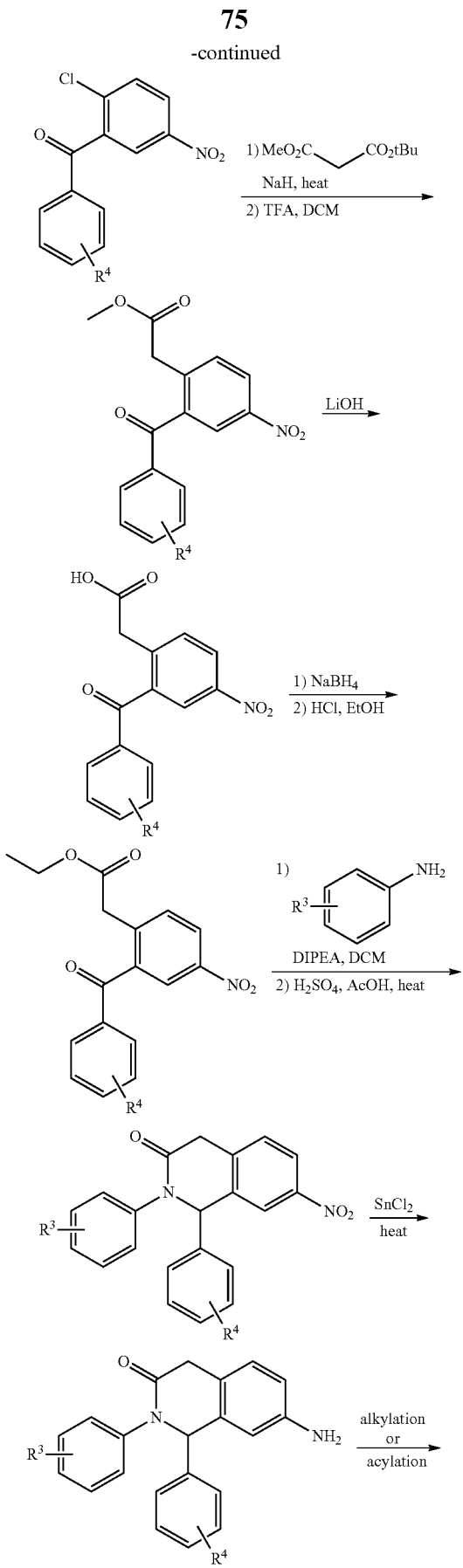

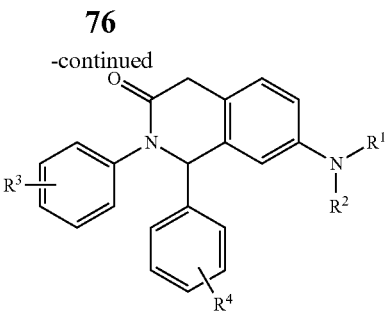

The benzaldehyde derivative is used in a Grignard type reaction typically in THF and typically at −78° C. to obtain the corresponding benzylalcohol. The alcohol derivative is oxidized by pyridinium dichromate (PDC) or other oxidizing reagents such as manganese dioxide.

The methyl acetate group is introduced using malonic acid tert-butyl ester methyl ester and a strong base typically NaH and using heat, typically the reaction is heated to 60° C. in an aprotic solvent such as DMSO. In a second step, the crude product was treated with typically with trifluoroacetic acid in an organic solvent such as DCM.

Saponification was done using LiOH in typically used methanol/water (2:1), typically at room temperature. After acidification with 2 M HCl, the precipitate was collected and extracted with organic solvents.

To a suspension of the free acid typically in EtOH, or other alcohol such as methanol, was added NaBH$_4$, typically at room temperature. To this solution the thionyl chloride was added, typically at 0° C. and the reaction is stirred at r.t.

Benzylchlorides were treated typically under basic conditions with DIPEA or triethyl amine, in DCM or other organic solvents such as dioxan, DMF, DMSO and substituted anilines at room temperature and then evaporated to dryness. To a solution of the resulting residue in acetic acid, was added sulfuric acid at RT and the mixture was heated at 80° C., stirred for 1 h then cooled to RT, and concentrated under vacuum.

The nitro group was reduced by treating the starting material with tin chloride typically in EtOH at RT. The slurry was heated at 80° C. and vigorously stirred 30 min.

The resulting aniline was further substituted with different acid chloride (acylation), e.g. propionyl chloride, or with different aldehydes or ketones using reductive amination conditions (AcOH, NaBH(OAc)$_3$, DCM, RT) to receive different alkylated products.

General Synthetic Scheme C.

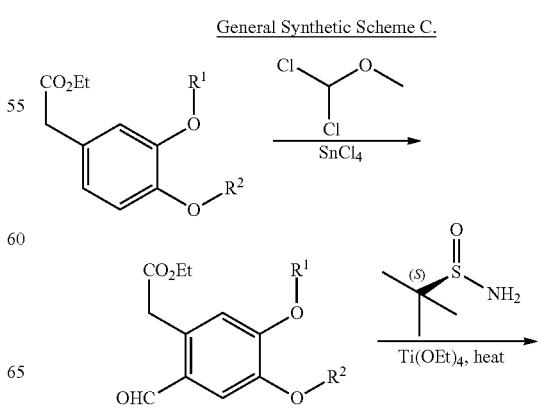

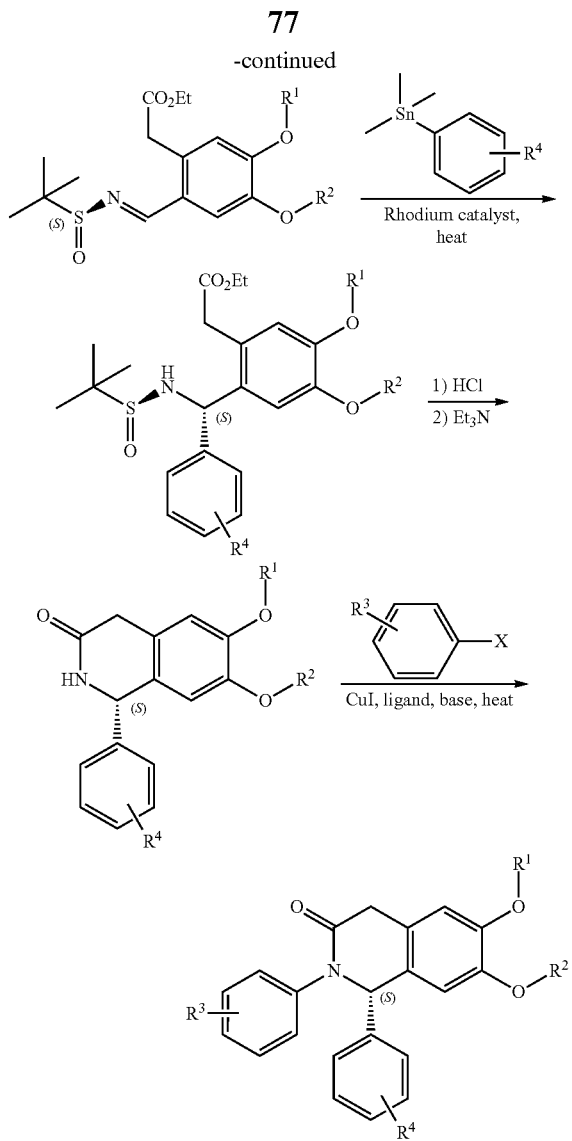

(3,4-Dialkoxy-phenyl)-acetic acid ethyl ester was treated with dichloro-methoxy-methane in typically DCM by slowly added $SnCl_4$ (1M solution in DCM), over typically 30 minutes. After the complete addition, the reaction was typically stirred at 0° C. for 1.5 hrs. The chiral auxiliar group was added following the procedure from Davis et a. (Frank A. Davis, Pradyumna K. Mohanty; *J. Org. Chem.*, 2002, 67, 4, 1290) using typically a Lewis acid such as $Ti(OEt)_4$ and typically an aprotic solvent such as DCM.

The enantioselevtive addition of the aryl group followed the procedure from Oi et al (S. Oi, M. Moro, H. Fukurhara, T. Kawanishi, Y. Inoue, *Tetrahedron*, 59, 2003, 4351). The tin reagent was added to a solution of starting material (sulfoximine) in an organic solvent such as THF, dioxane or acetonitrile, but typically THF in the presence of a rhodium catalyst, such as bis(acetonitrile)(1,5-cyclooctadiene)rhodium(I) tetrafluoroborate. The reaction is carried out typically at elevated temperature such as 60° C. Other reagents than the tin reagents can be utilized such as the corresponding borate salts. Deprotection od the sulfoxamine group was typically done under acidic conditions using acids such as HCl (e.g. 1.25 M in ethanol) in an organic solvent such as an alcohol, typically methanol. The free amine was evaporated to dryness, re-dissolved in typically methanol and a base is added, typically triethylamine and the reaction is stirred at typically room temperature.

The cross-coupling reaction is carried out following Buchwald's condition for the C—N amidation reaction, typically following Buchwald literature procedure (A. Klapars, Xiaohua Huang, S. L. Buchwald; *J. Am. Chem. Soc.*, 2002, 124, 7421). Under an inert argon atmosphere and using degassed aprotic solvents encompassing toluene, dioxane, THF and DMF, but typically dioxane, the starting materials (isoquinolinone and aryl halide) are mixed in the presence of a copper source, such as Cu powder, CuI, CuCN, $Cu_2O$, $CuCl_2$, but typically CuI and an diamine ligand, such as ethylenediamine, or other 1,2-diamine ligands, but typically trans-1,2-cyclohexanediamine in the presence of a base, such as $K_3PO_4$, $K_2CO_3$ or $CsCO_3$, but typically $K_3PO_4$. The reaction is heated to typically 100-110° C. and stirred for 4 to 16 hours depending the progress of the reaction.

General Synthetic Scheme D.

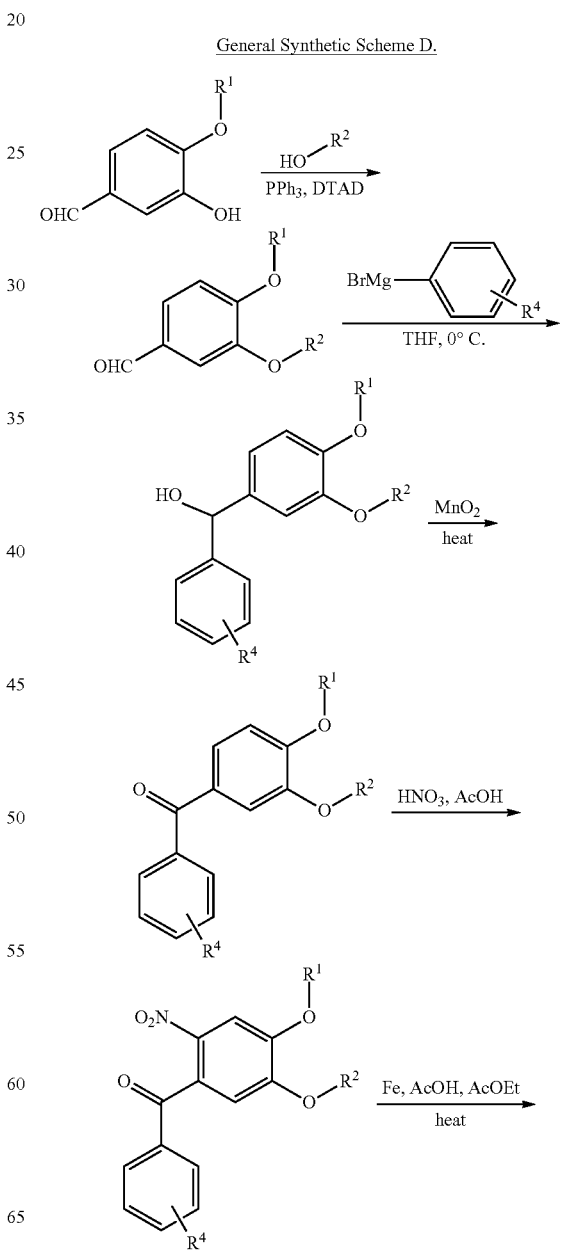

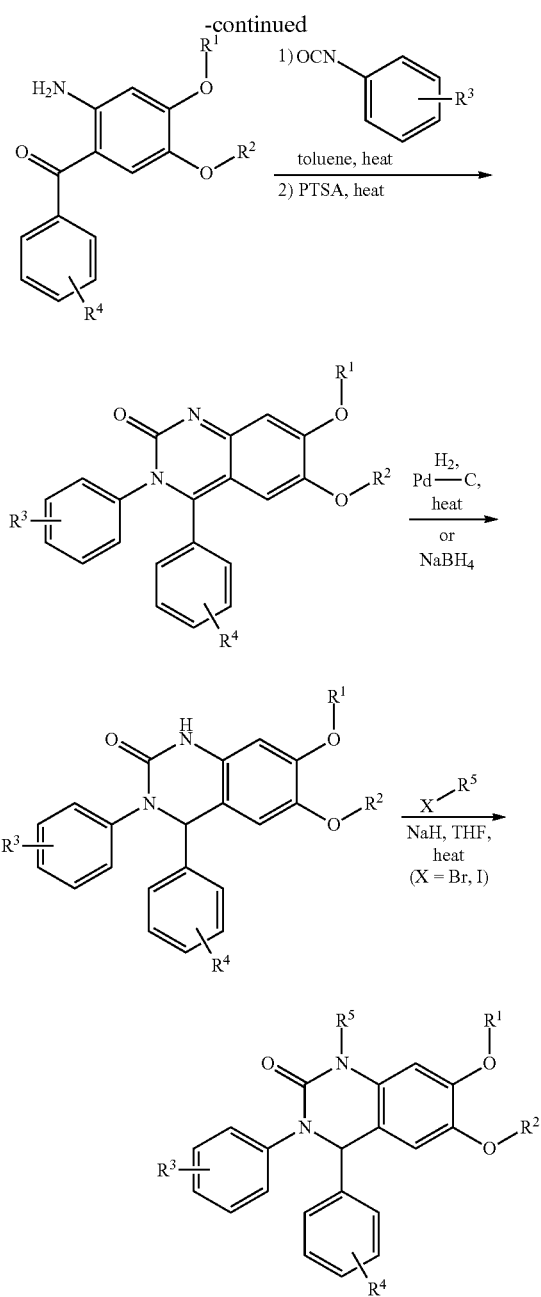

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described herein above.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

In another embodiment of the invention there is provided a compound of intermediate 75.6 below:

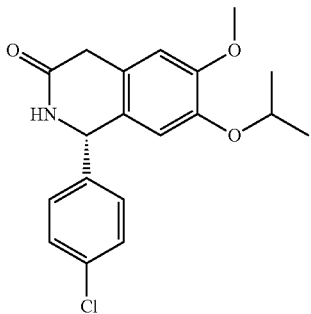 [SMILES: COc1cc2c(cc1OC(C)C)[C@H](c1ccc(Cl)cc1)NC(=O)C2]

In another embodiment of the invention there is provided an intermediate compound of the following formula as described in synthetic scheme C:

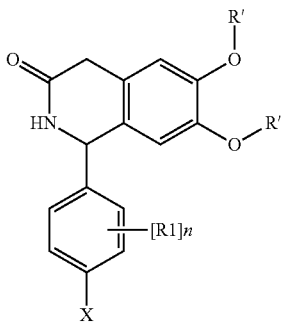

wherein R', $R^1$, n and X are as described herein. Preferably, in said intermediate, R' is independently selected from $C_1$-$C_6$-alkyl-, n is 0 and X is halo. In a particular embodiment, the intermediate has the following stereochemistry:

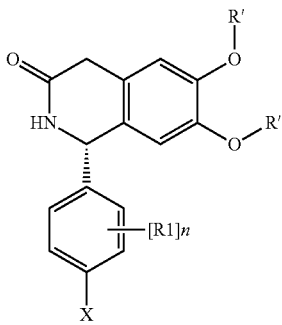

ABBREVIATIONS

Ac acetyl
AcOEt ethyl acetate
AcOH acetic acid
aq. aqueous
API-MS Atmospheric Pressure Ionization Mass Spectroscopy
$BH_3$.THF borane tetrahydrofuran complex
Boc t-butoxycarbonyl
brine saturated aqueous sodium chloride solution at RT
$^t$Bu t-butyl
$CDCl_3$ deuteriated chloroform
$CD_3OD$ deuteriated methanol
Celite trademark of Celite Corp. (World Minerals Inc.), Santa Barbara, Calif., USA, for filtering aid based on kieselguhr
$CHCl_3$ chloroform
conc. concentrated
$Cs_2CO_3$ cesium carbonate
CuI copper(I) iodide
$Cu_2O$ copper(I) oxide
DCM dichloromethane
DIPEA diisopropylethylamine
DMAP 4-dimethylaminopyridine
DME 1,2-dimethoxyethane
DMF N,N-dimethylformamide
DMSO dimethylsulfoxide
DTAD di-t-butyl azodicarboxylate
equiv. equivalent
Et ethyl
$Et_3N$ triethylamine
$Et_2O$ diethyl ether
EtOH ethanol
Fe iron metal
g gram(s)
h hour(s)
HATU O-(7-azabenzotriazol-1-yl)-N,N,N',N'-tetramethyluroniumhexafluorophosphat
HCl hydrogen chloride
$HNO_3$ nitric acid
HPLC high-pressure liquid chromatography
$H_2SO_4$ sulfuric acid
iPr isopropyl
$K_2CO_3$ potassium carbonate
KOH potassium hydroxide
$K_3PO_4$ potassium phosphate
LC-MS liquid chromatography mass spectroscopy
$LiBH_4$ lithium borohydride
LiOH lithium hydroxide
M molar
Me methyl
MeCN acetonitrile
mg milligram(s)
MeI methyl iodide
MeOH methanol
min minute(s)
ml milliliter(s)
mmol millimole(s)
$MnO_2$ manganese(IV) oxide
MS mass spectrometry
$NaBH_4$ sodium borohydride
$NaBH_3CN$ sodium cyanoborohydride
$NaBH(OAc)_3$ sodium triacetoxyborohydride
$Na_2CO_3$ sodium carbonate
NaH sodium hydride
$NaHCO_3$ sodium bicarbonate
$NaN_3$ sodium azide
NaOCN sodium cyanate
NaOH sodium hydroxide
$Na_2SO_4$ sodium sulfate
$NH_3$ ammoniac
$NH_4Cl$ ammonium chloride
NMM 4-methylmorpholine
NMR nuclear magnetic resonance
PDC pyridinium dichromate
Pd/C palladium over charcoal
$PdCl_2(PPh_3)_2$ dichlorobis(triphenylphosphine)-palladium (II)

Pd(PPh$_3$)$_4$ tetrakis(triphenylphosphine)palladium
Ph phenyl
PPh$_3$ triphenylphosphine
prep-HPLC preparative high-pressure liquid chromatography
PTSA p-toluenesulfonic acid
quant. quantitative
R$_F$ retention factor
RT room temperature
SiO$_2$ silica
SnCl$_2$ stannous chloride or Tin(II) chloride
SnCl$_4$ Tin(IV) chloride
SOCl$_2$ thionyl chloride
TBDMSCl tert-butyldimethylsilyl chloride
TBME tert-butyl-dimethyl ether
TFA trifluoroacetic acid
THF tetrahydrofurane
Ti(OEt)$_4$ titanium(IV) ethoxide
Ti(OiPr)$_4$ titanium(IV) isopropoxide
TLC thin layer chromatography
t$_{Ret}$ retention time
General Methods.

$^1$H-NMR measurements were performed on a Bruker Ultrashield™ 400 (400 MHz), Bruker Ultrashield™ 600 (600 MHz) or a 500 MHz DRX Bruker CryoProbe (500 MHz) spectrometer using or not trimethylsilane as an internal standard. Chemical shifts (d-values) are reported in ppm downfield from tetramethylsilane, coupling constants (J) are given in Hz, spectra splitting pattern are designated as singulet (s), doublet (d), doublet doublet (dd), triplet (t), quadruplet (q), multiplet or more overlapping signals (m), broad signal (br). Solvents are given in parentheses.

prep-HPLC purifications were performed using optimized gradient elution (CH$_3$CN water with 0.1% TFA) with a Waters HPLC prep-system equipped with a UV detector Waters 2487 Dual Absorbance Detector, a MS detector Waters micromassZQ, and a reversed phase column SunFire™ Prep, C18 OBD, 100×30 mm, 5 m, or 100×19 mm, 5 m. Generally products were obtained as TFA salts after lyophilization.

TLC were performed with precoated silica gel 60 F$_{254}$ glass plates (Merck, Darmstadt, Germany) using the respective named solvent systems. Visualization was generally done by UV light (254 nm).

LC-MS spectra were recorded on a Waters 2795 Alliance HT instrument with a Sunfire™ C18, 4.6×20 mm, 3.5 m column, eluting with a linear gradient of 5 to 100% MeCN (+0.1% TFA) in water (+0.1% TFA) in 4 min with a flow rate of 3 ml/min at 45° C., with positive ion electrospray ionization (Micromass ZQ Detector).

API-MS spectra were recorded on an Agilent 1100 instrument with a Ascentis Expresse™ C18, 2.1×30 mm, 2.7 m column, eluting with a linear gradient of 2 to 98% MeCN (+0.04% formic acid) in water (+0.05% formic acid+0.05% of a 7.5 M aqueous ammonium acetate solution) in 1.7 min with a flow rate of 1.2 ml/min at 50° C., with positive and/or negative ion electrospray ionization (ZMD Detector).

[M+H]$^+$ and [M−H]$^−$ refer to monoisotopic molecular weights.

HPLC retention times ($^X$t$_{Ret}$) were reported in min and were recorded using the following conditions:

Retention times for system A ($^A$t$_{Ret}$) were measured with a Waters 2795 Alliance HT instrument equipped with a Waters 2996 Photodiode Array Detector (PDA MaxPlot detection at 210.0 nm to 400.0 nm) and a Micromass ZQ Detector (positive ion electrospray ionization detection), eluting with a linear gradient of 5 to 100% MeCN (+0.1% TFA) in water (+0.1% TFA) in 4 min with a flow rate of 3 ml/min at 45° C. The column was a Sunfire™ C18, 4.6×20 mm, 3.5 m.

Retention times for system B ($^B$t$_{Ret}$) were measured with a Waters 2695 Alliance HT instrument equipped with a Waters 2996 Photodiode Array Detector (PDA MaxPlot detection at 210.0 nm to 400.0 nm), eluting with a linear gradient of 5 to 100% MeCN in water (+0.1% TFA) in 4 min with a flow rate of 3 ml/min at 35° C. The column was a Sunfire™ C18, 4.6×20 mm, 3.5 m.

Retention times for system C ($^C$t$_{Ret}$) were measured with an Agilent 1100 instrument equipped with an Agilent 1100 series Photodiode Array Detector (PDA MaxPlot detection at 210.0 nm to 400.0 nm), eluting with an isocratic of 40% MeCN in water (+5 mM ammonium formate) for 1 min then a gradient of 40 to 60% MeCN in water (+5 mM ammonium formate) in 7 min with a flow rate of 2 ml/min at 40° C. The column was a Sunfire™ C18, 4.6×50 mm, 5 m.

Retention times for system D ($^D$t$_{Ret}$) were measured with a Waters instrument equipped with a Waters Acquity UPLC PDA Detector (detection at 120 nm to 1200.0 nm), eluting with an isocratic from 0-1.40 min of 2 to 98% MeCN(0.04% HCOOH) in water (+0.05% HCOOH+0.05% Ammonium Acetate), 1.40-2.15 min. 98% MeCN(0.04% HCOOH), 2.15-2.19 min of 98% to 2% MeCN(+0.04% HCOOH) then 2.19-2.20 min of 2% MeCN(+0.04% HCOOH) with a flow rate of 1.2 ml/min at 50° C. The column was a Acquity HSS T3, 2.1×50 mm, 1.8 μm Retention times for system E ($^E$t$_{Ret}$) were measured with a Agilent 1100 instrument equipped with an Agilent 1100 series Dioden Array Detector (DAD detection at 215 nm), eluting with an isocratic from 0-5.0 min of 2 to 100% MeCN (0.1% TFA) in water (+0.1% TFA), 5.0-6.5 min. 100% MeCN (0.1% TFA) then 6.5-7.0 min of 100% to 2% MeCN(+0.1% TFA) with a flow rate of 1.0 ml/min at 30° C. The column was a Nucleosil 100-3 C18 HD, 4.0×70 mm Retention times for system F ($^F$t$_{Ret}$) were measured with a Waters instrument equipped with a Waters Acquity UPLC PDA Detector (PDA MaxPlot detection at 210.0 nm to 400.0 nm)), eluting with an isocratic from 0.1-1.60 min of 2 to 100% MeCN(0.05% HCOOH) in water (+0.05% HCOOH), 1.60-2.0 min. 100% MeCN(0.05% HCOOH) then 2.0-2.0 min of 100% to 2% MeCN(+0.05% HCOOH) with a flow rate of 1.0 ml/min at 40° C. The column was a Acquity BEH C18, 2.1×50 mm, 1.7 m.

Retention times for system G ($^G$t$_{Ret}$) were measured with a Agilent 1100 instrument equipped with an Agilent 1100 series Dioden Array Detector (DAD detection at 215 nm), eluting with an isocratic from 0-7.0 min of 2 to 100% MeCN (0.1% TFA) in water (+0.1% TFA), 7.0-9.0 min. 100% MeCN (0.1% TFA) then 9.0-10.0 min of 100% to 2% MeCN(+0.1% TFA) with a flow rate of 1.0 ml/min at 30° C. The column was a Nucleosil 100-3 C18 HD, 4.0×125 mm (Macherey-Nagel).

Retention times for system H ($^H$t$_{Ret}$) were measured with a Waters instrument equipped with a Waters Acquity UPLC PDA Detector (detection at 120 nm to 1200.0 nm), eluting with an isocratic from 0-3.0 min of 10 to 95% MeCN(0.1% HCOOH) in water (+0.1% HCOOH), 3.0-4.0 min. 95% MeCN(0.1% HCOOH) with a flow rate of 1.2 ml/min at 50° C. The column was a Acquity HSS T3 2.1×50 mm, 1.8 m.

Retention times for system I ($^I$t$_{Ret}$) were measured with a Agilent 1100 instrument equipped with an Agilent 1100 series Dioden Array Detector (DAD detection at 215 nm), eluting with an isocratic from 0-8.0 min of 2 to 100% MeCN (0.1% TFA) in water (+0.1% TFA), 8.0-10.0 min. 100% MeCN(0.1% TFA), 10.0-11.0 min of 100% to 2% MeCN(+0.1 TFA) then 11.0-13.0 min of 2% MeCN(+0.1% TFA) with a flow rate of 2.0 ml/min at 25° C. The column was a Chromolith Performance RP-18e, 4.6×100 mm (Merck)

Retention times for system J ($^{J}t_{Ret}$) were measured with a Thermo Finnigan instrument equipped with an UV 6000LP Photodiode Array Detector (DAD detection at 218 nm), eluting with an isocratic from 0-8.0 min of 2 to 100% MeCN (0.1% HCOOH) in water (+0.1% HCOOH), 8.0-10.0 min. 100% MeCN(0.1% HCOOH) then 10.0-11.0 min of 100% to 2% MeCN(+0.1% HCOOH) with a flow rate of 2.0 ml/min at 30° C. The column was a Chromolith Performance RP-18e, 4.6×100 mm (Merck)

Retention times for system K ($^{K}t_{Ret}$) were measured with a Agilent 1100 instrument equipped with an Agilent 1100 series Dioden Array Detector (DAD detection at 215 nm), eluting with an isocratic from 0-7.0 min of 2 to 100% MeCN (0.1% TFA) in water (+0.1% TFA), 7.0-9.0 min. 100% MeCN (0.1% TFA) then 9.0-10.0 min of 100% to 2% MeCN(+0.1% TFA) with a flow rate of 1.0 ml/min at 30° C. The column was a Nucleosil 100-3 C18 HD, 4.0×125 mm Retention times for system L ($^{L}t_{Ret}$) were measured with a Agilent 1100 instrument equipped with an Agilent 1100 series Dioden Array Detector (DAD detection at 215 nm), eluting with an isocratic from 0-5.0 min of 20 to 100% MeCN (0.1% TFA) in water (+0.1% TFA), 5.0-6.5 min. 100% MeCN (0.1% TFA) then 6.5-7.0 min of 100% to 20% MeCN(+0.1% TFA) with a flow rate of 1.0 ml/min at 30° C. The column was a Nucleosil 100-3 C18 HD, 4.0×125 mm Retention times for system M ($^{M}t_{Ret}$) were measured with a Waters instrument equipped with a Waters Acquity UPLC PDA Detector (detection at 120 nm to 1200.0 nm), eluting with an isocratic from 0-1.40 min of 2 to 98% MeCN(0.04% HCOOH) in water (+0.05% HCOOH+0.05% Ammonium Acetate), 1.40-2.15 min. 98% MeCN(0.04% HCOOH), 2.15-2.19 min of 98% to 2% MeCN(+0.04% HCOOH) then 2.19-2.20 min of 2% MeCN(+0.04% HCOOH) with a flow rate of 1.2 ml/min at 50° C. The column was a Acquity HSS T3, 2.1×50 mm, 1.8 μm Retention times for system N ($^{N}t_{Ret}$) were measured with a Agilent 1100 instrument equipped with an Agilent 1100 series Dioden Array Detector (DAD detection at 215 nm-350 nm), eluting with an isocratic from 0-1.40 min of 2 to 98% MeCN(0.04% HCOOH) in water (+0.5% HCOOH+0.05% Ammonium Acetate), 1.40-2.15 min. 98% MeCN(0.04% HCOOH), 2.15-2.19 min of 98% to 2% MeCN(+0.04% HCOOH) then 2.19-2.20 min of 2% MeCN(+0.04% HCOOH) with a flow rate of 1.2 ml/min at 50° C. The column was an Acentis Express C18, 2.1×30 mm, 2.7 μm Retention times for system O ($^{O}t_{Ret}$) were measured with a Waters 2690 instrument equipped with an Waters 996 series Photodiode Array Detector (detection at 215 nm and 254 nm), eluting with an isocratic from 1.0-11.0 min of 2 to 100% MeCN(0.1% TFA) in water (+0.1% TFA) then 11.0-13.0 min of 100% MeCN(+0.1% TFA) with a flow rate of 1.0 ml/min at 35° C. The column was Column Engineering, Inc., Matrix C18 4.6×150 mm (Lot#205), 3.0 μm

EXAMPLES

The following examples serve to illustrate the invention without limiting the scope thereof. Note that in some cases compounds mentioned as intermediates are also compounds of the formula I according to the invention (it is then mentioned that the compounds fall under formula I). Names of each examples or intermediates were automatically generated using AutoNom 2000 from IsisDraw. Where no specific source is indicated, starting materials and solvents are obtainable from customary suppliers, such as SigmaAldrich, Fluka, Alfa Aesar, Merck, or from providers indicated specifically. Abbreviations.

Example 1

7-((R)-sec-Butoxy)-1-(4-chloro-phenyl)-2-(4-dimethylamino-phenyl)-6-methoxy-1,4-dihydro-2H-isoquinolin-3-one

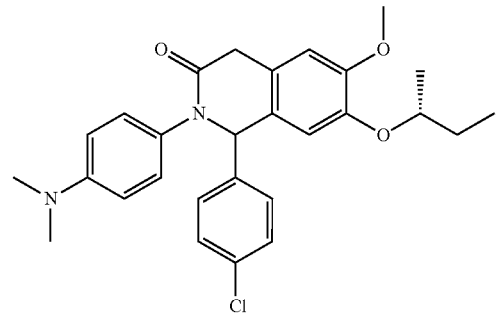

Intermediate 1.3 (41.4 mg, 0.16 mmol) was added to a solution of Intermediate 1.4 (40 mg, 0.16 mmol) in DCM (1 ml) at RT and the resulting yellow slurry was stirred for 1 h. Methanesulfonic acid (0.10 ml, 1.6 mmol) was added drop wise and the mixture was further stirred for 15 min at RT. The reaction mixture was concentrated under vacuum and the resulting residue was purified by reverse phase prep-HPLC (Waters system) to yield the title compound (TFA salt, 10 mg, 0.017 mmol, 10%). HPLC: $^{A}t_{Ret}$=2.03 min; API-MS: m/z 480.6 [M+H]$^{+}$; $^{1}$H NMR (400 MHz, CDCl$_{3}$): 0.93-1.03 (2t, J=7.5, 3H, mixture of diastereoisomers), 1.25-1.34 (2 d, J=6.1, 3H, mixture of diastereoisomers), 1.57-1.85 (m, 2H), 3.12 (s, 6H), 3.79 (d, J=19.8, 1H), 3.86-3.95 (m, 4H), 4.17-4.26 (m, 1H), 5.74 (s, 1H), 6.68-6.74 (m, 2H), 7.06-7.11 (m, 2H), 7.18-7.24 (m, 2H), 7.26-7.32 (m, 4H).

Intermediate 1.1: [4-((R)-sec-Butoxy)-3-methoxyphenyl]-acetic acid ethyl ester

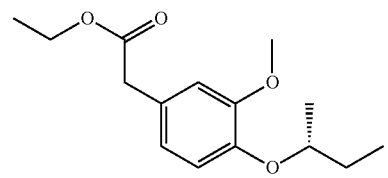 [SMILES: CCOC(=O)Cc1ccc(O[C@H](C)CC)c(OC)c1]

To a solution of (4-hydroxy-3-methoxy-phenyl)-acetic acid ethyl ester (700 mg, 3.33 mmol) in DCM (40 ml) were successively added (S)-butan-2-ol (0.37 ml, 4.0 mmol), supported PPh$_{3}$ (loading of 1.52 mmol/g, 4.38 g, 6.66 mmol) and DTAD (1.15 g, 5.0 mmol). The reaction mixture was shaken at RT for 3 h, then filtered and the resin was washed with DCM. The filtrate was evaporated to dryness and the resulting residue was purified by Combi-Flash Companion™ (Isco Inc.) column chromatography (SiO$_{2}$; gradient elution, heptane/TBME 95:5→1:1) to yield the title compound (818 mg, 3.07 mmol, 92%) as a colorless oil. TLC: R$_{F}$=0.85 (heptane/DCM/TBME 1:1:2); HPLC: $^{B}t_{Ret}$=2.46 min; API-MS: m/z 267.2 [M+H]$^{+}$; $^{1}$H NMR (400 MHz, CDCl$_{3}$): 1.00 (t, J=7.5, 3H), 1.28 (t, J=7.1, 3H), 1.33 (d, J=6.1, 3H), 1.60-1.70 (m, 1H), 1.77-1.89 (m, 1H), 3.56 (s, 2H), 3.86 (s, 3H), 4.17 (q, J=7.1, 2H), 4.25 (sxt, J=6.1, 1H), 6.79 (dd, J=8.3, 2.0, 1H), 6.83-6.87 (m, 2H).

Intermediate 1.2: [4-((R)-sec-Butoxy)-3-methoxy-phenyl]-acetic acid

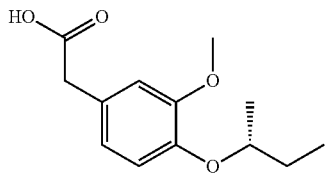 [SMILES: CC[C@@H](C)Oc1ccc(CC(=O)O)cc1OC]

A mixture of Intermediate 1.1 (818 mg, 3.07 mmol) in EtOH (8 ml) and water (2 ml) was treated with LiOH monohydrate (387 mg, 9.21 mmol) at RT and stirred for 1 h. The reaction mixture was neutralized by the addition of HCl 0.5 M in water then extracted with DCM. The organic fraction was dried over $Na_2SO_4$, filtered and evaporated to dryness to yield the title compound (740 mg, 3.07 mmol, quant) as a yellow oil, which was used in the next step without further purification. HPLC: $^Bt_{Ret}$=1.80 min; API-MS: m/z 237.2 [M−H]$^+$; $^1$H NMR (400 MHz, CDCl$_3$): 1.00 (t, J=7.5, 3H), 1.33 (d, J=6.1, 3H), 1.58-1.70 (m, 1H), 1.77-1.89 (m, 1H), 3.60 (s, 2H), 3.86 (s, 3H), 4.21-4.31 (m, 1H), 6.78-6.88 (m, 3H).

Intermediate 1.3: [4-((R)-sec-Butoxy)-3-methoxy-phenyl]-acetyl chloride

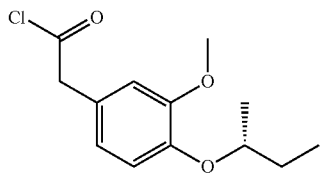 [SMILES: CC[C@@H](C)Oc1ccc(CC(=O)Cl)cc1OC]

To a solution of Intermediate 1.2 (372 mg, 1.56 mmol) in DCM (15 ml) were successively added oxalylchloride (0.2 ml, 2.3 mmol) and a catalytic amount of DMF (0.012 ml, 0.16 mmol) at 0° C. (ice bath). The reaction mixture was stirred at 0° C. for 30 min then evaporated to dryness under vacuum to yield the crude title compound (401 mg, 1.56 mmol, quant.) as an orange oil which was used in the next step without further purification.

Intermediate 1.4: N-[1-(4-Chloro-phenyl)-meth-(E)-ylidene]-N',N'-dimethyl-benzene-1,4-diamine

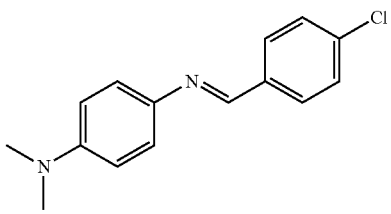 [SMILES: CN(C)c1ccc(/N=C/c2ccc(Cl)cc2)cc1]

To a mixture of 4-chloro-benzaldehyde (1.55 g, 11.0 mmol) and N,N-dimethyl-benzene-1,4-diamine (1.5 g, 11.0 mmol) in EtOH (15 ml) was added a catalytic amount of AcOH (0.063 ml, 1.1 mmol) at RT. The reaction mixture was heated at reflux and stirred for 14 h during which time precipitation took place. After cooling to RT, the slurry was filtered and washed with heptane. The solid was collected and dried under high vacuum to yield the title compound (2.09 g, 8.08 mmol, 73%) as a brownish solid. $^1$H NMR (400 MHz, CDCl$_3$): 3.01 (s, 6H), 6.78 (m, 2H), 7.29 (m, 2H), 7.44 (m, 2H), 7.84 (m, 2H), 8.49 (s, 1H).

Example 2

Compounds 2aa to 2bj were obtained analogously to Example 1 from various phenylacetyl chlorides (prepared analogously to Intermediate 1.3) and imines (prepared from commercially available aldehydes and anilines analogously to Intermediate 1.4).

| # | Structure | Name / HPLC / MS |
|---|---|---|
| 2aa | 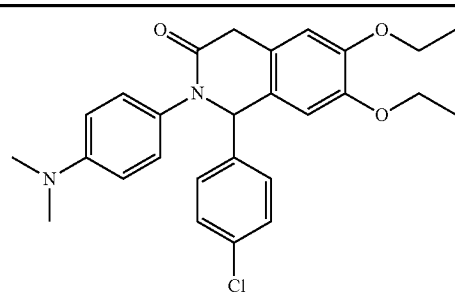 | 1-(4-Chloro-phenyl)-2-(4-dimethylamino-phenyl)-6,7-diethoxy-1,4-dihydro-2H-isoquinolin-3-one. HPLC: $^At_{Ret}$ = 1.88; API-MS: m/z 465.3 [M + H]$^+$. |
| 2ab | 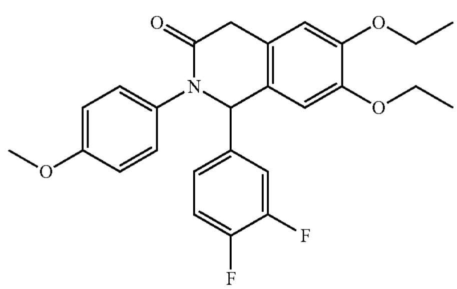 [SMILES: CCOc1cc2c(cc1OCC)C(c1ccc(F)c(F)c1)N(c1ccc(OC)cc1)C(=O)C2] | 1-(3,4-Difluoro-phenyl)-6,7-diethoxy-2-(4-methoxy-phenyl)-1,4-dihydro-2H-isoquinolin-3-one. HPLC: $^At_{Ret}$ = 2.51; API-MS: m/z 454.3 [M + H]$^+$. |

-continued

| # | Structure | Name / HPLC / MS |
|---|---|---|
| 2ac | 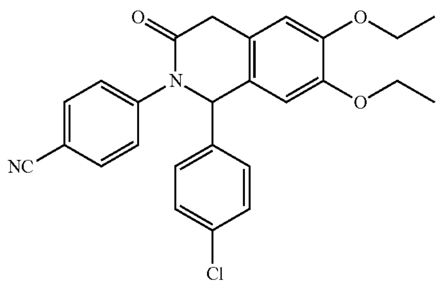 [SMILES: CCOc1cc2c(cc1OCC)C(c1ccc(Cl)cc1)N(c1ccc(C#N)cc1)C(=O)C2] | 4-[1-(4-Chloro-phenyl)-6,7-diethoxy-3-oxo-3,4-dihydro-1H-isoquinolin-2-yl]-benzonitrile.<br>HPLC: $^A t_{Ret}$ = 2.60; API-MS: m/z 447.1 [M + H]$^+$. |
| 2ad | 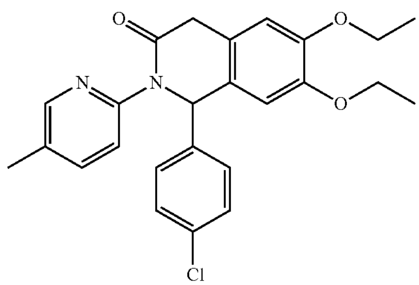 [SMILES: CCOc1cc2c(cc1OCC)C(c1ccc(Cl)cc1)N(c1ccc(C)cn1)C(=O)C2] | 1-(4-Chloro-phenyl)-6,7-diethoxy-2-(5-methyl-pyridin-2-yl)-1,4-dihydro-2H-isoquinolin-3-one.<br>HPLC: $^A t_{Ret}$ = 2.67; API-MS: m/z 437.2 [M + H]$^+$. |
| 2ae | 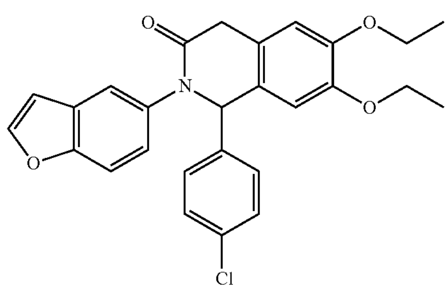 [SMILES: CCOc1cc2c(cc1OCC)C(c1ccc(Cl)cc1)N(c1ccc3occc3c1)C(=O)C2] | 2-Benzofuran-5-yl-1-(4-chloro-phenyl)-6,7-diethoxy-1,4-dihydro-2H-isoquinolin-3-one.<br>HPLC: $^A t_{Ret}$ = 2.67; API-MS: m/z 462.1 [M + H]$^+$. |
| 2am | 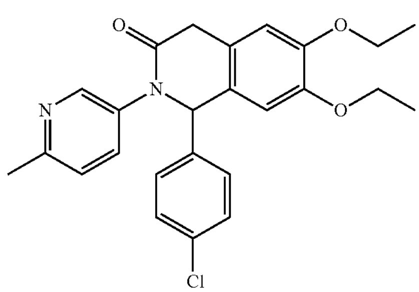 [SMILES: CCOc1cc2c(cc1OCC)C(c1ccc(Cl)cc1)N(c1ccc(C)nc1)C(=O)C2] | 1-(4-Chloro-phenyl)-6,7-diethoxy-2-(6-methyl-pyridin-3-yl)-1,4-dihydro-2H-isoquinolin-3-one.<br>HPLC: $^A t_{Ret}$ = 1.72; API-MS: m/z 437.2 [M + H]$^+$. |
| 2an | 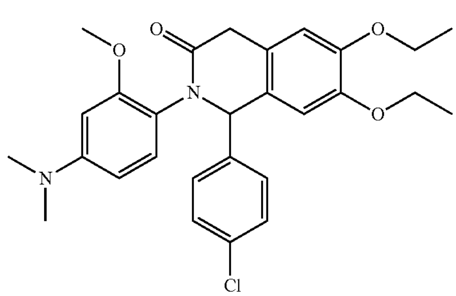 [SMILES: CCOc1cc2c(cc1OCC)C(c1ccc(Cl)cc1)N(c1ccc(N(C)C)cc1OC)C(=O)C2] | 1-(4-Chloro-phenyl)-2-(4-dimethylamino-2-methoxy-phenyl)-6,7-diethoxy-1,4-dihydro-2H-isoquinolin-3-one.<br>HPLC: $^A t_{Ret}$ = 1.96; LC-MS: m/z 496.2 [M + H]$^+$. |

-continued

| # | Structure | Name / HPLC / MS |
|---|---|---|
| 2ao | 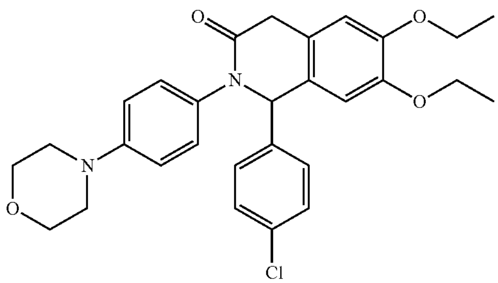 [SMILES: CCOc1cc2c(cc1OCC)C(c1ccc(Cl)cc1)N(c1ccc(N3CCOCC3)cc1)C(=O)C2] | 1-(4-Chloro-phenyl)-6,7-diethoxy-2-(4-morpholin-4-yl-phenyl)-1,4-dihydro-2H-isoquinolin-3-one.<br>HPLC: $^A t_{Ret}$ = 2.33; LC-MS: m/z 507.2 [M + H]$^+$. |
| 2ap | 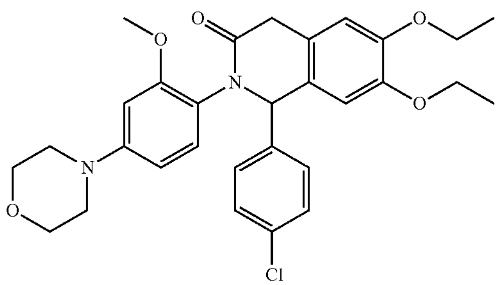 [SMILES: CCOc1cc2c(cc1OCC)C(c1ccc(Cl)cc1)N(c1ccc(N3CCOCC3)cc1OC)C(=O)C2] | 1-(4-Chloro-phenyl)-6,7-diethoxy-2-(2-methoxy-4-morpholin-4-yl-phenyl)-1,4-dihydro-2H-isoquinolin-3-one.<br>HPLC: $^A t_{Ret}$ = 2.36; LC-MS: m/z 537.2 [M + H]$^+$. |
| 2aq | 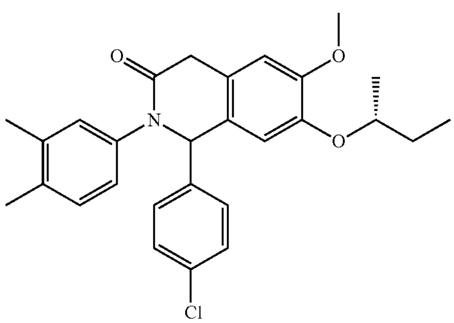 [SMILES: CC[C@@H](C)Oc1cc2c(cc1OC)CC(=O)N(c1ccc(C)c(C)c1)C2c1ccc(Cl)cc1] | 7-((R)-sec-Butoxy)-1-(4-chloro-phenyl)-2-(3,4-dimethyl-phenyl)-6-methoxy-1,4-dihydro-2H-isoquinolin-3-one.<br>HPLC: $^A t_{Ret}$ = 2.96; API-MS: m/z 465.6 [M + H]$^+$. |
| 2ar | 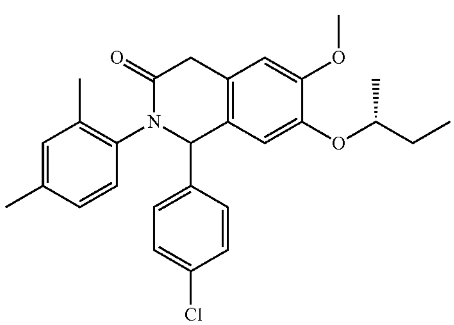 [SMILES: CC[C@@H](C)Oc1cc2c(cc1OC)CC(=O)N(c1ccc(C)cc1C)C2c1ccc(Cl)cc1] | 7-((R)-sec-Butoxy)-1-(4-chloro-phenyl)-2-(2,4-dimethyl-phenyl)-6-methoxy-1,4-dihydro-2H-isoquinolin-3-one.<br>HPLC: $^A t_{Ret}$ = 2.97; API-MS: m/z 465.6 [M + H]$^+$. |
| 2as | 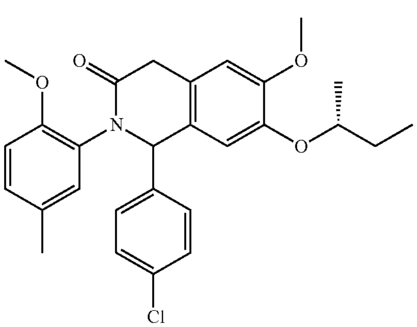 [SMILES: CC[C@@H](C)Oc1cc2c(cc1OC)CC(=O)N(c1cc(C)ccc1OC)C2c1ccc(Cl)cc1] | 7-((R)-sec-Butoxy)-1-(4-chloro-phenyl)-6-methoxy-2-(2-methoxy-5-methyl-phenyl)-1,4-dihydro-2H-isoquinolin-3-one.<br>HPLC: $^A t_{Ret}$ = 2.86; API-MS: m/z 481.9 [M + H]$^+$. |

| # | Structure | Name / HPLC / MS |
|---|---|---|
| 2at | 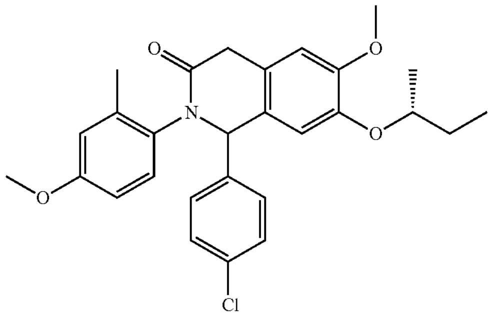 [SMILES: CC[C@@H](C)Oc1cc2c(cc1OC)CC(=O)N(c1ccc(OC)cc1C)C2c1ccc(Cl)cc1] | 7-((R)-sec-Butoxy)-1-(4-chloro-phenyl)-6-methoxy-2-(4-methoxy-2-methyl-phenyl)-1,4-dihydro-2H-isoquinolin-3-one.<br>HPLC: $^{A}t_{Ret}$ = 2.80; API-MS: m/z 481.6 [M + H]$^{+}$. |
| 2au | 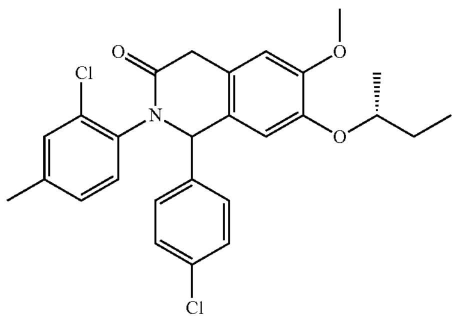 [SMILES: CC[C@@H](C)Oc1cc2c(cc1OC)CC(=O)N(c1ccc(C)cc1Cl)C2c1ccc(Cl)cc1] | 7-((R)-sec-Butoxy)-2-(2-chloro-4-methyl-phenyl)-1-(4-chloro-phenyl)-6-methoxy-1,4-dihydro-2H-isoquinolin-3-one.<br>HPLC: $^{A}t_{Ret}$ = 3.00; API-MS: m/z 485.9 [M + H]$^{+}$. |
| 2av | 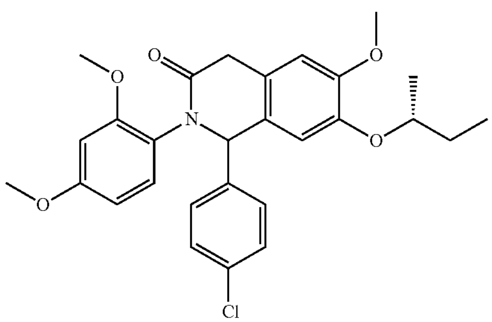 [SMILES: CC[C@@H](C)Oc1cc2c(cc1OC)CC(=O)N(c1ccc(OC)cc1OC)C2c1ccc(Cl)cc1] | 7-((R)-sec-Butoxy)-1-(4-chloro-phenyl)-2-(2,4-dimethoxy-phenyl)-6-methoxy-1,4-dihydro-2H-isoquinolin-3-one.<br>HPLC: $^{A}t_{Ret}$ = 2.74; API-MS: m/z 497.7 [M + H]$^{+}$. |
| 2aw | 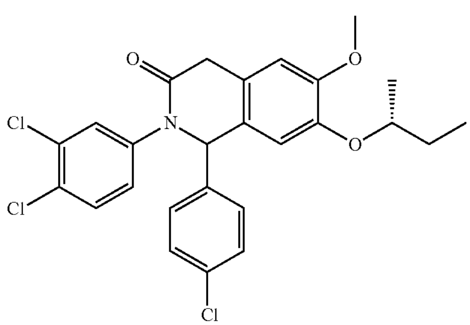 [SMILES: CC[C@@H](C)Oc1cc2c(cc1OC)CC(=O)N(c1ccc(Cl)c(Cl)c1)C2c1ccc(Cl)cc1] | 7-((R)-sec-Butoxy)-1-(4-chloro-phenyl)-2-(3,4-dichloro-phenyl)-6-methoxy-1,4-dihydro-2H-isoquinolin-3-one.<br>HPLC: $^{A}t_{Ret}$ = 3.14; API-MS: m/z 506.0 [M + H]$^{+}$. |
| 2ax | 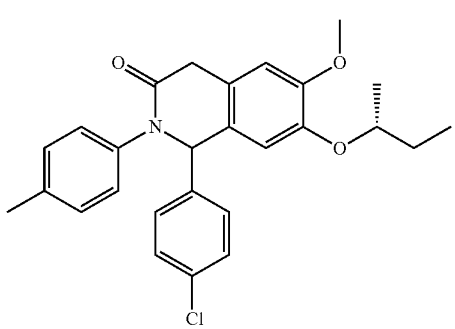 [SMILES: CC[C@@H](C)Oc1cc2c(cc1OC)CC(=O)N(c1ccc(C)cc1)C2c1ccc(Cl)cc1] | 7-((R)-sec-Butoxy)-1-(4-chloro-phenyl)-6-methoxy-2-p-tolyl-1,4-dihydro-2H-isoquinolin-3-one.<br>HPLC: $^{A}t_{Ret}$ = 2.88; API-MS: m/z 450.2 [M + H]$^{+}$. |

| # | Structure | Name / HPLC / MS |
|---|---|---|
| 2ay | 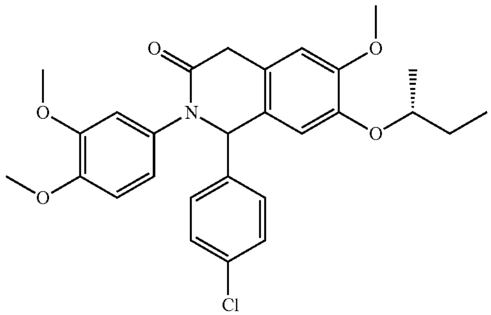 [SMILES: CC[C@@H](C)Oc1cc2c(cc1OC)CC(=O)N(c1ccc(OC)c(OC)c1)C2c1ccc(Cl)cc1] | 7-((R)-sec-Butoxy)-1-(4-chloro-phenyl)-2-(3,4-dimethoxy-phenyl)-6-methoxy-1,4-dihydro-2H-isoquinolin-3-one.<br>HPLC: $^A t_{Ret}$ = 2.59; API-MS: m/z 496.2 [M + H]$^+$. |
| 2az | 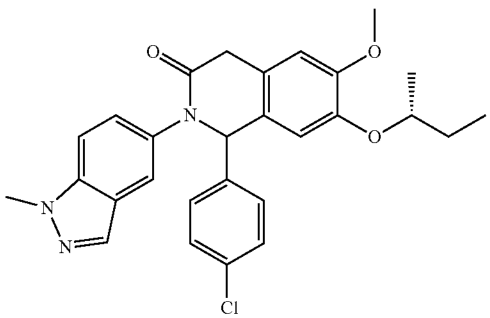 [SMILES: CC[C@@H](C)Oc1cc2c(cc1OC)CC(=O)N(c1ccc3c(cnn3C)c1)C2c1ccc(Cl)cc1] | 7-((R)-sec-Butoxy)-1-(4-chloro-phenyl)-6-methoxy-2-(1-methyl-1H-indazol-5-yl)-1,4-dihydro-2H-isoquinolin-3-one.<br>HPLC: $^A t_{Ret}$ = 2.53; API-MS: m/z 490.1 [M + H]$^+$. |
| 2ba | 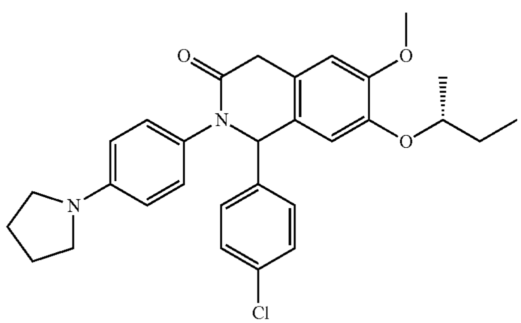 [SMILES: CC[C@@H](C)Oc1cc2c(cc1OC)CC(=O)N(c1ccc(N3CCCC3)cc1)C2c1ccc(Cl)cc1] | 7-((R)-sec-Butoxy)-1-(4-chloro-phenyl)-6-methoxy-2-(4-pyrrolidin-1-yl-phenyl)-1,4-dihydro-2H-isoquinolin-3-one.<br>HPLC: $^A t_{Ret}$ = 2.73; LC-MS: m/z 506.1 [M + H]$^+$. |
| 2bb | 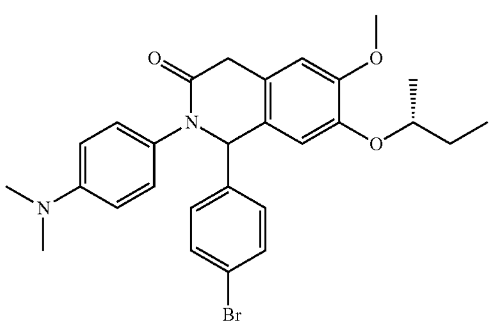 | 1-(4-Bromo-phenyl)-7-((R)-sec-butoxy)-2-(4-dimethylamino-phenyl)-6-methoxy-1,4-dihydro-2H-isoquinolin-3-one.<br>HPLC: $^A t_{Ret}$ = 2.10; LC-MS: m/z 523.4 [M + H]$^+$. |
| 2bc | 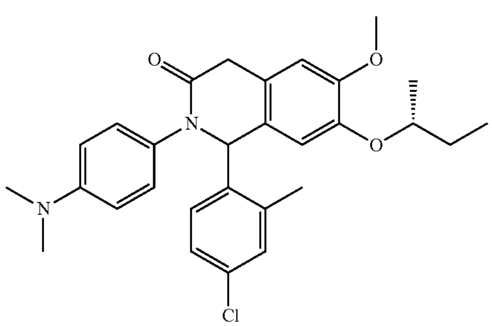 [SMILES: CC[C@@H](C)Oc1cc2c(cc1OC)CC(=O)N(c1ccc(N(C)C)cc1)C2c1ccc(Cl)cc1C] | 7-((R)-sec-Butoxy)-1-(4-chloro-2-methyl-phenyl)-2-(4-dimethylamino-phenyl)-6-methoxy-1,4-dihydro-2H-isoquinolin-3-one.<br>HPLC: $^A t_{Ret}$ = 2.13; LC-MS: m/z 493.5 [M + H]$^+$. |

| # | Structure | Name / HPLC / MS |
|---|---|---|
| 2bd | 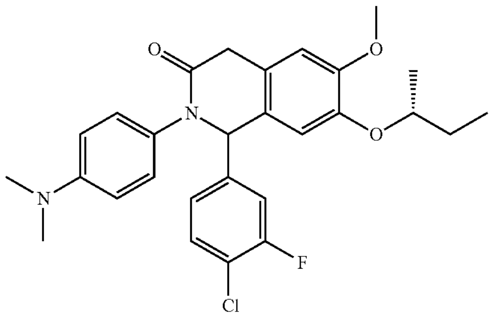 [SMILES: CC[C@@H](C)Oc1cc2c(cc1OC)CC(=O)N(c1ccc(N(C)C)cc1)C2c1ccc(Cl)c(F)c1] | 7-((R)-sec-Butoxy)-1-(4-chloro-3-fluoro-phenyl)-2-(4-dimethylamino-phenyl)-6-methoxy-1,4-dihydro-2H-isoquinolin-3-one.<br>HPLC: $^A t_{Ret}$ = 2.11; LC-MS: m/z 497.6 [M + H]$^+$. |
| 2be | 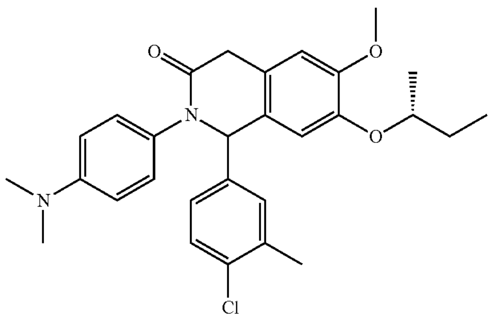 [SMILES: CC[C@@H](C)Oc1cc2c(cc1OC)CC(=O)N(c1ccc(N(C)C)cc1)C2c1ccc(Cl)c(C)c1] | 7-((R)-sec-Butoxy)-1-(4-chloro-3-methyl-phenyl)-2-(4-dimethylamino-phenyl)-6-methoxy-1,4-dihydro-2H-isoquinolin-3-one.<br>HPLC: $^A t_{Ret}$ = 2.17; LC-MS: m/z 493.4 [M + H]$^+$. |
| 2bf | 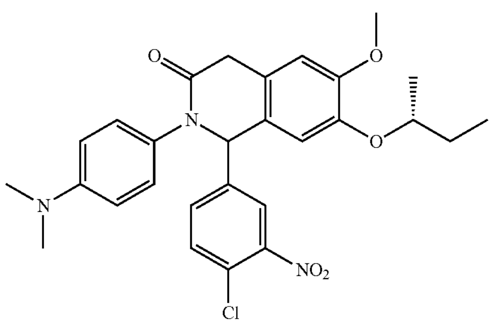 [SMILES: CC[C@@H](C)Oc1cc2c(cc1OC)CC(=O)N(c1ccc(N(C)C)cc1)C2c1ccc(Cl)c([N+](=O)[O-])c1] | 7-((R)-sec-Butoxy)-1-(4-chloro-3-nitro-phenyl)-2-(4-dimethylamino-phenyl)-6-methoxy-1,4-dihydro-2H-isoquinolin-3-one.<br>HPLC: $^A t_{Ret}$ = 2.08; LC-MS: m/z 524.5 [M + H]$^+$. |
| 2bg[1] | | 1-(3-Amino-4-chloro-phenyl)-7-((R)-sec-butoxy)-2-(4-dimethylamino-phenyl)-6-methoxy-1,4-dihydro-2H-isoquinolin-3-one.<br>HPLC: $^A t_{Ret}$ = 1.83; LC-MS: m/z 494.4 [M + H]$^+$. |
| 2bh | 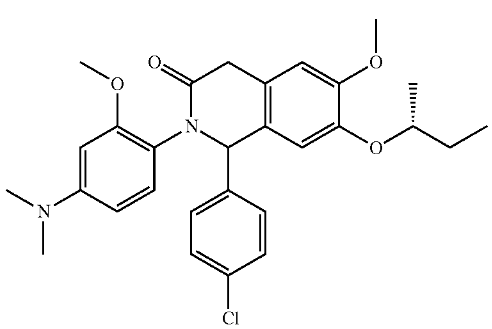 [SMILES: CC[C@@H](C)Oc1cc2c(cc1OC)CC(=O)N(c1ccc(N(C)C)cc1OC)C2c1ccc(Cl)cc1] | 7-((R)-sec-Butoxy)-1-(4-chloro-phenyl)-2-(4-dimethylamino-2-methoxy-phenyl)-6-methoxy-1,4-dihydro-2H-isoquinolin-3-one.<br>HPLC: $^A t_{Ret}$ = 2.10; LC-MS: m/z 510.4 [M + H]$^+$. |

| # | Structure | Name / HPLC / MS |
|---|---|---|
| 2bi | 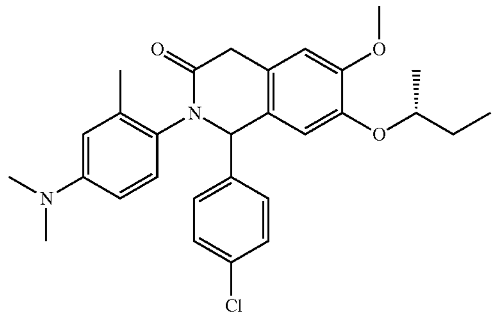 [SMILES: CC[C@@H](C)Oc1cc2c(cc1OC)CC(=O)N(c1ccc(N(C)C)cc1C)C2c1ccc(Cl)cc1] | 7-((R)-sec-Butoxy)-1-(4-chloro-phenyl)-2-(4-dimethylamino-2-methyl-phenyl)-6-methoxy-1,4-dihydro-2H-isoquinolin-3-one.<br>HPLC: $^A t_{Ret}$ = 2.03; LC-MS: m/z 493.2 [M + H]$^+$. |
| 2bj | 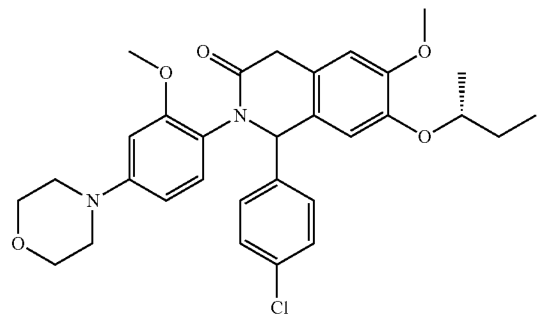 [SMILES: CC[C@@H](C)Oc1cc2c(cc1OC)CC(=O)N(c1ccc(N3CCOCC3)cc1OC)C2c1ccc(Cl)cc1] | 7-((R)-sec-Butoxy)-1-(4-chloro-phenyl)-6-methoxy-2-(2-methoxy-4-morpholin-4-yl-phenyl)-1,4-dihydro-2H-isoquinolin-3-one.<br>HPLC: $^A t_{Ret}$ = 2.50; LC-MS: m/z 551.2 [M + H]$^+$. |

[1]The title compound (TFA salt, 21.1 mg, 0.29 mmol, 37%) was obtained as a colorless solid by reduction of the nitro group of Example 2bf (41.5 mg, 0.079 mmol) analogously to Intermediate 3.3. Purification of the crude material was performed by reverse phase prep-HPLC (Waters system).

Example 3

{2-[7-((R)-sec-Butoxy)-2-(4-dimethylamino-phenyl)-6-methoxy-3-oxo-1,2,3,4-tetrahydro-isoquinolin-1-yl]-5-chloro-phenyl}-urea

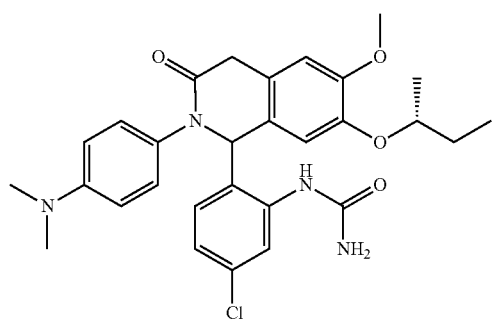 [SMILES: CC[C@@H](C)Oc1cc2c(cc1OC)CC(=O)N(c1ccc(N(C)C)cc1)C2c1ccc(Cl)cc1NC(N)=O]

A mixture of Intermediate 3.3 (20 mg, 0.040 mmol) and NaOCN (7.9 mg, 0.121 mmol) in AcOH (1 ml) and water (2 ml) was stirred at RT for 2 h. The reaction mixture was directly subjected to purification by reverse phase prep-HPLC (Waters system) to yield the title compound (TFA salt, 13.0 mg, 0.020 mmol, 49%) as a colorless solid. HPLC: $^A t_{Ret}$=1.62 min; LC-MS: m/z 537.4 [M+H]$^+$; $^1$H NMR (400 MHz, DMSO-d$_6$): 0.78-0.92 (2t, J=7.5, 3H, mixture of diastereoisomers), 1.04-1.21 (2 d, J=6.1, 3H, mixture of diastereoisomers), 1.41-1.67 (m, 2H, mixture of diastereoisomers), 2.88 (s, 6H), 3.64 (d, J=20.8, 1H), 3.73 (s, 3H), 4.02 (dd, J=20.8, 4.6, 1H), 4.08-4.18 (m, 1H), 6.15 (br. s., 2H), 6.25 (s, 1H), 6.65-6.73 (m, 2H), 6.79-6.85 (m, 2H), 6.86-6.93 (m, 2H), 7.01-7.08 (m, 1H), 7.31 (dd, J=8.6, 2.2, 1H), 7.74 (dd, J=17.6, 2.2, 1H), 7.99-8.05 (m, 1H).

Intermediate 3.1: N-[1-(4-Chloro-2-nitro-phenyl)-meth-(E)-ylidene]-N',N'-dimethylbenzene-1,4-diamine

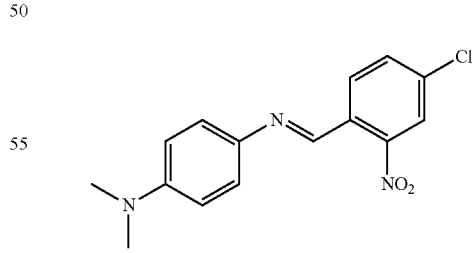

The title compound (660 mg, 2.17 mmol, 59%) was obtained as a black solid from N,N-dimethyl-benzene-1,4-diamine (500 mg, 3.67 mmol) and 4-chloro-2-nitro-benzaldehyde (681 mg, 3.67 mmol) analogously to Intermediate 1.4. $^1$H NMR (400 MHz, DMSO-d$_6$): 2.96 (s, 6H), 6.74-6.80 (m, 2H), 7.26-7.33 (m, 2H), 7.89 (dd, J=8.3, 2.0, 1H), 8.16-8.22 (m, 2H), 8.82 (s, 1H).

Intermediate 3.2: 7-((R)-sec-Butoxy)-1-(4-chloro-2-nitro-phenyl)-2-(4-dimethylamino-phenyl)-6-methoxy-1,4-dihydro-2H-isoquinolin-3-one

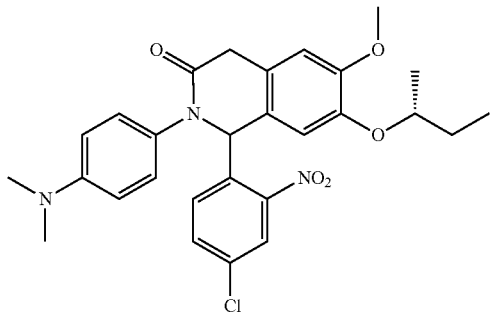

The title compound (322 mg, 0.61 mmol, 29%) was obtained as a brownish solid from Intermediate 3.1 (650 mg, 2.14 mmol) and Intermediate 1.3 (550 mg, 2.14 mmol) analogously to Example 1. Purification of the crude material was performed by Combi-Flash Companion™ (Isco Inc.) column chromatography (SiO$_2$; gradient elution, heptane/TBME 95:5→100% TBME). TLC: R$_F$=0.19 (heptane/DCM/TBME 1:1:2); HPLC: $^A$t$_{Ret}$=2.10 min; LC-MS: m/z 524.3 [M+H]$^+$; $^1$H NMR (400 MHz, DMSO-d$_6$): 0.79-0.91 (2t, J=7.5, 3H, mixture of diastereoisomers), 1.06-1.20 (2 d, J=6.1, 3H, mixture of diastereoisomers), 1.40-1.67 (m, 2H), 2.87 (s, 6H), 3.68 (d, J=20.8, 1H), 3.77 (s, 3H), 4.02-4.17 (m, 2H), 6.42 (br. s., 1H), 6.58-6.66 (m, 3H), 6.76-6.84 (m, 2H), 6.89 (s, 1H), 7.61-7.66 (m, 1H), 7.71 (dd, J=8.6, 2.2, 1H), 7.91 (d, J=2.0, 1H).

Intermediate 3.3: 1-(2-Amino-4-chloro-phenyl)-7-(R)-sec-butoxy)-2-(4-dimethylamino-phenyl)-6-methoxy-1,4-dihydro-2H-isoquinolin-3-one

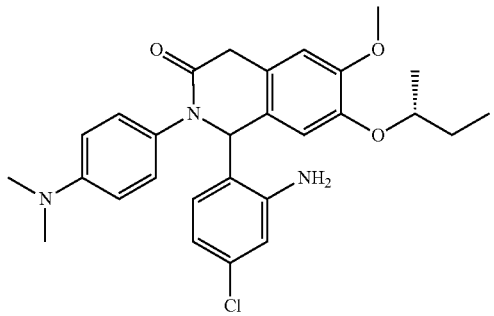 [SMILES: CC[C@@H](C)Oc1cc2c(cc1OC)CC(=O)N(c1ccc(N(C)C)cc1)C2c1ccc(Cl)cc1[N+](=O)[O-]]

In a sealed reaction flask, a mixture of Intermediate 3.2 (322 mg, 0.61 mmol) and Fe (343 mg, 6.1 mmol) in AcOH (1.8 ml), water (2.4 ml) and AcOEt (0.6 ml) was heated at 110° C. and stirred for 1 h. The suspension was cooled to RT, filtered through a Celite pad and the solid washed with AcOEt. The filtrate was concentrated under vacuum, the resulting residue was dissolved in AcOEt and washed with Na$_2$CO$_3$ 2M in water (2×). The organic phase was dried over Na$_2$SO$_4$, filtered and evaporated to dryness. The resulting crude material was purified by Combi-Flash Companion™ (Isco Inc.) column chromatography (SiO$_2$; gradient elution, [heptane/DCM 1:1]/TBME containing 5% of 7M NH$_3$ in MeOH 95:5→4:6) to yield the title compound (253 mg, 0.51 mmol, 83%) as a brownish solid. TLC: R$_F$=0.31 (heptane/DCM/TBME containing 5% of 7M NH$_3$ in MeOH 1:1:2); HPLC: $^A$t$_{Ret}$=1.87 min; LC-MS: m/z 494.5 [M+H]$^+$; $^1$H NMR (400 MHz, DMSO-d$_6$): 0.81-0.94 (m, 3H), 1.11-1.22 (2 d, J=6.1, 3H, mixture of diastereoisomers), 1.41-1.69 (m, 2H), 2.86 (s, 6H), 3.60 (d, J=20.5, 1H), 3.73 (s, 3H), 4.00 (d, J=20.3, 1H), 4.05-4.15 (m, 1H), 5.42-5.48 (m, 2H), 6.17 (br. s., 1H), 6.46-6.51 (m, 1H), 6.54-6.57 (m, 1H), 6.58-6.64 (m, 2H), 6.79 (s, 1H), 6.90-6.99 (m, 3H), 7.05 (dd, J=8.2, 1.8, 1H).

Example 4

1-{2-[7-((R)-sec-Butoxy)-2-(4-dimethylamino-phenyl)-6-methoxy-3-oxo-1,2,3,4-tetrahydro-isoquinolin-1-yl]-5-chloro-phenyl}-3-methyl-urea

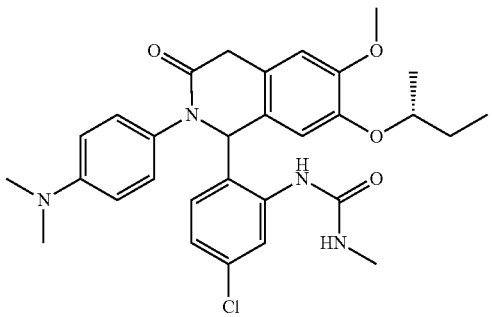 [SMILES: CC[C@@H](C)Oc1cc2c(cc1OC)CC(=O)N(c1ccc(N(C)C)cc1)C2c1ccc(Cl)cc1NC(=O)NC]

To a solution of Intermediate 3.3 (33 mg, 0.067 mmol) and pyridine (0.086 ml, 1.07 mmol) in MeCN (0.5 ml) was added methyl isocyanate (0.045 ml, 0.77 mmol) in portions over a period of 4 h at RT. The reaction mixture was further stirred at RT for 14 h then directly subjected to purification by reverse phase prep-HPLC (Waters system) to yield the title compound (TFA salt, 28.0 mg, 0.042 mmol, 63%) as a colorless solid. HPLC: $^A$t$_{Ret}$=1.70 min; LC-MS: m/z 551.5 [M+H]$^+$; $^1$H NMR (400 MHz, DMSO-d$_6$): 0.79-0.91 (2t, J=7.5, 3H, mixture of diastereoisomers), 1.04-1.19 (2 d, J=6.1, 3H, mixture of diastereoisomers), 1.41-1.66 (m, 2H), 2.60-2.66 (m, 3H), 2.88 (s, 6H), 3.59-3.67 (m, J=20.8, 1H), 3.73 (s, 3H), 3.96-4.13 (m, 2H), 6.24 (s, 1H), 6.28-6.36 (m, 1H), 6.64-6.72 (m, 2H), 6.79 (d, J=2.7, 1H), 6.83 (s, 1H), 6.86-6.93 (m, 2H), 7.01-7.07 (m, 1H), 7.30 (dd, J=8.6, 3.9, 1H), 7.69 (dd, J=19.3, 2.2, 1H), 7.96-8.03 (m, 1H).

Example 5

N-{2-[7-((R)-sec-Butoxy)-2-(4-dimethylamino-phenyl)-6-methoxy-3-oxo-1,2,3,4-tetrahydro-isoquinolin-1-yl]-5-chloro-phenyl}-acetamide

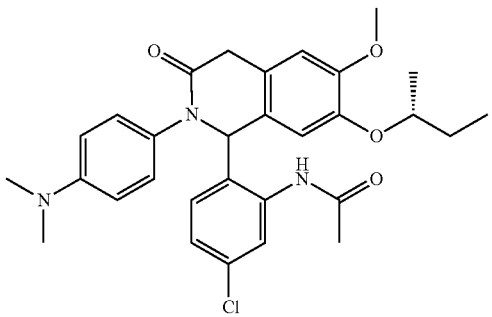 [SMILES: CC[C@@H](C)Oc1cc2c(cc1OC)CC(=O)N(c1ccc(N(C)C)cc1)C2c1ccc(Cl)cc1NC(C)=O]

To a mixture of Intermediate 3.3 (20 mg, 0.040 mmol) and pyridine (0.010 ml, 0.12 mmol) in MeCN (0.5 ml) was added acetyl chloride (0.006 ml, 0.081 mmol) at RT. The reaction mixture was stirred for 14 h then directly subjected to purification by reverse phase prep-HPLC (Waters system) to yield the title compound (TFA salt, 13.1 mg, 0.020 mmol, 50%) as a colorless solid. HPLC: $^A$t$_{Ret}$=1.71 min; LC-MS: m/z 536.3

[M+H]+; 1H NMR (400 MHz, DMSO-d6): 0.79-0.92 (2t, J=7.5, 3H, mixture of diastereoisomers), 1.04-1.19 (2 d, J=6.1, 3H, mixture of diastereoisomers), 1.42-1.65 (m, 2H), 1.90-1.99 (m, 3H), 2.90 (s, 6H), 3.59-3.67 (m, 1H), 3.76 (d, J=1.5, 3H), 3.96-4.05 (m, 1H), 4.05-4.17 (m, 1H), 6.34 (s, 1H), 6.67-6.76 (m, 2H), 6.78-6.89 (m, 4H), 7.15-7.26 (m, 2H), 7.40-7.46 (m, 1H), 9.32 (d, J=17.1, 1H).

Example 6

7-((R)-sec-Butoxy)-1-(4-chloro-2-dimethylamino-phenyl)-2-(4-dimethylamino-phenyl)-6-methoxy-1,4-dihydro-2H-isoquinolin-3-one

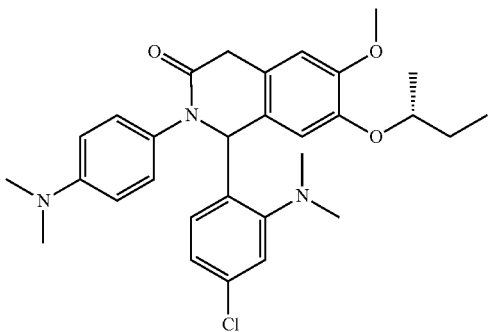 [SMILES: CC[C@@H](C)Oc1cc2c(cc1OC)CC(=O)N(c1ccc(N(C)C)cc1)C2c1ccc(Cl)cc1N(C)C]

To a solution of Intermediate 3.3 (29 mg, 0.059 mmol) in DCM (1 ml) were successively added AcOH (0.017 ml, 0.29 mmol), formaldehyde (37% in water, 0.013 ml, 0.18 mmol) and NaBH(OAc)3 (62.2 mg, 0.29 mmol) at RT. The reaction mixture was stirred for 4 h then Na2CO3 2 M in water was added, the two phases were separated and the aqueous layer was further extracted with DCM (2x). The combined organic fractions were evaporated to dryness and the resulting crude material was purified by reverse phase prep-HPLC (Waters system) to yield the title compound (TFA salt, 18 mg, 0.024 mmol, 41%) as a colorless solid. HPLC: $^A t_{Ret}$=2.17 min; LC-MS: m/z 522.6 [M+H]+; 1H NMR (400 MHz, DMSO-d6): 0.79-0.91 (2t, J=7.5, 3H, mixture of diastereoisomers), 1.04-1.19 (2 d, J=6.1, 3H, mixture of diastereoisomers), 1.42-1.66 (m, 2H), 2.29-2.37 (m, 6H), 2.85 (s, 6H), 3.62 (d, J=20.8, 1H), 3.73 (s, 3H), 4.02-4.16 (m, 2H), 6.44 (br. s., 1H), 6.62-6.71 (m, 2H), 6.78-6.91 (m, 4H), 7.11-7.16 (m, 1H), 7.21-7.25 (m, 1H), 7.39 (d, J=8.3, 1H).

Example 7

2-[7-((R)-sec-Butoxy)-2-(4-dimethylamino-phenyl)-6-methoxy-3-oxo-1,2,3,4-tetrahydro-isoquinolin-1-yl]-5-chloro-benzamide

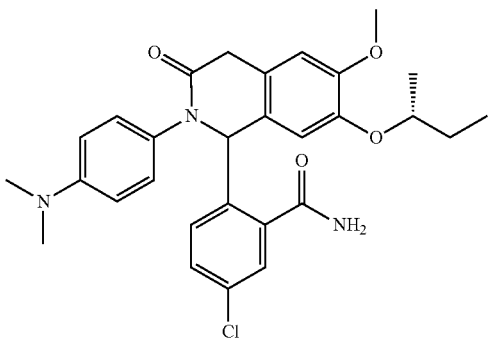 [SMILES: CC[C@@H](C)Oc1cc2c(cc1OC)CC(=O)N(c1ccc(N(C)C)cc1)C2c1ccc(Cl)cc1C(N)=O]

To a solution of Intermediate 7.4 (30 mg, 0.057 mmol) in DMF (0.3 ml) were successively added NH4Cl (15.3 mg, 0.29 mmol), Et3N (0.024 ml, 0.17 mmol) and HATU (28.4 mg, 0.075 mmol). The reaction mixture was stirred at RT for 1 h then directly subjected to purification by reverse phase prep-HPLC (Waters system) to yield the title compound (TFA salt, 19.3 mg, 0.030 mmol, 53%) as a colorless solid. HPLC: $^A t_{Ret}$=1.65 min; LC-MS: m/z 522.4 [M+H]+; 1H NMR (400 MHz, DMSO-d6): 0.80-0.92 (2t, J=7.3, 3H, mixture of diastereoisomers), 1.08-1.21 (2 d, J=6.1, 3H, mixture of diastereoisomers), 1.42-1.66 (m, 2H), 2.87 (s, 6H), 3.64 (d, J=20.5, 1H), 3.73 (s, 3H), δ 4.05-4.16 (m, 2H), 6.61-6.68 (m, 2H), 6.72-6.75 (m, 1H), 6.78-6.85 (m, 3H), 7.17 (s, 1H), 7.39-7.42 (m, 1H), 7.44-7.49 (m, 1H), 7.50-7.54 (m, 1H), 7.55-7.61 (m, 1H), 7.77-7.84 (m, 1H).

Intermediate 7.1: 5-Chloro-2-formyl-benzoic acid methyl ester

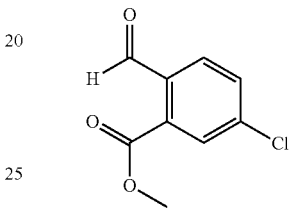

To a heterogeneous mixture of 5-chloro-2-formyl-benzoic acid (1.0 g, 5.42 mmol) and K2CO3 (1.12 g, 8.13 mmol) in DMF (7 ml) was added MeI (0.41 ml, 6.5 mmol) at RT. The reaction mixture was stirred for 4 h then diluted into Et2O and washed with water (2x). The organic layer was dried over Na2SO4, filtered and evaporated to dryness to yield the crude title compound (700 mg, 3.52 mmol, 65%) as a light yellow solid, which was used without further purification. HPLC: $^A t_{Ret}$=1.84 min; LC-MS: m/z 199.3 [M+H]+; 1H NMR (400 MHz, DMSO-d6): 3.91 (s, 3H), 7.84-7.94 (m, 3H), 10.33 (s, 1H).

Intermediate 7.2: 5-Chloro-2-{[(E)-4-dimethylamino-phenylimino]-methyl}-benzoic acid methyl ester

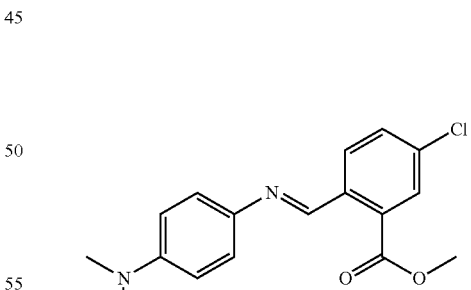

The title compound (653 mg, 2.06 mmol, 50%) was obtained as a black solid from N,N-dimethyl-benzene-1,4-diamine (555 mg, 4.08 mmol) and Intermediate 7.1 (810 mg, 4.08 mmol) analogously to Intermediate 1.4. 1H NMR (400 MHz, DMSO-d6): 2.94 (s, 6H), 3.89 (s, 3H), 6.74-6.79 (m, 2H), 7.23-7.29 (m, 2H), 7.74 (dd, J=8.4, 2.1, 1H), 7.84 (d, J=2.2, 1H), 8.15 (d, J=8.6, 1H), 9.03 (s, 1H).

Intermediate 7.3: 2-[7-((R)-sec-Butoxy)-2-(4-dimethylamino-phenyl)-6-methoxy-3-oxo-1,2,3,4-tetrahydro-isoquinolin-1-yl]-5-chloro-benzoic acid methyl ester

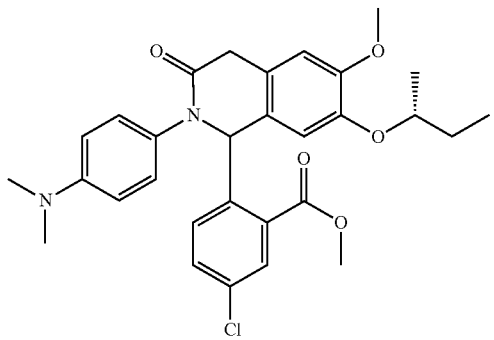 [SMILES: CC[C@@H](C)Oc1cc2c(cc1OC)CC(=O)N(c1ccc(N(C)C)cc1)C2c1ccc(Cl)cc1C(=O)OC]

The title compound (537 mg, 1.0 mmol, 48%) was obtained as a brownish solid from Intermediate 7.2 (653 mg, 2.06 mmol) and Intermediate 1.3 (530 mg, 2.06 mmol) analogously to Example 1. Purification of the crude material was performed by Combi-Flash Companion™ (Isco Inc.) column chromatography (SiO$_2$; gradient elution, [heptane/DCM 1:1]/TBME 95:5→3:7). TLC: R$_F$=0.20 (heptane/DCM/TBME 1:1:2); HPLC: $^A$t$_{Ret}$=2.07 min; LC-MS: m/z 537.4 [M+H]$^+$; $^1$H NMR (400 MHz, DMSO-d$_6$): 0.78-0.91 (2t, J=7.3, 3H, mixture of diastereoisomers), 1.04-1.18 (2 d, J=6.1, 3H, mixture of diastereoisomers), 1.40-1.68 (m, 2H), 2.85 (s, 6H), 3.67 (d, J=21.0, 1H), 3.73 (s, 3H), 3.76 (s, 3H), 3.99-4.09 (m, 1H), 4.14 (d, J=21.0, 1H), 6.54-6.61 (m, 2H), 6.65-6.69 (m, 1H), 6.71-6.77 (m, 2H), 6.80-6.84 (m, 1H), 6.86 (s, 1H), 7.51 (dd, J=8.6, 2.4, 1H), 7.55-7.62 (m, 2H).

Intermediate 7.4: 2-[7-((R)-sec-Butoxy)-2-(4-dimethylamino-phenyl)-6-methoxy-3-oxo-1,2,3,4-tetrahydro-isoquinolin-1-yl]-5-chloro-benzoic acid

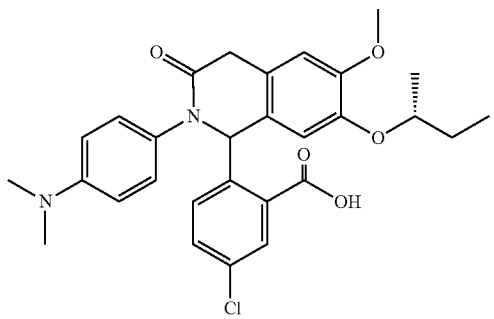 [SMILES: CC[C@@H](C)Oc1cc2c(cc1OC)CC(=O)N(c1ccc(N(C)C)cc1)C2c1ccc(Cl)cc1C(=O)O]

A mixture of Intermediate 7.3 (100 mg, 0.19 mmol) and LiOH monohydrate (39.1 mg, 0.93 mmol) in MeOH (1 ml) and water (0.5 ml) was heated at 50° C. and stirred for 3 h. The reaction mixture was cooled to RT, concentrated under vacuum, diluted into water and neutralized by the addition of HCl 2 M in water (0.47 ml). The resulting slurry was extracted with DCM (3×) and the combined organic fractions were dried over Na$_2$SO$_4$, filtered and evaporated to dryness to yield the crude title compound (87.5 mg, 0.17 mmol, 90%) as a brownish solid, which was used in the next step without further purification. HPLC: $^A$t$_{Ret}$=1.78 min; LC-MS: m/z 523.5 [M+H]$^+$; $^1$H NMR (400 MHz, DMSO-d$_6$): 0.78-0.91 (2t, J=7.3, 3H, mixture of diastereoisomers), 1.05-1.19 (2 d, J=6.1, 3H, mixture of diastereoisomers), 1.38-1.65 (m, 2H), 2.86 (s, 6H), 3.63-3.70 (m, J=20.8, 1H), 3.75 (s, 3H), 3.99-4.09 (m, 1H), 4.15 (d, J=21.0, 1H), 6.60-6.67 (m, 2H), 6.76- 6.82 (m, 2H), 6.84 (s, 1H), 6.88 (d, J=2.9, 1H), 7.03-7.07 (m, 1H), 7.55-7.58 (m, 2H), 7.65-7.68 (m, 1H), 13.60 (br. s., 1H).

Example 8

7-((R)-sec-Butoxy)-1-(4-chloro-2-hydroxymethyl-phenyl)-2-(4-dimethylamino-phenyl)-6-methoxy-1,4-dihydro-2H-isoquinolin-3-one

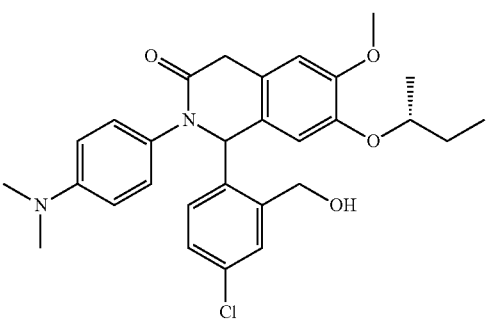 [SMILES: CC[C@@H](C)Oc1cc2c(cc1OC)CC(=O)N(c1ccc(N(C)C)cc1)C2c1ccc(Cl)cc1CO]

To a solution of Intermediate 7.3 (150 mg, 0.28 mmol) in THF (3 ml) were successively added LiBH$_4$ (18.3 mg, 0.84 mmol) and MeOH (0.034 ml, 0.84 mmol) at RT. The reaction mixture was stirred at RT for 3 h then quenched cautiously by the addition of HCl 2 M in water, diluted into DCM and washed with Na$_2$CO$_3$ 2 M in water. The aqueous layer was further extracted with DCM (2×) and the combined organic fractions were dried over Na$_2$SO$_4$, filtered and evaporated to dryness. The resulting crude material was purified by Combi-Flash Companion™ (Isco Inc.) column chromatography (SiO$_2$; gradient elution, [heptane/DCM 1:1]/TBME containing 5% of 7 M NH$_3$ in MeOH 95:5→3:7) to yield the title compound (95.2 mg, 0.19 mmol, 67%) as an off-white solid. TLC: R$_F$=0.18 (heptane/DCM/TBME containing 1% of 7 M NH$_3$ in MeOH 1:1:2); HPLC: $^A$t$_{Ret}$=1.73 min; LC-MS: m/z 509.4 [M+H]$^+$; $^1$H NMR (400 MHz, DMSO-d$_6$): 0.76-0.88 (2t, J=7.5, 3H, mixture of diastereoisomers), 1.02-1.14 (2 d, J=6.1, 3H, mixture of diastereoisomers), 1.37-1.65 (m, 2H), 2.85 (s, 6H), 3.67 (d, J=21.3, 1H), 3.76 (s, 3H), 3.99-4.27 (m, 4H), 5.46 (br. s., 1H), 6.22 (br. s., 1H), 6.54-6.61 (m, 2H), 6.69-6.75 (m, 2H), 6.78 (s, 1H), 6.83 (s, 1H), 7.26 (s, 3H).

Example 9

1-(2-Aminomethyl-4-chloro-phenyl)-7-((R)-sec-butoxy)-2-(4-dimethylamino-phenyl)-6-methoxy-1,4-dihydro-2H-isoquinolin-3-one

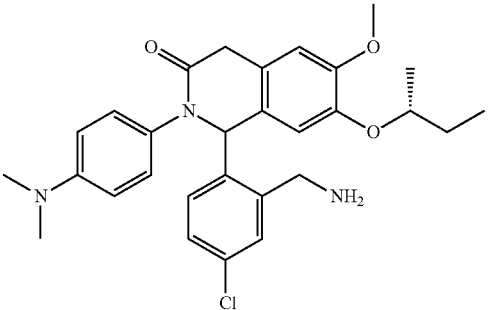 [SMILES: CC[C@@H](C)Oc1cc2c(cc1OC)CC(=O)N(c1ccc(N(C)C)cc1)C2c1ccc(Cl)cc1CN]

In a sealed reaction flask, a mixture of Example 8 (20 mg, 0.039 mmol) and SOCl$_2$ (0.014 ml, 0.20 mmol) in DCM (0.4 ml) was heated at 40° C. and stirred for 1 h. The reaction mixture was cooled to RT and evaporated to dryness. To the residue was added a 7 M solution of NH$_3$ in MeOH (1.0 ml, 7.03 mmol) and the resulting solution was heated at 70° C. and stirred for 14 h. The reaction mixture was cooled to RT and directly subjected to purification by reverse phase prep- HPLC (Waters system) to yield the title compound (TFA salt, 6.8 mg, 0.009 mmol, 23%) as a colorless solid. HPLC: $^At_{Ref}$=1.38 min; LC-MS: m/z 508.3 [M+H]$^+$; $^1$H NMR (400 MHz, DMSO-d$_6$): 0.78-0.90 (2t, J=7.5, 3H, mixture of diastereoisomers), 1.03-1.16 (2 d, J=6.1, 3H, mixture of diastereoisomers), 1.41-1.62 (m, 2H), 2.88 (s, 6H), 3.70 (d, J=21.0, 1H), 3.79 (s, 3H), 3.88-3.98 (m, 2H), 4.05 (d, J=20.8, 1H), 4.09-4.21 (m, 1H), 6.20 (br. s., 1H), 6.55-6.59 (m, 1H), 6.60-6.65 (m, 2H), 6.70-6.76 (m, 2H), 6.91 (s, 1H), 7.19 (d, J=8.3, 1H), 7.35-7.41 (m, 2H), 8.13 (br. s., 2H).

Example 10

N-{2-[7-((R)-sec-Butoxy)-2-(4-dimethylamino-phenyl)-6-methoxy-3-oxo-1,2,3,4-tetrahydro-isoquinolin-1-yl]-5-chloro-benzyl}-acetamide

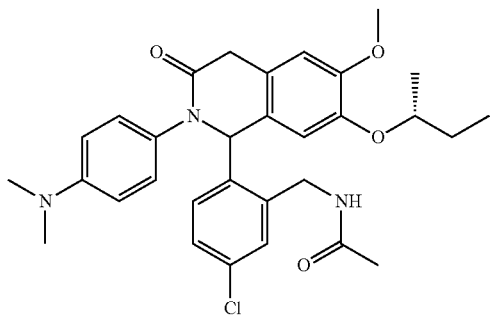 [SMILES: CC[C@@H](C)Oc1cc2c(cc1OC)CC(=O)N(c1ccc(N(C)C)cc1)C2c1ccc(Cl)cc1CNC(C)=O]

To a mixture of crude Example 9 (24 mg, 0.047 mmol) and Et$_3$N (0.020 ml, 0.14 mmol) in DCM (0.4 ml) was added acetyl chloride (0.007 ml, 0.094 mmol) at RT. The reaction mixture was stirred for 30 min and evaporated to dryness. The resulting crude material was purified by reverse phase prep-HPLC (Waters system) to yield the title compound (TFA salt, 12 mg, 0.018 mmol, 38%) as a colorless solid. HPLC: $^At_{Ret}$=1.70 min; LC-MS: m/z 550.5 [M+H]$^+$; $^1$H NMR (400 MHz, DMSO-d$_6$): 0.76-0.89 (2t, J=7.5, 3H, mixture of diastereoisomers), 1.00-1.16 (2 d, J=6.1, 3H, mixture of diastereoisomers), 1.38-1.62 (m, 2H), 1.82 (s, 3H), 2.87 (s, 6H), 3.68 (d, J=21.3, 1H), 3.77 (s, 3H), 4.04-4.18 (m, 2H), 4.19-4.29 (m, 1H), 6.29 (br. s., 1H), 6.57-6.65 (m, 3H), 6.70-6.76 (m, 2H), 6.85 (s, 1H), 7.13-7.20 (m, 2H), 7.22-7.27 (m, 1H), 8.28-8.35 (m, 1H).

Example 11

Compounds 11a to 11f were obtained by reaction of Intermediate 3.3 (or analogues prepared similarly) with various isocyanates, acyl chlorides or aldehydes analogously to Example 4, 5 and 6 respectively, or by reaction of Intermediate 7.4 (or analogues prepared similarly) with various amines analogously to Example 7, or by reaction of Example 8 (or analogues prepared similarly) with various amines analogously to Example 9.

| # | Structure | Name / HPLC / MS |
|---|-----------|------------------|
| 11a | 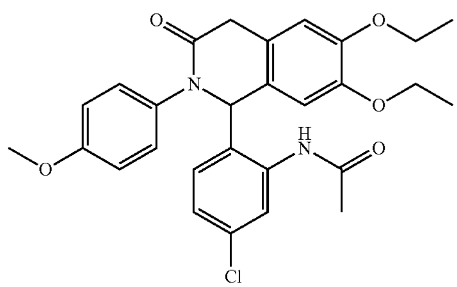 [SMILES: CCOc1cc2c(cc1OCC)C(c1ccc(Cl)cc1NC(C)=O)N(c1ccc(OC)cc1)C(=O)C2] | N-{5-Chloro-2-[6,7-diethoxy-2-(4-methoxy-phenyl)-3-oxo-1,2,3,4-tetrahydro-isoquinolin-1-yl]-phenyl}-acetamide.<br>HPLC: $^At_{Ret}$ = 2.08; API-MS: m/z 509.2 [M + H]$^+$. |
| 11b | 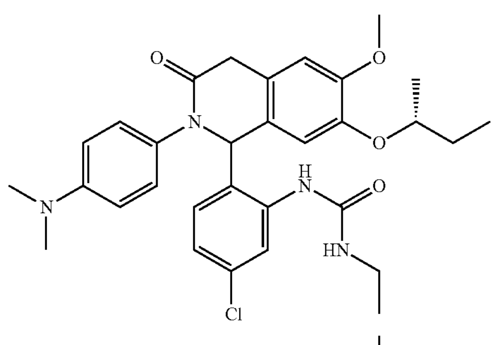 | 1-{2-[7-((R)-sec-Butoxy)-2-(4-dimethylamino-phenyl)-6-methoxy-3-oxo-1,2,3,4-tetrahydro-isoquinolin-1-yl]-5-chloro-phenyl}-3-ethyl-urea.<br>HPLC: $^At_{Ret}$ = 1.80; LC-MS: m/z 565.5 [M + H]$^+$. |
| 11c | 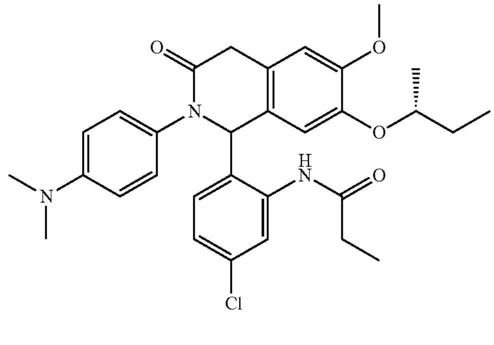 [SMILES: CCC(=O)Nc1cc(Cl)ccc1C1c2cc(O[C@H](C)CC)c(OC)cc2CC(=O)N1c1ccc(N(C)C)cc1] | N-{2-[7-((R)-sec-Butoxy)-2-(4-dimethylamino-phenyl)-6-methoxy-3-oxo-1,2,3,4-tetrahydro-isoquinolin-1-yl]-5-chloro-phenyl}-propionamide.<br>HPLC: $^At_{Ret}$ = 1.82; LC-MS: m/z 550.3 [M + H]$^+$. |

| # | Structure | Name / HPLC / MS |
|---|---|---|
| 11d | 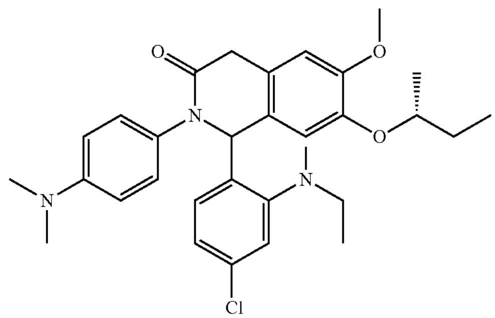 [SMILES: CC[C@@H](C)Oc1cc2c(cc1OC)CC(=O)N(c1ccc(N(C)C)cc1)C2c1ccc(Cl)cc1N(C)CC] | 7-((R)-sec-Butoxy)-1-[4-chloro-2-(ethyl-methyl-amino)-phenyl]-2-(4-dimethylamino-phenyl)-6-methoxy-1,4-dihydro-2H-isoquinolin-3-one.<br>HPLC: $^A t_{Ret}$ = 2.29; LC-MS: m/z 536.6 [M + H]$^+$. |
| 11e | 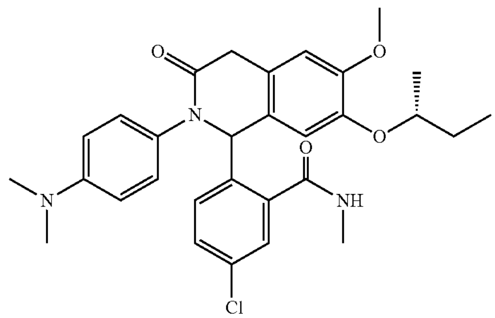 [SMILES: CC[C@@H](C)Oc1cc2c(cc1OC)CC(=O)N(c1ccc(N(C)C)cc1)C2c1ccc(Cl)cc1C(=O)NC] | 2-[7-((R)-sec-Butoxy)-2-(4-dimethylamino-phenyl)-6-methoxy-3-oxo-1,2,3,4-tetrahydro-isoquinolin-1-yl]-5-chloro-N-methyl-benzamide.<br>HPLC: $^A t_{Ret}$ = 1.75; LC-MS: m/z 536.4 [M + H]$^+$. |
| 11f | 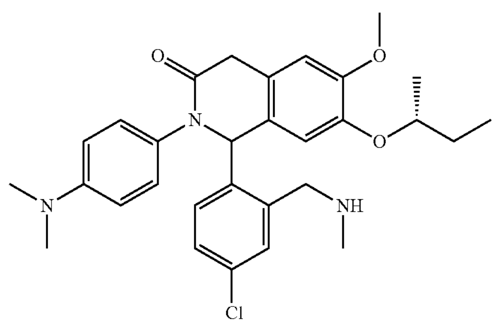 [SMILES: CC[C@@H](C)Oc1cc2c(cc1OC)CC(=O)N(c1ccc(N(C)C)cc1)C2c1ccc(Cl)cc1CNC] | 7-((R)-sec-Butoxy)-1-(4-chloro-2-methylaminomethyl-phenyl)-2-(4-dimethylamino-phenyl)-6-methoxy-1,4-dihydro-2H-isoquinolin-3-one.<br>HPLC: $^A t_{Ret}$ = 1.40; LC-MS: m/z 522.3 [M + H]$^+$ |

Example 12

1-(4-Chloro-phenyl)-6,7-diethoxy-2-[4-methyl-2-(3-morpholin-4-yl-propoxy)-phenyl]-1,4-dihydro-2H-isoquinolin-3-one. (Methode A)

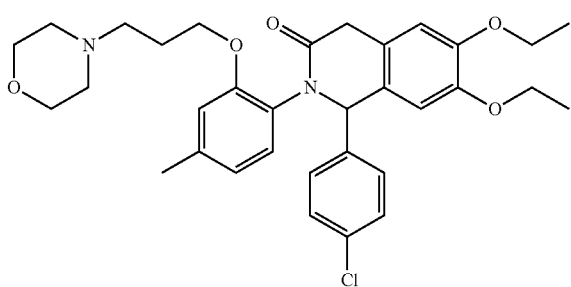 [SMILES: CCOc1cc2c(cc1OCC)C(c1ccc(Cl)cc1)N(c1ccc(C)cc1OCCCN1CCOCC1)C(=O)C2]

To a solution of Intermediate 12.3 (25 mg, 0.055 mmol) in DCM (1.5 ml) were successively added 3-morpholin-4-yl-propan-1-ol (0.009 ml, 0.066 mmol), supported PPh$_3$ (loading of 1.52 mmol/g, 109 mg, 0.166 mmol) and DTAD (19.1 mg, 0.083 mmol). The reaction mixture was shaken at RT for 3 h, then filtered and the resin was washed with DCM. The filtrate was evaporated to dryness and the resulting residue was purified by reverse phase prep-HPLC (Waters system) to yield the title compound (TFA salt, 9.9 mg, 0.014 mmol, 26%). HPLC: $^A t_{Ret}$=1.98 min; API-MS: m/z 580.6 [M+H]$^+$; $^1$H NMR (400 MHz, CD$_3$OD): 1.27-1.52 (m, 6H), 1.97-2.15 (m, 2H), 2.36 (s, 3H), 2.50-2.82 (m, 1H), 2.83-3.28 (m, 4H), 3.38-4.25 (m, 13H), 5.66 (s, 1H), 6.54-6.80 (m, 2H), 6.82-7.07 (m, 3H), 7.15-7.40 (m, 4H).

Intermediate 12.1: 2-(tert-Butyl-dimethyl-silanyloxy)-4-methyl-phenylamine

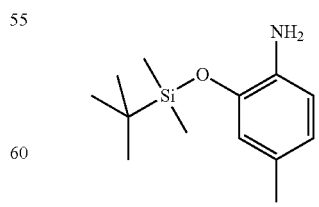

To a solution of 2-amino-5-methyl-phenol (500 mg, 4.0 mmol) and imidazole (298 mg, 4.4 mmol) in DMF (5 ml) was added TBDMSCl (660 mg, 4.4 mmol). The reaction mixture was stirred at RT for 3 h then diluted into water and extracted with AcOEt. The organic fraction was dried over Na$_2$SO$_4$, filtered and evaporated to dryness. The resulting residue was purified by Combi-Flash Companion™ (Isco Inc.) column chromatography (SiO$_2$; gradient elution, heptane/TBME containing 5% of 7M NH$_3$ in MeOH 95:5→8:2) to yield the title compound (724 mg, 3.1 mmol, 77%) as a reddish oil. TLC: R$_F$=0.94 (heptane/DCM/TBME 1:1:2 containing 5% of 7M NH$_3$ in MeOH); HPLC: $^At_{Ret}$=1.80 min; API-MS: m/z 238.1 [M+H]$^+$; $^1$H NMR (400 MHz, CDCl$_3$): 0.26 (s, 6H), 1.04 (s, 9H), 2.23 (s, 3H), 3.56 (br. s., 1H), 6.56-6.67 (m, 3H).

Intermediate 12.2: [2-(tert-Butyl-dimethyl-silanyloxy)-4-methyl-phenyl]-[1-(4-chloro-phenyl)-meth-(E)-ylidene]-amine

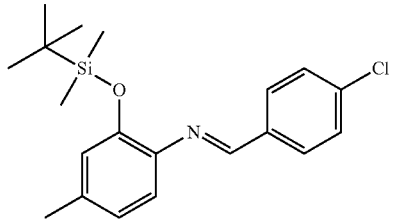 [SMILES: Cc1ccc(/N=C/c2ccc(Cl)cc2)c(O[Si](C)(C)C(C)(C)C)c1]

The title intermediate (1.06 g, 2.94 mmol, 97%) was obtained as a brownish solid from Intermediate 12.1 (724 mg, 3.05 mmol) and 4-chloro-benzaldehyde (429 mg, 3.05 mmol) analogously to Intermediate 1.4. $^1$H NMR (400 MHz, CDCl$_3$): 0.17 (s, 6H), 0.99 (s, 9H), 2.33 (s, 3H), 6.73-6.83 (m, 2H), 6.94 (d, J=7.8, 1H), 7.42-7.48 (m, 2H), 7.81-7.87 (m, 2H), 8.43 (s, 1H).

Intermediate 12.3: (3,4-Diethoxy-phenyl)-acetyl chloride

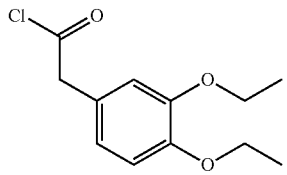 [SMILES: CCOc1ccc(CC(=O)Cl)cc1OCC]

To a solution of (3,4-diethoxy-phenyl)-acetic acid (2.0 g, 8.9 mmol) in DCM (6 ml) were successively added oxalylchloride (1.13 ml, 13.4 mmol) and a catalytic amount of DMF (0.069 ml, 0.89 mmol) at 0° C. (ice bath). The reaction mixture was stirred at 0° C. for 1 h then evaporated to dryness under vacuum to yield the crude (3,4-diethoxy-phenyl)-acetyl chloride (2.2 g, 8.9 mmol, quant.) as a brownish oil which was used in the next step without further purification.

Intermediate 12.4: 1-(4-Chloro-phenyl)-6,7-diethoxy-2-(2-hydroxy-4-methyl-phenyl)-1,4-dihydro-2H-isoquinolin-3-one

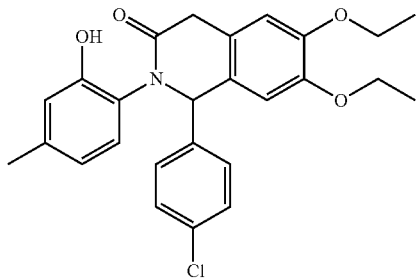 [SMILES: CCOc1cc2c(cc1OCC)C(c1ccc(Cl)cc1)N(c1ccc(C)cc1O)C(=O)C2]

The title intermediate (600 mg, 1.33 mmol, 45%) was obtained as a yellow foam from Intermediate 12.2 (1.06 g, 2.94 mmol) and Intermediate 12.3 (715 mg, 2.94 mmol) analogously to Example 1. Longer reaction time (14 h) was required after the addition of methanesulfonic acid to cleave the silyl group in-situ. The title compound was purified by Combi-Flash Companion™ (Isco Inc.) column chromatography (SiO$_2$; gradient elution, [heptane/DCM 1:1]/TBME 95:5→4:6). TLC: R$_F$=0.33 (heptane/DCM/TBME 1:1:2); HPLC: $^At_{Ret}$=2.51 min; API-MS: m/z 452.2 [M+H]$^+$; $^1$H NMR (400 MHz, CDCl$_3$): 1.44-1.52 (m, 6H), 2.33 (s, 3H), 3.73 (s, 2H), 4.04-4.17 (m, 4H), 5.95 (s, 1H), 6.73-6.82 (m, 4H), 6.87-6.91 (m, 1H), 7.00-7.07 (m, 3H), 7.21-7.26 (m, 2H).

Example 13

{2-[1-(4-Chloro-phenyl)-6,7-diethoxy-3-oxo-3,4-dihydro-1H-isoquinolin-2-yl]-5-methyl-phenoxy}-acetic acid

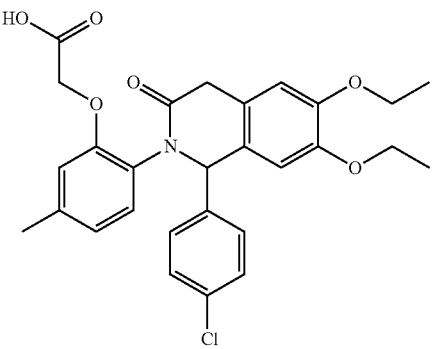 [SMILES: CCOc1cc2c(cc1OCC)C(c1ccc(Cl)cc1)N(c1ccc(C)cc1OCC(=O)O)C(=O)C2]

A mixture of Intermediate 13.1 (44 mg, 0.084 mmol) in MeOH (0.8 ml) and water (0.2 ml) was treated with LiOH monohydrate (10.6 mg, 0.25 mmol) at RT and stirred for 1 h. The reaction mixture was neutralized by the addition of HCl 0.5 M in water then extracted with DCM. The organic fraction was dried over Na$_2$SO$_4$, filtered and evaporated to dryness. The resulting residue was purified by reverse phase prep-HPLC (Waters system) to yield the title compound (8.5 mg, 0.017 mmol, 20% for 2 steps). HPLC: $^At_{Ret}$=2.41 min; LC-MS: m/z 510.8 [M+H]$^+$; $^1$H NMR (400 MHz, DMSO-d$_6$): 1.26 (t, J=6.9, 3H), 1.33 (t, J=6.9, 3H), 2.26 (s, 3H), 3.53 (d, J=19.6, 1H), 3.89 (d, J=19.5, 1H), 3.90-4.01 (m, 2H), 4.05 (q, J=6.9 Hz, 2H), 4.44 (d, J=15.9, 1H), 4.59 (d, J=15.9, 1H), 5.98 (s, 1H), 6.64-6.69 (m, 1H), 6.72 (s, 1H), 6.77 (d, J=7.8, 1H), 6.81 (s, 2H), 7.23 (d, J=2.1, 4H).

Intermediate 13.1: {2-[1-(4-Chloro-phenyl)-6,7-diethoxy-3-oxo-3,4-dihydro-1H-isoquinolin-2-yl]-5-methyl-phenoxy}-acetic acid methyl ester. (Methode B)

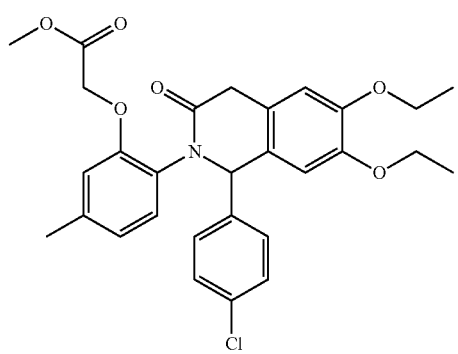 [SMILES: CCOc1cc2c(cc1OCC)C(c1ccc(Cl)cc1)N(c1ccc(C)cc1OCC(=O)OC)C(=O)C2]

To a solution of Intermediate 12.4 (38 mg, 0.084 mmol) in DMF (0.5 ml) were successively added Cs$_2$CO$_3$ (54.8 mg, 0.17 mmol) and bromo-acetic acid methyl ester (0.012 ml, 0.13 mmol). The reaction mixture was stirred at RT for 30 min then partitioned between water and AcOEt. The organic phase was separated, dried over Na$_2$SO$_4$, filtered and evaporated to dryness to yield the crude title intermediate (44.1 mg) as a yellow oil, which was used in the next step without further purification. HPLC: $^At_{Ret}$=2.66 min; LC-MS: m/z 525.9 [M+H]$^+$.

Example 14

1-(4-Chloro-phenyl)-6,7-diethoxy-2-[4-methyl-2-(2H-tetrazol-5-ylmethoxy)-phenyl]-1,4-dihydro-2H-isoquinolin-3-one

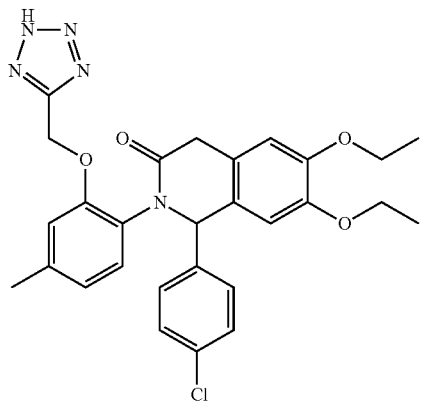 [SMILES: CCOc1cc2c(cc1OCC)C(c1ccc(Cl)cc1)N(c1ccc(C)cc1OCc1nn[nH]n1)C(=O)C2]

To a solution of Intermediate 12.4 (50 mg, 0.11 mmol) in acetone (1 ml) were successively added K$_2$CO$_3$ (45.4 mg, 0.33 mmol) and bromo-acetonitrile (0.011 ml, 0.17 mmol). The reaction mixture was stirred at RT for 3 h then diluted into AcOEt and washed with water. The organic phase was dried over Na$_2$SO$_4$, filtered and evaporated to dryness. The resulting residue was dissolved in DMF (0.5 ml) then NH$_4$Cl (19.6 mg, 0.33 mmol) and NaN$_3$ (21.4 mg, 0.033 mmol) were added and the heterogeneous mixture was heated at 100° C. and stirred for 24 h. The reaction mixture was cooled to RT, filtered and directly subjected to purification by reverse phase prep-HPLC (Waters system) to yield the title compound (25 mg, 0.047 mmol, 43%). HPLC: $^At_{Ret}$=2.47 min; LC-MS: m/z 535.8 [M+H]$^+$; $^1$H NMR (400 MHz, CD$_3$OD): 1.35 (t, J=7.0, 3H), 1.43 (t, J=7.0, 3H), 2.34 (s, 3H), 3.60-3.78 (m, 1H), 3.83-4.20 (m, 5H), 5.16-6.05 (m, 3H), 6.55-7.38 (m, 9H).

Example 15

Compounds 15a to 15l were obtained by reaction of Intermediate 12.4 (or analogues prepared similarly) with various aliphatic alcohols or halogenides analogously to Example 12 (Methode A) or Intermediate 13.1 (Methode B) respectively.

| # | Structure | Name/HPLC/MS |
|---|-----------|--------------|
| 15a | 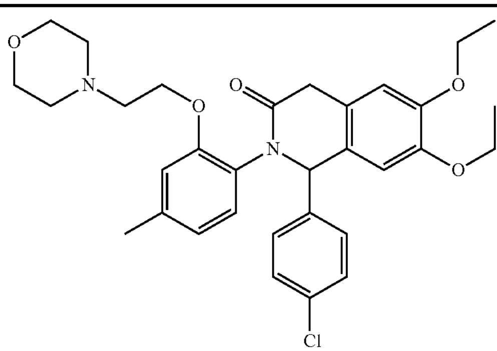 | 1-(4-Chloro-phenyl)-6,7-diethoxy-2-[4-methyl-2-(2-morpholin-4-yl-ethoxy)-phenyl]-1,4-dihydro-2H-isoquinolin-3-one.<br>HPLC: $^At_{Ret}$ = 1.95; LC-MS: m/z 566.9 [M + H]$^+$. |
| 15b | 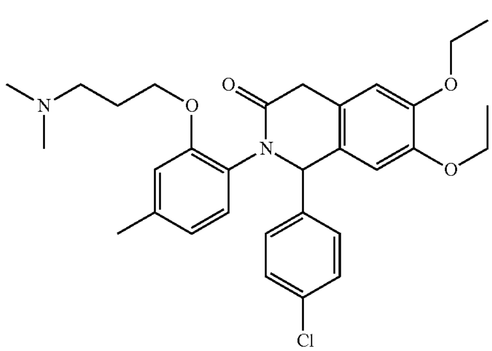 [SMILES: CCOc1cc2c(cc1OCC)C(c1ccc(Cl)cc1)N(c1ccc(C)cc1OCCCN(C)C)C(=O)C2] | 1-(4-Chloro-phenyl)-2-[2-(3-dimethylamino-propoxy)-4-methyl-phenyl]-6,7-diethoxy-1,4-dihydro-2H-isoquinolin-3-one.<br>HPLC: $^At_{Ret}$ = 1.97; LC-MS: m/z 537.9 [M + H]$^+$. |

-continued

| # | Structure | Name/HPLC/MS |
|---|---|---|
| 15c | 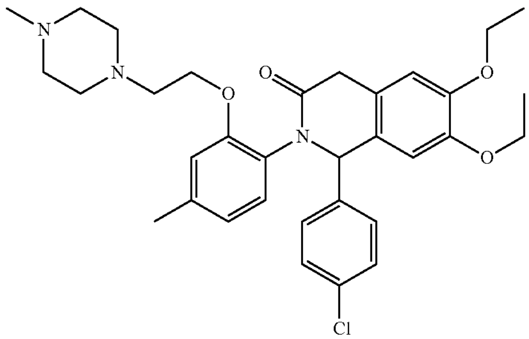 [SMILES: CCOc1cc2c(cc1OCC)C(c1ccc(Cl)cc1)N(c1ccc(C)cc1OCCN1CCN(C)CC1)C(=O)C2] | 1-(4-Chloro-phenyl)-6,7-diethoxy-2-{4-methyl-2-[2-(4-methyl-piperazin-1-yl)-ethoxy]-phenyl}-1,4-dihydro-2H-isoquinolin-3-one.<br>HPLC: $^{A}t_{Ret}$ = 1.77; API-MS: m/z 579.7 [M + H]$^+$. |
| 15d | 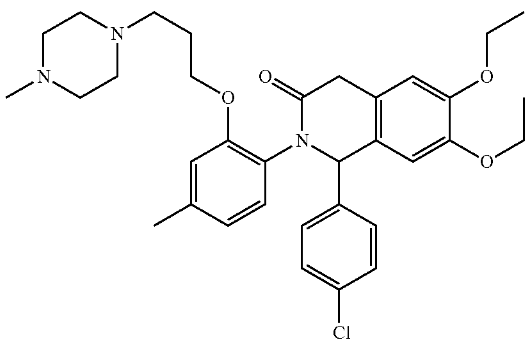 [SMILES: CCOc1cc2c(cc1OCC)C(c1ccc(Cl)cc1)N(c1ccc(C)cc1OCCCN1CCN(C)CC1)C(=O)C2] | 1-(4-Chloro-phenyl)-6,7-diethoxy-2-{4-methyl-2-[3-(4-methyl-piperazin-1-yl)-propoxy]-phenyl}-1,4-dihydro-2H-isoquinolin-3-one.<br>HPLC: $^{A}t_{Ret}$ = 1.77; API-MS: m/z 592.4 [M + H]$^+$. |
| 15e | 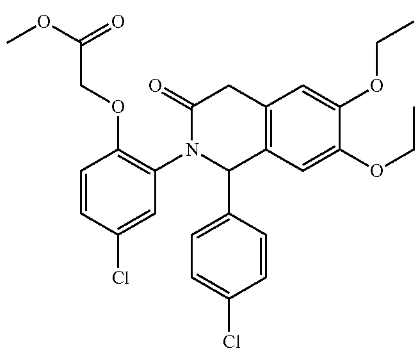 [SMILES: CCOc1cc2c(cc1OCC)C(c1ccc(Cl)cc1)N(c1cc(Cl)ccc1OCC(=O)OC)C(=O)C2] | {4-Chloro-2-[1-(4-chloro-phenyl)-6,7-diethoxy-3-oxo-3,4-dihydro-1H-isoquinolin-2-yl]-phenoxy}-acetic acid methyl ester.<br>HPLC: $^{A}t_{Ret}$ = 2.76; LC-MS: m/z 545.8 [M + H]$^+$. |
| 15f | 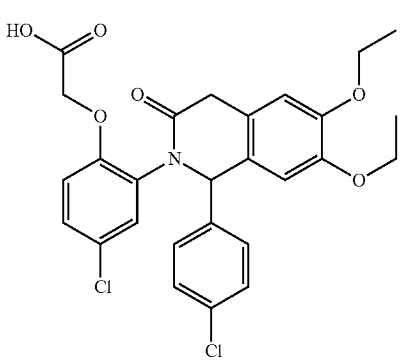 [SMILES: CCOc1cc2c(cc1OCC)C(c1ccc(Cl)cc1)N(c1cc(Cl)ccc1OCC(=O)O)C(=O)C2] | {4-Chloro-2-[1-(4-chloro-phenyl)-6,7-diethoxy-3-oxo-3,4-dihydro-1H-isoquinolin-2-yl]-phenoxy}-acetic acid.<br>HPLC: $^{A}t_{Ret}$ = 2.49; LC-MS: m/z 531.8 [M + H]$^+$. |

-continued

| # | Structure | Name/HPLC/MS |
|---|---|---|
| 15g | 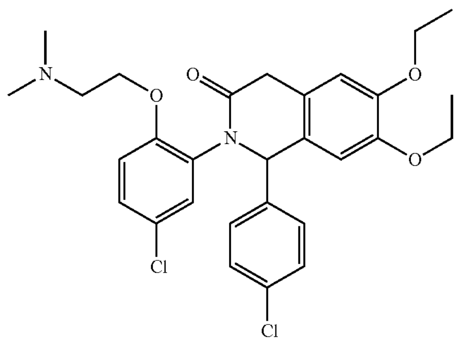 [SMILES: CCOc1cc2c(cc1OCC)C(c1ccc(Cl)cc1)N(c1cc(Cl)ccc1OCCN(C)C)C(=O)C2] | 2-[5-Chloro-2-(2-dimethylamino-ethoxy)-phenyl]-1-(4-chloro-phenyl)-6,7-diethoxy-1,4-dihydro-2H-isoquinolin-3-one.<br>HPLC: $^{A}t_{Ret}$ = 2.00; API-MS: m/z 544.7 [M + H]$^{+}$. |
| 15h | 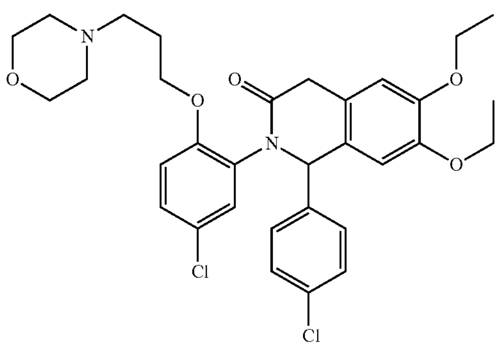 [SMILES: CCOc1cc2c(cc1OCC)C(c1ccc(Cl)cc1)N(c1cc(Cl)ccc1OCCCN1CCOCC1)C(=O)C2] | 2-[5-Chloro-2-(3-morpholin-4-yl-propoxy)-phenyl]-1-(4-chloro-phenyl)-6,7-diethoxy-1,4-dihydro-2H-isoquinolin-3-one.<br>HPLC: $^{A}t_{Ret}$ = 2.03; LC-MS: m/z 601.8 [M + H]$^{+}$. |
| 15i | 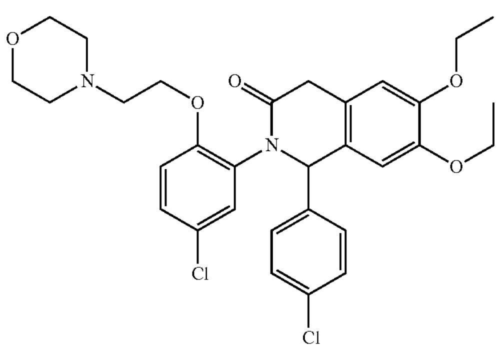 [SMILES: CCOc1cc2c(cc1OCC)C(c1ccc(Cl)cc1)N(c1cc(Cl)ccc1OCCN1CCOCC1)C(=O)C2] | 2-[5-Chloro-2-(2-morpholin-4-yl-ethoxy)-phenyl]-1-(4-chloro-phenyl)-6,7-diethoxy-1,4-dihydro-2H-isoquinolin-3-one.<br>HPLC: $^{A}t_{Ret}$ = 2.03; LC-MS: m/z 586.8 [M + H]$^{+}$. |
| 15j | 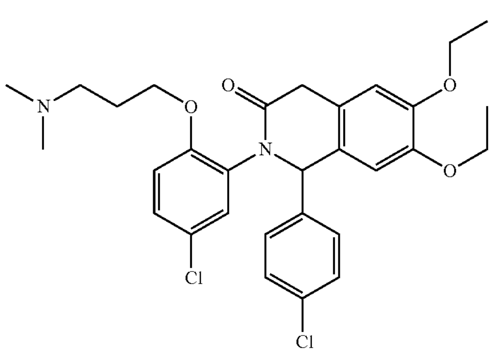 [SMILES: CCOc1cc2c(cc1OCC)C(c1ccc(Cl)cc1)N(c1cc(Cl)ccc1OCCCN(C)C)C(=O)C2] | 2-[5-Chloro-2-(3-dimethylamino-propoxy)-phenyl]-1-(4-chloro-phenyl)-6,7-diethoxy-1,4-dihydro-2H-isoquinolin-3-one.<br>HPLC: $^{A}t_{Ret}$ = 2.03; LC-MS: m/z 558.9 [M + H]$^{+}$. |

| # | Structure | Name/HPLC/MS |
|---|---|---|
| 15k | 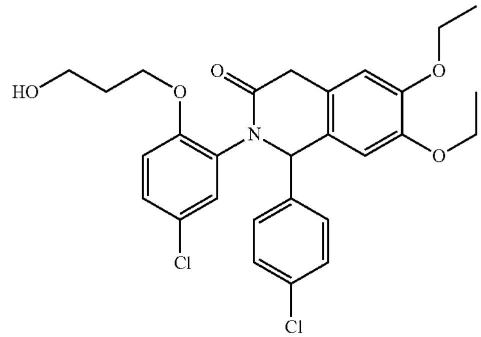 [SMILES: CCOc1cc2c(cc1OCC)C(c1ccc(Cl)cc1)N(c1cc(Cl)ccc1OCCCO)C(=O)C2] | 2-[5-Chloro-2-(3-hydroxy-propoxy)-phenyl]-1-(4-chloro-phenyl)-6,7-diethoxy-1,4-dihydro-2H-isoquinolin-3-one.<br>HPLC: $^A t_{Ret}$ = 2.57; LC-MS: m/z 531.7 [M + H]$^+$. |
| 15l$^{(1)}$ | 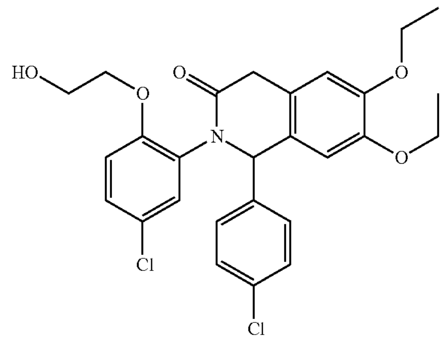 [SMILES: CCOc1cc2c(cc1OCC)C(c1ccc(Cl)cc1)N(c1cc(Cl)ccc1OCCO)C(=O)C2] | 2-[5-Chloro-2-(2-hydroxy-ethoxy)-phenyl]-1-(4-chloro-phenyl)-6,7-diethoxy-1,4-dihydro-2H-isoquinolin-3-one.<br>HPLC: $^A t_{Ret}$ = 2.55; LC-MS: m/z 517.8 [M + H]$^+$. |

$^{(1)}$The title compound (2.5 mg, 0.005 mmol, 15%) was obtained by reduction of the methyl ester function of Example 15e (17.4 mg, 0.032 mmol) analogously to Example 8. Purification of the crude material was performed by reverse phase prep-HPLC (Waters system).

Example 16

6-((R)-sec-Butoxy)-4-(4-chloro-phenyl)-3-(4-dimethylamino-phenyl)-7-methoxy-3,4-dihydro-1H-quinazolin-2-one. (Methode A)

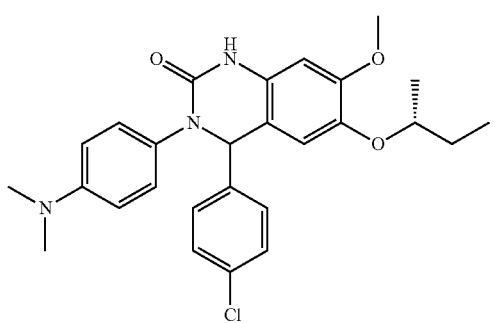 [SMILES: CC[C@@H](C)Oc1cc2c(cc1OC)NC(=O)N(c1ccc(N(C)C)cc1)C2c1ccc(Cl)cc1]

To a mixture of Intermediate 16.7 (90 mg, 0.19 mmol) and ammonium formate (237 mg, 3.77 mmol) in MeOH (2 ml) was added Pd/C (2 mg, 0.019 mmol). The reaction mixture was heated at 60° C., stirred for 14 h, then cooled to RT and filtered through a Celite pad. The filter cake was washed with MeOH and the filtrate was concentrated under vacuum. The resulting residue was dissolved in AcOEt and washed successively with water and Na$_2$CO$_3$ 2M. The organic phase was dried over Na$_2$SO$_4$, filtered and evaporated to dryness. The resulting residue was purified by Combi-Flash Companion™ (Isco Inc.) column chromatography (SiO$_2$; gradient elution, [heptane/DCM 1:1]/TBME 95:5→100% TBME) to yield the title compound (49 mg, 0.10 mmol, 54%) as an off-white solid. TLC: R$_F$=0.14 (heptane/DCM/TBME 1:1:2); HPLC: $^A t_{Ret}$=1.98 min; LC-MS: m/z 480.2 [M+H]$^+$; $^1$H NMR (400 MHz, DMSO-d$_6$): 0.81-0.93 (m, 3H, mixture of diastereoisomers), 1.06-1.16 (2 d, J=6.1, 3H, mixture of diastereoisomers), 1.40-1.64 (m, 2H), 2.85 (s, 6H), 3.70 (s, 3H), 3.99-4.13 (m, 1H), 5.83 (s, 1H), 6.51-6.54 (m, 1H), 6.59-6.64 (m, 2H), 6.77-6.80 (m, 1H), 6.88-6.94 (m, 2H), 7.27-7.39 (m, 4H), 9.36 (s, 1H).

Intermediate 16.1:
3-((R)-sec-Butoxy)-4-methoxy-benzaldehyde

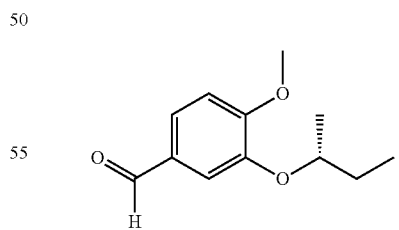

To a solution of 3-hydroxy-4-methoxy-benzaldehyde (4 g, 26.3 mmol), PPh$_3$ (9.65 g, 36.8 mmol) and (S)-butan-2-ol (2.9 ml, 31.5 mmol) in DCM (100 ml) was slowly added DTAD (9.08 g, 39.4 mmol) at 0° C. (ice bath). After the addition, the yellow solution was allowed to warm to RT and further stirred for 30 min. The reaction mixture was washed successively with HCl 2M in water (2×) and Na$_2$CO$_3$ 2M. The organic phase was dried over Na$_2$SO$_4$, filtered and evaporated to dryness. The resulting crude material was purified by Combi-Flash Companion™ (Isco Inc.) column chromatography (SiO$_2$; gradient elution, heptane/TBME 95:5→7:3) to yield the title compound (2.42 g, 11.6 mmol, 44%) as a light yellow oil. TLC: R$_F$=0.4 (heptane/TBME 1:1); HPLC: $^At_{Ret}$=1.93 min; LC-MS: m/z 209.2 [M+H]$^+$; $^1$H NMR (400 MHz, DMSO-d$_6$): 0.93 (t, J=7.5, 3H), 1.24 (d, J=6.1, 3H), 1.53-1.75 (m, 2H), 3.87 (s, 3H), 4.38-4.47 (m, 1H), 7.18 (d, J=8.3, 1H), 7.39 (d, J=1.7, 1H), 7.54 (dd, J=8.3, 2.0, 1H), 9.83 (s, 1H).

Intermediate 16.2: [3-((R)-sec-Butoxy)-4-methoxy-phenyl]-(4-chloro-phenyl)-methanol

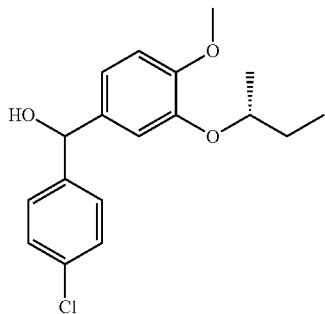 [SMILES: CC[C@@H](C)Oc1cc(C(O)c2ccc(Cl)cc2)ccc1OC]

A solution of Intermediate 16.1 (576 mg, 2.77 mmol) in THF (20 ml) was cooled to 0° C. (ice bath) and treated with 4-chlorophenylmagnesium bromide (1M THF solution, 4.15 ml, 4.15 mmol). After the addition, the reaction mixture was further stirred for 1.5 h at 0° C. then quenched by the addition of a saturated aqueous NH$_4$Cl solution (20 ml). The resulting slurry was diluted into water and extracted with DCM (2x). The combined organic fractions were dried over Na$_2$SO$_4$, filtered and evaporated to dryness to yield the crude title compound (1.01 g) as a yellow oil, which was used in the next step without further purification. HPLC: $^At_{Ret}$=2.51 min; API-MS: m/z 319.2 [M−H]$^+$; $^1$H NMR (400 MHz, DMSO-d$_6$): 0.86-0.93 (m, 3H, mixture of diastereoisomers), 1.13-1.21 (m, 3H, mixture of diastereoisomers), 1.47-1.70 (m, 2H), 3.71 (s, 3H), 4.19-4.28 (m, 1H), 5.62 (d, J=3.9, 1H), 5.86 (d, J=4.2, 1H), 6.81-6.90 (m, 2H), 6.93 (d, J=1.7, 1H), 7.33-7.38 (m, 4H).

Intermediate 16.3: [3-((R)-sec-Butoxy)-4-methoxy-phenyl]-(4-chloro-phenyl)-methanone

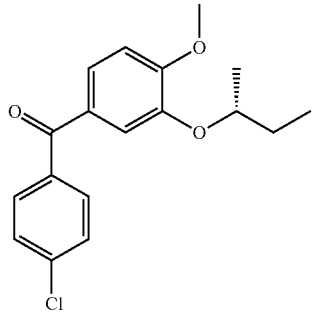 [SMILES: CC[C@@H](C)Oc1cc(C(=O)c2ccc(Cl)cc2)ccc1OC]

To a solution of Intermediate 16.2 (1.01 g) in CHCl$_3$ (15 ml) was added MnO$_2$ (2.88 g, 33.1 mmol) in one portion. The suspension was refluxed for 3 h, then cooled to RT and filtered through a Celite pad. The filter cake was washed with DCM and the filtrate was evaporated to dryness to yield the crude title compound (965 mg) as an orange oil, which was used in the next step without further purification. HPLC: $^At_{Ret}$=2.85 min; LC-MS: m/z 319.0 [M+H]$^+$; $^1$H NMR (400 MHz, DMSO-d$_6$): 0.92 (t, J=7.3, 3H), 1.24 (d, J=6.1, 3H), 1.53-1.74 (m, 2H), 3.87 (s, 3H), 4.33-4.42 (m, 1H), 7.11 (d, J=8.3, 1H), 7.28-7.36 (m, 2H), 7.60-7.65 (m, 2H), 7.69-7.75 (m, 2H).

Intermediate 16.4: [5-((R)-sec-Butoxy)-4-methoxy-2-nitro-phenyl]-(4-chloro-phenyl)-methanone

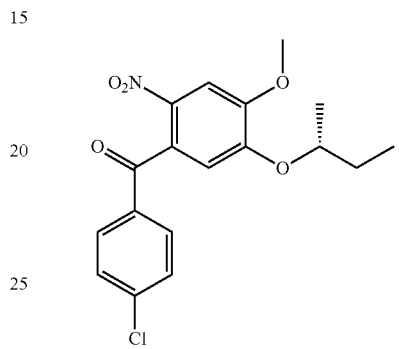

To a solution of Intermediate 16.3 (965 mg) in AcOH (10 ml) was slowly added HNO$_3$ (0.86 ml, 19.3 mmol) at 0° C. (ice bath). After the addition, the reaction mixture was allowed to warm to RT, then further stirred for 1 h and poured into cold water. The resulting precipitate was collected by filtration and washed with 2M aqueous NaHCO$_3$ solution. The solid was dissolved in DCM, dried over Na$_2$SO$_4$, filtered and evaporated to dryness to yield the title compound (1.0 g, 2.76 mmol) as a brownish solid, which was used in the next step without further purification. HPLC: $^At_{Ret}$=2.82 min; LC-MS: m/z 364.0 [M+H]$^+$; $^1$H NMR (400 MHz, DMSO-d$_6$): 0.89 (t, J=7.3, 3H), 1.23 (d, J=5.9, 3H), 1.54-1.76 (m, 2H), 3.96 (s, 3H), 4.61-4.71 (m, 1H), 7.26 (s, 1H), 7.57-7.63 (m, 2H), 7.69-7.75 (m, 2H), 7.79 (s, 1H).

Intermediate 16.5: 5-((R)-sec-Butoxy)-3-(4-chloro-phenyl)-6-methoxy-benzo[c]isoxazole

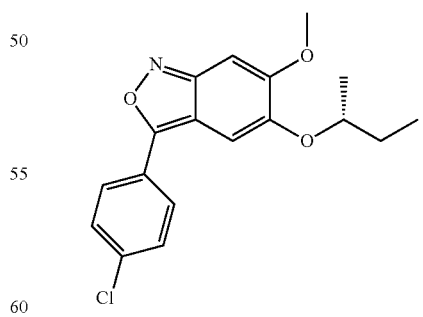

In a sealed reaction flask, a mixture of Intermediate 16.4 (1.0 g, 2.76 mmol) and SnCl$_2$ (5.24 g, 27.6 mmol) in EtOH (10 ml) was heated at 80° C. and stirred for 1 h. The resulting suspension was cooled to RT and filtered. The solid was dissolved in DCM (200 ml) and washed with a 1M aqueous NaOH solution (2x). The organic layer was dried over Na₂SO₄, filtered and evaporated to dryness to yield the title compound (581 mg, 1.75 mmol, 63%) as a yellow solid, which was used in the next step without further purification. HPLC: $^At_{Ret}$=2.97 min; LC-MS: m/z 332.1 [M+H]⁺; ¹H NMR (400 MHz, DMSO-d₆): 0.95 (t, J=7.5, 3H), 1.29 (d, J=6.1, 3H), 1.58-1.79 (m, 2H), 3.89 (s, 3H), 4.60-4.71 (m, 1H), 6.94 (s, 1H), 7.12 (s, 1H), 7.62-7.69 (m, 2H), 8.01-8.08 (m, 2H).

Intermediate 16.6: [2-Amino-5-((R)-sec-butoxy)-4-methoxy-phenyl]-(4-chloro-phenyl)-methanone

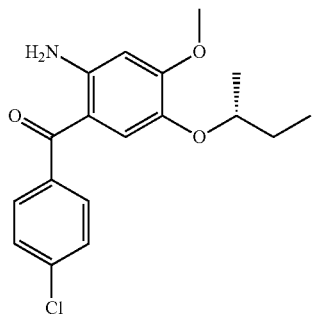 [SMILES: CC[C@@H](C)Oc1cc(C(=O)c2ccc(Cl)cc2)c([N+](=O)[O-])cc1OC]

In a sealed reaction flask, a mixture of Intermediate 16.5 (522 mg, 1.57 mmol) and Fe (879 mg, 15.7 mmol) in AcOH (3 ml), water (4 ml) and AcOEt (1 ml) was heated at 110° C. and stirred for 30 min. The resulting suspension was cooled to RT, neutralized by the addition of a saturated aqueous NaHCO₃ solution to pH 7 and filtered through a Celite pad. The solid was washed with AcOEt and the biphasic filtrate was transferred into a separating funnel. The aqueous layer was separated and further extracted with AcOEt (3×). The combined organic fractions were dried over Na₂SO₄, filtered and evaporated to dryness. The resulting crude material was purified by Combi-Flash Companion™ (Isco Inc.) column chromatography (SiO₂; isocratic elution, [heptane/DCM 1:1]/TBME 95:5) to yield the title compound (525 mg, 1.57 mmol, quant.) as a brownish solid. TLC: RE=0.57 (heptane/DCM/TBME 1:1:2); HPLC: $^At_{Ret}$=2.64 min; LC-MS: m/z 334.1 [M+H]⁺; ¹H NMR (400 MHz, DMSO-d₆): 0.82 (t, J=7.5, 3H), 1.07 (d, J=6.1, 3H), 1.36-1.60 (m, 2H), 3.79 (s, 3H), 3.80-3.88 (m, 1H), 6.43 (s, 1H), 6.68 (s, 1H), 7.20 (s, 2H), 7.49-7.59 (m, 4H).

Intermediate 16.7: 6-((R)-sec-Butoxy)-4-(4-chloro-phenyl)-3-(4-dimethylamino-phenyl)-7-methoxy-3H-quinazolin-2-one

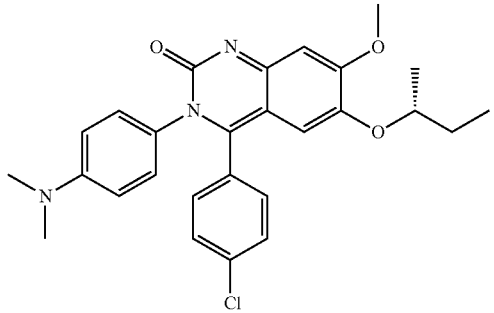 [SMILES: CC[C@@H](C)Oc1cc2c(-c3ccc(Cl)cc3)n(-c3ccc(N(C)C)cc3)c(=O)nc2cc1OC]

To a solution of Intermediate 16.6 (300 mg, 0.9 mmol) in toluene (8 ml) was added (4-isocyanato-phenyl)-dimethyl-amine (219 mg, 1.35 mmol). The reaction mixture was heated at 110° C. and stirred for 4.5 days. PTSA (15.48 mg, 0.09 mmol) was then added and the mixture was further stirred at 110° C. for additional 14 h. The reaction mixture was cooled to RT and evaporated to dryness. The resulting residue was purified by Combi-Flash Companion™ (Isco Inc.) column chromatography (SiO₂; gradient elution, DCM/MeOH 99:1→9:1) to yield the title compound (100 mg, 0.21 mmol, 23%) as a dark solid. TLC: R_F=0.29 (DCM/MeOH 9:1); HPLC: $^At_{Ret}$=2.07 min; LC-MS: m/z 478.0 [M+H]⁺.

Example 17

4-(4-Chloro-phenyl)-6,7-dimethoxy-3-(4-methoxy-phenyl)-3,4-dihydro-1H-quinazolin-2-one. (Methode B)

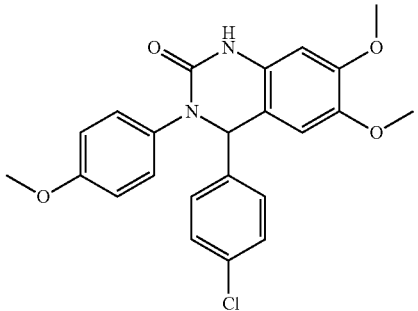

To a solution of the crude Intermediate 17.1 (25 mg) in MeOH (1 ml) was added NaBH₄ (4.7 mg, 0.12 mmol) in one portion at RT. The reaction mixture was stirred for 3 h and concentrated under vacuum. The residue was dissolved in DCM, washed with water and the organic phase was dried over Na₂SO₄, filtered and evaporated to dryness. The resulting crude material was purified by reverse phase prep-HPLC (Waters system) to yield the title compound (9.5 mg, 0.022 mmol, 38%). HPLC: $^At_{Ret}$=2.17 min; API-MS: m/z 425.2 [M+H]⁺; ¹H NMR (400 MHz, CD₃OD): 3.70 (s, 3H), 3.78 (s, 3H), 3.85 (s, 3H), 5.81 (s, 1H), 6.60 (s, 1H), 6.62 (s, 1H), 6.83-6.89 (m, 2H), 6.95-7.01 (m, 2H), 7.17-7.23 (m, 2H), 7.26-7.32 (m, 2H).

Intermediate 17.1: 4-(4-Chloro-phenyl)-6,7-dimethoxy-3-(4-methoxy-phenyl)-3H-quinazolin-2-one

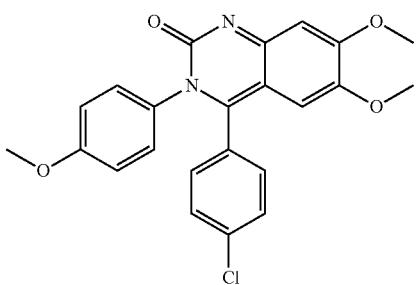

The crude title intermediate (136 mg) was obtained as a light yellow solid from (2-amino-4,5-dimethoxy-phenyl)-(4-chloro-phenyl)-methanone (100 mg, 0.34 mmol, purchased by ChemCollect GmbH) and 1-isocyanato-4-methoxy-benzene (0.044 ml, 0.34 mmol) analogously to Intermediate 16.7.

The crude intermediate was used in the next step without further purification. HPLC: $^At_{Ret}$=2.53 min; API-MS: m/z 441.1 [M+H]$^+$.

Example 18

6-((R)-sec-Butoxy)-4-(4-chloro-phenyl)-3-(4-dimethylamino-phenyl)-7-methoxy-1-methyl-3,4-dihydro-1H-quinazolin-2-one

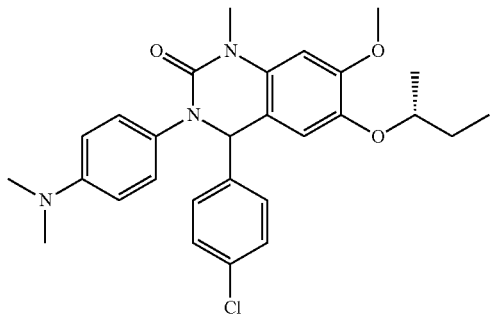 [SMILES: CC[C@@H](C)Oc1cc2c(cc1OC)N(C)C(=O)N(c1ccc(N(C)C)cc1)C2c1ccc(Cl)cc1]

To a solution of Example 16 (20 mg, 0.042 mmol) in THF (0.3 ml) was cautiously added NaH (60% in mineral oil, 3.3 mg, 0.083 mmol) at RT. The mixture was heated at 50° C. and stirred for 30 min. MeI (0.005 ml, 0.083 mmol) was added at 50° C. and the reaction mixture was further stirred for 1 h then cooled to RT and quenched by the addition of MeOH. The resulting clear solution was directly subjected to purification by reverse phase prep-HPLC (Waters system) to yield the title compound (TFA salt, 9.4 mg, 0.015 mmol, 37%) as an off-white solid. HPLC: $^At_{Ret}$=2.10 min; LC-MS: m/z 494.4 [M+H]$^+$; $^1$H NMR (400 MHz, DMSO-d$_6$): 0.84-0.94 (m, 3H, mixture of diastereoisomers), 1.09-1.19 (m, 3H, mixture of diastereoisomers), 1.43-1.66 (m, 2H), 2.88 (s, 6H), 3.30 (s, 3H), 3.80 (s, 3H), 4.08-4.21 (m, 1H), 5.83 (s, 1H), 6.63 (s, 1H), 6.67-6.78 (m, 2H), 6.91-7.02 (m, 3H), 7.25-7.32 (m, 2H), 7.34-7.41 (m, 2H).

Example 19

Compounds 19a to 19f were obtained by reaction of Intermediate 16.6 (or analogues prepared similarly) or the commercially available (2-amino-4,5-dimethoxy-phenyl)-(4-chloro-phenyl)-methanone with various isocyanates analogously to Example 16 (Methods A) or Example 17 (Methods 8), or by alkylation of Example 16 (or analogues prepared similarly) with various alkyl halogenides as described for Example 18.

| # | Structure | Name/HPLC/MS/NMR |
|---|---|---|
| 19a | 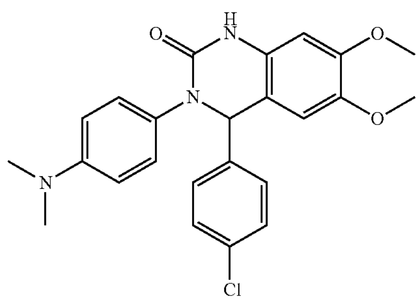 | 4-(4-Chloro-phenyl)-3-(4-dimethylamino-phenyl)-6,7-dimethoxy-3,4-dihydro-1H-quinazolin-2-one. HPLC: $^At_{Ret}$ = 1.54; LC-MS: m/z 438.1 [M + H]$^+$. |
| 19b | 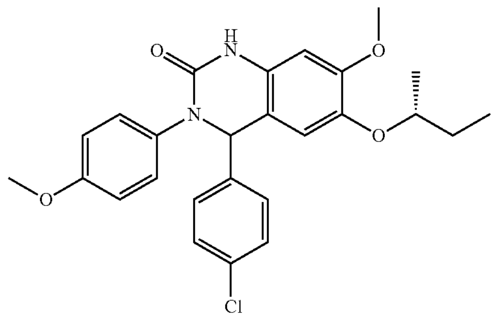 [SMILES: CC[C@@H](C)Oc1cc2c(cc1OC)NC(=O)N(c1ccc(OC)cc1)C2c1ccc(Cl)cc1] | 6-((R)-sec-Butoxy-4-(4-chloro-phenyl)-7-methoxy-3-(4-methoxy-phenyl)-3,4-dihydro-1H-quinazolin-2-one. HPLC: $^At_{Ret}$ = 2.65; LC-MS: m/z 467.1 [M + H]$^+$. |
| 19c | 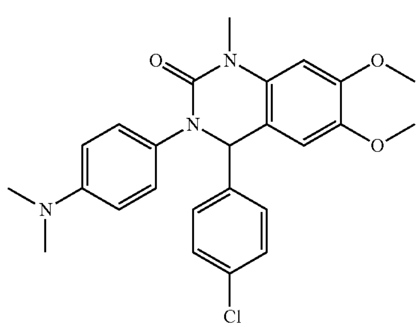 | 4-(4-Chloro-phenyl)-3-(4-dimethylamino-phenyl)-6,7-dimethoxy-1-methyl-3,4-dihydro-1H-quinazolin-2-one. HPLC: $^At_{Ret}$ = 1.69; LC-MS: m/z 452.0 [M + H]$^+$. |

-continued

| # | Structure | Name/HPLC/MS/NMR |
|---|---|---|
| 19d | 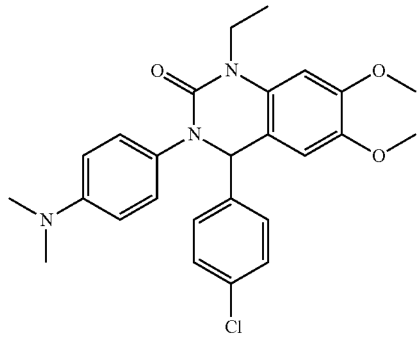 | 4-(4-Chloro-phenyl)-3-(4-dimethylamino-phenyl)-1-ethyl-6,7-dimethoxy-3,4-dihydro-1H-quinazolin-2-one.<br>HPLC: $^A t_{Ret}$ = 1.79; LC-MS: m/z 466.1 [M + H]$^+$. |
| 19e | 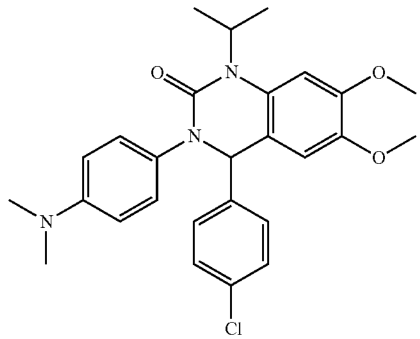 | 4-(4-Chloro-phenyl)-3-(4-dimethylamino-phenyl)-1-isopropyl-6,7-dimethoxy-3,4-dihydro-1H-quinazolin-2-one.<br>HPLC: $^A t_{Ret}$ = 1.94; LC-MS: m/z 480.1 [M + H]$^+$. |
| 19f | 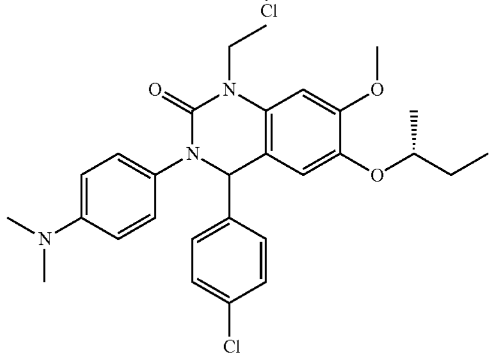 | 6-((R)-sec-Butoxy)-4-(4-chloro-phenyl)-3-(4-dimethylamino-phenyl)-1-ethyl-7-methoxy-3,4-dihydro-1H-quinazolin-2-one.<br>HPLC: $^A t_{Ret}$ = 2.17; LC-MS: m/z 508.6 [M + H]$^+$. |

Example 20

1-(4-Chloro-phenyl)-7-methoxy-2-(4-methoxy-phenyl)-6-(2-morpholin-4-yl-ethoxy)-1,4-dihydro-2H-isoquinolin-3-one

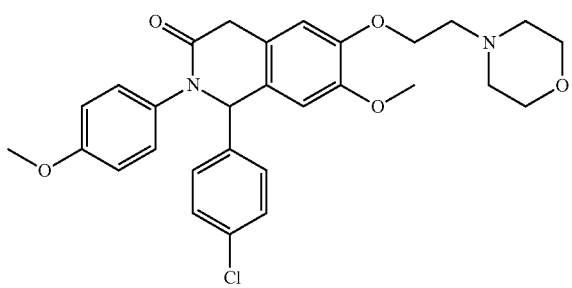 [SMILES: COc1ccc(N2C(=O)Cc3cc(OCCN4CCOCC4)c(OC)cc3C2c2ccc(Cl)cc2)cc1]

To a solution of Intermediate 20.3 (15 mg, 0.037 mmol) in DCM (0.5 ml) were successively added 2-morpholin-4-yl-ethanol (0.005 ml, 0.044 mmol), supported PPh$_3$ (loading of 1.52 mmol/g, 72.2 mg, 0.11 mmol) and DTAD (12.6 mg, 0.055 mmol). The reaction mixture was shaken at RT for 3 h, then filtered and the resin was washed with DCM. The filtrate was evaporated to dryness and the resulting residue was purified by reverse phase prep-HPLC (Waters system) to yield the title compound (TFA salt, 5 mg, 0.008 mmol, 21%). HPLC: $^A t_{Ret}$=1.66 min; API-MS: m/z 523.2 [M+H]$^+$.

Intermediate 20.1: [1-(4-Chloro-phenyl)-meth-(E)-ylidene]-(4-methoxy-phenyl)-amine

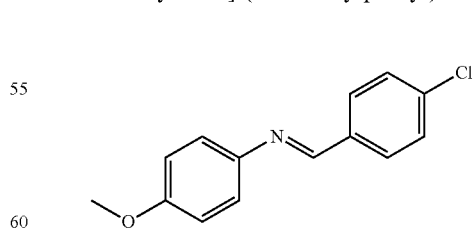

The title intermediate (1.88 g, 7.65 mmol, 94%) was obtained as a colorless solid from 4-methoxy-phenylamine (1 g, 8.12 mmol) and 4-chloro-benzaldehyde (1.14 g, 8.12 mmol) analogously to Intermediate 1.4. $^1$H NMR (400 MHz, CDCl$_3$): 3.86 (s, 3H), 6.93-6.98 (m, 2H), 7.24-7.28 (m, 2H), 7.43-7.48 (m, 2H), 7.83-7.87 (m, 2H), 8.47 (s, 1H).

Intermediate 20.2: (3-Benzyloxy-4-methoxy-phenyl)-acetyl chloride

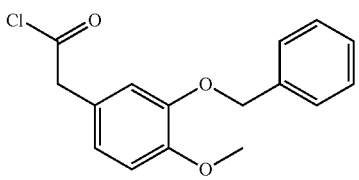 [SMILES: COc1ccc(CC(=O)Cl)cc1OCc1ccccc1]

The title intermediate (534 mg, 1.84 mmol, quant.) was obtained as a yellow solid from (3-benzyloxy-4-methoxy-phenyl)-acetic acid (500 mg, 1.84 mmol) analogously to Intermediate 1.3.

Intermediate 20.3: 1-(4-Chloro-phenyl)-6-hydroxy-7-methoxy-2-(4-methoxy-phenyl)-1,4-dihydro-2H-isoquinolin-3-one

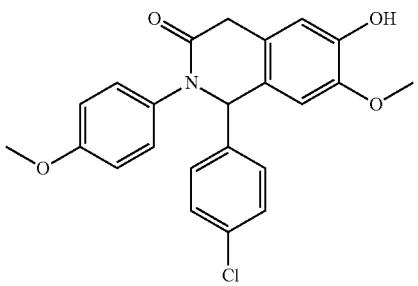

The title intermediate (340 mg, 0.83 mmol, 45%) was obtained from Intermediate 20.1 (452 mg, 1.84 mmol) and Intermediate 20.2 (535 mg, 1.84 mmol) analogously to Example 1. The benzyl protecting group was cleaved in-situ under the reaction conditions. Purification of the crude material was performed by Combi-Flash Companion™ (Isco Inc.) column chromatography (SiO$_2$; gradient elution, heptane/TBME containing 5% of formic acid 95:5→100% TBME containing 5% of formic acid). HPLC: $^A t_{Ret}$=2.09 min; API-MS: m/z 410.1 [M+H]$^+$; $^1$H NMR (400 MHz, DMSO-d$_6$): 3.47 (d, J=19.8, 1H), 3.66-3.72 (m, 6H), 3.87 (d, J=19.7, 1H), 5.92 (s, 1H), 6.61 (s, 1H), 6.82-6.89 (m, 2H), 6.95 (s, 1H), 6.97-7.04 (m, 2H), 7.26-7.34 (m, 4H), 9.06 (br. s., 1H).

Example 21

6-(2-Amino-ethoxy)-1-(4-chloro-phenyl)-7-methoxy-2-(4-methoxy-phenyl)-1,4-dihydro-2H-isoquinolin-3-one

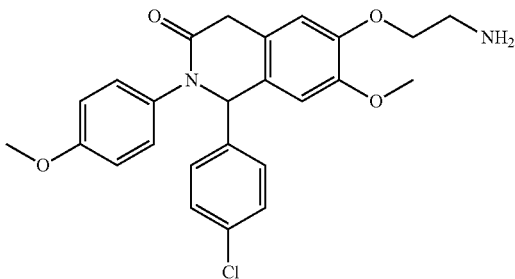 [SMILES: COc1ccc(N2C(=O)Cc3cc(OCCN)c(OC)cc3C2c2ccc(Cl)cc2)cc1]

To a solution of Intermediate 20.3 (15 mg, 0.037 mmol) in DMF (0.5 ml) were successively added Cs$_2$CO$_3$ (23.8 mg, 0.073 mmol) and (2-bromo-ethyl)-carbamic acid tert-butyl ester (12.3 mg, 0.055 mmol). The reaction mixture was stirred at RT for 30 min and partitioned between water and AcOEt. The organic phase was separated, dried over Na$_2$SO$_4$, filtered and evaporated to dryness. The resulting yellow residue was dissolved in DCM (0.5 ml) and treated with TFA (0.028 ml, 0.37 mmol). The reaction mixture was stirred at RT for 30 min, evaporated to dryness and the resulting crude material was purified by reverse phase prep-HPLC (Waters system) to yield the title compound (TFA salt, 8.5 mg, 0.015 mmol, 41%). HPLC: $^A t_{Ret}$=1.61 min; API-MS: m/z 453.3 [M+H]$^+$; $^1$H NMR (400 MHz, DMSO-d$_6$): 3.14-3.24 (m, 2H), 3.59 (d, J=19.8, 1H), 3.71 (s, 3H), 3.73 (s, 3H), 3.93 (d, J=19.7, 1H), 4.07-4.16 (m, 2H), 6.00 (s, 1H), 6.83-6.89 (m, 2H), 6.91 (s, 1H), 6.98-7.04 (m, 2H), 7.08 (s, 1H), 7.33 (s, 4H), 7.89 (br. s., 2H).

Example 22

7-((R)-sec-Butoxy)-1-(4-chloro-phenyl)-6-ethoxy-2-(4-methoxy-phenyl)-1,4-dihydro-2H-isoquinolin-3-one

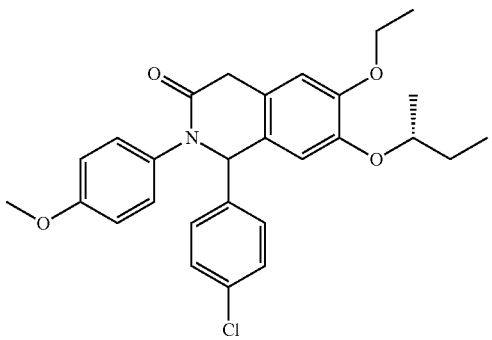 [SMILES: CCOc1cc2c(cc1O[C@H](C)CC)C(c1ccc(Cl)cc1)N(c1ccc(OC)cc1)C(=O)C2]

To a solution of Intermediate 22.4 (15 mg, 0.033 mmol) in DMF (0.5 ml) were successively added Cs$_2$CO$_3$ (21.6 mg, 0.066 mmol) and iodo-ethane (0.004 ml, 0.05 mmol). The reaction mixture was stirred at RT for 3 h and partitioned between water and AcOEt. The organic phase was separated, dried over Na$_2$SO$_4$, filtered and evaporated to dryness. The resulting crude material was purified by reverse phase prep-HPLC (Waters system) to yield the title compound (6.5 mg, 0.014 mmol, 41%). HPLC: $^A t_{Ret}$=2.92 min; API-MS: m/z 480.2 [M+H]$^+$; $^1$H NMR (400 MHz, CD$_3$OD): 0.90-1.01 (m, 3H), 1.14-1.24 (2 d, J=6.1, 3H, mixture of diastereoisomers), 1.42 (t, J=7.0, 3H), 1.50-1.75 (m, 2H), 3.72 (d, J=20.3, 1H), 3.78 (s, 3H), 3.99-4.12 (m, 3H), 4.17-4.27 (m, 1H), 5.91 (s, 1H), 6.78 (d, J=2.9, 1H), 6.85-6.92 (m, 3H), 6.97-7.02 (m, 2H), 7.14-7.19 (m, 2H), 7.27-7.32 (m, 2H).

Intermediate 22.1: [3-Benzyloxy-4-((R)-sec-butoxy)-phenyl]-acetonitrile

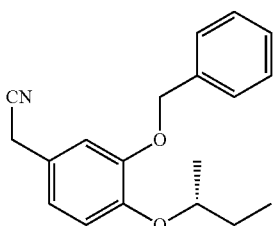

The title intermediate (519 mg, 1.76 mmol, 84%) was obtained as a colorless foam from (3-benzyloxy-4-hydroxy-phenyl)-acetonitrile (500 mg, 2.09 mmol) and (S)-butan-2-ol (0.23 ml, 2.51 mmol) analogously to Intermediate 1.1. Purification of the crude material was performed by Combi-Flash Companion™ (Isco Inc.) column chromatography (SiO$_2$;

gradient elution, heptane/TBME 95:5→1:1). TLC: $R_F$=0.84 (heptane/DCM/TBME 1:1:2); HPLC: $^At_{Ret}$=2.72 min; LC-MS: m/z 296.1 [M+H]$^+$; $^1$H NMR (400 MHz, CDCl$_3$): 1.00 (t, J=7.3, 3H), 1.32 (d, J=6.1, 3H), 1.60-1.72 (m, 1H), 1.75-1.87 (m, 1H), 3.67 (s, 2H), 4.31 (sxt, J=6.1, 1H), 5.14 (s, 2H), 6.84-6.95 (m, 3H), 7.30-7.43 (m, 3H), 7.44-7.50 (m, 2H).

Intermediate 22.2: [3-Benzyloxy-4-((R)-sec-butoxy)-phenyl]-acetic acid

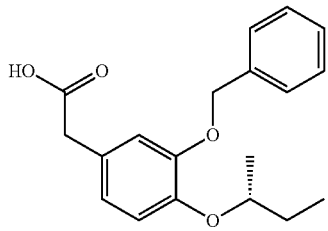 [SMILES: CC[C@@H](C)Oc1ccc(CC(=O)O)cc1OCc1ccccc1]

A mixture of Intermediate 22.1 (519 mg, 1.76 mmol) in 4M NaOH in water (3 ml) and EtOH (3 ml) was heated at 80° C. and stirred for 14 h. The reaction mixture was cooled to RT, concentrated under vacuum then acidified carefully by the addition of 2M HCl in water and extracted with DCM. The organic fraction was dried over Na$_2$SO$_4$, filtered and evaporated to dryness to give the title compound (538 mg, 1.71 mmol, 97%) as an orange oil, which was used in the next step without further purification. HPLC: $^At_{Ret}$=2.42 min; LC-MS: m/z 313.2 [M–H]$^+$; $^1$H NMR (400 MHz, CDCl$_3$): 0.99 (t, J=7.3, 3H), 1.32 (d, J=6.1, 3H), 1.59-1.71 (m, 1H), 1.75-1.87 (m, 1H), 3.58 (s, 2H), 4.29 (sxt, J=6.1, 1H), 5.12 (s, 2H), 6.82-6.87 (m, 1H), 6.88-6.92 (m, 2H), 7.30-7.34 (m, 1H), 7.35-7.41 (m, 2H), 7.43-7.49 (m, 2H).

Intermediate 22.3: 3-Benzyloxy-4-((R)-sec-butoxy)-phenyl]-acetyl chloride

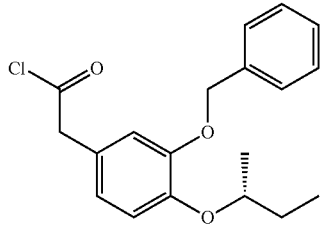 [SMILES: CC[C@@H](C)Oc1ccc(CC(=O)Cl)cc1OCc1ccccc1]

The title intermediate (571 mg, 1.71 mmol, quant.) was obtained as an orange oil from Intermediate 22.2 (539 mg, 1.71 mmol) analogously to Intermediate 1.3.

Intermediate 22.4: 7-((R)-sec-Butoxy)-1-(4-chloro-phenyl)-6-hydroxy-2-(4-methoxy-phenyl)-1,4-dihydro-2H-isoquinolin-3-one

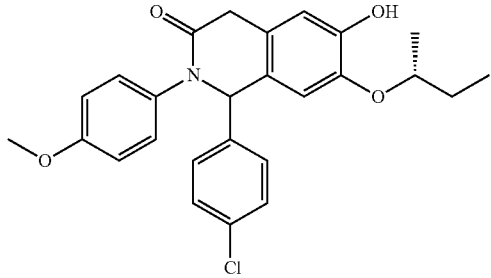 [SMILES: CC[C@@H](C)Oc1cc2c(cc1O)CC(=O)N(c1ccc(OC)cc1)C2c1ccc(Cl)cc1]

The title intermediate (270 mg, 0.60 mmol, 35%) was obtained as an off-white foam from Intermediate 20.1 (423 mg, 1.72 mmol) and Intermediate 22.3 (573 mg, 1.72 mmol) analogously to Example 1. The benzyl protecting group was cleaved in-situ under the reaction conditions. Purification of the crude material was performed by Combi-Flash Companion™ (Isco Inc.) column chromatography (SiO$_2$; gradient elution, heptane/TBME containing 5% of formic acid 95:5→4:6). TLC: $R_F$=0.76 (heptane/DCM/TBME containing 5% of formic acid 1:1:2); HPLC: $^At_{Ret}$=2.53 min; API-MS: m/z 452.1 [M+H]$^+$; $^1$H NMR (400 MHz, CD$_3$OD): 0.88-1.01 (2t, J=7.5, 3H, mixture of diastereoisomers), 1.15-1.29 (2 d, J=6.1, 3H, mixture of diastereoisomers), 1.49-1.81 (m, 2H), 3.64 (d, J=20.3, 1H), 3.79 (s, 3H), 3.98 (d, J=20.1, 1H), 4.22-4.31 (m, 1H), 5.89 (s, 1H), 6.72 (s, 1H), 6.74-6.78 (m, 1H), 6.87-6.93 (m, 2H), 6.96-7.02 (m, 2H), 7.13-7.19 (m, 2H), 7.26-7.33 (m, 2H).

Example 23

7-((R)-sec-Butoxy)-1-(4-chloro-phenyl)-2-(4-methoxy-phenyl)-6-[2-(4-methyl-piperazin-1-yl)-2-oxo-ethoxy]-1,4-dihydro-2H-isoquinolin-3-one

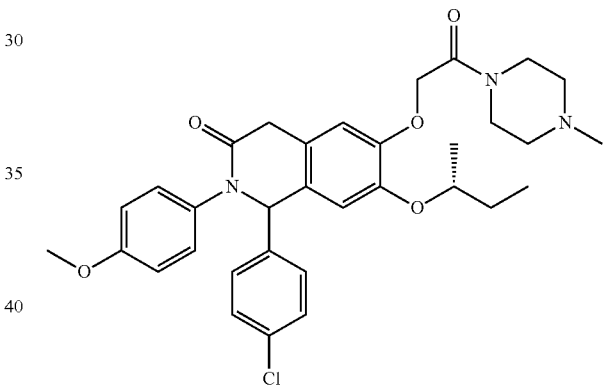

To a solution of Intermediate 23.1 (15 mg, 0.029 mmol) in DMF (0.5 ml) were successively added 1-methyl-piperazine (0.016 ml, 0.15 mmol), NMM (0.016 ml, 0.15 mmol) and HATU (16.8 mg, 0.044 mmol). The reaction mixture was stirred at RT for 1 h then partitioned between AcOEt and water. The organic phase was separated, dried over Na$_2$SO$_4$, filtered and evaporated to dryness. The resulting crude material was purified by reverse phase prep-HPLC (Waters system) to yield the title compound (TFA salt, 11.1 mg, 0.016 mmol, 54%). HPLC: $^At_{Ret}$=1.92 min; API-MS: m/z 592.0 [M+H]$^+$; $^1$H NMR (400 MHz, DMSO-d$_6$): 0.84-0.95 (2t, J=7.3, 3H, mixture of diastereoisomers), 1.11-1.25 (2 d, J=6.1, 3H, mixture of diastereoisomers), 1.45-1.70 (m, 2H), 2.81 (s, 3H), 2.88-3.14 (m, 3H), 3.29-3.48 (m, 3H), 3.52 (d, J=19.8, 1H), 3.71 (s, 3H), 3.92 (d, J=19.1, 1H), 3.99-4.15 (m, 1H), 4.23-4.34 (m, 1H), 4.34-4.47 (m, 1H), 4.81 (s, 2H), 6.01 (m, 1H), 6.78 (s, 1H), 6.83-6.90 (m, 2H), 6.98-7.09 (m, 3H), 7.29-7.37 (m, 4H).

Intermediate 23.1: [7-((R)-sec-Butoxy)-1-(4-chloro-phenyl)-2-(4-methoxy-phenyl)-3-oxo-1,2,3,4-tetrahydro-isoquinolin-6-yloxy]-acetic acid

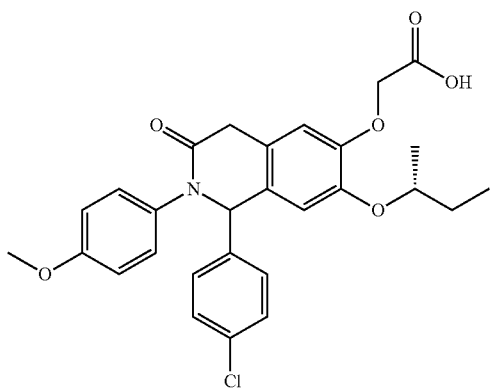 [SMILES: CC[C@@H](C)Oc1cc2c(cc1OCC(=O)O)CC(=O)N(c1ccc(OC)cc1)C2c1ccc(Cl)cc1]

The title compound (116 mg, 0.23 mmol, 90% over 2 steps) was obtained as an off-white solid from Intermediate 22.4 (120 mg, 0.27 mmol) following the same 2 steps sequence as described for Example 13. Purification of the crude material was performed by precipitation into water and filtration. HPLC: $^A t_{Ret}$=2.42 min; API-MS: m/z 509.8 [M+H]$^+$; $^1$H NMR (400 MHz, DMSO-d$_6$): 0.84-0.94 (2t, J=7.4, 3H, mixture of diastereoisomers), 1.11-1.22 (2 d, J=6.1, 3H, mixture of diastereoisomers), 1.46-1.67 (m, 2H), 3.53 (d, J=19.7, 1H), 3.70 (s, 3H), 3.86 (d, J=20.2, 1H), 4.21-4.31 (m, 1H), 4.62 (s, 2H), 5.99 (m, 1H), 6.73 (s, 1H), 6.82-6.89 (m, 2H), 7.01-7.06 (m, 3H), 7.29-7.35 (m, 4H), 12.87 (br. s., 1H).

Example 24

1-(4-Chloro-phenyl)-6-methoxy-2-(4-methoxy-phenyl)-7-propoxy-1,4-dihydro-2H-isoquinolin-3-one

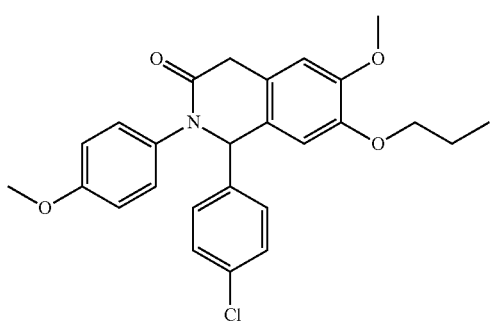 [SMILES: CCCOc1cc2c(cc1OC)CC(=O)N(c1ccc(OC)cc1)C2c1ccc(Cl)cc1]

To a solution of Intermediate 24.2 (25 mg, 0.061 mmol) in DMF (0.5 ml) were successively added Cs$_2$CO$_3$ (39.7 mg, 0.12 mmol) and 1-iodo-propane (0.015 ml, 0.15 mmol). The reaction mixture was heated at 50° C. and stirred for 3 h, then cooled to RT and partitioned between water and AcOEt. The organic phase was separated, dried over Na$_2$SO$_4$, filtered and evaporated to dryness. The resulting crude material was purified by reverse phase prep-HPLC (Waters system) to yield the title compound (12.2 mg, 0.027 mmol, 44%). HPLC: $^A t_{Ret}$=2.64 min; API-MS: m/z 452.2 [M+H]$^+$; $^1$H NMR (400 MHz, CD$_3$OD): 1.01 (t, J=7.3, 3H), 1.71-1.82 (m, 2H), 3.73 (d, J=20.3, 1H), 3.79 (s, 3H), 3.80-3.95 (m, 2H), 3.87 (s, 3H), 4.05 (d, J=20.3, 1H), 5.91 (s, 1H), 6.78 (s, 1H), 6.86-6.93 (m, 3H), 6.96-7.02 (m, 2H), 7.14-7.19 (m, 2H), 7.30 (m, 2H).

Intermediate 24.1: (4-Benzyloxy-3-methoxy-phenyl)-acetyl chloride

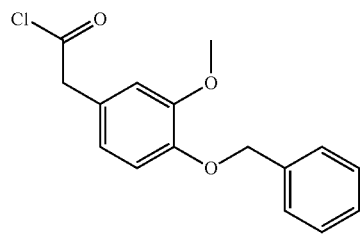 [SMILES: COc1cc(CC(=O)Cl)ccc1OCc1ccccc1]

The title intermediate (1.0 g, 3.44 mmol, quant.) was obtained as an orange oil from (4-benzyloxy-3-methoxy-phenyl)-acetic acid (937 mg, 3.44 mmol) analogously to Intermediate 1.3.

Intermediate 24.2: 1-(4-Chloro-phenyl)-7-hydroxy-6-methoxy-2-(4-methoxy-phenyl)-1,4-dihydro-2H-isoquinolin-3-one

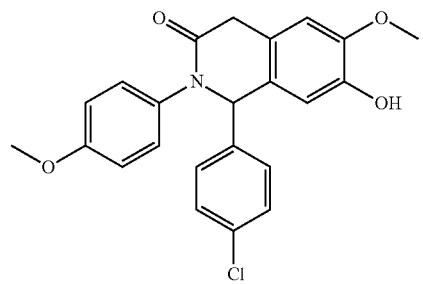

The title intermediate (681 mg, 1.66 mmol, 48%) was obtained as an off-white solid from Intermediate 20.1 (845 mg, 3.44 mmol) and Intermediate 24.1 (1.0 g, 3.44 mmol) analogously to Example 1. The benzyl protecting group was cleaved in-situ under the reaction conditions. Purification of the crude material was performed by Combi-Flash Companion™ (Isco Inc.) column chromatography (SiO$_2$; gradient elution, [heptane/DCM 1:1]/TBME containing 5% of formic acid 95:5→3:7). HPLC: $^A t_{Ret}$=2.07 min; API-MS: m/z 410.1 [M+H]$^+$; $^1$H NMR (400 MHz, DMSO-d$_6$): 3.56 (d, J=20.0, 1H), 3.70 (s, 3H), 3.74 (s, 3H), 3.90 (d, J=19.8, 1H), 5.92 (s, 1H), 6.70 (s, 1H), 6.77 (s, 1H), 6.81-6.87 (m, 2H), 6.95-7.01 (m, 2H), 7.22-7.27 (m, 2H), 7.28-7.34 (m, 2H), 8.91 (br. s., 1H).

Example 25

7-((R)-sec-Butoxy)-1-(4-chloro-phenyl)-6-methoxy-2-(4-methoxy-phenyl)-1,4-dihydro-2H-isoquinolin-3-one

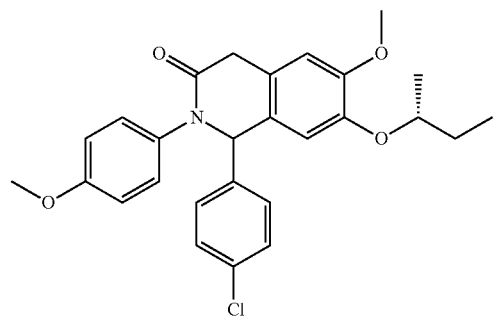 [SMILES: CC[C@@H](C)Oc1cc2c(cc1OC)CC(=O)N(c1ccc(OC)cc1)C2c1ccc(Cl)cc1]

To a solution of Intermediate 24.2 (200 mg, 0.49 mmol) in DCM (13 ml) were successively added (S)-butan-2-ol (0.054 ml, 0.59 mmol), supported PPh$_3$ (loading 1.52 mmol/g, 963 mg, 1.46 mmol) and DTAD (169 mg, 0.73 mmol). The reaction mixture was shaken at RT for 3 h, then filtered and the resin was washed with DCM. The filtrate was evaporated to dryness and the resulting residue was purified by Combi-Flash Companion™ (Isco Inc.) column chromatography (SiO$_2$; gradient elution, [heptane/DCM 1:1]/TBME 95:5→1:1) to yield the title compound (136 mg, 0.29 mmol, 60%) as a colorless foam. TLC: R$_F$=0.39 (heptane/DCM/TBME 1:1:2); HPLC: $^A$t$_{Ret}$=2.74 min; API-MS: m/z 466.2 [M+H]$^+$; NMR (400 MHz, CDCl$_3$): 0.93-1.03 (m, 3H, 2 diastereoisomers visible), 1.23-1.35 (m, 3H, 2 diastereoisomers visible), 1.59-1.69 (m, 1H), 1.71-1.84 (m, 1H), 3.74 (d, J=20.1, 1H), 3.81 (s, 3H), 3.85-3.94 (m, 4H), 4.14-4.24 (m, 1H), 5.70 (s, 1H), 6.67 (d, J=4.6, 1H), 6.71 (s, 1H), 6.84-6.91 (m, 2H), 6.99-7.10 (m, 4H), 7.23-7.28 (m, 2H).

Example 26

1-(4-Chloro-phenyl)-2-(4-dimethylamino-phenyl)-7-isopropoxy-6-methoxy-1,4-dihydro-2H-isoquinolin-3-one

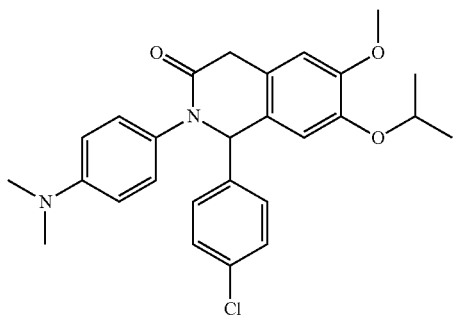

To a solution of Intermediate 26.3 (20 mg, 0.047 mmol) in DCM (1.5 ml) were successively added propan-2-ol (0.011 ml, 0.14 mmol), supported PPh$_3$ (loading 1.52 mmol/g, 93 mg, 0.14 mmol) and DTAD (32.7 mg, 0.14 mmol). The reaction mixture was shaken at RT for 14 h, then filtered and the resin was washed with DCM. The filtrate was evaporated to dryness and the resulting residue was purified by reverse phase prep-HPLC (Waters system) to yield the title compound (TFA salt, 17 mg, 0.029 mmol, 62%) as a colorless solid. HPLC: $^A$t$_{Ret}$=1.88 min; LC-MS: m/z 465.3 [M+H]$^+$; $^1$H NMR (400 MHz, DMSO-d$_6$): 1.19 (d, J=6.1, 3H), 1.24 (d, J=5.9, 3H), 2.89 (s, 6H), 3.58 (d, J=19.8, 1H), 3.73 (s, 3H), 3.91 (d, J=19.8, 1H), 4.45 (spt, J=5.9, 1H), 5.98 (s, 1H), 6.69-6.80 (m, 2H), 6.84 (s, 1H), 6.94-7.00 (m, 2H), 7.03 (s, 1H), 7.35 (s, 4H).

Intermediate 26.1: (4-Hydroxy-3-methoxy-phenyl)-acetic acid

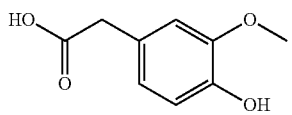

A mixture of (4-hydroxy-3-methoxy-phenyl)-acetic acid ethyl ester (2 g, 9.51 mmol) and LiOH monohydrate (1.2 g, 28.5 mmol) in MeOH (20 ml) and water (10 ml) was stirred at RT for 14 h. The reaction mixture was concentrated under vacuum, diluted into water and neutralized by the addition of HCl 2 M in water (14.3 ml). The resulting slurry was extracted with DCM (3×) and AcOEt (2×) and the combined organic fractions were dried over Na$_2$SO$_4$, filtered and evaporated to dryness to yield the crude title compound (1.67 g, 9.17 mmol, 96%) as a brownish solid, which was used in the next step without further purification. HPLC: $^A$t$_{Ret}$=0.77 min; LC-MS: m/z 183.4 [M+H]$^+$; NMR (400 MHz, DMSO-d$_6$): 3.43 (s, 2H), 3.74 (s, 3H), 6.61-6.66 (m, J=8.1, 2.0, 1H), 6.67-6.72 (m, 1H), 6.81 (d, J=2.0, 1H), 8.81 (s, 1H), 12.17 (s, 1H).

Intermediate 26.2: (4-Hydroxy-3-methoxy-phenyl)-acetyl chloride

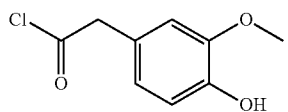

The title intermediate (1.78 g, 8.89 mmol, quant.) was obtained from Intermediate 26.1 (1.62 g, 8.89 mmol) analogously to Intermediate 1.3.

Intermediate 26.3: 1-(4-Chloro-phenyl)-2-(4-dimethylamino-phenyl)-7-hydroxy-6-methoxy-1,4-dihydro-2H-isoquinolin-3-one

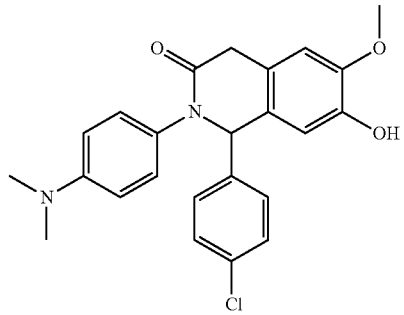 [SMILES: COc1cc2c(cc1O)C(c1ccc(Cl)cc1)N(c1ccc(N(C)C)cc1)C(=O)C2]

The title compound (1.35 g, 3.19 mmol, 36%) was obtained as a brownish solid from Intermediate 1.4 (2.3 g, 8.89 mmol) and Intermediate 26.2 (1.62 g, 8.9 mmol) analogously to Example 1. Purification of the crude material was performed by Combi-Flash Companion™ (Isco Inc.) column chromatography (SiO$_2$; gradient elution, [heptane/DCM 1:1]/TBME containing 5% of 7 M NH$_3$ in MeOH 95:5→4:6). TLC: R$_F$=0.16 (heptane/DCM/TBME containing 5% of 7 M NH$_3$ in MeOH 1:1:2); HPLC: $^A$t$_{Ret}$=1.44 min; LC-MS: m/z 423.2 [M+H]$^+$; $^1$H NMR (400 MHz, DMSO-d$_6$): 2.89 (s, 6H), 3.56 (d, J=20.1, 1H), 3.76 (s, 3H), 3.91 (d, J=19.8, 1H), 5.91 (s, 1H), 6.70-6.77 (m, 3H), 6.80 (s, 1H), 6.91-6.98 (m, 2H), 7.26-7.37 (m, 4H), 8.99 (br. s., 1H).

Example 27

Compounds 27aa to 27 bp were obtained from Intermediate 20.3 (or analogues prepared similarly) analogously to Example 20 or 21, from Intermediate 22.4 (or analogues prepared similarly) analogously to Example 22 or 23, from Intermediate 24.2 (or analogues prepared similarly) analogously to Example 24 or 25, or from Intermediate 26.3 (or analogues prepared similarly) analogously to Example 26.

| # | Structure | Name/HPLC/MS |
|---|---|---|
| 27aa | 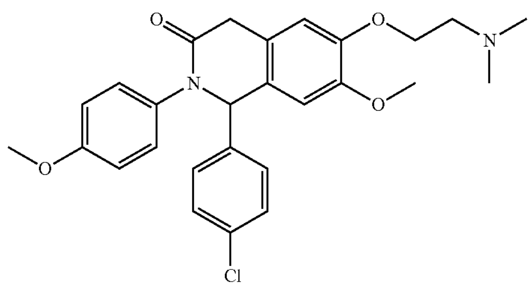 | 1-(4-Chloro-phenyl)-6-(2-dimethylamino-ethoxy)-7-methoxy-2-(4-methoxy-phenyl)-1,4-dihydro-2H-isoquinolin-3-one.<br>HPLC: $^{A}t_{Ret}$ = 1.65; API-MS: m/z 481.2 [M + H]$^+$. |
| 27ab[(1)] | | 1-(4-Chloro-phenyl)-6-(2-hydroxy-ethoxy)-7-methoxy-2-(4-methoxy-phenyl)-1,4-dihydro-2H-isoquinolin-3-one.<br>HPLC: $^{A}t_{Ret}$ = 1.99; API-MS: m/z 454.2 [M + H]$^+$. |
| 27ac | 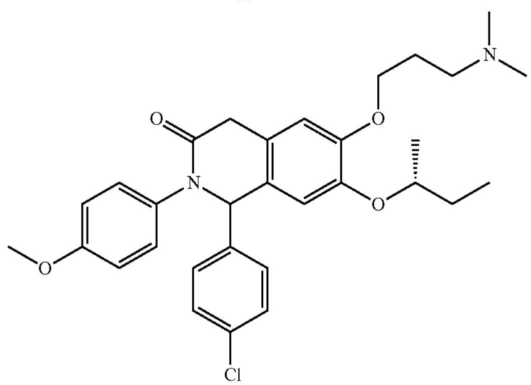 | 7-((R)-sec-Butoxy)-1-(4-chloro-phenyl)-6-(3-dimethylamino-propoxy)-2-(4-methoxy-phenyl)-1,4-dihydro-2H-isoquinolin-3-one.<br>HPLC: $^{A}t_{Ret}$ = 1.96; API-MS: m/z 537.2 [M + H]$^+$. |
| 27ad | 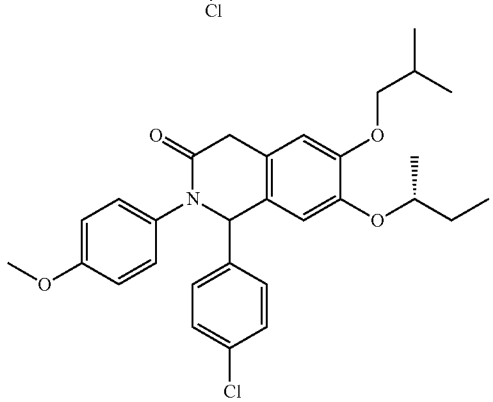 | 7-((R)-sec-Butoxy)-1-(4-chloro-phenyl)-6-isobutoxy-2-(4-methoxy-phenyl)-1,4-dihydro-2H-isoquinolin-3-one.<br>HPLC: $^{A}t_{Ret}$ = 3.29; API-MS: m/z 509.7 [M + H]$^+$. |
| 27ae | 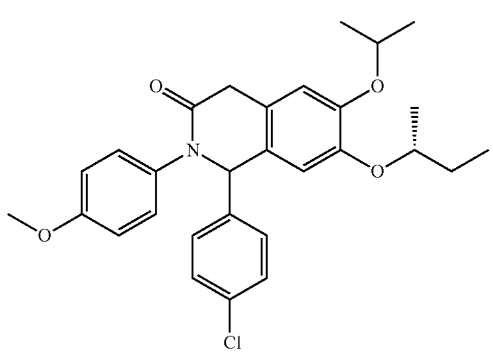 [SMILES: CC[C@@H](C)Oc1cc2c(cc1OC(C)C)CC(=O)N(c1ccc(OC)cc1)C2c1ccc(Cl)cc1] | 7-((R)-sec-Butoxy)-1-(4-chloro-phenyl)-6-isopropoxy-2-(4-methoxy-phenyl)-1,4-dihydro-2H-isoquinolin-3-one.<br>HPLC: $^{A}t_{Ret}$ = 3.06; API-MS: m/z 494.2 [M + H]$^+$. |

| # | Structure | Name/HPLC/MS |
|---|---|---|
| 27af | 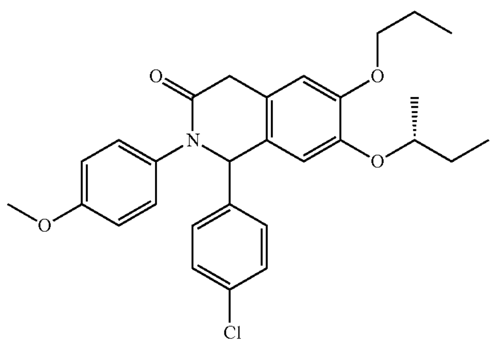 [SMILES: CCCOc1cc2c(cc1O[C@H](C)CC)C(c1ccc(Cl)cc1)N(c1ccc(OC)cc1)C(=O)C2] | 7-((R)-sec-Butoxy)-1-(4-chloro-phenyl)-2-(4-methoxy-phenyl)-6-propoxy-1,4-dihydro-2H-isoquinolin-3-one.<br>HPLC: $^A t_{Ret}$ = 3.13; API-MS: m/z 494.3 [M + H]$^+$. |
| 27ag | 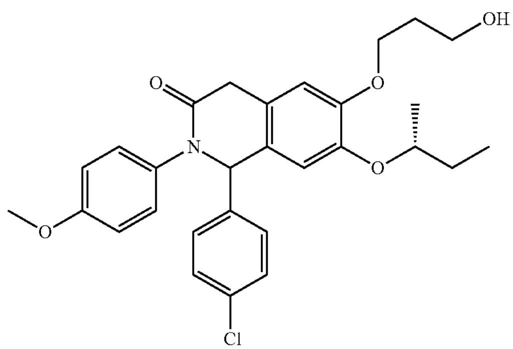 [SMILES: CC[C@@H](C)Oc1cc2c(cc1OCCCO)CC(=O)N(c1ccc(OC)cc1)C2c1ccc(Cl)cc1] | 7-((R)-sec-Butoxy)-1-(4-chloro-phenyl)-6-(3-hydroxy-propoxy)-2-(4-methoxy-phenyl)-1,4-dihydro-2H-isoquinolin-3-one.<br>HPLC: $^A t_{Ret}$ = 2.48; API-MS: m/z 510.2 [M + H]$^+$. |
| 27ah | 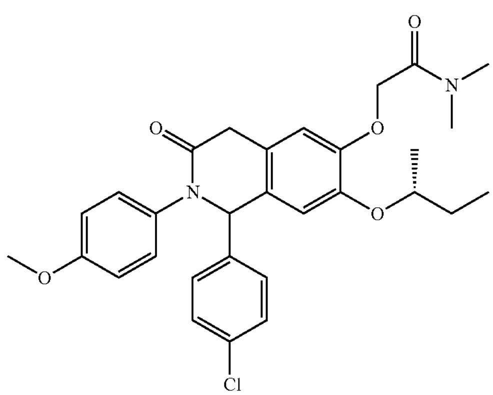 | 2-[7-((R)-sec-Butoxy)-1-(4-chloro-phenyl)-2-(4-methoxy-phenyl)-3-oxo-1,2,3,4-tetrahydro-isoquinolin-6-yloxy]-N,N-dimethyl-acetamide.<br>HPLC: $^A t_{Ret}$ = 2.45; API-MS: m/z 538.5 [M + H]$^+$. |
| 27ai | 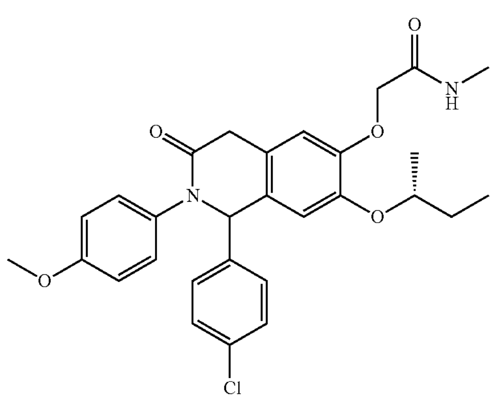 | 2-[7-((R)-sec-Butoxy)-1-(4-chloro-phenyl)-2-(4-methoxy-phenyl)-3-oxo-1,2,3,4-tetrahydro-isoquinolin-6-yloxy]-N-methyl-acetamide.<br>HPLC: $^A t_{Ret}$ = 2.41; API-MS: m/z 524.5 [M + H]$^+$. |

-continued

| # | Structure | Name/HPLC/MS |
|---|---|---|
| 27aj | 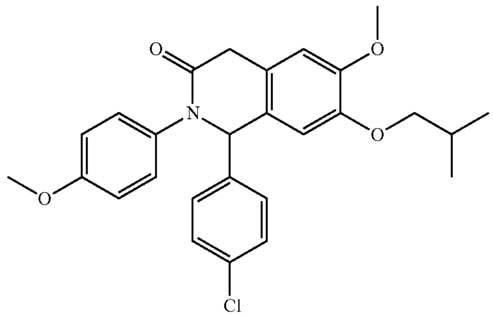 | 1-(4-Chloro-phenyl)-7-isobutoxy-6-methoxy-2-(4-methoxy-phenyl)-1,4-dihydro-2H-isoquinolin-3-one. HPLC: $^A$t$_{Ret}$ = 2.84; API-MS: m/z 466.2 [M + H]$^+$. |
| 27ak | 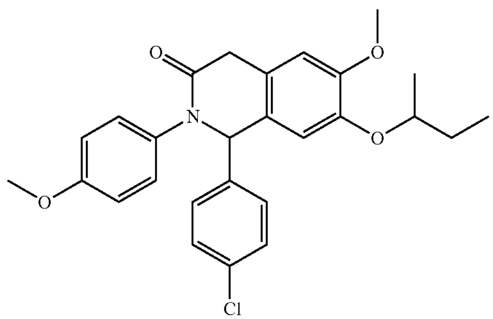 | 7-sec-Butoxy-1-(4-chloro-phenyl)-6-methoxy-2-(4-methoxy-phenyl)-1,4-dihydro-2H-isoquinolin-3-one. HPLC: $^A$t$_{Ret}$ = 2.76; API-MS: m/z 466.2 [M + H]$^+$. |
| 27al | 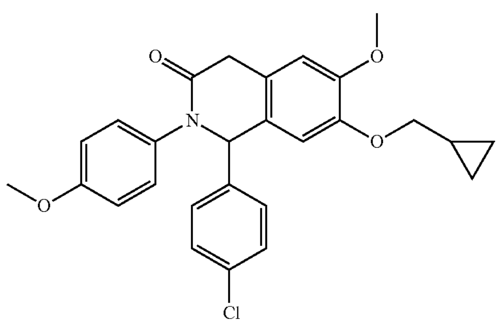 [SMILES: COc1ccc(N2C(=O)Cc3cc(OC)c(OCC4CC4)cc3C2c2ccc(Cl)cc2)cc1] | 1-(4-Chloro-phenyl)-7-cyclopropylmethoxy-6-methoxy-2-(4-methoxy-phenyl)-1,4-dihydro-2H-isoquinolin-3-one. HPLC: $^A$t$_{Ret}$ = 2.61; API-MS: m/z 464.2 [M + H]$^+$. |
| 27am | 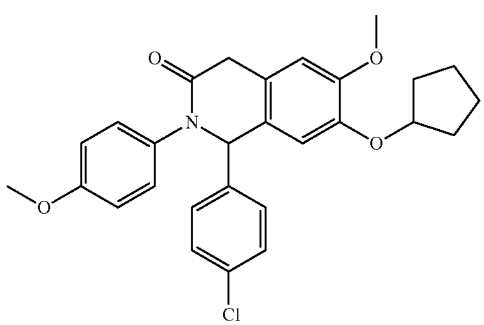 [SMILES: COc1ccc(N2C(=O)Cc3cc(OC)c(OC4CCCC4)cc3C2c2ccc(Cl)cc2)cc1] | 1-(4-Chloro-phenyl)-7-cyclopentyloxy-6-methoxy-2-(4-methoxy-phenyl)-1,4-dihydro-2H-isoquinolin-3-one. HPLC: $^A$t$_{Ret}$ = 2.81; API-MS: m/z 478.2 [M + H]$^+$. |
| 27an | 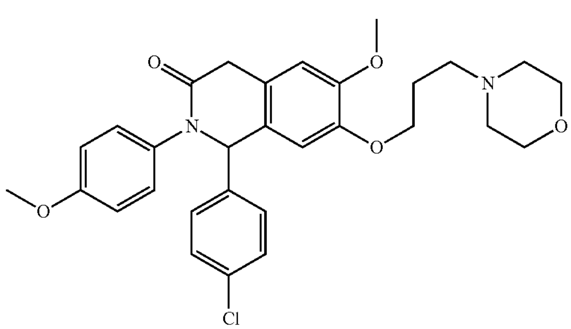 [SMILES: COc1ccc(N2C(=O)Cc3cc(OC)c(OCCCN4CCOCC4)cc3C2c2ccc(Cl)cc2)cc1] | 1-(4-Chloro-phenyl)-6-methoxy-2-(4-methoxy-phenyl)-7-(3-morpholin-4-yl-propoxy)-1,4-dihydro-2H-isoquinolin-3-one. HPLC: $^A$t$_{Ret}$ = 1.61; API-MS: m/z 538.6 [M + H]$^+$. |

-continued

| # | Structure | Name/HPLC/MS |
|---|---|---|
| 27ao | 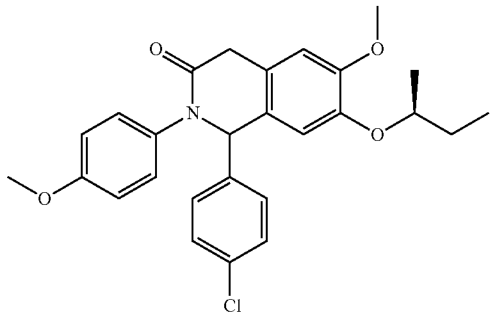 | 7-((S)-sec-Butoxy)-1-(4-chloro-phenyl)-6-methoxy-2-(4-methoxy-phenyl)-1,4-dihydro-2H-isoquinolin-3-one.<br>HPLC: $^A t_{Ret}$ = 2.73; API-MS: m/z 466.2 [M + H]$^+$. |
| 27ap | 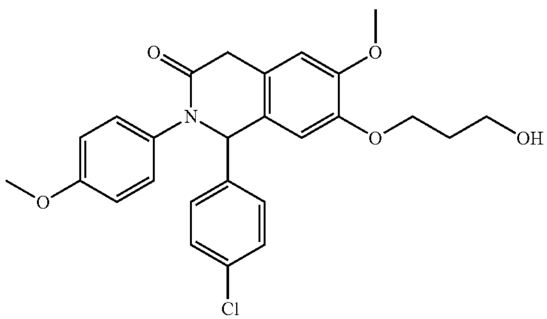 [SMILES: COc1ccc(N2C(=O)Cc3cc(OC)c(OCCCO)cc3C2c2ccc(Cl)cc2)cc1] | 1-(4-Chloro-phenyl)-7-(3-hydroxy-propoxy)-6-methoxy-2-(4-methoxy-phenyl)-1,4-dihydro-2H-isoquinolin-3-one.<br>HPLC: $^A t_{Ret}$ = 1.99; API-MS: m/z 468.2 [M + H]$^+$. |
| 27aq | 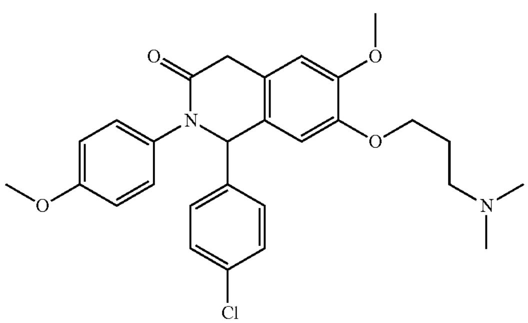 | 1-(4-Chloro-phenyl)-7-(3-dimethylamino-propoxy)-6-methoxy-2-(4-methoxy-phenyl)-1,4-dihydro-2H-isoquinolin-3-one.<br>HPLC: $^A t_{Ret}$ = 1.61; API-MS: m/z 495.2 [M + H]$^+$. |
| 27r | 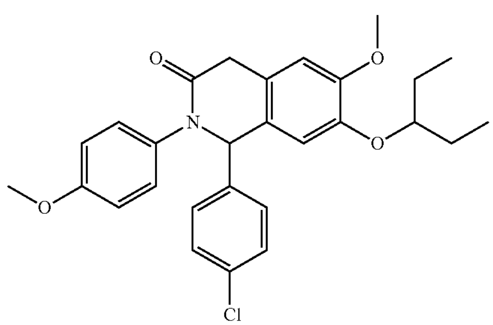 [SMILES: CCC(CC)Oc1cc2c(cc1OC)CC(=O)N(c1ccc(OC)cc1)C2c1ccc(Cl)cc1] | 1-(4-Chloro-phenyl)-7-(1-ethyl-propoxy)-6-methoxy-2-(4-methoxy-phenyl)-1,4-dihydro-2H-isoquinolin-3-one.<br>HPLC: $^A t_{Ret}$ = 2.88; API-MS: m/z 480.2 [M + H]$^+$. |
| 27as | 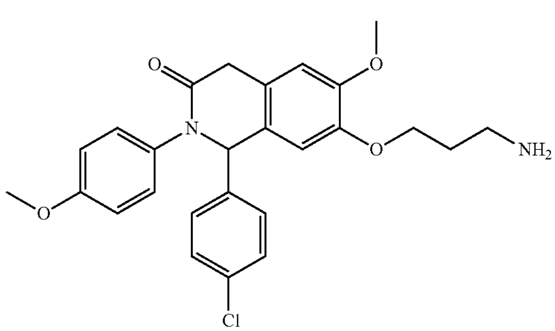 [SMILES: COc1ccc(N2C(=O)Cc3cc(OC)c(OCCCN)cc3C2c2ccc(Cl)cc2)cc1] | 7-(3-Amino-propoxy)-1-(4-chloro-phenyl)-6-methoxy-2-(4-methoxy-phenyl)-1,4-dihydro-2H-isoquinolin-3-one.<br>HPLC: $^A t_{Ret}$ = 1.57; API-MS: m/z 467.2 [M + H]$^+$. |

-continued

| # | Structure | Name/HPLC/MS |
|---|---|---|
| 27at | 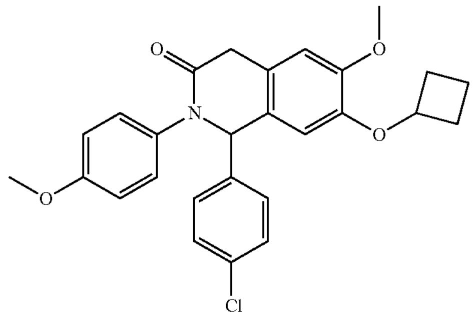 [SMILES: COc1ccc(N2C(=O)Cc3cc(OC)c(OC4CCC4)cc3C2c2ccc(Cl)cc2)cc1] | 1-(4-Chloro-phenyl)-7-cyclobutoxy-6-methoxy-2-(4-methoxy-phenyl)-1,4-dihydro-2H-isoquinolin-3-one.<br>HPLC: $^A t_{Ret}$ = 2.63; API-MS: m/z 464.2 [M + H]$^+$. |
| 27au | 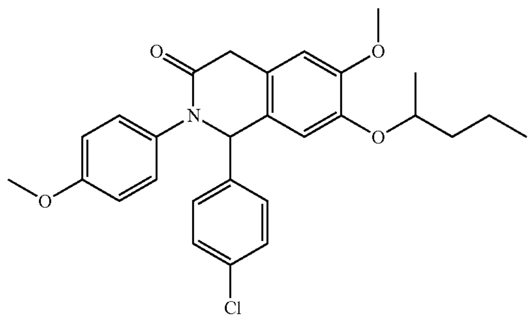 [SMILES: CCCC(C)Oc1cc2c(cc1OC)CC(=O)N(c1ccc(OC)cc1)C2c1ccc(Cl)cc1] | 1-(4-Chloro-phenyl)-6-methoxy-2-(4-methoxy-phenyl)-7-(1-methyl-butoxy)-1,4-dihydro-2H-isoquinolin-3-one.<br>HPLC: $^A t_{Ret}$ = 2.90; API-MS: m/z 480.2 [M + H]$^+$. |
| 27av | 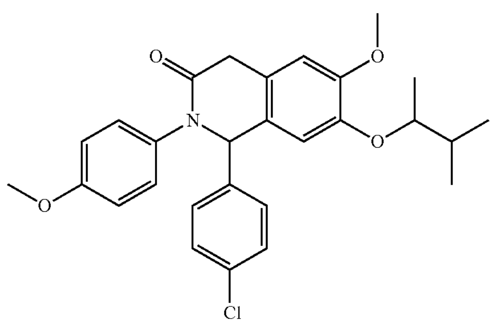 [SMILES: COc1ccc(N2C(=O)Cc3cc(OC)c(OC(C)C(C)C)cc3C2c2ccc(Cl)cc2)cc1] | 1-(4-Chloro-phenyl)-7-(1,2-dimethyl-propoxy)-6-methoxy-2-(4-methoxy-phenyl)-1,4-dihydro-2H-isoquinolin-3-one.<br>HPLC: $^A t_{Ret}$ = 2.92; API-MS: m/z 480.2 [M + H]$^+$. |
| 27aw | 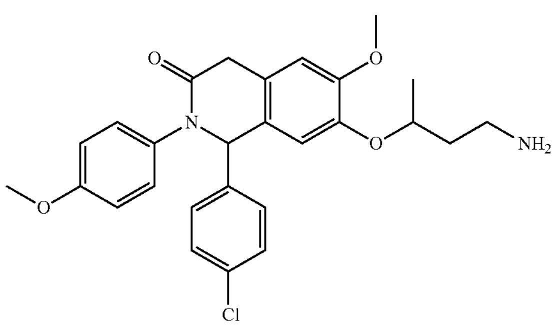 [SMILES: COc1ccc(N2C(=O)Cc3cc(OC)c(OC(C)CCN)cc3C2c2ccc(Cl)cc2)cc1] | 7-(3-Amino-1-methyl-propoxy)-1-(4-chloro-phenyl)-6-methoxy-2-(4-methoxy-phenyl)-1,4-dihydro-2H-isoquinolin-3-one.<br>HPLC: $^A t_{Ret}$ = 1.64; API-MS: m/z 481.3 [M + H]$^+$. |
| 27ax | 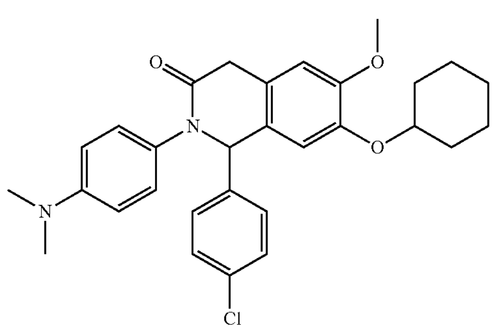 [SMILES: COc1cc2c(cc1OC1CCCCC1)C(c1ccc(Cl)cc1)N(c1ccc(N(C)C)cc1)C(=O)C2] | 1-(4-Chloro-phenyl)-7-cyclohexyloxy-2-(4-dimethylamino-phenyl)-6-methoxy-1,4-dihydro-2H-isoquinolin-3-one.<br>HPLC: $^A t_{Ret}$ = 2.22; LC-MS: m/z 505.3 [M + H]$^+$. |

-continued

| # | Structure | Name/HPLC/MS |
|---|---|---|
| 27ay | 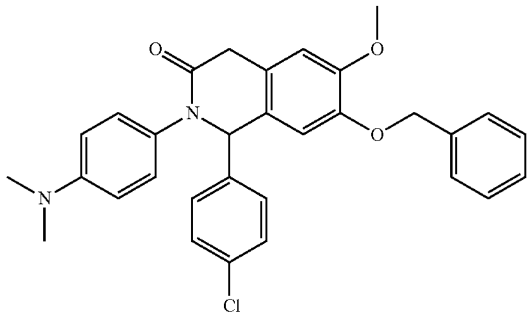 [SMILES: COc1cc2c(cc1OCc1ccccc1)C(c1ccc(Cl)cc1)N(c1ccc(N(C)C)cc1)C(=O)C2] | 7-Benzyloxy-1-(4-chloro-phenyl)-2-(4-dimethylamino-phenyl)-6-methoxy-1,4-dihydro-2H-isoquinolin-3-one.<br>HPLC: $^{A}t_{Ret}$ = 2.07; LC-MS: m/z 513.3 [M + H]$^{+}$. |
| 27az | 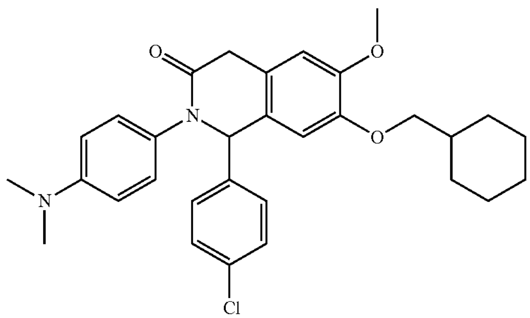 [SMILES: COc1cc2c(cc1OCC1CCCCC1)C(c1ccc(Cl)cc1)N(c1ccc(N(C)C)cc1)C(=O)C2] | 1-(4-Chloro-phenyl)-7-cyclohexylmethoxy-2-(4-dimethylamino-phenyl)-6-methoxy-1,4-dihydro-2H-isoquinolin-3-one.<br>HPLC: $^{A}t_{Ret}$ = 2.45; LC-MS: m/z 519.3 [M + H]$^{+}$. |
| 27ba | 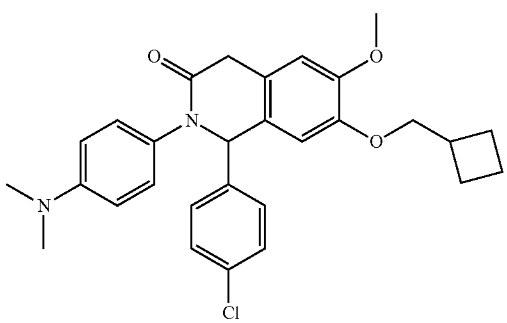 [SMILES: COc1cc2c(cc1OCC1CCC1)C(c1ccc(Cl)cc1)N(c1ccc(N(C)C)cc1)C(=O)C2] | 1-(4-Chloro-phenyl)-7-cyclobutylmethoxy-2-(4-dimethylamino-phenyl)-6-methoxy-1,4-dihydro-2H-isoquinolin-3-one.<br>HPLC: $^{A}t_{Ret}$ = 2.17; LC-MS: m/z 491.3 [M + H]$^{+}$. |
| 27bb | 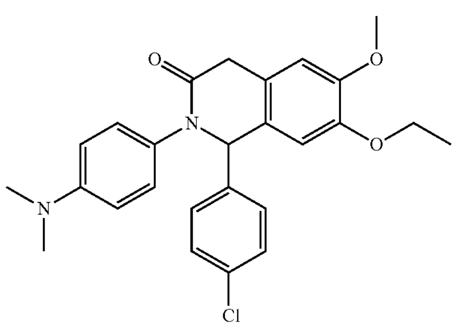 | 1-(4-Chloro-phenyl)-2-(4-dimethylamino-phenyl)-7-ethoxy-6-methoxy-1,4-dihydro-2H-isoquinolin-3-one.<br>HPLC: $^{A}t_{Ret}$ = 1.76; LC-MS: m/z 451.3 [M + H]$^{+}$. |
| 27bc | 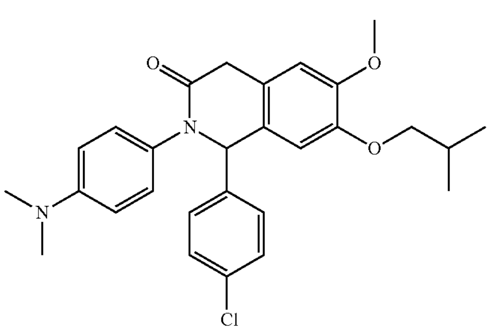 [SMILES: COc1cc2c(cc1OCC(C)C)C(c1ccc(Cl)cc1)N(c1ccc(N(C)C)cc1)C(=O)C2] | 1-(4-Chloro-phenyl)-2-(4-dimethylamino-phenyl)-7-isobutoxy-6-methoxy-1,4-dihydro-2H-isoquinolin-3-one.<br>HPLC: $^{A}t_{Ret}$ = 2.13; LC-MS: m/z 479.3 [M + H]$^{+}$. |

-continued

| # | Structure | Name/HPLC/MS |
|---|---|---|
| 27bd | 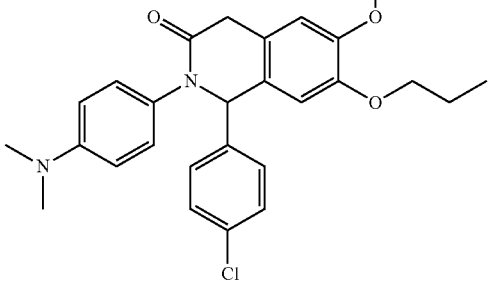 | 1-(4-Chloro-phenyl)-2-(4-dimethylamino-phenyl)-6-methoxy-7-propoxy-1,4-dihydro-2H-isoquinolin-3-one.<br>HPLC: $^A t_{Ret}$ = 1.96; LC-MS: m/z 465.3 [M + H]$^+$. |
| 27be | 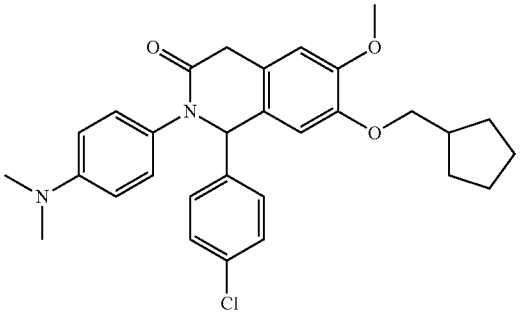 [SMILES: COc1cc2c(cc1OCC1CCCC1)C(c1ccc(Cl)cc1)N(c1ccc(N(C)C)cc1)C(=O)C2] | 1-(4-Chloro-phenyl)-7-cyclopentylmethoxy-2-(4-dimethylamino-phenyl)-6-methoxy-1,4-dihydro-2H-isoquinolin-3-one.<br>HPLC: $^A t_{Ret}$ = 2.31; LC-MS: m/z 505.3 [M + H]$^+$. |
| 27bf | 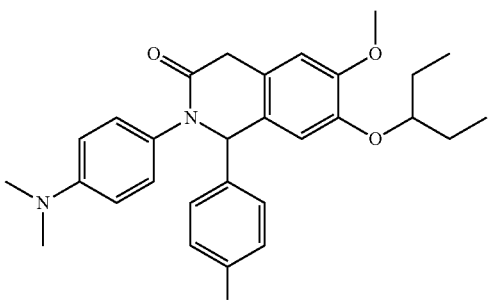 | 1-(4-Chloro-phenyl)-2-(4-dimethylamino-phenyl)-7-(1-ethyl-propoxy)-6-methoxy-1,4-dihydro-2H-isoquinolin-3-one.<br>HPLC: $^A t_{Ret}$ = 2.17; LC-MS: m/z 493.3 [M + H]$^+$. |
| 27bg | 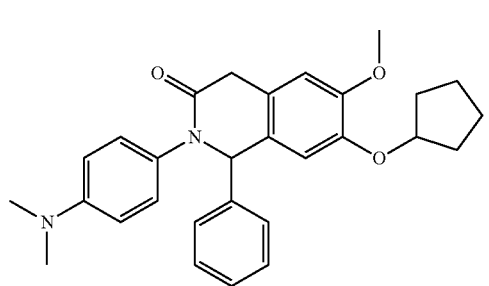 | 1-(4-Chloro-phenyl)-7-cyclopentyloxy-2-(4-dimethylamino-phenyl)-6-methoxy-1,4-dihydro-2H-isoquinolin-3-one.<br>HPLC: $^A t_{Ret}$ = 2.08; LC-MS: m/z 491.2 [M + H]$^+$. |
| 27bh | 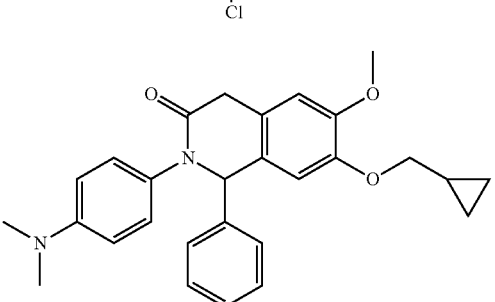 | 1-(4-Chloro-phenyl)-7-cyclopropylmethoxy-2-(4-dimethylamino-phenyl)-6-methoxy-1,4-dihydro-2H-isoquinolin-3-one.<br>HPLC: $^A t_{Ret}$ = 1.92; LC-MS: m/z 477.3 [M + H]$^+$. |

-continued

| # | Structure | Name/HPLC/MS |
|---|---|---|
| 27bi | 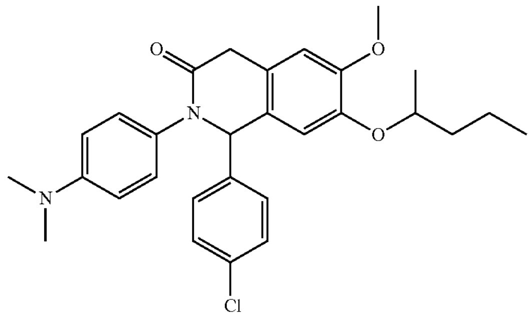 [SMILES: CCCC(C)Oc1cc2c(cc1OC)CC(=O)N(c1ccc(N(C)C)cc1)C2c1ccc(Cl)cc1] | 1-(4-Chloro-phenyl)-2-(4-dimethylamino-phenyl)-6-methoxy-7-(1-methyl-butoxy)-1,4-dihydro-2H-isoquinolin-3-one.<br>HPLC: $^A t_{Ret}$ = 2.19; LC-MS: m/z 493.3 [M + H]$^+$. |
| 27bj | 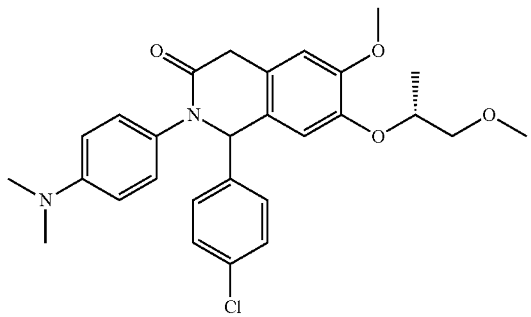 | 1-(4-Chloro-phenyl)-2-(4-dimethylamino-phenyl)-6-methoxy-7-((R)-2-methoxy-1-methyl-ethoxy)-1,4-dihydro-2H-isoquinolin-3-one.<br>HPLC: $^A t_{Ret}$ = 1.77; LC-MS: m/z 495.3 [M + H]$^+$. |
| 27bk | 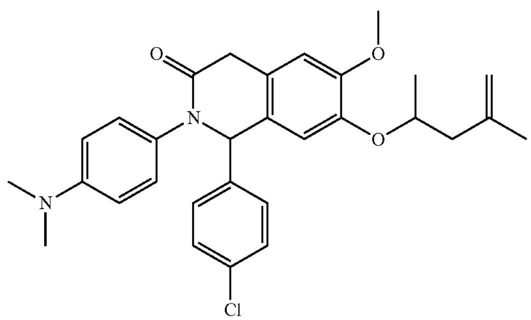 [SMILES: C=C(C)CC(C)Oc1cc2c(cc1OC)CC(=O)N(c1ccc(N(C)C)cc1)C2c1ccc(Cl)cc1] | 1-(4-Chloro-phenyl)-2-(4-dimethylamino-phenyl)-7-(1,3-dimethyl-but-3-enyloxy)-6-methoxy-1,4-dihydro-2H-isoquinolin-3-one.<br>HPLC: $^A t_{Ret}$ = 2.21; LC-MS: m/z 505.3 [M + H]$^+$. |
| 27bl | 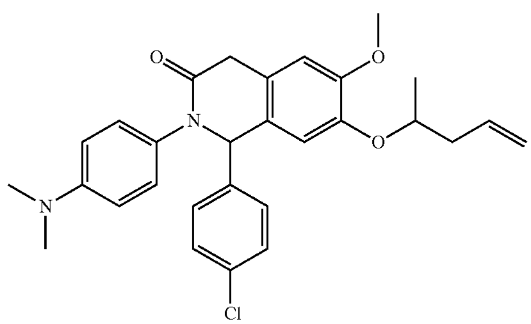 [SMILES: C=CCC(C)Oc1cc2c(cc1OC)CC(=O)N(c1ccc(N(C)C)cc1)C2c1ccc(Cl)cc1] | 1-(4-Chloro-phenyl)-2-(4-dimethylamino-phenyl)-6-methoxy-7-(1-methyl-but-3-enyloxy)-1,4-dihydro-2H-isoquinolin-3-one.<br>HPLC: $^A t_{Ret}$ = 2.09; LC-MS: m/z 491.3 [M + H]$^+$. |
| 27bm | 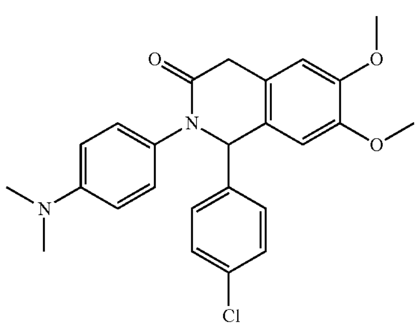 | 1-(4-Chloro-phenyl)-2-(4-dimethylamino-phenyl)-6,7-dimethoxy-1,4-dihydro-2H-isoquinolin-3-one.<br>HPLC: $^A t_{Ret}$ = 1.61; LC-MS: m/z 437.4 [M + H]$^+$. |

| # | Structure | Name/HPLC/MS |
|---|---|---|
| 27bn | 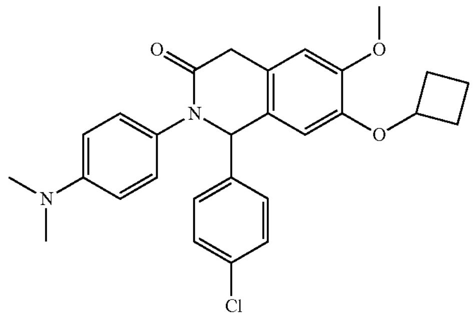 [SMILES: COc1cc2c(cc1OC1CCC1)C(c1ccc(Cl)cc1)N(c1ccc(N(C)C)cc1)C(=O)C2] | 1-(4-Chloro-phenyl)-7-cyclobutoxy)-2-(4-dimethylamino-phenyl)-6-methoxy-1,4-dihydro-2H-isoquinolin-3-one.<br>HPLC: $^A t_{Ret}$ = 1.96; LC-MS: m/z 477.4 [M + H]$^+$. |
| 27bo | 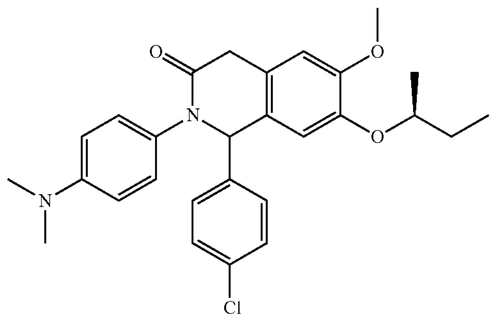 | 7-((S)-sec-Butoxy)-1-(4-chloro-phenyl)-2-(4-dimethylamino-phenyl)-6-methoxy-1,4-dihydro-2H-isoquinolin-3-one.<br>HPLC: $^A t_{Ret}$ = 2.04; LC-MS: m/z 479.4 [M + H]$^+$. |
| 27bp | 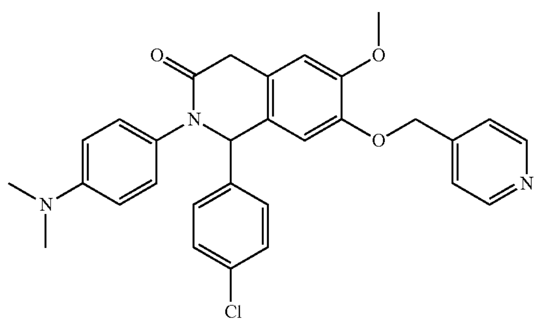 [SMILES: COc1cc2c(cc1OCc1ccncc1)C(c1ccc(Cl)cc1)N(c1ccc(N(C)C)cc1)C(=O)C2] | 1-(4-Chloro-phenyl)-2-(4-dimethylamino-phenyl)-6-methoxy-7-(pyridin-4-ylmethoxy)-1,4-dihydro-2H-isoquinolin-3-one.<br>HPLC: $^A t_{Ret}$ = 1.22; LC-MS: m/z 514.3 [M + H]$^+$. |

(1)The title compound (11.8 mg, 0.021 mmol, 57% over 2 steps) was obtained from Intermediate 20.3 (15 mg, 0.037 mmol) following the same 2 steps sequence as described for Example 15l. Purification of the crude material was performed by reverse phase prep-HPLC (Waters system).

Example 28

1-(4-Chloro-phenyl)-7-isopropylamino-2-[4-(methyl-pyridin-4-ylmethyl-amino)-phenyl]-1,4-dihydro-2H-isoquinolin-3-one

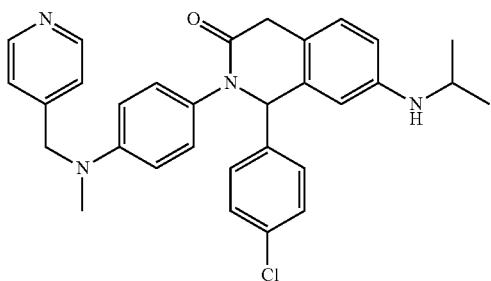 [SMILES: CC(C)Nc1ccc2c(c1)C(c1ccc(Cl)cc1)N(c1ccc(N(C)Cc3ccncc3)cc1)C(=O)C2]

To a solution of Intermediate 28.9 (400 mg, 0.85 mmol) in DCM (5 ml) were successively added AcOH (0.176 ml, 3.07 mmol), acetone (0.125 ml, 1.71 mmol) and NaBH(OAc)$_3$ (651 mg, 3.07 mmol) at RT. The reaction mixture was stirred at RT for 4 h then diluted with DCM and washed with a 2M aqueous Na$_2$CO$_3$ solution (2×). The organic phase was dried over Na$_2$SO$_4$, filtered and evaporated to dryness. The resulting crude material was purified by Combi-Flash Companion™ (Isco Inc.) column chromatography (SiO$_2$; gradient elution, DCM/MeOH 99.5:0.5→9:1) to yield the title compound (392 mg, 0.77 mmol, 90%) as a brownish resin. TLC: R$_F$=0.41 (DCM/MeOH 9:1); HPLC: $^A t_{Ret}$=1.30 min; LC-MS: m/z 511.3 [M+H]$^+$; $^1$H NMR (400 MHz, DMSO-d$_6$): 1.03-1.13 (2 d, J=6.2, 6H), 3.03 (s, 3H), 3.40-3.55 (m, 2H), 3.77 (d, J=19.6, 1H), 4.58 (s, 2H), 5.34 (d, J=8.1, 1H), 5.87 (s, 1H), 6.47 (dd, J=8.2, 2.1, 1H), 6.56-6.64 (m, 3H), 6.87-6.94 (m, 3H), 7.15-7.20 (m, 2H), 7.28-7.38 (m, 4H), 8.45-8.50 (m, 2H).

Intermediate 28.1: (2-Chloro-5-nitro-phenyl)-(4-chloro-phenyl)-methanol

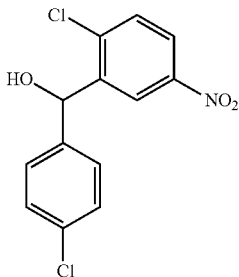 [SMILES: O=[N+]([O-])c1ccc(Cl)c(C(O)c2ccc(Cl)cc2)c1]

To a solution of (4-chlorophenyl)magnesium bromide (1M in Et$_2$O, 81 ml, 81 mmol) in THF (200 ml) was added drop wise a solution of 2-chloro-5-nitrobenzaldehyde (10 g, 53.9 mmol) in THF (100 ml) at −78° C. (dry ice/acetone bath). After the addition, the reaction mixture was further stirred at −78° C. for 1 h then 10 min at 0° C. (ice bath). A saturated aqueous NH$_4$Cl solution (400 ml) was added and the resulting mixture was extracted with AcOEt (2×400 ml). The combined organic layers were washed with brine then dried over Na$_2$SO$_4$, filtered and evaporated to dryness. The resulting crude material was purified by Combi-Flash Companion™ (Isco Inc.) column chromatography (SiO$_2$; gradient elution, heptane/TBME 95:5→6:4) to yield the title compound (14.4 g, 48.4 mmol, 90%) as a beige solid. TLC: R$_F$=0.80 (heptane/DCM/TBME 1:1:2); HPLC: $^A$t$_{Ret}$=2.43 min; LC-MS: m/z not detected; $^1$H NMR (400 MHz, CDCl$_3$): 6.20 (s, 1H), 7.36 (s, 4H), 7.53 (d, J=8.6, 1H), 8.13 (dd, J=8.8, 2.9, 1H), 8.66 (d, J=2.7, 1H).

Intermediate 28.2: (2-Chloro-5-nitro-phenyl)-(4-chloro-phenyl)-methanone

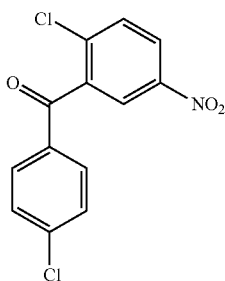 [SMILES: O=C(c1ccc(Cl)cc1)c1cc([N+](=O)[O-])ccc1Cl]

To a solution of Intermediate 28.1 (14.07 g, 47.2 mmol) in DCM (236 ml) was added PDC (26.6 g, 70.8 mmol) in one portion at RT and the resulting suspension was vigorously stirred at RT for 14 h. The reaction mixture was filtered through a Celite pad, the solids were washed with DCM and the filtrate evaporated to dryness. The resulting crude material was purified by Combi-Flash Companion™ (Isco Inc.) column chromatography (gradient elution, heptane/AcOEt 95:5 to 9:1) to yield the title compound (11.7 g, 39.5 mmol, 84%) as an orange viscous oil. TLC: R$_F$=0.47 (heptane/AcOEt 4:1); HPLC: $^A$t$_{Ret}$=2.64 min; LC-MS: m/z 296.5 [M+H]$^+$; $^1$H NMR (400 MHz, CDCl$_3$): 7.51 (m, 2H), 7.65-7.81 (m, 3H), 8.23-8.39 (m, 2H).

Intermediate 28.3: [2-(4-Chloro-benzoyl)-4-nitro-phenyl]-acetic acid methyl ester

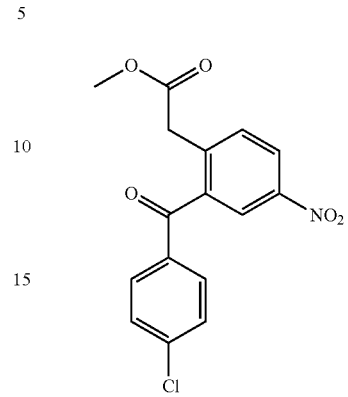

To a suspension of NaH (60% in mineral oil, 3.46 g, 86 mmol) in DMSO was slowly added tert-butylmethylmalonate (14.6 ml, 86 mmol) at 0° C. (ice bath). After the addition, the reaction mixture was heated at 60° C. and stirred for 30 min then cooled to RT. A solution of Intermediate 28.2 (11.63 g, 39.3 mmol) in DMSO (40 ml) was added, then the mixture was heated again at 60° C. and stirred for 1 h30. The reaction mixture was cooled to RT then diluted into Et$_2$O and washed with brine. The organic layer was dried over Na$_2$SO$_4$, filtered and evaporated to dryness. The resulting reddish oil was dissolved in DCM (30 ml) and TFA (30 ml) was slowly added at RT (Warning: important gas evolution occurred!). The reaction mixture was stirred at RT for 30 min then concentrated under vacuum. The resulting crude material was purified by Combi-Flash Companion™ (Isco Inc.) column chromatography (gradient elution, heptane/TBME 95:5 to 100% TBME) to yield the title compound (13.7 g, 39.4 mmol, quant.) as an off-white solid. TLC: R$_F$=0.36 (heptane/TBME 1:1); HPLC: $^A$t$_{Ret}$=2.42 min; LC-MS: m/z 334.4 [M+H]$^+$; $^1$H NMR (400 MHz, DMSO-d$_6$): 3.48 (s, 3H), 4.01 (s, 2H), 7.62-7.69 (m, 2H), 7.74-7.83 (m, 3H), 8.19 (d, J=2.4, 1H), 8.42 (dd, J=8.4, 2.6, 1H).

Intermediate 28.4: [2-(4-Chloro-benzoyl)-4-nitro-phenyl]-acetic acid

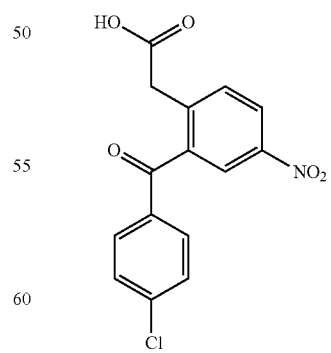

A suspension of Intermediate 28.3 (13.7 g, 39.4 mmol) and LiOH monohydrate (8.64 g, 206 mmol) in MeOH (100 ml) and water (50 ml) was stirred at RT for 1 h then concentrated under vacuum. The resulting residue was diluted with water and neutralized by the addition of 2M HCl in water. The resulting precipitate was filtered, washed with water, and dissolved in DCM. The organic fraction was dried over $Na_2SO_4$, filtered and evaporated to dryness to yield the crude title compound (10.16 g, 31.8 mmol, 81%) as a beige solid. HPLC: $^At_{Ret}$=2.06 min; LC-MS: m/z 320.5 [M+H]$^+$.

Intermediate 28.5: {2-[Chloro-(4-chloro-phenyl)-methyl]-4-nitro-phenyl}-acetic acid ethyl ester

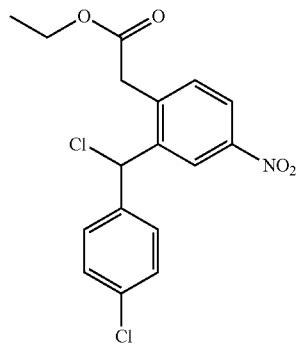 [SMILES: CCOC(=O)Cc1ccc([N+](=O)[O-])cc1C(Cl)c1ccc(Cl)cc1]

To a suspension of Intermediate 28.4 (2.5 g, 7.82 mmol) in EtOH (40 ml) was added $NaBH_4$ (888 mg, 23.46 mmol) at RT (Warning: important gaz evolution occurred!). The resulting red solution was stirred at RT for 15 min then cooled to 0° C. (ice bath) before $SOCl_2$ (8.56 ml, 117 mmol) was cautiously added. The resulting slurry was stirred at 0° C. for 30 min then concentrated under vacuum. The resulting residue was diluted with AcOEt and washed with a 2M aqueous $Na_2CO_3$ solution (2×). The organic phase was dried over $Na_2SO_4$, filtered and evaporated to dryness. The resulting crude material was purified by Combi-Flash Companion™ (Isco Inc.) column chromatography (gradient elution, heptane/AcOEt 95:5 to 1:1) to yield the title compound (2.5 g, 6.79 mmol, 87%) as a yellow oil which crystallized on standing into a yellow solid. TLC: $R_F$=0.63 (heptane 15/AcOEt 1:1); HPLC: $^At_{Ret}$=2.85 min; $^1$H NMR (400 MHz, DMSO-d$_6$): 1.09 (t, J=7.2, 3H), 3.81-4.04 (m, 4H), 6.91 (s, 1H), 7.40-7.50 (m, 4H), 7.61 (d, J=8.6, 1H), 8.21 (dd, J=8.3, 2.2, 1H), 8.34 (d, J=2.0, 1H).

Intermediate 28.6:
Methyl-(4-nitro-phenyl)-pyridin-4-ylmethyl-amine

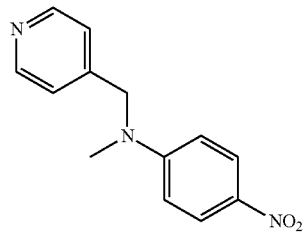 [SMILES: CN(Cc1ccncc1)c1ccc([N+](=O)[O-])cc1]

To a solution of N-methyl-4-nitroaniline (5 g, 32.9 mmol) in DMF (75 ml) was slowly added NaH (60% in mineral oil, 4.21 g, 105 mmol) at RT (Warning: important gaz evolution occurred!). The suspension was vigorously stirred at RT for 15 min then cooled to 0° C. (ice bath). 4-(Chloromethyl) pyridine hydrochloride (8.09 g, 49.3 mmol) was added carefully then the slurry was allowed to warm to RT and further stirred for 45 min. The reaction mixture was poured into water and extracted with $Et_2O$ (3×). The combined organic phases were dried over $Na_2SO_4$, filtered and evaporated to dryness to yield the crude title compound (10.13 g) as an orange solid, which was used in the next step without further purification. HPLC: $^At_{Ret}$=1.01 min; LC-MS: m/z 244.5 [M+H]$^+$; $^1$H NMR (400 MHz, DMSO-d$_6$): 3.23 (s, 3H), 4.82 (s, 2H), 6.77-6.83 (m, 2H), 7.17-7.22 (m, 2H), 8.02-8.08 (m, 2H), 8.49-8.54 (m, 2H).

Intermediate 28.7:
N-Methyl-N-pyridin-4-ylmethyl-benzene-1,4-diamine

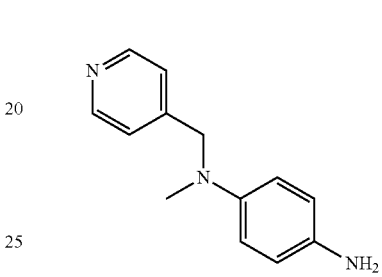

A suspension of Intermediate 28.6 (10.13 g) and Fe in powder (18.34 g, 328 mmol) in AcOH (65.7 ml), water (82 ml) and AcOEt (16.4 ml) was heated at 80° C. and stirred for 30 min. The reaction mixture was cooled to RT and concentrated under vacuum. The resulting aqueous mixture was basified by the addition of a 2M aqueous $Na_2CO_3$ solution until pH 8-9 then filtered through a Celite pad and the filter cake was washed with AcOEt. The biphasic filtrate was separated and the organic phase was dried over $Na_2SO_4$, filtered and evaporated to dryness. The resulting crude material was purified by Combi-Flash Companion™ (Isco Inc.) column chromatography (gradient elution, DCM/7M $NH_3$ in MeOH 99.7:0.3 to 95:5) to yield the title compound (4.14 g, 19.41 mmol, 59% for 2 steps) as a brownish solid. TLC: $R_F$=0.37 (DCM/7M $NH_3$ in MeOH 95:5); HPLC: $^At_{Ret}$=0.73 min; LC-MS: m/z 214.6 [M+H]$^+$; $^1$H NMR (400 MHz, DMSO-d$_6$): 2.80 (s, 3H), 4.35 (s, 2H), 4.42 (br. s., 2H), 6.44-6.50 (m, 2H), 6.51-6.58 (m, 2H), 7.20 (d, J=5.4, 2H), 8.46 (d, J=5.6, 2H).

Intermediate 28.8: 1-(4-Chloro-phenyl)-2-[4-(methyl-pyridin-4-ylmethyl-amino)-phenyl]-7-nitro-1,4-dihydro-2H-isoquinolin-3-one

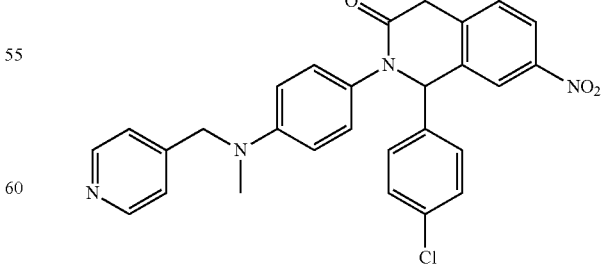

To a solution of Intermediate 28.7 (1.46 g, 6.84 mmol) in DCM (10 ml) were successively added DIPEA (1.49 ml, 8.55 mmol) and a solution of Intermediate 28.5 (2.1 g, 5.70 mmol)

in DCM (10 ml) at RT. The reaction mixture was stirred at RT for 45 min then evaporated to dryness. To a solution of the resulting residue in AcOH (20 ml) was added H$_2$SO$_4$ (0.456 ml, 8.55 mmol) at RT. The mixture was heated at 80° C., stirred for 1 h then cooled to RT, and concentrated under vacuum. The resulting residue was diluted with AcOEt and washed with a 2M aqueous Na$_2$CO$_3$ solution (2×). The organic phase was dried over Na$_2$SO$_4$, filtered and evaporated to dryness. The resulting crude material was purified by Combi-Flash Companion™ (Isco Inc.) column chromatography (gradient elution, DCM/MeOH 99.5: 0.5 to 9:1) to yield the title compound (2.08 g, 4.17 mmol, 73%) as a brown solid. TLC: R$_F$=0.43 (DCM/MeOH 9:1); HPLC: $^A$t$_{Ret}$=1.87 min; LC-MS: m/z 499.3 [M+H]$^+$; $^1$H NMR (500 MHz, DMSO-d$_6$): 3.02 (s, 3H), 3.86 (d, J=20.3, 1H), 4.15 (d, J=20.3, 1H), 4.58 (s, 2H), 6.34 (s, 1H), 6.58-6.64 (m, 2H), 6.90-6.96 (m, 2H), 7.17 (d, J=5.5, 2H), 7.34-7.46 (m, 4H), 7.55 (d, J=8.5, 1H), 8.13 (dd, J=8.4, 2.3, 1H), 8.41 (d, J=2.0, 1H), 8.44-8.49 (m, 2H).

Intermediate 28.9: 7-Amino-1-(4-chloro-phenyl)-2-[4-(methyl-pyridin-4-ylmethyl-amino)-phenyl]-1,4-dihydro-2H-isoquinolin-3-one

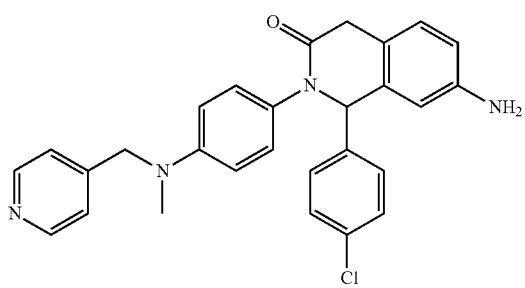 [SMILES: CN(Cc1ccncc1)c1ccc(N2C(=O)Cc3ccc([N+](=O)[O-])cc3C2c2ccc(Cl)cc2)cc1]

To a solution of Intermediate 28.8 (2.08 g, 4.17 mmol) in EtOH (30 ml) was added SnCl$_2$ dihydrate (9.41 g, 41.7 mmol) at RT. The slurry was heated at 80° C. and vigorously stirred 30 min. The reaction mixture was cooled to RT and poured into NaOH 2M in water (62.5 ml). The resulting slurry was stirred at RT for 10 min then filtered through a Celite pad and the filter cake was washed with Et$_2$O. The biphasic filtrate was separated and the aqueous phase further extracted with Et$_2$O (2×). The combined organic fractions were dried over Na$_2$SO$_4$, filtered and evaporated to dryness. The resulting crude material was purified by Combi-Flash Companion™ (Isco Inc.) column chromatography (gradient elution, DCM/MeOH 99.5:0.5 to 9:1) to yield the title compound (1.17 g, 2.50 mmol, 60%) as a brown solid. TLC: R$_F$=0.43 (DCM/MeOH 9:1); HPLC: $^A$t$_{Ret}$=1.20 min; LC-MS: m/z 469.2 [M+H]$^+$; $^1$H NMR (400 MHz, DMSO-d$_6$): 3.02 (s, 3H), 3.45 (d, J=19.6, 1H), 3.78 (d, J=19.6, 1H), 4.57 (s, 2H), 5.03 (br. s., 2H), 5.84 (s, 1H), 6.48 (dd, J=8.2, 1.8, 1H), 6.52-6.55 (m, 1H), 6.56-6.64 (m, 2H), 6.84-6.93 (m, 3H), 7.18 (d, J=5.4, 2H), 7.24-7.38 (m, 4H), 8.48 (d, J=5.9, 2H).

Example 29

N-{1-(4-Chloro-phenyl)-2-[4-(methyl-pyridin-4-ylmethyl-amino)-phenyl]-3-oxo-1,2,3,4-tetrahydro-isoquinolin-7-yl}-propionamide

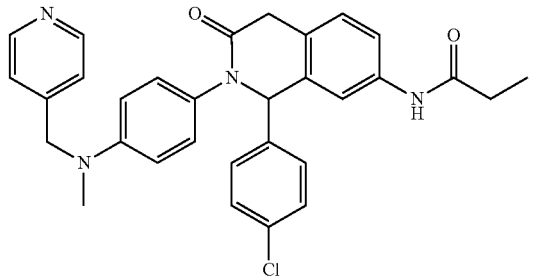 [SMILES: CCC(=O)Nc1ccc2c(c1)C(c1ccc(Cl)cc1)N(c1ccc(N(C)Cc3ccncc3)cc1)C(=O)C2]

To a solution of Intermediate 28.9 (30 mg, 0.064 mmol) in MeCN (0.5 ml) were successively added pyridine (0.010 ml, 0.128 mmol) and propionyl chloride (0.008 ml, 0.096 mmol) at RT. The reaction mixture was stirred at RT for 30 min then directly subjected to purification by reverse phase prep-HPLC (Waters system) to yield the title compound (TFA salt, 20.2 mg, 0.032 mmol, 49%) as a yellow solid. HPLC: $^A$t$_{Ret}$=1.60 min; LC-MS: m/z 525.2 [M+H]$^+$; $^1$H NMR (400 MHz, DMSO-d$_6$): 1.05 (t, J=7.6, 3H), 2.28 (q, J=7.6, 2H), 3.07 (s, 3H), 3.61 (d, J=20.1, 1H), 3.95 (d, J=20.1, 1H), 4.78 (s, 2H), 6.01 (s, 1H), 6.58-6.65 (m, 2H), 6.89-6.96 (m, 2H), 7.17 (d, J=8.3, 1H), 7.26-7.38 (m, 4H), 7.41 (dd, J=8.3, 1.5, 1H), 7.62-7.69 (m, 3H), 8.70-8.76 (m, 2H), 9.89 (s, 1H).

Example 30

1-(4-Chloro-phenyl)-7-(isopropyl-propyl-amino)-2-[4-(methyl-pyridin-4-ylmethyl-amino)-phenyl]-1,4-dihydro-2H-isoquinolin-3-one

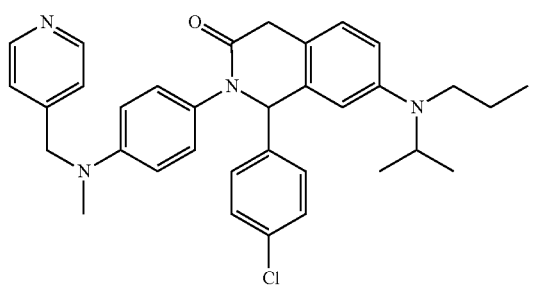 [SMILES: CCCN(c1ccc2c(c1)C(c1ccc(Cl)cc1)N(c1ccc(N(C)Cc3ccncc3)cc1)C(=O)C2)C(C)C]

To a solution of Example 28 (20 mg, 0.039 mmol) in MeCN (0.5 ml) were successively added AcOH (0.007 ml, 0.117 mmol), propionaldehyde (0.009 ml, 0.117 mmol) and NaBH(OAc)$_3$ (24.9 mg, 0.117 mmol) at RT. The reaction mixture was stirred at RT for 3 h30 then directly subjected to purification by reverse phase prep-HPLC (Waters system) to yield the title compound (TFA salt, 21 mg, 0.027 mmol, 69%) as a yellow solid. HPLC: $^A t_{Ret}$=1.37 min; LC-MS: m/z 553.5 [M+H]$^+$; $^1$H NMR (400 MHz, DMSO-d$_6$): 0.86 (t, J=7.3, 3H), 1.11 (d, J=6.7, 3H), 1.14 (d, J=6.6, 3H), 1.37-1.51 (m, 2H), 3.00 (s, 3H), 3.04-3.11 (m, 2H), 3.51 (d, J=19.6, 1H), 3.75 (d, J=19.6, 1H), 3.86-3.96 (m, 1H), 4.57 (s, 2H), 5.91 (s, 1H), 6.61-6.68 (m, 2H), 6.70-6.79 (m, 2H), 6.90-6.96 (m, 2H), 7.00-7.06 (m, 1H), 7.21-7.35 (m, 6H), 8.47-8.54 (m, 2H).

Example 31

1-(4-Chloro-phenyl)-7-[(2-dimethylamino-ethyl)-isopropyl-amino]-2-[4-(methyl-pyridin-4-ylmethyl-amino)-phenyl]-1,4-dihydro-2H-isoquinolin-3-one

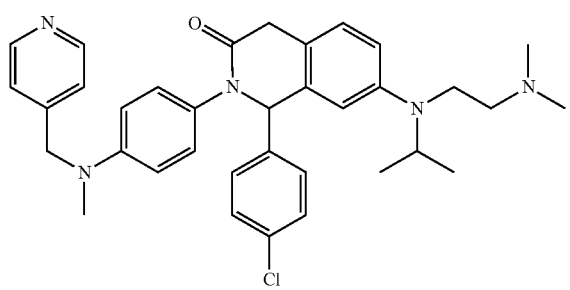 [SMILES: CC(C)N(CCN(C)C)c1ccc2c(c1)C(c1ccc(Cl)cc1)N(c1ccc(N(C)Cc3ccncc3)cc1)C(=O)C2]

To a solution of the crude Intermediate 31.2 (138 mg) in MeCN (0.5 ml) were successively added AcOH (0.018 ml, 0.314 mmol), formaldehyde (37% in water, 0.024 ml, 0.314 mmol) and NaBH(OAc)$_3$ (66.5 mg, 0.314 mmol) at RT. The reaction mixture was stirred at RT for 2 h then directly subjected to purification by reverse phase prep-HPLC (Waters system) to yield the title compound (TFA salt, 13 mg, 0.016 mmol, 31% over 3 steps) as a light yellow solid. HPLC: $^A t_{Ret}$=1.48 min; LC-MS: m/z 580.4 [M+H]$^+$.

Intermediate 31.1: [2-({1-(4-Chloro-phenyl)-2-[4-(methyl-pyridin-4-ylmethyl-amino)-phenyl]-3-oxo-1,2,3,4-tetrahydro-isoquinolin-7-yl}-isopropyl-amino)-ethyl]-carbamic acid tert-butyl ester

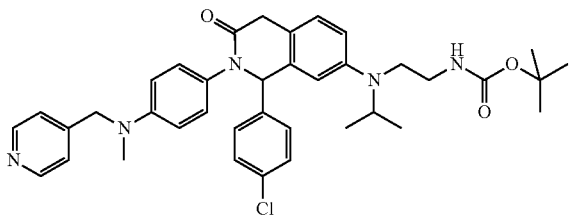 [SMILES: CC(C)N(CCNC(=O)OC(C)(C)C)c1ccc2c(c1)C(c1ccc(Cl)cc1)N(c1ccc(N(C)Cc3ccncc3)cc1)C(=O)C2]

The crude title compound (174 mg) was obtained as a brown solid from Example 28 (80 mg, 0.157 mmol) and N-Boc-2-aminoacetaldehyde (100 mg, 0.626 mmol) analogously to Example 30. The crude material was used in the next step without further purification. HPLC: $^A t_{Ret}$=1.63 min; LC-MS: m/z 654.5 [M+H]$^+$.

Intermediate 31.2: 7-[(2-Amino-ethyl)-isopropyl-amino]-1-(4-chloro-phenyl)-2-[4-(methyl-pyridin-4-ylmethyl-amino)-phenyl]-1,4-dihydro-2H-isoquinolin-3-one

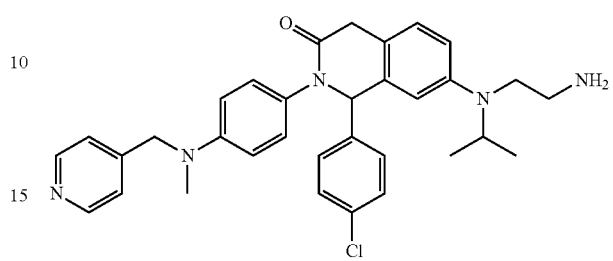

A solution of the crude Intermediate 31.1 (174 mg) in DCM (2 ml) and TFA (1 ml) was stirred at RT for 1 h30 then evaporated to dryness to yield the crude title compound (415 mg) as a dark resin which was used in the next step without further purification. HPLC: $^A t_{Ret}$=1.37 min; LC-MS: m/z 554.4 [M+H]$^+$; $^1$H NMR (400 MHz, DMSO-d$_6$): 1.10 (t, J=6.8, 6H), 2.76-2.90 (m, 2H), 3.07 (s, 3H), 3.28-3.36 (m, 2H), 3.52 (d, J=19.6, 1H), 3.80 (d, J=19.6, 1H), 3.97-4.06 (m, 1H), 4.73 (s, 2H), 5.94 (s, 1H), 6.59-6.66 (m, 2H), 6.77 (dd, J=8.4, 2.3, 1H), 6.91-6.99 (m, 3H), 7.07 (d, J=8.3, 1H), 7.33-7.42 (m, 4H), 7.47-7.53 (m, 2H), 7.71-7.80 (m, 2H), 8.66 (d, J=6.1, 2H).

Example 32

N-[2-({1-(4-Chloro-phenyl)-2-[4-(methyl-pyridin-4-ylmethyl-amino)-phenyl]-3-oxo-1,2,3,4-tetrahydro-isoquinolin-7}-isopropyl-amino)-ethyl]-acetamide

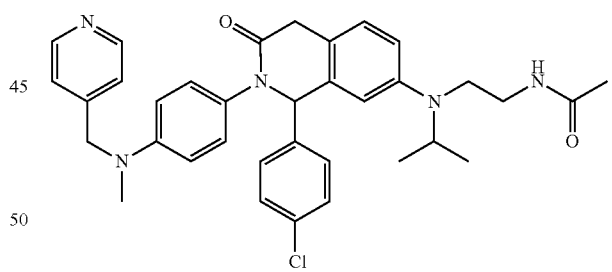

The title compound (10.8 mg, 0.013 mmol, 25% over 3 steps) was obtained as a beige solid from the crude Intermediate 31.2 (138 mg) and acetylchloride (0.033 ml, 0.471 mmol) analogously to Example 29. Purification of the crude material was performed by reverse phase prep-HPLC (Waters system). HPLC: $^A t_{Ret}$=1.28 min; LC-MS: m/z 596.4 [M+H]$^+$.

Example 33

Compounds 33a to 33r were obtained from Intermediate 28.9 (or analogues prepared similarly) analogously to Example 28 or 29, or from Example 28 (or analogues prepared similarly) analogously to Example 30, 31 or 32.

| # | Structure | Name/HPLC/MS/NMR |
|---|---|---|
| 33a | 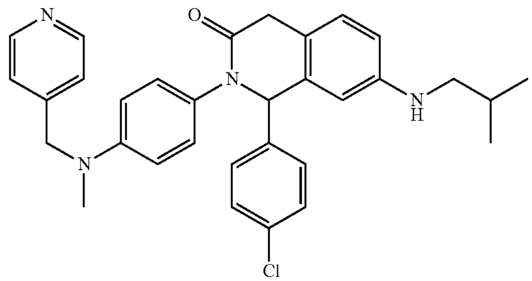 [SMILES: CC(C)CNc1ccc2c(c1)C(c1ccc(Cl)cc1)N(c1ccc(N(C)Cc3ccncc3)cc1)C(=O)C2] | 1-(4-Chloro-phenyl)-7-isobutylamino-2-[4-(methyl-pyridin-4-ylmethyl-amino)-phenyl]-1,4-dihydro-2H-isoquinolin-3-one.<br>HPLC: $^{A}t_{Ret}$ = 1.64; LC-MS: m/z 525.3 [M + H]$^{+}$. |
| 33b | 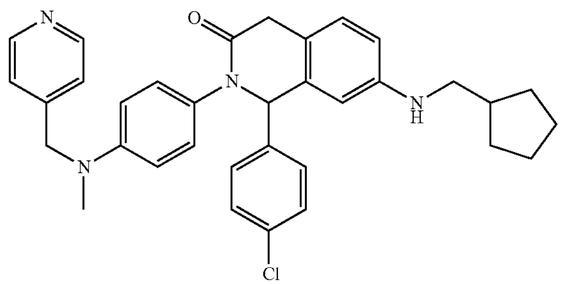 [SMILES: CN(Cc1ccncc1)c1ccc(N2C(=O)Cc3ccc(NCC4CCCC4)cc3C2c2ccc(Cl)cc2)cc1] | 1-(4-Chloro-phenyl)-7-(cyclopentylmethyl-amino)-2-[4-(methyl-pyridin-4-ylmethyl-amino)-phenyl]-1,4-dihydro-2H-isoquinolin-3-one.<br>HPLC: $^{A}t_{Ret}$ = 1.72; LC-MS: m/z 551.2 [M + H]$^{+}$. |
| 33c | 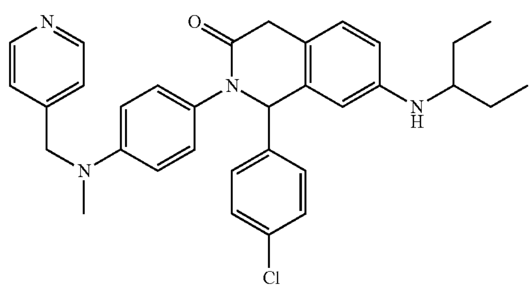 [SMILES: CCC(CC)Nc1ccc2c(c1)C(c1ccc(Cl)cc1)N(c1ccc(N(C)Cc3ccncc3)cc1)C(=O)C2] | 1-(4-Chloro-phenyl)-7-(1-ethyl-propylamino)-2-[4-(methyl-pyridin-4-ylmethyl-amino)-phenyl]-1,4-dihydro-2H-isoquinolin-3-one.<br>HPLC: $^{A}t_{Ret}$ = 1.63; LC-MS: m/z 539.3 [M + H]$^{+}$. |
| 33d | 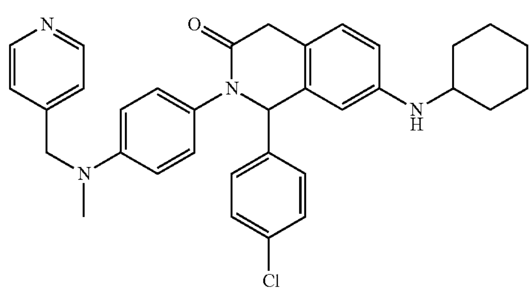 [SMILES: CN(Cc1ccncc1)c1ccc(N2C(=O)Cc3ccc(NC4CCCCC4)cc3C2c2ccc(Cl)cc2)cc1] | 1-(4-Chloro-phenyl)-7-cyclohexylamino-2-[4-(methyl-pyridin-4-ylmethyl-amino)-phenyl]-1,4-dihydro-2H-isoquinolin-3-one.<br>HPLC: $^{A}t_{Ret}$ = 1.51; LC-MS: m/z 551.3 [M + H]$^{+}$. |
| 33e | 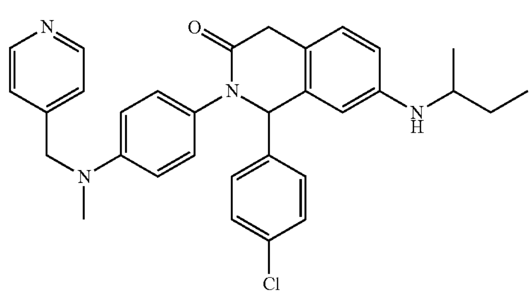 [SMILES: CCC(C)Nc1ccc2c(c1)C(c1ccc(Cl)cc1)N(c1ccc(N(C)Cc3ccncc3)cc1)C(=O)C2] | 7-sec-Butylamino-1-(4-chloro-phenyl)-2-+4-(methyl-pyridin-4-ylmethyl-amino)-phenyl]-1,4-dihydro-2H-isoquinolin-3-one.<br>HPLC: $^{A}t_{Ret}$ = 1.42; LC-MS: m/z 525.2 [M + H]$^{+}$. |

| # | Structure | Name/HPLC/MS/NMR |
|---|---|---|
| 33f | 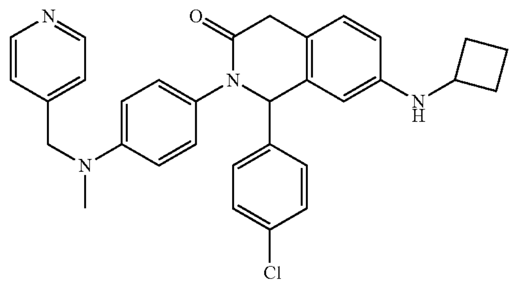 [SMILES: CN(Cc1ccncc1)c1ccc(N2C(=O)Cc3ccc(NC4CCC4)cc3C2c2ccc(Cl)cc2)cc1] | 1-(4-Chloro-phenyl)-7-cyclobutylamino-2-[4-(methyl-pyridin-4-ylmethyl-amino)-phenyl]-1,4-dihydro-2H-isoquinolin-3-one.<br>HPLC: $^A t_{Ret}$ = 1.50; LC-MS: m/z 523.2 [M + H]$^+$. |
| 33g | 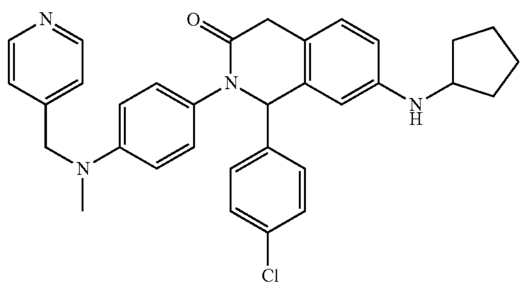 [SMILES: CN(Cc1ccncc1)c1ccc(N2C(=O)Cc3ccc(NC4CCCC4)cc3C2c2ccc(Cl)cc2)cc1] | 1-(4-Chloro-phenyl)-7-cyclopentylamino-2-[4-(methyl-pyridin-4-ylmethyl-amino)-phenyl]-1,4-dihydro-2H-isoquinolin-3-one.<br>HPLC: $^A t_{Ret}$ = 1.47; LC-MS: m/z 537.2 [M + H]$^+$. |
| 33h | 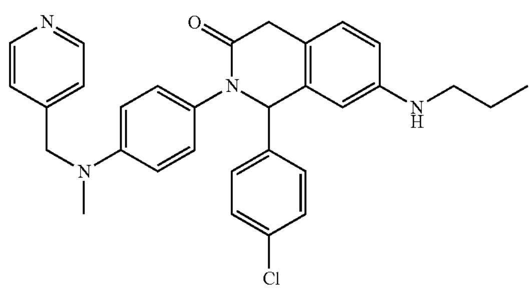 [SMILES: CCCNc1ccc2c(c1)C(c1ccc(Cl)cc1)N(c1ccc(N(C)Cc3ccncc3)cc1)C(=O)C2] | 1-(4-Chloro-phenyl)-2-[4-(methyl-pyridin-4-ylmethyl-amino)-phenyl]-7-propylamino-1,4-dihydro-2H-isoquinolin-3-one.<br>HPLC: $^A t_{Ret}$ = 1.40; LC-MS: m/z 511.2 [M + H]$^+$. |
| 33i | 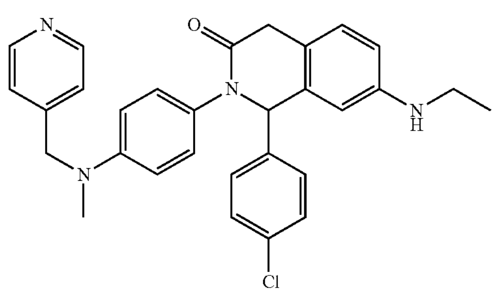 [SMILES: CCNc1ccc2c(c1)C(c1ccc(Cl)cc1)N(c1ccc(N(C)Cc3ccncc3)cc1)C(=O)C2] | 1-(4-Chloro-phenyl)-7-ethylamino-2-[4-(methyl-pyridin-4-ylmethyl-amino)-phenyl]-1,4-dihydro-2H-isoquinolin-3-one.<br>HPLC: $^A t_{Ret}$ = 1.27; LC-MS: m/z 497.2 [M + H]$^+$. |
| 33j | 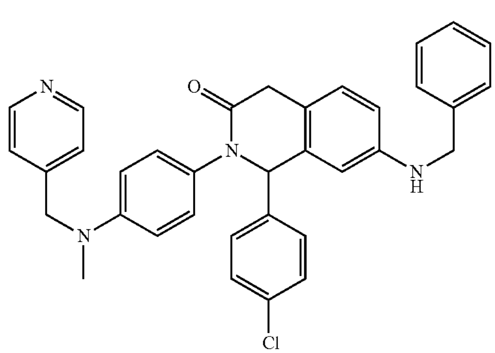 [SMILES: CN(Cc1ccncc1)c1ccc(N2C(=O)Cc3ccc(NCc4ccccc4)cc3C2c2ccc(Cl)cc2)cc1] | 7-Benzylamino-1-(4-chloro-phenyl)-2-[4-(methyl-pyridin-4-ylmethyl-amino)-phenyl]-1,4-dihydro-2H-isoquinolin-3-one.<br>HPLC: $^A t_{Ret}$ = 1.79; LC-MS: m/z 559.2 [M + H]$^+$. |

-continued

| # | Structure | Name/HPLC/MS/NMR |
|---|---|---|
| 33k | 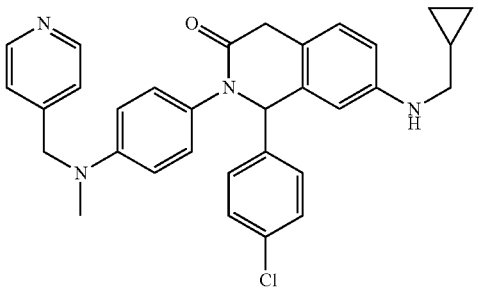 [SMILES: CN(Cc1ccncc1)c1ccc(N2C(=O)Cc3ccc(NCC4CC4)cc3C2c2ccc(Cl)cc2)cc1] | 1-(4-Chloro-phenyl)-7-(cyclopropylmethyl-amino)-2-[4-(methyl-pyridin-4-ylmethyl-amino)-phenyl]-1,4-dihydro-2H-isoquinolin-3-one.<br>HPLC: $^A t_{Ret}$ = 1.40; LC-MS: m/z 523.3 [M + H]$^+$. |
| 33l | 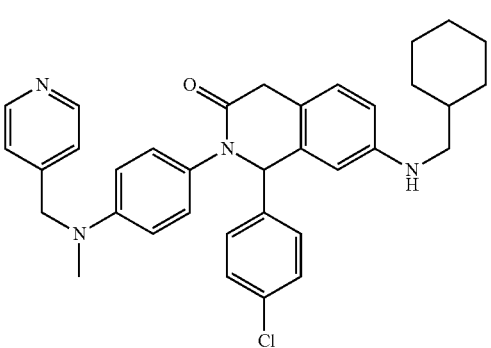 [SMILES: CN(Cc1ccncc1)c1ccc(N2C(=O)Cc3ccc(NCC4CCCCC4)cc3C2c2ccc(Cl)cc2)cc1] | 1-(4-Chloro-phenyl)-7-(cyclohexylmethyl-amino)-2-[4-(methyl-pyridin-4-ylmethyl-amino)-phenyl]-1,4-dihydro-2H-isoquinolin-3-one.<br>HPLC: $^A t_{Ret}$ = 1.87; LC-MS: m/z 565.2 [M + H]$^+$. |
| 33m | 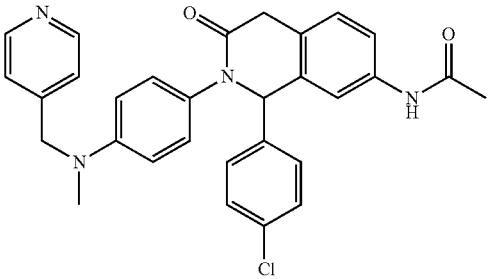 [SMILES: CC(=O)Nc1ccc2c(c1)C(c1ccc(Cl)cc1)N(c1ccc(N(C)Cc3ccncc3)cc1)C(=O)C2] | N-{1-(4-Chloro-phenyl)-2-[4-(methyl-pyridin-4-ylmethyl-amino)-phenyl]-3-oxo-1,2,3,4-tetrahydro-isoquinolin-7-yl}-acetamide.<br>HPLC: $^A t_{Ret}$ = 1.49; LC-MS: m/z 511.1 [M + H]$^+$. |
| 33n | 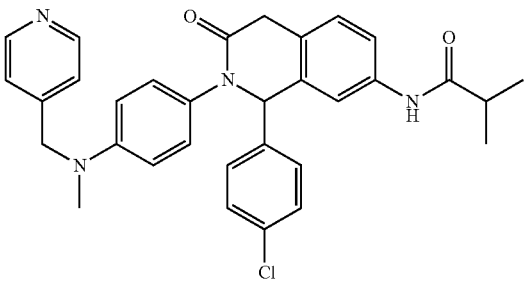 [SMILES: CC(C)C(=O)Nc1ccc2c(c1)C(c1ccc(Cl)cc1)N(c1ccc(N(C)Cc3ccncc3)cc1)C(=O)C2] | N-{1-(4-Chloro-phenyl)-2-[4-(methyl-pyridin-4-ylmethyl-amino)-phenyl]-3-oxo-1,2,3,4-tetrahydro-isoquinolin-7-yl}-isobutyramide.<br>HPLC: $^A t_{Ret}$ = 1.71; LC-MS: m/z 539.2 [M + H]$^+$. |
| 33o | 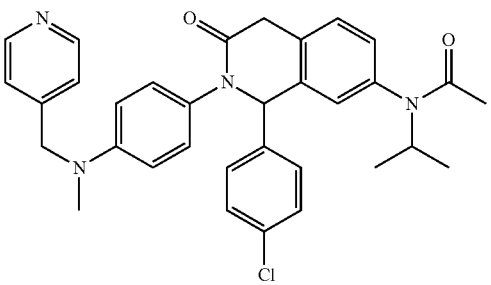 [SMILES: CC(=O)N(c1ccc2c(c1)C(c1ccc(Cl)cc1)N(c1ccc(N(C)Cc3ccncc3)cc1)C(=O)C2)C(C)C] | N-{1-(4-Chloro-phenyl)-2-[4-(methyl-pyridin-4-ylmethyl-amino)-phenyl]-3-oxo-1,2,3,4-tetrahydro-isoquinolin-7-yl}-N-isopropyl-acetamide.<br>HPLC: $^A t_{Ret}$ = 1.67; LC-MS: m/z 553.3 [M + H]$^+$. |

| # | Structure | Name/HPLC/MS/NMR |
|---|---|---|
| 33p | 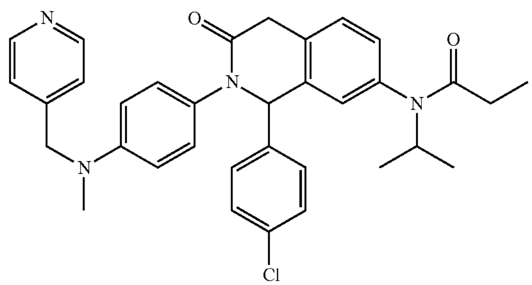 [SMILES: CCC(=O)N(c1ccc2c(c1)C(c1ccc(Cl)cc1)N(c1ccc(N(C)Cc3ccncc3)cc1)C(=O)C2)C(C)C] | N-{1-(4-Chloro-phenyl)-2-[4-(methyl-pyridin-4-ylmethyl-amino)-phenyl]-3-oxo-1,2,3,4-tetrahydro-isoquinolin-7-yl}-N-isopropyl-propionamide.<br>HPLC: $^At_{Ret}$ = 1.77; LC-MS: m/z 567.3 [M + H]$^+$. |
| 33q | 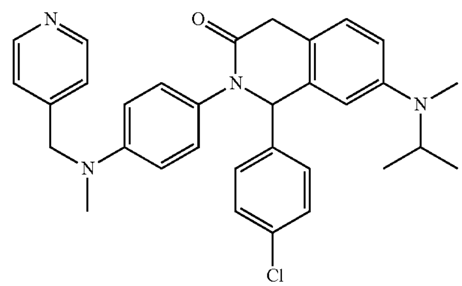 [SMILES: CC(C)N(C)c1ccc2c(c1)C(c1ccc(Cl)cc1)N(c1ccc(N(C)Cc3ccncc3)cc1)C(=O)C2] | 1-(4-Chloro-phenyl)-7-(isopropyl-methyl-amino)-2-[4-(methyl-pyridin-4-ylmethyl-amino)-phenyl]-1,4-dihydro-2H-isoquinolin-3-one.<br>HPLC: $^At_{Ret}$ = 1.27; LC-MS: m/z 525.4 [M + H]$^+$. |
| 33r | 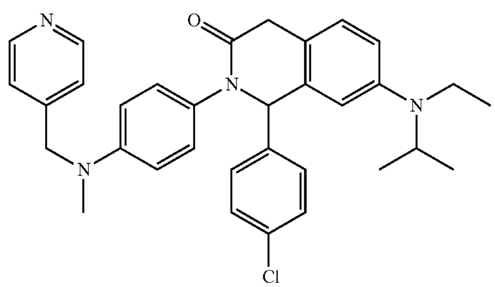 [SMILES: CCN(c1ccc2c(c1)C(c1ccc(Cl)cc1)N(c1ccc(N(C)Cc3ccncc3)cc1)C(=O)C2)C(C)C] | 1-(4-Chloro-phenyl)-7-(ethyl-isopropyl-amino)-2-[4-(methyl-pyridin-4-ylmethyl-amino)-phenyl]-1,4-dihydro-2H-isoquinolin-3-one.<br>HPLC: $^At_{Ret}$ = 1.29; LC-MS: m/z 539.4 [M + H]$^+$. |

Example 34

7-((R)-sec-Butoxy)-1-(4-chloro-phenyl)-6-methoxy-2-[4-(2-oxo-pyrrolidin-1-yl)-phenyl]-1,4-dihydro-2H-isoquinolin-3-one

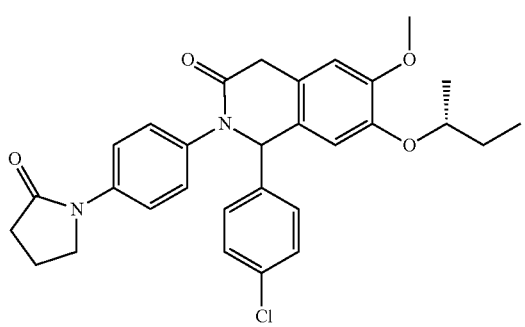 [SMILES: CC[C@@H](C)Oc1cc2c(cc1OC)CC(=O)N(c1ccc(N3CCCC3=O)cc1)C2c1ccc(Cl)cc1]

A reaction flask was charged with CuI (0.51 mg, 0.003 mmol) and K$_3$PO$_4$ (22.67 mg, 0.11 mmol) then evacuated and backfilled with argon (3 times). N,N'-Dimethylethylenediamine (0.006 ml, 0.006 mmol), pyrrolidin-2-one (5 l, 0.064 mmol), Intermediate 34.3 (30 mg, 0.053 mmol) and toluene (0.5 ml) were added, the reaction flask was sealed, heated at 80° C. and stirred for 1 h30. The reaction mixture was cooled to RT, filtered through a Celite pad and the solid was washed with MeOH. The filtrate was evaporated to dryness and the resulting residue was purified by reverse phase prep-HPLC (Waters system) to yield the title compound (8 mg, 0.015 mmol, 28%). HPLC: $^At_{Ret}$=2.50 min; API-MS: m/z 519.2 [M+H]$^+$; $^1$H NMR (400 MHz, CDCl$_3$): 0.92-1.03 (m, 3H, mixture of diastereoisomers), 1.23-1.33 (2 d, J=6.1, 3H, mixture of diastereoisomers), 1.56-1.84 (m, 2H), 2.20 (quin, J=7.5, 2H), 2.67 (t, J=8.1, 2H), 3.79 (d, J=19.8, 1H), 3.85-3.97 (m, 6H), 4.20 (sxt, J=6.1, 1H), 5.75 (s, 1H), 6.67 (d, J=3.9, 1H), 6.72 (s, 1H), 7.03-7.09 (m, 2H), 7.10-7.16 (m, 2H), 7.24-7.30 (m, 2H), 7.58-7.64 (m, 2H).

Intermediate 34.1: [1-(4-Chloro-phenyl)-meth-(E)-ylidene]-(4-iodo-phenyl)-amine

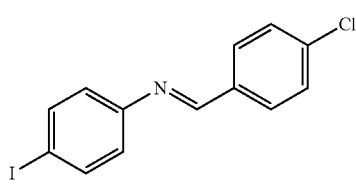 [SMILES: Clc1ccc(/C=N/c2ccc(I)cc2)cc1]

The title compound (2.08 g, 6.10 mmol, 89%) was obtained as a brownish solid from 4-iodo-phenylamine (1.5 g, 6.85 mmol) and 4-chloro-benzaldehyde (963 mg, 6.85 mmol) analogously to Intermediate 1.4. ¹H NMR (400 MHz, CDCl₃): 6.94-7.02 (m, 2H), 7.44-7.51 (m, 2H), 7.69-7.76 (m, 2H), 7.82-7.89 (m, 2H), 8.40 (s, 1H).

Intermediate 34.2: 1-(4-Chloro-phenyl)-7-hydroxy-2-(4-iodo-phenyl)-6-methoxy-1,4-dihydro-2H-isoquinolin-3-one

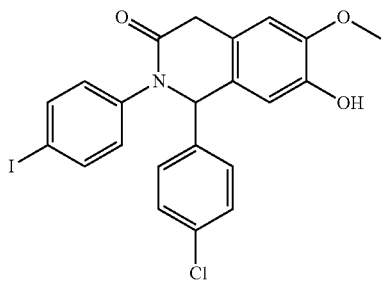 [SMILES: COc1cc2c(cc1O)C(c1ccc(Cl)cc1)N(c1ccc(I)cc1)C(=O)C2]

The title intermediate (496 mg, 0.98 mmol, 36%) was obtained as a light yellow solid from Intermediate 34.1 (939 mg, 2.75 mmol) and Intermediate 24.1 (799 mg, 2.75 mmol) analogously to Example 1. The benzyl protecting group was cleaved in-situ under the reaction conditions. Purification of the crude material was performed by Combi-Flash Companion™ (Isco Inc.) column chromatography (SiO₂; gradient elution, [heptane/DCM 1:1]/TBME containing 5% of formic acid 95:5→7:3). TLC: R_F=0.40 (heptane/DCM/TBME 1:1:2); HPLC: $^{A}t_{Ret}$=2.42 min; API-MS: m/z 506.0 [M+H]⁺; ¹H NMR (400 MHz, CDCl₃): 3.71 (d, J=19.6, 1H), 3.84 (d, J=19.8, 1H), 3.93 (s, 3H), 5.62 (s, 1H), 5.71 (s, 1H), 6.69 (s, 1H), 6.79 (s, 1H), 6.88-6.94 (m, 2H), 7.07-7.13 (m, 2H), 7.25-7.31 (m, 2H), 7.65-7.71 (m, 2H).

Intermediate 34.3: 7-((R)-sec-Butoxy)-1-(4-chlorophenyl)-2-(4-iodo-phenyl)-6-methoxy-1,4-dihydro-2H-isoquinolin-3-one

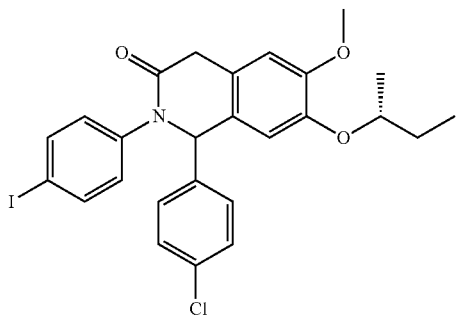 [SMILES: CC[C@@H](C)Oc1cc2c(cc1OC)CC(=O)N(c1ccc(I)cc1)C2c1ccc(Cl)cc1]

The title compound (350 mg, 0.62 mmol, 64%) was obtained as a yellow foam from Intermediate 34.2 (496 mg, 0.98 mmol) and (S)-butan-2-ol (0.11 ml, 1.18 mmol) analogously to Example 25. Purification of the crude material was performed by Combi-Flash Companion™ (Isco Inc.) column chromatography (SiO₂; gradient elution, [heptane DCM 1:1]/TBME 95:5→4:6). TLC: R_F=0.64 (heptane/DCM/TBME 1:1:2); HPLC: $^{A}t_{Ret}$=3.06 min; API-MS: m/z 562.0 [M+H]⁺; ¹H NMR (400 MHz, CD₃OD): 0.89-1.00 (2t, J=7.5, 3H, mixture of diastereoisomers), 1.14-1.25 (2 d, J=6.1, 3H, mixture of diastereoisomers), 1.50-1.75 (m, 2H), 3.75 (d, J=20.3, 1H), 3.86 (s, 3H), 4.02 (d, 0.1=20.3, 1H), 4.19-4.29 (m, 1H), 5.99 (s, 1H), 6.81 (d, J=3.4, 1H), 6.87-6.95 (m, 3H), 7.15-7.21 (m, 2H), 7.28-7.34 (m, 2H), 7.68-7.75 (m, 2H).

Example 35

7-((R)-sec-Butoxy)-1-(4-chloro-phenyl)-6-methoxy-2-(4-pyrazol-1-yl-phenyl)-1,4-dihydro-2H-isoquinolin-3-one

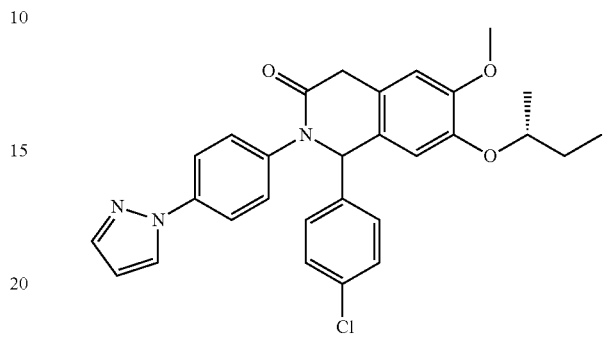

A reaction flask was charged with Intermediate 34.3 (25 mg, 0.044 mmol), 1H-pyrazole (4.5 mg, 0.067 mmol), Cu₂O (0.3 mg, 0.002 mmol), salicylaldoxime (1.2 mg, 0.009 mmol) and Cs₂CO₃ (29.0 mg, 0.089 mmol) then evacuated and backfilled with argon (3 times). MeCN (0.5 ml) was added, the reaction flask was sealed, heated at 80° C. and stirred for 14 h. The reaction mixture was cooled to RT, diluted with DCM and filtered through a Celite pad. The solid was washed with DCM, the filtrate was evaporated to dryness and the resulting residue was purified by reverse phase prep-HPLC (Waters system) to yield the title compound (12.5 mg, 0.02 mmol, 46%). HPLC: $^{A}t_{Ret}$=2.71 min; API-MS: m/z 503.5 [M+H]⁺; ¹H NMR (400 MHz, DMSO-d₆): 0.83-0.93 (m, 3H, mixture of diastereoisomers), 1.10-1.21 (2 d, J=6.1, 3H, mixture of diastereoisomers), 1.44-1.67 (m, 2H), 3.63 (d, J=20.0, 1H), 3.73 (s, 3H), 3.88-3.97 (m, 1H), 4.15-4.28 (m, 1H), 6.13 (d, J=3.3, 1H), 6.49-6.52 (m, 1H), 6.84 (s, 1H), 7.00 (d, J=6.7, 1H), 7.23-7.29 (m, 2H), 7.31-7.34 (m, 4H), 7.70 (d, J=1.8, 1H), 7.74-7.79 (m, 2H), 8.42 (d, J=2.5, 1H).

Example 36

7-((R)-sec-Butoxy)-1-(4-chloro-phenyl)-6-methoxy-2-[4-(1H-pyrazol-4-yl)-phenyl]-1,4-dihydro-2H-isoquinolin-3-one

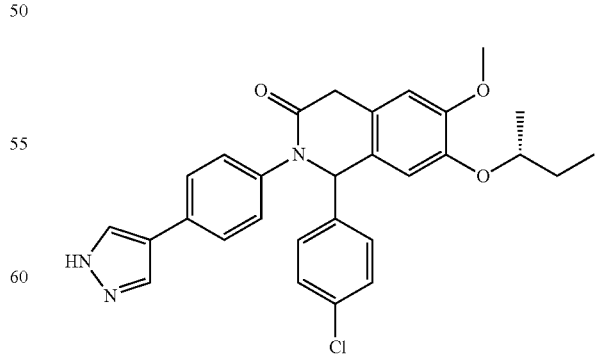

A mixture of Intermediate 34.3 (20 mg, 0.036 mmol), 4-(4,4,5,5-tetramethyl-1,3,2-dioxaborolan-2-yl)-1H-pyrazole (10.36 mg, 0.053 mmol) and aqueous Na₂CO₃ 2M (0.062 ml, 0.125 mmol) in DME (0.6 ml) was evacuated under vacuum and backfilled with argon (3 times). PdCl$_2$(PPh$_3$)$_2$ (1.25 mg, 0.0018 mmol) was added, the reaction flask was sealed and irradiated in a microwave oven at 150° C. for 15 min. The reaction mixture was cooled to RT, diluted into AcOEt and washed with water. The organic layer was dried over Na$_2$SO$_4$, filtered and evaporated to dryness. The crude material was purified by reverse phase prep-HPLC (Waters system) to yield the title compound (TFA salt, 5 mg, 0.008 mmol, 23%). HPLC: $^A t_{Ret}$=2.38 min; LC-MS: m/z 502.2 [M+H]$^+$; $^1$H NMR (500 MHz, DMSO-ds): 0.84-0.92 (2t, J=7.5, 3H, mixture of diastereoisomers), 1.11-1.21 (2 d, J=6.1, 3H, mixture of diastereoisomers), 1.45-1.67 (m, 2H), 3.61 (d, J=20.0, 1H), 3.73 (s, 3H), 3.92 (dd, J=19.8, 3.7, 1H), 4.18-4.28 (m, 1H), 6.10 (d, J=4.1, 1H), 6.85 (s, 1H), 7.01-7.04 (m, 1H), 7.10-7.15 (m, 2H), 7.33-7.37 (m, 4H), 7.53-7.58 (m, 2H), 8.02 (br. s., 2H).

Example 37

Compounds 37a to 37c were obtained from Intermediate 34.3 (or analogues prepared similarly) analogously to Example 34, 35 or 36.

| # | Structure | Name/HPLC/MS |
|---|-----------|--------------|
| 37a | 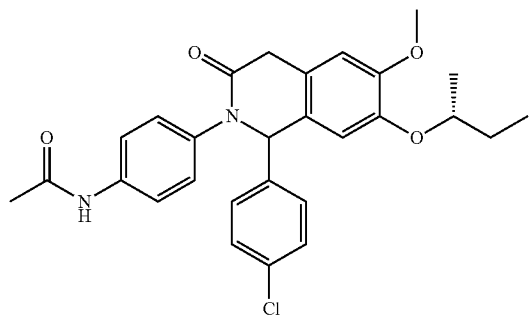 [SMILES: CC[C@@H](C)Oc1cc2c(cc1OC)CC(=O)N(c1ccc(NC(C)=O)cc1)C2c1ccc(Cl)cc1] | N-{4-[7-((R)-sec-Butoxy)-1-(4-chloro-phenyl)-6-methoxy-3-oxo-3,4-dihydro-1H-isoquinolin-2-yl]-phenyl}-acetamide.<br>HPLC: $^A t_{Ret}$ = 2.33; API-MS: m/z 493.2 [M + H]$^+$. |
| 37b | 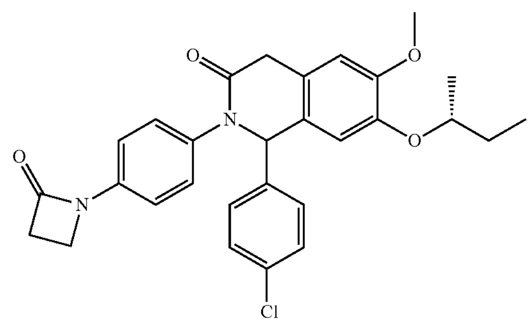 | 7-((R)-sec-Butoxy)-1-(4-chloro-phenyl)-6-methoxy-2-[4-(2-oxo-azetidin-1-yl)-phenyl]-1,4-dihydro-2H-isoquinolin-3-one.<br>HPLC: $^A t_{Ret}$ = 2.49; API-MS: m/z 505.1 [M + H]$^+$. |
| 37c[1] | | 7-((R)-sec-Butoxy)-1-(4-chloro-phenyl)-2-[4-(3,5-dimethyl-1H-pyrazol-4-yl)-phenyl]-6-methoxy-1,4-dihydro-2H-isoquinolin-3-one.<br>HPLC: $^A t_{Ret}$ = 2.14; LC-MS: m/z 530.2 [M + H]$^+$. |

[1]The title compound (TFA salt, 15 mg, 0.023 mmol, 44%) was obtained from Intermediate 34.3 (30 mg, 0.053 mmol), 3,5-dimethyl-4-(4,4,5,5-tetramethyl-1,3,2-dioxaborolan-2-yl)-1H-pyrazole (11.9 mg, 0.053 mmol) and Pd(PPh$_3$)$_4$ (3.1 mg, 0.003 mmol) as a catalyst analogously to Example 36. Purification of the crude material was performed by reverse phase prep-HPLC (Waters system).

Example 38

4-[7-((R)-sec-Butoxy)-1-(4-chloro-phenyl)-6-methoxy-3-oxo-3,4-dihydro-1H-isoquinolin-2-yl]-N-ethyl-N-methyl-benzamide

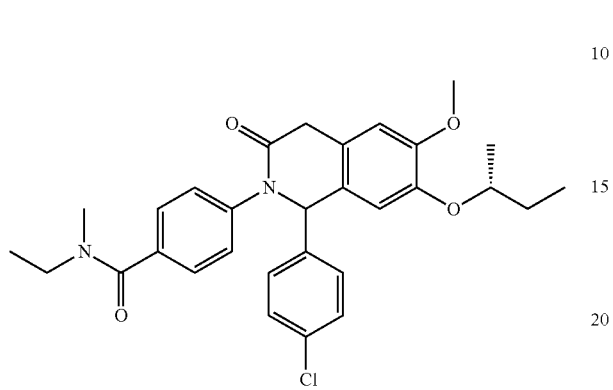

To a solution of Intermediate 38.3 (25 mg, 0.052 mmol) in DMF (0.5 ml) were successively added ethyl-methyl-amine (0.013 ml, 0.156 mmol), NMM (0.017 ml, 0.156 mmol) and HATU (23.77 mg, 0.063 mmol) at RT. The reaction mixture was stirred at RT for 2 h then directly subjected to purification by reverse phase prep-HPLC (Waters system) to yield the title compound (12.7 mg, 0.024 mmol, 47%). HPLC: $^A t_{Ret}$=2.46 min; LC-MS: m/z 521.7 [M+H]$^+$; $^1$H NMR (400 MHz, CD$_3$OD): 0.89-1.00 (2t, J=7.5, 3H, mixture of diastereoisomers), 1.11-1.28 (m, 6H), 1.50-1.77 (m, 2H), 2.95-3.10 (m, 3H), 3.53-3.62 (m, 1H), 3.77 (d, J=20.3, 1H), 3.86 (s, 3H), 4.05 (d, J=20.3, 1H), 4.20-4.30 (m, 1H), 6.07 (br. s., 1H), 6.80-6.85 (m, 1H), 6.90 (s, 1H), 7.18-7.33 (m, 6H), 7.37-7.46 (m, 2H).

Intermediate 38.1: 4-{[1-(4-Chloro-phenyl)-meth-(E)-ylidene]-amino}-benzoic acid methyl ester

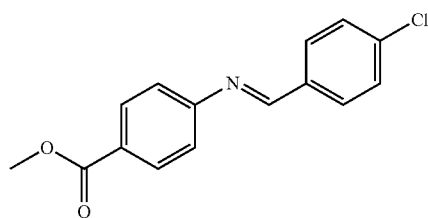 [SMILES: COC(=O)c1ccc(/N=C/c2ccc(Cl)cc2)cc1]

The title compound (2.35 g, 8.59 mmol, 87%) was obtained as a light yellow solid from methyl 4-aminobenzoate (1.5 g, 9.92 mmol) and 4-chloro-benzaldehyde (1.40 g, 9.92 mmol) analogously to Intermediate 1.4. $^1$H NMR (400 MHz, CDCl$_3$): 3.95 (s, 3H), 7.20-7.25 (m, 2H), 7.46-7.52 (m, 2H), 7.84-7.91 (m, 2H), 8.07-8.13 (m, 2H), 8.42 (s, 1H).

Intermediate 38.2: 4-[7-((R)-sec-Butoxy)-1-(4-chloro-phenyl)-6-methoxy-3-oxo-3,4-dihydro-1H-isoquinolin-2-yl]-benzoic acid methyl ester

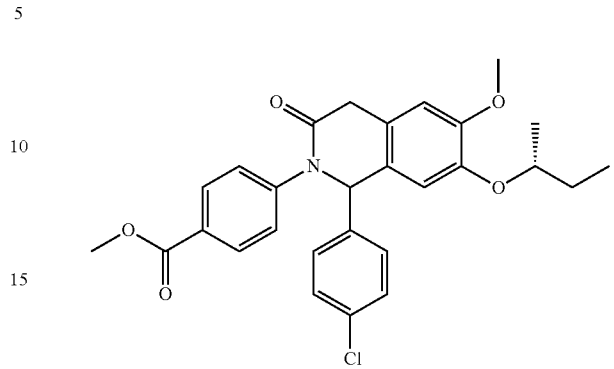

The title compound (780 mg, 1.58 mmol, 64%) was obtained from Intermediate 38.1 (672 mg, 2.45 mmol) and Intermediate 1.3 (630 mg, 2.45 mmol) analogously to Example 1. Purification of the crude material was performed by reverse phase column chromatography (C18; gradient elution, water containing 0.5% TFA/MeCN 95:5→1:9). HPLC: $^A t_{Ret}$=2.75 min; LC-MS: m/z 494.3 [M+H]$^+$; $^1$H NMR (400 MHz, CDCl$_3$): 0.94-1.03 (2t, J=7.5, 3H, mixture of diastereoisomers), 1.26-1.35 (2 d, J=6.1, 3H, mixture of diastereoisomers), 1.56-1.85 (m, 2H), 3.72-3.87 (m, 2H), 3.88 (s, 3H), 3.93 (s, 3H), 4.17-4.28 (m, 1H), 5.82 (s, 1H), 6.73 (s, 1H), 6.75 (d, J=4.9, 1H), 7.06-7.12 (m, 2H), 7.25-7.32 (m, 4H), 8.01-8.08 (m, 2H).

Intermediate 38.3: 4-[7-((R)-sec-Butoxy)-1-(4-chloro-phenyl)-6-methoxy-3-oxo-3,4-dihydro-1H-isoquinolin-2-yl]-benzoic acid

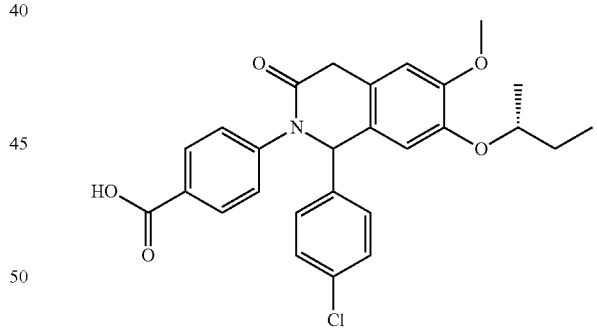

A mixture of Intermediate 38.2 (400 mg, 0.81 mmol) and LiOH monohydrate (170 mg, 4.05 mmol) in MeOH (8 ml) and water (2 ml) was stirred at RT for 5 h. The reaction mixture was concentrated under vacuum, diluted into water and neutralized by the addition of HCl 2 M in water. The resulting slurry was extracted with DCM (3×) and the combined organic fractions were dried over Na$_2$SO$_4$, filtered and evaporated to dryness to yield the crude title compound (461 mg, quant.) as an orange oil, which was used in the next step without further purification. HPLC: $^A t_{Ret}$=2.41 min; LC-MS: m/z 480.5 [M+H]$^+$; $^1$H NMR (400 MHz, CDCl$_3$): 0.95-1.03 (2t, J=7.5, 3H, mixture of diastereoisomers), 1.29-1.34 (2 d, J=6.1, 3H, mixture of diastereoisomers), 1.58-1.85 (m, 2H), 3.72-3.87 (m, 2H), 3.88 (s, 3H), 4.19-4.28 (m, 1H), 5.83 (s, 1H), 6.73 (s, 1H), 6.77 (d, J=4.9, 1H), 7.07-7.13 (m, 2H), 7.26-7.35 (m, 4H), 8.05-8.11 (m, 2H).

Example 39

(2S,4R)-1-{4-[7-((R)-sec-Butoxy)-1-(4-chloro-phenyl)-6-methoxy-3-oxo-3,4-dihydro-1H-isoquinolin-2-yl]-benzoyl}-4-hydroxy-pyrrolidine-2-carboxylic acid methylamide

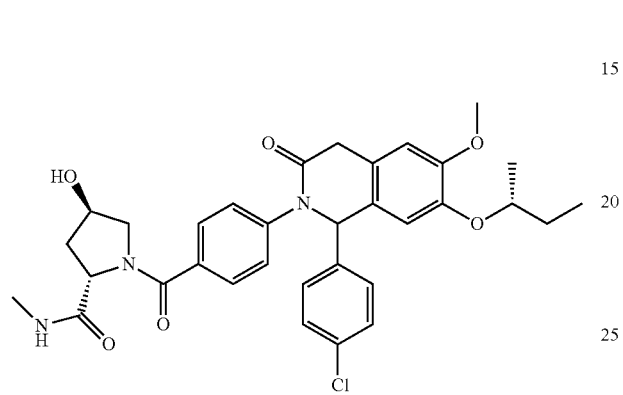

To a solution of Intermediate 39.1 (30 mg, 0.051 mmol) in DMF (0.5 ml) were successively added methylamine (2M solution in THF, 0.25 ml, 0.50 mmol), NMM (0.017 ml, 0.156 mmol) and HATU (28.9 mg, 0.076 mmol) at RT. The reaction mixture was stirred at RT for 2 h then diluted into AcOEt and washed with a 2M aqueous Na$_2$CO$_3$ solution. The organic layer was dried over Na$_2$SO$_4$, filtered and evaporated to dryness. The crude material was purified by reverse phase prep-HPLC (Waters system) to yield the title compound (19.9 mg, 0.033 mmol, 65%) as a yellow solid. HPLC: $^A$t$_{Ret}$=2.00 min; LC-MS: m/z 606.2 [M+H]$^+$; $^1$H NMR (500 MHz, DMSO-d$_6$): 0.83-0.94 (2t, J=7.5, 3H, mixture of diastereoisomers), 1.11-1.22 (2 d, J=6.1, 3H, mixture of diastereoisomers), 1.47-1.68 (m, 2H), 1.79-1.88 (m, 1H), 2.04-2.12 (m, 1H), 2.55-2.60 (m, 2H), 3.26 (d, J=11.0, 1H), 3.51-3.77 (m, 5H), 3.89 (dd, J=19.8, 7.3, 1H), 4.17-4.29 (m, 2H), 4.46 (t, J=8.5, 1H), 6.18 (d, J=2.9, 1H), 6.86 (s, 1H), 7.07 (d, J=10.5, 1H), 7.24-7.29 (m, 2H), 7.30-7.38 (m, 3H), 7.52-7.58 (m, 2H), 7.81-7.89 (m, 1H).

Intermediate 39.1: (2S,4R)-1-{4-[7-((R)-sec-Butoxy)-1-(4-chloro-phenyl)-6-methoxy-3-oxo-3,4-dihydro-1H-isoquinolin-2-yl]-benzoyl}-4-hydroxy-pyrrolidine-2-carboxylic acid

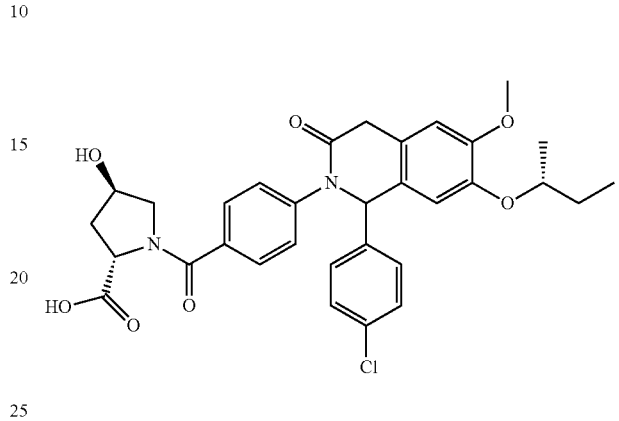

To a solution of Intermediate 38.3 (73 mg, 0.15 mmol) in DCM (1 ml) were successively added oxalylchloride (0.020 ml, 0.23 mmol) and a catalytic amount of DMF (0.001 ml, 0.015 mmol) at 0° C. (ice bath). The reaction mixture was stirred at 0° C. for 30 min then DIPEA (0.106 ml, 0.608 mmol) and (2S,4R)-4-hydroxy-pyrrolidine-2-carboxylic acid methyl ester hydrochloride (41.4 mg, 0,228 mmol) were successively added. The reaction mixture was allowed to warm to RT and stirred for 1 h. A 2M aqueous KOH solution was added then the heterogeneous mixture was stirred for 30 min and extracted with Et$_2$O. The organic layer was dried over Na$_2$SO$_4$, filtered and evaporated to dryness to yield the crude title compound (71 mg, 0.12 mmol, 79%) as a yellow resin, which was used in the next step without further purification. HPLC: $^A$t$_{Ret}$=2.04 min; LC-MS: m/z 593.4 [M+H]$^+$.

Example 40

Compounds 40a to 40l were obtained from Intermediate 38.3 (or analogues prepared similarly) analogously to Example 38 or 39.

| # | Structure | Name/HPLC/MS/NMR |
|---|---|---|
| 40a | 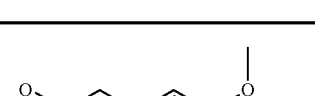 | 7-((R)-sec-Butoxy)-1-[4-chloro-phenyl)-6-methoxy-2-[4-(piperidine-1-carbonyl)-phenyl]-1,4-dihydro-2H-isoquinolin-3-one.<br>HPLC: $^A$t$_{Ret}$ = 2.63; LC-MS: m/z 547.5 [M + H]$^+$. |

-continued

| # | Structure | Name/HPLC/MS/NMR |
|---|-----------|------------------|
| 40b | 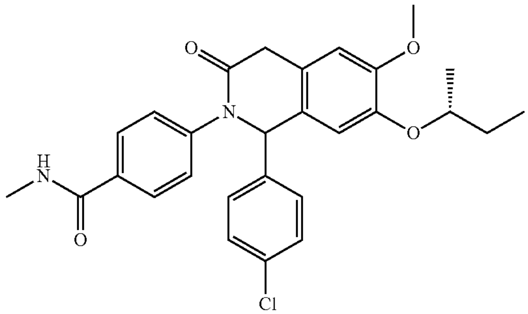 [SMILES: CC[C@@H](C)Oc1cc2c(cc1OC)CC(=O)N(c1ccc(C(=O)OC)cc1)C2c1ccc(Cl)cc1] | 4-[7-((R)-sec-Butoxy)-1-[4-chloro-phenyl)-6-methoxy-3-oxo-3,4-dihydro-1H-isoquinolin-2-yl]-N-methyl-benzamide.<br>HPLC: $^{A}t_{Ret}$ = 2.29; LC-MS: m/z 493.4 [M + H]$^{+}$. |
| 40c | 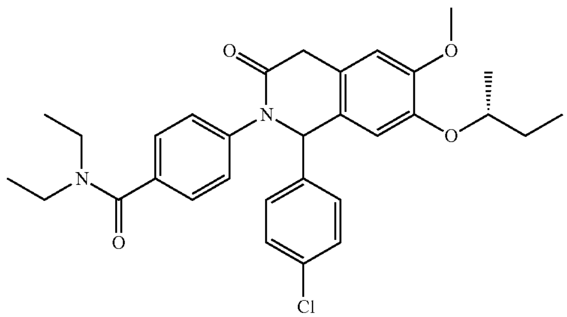 [SMILES: CC[C@@H](C)Oc1cc2c(cc1OC)CC(=O)N(c1ccc(C(=O)N(CC)CC)cc1)C2c1ccc(Cl)cc1] | 4-[7-((R)-sec-Butoxy)-1-(4-chloro-phenyl)-6-methoxy-3-oxo-3,4-dihydro-1H-isoquinolin-2-yl]-N,N-diethyl-benzamide.<br>HPLC: $^{A}t_{Ret}$ = 2.58; LC-MS: m/z 535.5 [M + H]$^{+}$. |
| 40d | 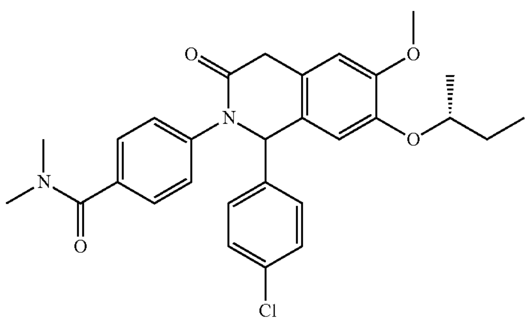 | 4-[7-((R)-sec-Butoxy)-1-(4-chloro-phenyl)-6-methoxy-3-oxo-3,4-dihydro-1H-isoquinolin-2-yl]-N,N-dimethyl-benzamide.<br>HPLC: $^{A}t_{Ret}$ = 2.35; LC-MS: m/z 507.4 [M + H]$^{+}$. |
| 40e | 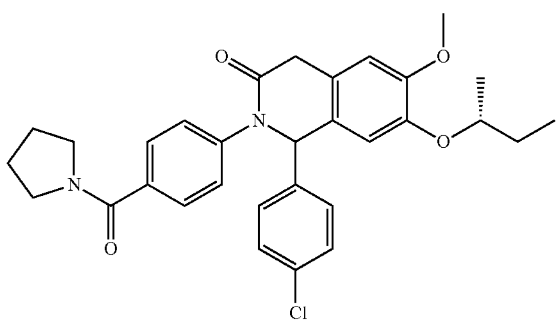 [SMILES: CC[C@@H](C)Oc1cc2c(cc1OC)CC(=O)N(c1ccc(C(=O)N3CCCC3)cc1)C2c1ccc(Cl)cc1] | 7-((R)-sec-Butoxy)-1-(4-chloro-phenyl)-6-methoxy-2-[4-(pyrrolidine-1-carbonyl)-phenyl]-1,4-dihydro-2H-isoquinolin-3-one.<br>HPLC: $^{A}t_{Ret}$ = 2.47; LC-MS: m/z 533.5 [M + H]$^{+}$. |
| 40f | 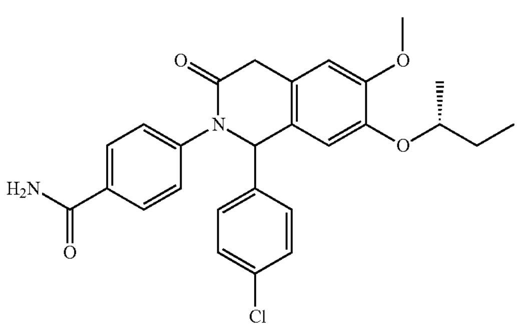 | 4-[7-((R)-sec-Butoxy)-1-(4-chloro-phenyl)-6-methoxy-3-oxo-3,4-dihydro-1H-isoquinolin-2-yl]-benzamide.<br>HPLC: $^{A}t_{Ret}$ = 2.19; LC-MS: m/z 497.4 [M + H]$^{+}$. |

| # | Structure | Name/HPLC/MS/NMR |
|---|---|---|
| 40g | 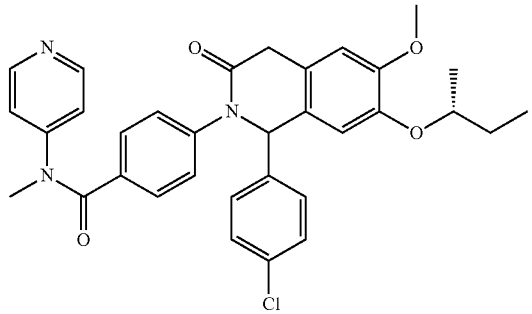 [SMILES: CC[C@@H](C)Oc1cc2c(cc1OC)CC(=O)N(c1ccc(C(=O)N(C)c3ccncc3)cc1)C2c1ccc(Cl)cc1] | 4-[7-((R)-sec-Butoxy)-1-(4-chloro-phenyl)-6-methoxy-3-oxo-3,4-dihydro-1H-isoquinolin-2-yl]-N-methyl-N-pyridin-4-yl-benzamide. HPLC: $^{A}t_{Ret}$ = 1.98; LC-MS: m/z 570.3 [M + H]$^{+}$. |
| 40h | 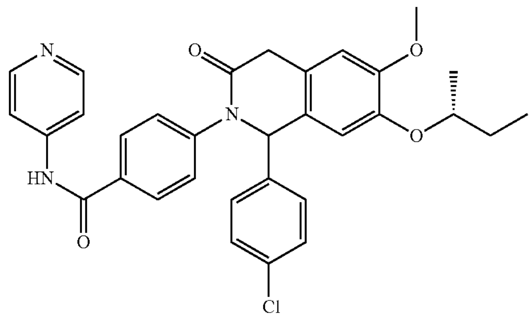 [SMILES: CC[C@@H](C)Oc1cc2c(cc1OC)CC(=O)N(c1ccc(C(=O)Nc3ccncc3)cc1)C2c1ccc(Cl)cc1] | 4-[7-((R)-sec-Butoxy)-1-(4-chloro-phenyl)-6-methoxy-3-oxo-3,4-dihydro-1H-isoquinolin-2-yl]-N-pyridin-4-yl-benzamide. HPLC: $^{A}t_{Ret}$ = 2.04; LC-MS: m/z 556.3 [M + H]$^{+}$. |
| 40i | 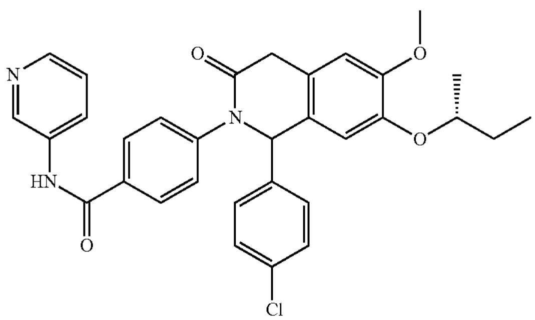 | 4-[7-((R)-sec-Butoxy)-1-(4-chloro-phenyl)-6-methoxy-3-oxo-3,4-dihydro-1H-isoquinolin-2-yl]-N-pyridin-3-yl-benzamide. HPLC: $^{A}t_{Ret}$ = 1.99; LC-MS: m/z 566.3 [M + H]$^{+}$. |
| 40j | 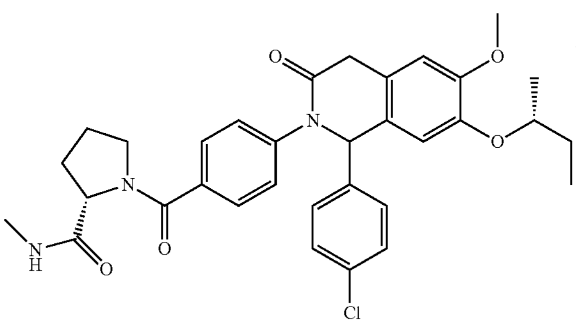 [SMILES: CC[C@@H](C)Oc1cc2c(cc1OC)CC(=O)N(c1ccc(C(=O)N3CCC[C@H]3C(=O)NC)cc1)C2c1ccc(Cl)cc1] | (S)-1-{4-[7-((R)-sec-Butoxy)-1-(4-chloro-phenyl)-6-methoxy-3-oxo-3,4-dihydro-1H-isoquinolin-2-yl]-benzoyl}-pyrrolidine-2-carboxylic acid methylamide. HPLC: $^{A}t_{Ret}$ = 2.18; LC-MS: m/z 590.3 [M + H]$^{+}$. |
| 40k | 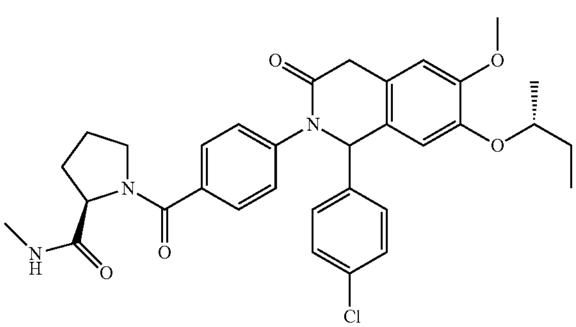 [SMILES: CC[C@@H](C)Oc1cc2c(cc1OC)CC(=O)N(c1ccc(C(=O)N3CCC[C@@H]3C(=O)NC)cc1)C2c1ccc(Cl)cc1] | (R)-1-{4-[7-((R)-sec-Butoxy)-1-(4-chloro-phenyl)-6-methoxy-3-oxo-3,4-dihydro-1H-isoquinolin-2-yl]-benzoyl}-pyrrolidine-2-carboxylic acid methylamide. HPLC: $^{A}t_{Ret}$ = 2.18; LC-MS: m/z 590.2 [M + H]$^{+}$. |

| # | Structure | Name/HPLC/MS/NMR |
|---|---|---|
| 401 | | (2R,4S)-1-{4-[7-((R)-sec-Butoxy)-1-(4-chloro-phenyl)-6-methoxy-3-oxo-3,4-dihydro-1H-isoquinolin-2-yl]-benzoyl}-4-hydroxy-pyrrolidine-2-carboxylic acid methylamide.<br>HPLC: $^{A}t_{Ret}$ = 1.99; LC-MS: m/z 606.3 [M + H]$^{+}$. |

Example 41

7-((R)-sec-Butoxy)-1-(4-chloro-phenyl)-2-(4-hydroxymethyl-phenyl)-6-methoxy-1,4-dihydro-2H-isoquinolin-3-one

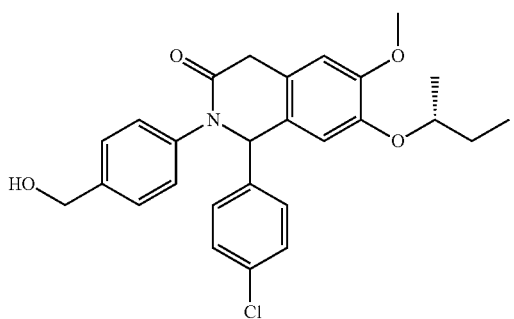 [SMILES: CC[C@@H](C)Oc1cc2c(cc1OC)CC(=O)N(c1ccc(CO)cc1)C2c1ccc(Cl)cc1]

Example 42

7-((R)-sec-Butoxy)-1-(4-chloro-phenyl)-6-methoxy-2-[4-(methyl-pyridin-4-ylmethyl-amino)-phenyl]-1,4-dihydro-2H-isoquinolin-3-one

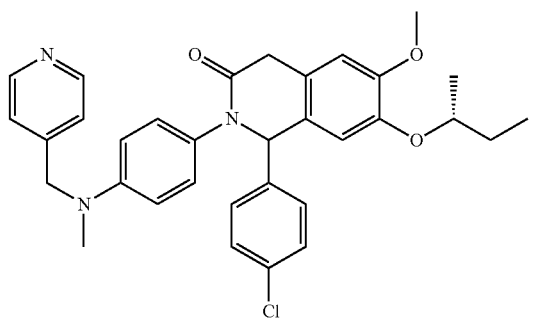

To a solution of Intermediate 38.2 (50 mg, 0.10 mmol) in THF (1 ml) were successively added LiBH$_4$ (6.6 mg, 0.30 mmol) and MeOH (0.012 ml, 0.30 mmol) at RT. The reaction mixture was stirred at RT for 2 h then quenched cautiously by the addition of HCl 2M in water, diluted into DCM and washed with Na$_2$CO$_3$ 2M in water. The aqueous layer was further extracted with DCM (2×) and the combined organic fractions were dried over Na$_2$SO$_4$, filtered and evaporated to dryness. The resulting crude material was purified by Combi-Flash Companion™ (Isco Inc.) column chromatography (SiO$_2$; gradient elution, [heptane/DCM 1:1]/TBME 95:5→100% TBME) to yield the title compound (22 mg, 0.047 mmol, 47%) as a foam. TLC: R$_F$=0.13 (heptane/DCM/TBME 1:1:2); HPLC: $^{A}t_{Ret}$=2.33 min; LC-MS: m/z 466.3 [M+H]$^{+}$; $^{1}$H NMR (400 MHz, CDCl$_3$): 0.93-1.03 (2t, J=7.5, 3H, mixture of diastereoisomers), 1.24-1.34 (2 d, J=6.1, 3H, mixture of diastereoisomers), 1.61-1.86 (m, 2H), 3.76 (d, J=19.8, 1H), 3.84-3.92 (m, 4H), 4.15-4.26 (m, 1H), 4.70 (s, 2H), 5.76 (s, 1H), 6.68-6.74 (m, 2H), 7.05-7.11 (m, 2H), 7.12-7.17 (m, 2H), 7.24-7.30 (m, 2H), 7.34-7.40 (m, 2H).

To a solution of Intermediate 42.3 (25 mg, 0.055 mmol) in DCM (1 ml) were successively added AcOH (0.009 ml, 0.15 mmol), pyridine-4-carbaldehyde (0.006 ml, 0.061 mmol) and NaBH(OAc)$_3$ (19.4 mg, 0.091 mmol) at RT. The reaction mixture was stirred for 2 h, then additional AcOH (0.008 ml, 0.14 mmol), formaldehyde (37% in water, 0.008 ml, 0.11 mmol) and additional NaBH(OAc)$_3$ (17 mg, 0.083 mmol) were added. The reaction mixture was stirred at RT for 2 h then water was added and the two phases were separated. The aqueous layer was extracted with DCM (2×) and the combined organic fractions were evaporated to dryness. The resulting residue was purified by reverse phase prep-HPLC (Waters system) to yield the title compound (TFA salt, 10.8 mg, 0.016 mmol, 29%). HPLC: $^{A}t_{Ret}$=2.05 min; LC-MS: m/z 556.3 [M+H]$^{+}$; $^{1}$H NMR (400 MHz, DMSO-d$_6$): 0.83-0.94 (m, 3H, mixture of diastereoisomers), 1.09-1.22 (2 d, J=6.1, 3H, mixture of diastereoisomers), 1.43-1.68 (m, 2H), 3.03 (s, 3H), 3.56 (d, J=19.8, 1H), 3.72 (s, 3H), 3.83-3.93 (m, 1H), 4.16-4.30 (m, 1H), 4.58 (s, 2H), 5.93-5.98 (m, 1H), 6.57-6.64 (m, 2H), 6.83 (s, 1H), 6.87-6.95 (m, 2H), 7.03 (d, J=6.6, 1H), 7.18 (d, J=5.4, 2H), 7.34 (s, 4H), 8.48 (d, J=4.9, 2H).

Intermediate 42.1: [1-(4-Chloro-phenyl)-meth-(E)-ylidene]-(4-nitro-phenyl)-amine

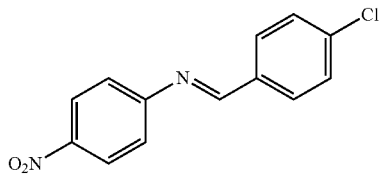 [SMILES: O=[N+]([O-])c1ccc(/N=C/c2ccc(Cl)cc2)cc1]

The title compound (2.27 g, 8.69 mmol, 80%) was obtained as a yellow solid from 4-nitro-phenylamine (1.5 g, 10.86 mmol) and 4-chloro-benzaldehyde (1.53 g, 10.86 mmol) analogously to Intermediate 1.4. $^1$H NMR (400 MHz, CDCl$_3$): 7.23-7.31 (m, 2H), 7.48-7.54 (m, 2H), 7.85-7.92 (m, 2H), 8.26-8.34 (m, 2H), 8.42 (s, 1H).

Intermediate 42.2: 7-((R)-sec-Butoxy)-1-(4-chloro-phenyl)-6-methoxy-2-(4-nitro-phenyl)-1,4-dihydro-2H-isoquinolin-3-one

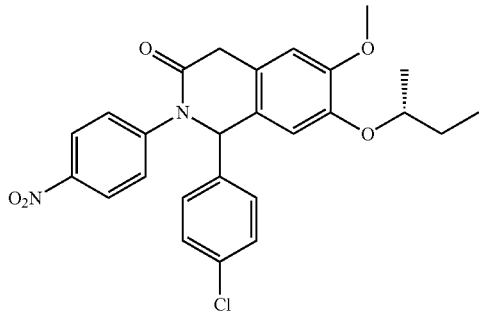 [SMILES: CC[C@@H](C)Oc1cc2c(cc1OC)CC(=O)N(c1ccc([N+](=O)[O-])cc1)C2c1ccc(Cl)cc1]

The title compound (700 mg, 1.46 mmol, 47%) was obtained as a yellow foam from Intermediate 42.1 (812 mg, 3.12 mmol) and Intermediate 1.3 (800 mg, 3.12 mmol) analogously to Example 1. Purification of the crude material was performed by reverse phase prep-HPLC (Waters system). HPLC: $^A t_{Ret}$=2.81 min; LC-MS: m/z 481.4 [M+H]$^+$; $^1$H NMR (400 MHz, CDCl$_3$): 0.96-1.04 (m, 3H, mixture of diastereoisomers), 1.28-1.35 (2 d, J=6.1, 3H, mixture of diastereoisomers), 1.60-1.87 (m, 2H, mixture of diastereoisomers), 3.75-3.80 (m, 2H), 3.88 (s, 3H), 4.19-4.31 (m, 1H), 5.85 (s, 1H), 6.73 (s, 1H), 6.80 (d, J=4.9, 1H), 7.09-7.15 (m, 2H), 7.29-7.34 (m, 2H), 7.39-7.46 (m, 2H), 8.20-8.27 (m, 2H).

Intermediate 42.3: 2-(4-Amino-phenyl)-7-((R)-sec-butoxy)-1-(4-chloro-phenyl)-6-methoxy-1,4-dihydro-2H-isoquinolin-3-one

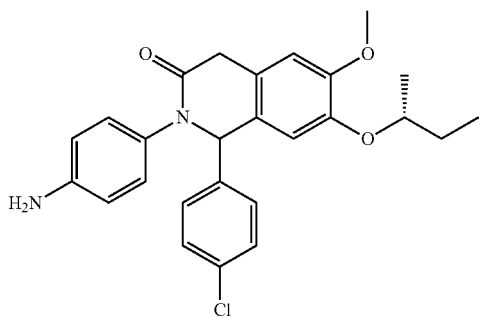

In a sealed reaction flask, a mixture of Intermediate 42.2 (700 mg, 1.46 mmol) and Fe (813 mg, 14.6 mmol) in AcOH (2.8 ml), water (4 ml) and AcOEt (0.8 ml) was heated at 80° C. and stirred for 1 h. The suspension was cooled to RT, neutralized by the addition of a saturated aqueous NaHCO$_3$ solution to pH 7 and filtered through a Celite pad. The solid was washed with AcOEt and the biphasic filtrate was transferred into a separating funnel. The aqueous layer was separated and further extracted with AcOEt (3×). The combined organic fractions were dried over Na$_2$SO$_4$, filtered and evaporated to dryness to yield the crude title compound (651 mg, 1.44 mmol, 99%) as a yellow foam, which was used in the next step without further purification. HPLC: $^A t_{Ret}$=1.88 min; LC-MS: m/z 451.2 [M+H]$^+$; $^1$H NMR (400 MHz, CDCl$_3$): 0.91-1.02 (2t, J=7.5, 3H, mixture of diastereoisomers), 1.21-1.32 (2 d, J=6.1, 3H, mixture of diastereoisomers), 1.54-1.83 (m, 2H), 3.83 (d, J=20.3, 1H), 3.89 (s, 3H), 3.97 (d, J=20.1, 1H), 4.12-4.23 (m, 1H), 5.69 (s, 1H), 6.61 (d, J=4.6, 1H), 6.72 (s, 1H), 6.81-6.93 (m, 4H), 6.99-7.04 (m, 2H), 7.23-7.28 (m, 2H).

Example 43

N-{4-[7-((R)-sec-Butoxy)-1-(4-chloro-phenyl)-6-methoxy-3-oxo-3,4-dihydro-1H-isoquinolin-2-yl]-phenyl}-N-methyl-acetamide

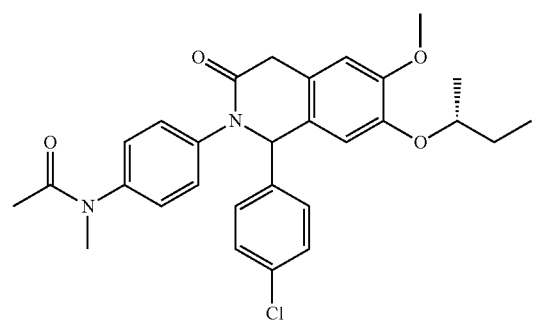 [SMILES: CC[C@@H](C)Oc1cc2c(cc1OC)CC(=O)N(c1ccc(N(C)C(C)=O)cc1)C2c1ccc(Cl)cc1]

The title compound (50.7 mg, 0.10 mmol, 57%) was obtained from Intermediate 43.3 (50 mg, 0.17 mmol) and Intermediate 1.3 (44.8 mg, 0.17 mmol) analogously to Example 1. Purification of the crude material was performed by reverse phase prep-HPLC (Waters system). HPLC: $^A t_{Ret}$=2.37 min; LC-MS: m/z 507.3 [M+H]$^+$; $^1$H NMR (400 MHz, CDCl$_3$): 0.94-1.03 (2t, J=7.5, 3H, mixture of diastereoisomers), 1.26-1.34 (2 d, J=6.1, 3H, mixture of diastereoisomers), 1.56-1.84 (m, 2H), 1.93 (s, 3H), 3.28 (s, 3H), 3.78 (d, J=19.8, 1H), 3.88 (d, J=19.6, 1H), 3.88 (s, 3H), 4.17-4.26 (m, 1H), 5.79 (br. s., 1H), 6.71-6.76 (m, 2H), 7.09-7.14 (m, 2H), 7.17-7.32 (m, 6H).

Intermediate 43.1: N-Methyl-N-(4-nitro-phenyl)-acetamide

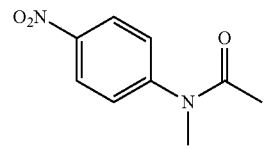

To a solution of N-methyl-4-nitroaniline (200 mg, 1.31 mmol) in THF (5 ml) were successively added Et$_3$N (0.364 ml, 2.63 mmol), acetyl chloride (0.14 ml, 1.97 mmol) and DMAP (8.0 mg, 0.066 mmol) at RT. The reaction mixture was stirred at RT for 2 h then diluted into AcOEt and washed with water. The organic layer was dried over Na$_2$SO$_4$, filtered and evaporated to dryness to yield the crude title compound (275 mg) as a brownish solid, which was used in the next step without further purification. HPLC: $^A$t$_{Ret}$=1.17 min; LC-MS: m/z 195.4 [M+H]$^+$; $^1$H NMR (400 MHz, CDCl$_3$): 2.05 (br. s., 3H), 3.37 (s, 3H), 7.36-7.46 (m, 2H), 8.27-8.36 (m, 2H).

Intermediate 43.2:
N-(4-Amino-phenyl)-N-methyl-acetamide

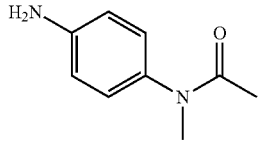

A solution of Intermediate 43.1 (275 mg, 1.232 mmol) in EtOH (5 ml) was degassed under vacuum and backfilled with argon. Pd/C (1.31 mg, 0.012 mmol) and ammonium formate (155 mg, 2.46 mmol) were successively added and the heterogeneous mixture was well stirred at RT for 2 h then filtered over a Celite pad and the catalyst washed with DCM. The filtrate was evaporated to dryness and the resulting crude material was purified by Combi-Flash Companion™ (Isco Inc.) column chromatography (SiO$_2$; gradient elution, [heptane/DCM 1:1]/TBME containing 5% of 7 M NH$_3$ in MeOH 95:5→100% TBME containing 5% of 7 M NH$_3$ in MeOH) to yield the title compound (190 mg, 1.16 mmol, 94%) as a yellow oil. TLC: R$_F$=0.35 (heptane/DCM/TBME containing 5% of 7 M NH$_3$ in MeOH 1:1:2); HPLC: $^B$t$_{Ret}$=0.17 and 0.24 min; API-MS: m/z 165.1 [M+H]$^+$; $^1$H NMR (400 MHz, CDCl$_3$): 1.87 (s, 3H), 3.22 (s, 3H), 6.67-6.73 (m, 2H), 6.94-6.99 (m, 2H).

Intermediate 43.3: N-(4-{([1-(4-Chloro-phenyl)-meth-(E)-ylidene]-amino}-phenyl)-N-methyl-acetamide

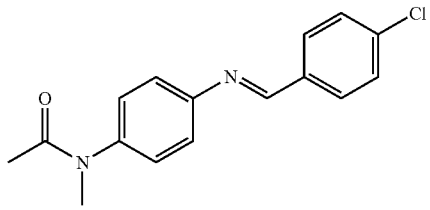 [SMILES: CC(=O)N(C)c1ccc(/N=C/c2ccc(Cl)cc2)cc1]

The title compound (160 mg, 0.56 mmol, 92%) was obtained as a yellow solid from Intermediate 43.2 (100 mg, 0.61 mmol) and 4-chloro-benzaldehyde (86 mg, 0.61 mmol) analogously to Intermediate 1.4. $^1$H NMR (400 MHz, CDCl$_3$): 1.93 (s, 3H), 3.31 (s, 3H), 7.19-7.30 (m, 4H), 7.45-7.52 (m, 2H), 7.84-7.92 (m, 2H), 8.45 (s, 1H).

Example 44

N-{4-[7-((R)-sec-Butoxy)-1-(4-chloro-phenyl)-6-methoxy-3-oxo-3,4-dihydro-1H-isoquinolin-2-yl]-phenyl}-N-cyclopentylmethyl-acetamide

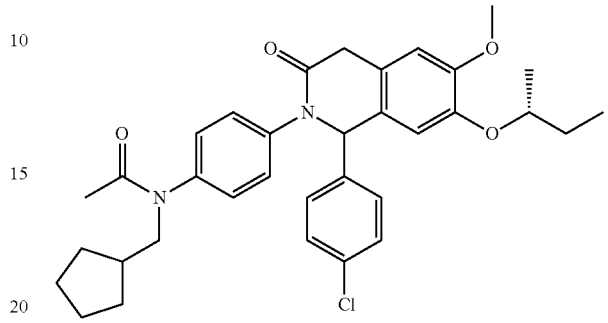

To a solution of Intermediate 44.1 (24 mg, 0.045 mmol) in THF (1 ml) were successively added Et$_3$N (0.012 ml, 0.090 mmol), DMAP (0.28 mg, 0.002 mmol) and acetyl chloride (0.007 ml, 0.090 mmol) at RT. The reaction mixture was stirred at RT for 2 h, diluted in DCM and washed with water. The organic layer was dried over Na$_2$SO$_4$, filtered and evaporated to dryness. The crude material was purified by reverse phase prep-HPLC (Waters system). HPLC: $^A$t$_{Ret}$=2.89 min; LC-MS: m/z 575.4 [M+H]$^+$; $^1$H NMR (400 MHz, CDCl$_3$): 0.94-1.03 (2t, J=7.5, 3H, mixture of diastereoisomers), 1.18-1.26 (m, 2H), 1.26-1.34 (2 d, J=6.1, 3H, mixture of diastereoisomers), 1.47-1.84 (m, 8H), 1.88 (s, 3H), 1.97-2.06 (m, 1H), 3.66-3.73 (m, 2H), 3.75-3.91 (m, 2H), 3.89 (s, 3H), 4.17-4.26 (m, 1H), 5.81 (s, 1H), 6.71-6.76 (m, 2H), 7.08-7.13 (m, 2H), 7.14-7.20 (m, 2H), 7.22-7.32 (m, 4H).

Intermediate 44.1: 7-((R)-sec-Butoxy)-1-(4-chloro-phenyl)-2-[4-(cyclopentylmethyl-amino)-phenyl]-6-methoxy-1,4-dihydro-2H-isoquinolin-3-one

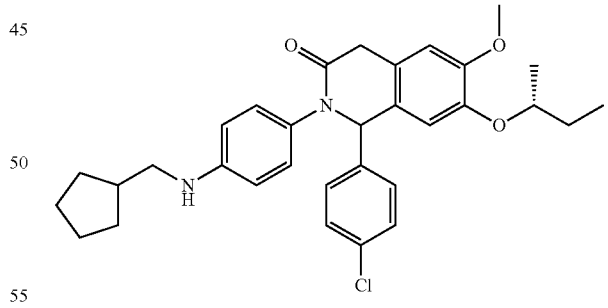

To a solution of Intermediate 42.3 (25 mg, 0.044 mmol) in DCM (1 ml) were successively added AcOH (0.006 ml, 0.11 mmol), cyclopentanecarbaldehyde (0.006 ml, 0.053 mmol) and NaBH(OAc)$_3$ (14.1 mg, 0.066 mmol) at RT. The reaction mixture was stirred at RT for 2 h then Na$_2$CO$_3$ 2 M in water was added, the two phases were separated and the aqueous layer was further extracted with DCM (2×). The combined organic fractions were evaporated to dryness to yield the crude title compound (23.6 mg, 0.044 mmol, quant.) as a brownish solid. HPLC: $^A$t$_{Ret}$=2.57 min; LC-MS: m/z 533.4 [M+H]$^+$; $^1$H NMR (400 MHz, CDCl$_3$): 0.93-1.02 (m, 3H), 1.23-1.33 (m, 5H), 1.51-1.88 (m, 8H), 2.11-2.22 (m, 1H), 3.01 (d, J=7.3, 2H), 3.74 (d, J=19.8, 1H), 3.85-3.92 (m, 4H), 4.14-4.24 (m, 1H), 5.68 (s, 1H), 6.52-6.58 (m, 2H), 6.66 (d, J=4.2, 1H), 6.70 (s, 1H), 6.85-6.90 (m, 2H), 7.05-7.10 (m, 2H), 7.22-7.27 (m, 2H).

Example 45

7-((R)-sec-Butoxy)-1-(4-chloro-phenyl)-6-methoxy-2-[4-(methyl-piperidin-3-ylmethyl-amino)-phenyl]-1,4-dihydro-2H-isoquinolin-3-one

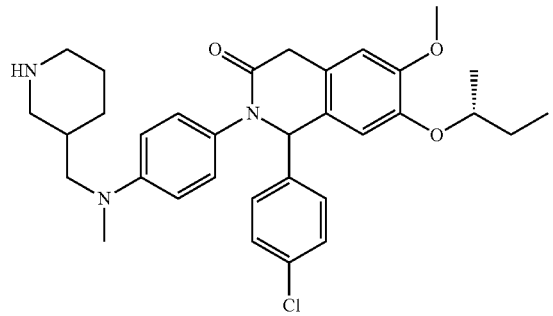 [SMILES: CC[C@@H](C)Oc1cc2c(cc1OC)CC(=O)N(c1ccc(N(C)CC3CCCNC3)cc1)C2c1ccc(Cl)cc1]

To a solution of Intermediate 42.3 (25 mg, 0.055 mmol) in DCM (0.5 ml) were successively added AcOH (0.006 ml, 0.111 mmol), tert-butyl 3-formylpiperidine-1-carboxylate (13.0 mg, 0.061 mmol) and NaBH(OAc)$_3$ (23.5 mg, 0.111 mmol) at RT. The reaction mixture was stirred at RT for 1 h, then diluted with DCM and washed with water. The organic phase was dried over Na$_2$SO$_4$, filtered and evaporated to dryness. The resulting yellow resin was dissolved in DCM (0.5 ml) then AcOH (0.006 ml, 0.111 mmol), formaldehyde (37% in water, 0.008 ml, 0.111 mmol) and NaBH(OAc)$_3$ (23.5 mg, 0.111 mmol) were successively added at RT. The reaction mixture was stirred at RT for 1 h, then diluted with DCM and washed with water. The organic phase was dried over Na$_2$SO$_4$, filtered and evaporated to dryness. The resulting yellow resin was dissolved in DCM (1 ml) and TFA (0.021 ml, 0.272 mmol) was added at RT. The reaction mixture was stirred at RT for 30 min then evaporated to dryness. The resulting crude material was purified by reverse phase prep-HPLC (Waters system) to yield the title compound (TFA salt, 7 mg, 0.01 mmol, 19%) as a colorless solid. HPLC: $^A$t$_{Ret}$=2.11 min; LC-MS: m/z 562.6 [M+H]$^+$; $^1$H NMR (400 MHz, DMSO-d$_6$): 0.83-0.95 (2t, J=7.5, 3H, mixture of diastereoisomers), 1.10-1.26 (m, 4H), 1.44-1.69 (m, 3H), 1.69-1.84 (m, 2H), 2.01-2.15 (m, 1H), 2.59-2.80 (m, 2H), 2.89 (s, 3H), 3.10-3.26 (m, 4H), 3.58 (d, J=19.8, 1H), 3.73 (s, 3H), 3.87-3.97 (m, 1H), 4.17-4.31 (m, 1H), 5.92-5.99 (m, 1H), 6.58-6.66 (m, 2H), 6.84 (s, 1H), 6.89-6.96 (m, 2H), 6.99-7.05 (m, 1H), 7.36 (s, 4H).

Example 46

7-((R)-sec-Butoxy)-1-(4-chloro-phenyl)-6-methoxy-2-{4-[methyl-(1-methyl-piperidin-3-ylmethyl)-amino]-phenyl}-1,4-dihydro-2H-isoquinolin-3-one

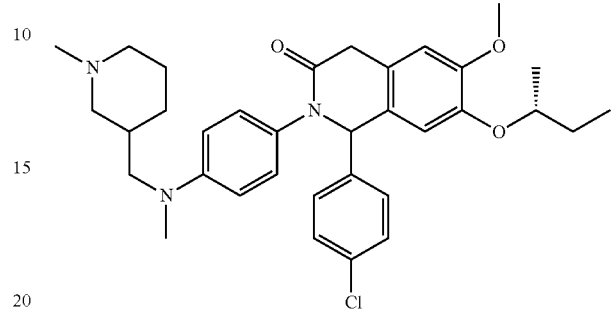

To a solution of Example 45 (TFA salt, 7 mg, 0.01 mmol) in DCM (0.5 ml) were successively added AcOH (0.001 ml, 0.021 mmol), formaldehyde (37% in water, 0.002 ml, 0.021 mmol) and NaBH(OAc)$_3$ (4.4 mg, 0.021 mmol) at RT. The reaction mixture was stirred at RT for 1 h, then diluted into DCM and washed with a 2M aqueous Na$_2$CO$_3$ solution. The organic phase was dried over Na$_2$SO$_4$, filtered and evaporated to dryness. The crude material was purified by reverse phase prep-HPLC (Waters system) to yield the title compound (TFA salt, 7.4 mg, 0.01 mmol, quant.) as a colorless solid. HPLC: $^A$t$_{Ret}$=2.11 min; LC-MS: m/z 576.3 [M+H]$^+$; $^1$H NMR (500 MHz, DMSO-d$_6$): 0.83-0.92 (2t, J=7.5, 3H, mixture of diastereoisomers), 1.10-1.20 (2t, J=6.1, 3H, mixture of diastereoisomers), 1.44-1.67 (m, 4H), 1.69-1.87 (m, 2H), 2.04-2.19 (m, 1H), 2.65-2.81 (m, 5H), 2.84-2.93 (m, 3H), 3.08-3.19 (m, 1H), 3.22-3.41 (m, 3H), 3.56 (d, J=20.0, 1H), 3.72 (s, 3H), 3.91 (d, J=20.0, 1H), 4.17-4.27 (m, 1H), 5.91-5.96 (m, 1H), 6.58-6.63 (m, 2H), 6.83 (s, 1H), 6.88-6.94 (m, 2H), 6.98-7.02 (m, 1H), 7.32-7.37 (m, 4H).

Example 47

7-((R)-sec-Butoxy)-1-(4-chloro-phenyl)-6-methoxy-2-[4-(methyl-piperidin-4-ylmethyl-amino)-phenyl]-1,4-dihydro-2H-isoquinolin-3-one

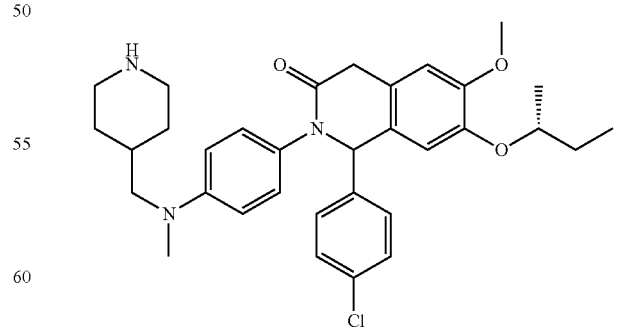

The title compound (TFA salt, 27 mg, 0.04 mmol, 36%) was obtained as a light yellow solid from Intermediate 42.3 (50 mg, 0.111 mmol) and benzyl 4-formylpiperidine-1-carboxylate (30.2 mg, 0.122 mmol) analogously to Example 45.

Cleavage of the benzyloxy carbamate protecting group was achieved by hydrogenolysis with ammonium formate (1.5 equiv.) and Pd/C (0.05 equiv.) as a catalyst in EtOH (0.1 M) at RT for 2 h. Purification of the crude material was performed by reverse phase prep-HPLC (Waters system). HPLC: $^A t_{Ret}$=2.01 min; LC-MS: m/z 562.5 [M+H]$^+$; $^1$H NMR (400 MHz, DMSO-d$_6$): 0.83-0.95 (2t, J=7.5, 3H, mixture of diastereoisomers), 1.10-1.22 (2 d, J=6.1, 3H, mixture of diastereoisomers), 1.23-1.37 (m, 2H), 1.45-1.69 (m, 2H), 1.71-1.82 (m, 2H), 1.87-1.98 (m, 1H), 2.75-2.88 (m, 2H), 2.91 (s, 3H), 3.16-3.30 (m, 4H), 3.60 (d, J=20.1, 1H), 3.73 (s, 3H), 3.86-3.95 (m, 1H), 4.18-4.31 (m, 1H), 5.95 (d, J=2.9, 1H), 6.56-6.64 (m, 2H), 6.84 (s, 1H), 6.88-6.96 (m, 2H), 7.03 (d, J=5.9, 1H), 7.36 (s, 4H), 8.06-8.20 (m, 1H), 8.41-8.54 (m, 1H).

Example 48

2-{4-[(1-Acetyl-piperidin-4-ylmethyl)-methyl-amino]-phenyl}-7-((R)-sec-butoxy)-1-(4-chloro-phenyl)-6-methoxy-1,4-dihydro-2H-isoquinolin-3-one

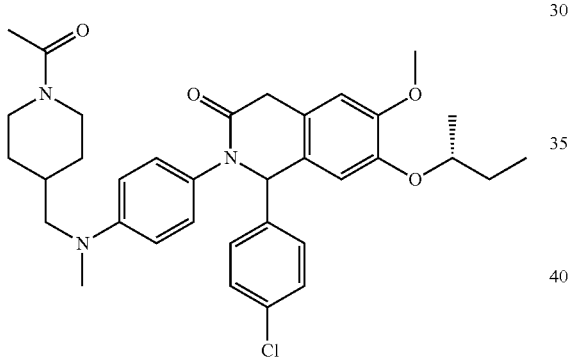

To a solution of Example 47 (TFA salt, 12 mg, 0.018 mmol) in DCM (0.5 ml) were successively added pyridine (0.009 ml, 0.107 mmol) and acetic anhydride (0.002 ml, 0.026 mmol) at RT. The reaction mixture was stirred at RT for 1 h then diluted with AcOEt and washed with water and brine. The organic phase was dried over Na$_2$SO$_4$, filtered and evaporated to dryness. The resulting crude material was purified by reverse phase prep-HPLC (Waters system) to yield the title compound (TFA salt, 7.1 mg, 0.01 mmol, 55%) as a colorless solid. HPLC: $^A t_{Ret}$=2.24 min; LC-MS: m/z 604.3 [M+H]$^+$; $^1$H NMR (500 MHz, DMSO-d$_6$): 0.82-0.92 (2t, J=7.5, 3H, mixture of diastereoisomers), 0.93-1.03 (m, 1H), 1.05-1.21 (m, 4H), 1.45-1.65 (m, 4H), 1.82-1.92 (m, 1H), 1.95 (s, 3H), 2.37-2.45 (m, 1H), 2.84-2.98 (m, 4H), 3.12-3.20 (m, 2H), 3.56 (d, J=19.8, 1H), 3.72 (s, 3H), 3.74-3.81 (m, 1H), 3.84-3.92 (m, 1H), 4.18-4.28 (m, 1H), 4.31-4.39 (m, 1H), 5.94 (d, J=4.1, 1H), 6.55-6.62 (m, 2H), 6.82 (s, 1H), 6.86-6.92 (m, 2H), 7.02 (d, J=7.3, 1H), 7.34 (s, 4H).

Example 49

7-((R)-sec-Butoxy)-1-(4-chloro-phenyl)-2-{4-[(1-methanesulfonyl-piperidin-4-ylmethyl)-methyl-amino]-phenyl}-6-methoxy-1,4-dihydro-2H-isoquinolin-3-one

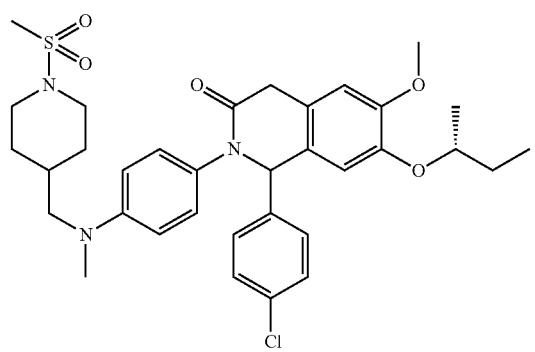 [SMILES: CC[C@@H](C)Oc1cc2c(cc1OC)CC(=O)N(c1ccc(N(C)CC3CCN(S(C)(=O)=O)CC3)cc1)C2c1ccc(Cl)cc1]

To a solution of Example 47 (20 mg, 0.036 mmol) in MeCN (0.5 ml) were successively added Et$_3$N (0.015 ml, 0.11 mmol) and methanesulfonyl chloride (8.2 mg, 0.071 mmol) at RT. The reaction mixture was stirred at RT for 1 h then directly subjected to purification by reverse phase prep-HPLC (Waters system) to yield the title compound (TFA salt, 16.1 mg, 0.021 mmol, 60%) as a colorless solid. HPLC: $^A t_{Ret}$=2.53 min; LC-MS: m/z 640.4 [M+H]$^+$.

Example 50

4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-piperidine-1-carboxylic acid dimethylamide

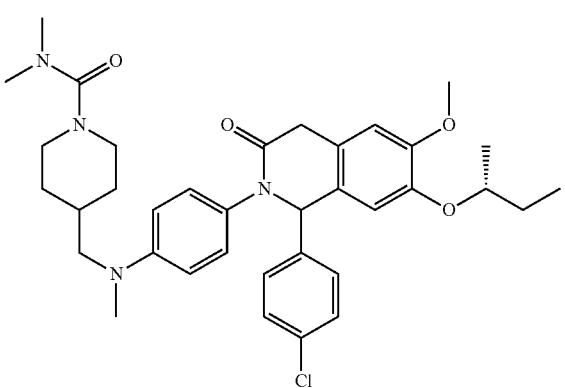 [SMILES: CC[C@@H](C)Oc1cc2c(cc1OC)CC(=O)N(c1ccc(N(C)CC3CCN(C(=O)N(C)C)CC3)cc1)C2c1ccc(Cl)cc1]

To a solution of Example 47 (20 mg, 0.036 mmol) in MeCN (0.5 ml) were successively added Et$_3$N (0.015 ml, 0.11 mmol) and dimethylcarbamoyl chloride (0.007 ml, 0.071 mmol) at RT. The reaction mixture was stirred at RT for 30 min then directly subjected to purification by reverse phase prep-HPLC (Waters system) to yield the title compound (TFA salt, 17.4 mg, 0.023 mmol, 65%) as a colorless solid. HPLC: $^At_{Ret}$=2.39 min; LC-MS: m/z 633.4 [M+H]$^+$.

Example 51

2-{4-[(Trans-4-amino-cyclohexylmethyl)-methyl-amino]-phenyl}-7-((R)-sec-butoxy)-1-(4-chloro-phenyl)-6-methoxy-1,4-dihydro-2H-isoquinolin-3-one

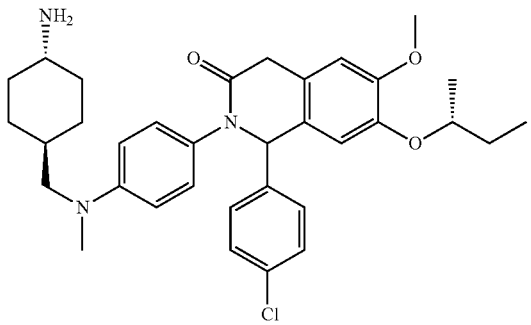 [SMILES: CC[C@@H](C)Oc1cc2c(cc1OC)CC(=O)N(c1ccc(N(C)C[C@H]3CC[C@H](N)CC3)cc1)C2c1ccc(Cl)cc1]

To a solution of Intermediate 51.1 (1.35 g, 2.0 mmol) in DCM (16 ml) was added TFA (8.0 ml, 104 mmol) at RT. The reaction mixture was stirred at RT for 30 min then evaporated to dryness. The resulting crude material was dissolved in AcOEt and washed with a 2M aqueous Na$_2$CO$_3$ solution (2×). The organic layer was dried over Na$_2$SO$_4$, filtered and evaporated to dryness. The resulting crude material was purified by Combi-Flash Companion™ (Isco Inc.) column chromatography (SiO$_2$; gradient elution, DCM/7M NH$_3$ in MeOH 99.5: 0.5→9:1) to yield the title compound (761 mg, 1.32 mmol, 66%) as a brown solid. TLC: R$_F$=0.26 (DCM/7M NH$_3$ in MeOH 9:1); HPLC: $^At_{Ret}$=1.91 min; LC-MS: m/z 576.4 [M+H]$^+$; $^1$H NMR (400 MHz, DMSO-d$_6$): 0.84-0.97 (m, 6H), 1.11-1.23 (2 d, J=6.1, 3H, mixture of diastereoisomers), 1.43-1.78 (m, 8H), 2.39-2.48 (m, 1H), 2.87 (s, 3H), 3.04-3.14 (m, 2H), 3.57 (d, J=19.8, 1H), 3.73 (s, 3H), 3.89 (d, J=19.8, 1H), 4.18-4.31 (m, 1H), 5.95 (d, J=3.4, 1H), 6.51-6.61 (m, 2H), 6.84 (s, 1H), 6.86-6.93 (m, 2H), 7.04 (d, J=5.9, 1H), 7.35 (s, 4H).

Intermediate 51.1: {4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-carbamic acid tert-butyl ester

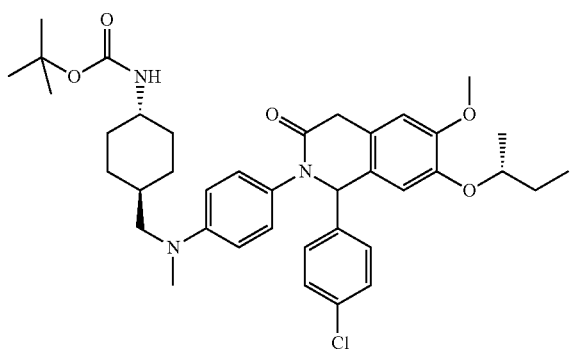 [SMILES: CC[C@@H](C)Oc1cc2c(cc1OC)CC(=O)N(c1ccc(N(C)C[C@H]3CC[C@H](NC(=O)OC(C)(C)C)CC3)cc1)C2c1ccc(Cl)cc1]

To a solution of Intermediate 42.3 (1.0 g, 2.23 mmol) in DCM (13 ml) were successively added AcOH (0.26 ml, 4.46 mmol), (trans)-(4-formyl-cyclohexyl)-carbamic acid tert-butyl ester (557 mg, 2.45 mmol) and NaBH(OAc)$_3$ (945 mg, 4.46 mmol) at RT. The reaction mixture was stirred at RT for 1 h, then diluted with DCM and washed with a 2M aqueous Na$_2$CO$_3$ solution (2×). The organic phase was dried over Na$_2$SO$_4$, filtered and evaporated to dryness. The resulting yellow solid was dissolved in DCM (13 ml) then AcOH (0.25 ml, 4.44 mmol), formaldehyde (37% in water, 0.33 ml, 4.44 mmol) and NaBH(OAc)$_3$ (940 mg, 4.44 mmol) were successively added at RT. The reaction mixture was stirred at RT for 1 h, then diluted with DCM and washed with a 2M aqueous Na$_2$CO$_3$ solution (2×). The organic phase was dried over Na$_2$SO$_4$, filtered and evaporated to dryness. The resulting crude material was purified by Combi-Flash Companion™ (Isco Inc.) column chromatography (SiO$_2$; gradient elution, [heptane/DCM 1:1]/TBME containing 5% of 7M NH$_3$ in MeOH 95:5→100% TBME containing 55 of 7M NH$_3$ in MeOH) to yield the title compound (1.35 g, 2.0 mmol, 90%) as a yellow solid. TLC: R$_F$=0.32 (heptane/DCM/TBME containing 1% of 7M NH$_3$ in MeOH 1:1:2); HPLC: $^At_{Ret}$=2.80 min; LC-MS: m/z 676.6 [M+H]$^+$.

Example 52

7-((R)-sec-Butoxy)-1-(4-chloro-phenyl)-2-{4-[(trans-4-ethylamino-cyclohexylmethyl)-methyl-amino]-phenyl}-6-methoxy-1,4-dihydro-2H-isoquinolin-3-one

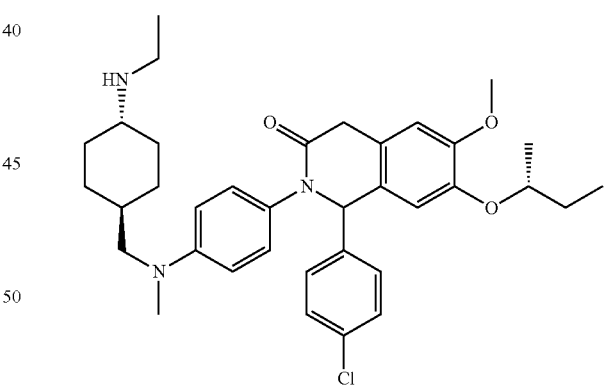

To a solution of Example 51 (60 mg, 0.10 mmol) in DCM (1.5 ml) were successively added AcOH (0.06 ml, 1.04 mmol), acetaldehyde (0.032 ml, 0.57 mmol) and NaBH(OAc)$_3$ (221 mg, 1.04 mmol) at RT. The reaction mixture was stirred at RT for 14 h, diluted with DCM and washed with a 2M aqueous Na$_2$CO$_3$ solution (2×). The organic phase was dried over Na$_2$SO$_4$, filtered and evaporated to dryness to yield the crude title compound (55 mg, 0.091 mmol, 88%) as a yellow solid which was used in the next step without further purification. HPLC: $^At_{Ret}$=1.97 min; LC-MS: m/z 604.3 [M+H]$^+$.

Example 53

7-((R)-sec-Butoxy)-1-(4-chloro-phenyl)-2-(4-{[4-(ethyl-methyl-amino)-trans-cyclohexylmethyl]-methyl-amino}-phenyl)-6-methoxy-1,4-dihydro-2H-isoquinolin-3-one

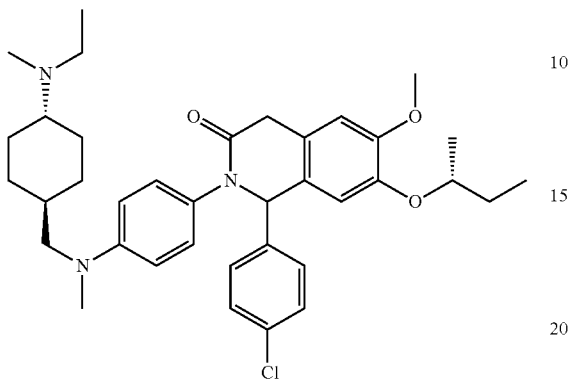

To a solution of Example 52 (13.8 mg, 0.023 mmol) in MeCN (0.5 ml) were successively added AcOH (0.003 ml, 0.046 mmol), formaldehyde (37% in water, 0.003 ml, 0.046 mmol) and NaBH(OAc)$_3$ (9.7 mg, 0.046 mmol) at RT. The reaction mixture was stirred at RT for 2 h then directly subjected to purification by reverse phase prep-HPLC (Waters system) to yield the title compound (TFA salt, 7.4 mg, 0.010 mmol, 44%) as a colorless solid. HPLC: $^A t_{Ret}$=2.01 min; LC-MS: m/z 618.4 [M+H]$^+$.

Example 54

Compounds 54aa to 54ce were obtained from Intermediate 42.3 (or analogues prepared similarly), Example 47 (or analogues prepared similarly), Example 51 (or analogues prepared similarly) or Example 52 (or analogues prepared similarly), analogously to Intermediate 44.1, Example 42, 46, 48, 49, 50, 52, or 53.

| # | Structure | Name/HPLC/MS |
|---|---|---|
| 54aa | 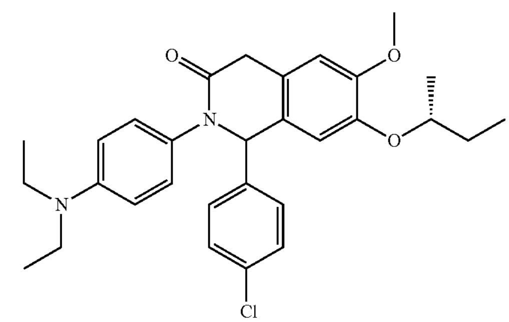 [SMILES: CC[C@@H](C)Oc1cc2c(cc1OC)CC(=O)N(c1ccc(N(CC)CC)cc1)C2c1ccc(Cl)cc1] | 7-((R)-sec-Butoxy)-1-(4-chloro-phenyl)-2-(4-diethylamino-phenyl)-6-methoxy-1,4-dihydro-2H-isoquinolin-3-one.<br>HPLC: $^A t_{Ret}$ = 2.01; LC-MS: m/z 507.1 [M + H]$^+$. |
| 54ab | 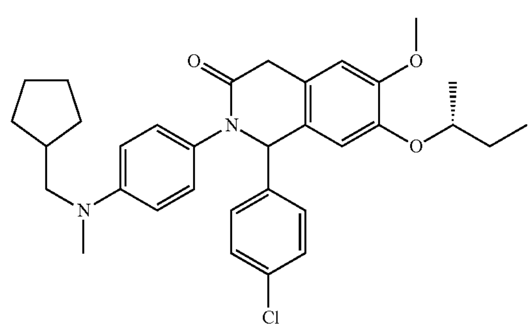 [SMILES: CC[C@@H](C)Oc1cc2c(cc1OC)CC(=O)N(c1ccc(N(C)CC3CCCC3)cc1)C2c1ccc(Cl)cc1] | 7-((R)-sec-Butoxy)-1-(4-chloro-phenyl)-2-[4-(cyclopentylmethyl-methyl-amino)-phenyl]-6-methoxy-1,4-dihydro-2H-isoquinolin-3-one.<br>HPLC: $^A t_{Ret}$ = 2.52; LC-MS: m/z 547.6 [M + H]$^+$. |
| 54ac | 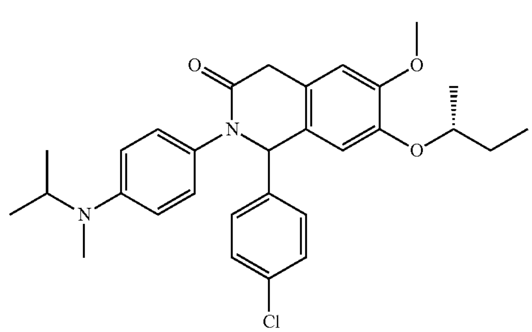 [SMILES: CC[C@@H](C)Oc1cc2c(cc1OC)CC(=O)N(c1ccc(N(C)C(C)C)cc1)C2c1ccc(Cl)cc1] | 7-((R)-sec-Butoxy)-1-(4-chloro-phenyl)-2-[4-(isopropyl-methyl-amino)-phenyl]-6-methoxy-1,4-dihydro-2H-isoquinolin-3-one.<br>HPLC: $^A t_{Ret}$ = 2.02; LC-MS: m/z 507.5 [M + H]$^+$. |

| # | Structure | Name/HPLC/MS |
|---|---|---|
| 54ad | 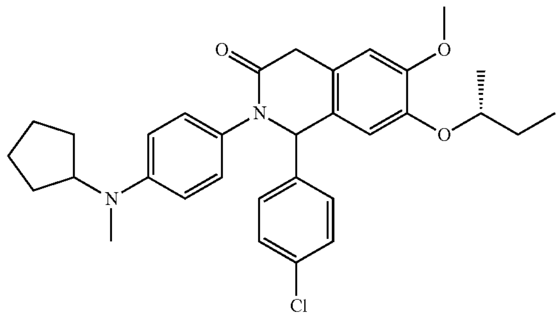 | 7-((R)-sec-Butoxy)-1-(4-chloro-phenyl)-2-[4-(cyclopentyl-methyl-amino)-phenyl]-6-methoxy-1,4-dihydro-2H-isoquinolin-3-one.<br>HPLC: $^{A}t_{Ret}$ = 2.11; LC-MS: m/z 533.5 [M + H]$^{+}$. |
| 54ae | 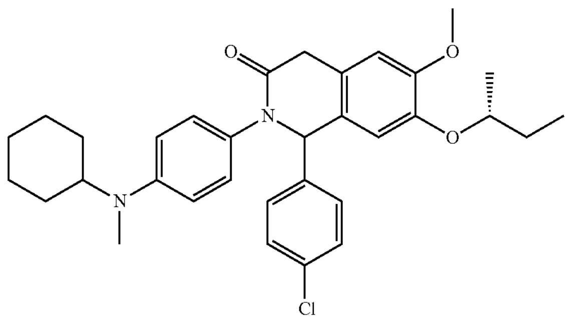 [SMILES: CC[C@@H](C)Oc1cc2c(cc1OC)CC(=O)N(c1ccc(N(C)C3CCCCC3)cc1)C2c1ccc(Cl)cc1] | 7-((R)-sec-Butoxy)-1-(4-chloro-phenyl)-2-[4-(cyclohexyl-methyl-amino)-phenyl]-6-methoxy-1,4-dihydro-2H-isoquinolin-3-one.<br>HPLC: $^{A}t_{Ret}$ = 2.22; LC-MS: m/z 547.5 [M + H]$^{+}$. |
| 54af | 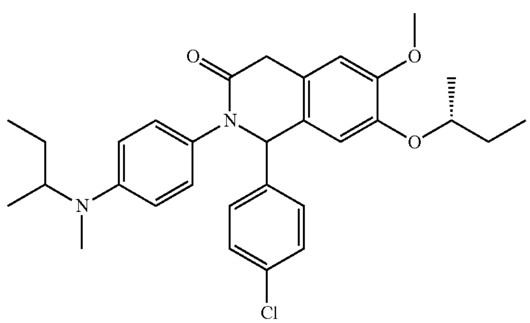 [SMILES: CCC(C)N(C)c1ccc(N2C(=O)Cc3cc(OC)c(O[C@H](C)CC)cc3C2c2ccc(Cl)cc2)cc1] | 7-((R)-sec-Butoxy)-2-[4-(sec-butyl-methyl-amino)-phenyl]-1-(4-chloro-phenyl)-6-methoxy-1,4-dihydro-2H-isoquinolin-3-one.<br>HPLC: $^{A}t_{Ret}$ = 2.19; LC-MS: m/z 521.5 [M + H]$^{+}$. |
| 54ag | 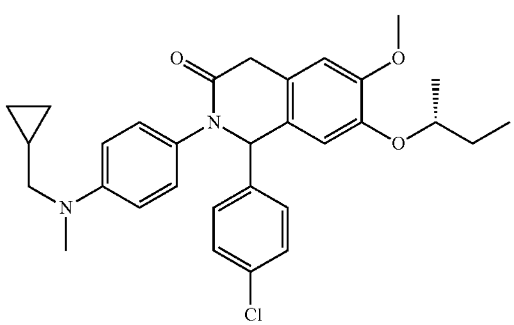 [SMILES: CC[C@@H](C)Oc1cc2c(cc1OC)CC(=O)N(c1ccc(N(C)CC3CC3)cc1)C2c1ccc(Cl)cc1] | 7-((R)-sec-Butoxy)-1-(4-chloro-phenyl)-2-[4-(cyclopropylmethyl-methyl-amino)-phenyl]-6-methoxy-1,4-dihydro-2H-isoquinolin-3-one.<br>HPLC: $^{A}t_{Ret}$ = 2.12; LC-MS: m/z 519.4 [M + H]$^{+}$. |
| 54ah | 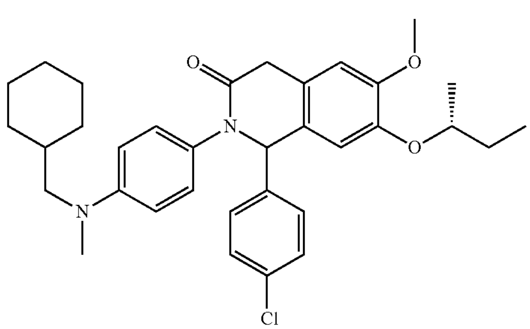 [SMILES: CC[C@@H](C)Oc1cc2c(cc1OC)CC(=O)N(c1ccc(N(C)CC3CCCCC3)cc1)C2c1ccc(Cl)cc1] | 7-((R)-sec-Butoxy)-1-(4-chloro-phenyl)-2-[4-(cyclohexylmethyl-methyl-amino)-phenyl]-6-methoxy-1,4-dihydro-2H-isoquinolin-3-one.<br>HPLC: $^{A}t_{Ret}$ = 2.85; LC-MS: m/z 561.4 [M + H]$^{+}$. |

| # | Structure | Name/HPLC/MS |
|---|---|---|
| 54ai | 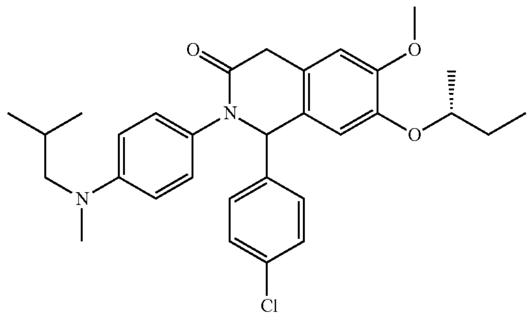 [SMILES: CC[C@@H](C)Oc1cc2c(cc1OC)CC(=O)N(c1ccc(N(C)CC(C)C)cc1)C2c1ccc(Cl)cc1] | 7-((R)-sec-Butoxy)-1-(4-chloro-phenyl)-2-[4-(isobutyl-methyl-amino)-phenyl]-6-methoxy-1,4-dihydro-2H-isoquinolin-3-one.<br>HPLC: $^A t_{Ret}$ = 2.57; LC-MS: m/z 521.4 [M + H]$^+$. |
| 54aj | 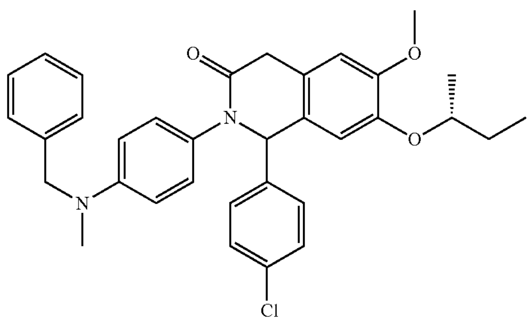 | 2-[4-(Benzyl-methyl-amino)-phenyl]-7-((R)-sec-butoxy)-1-(4-chloro-phenyl)-6-methoxy-1,4-dihydro-2H-isoquinolin-3-one.<br>HPLC: $^A t_{Ret}$ = 2.81; LC-MS: m/z 555.4 [M + H]$^+$. |
| 54ak | 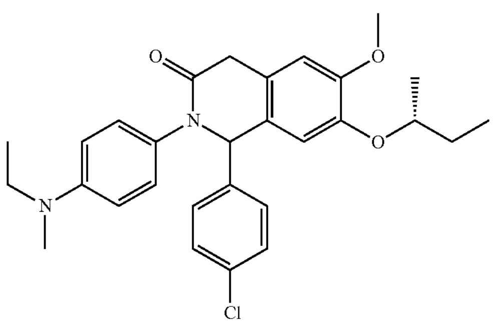 [SMILES: CC[C@@H](C)Oc1cc2c(cc1OC)CC(=O)N(c1ccc(N(C)CC)cc1)C2c1ccc(Cl)cc1] | 7-((R)-sec-Butoxy)-1-(4-chloro-phenyl)-2-[4-(ethyl-methyl-amino)-phenyl]-6-methoxy-1,4-dihydro-2H-isoquinolin-3-one.<br>HPLC: $^A t_{Ret}$ = 2.01; LC-MS: m/z 493.4 [M + H]$^+$. |
| 54al | 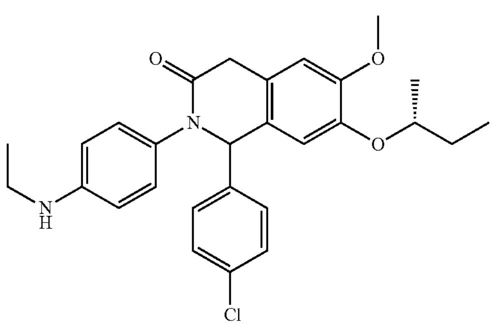 [SMILES: CCNc1ccc(N2C(=O)Cc3cc(OC)c(O[C@H](C)CC)cc3C2c2ccc(Cl)cc2)cc1] | 7-((R)-sec-Butoxy)-1-(4-chloro-phenyl)-2-(4-ethylamino-phenyl)-6-methoxy-1,4-dihydro-2H-isoquinolin-3-one.<br>HPLC: $^A t_{Ret}$ = 1.99; LC-MS: m/z 479.6 [M + H]$^+$. |
| 54am | 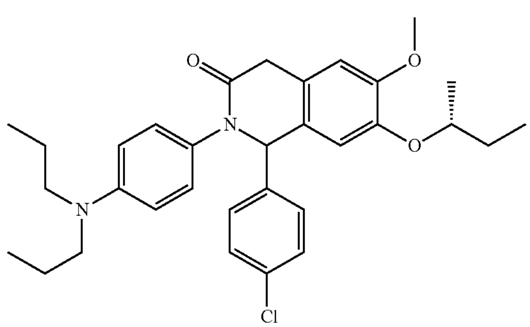 [SMILES: CCCN(CCC)c1ccc(N2C(=O)Cc3cc(OC)c(O[C@H](C)CC)cc3C2c2ccc(Cl)cc2)cc1] | 7-((R)-sec-Butoxy)-1-(4-chloro-phenyl)-2-(4-dipropylamino-phenyl)-6-methoxy-1,4-dihydro-2H-isoquinolin-3-one.<br>HPLC: $^A t_{Ret}$ = 2.28; LC-MS: m/z 535.6 [M + H]$^+$. |

| # | Structure | Name/HPLC/MS |
|---|---|---|
| 54an | 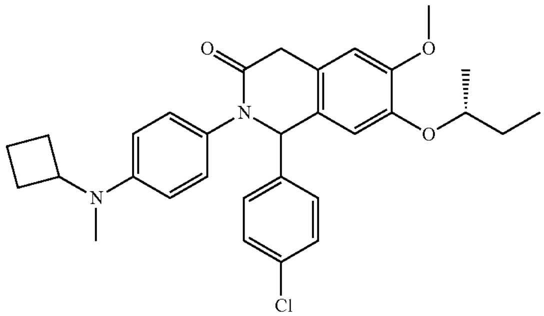 [SMILES: CC[C@@H](C)Oc1cc2c(cc1OC)CC(=O)N(c1ccc(N(C)C3CCC3)cc1)C2c1ccc(Cl)cc1] | 7-((R)-sec-Butoxy)-1-(4-chloro-phenyl)-2-[4-(cyclobutyl-methyl-amino)-phenyl]-6-methoxy-1,4-dihydro-2H-isoquinolin-3-one.<br>HPLC: $^A t_{Ret}$ = 2.08; LC-MS: m/z 519.4 [M + H]$^+$. |
| 54ao | 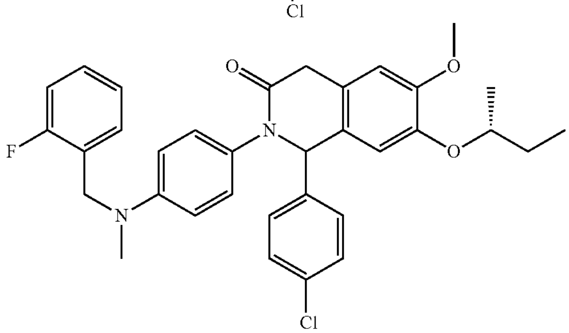 | 7-((R)-sec-Butoxy)-1-(4-chloro-phenyl)-2-{4-[(2-fluoro-benzyl)-methyl-amino]-phenyl}-6-methoxy-1,4-dihydro-2H-isoquinolin-3-one.<br>HPLC: $^A t_{Ret}$ = 2.99; LC-MS: m/z 573.2 [M + H]$^+$. |
| 54ap | 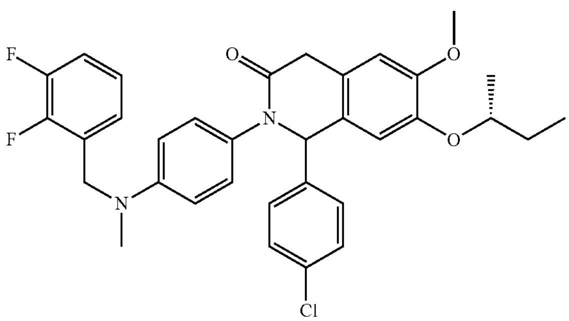 [SMILES: CC[C@@H](C)Oc1cc2c(cc1OC)CC(=O)N(c1ccc(N(C)Cc3cccc(F)c3F)cc1)C2c1ccc(Cl)cc1] | 7-((R)-sec-Butoxy)-1-(4-chloro-phenyl)-2-{4-[(2,3-difluoro-benzyl}-methyl-amino]-phenyl}-6-methoxy-1,4-dihydro-2H-isoquinolin-3-one.<br>HPLC: $^A t_{Ret}$ = 3.13; LC-MS: m/z 591.2 [M + H]$^+$. |
| 54aq | 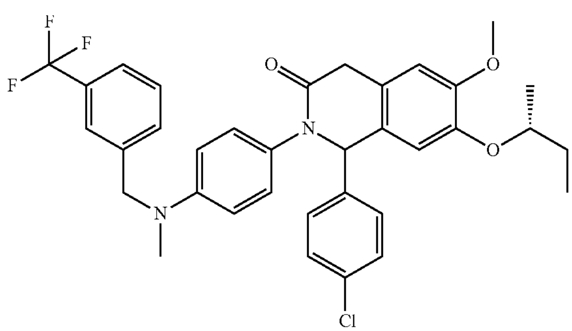 [SMILES: CC[C@@H](C)Oc1cc2c(cc1OC)CC(=O)N(c1ccc(N(C)Cc3cccc(C(F)(F)F)c3)cc1)C2c1ccc(Cl)cc1] | 7-((R)-sec-Butoxy)-1-(4-chloro-phenyl)-6-methoxy-2-{4-[methyl-(3-trifluoromethyl-benzyl)-amino]-phenyl}-1,4-dihydro-2H-isoquinolin-3-one.<br>HPLC: $^A t_{Ret}$ = 3.21; LC-MS: m/z 623.2 [M + H]$^+$. |
| 54ar | 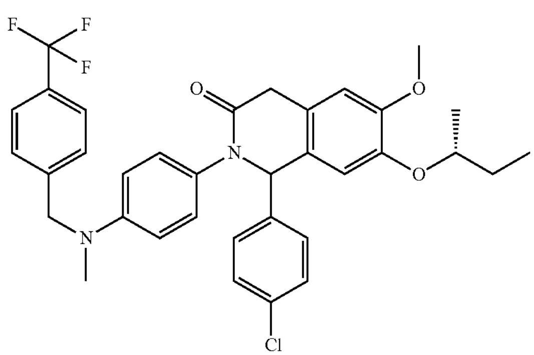 [SMILES: CC[C@@H](C)Oc1cc2c(cc1OC)CC(=O)N(c1ccc(N(C)Cc3ccc(C(F)(F)F)cc3)cc1)C2c1ccc(Cl)cc1] | 7-((R)-sec-Butoxy)-1-(4-chloro-phenyl)-6-methoxy-2-{4-[methyl-(4-trifluoromethyl-benzyl)-amino]-phenyl}-1,4-dihydro-2H-isoquinolin-3-one.<br>HPLC: $^A t_{Ret}$ = 3.23; LC-MS: m/z 623.2 [M + H]$^+$. |

-continued

| # | Structure | Name/HPLC/MS |
|---|---|---|
| 54as | 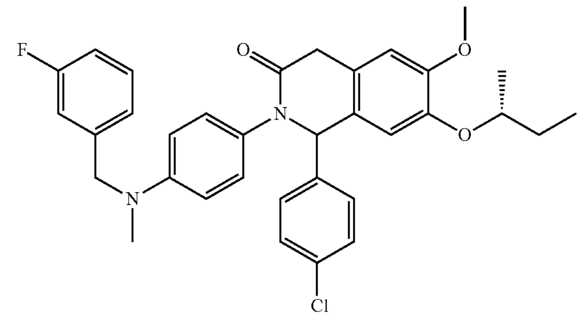 [SMILES: CC[C@@H](C)Oc1cc2c(cc1OC)CC(=O)N(c1ccc(N(C)Cc3cccc(F)c3)cc1)C2c1ccc(Cl)cc1] | 7-((R)-sec-Butoxy)-1-(4-chloro-phenyl)-2-{4-[(3-fluoro-benzyl)-methyl-amino]-phenyl}-6-methoxy-1,4-dihydro-2H-isoquinolin-3-one.<br>HPLC: $^A t_{Ret}$ = 3.00; LC-MS: m/z 573.2 [M + H]$^+$. |
| 54at | 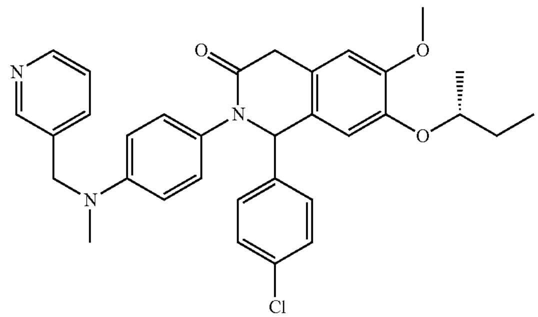 [SMILES: CC[C@@H](C)Oc1cc2c(cc1OC)CC(=O)N(c1ccc(N(C)Cc3cccnc3)cc1)C2c1ccc(Cl)cc1] | 7-((R)-sec-Butoxy)-1-(4-chloro-phenyl)-6-methoxy-2-[4-(methyl-pyridin-3-ylmethyl-amino)-phenyl]-1,4-dihydro-2H-isoquinolin-3-one.<br>HPLC: $^A t_{Ret}$ = 2.05; LC-MS: m/z 556.2 [M + H]$^+$. |
| 54au | 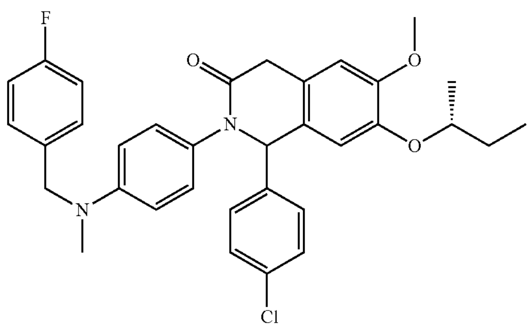 [SMILES: CC[C@@H](C)Oc1cc2c(cc1OC)CC(=O)N(c1ccc(N(C)Cc3ccc(F)cc3)cc1)C2c1ccc(Cl)cc1] | 7-((R)-sec-Butoxy)-1-(4-chloro-phenyl)-2-{4-[(4-fluoro-benzyl)-methyl-amino]-phenyl}-6-methoxy-1,4-dihydro-2H-isoquinolin-3-one.<br>HPLC: $^A t_{Ret}$ = 2.84; LC-MS: m/z 573.2 [M + H]$^+$. |
| 54av | 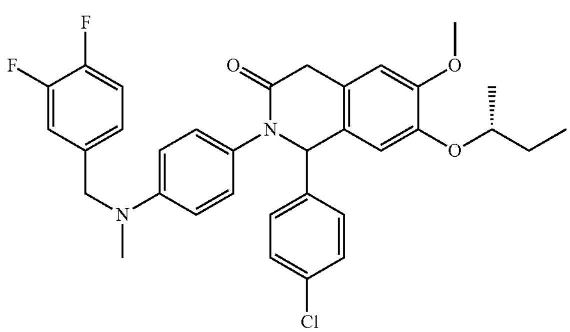 [SMILES: CC[C@@H](C)Oc1cc2c(cc1OC)CC(=O)N(c1ccc(N(C)Cc3ccc(F)c(F)c3)cc1)C2c1ccc(Cl)cc1] | 7-((R)-sec-Butoxy)-1-(4-chloro-phenyl)-2-{4-[(3,4-difluoro-benzyl)-methyl-amino]-phenyl}-6-methoxy-1,4-dihydro-2H-isoquinolin-3-one.<br>HPLC: $^A t_{Ret}$ = 3.06; LC-MS: m/z 591.2 [M + H]$^+$. |
| 54aw | 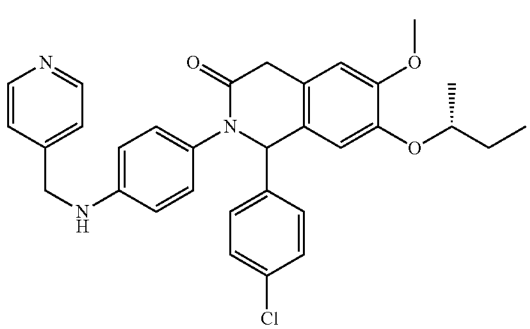 | 7-((R)-sec-Butoxy)-1-(4-chloro-phenyl)-6-methoxy-2-{4-[(pyridin-4-ylmethyl)-amino]-phenyl}-1,4-dihydro-2H-isoquinolin-3-one.<br>HPLC: $^A t_{Ret}$ = 1.97; LC-MS: m/z 542.5 [M + H]$^+$. |

-continued

| # | Structure | Name/HPLC/MS |
|---|---|---|
| 54ax | 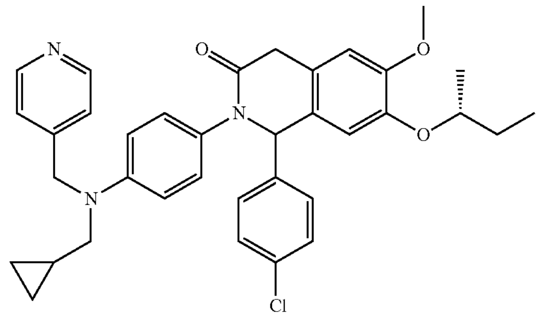 [SMILES: CC[C@@H](C)Oc1cc2c(cc1OC)CC(=O)N(c1ccc(N(Cc3ccncc3)CC3CC3)cc1)C2c1ccc(Cl)cc1] | 7-((R)-sec-Butoxy)-1-(4-chloro-phenyl)-2-[4-(cyclopropylmethyl-pyridin-4-ylmethyl-amino)-phenyl]-6-methoxy-1,4-dihydro-2H-isoquinolin-3-one.<br>HPLC: $^A t_{Ret}$ = 2.23; LC-MS: m/z 596.5 [M + H]$^+$. |
| 54ay | 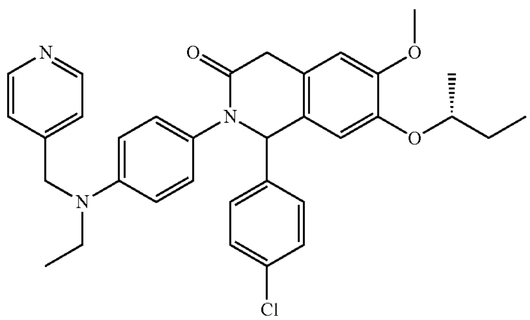 [SMILES: CC[C@@H](C)Oc1cc2c(cc1OC)CC(=O)N(c1ccc(N(CC)Cc3ccncc3)cc1)C2c1ccc(Cl)cc1] | 7-((R)-sec-Butoxy)-1-(4-chloro-phenyl)-2-[4-(ethyl-pyridin-4-ylmethyl-amino)-phenyl]-6-methoxy-1,4-dihydro-2H-isoquinolin-3-one.<br>HPLC: $^A t_{Ret}$ = 2.13; LC-MS: m/z 570.3 [M + H]$^+$. |
| 54az | 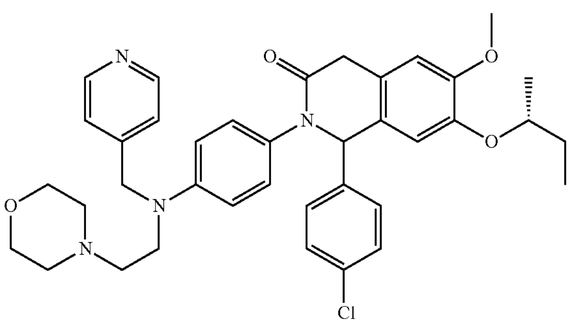 [SMILES: CC[C@@H](C)Oc1cc2c(cc1OC)CC(=O)N(c1ccc(N(CCN3CCOCC3)Cc3ccncc3)cc1)C2c1ccc(Cl)cc1] | 7-((R)-sec-Butoxy)-1-(4-chloro-phenyl)-6-methoxy-2-{4-[(2-morpholin-4-yl-ethyl)-pyridin-4-ylmethyl-amino]-phenyl}-1,4-dihydro-2H-isoquinolin-3-one.<br>HPLC: $^A t_{Ret}$ = 1.72; LC-MS: m/z 655.4 [M + H]$^+$. |
| 54ba | 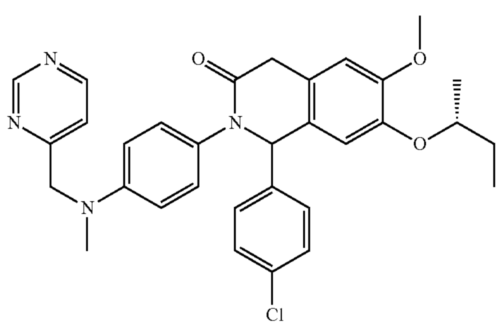 [SMILES: CC[C@@H](C)Oc1cc2c(cc1OC)CC(=O)N(c1ccc(N(C)Cc3ccncn3)cc1)C2c1ccc(Cl)cc1] | 7-((R)-sec-Butoxy)-1-(4-chloro-phenyl)-6-methoxy-2-[4-(methyl-pyrimidin-4-ylmethyl-amino)-phenyl]-1,4-dihydro-2H-isoquinolin-3-one.<br>HPLC: $^A t_{Ret}$ = 2.48; LC-MS: m/z 557.1 [M + H]$^+$. |
| 54bb | 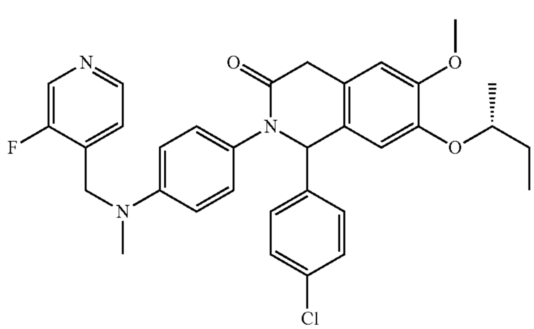 [SMILES: CC[C@@H](C)Oc1cc2c(cc1OC)CC(=O)N(c1ccc(N(C)Cc3ccncc3F)cc1)C2c1ccc(Cl)cc1] | 7-((R)-sec-Butoxy)-1-(4-chloro-phenyl)-2-{4-[(3-fluoro-pyridin-4-ylmethyl)-methyl-amino]-phenyl}-6-methoxy-1,4-dihydro-2H-isquinolin-3-one.<br>HPLC: $^A t_{Ret}$ = 2.40; LC-MS: m/z 574.2 [M + H]$^+$. |

| # | Structure | Name/HPLC/MS |
|---|---|---|
| 54bc | 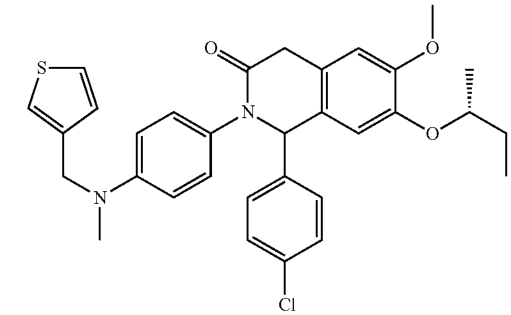 [SMILES: CC[C@@H](C)Oc1cc2c(cc1OC)CC(=O)N(c1ccc(N(C)Cc3ccsc3)cc1)C2c1ccc(Cl)cc1] | 7-((R)-sec-Butoxy)-1-(4-chloro-phenyl)-6-methoxy-2-[4-(methyl-thiophen-3-ylmethyl-amino)-phenyl]-1,4-dihydro-2H-isoquinolin-3-one.<br>HPLC: $^A t_{Ret}$ = 2.58; LC-MS: m/z 561.2 [M + H]$^+$. |
| 54bd | 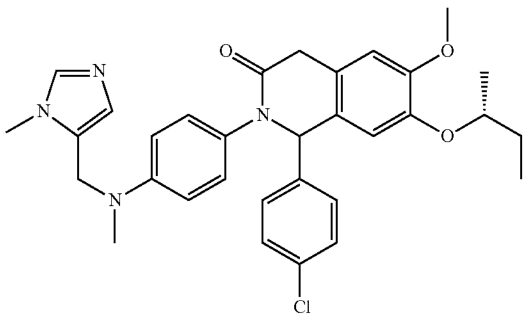 | 7-((R)-sec-Butoxy)-1-(4-chloro-phenyl)-6-methoxy-2-{4-[methyl-(3-methyl-3H-imidazol-4-ylmethyl)-amino]-phenyl}-1,4-dihydro-2H-isoquinolin-3-one.<br>HPLC: $^A t_{Ret}$ = 2.04; LC-MS: m/z 599.2 [M + H]$^+$. |
| 54be | 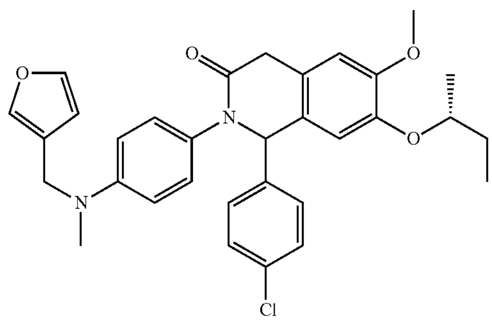 [SMILES: CC[C@@H](C)Oc1cc2c(cc1OC)CC(=O)N(c1ccc(N(C)Cc3ccoc3)cc1)C2c1ccc(Cl)cc1] | 7-((R)-sec-Butoxy)-1-(4-chloro-phenyl)-2-[4-(furan-3-ylmethyl-methyl-amino)-phenyl]-6-methoxy-1,4-dihydro-2H-isoquinolin-3-one.<br>HPLC: $^A t_{Ret}$ = 2.40; LC-MS: m/z 545.2 [M + H]$^+$. |
| 54bf | 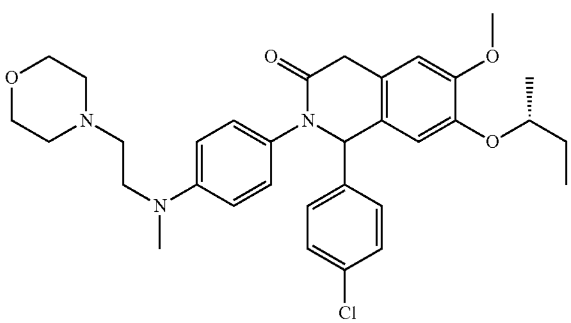 [SMILES: CC[C@@H](C)Oc1cc2c(cc1OC)CC(=O)N(c1ccc(N(C)CCN3CCOCC3)cc1)C2c1ccc(Cl)cc1] | 7-((R)-sec-Butoxy)-1-(4-chloro-phenyl)-6-methoxy-2-{4-[methyl-(2-morpholin-4-yl-ethyl)-amino]-phenyl}-1,4-dihydro-2H-isoquinolin-3-one.<br>HPLC: $^A t_{Ret}$ = 2.03; LC-MS: m/z 578.3 [M + H]$^+$. |
| 54bg | 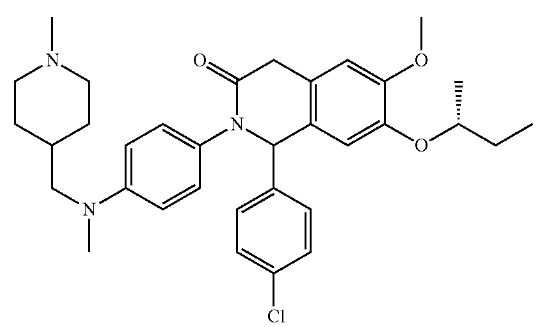 [SMILES: CC[C@@H](C)Oc1cc2c(cc1OC)CC(=O)N(c1ccc(N(C)CC3CCN(C)CC3)cc1)C2c1ccc(Cl)cc1] | 7-((R)-sec-Butoxy)-1-(4-chloro-phenyl)-6-methoxy-2-{4-[methyl-(1-methyl-piperidin-4-ylmethyl)-amino]-phenyl}-1,4-dihydro-2H-isoquinolin-3-one.<br>HPLC: $^A t_{Ret}$ = 2.04; LC-MS: m/z 576.3 [M + H]$^+$. |

| # | Structure | Name/HPLC/MS |
|---|---|---|
| 54bh | 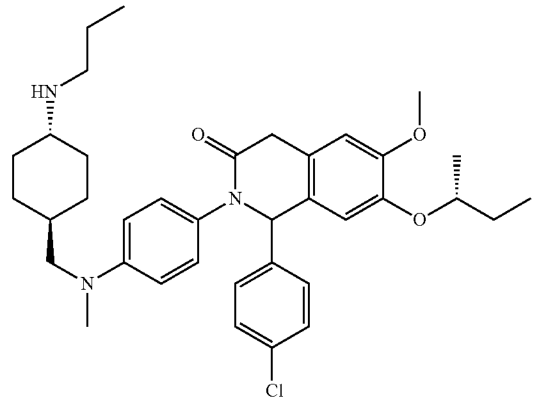 [SMILES: CCCN[C@H]1CC[C@H](CN(C)c2ccc(N3C(=O)Cc4cc(OC)c(O[C@H](C)CC)cc4C3c3ccc(Cl)cc3)cc2)CC1] | 7-((R)-sec-Butoxy)-1-(4-chloro-phenyl)-6-methoxy-2-{4-[methyl-(4-propylamino-trans-cyclohexylmethyl)-amino]-phenyl}-1,4-dihydro-2H-isoquinolin-3-one.<br>HPLC: $^A t_{Ret}$ = 2.03; LC-MS: m/z 618.5 [M + H]$^+$. |
| 54bi[(1)] | 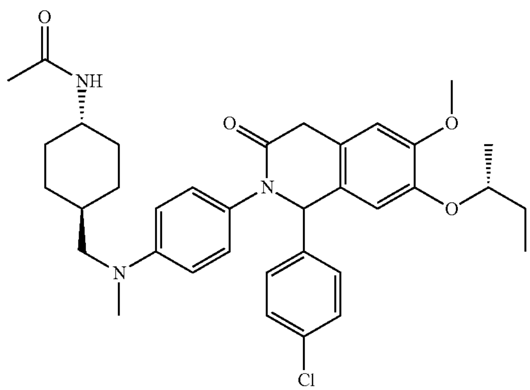 [SMILES: CC[C@@H](C)Oc1cc2c(cc1OC)CC(=O)N(c1ccc(N(C)C[C@H]3CC[C@H](NC(C)=O)CC3)cc1)C2c1ccc(Cl)cc1] | N-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-acetamide.<br>HPLC: $^A t_{Ret}$ = 2.13; LC-MS: m/z 618.3 [M + H]$^+$. |
| 54bj | 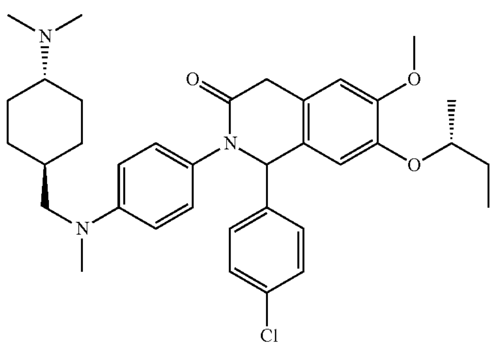 [SMILES: CC[C@@H](C)Oc1cc2c(cc1OC)CC(=O)N(c1ccc(N(C)C[C@H]3CC[C@H](N(C)C)CC3)cc1)C2c1ccc(Cl)cc1] | 7-((R)-sec-Butoxy)-1-(4-chloro-phenyl)-2-{4-[(4-dimethylamino-trans-cyclohexylmethyl)-methyl-amino]-phenyl}-6-methoxy-1,4-dihydro-2H-isoquinolin-3-one.<br>HPLC: $^A t_{Ret}$ = 1.98; LC-MS: m/z 604.3 [M + H]$^+$. |
| 54bk | 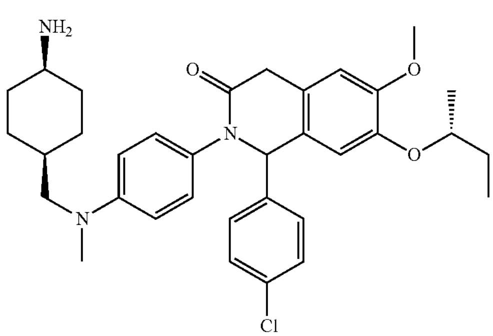 [SMILES: CC[C@@H](C)Oc1cc2c(cc1OC)CC(=O)N(c1ccc(N(C)C[C@H]3CC[C@@H](N)CC3)cc1)C2c1ccc(Cl)cc1] | 2-{4-[(Trans-4-amino-cyclohexylmethyl)-methyl-amino]-phenyl}-7-((R)-sec-butoxy)-1-(4-chloro-phenyl)-6-methoxy-1,4-dihydro-2H-isoquinolin-3-one.<br>HPLC: $^A t_{Ret}$ = 1.91; LC-MS: m/z 576.3 [M + H]$^+$. |

-continued

| # | Structure | Name/HPLC/MS |
|---|---|---|
| 54bl[(1)] | | N-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-acetamide.<br>HPLC: $^A t_{Ret}$ = 2.15; LC-MS: m/z 618.3 [M + H]$^+$. |
| 54bm | 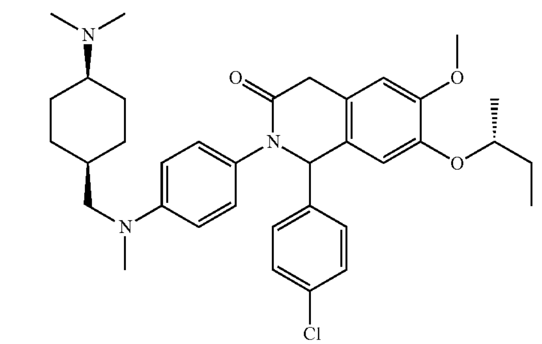 [SMILES: CC[C@@H](C)Oc1cc2c(cc1OC)CC(=O)N(c1ccc(N(C)C[C@H]3CC[C@@H](N(C)C)CC3)cc1)C2c1ccc(Cl)cc1] | 7-((R)-sec-Butoxy)-1-(4-chloro-phenyl)-2-{4-[(4-dimethylamino-trans-cyclohexylmethyl)-methyl-amino]-phenyl}-6-methoxy-1,4-dihydro-2H-isoquinolin-3-one.<br>HPLC: $^A t_{Ret}$ = 1.89; LC-MS: m/z 604.3 [M + H]$^+$. |
| 54bn | 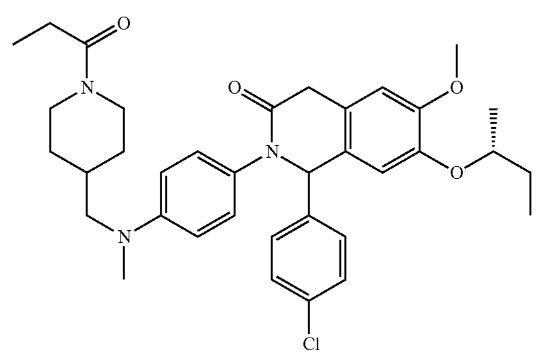 [SMILES: CCC(=O)N1CCC(CN(C)c2ccc(N3C(=O)Cc4cc(OC)c(O[C@H](C)CC)cc4C3c3ccc(Cl)cc3)cc2)CC1] | 7-((R)-sec-Butoxy)-1-(4-chloro-phenyl)-6-methoxy-2-{4-[methyl-(1-propionyl-piperidin-4-ylmethyl)-amino]-phenyl}-1,4-dihydro-2H-isoquinolin-3-one.<br>HPLC: $^A t_{Ret}$ = 2.41; LC-MS: m/z 618.3 [M + H]$^+$. |
| 54bo | 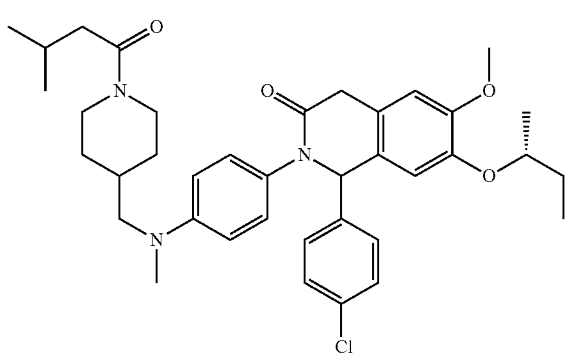 [SMILES: CC[C@@H](C)Oc1cc2c(cc1OC)CC(=O)N(c1ccc(N(C)CC3CCN(C(=O)CC(C)C)CC3)cc1)C2c1ccc(Cl)cc1] | 7-((R)-sec-Butoxy)-1-(4-chloro-phenyl)-6-methoxy-2-(4-{methyl-[1-(3-methyl-butyryl)-piperidin-4-ylmethyl]-amino}-phenyl)-1,4-dihydro-2H-isoquinolin-3-one.<br>HPLC: $^A t_{Ret}$ = 2.66; LC-MS: m/z 646.5 [M + H]$^+$. |

| # | Structure | Name/HPLC/MS |
|---|---|---|
| 54bp | 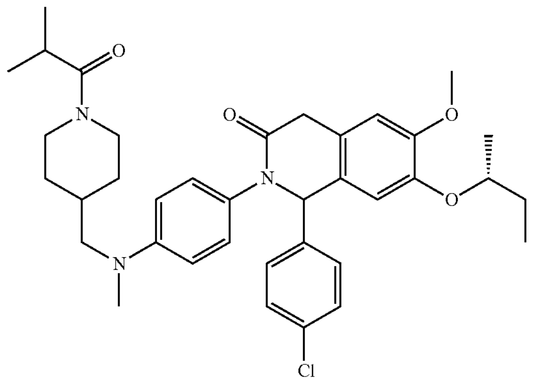 [SMILES: CC[C@@H](C)Oc1cc2c(cc1OC)CC(=O)N(c1ccc(N(C)CC3CCN(C(=O)C(C)C)CC3)cc1)C2c1ccc(Cl)cc1] | 7-((R)-sec-Butoxy)-1-(4-chloro-phenyl)-2-{4-[(1-isobutyryl-piperidin-4-ylmethyl)-methyl-amino]-phenyl}-6-methoxy-1,4-dihydro-2H-isoquinolin-3-one.<br>HPLC: $^{A}t_{Ret}$ = 2.54; LC-MS: m/z 632.5 [M + H]$^+$. |
| 54bq | 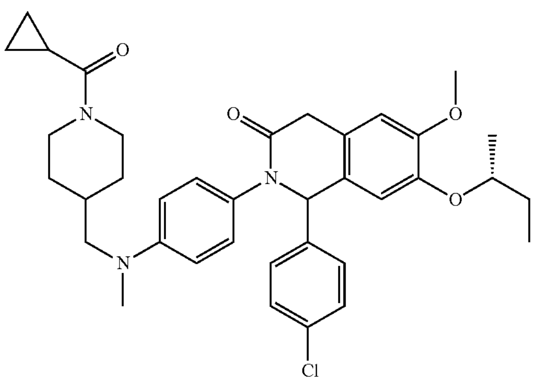 [SMILES: CC[C@@H](C)Oc1cc2c(cc1OC)CC(=O)N(c1ccc(N(C)CC3CCN(C(=O)C4CC4)CC3)cc1)C2c1ccc(Cl)cc1] | 7-((R)-sec-Butoxy)-1-(4-chloro-phenyl)-2-{4-[(1-cyclopropanecarbonyl-piperidin-4-ylmethyl)-methyl-amino]-phenyl}-6-methoxy-1,4-dihydro-2H-isoquinolin-3-one.<br>HPLC: $^{A}t_{Ret}$ = 2.47; LC-MS: m/z 630.4 [M + H]$^+$. |
| 54br | 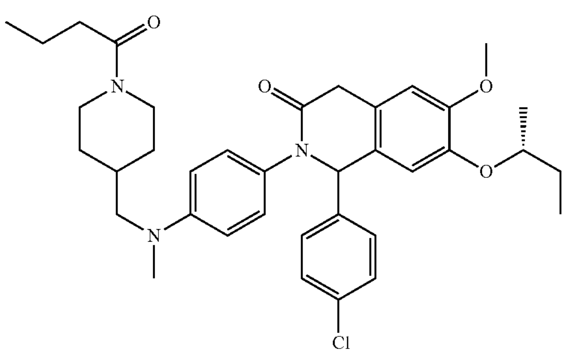 [SMILES: CCCC(=O)N1CCC(CN(C)c2ccc(N3C(=O)Cc4cc(OC)c(O[C@H](C)CC)cc4C3c3ccc(Cl)cc3)cc2)CC1] | 7-((R)-sec-Butoxy)-2-{4-[(1-butyryl-piperidin-4-ylmethyl)-methyl-amino]-phenyl}-1-(4-chloro-phenyl)-6-methoxy-1,4-dihydro-2H-isoquinolin-3-one.<br>HPLC: $^{A}t_{Ret}$ = 2.54; LC-MS: m/z 632.4 [M + H]$^+$. |
| 54bs$^{(1)}$ | 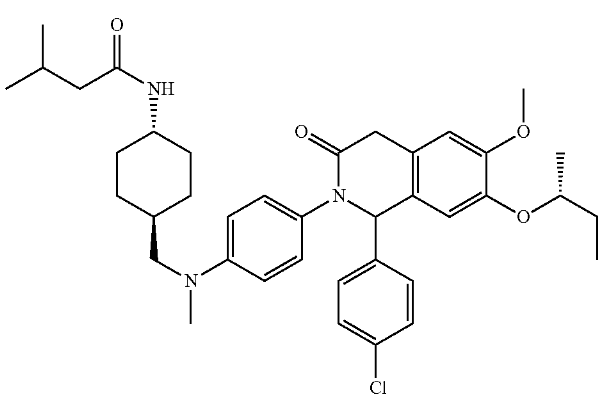 [SMILES: CC[C@@H](C)Oc1cc2c(cc1OC)CC(=O)N(c1ccc(N(C)C[C@H]3CC[C@H](NC(=O)CC(C)C)CC3)cc1)C2c1ccc(Cl)cc1] | N-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-3-methyl-butyramide.<br>HPLC: $^{A}t_{Ret}$ = 2.45; LC-MS: m/z 660.5 [M + H]$^+$. |

| # | Structure | Name/HPLC/MS |
|---|---|---|
| 54bt[(1)] | 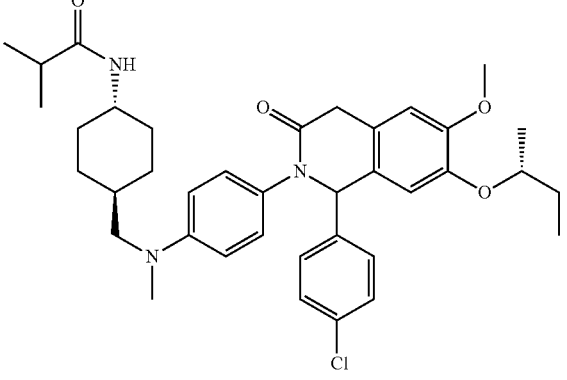 | N-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-isobutyramide.<br>HPLC: $^A t_{Ret}$ = 2.36; LC-MS: m/z 646.4 [M + H]$^+$. |
| 54bu[(1)] | 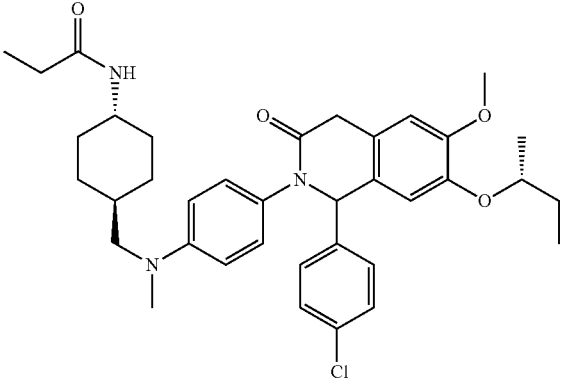 [SMILES: CCC(=O)N[C@H]1CC[C@H](CN(C)c2ccc(N3C(=O)Cc4cc(OC)c(O[C@H](C)CC)cc4C3c3ccc(Cl)cc3)cc2)CC1] | N-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-propionamide.<br>HPLC: $^A t_{Ret}$ = 2.25; LC-MS: m/z 632.4 [M + H]$^+$. |
| 54bv[(1)] | 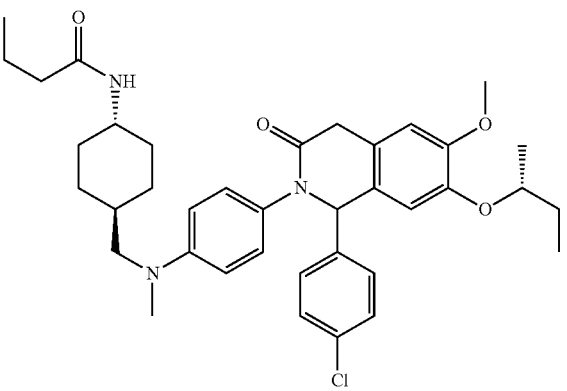 [SMILES: CCCC(=O)N[C@H]1CC[C@H](CN(C)c2ccc(N3C(=O)Cc4cc(OC)c(O[C@H](C)CC)cc4C3c3ccc(Cl)cc3)cc2)CC1] | N-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-butyramide.<br>HPLC: $^A t_{Ret}$ = 2.35; LC-MS: m/z 646.4 [M + H]$^+$. |
| 54bw[(1)] | 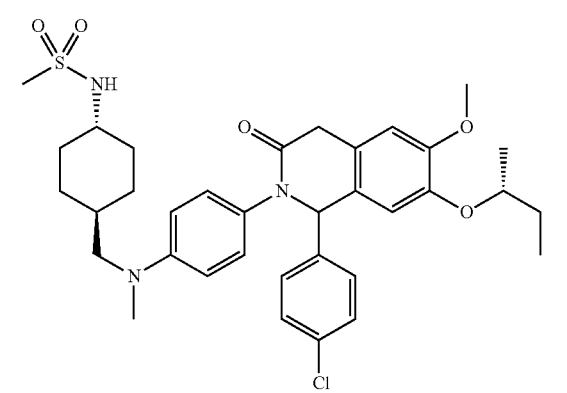 [SMILES: CC[C@@H](C)Oc1cc2c(cc1OC)CC(=O)N(c1ccc(N(C)C[C@H]3CC[C@H](NS(C)(=O)=O)CC3)cc1)C2c1ccc(Cl)cc1] | N-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-methanesulfonamide.<br>HPLC: $^A t_{Ret}$ = 2.33; LC-MS: m/z 654.3 [M + H]$^+$. |

-continued

| # | Structure | Name/HPLC/MS |
|---|---|---|
| 54bx[(1)] | | 3-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-1,1-dimethyl-urea.<br>HPLC: $^A t_{Ret}$ = 2.20; LC-MS: m/z 647.4 [M + H]$^+$. |
| 54by | | 7-((R)-sec-Butoxy)-1-(4-chloro-phenyl)-2-{4-[(1-cyclobutanecarbonyl-piperidin-4-ylmethyl)-methyl-amino]-phenyl}-6-methoxy-1,4-dihydro-2H-isoquinolin-3-one.<br>HPLC: $^A t_{Ret}$ = 2.61; LC-MS: m/z 644.5 [M + H]$^+$. |
| 54bz[(1)] | | N-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-N-ethyl-acetamide.<br>HPLC: $^A t_{Ret}$ = 2.42; LC-MS: m/z 646.4 [M + H]$^+$. |
| 54ca[(1)] | | N-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-N-ethyl-methanesulfonamide.<br>HPLC: $^A t_{Ret}$ = 2.62; LC-MS: m/z 682.4 [M + H]$^+$. |

-continued

| # | Structure | Name/HPLC/MS |
|---|---|---|
| 54cb[(1)] | 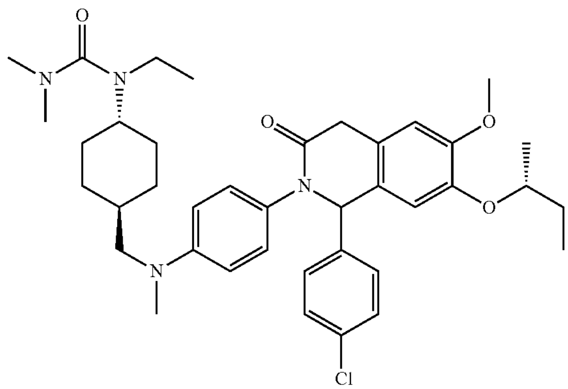 [SMILES: CC[C@@H](C)Oc1cc2c(cc1OC)CC(=O)N(c1ccc(N(C)C[C@H]3CC[C@H](N(CC)C(=O)N(C)C)CC3)cc1)C2c1ccc(Cl)cc1] | 1-{4-[({4-[7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-1-ethyl-3,3-dimethyl-urea.<br>HPLC: $^{A}t_{Ret}$ = 2.58; LC-MS: m/z 675.5 [M + H]$^{+}$. |
| 54cc | 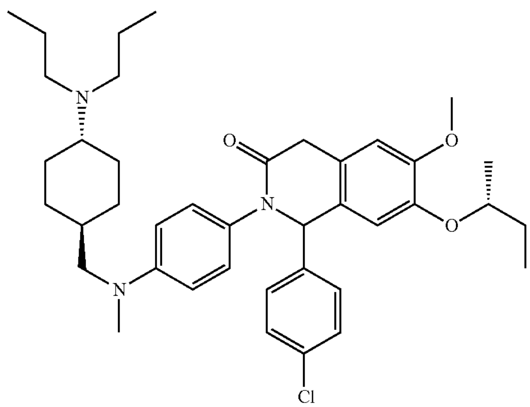 [SMILES: CCCN(CCC)[C@H]1CC[C@H](CN(C)c2ccc(N3C(=O)Cc4cc(OC)c(O[C@H](C)CC)cc4C3c3ccc(Cl)cc3)cc2)CC1] | 7-((R)-sec-Butoxy)-1-(4-chloro-phenyl)-2-{4-[(trans-4-dipropylamino-cyclohexylmethyl)-methyl-amino]-phenyl}-6-methoxy-1,4-dihydro-2H-isoquinolin-3-one.<br>HPLC: $^{A}t_{Ret}$ = 2.26; LC-MS: m/z 659.5 [M + H]$^{+}$. |
| 54cd | 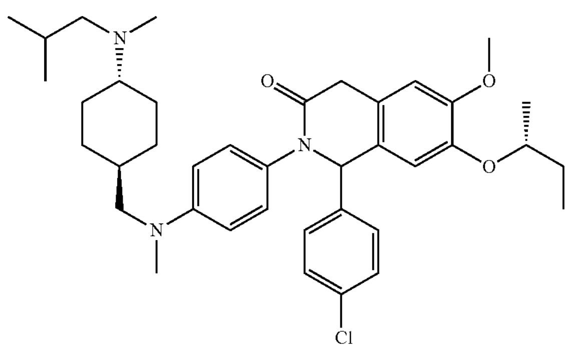 [SMILES: CC[C@@H](C)Oc1cc2c(cc1OC)CC(=O)N(c1ccc(N(C)C[C@H]3CC[C@H](N(C)CC(C)C)CC3)cc1)C2c1ccc(Cl)cc1] | 7-((R)-sec-Butoxy)-1-(4-chloro-phenyl)-2-(4-{[trans-4-(isobutyl-methyl-amino)-cyclohexylmethyl]-methyl-amino}-phenyl)-6-methoxy-1,4-dihydro-2H-isoquinolin-3-one.<br>HPLC: $^{A}t_{Ret}$ = 2.13; LC-MS: m/z 646.4 [M + H]$^{+}$. |
| 54ce | 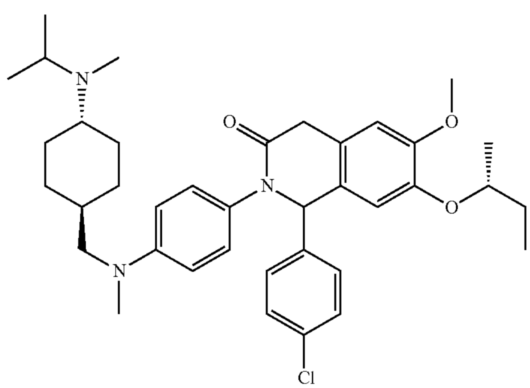 [SMILES: CC[C@@H](C)Oc1cc2c(cc1OC)CC(=O)N(c1ccc(N(C)C[C@H]3CC[C@H](N(C)C(C)C)CC3)cc1)C2c1ccc(Cl)cc1] | 7-((R)-sec-Butoxy)-1-(4-chloro-phenyl)-2-(4-{[trans-4-(isopropyl-methyl-amino)-cyclohexylmethyl]-methyl-amino}-phenyl)-6-methoxy-1,4-dihydro-2H-isoquinolin-3-one.<br>HPLC: $^{A}t_{Ret}$ = 2.05; LC-MS: m/z 632.4 [M + H]$^{+}$. |

[(1)]Title compounds were obtained from the corresponding amine analogously to Example 48, 49 or 50 using various acyl chlorides, sulfonyl chlorides or carbamoyl chlorides.

Example 55

7-((R)-sec-Butoxy)-1-(4-chloro-phenyl)-6-methoxy-2-[4-(1-pyrrolidin-1-yl-ethyl)-phenyl]-1,4-dihydro-2H-isoquinolin-3-one. (Methode A)

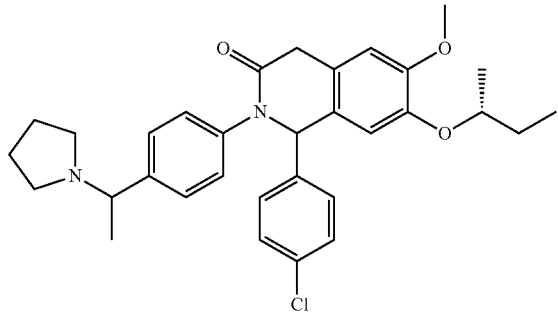 [SMILES: CC[C@@H](C)Oc1cc2c(cc1OC)CC(=O)N(c1ccc(C(C)N3CCCC3)cc1)C2c1ccc(Cl)cc1]

To a solution of Intermediate 55.2 (35 mg, 0.073 mmol) in MeOH (1 ml) were successively added AcOH (0.017 ml, 0.29 mmol), pyrrolidine (0.018 ml, 0.22 mmol) and NaBH$_3$CN (13.8 mg, 0.22 mmol) at RT. The reaction mixture was stirred at RT for 2 h then Na$_2$CO$_3$ 2M in water and DCM were added. The two phases were separated, the aqueous layer was further extracted with DCM (2×) and the combined organic fractions were dried over Na$_2$SO$_4$, filtered and evaporated to dryness. The crude material was purified by reverse phase prep-HPLC (Waters system) to yield the title compound (24.1 mg, 0.037 mmol, 51%). HPLC: $^A$t$_{Ret}$=2.01 min; LC-MS: m/z 533.3 [M+H]$^+$; $^1$H NMR (400 MHz, CD$_3$OD): 0.89-1.00 (2t, J=7.5, 3H, mixture of diastereoisomers), 1.14-1.25 (2 d, J=6.1, 3H, mixture of diastereoisomers), 1.50-1.71 (m, 2H), 1.70-1.76 (m, 3H), 1.86-2.00 (m, 1H), 2.01-2.28 (m, 3H), 2.92-3.17 (m, 2H), 3.19-3.29 (m, 1H), 3.73-3.82 (m, 2H), 3.86 (s, 3H), 4.06 (d, J=20.5, 1H), 4.18-4.29 (m, 1H), 4.34-4.44 (m, 1H), 6.06 (s, 1H), 6.78-6.83 (m, 1H), 6.90 (s, 1H), 7.19-7.25 (m, 2H), 7.26-7.34 (m, 4H), 7.46-7.52 (m, 2H).

Intermediate 55.1: 1-(4-{[1-(4-Chloro-phenyl)-meth-(E)-ylidene]-amino}-phenyl)-ethanone

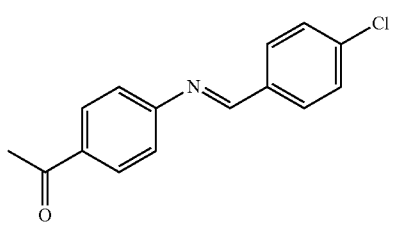 [SMILES: CC(=O)c1ccc(/N=C/c2ccc(Cl)cc2)cc1]

The title compound (460 mg, 1.80 mmol, 49%) was obtained as a light yellow solid from 1-(4-amino-phenyl)-ethanone (500 mg, 3.7 mmol) and 4-chloro-benzaldehyde (520 mg, 3.7 mmol) analogously to Intermediate 1.4. $^1$H NMR (400 MHz, CDCl$_3$): 2.64 (s, 3H), 7.22-7.27 (m, 2H), 7.47-7.53 (m, 2H), 7.85-7.92 (m, 2H), 8.00-8.06 (m, 2H), 8.43 (s, 1H).

Intermediate 55.2: 2-(4-Acetyl-phenyl)-7-((R)-sec-butoxy)-1-(4-chloro-phenyl)-6-methoxy-1,4-dihydro-2H-isoquinolin-3-one

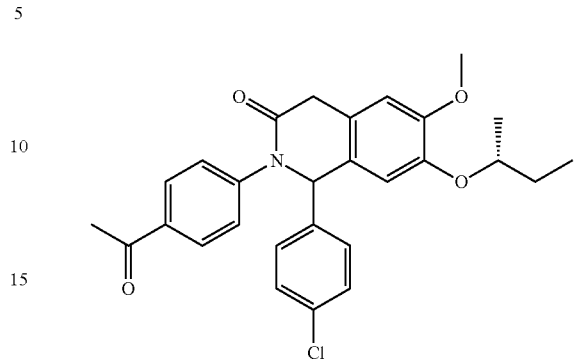

The title compound (286 mg, 0.60 mmol, 62%) was obtained as a yellow foam from Intermediate 55.1 (248 mg, 0.96 mmol) and Intermediate 1.3 (247 mg, 0.96 mmol) analogously to Example 1. Purification of the crude material was performed by reverse phase column chromatography (C18; gradient elution, water containing 0.5% TFA/MeCN 95:5→3:7). HPLC: $^A$t$_{Ret}$=2.63 min; LC-MS: m/z 478.5 [M+H]$^+$; $^1$H NMR (400 MHz, DMSO-d$_6$): 0.85-0.95 (2t, J=7.5, 3H, mixture of diastereoisomers), 1.13-1.23 (2 d, J=6.1, 3H, mixture of diastereoisomers), 1.46-1.69 (m, 2H), 2.55 (s, 3H), 3.66 (d, J=19.8, 1H), 3.74 (s, 3H), 3.90 (dd, J=19.8, 3.9, 1H), 4.20-4.31 (m, 1H), 6.25 (d, J=3.4, 1H), 6.88 (s, 1H), 7.10 (d, J=7.1, 1H), 7.32-7.42 (m, 6H), 7.91-7.97 (m, 2H).

Example 56

7-((R)-sec-Butoxy)-1-(4-chloro-phenyl)-6-methoxy-2-[4-(1-morpholin-4-yl-ethyl)-phenyl]-1,4-dihydro-2H-isoquinolin-3-one. (Methode B)

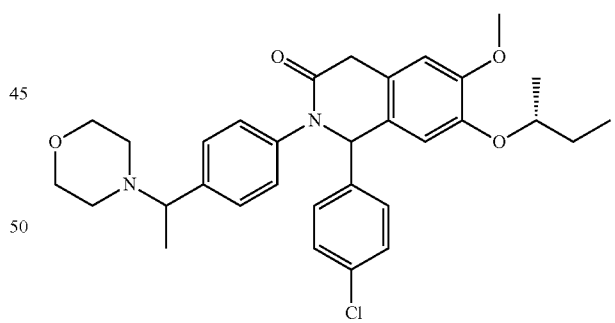

To a solution of Intermediate 55.2 (30 mg, 0.063 mmol) in THF (0.5 ml) were successively added morpholine (0.016 ml, 0.188 mmol) and Ti(OiPr)$_4$ (0.056 ml, 0.188 mmol) at RT. The reaction mixture was heated at reflux, stirred for 14 h and cooled to RT. MeOH (0.2 ml) followed by NaBH$_4$ (2.4 mg, 0.063 mmol) were added and the mixture was stirred at RT for 1 h. Celite and water were added, the heterogenous mixture was vigorously stirred for 15 min, filtered and the filter cake was washed with AcOEt. The filtrate was washed with a 2M aqueous Na$_2$CO$_3$ solution and the organic phase was dried over Na$_2$SO$_4$, filtered and evaporated to dryness. The resulting crude material was purified by reverse phase prep-HPLC (Waters system) to yield the title compound (TFA salt, 19.8 mg, 0.038 mmol, 48%) as a colorless solid. HPLC: $^A t_{Ret}$=1.91 min; LC-MS: m/z 549.3 [M+H]$^+$; $^1$H NMR (400 MHz, CD$_3$OD): 0.89-1.00 (2t, J=7.5, 3H, mixture of diastereoisomers), 1.14-1.26 (2 d, J=6.1, 3H, mixture of diastereoisomers), 1.50-1.73 (m, 2H), 1.76 (t, J=6.4, 3H), 2.93-3.20 (m, 3H), 3.60-3.84 (m, 3H), 3.79 (d, J=20.3, 1H), 3.86 (s, 3H), 3.94-4.16 (m, 2H), 4.07 (d, J=20.5, 1H), 4.18-4.29 (m, 1H), 4.43-4.52 (m, 1H), 6.06 (br. s., 1H), 6.78-6.83 (m, 1H), 6.90 (s, 1H), 7.19-7.26 (m, 2H), 7.28-7.35 (m, 4H), 7.48-7.55 (m, 2H).

Example 57

7-((R)-sec-Butoxy)-1-(4-chloro-phenyl)-2-[4-(1-hydroxy-ethyl)-phenyl]-6-methoxy-1,4-dihydro-2H-isoquinolin-3-one

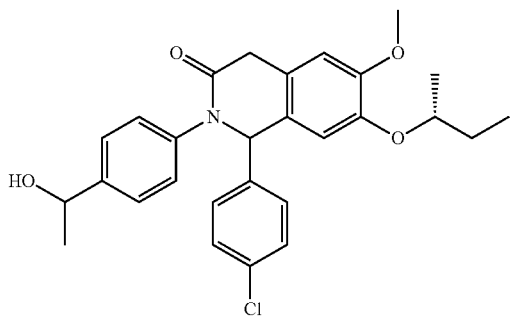

To a solution of Intermediate 55.2 (25 mg, 0.052 mmol) in MeOH (1 ml) was added NaBH$_4$ (4 mg, 0.11 mmol) at RT. The reaction mixture was stirred at RT for 2 h and concentrated under vacuum. The resulting residue was dissolved in DCM and washed with water. The organic layer was dried over Na$_2$SO$_4$, filtered and evaporated to dryness. The crude material was purified by reverse phase prep-HPLC (Waters system) to yield the title compound (11 mg, 0.021 mmol, 39%). HPLC: $^A t_{Ret}$=2.42 min; LC-MS: m/z 480.5 [M+H]$^+$; $^1$H NMR (500 MHz, DMSO-d$_6$): 0.84-0.93 (2t, J=7.5, 3H, mixture of diastereoisomers), 1.11-1.21 (2 d, J=6.1, 3H, mixture of diastereoisomers), 1.28 (d, J=6.6, 3H), 1.45-1.67 (m, 2H), 3.59 (d, J=19.7, 1H), 3.72 (s, 3H), 3.89 (dd, J=19.6, 3.6, 1H), 4.18-4.29 (m, 1H), 4.64-4.70 (m, 1H), 6.07 (d, J=4.3, 1H), 6.84 (s, 1H), 7.06 (d, J=7.8, 1H), 7.08-7.12 (m, 2H), 7.26-7.31 (m, 2H), 7.33-7.38 (m, 4H).

Example 58

N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-ethyl-acetamide

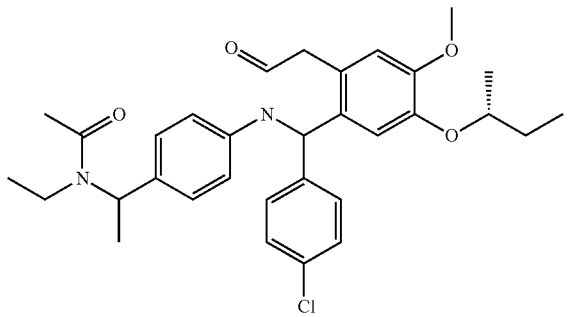 [SMILES: CC[C@@H](C)Oc1cc(C(Nc2ccc(C(C)N(CC)C(C)=O)cc2)c2ccc(Cl)cc2)c(CC=O)cc1OC]

To a solution Intermediate 58.1 (272 mg, 0.54 mmol) in DCM (5 ml) were successively added pyridine (0.22 ml, 2.68 mmol) and acetic anhydride (0.061 ml, 0.64 mmol) at RT. The reaction mixture was stirred at RT for 1 h, diluted into AcOEt and washed with water and brine. The organic phase was dried over Na$_2$SO$_4$, filtered and evaporated to dryness. The resulting crude material was purified by Combi-Flash Companion™ (Isco Inc.) column chromatography (SiO$_2$; gradient elution, DCM/[DCM/MeOH 9:1] 95:5→1:1) to yield the title compound (215 mg, 0.39 mmol, 73%) as a yellow resin. TLC: R$_F$=0.31 (DCM/MeOH 95:5); HPLC: $^A t_{Ret}$=2.54 min; LC-MS: m/z 549.3 [M+H]$^+$; $^1$H NMR (400 MHz, DMSO-d$_6$): 0.74-0.96 (m, 6H), 1.10-1.23 (m, 3H, mixture of diastereoisomers), 1.38-1.71 (m, 5H), 2.02-2.14 (m, 3H), 2.82-3.26 (m, 2H), 3.58-3.67 (m, 1H), 3.74 (s, 3H), 3.85-3.95 (m, 1H), 4.17-4.30 (m, 1H), 5.04-5.74 (m, 1H, mixture of diastereoisomers), 6.07-6.15 (m, 1H), 6.86 (s, 1H), 7.02-7.08 (m, 1H), 7.10-7.21 (m, 2H), 7.22-7.31 (m, 2H), 7.31-7.39 (m, 4H).

Intermediate 58.1: 7-((R)-sec-Butoxy)-1-(4-chloro-phenyl)-2-[4-(1-ethylamino-ethyl)-phenyl]-6-methoxy-1,4-dihydro-2H-isoquinolin-3-one

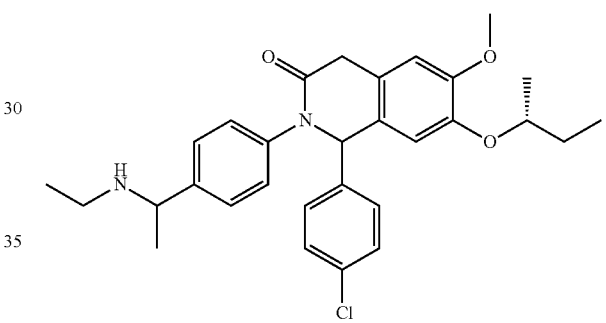

To a solution of Intermediate 55.2 (500 mg, 1.05 mmol) in dry THF (5 ml) were successively added Ti(OiPr)$_4$ (0.929 ml, 3.14 mmol) and ethylamine (2M solution in THF, 2.62 ml, 5.23 mmol) at RT. The reaction mixture was heated at reflux for 3 h then cooled to RT. NaBH$_3$CN (197 mg, 3.14 mmol) was added and the reaction mixture was stirred at RT for 14 h. Celite and water were added, the heterogenous mixture was vigorously stirred for 15 min, filtered and the filter cake was washed with AcOEt. The filtrate was washed with a 2M aqueous Na$_2$CO$_3$ solution and the organic phase was dried over Na$_2$SO$_4$, filtered and evaporated to dryness. The resulting crude material was purified by Combi-Flash Companion™ (Isco Inc.) column chromatography (SiO$_2$; gradient elution, heptane/TBME containing 5% of 7M NH$_3$ in MeOH 95:5→100% of TBME containing 5% of 7M NH$_3$ in MeOH) to yield the title compound (272 mg, 0.54 mmol, 51%) as a yellow foam. HPLC: $^A t_{Ret}$=1.95 min; LC-MS: m/z 507.2 [M+H]$^+$; $^1$H NMR (500 MHz, DMSO-d$_6$): 0.83-0.98 (m, 6H), 1.12-1.22 (m, 3H), 1.45-1.68 (m, 3H), 1.80-1.94 (m, 1H), 2.20-2.38 (m, 3H), 3.54-3.67 (m, 2H), 3.72 (s, 3H), 3.80-3.88 (m, 1H), 4.17-4.30 (m, 1H), 6.05-6.11 (m, 1H), 6.84 (s, 1H), 7.05-7.13 (m, 3H), 7.23-7.30 (m, 2H), 7.35 (s, 4H).

Example 59

1-Acetyl-piperidine-4-carboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethyl-amide

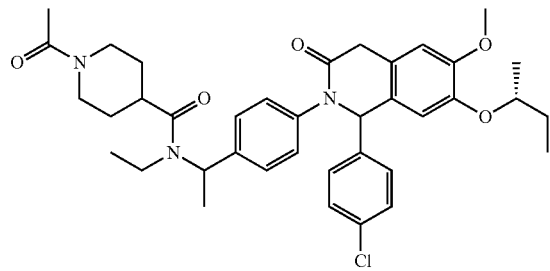 [SMILES: CC[C@@H](C)Oc1cc2c(cc1OC)CC(=O)N(c1ccc(C(C)N(CC)C(=O)C3CCN(C(C)=O)CC3)cc1)C2c1ccc(Cl)cc1]

To a solution of Intermediate 58.1 (25 mg, 0.049 mmol) in DMF (0.5 ml) were successively added 1-acetylpiperidine-4-carboxylic acid (16.9 mg, 0.099 mmol), NMM (0.016 ml, 0.148 mmol) and HATU (28.1 mg, 0.074 mmol) at RT. The reaction mixture was heated at 50° C. and stirred for 24 h then cooled to RT, diluted with AcOEt and washed with a 2M aqueous $Na_2CO_3$ solution. The organic phase was dried over $Na_2SO_4$, filtered and evaporated to dryness. The resulting crude material was purified by reverse phase prep-HPLC (Waters system) to yield the title compound (8.6 mg, 0.013 mmol, 26%) as a colorless solid. HPLC: $^A t_{Ret}$=2.47 min; LC-MS: m/z 660.6 [M+H]$^+$; $^1$H NMR (400 MHz, $CD_3OD$): 0.87-1.07 (m, 6H), 1.11-1.27 (2 d, J=6.1, 3H, mixture of diastereoisomers), 1.48-1.87 (m, 9H), 2.10-2.15 (m, 3H), 2.60-2.79 (m, 1H), 2.83-2.97 (m, 1H), 2.98-3.27 (m, 2H), 3.71-3.82 (m, 1H), 3.86 (s, 3H), 3.89-4.11 (m, 2H), 4.16-4.30 (m, 1H), 4.48-4.66 (m, 1H), 5.30-5.45 (m, 1H), 5.80-5.93 (m, 1H), 5.97-6.08 (m, 1H), 6.79 (d, J=3.4, 1H), 6.89 (s, 1H), 7.10-7.22 (m, 4H), 7.26-7.37 (m, 4H).

Example 60

Piperidine-4-carboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethyl-amide

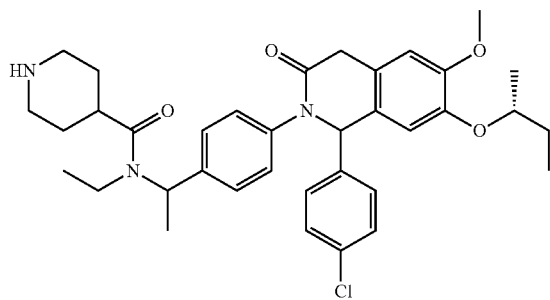 [SMILES: CC[C@@H](C)Oc1cc2c(cc1OC)CC(=O)N(c1ccc(C(C)N(CC)C(=O)C3CCNCC3)cc1)C2c1ccc(Cl)cc1]

To a solution of Intermediate 60.1 (13.7 mg, 0.019 mmol) in DCM (1 ml) was added TFA (0.058 ml, 0.76 mmol) at RT. The reaction mixture was stirred for 1 h then evaporated to dryness. The resulting crude material was purified by reverse phase prep-HPLC (Waters system) to yield the title compound (TFA salt, 8.2 mg, 0.011 mmol, 58%) as a colorless solid. HPLC: $^A t_{Ret}$=2.01 min; LC-MS: m/z 618.7 [M+H]$^+$; $^1$H NMR (400 MHz, $CD_3OD$): 0.84-1.04 (m, 6H), 1.10-1.25 (2 d, J=6.1, 3H, mixture of diastereoisomers), 1.45-1.76 (m, 5H), 1.83-2.07 (m, 4H), 2.89-3.54 (m, 5H), 3.69-3.81 (m, 1H), 3.85 (s, 3H), 3.99-4.11 (m, 1H), 4.15-4.31 (m, 1H), 5.27-5.41 (m, 1H), 5.77-5.90 (m, 1H), 5.95-6.05 (m, 1H), 6.72-6.82 (m, 1H), 6.89 (s, 1H), 7.08-7.41 (m, 8H).

Intermediate 60.1: 4-[(1-{4-[7-((R)-sec-Butoxy)-1-(4-chloro-phenyl)-6-methoxy-3-oxo-3,4-dihydro-1H-isoquinolin-2-yl]-phenyl}-ethyl)-ethyl-carbamoyl]-piperidine-1-carboxylic acid tert-butyl ester

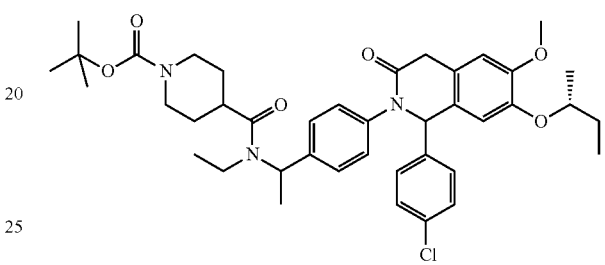

The title compound (15 mg, 0.02 mmol, 40%) was obtained as a colorless solid from Intermediate 58.1 (25 mg, 0.049 mmol) and piperidine-1,4-dicarboxylic acid mono-tert-butyl ester (22.6 mg, 0.099 mmol) analogously to Example 59. Purification of the crude material was performed by reverse phase prep-HPLC (Waters system). HPLC: $^A t_{Ret}$=3.07 min; LC-MS: m/z 718.8 [M+H]$^+$; $^1$H NMR (400 MHz, $CD_3OD$): 0.86-1.06 (m, 6H), 1.11-1.27 (2 d, J=6.1, 3H, mixture of diastereoisomers), 1.48 (s, 9H), 1.51-1.78 (m, 9H), 2.70-3.26 (m, 4H), 3.71-3.81 (m, 1H), 3.86 (s, 3H), 3.98-4.31 (m, 4H), 5.28-5.42 (m, 1H), 5.80-5.91 (m, 1H), 5.96-6.06 (m, 1H), 6.77-6.80 (m, 1H), 6.89 (s, 1H), 7.09-7.21 (m, 4H), 7.26-7.36 (m, 4H).

Example 61

7-((R)-sec-Butoxy)-1-(4-chloro-phenyl)-6-methoxy-2-{4-[1-(piperidin-4-ylamino)-ethyl]-phenyl}-1,4-dihydro-2H-isoquinolin-3-one

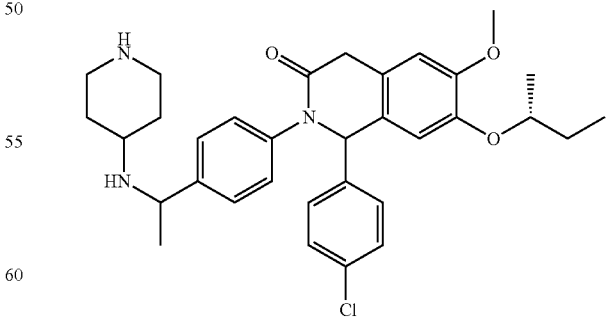

To a solution of Intermediate 61.1 (20 mg, 0.030 mmol) in DCM (0.5 ml) was added TFA (0.023 ml, 0.300 mmol) at RT. The reaction mixture was stirred at RT for 30 min then evaporated to dryness. The resulting crude material was purified by reverse phase prep-HPLC (Waters system) to yield the title compound (TFA salt, 7 mg, 0.01 mmol, 34%) as a yellow solid. HPLC: $^At_{Ret}$=1.69 min; LC-MS: m/z 562.3 [M+H]$^+$; $^1$H NMR (400 MHz, CD$_3$OD): 0.89-1.00 (2t, J=7.5, 3H, mixture of diastereoisomers), 1.14-1.26 (2 d, J=6.1, 3H, mixture of diastereoisomers), 1.49-1.78 (m, 5H), 1.79-1.99 (m, 2H), 2.18-2.30 (m, 1H), 2.34-2.47 (m, 1H), 2.92-3.10 (m, 2H), 3.24-3.35 (m, 2H), 3.45-3.61 (m, 2H), 3.79 (d, J=20.3, 1H), 3.86 (s, 3H), 4.09 (d, J=20.8, 1H), 4.18-4.30 (m, 1H), 4.56-4.66 (m, 1H), 6.05 (s, 1H), 6.79-6.83 (m, 1H), 6.90 (s, 1H), 7.21-7.26 (m, 2H), 7.27-7.35 (m, 4H), 7.49-7.56 (m, 2H).

Intermediate 61.1: 4-(1-{4-[7-((R)-sec-Butoxy)-1-(4-chloro-phenyl)-6-methoxy-3-oxo-3,4-dihydro-1H-isoquinolin-2-yl]-phenyl}-ethylamino)-piperidine-1-carboxylic acid tert-butyl ester

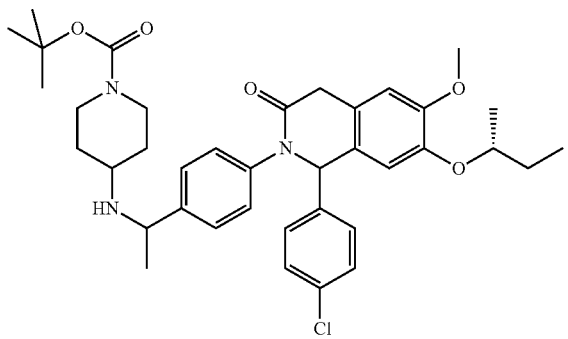 [SMILES: CC[C@@H](C)Oc1cc2c(cc1OC)CC(=O)N(c1ccc(C(C)NC3CCN(C(=O)OC(C)(C)C)CC3)cc1)C2c1ccc(Cl)cc1]

To a solution of Intermediate 55.2 (136 mg, 0.285 mmol) in THF (1 ml) were successively added tert-butyl 4-aminopiperidine-1-carboxylate (171 mg, 0.854 mmol) and Ti(OiPr)$_4$ (0.253 ml, 0.854 mmol) at RT. The reaction mixture was heated at reflux, stirred for 14 h and cooled to RT. MeOH (0.2 ml) followed by NaBH$_4$ (10.76 mg, 0.285 mmol) were added and the mixture was stirred at RT for 1 h. Celite and water were added, the heterogenous mixture was vigorously stirred for 15 min, filtered and the filter cake was washed with AcOEt. The filtrate was washed with a 2M aqueous Na$_2$CO$_3$ solution and the organic phase was dried over Na$_2$SO$_4$, filtered and evaporated to dryness. The resulting crude material was purified by Combi-Flash Companion™ (Isco Inc.) column chromatography (SiO$_2$; gradient elution, DCM/[DCM/MeOH 9:1] 95:5→2:8) to yield the title compound (162 mg, 0.245 mmol, 86%) as a yellow foam. TLC: R$_F$=0.31 (DCM/MeOH 95:5); HPLC: $^At_{Ret}$=2.20 min; LC-MS: m/z 662.3 [M+H]$^+$; $^1$H NMR (400 MHz, DMSO-d$_6$): 0.84-0.95 (2t, 3H, mixture of diastereoisomers), 0.98-1.28 (m, 7H), 1.32-1.44 (m, 9H), 1.45-1.72 (m, 3H), 1.74-1.85 (m, 1H), 1.89-2.04 (m, 1H), 2.24-2.37 (m, 1H), 2.57-2.80 (m, 2H), 3.60 (d, J=19.6, 1H), 3.68-3.92 (m, 7H), 4.18-4.31 (m, 1H), 6.07-6.14 (m, 1H), 6.85 (s, 1H), 7.05-7.14 (m, 3H), 7.27-7.40 (m, 6H).

Example 62

N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-piperidin-4-yl-acetamide

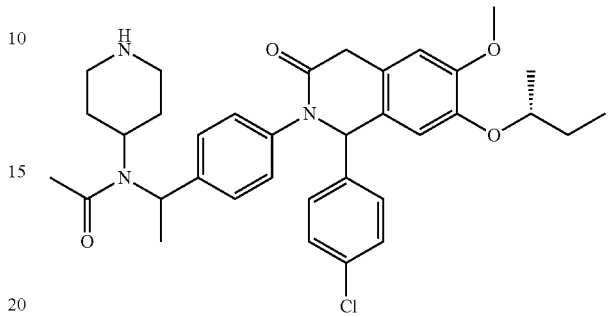

To a solution of Intermediate 61.1 (20 mg, 0.030 mmol) in DCM (0.5 ml) were successively added acetyl chloride (0.003 ml, 0.045 mmol) and Et$_3$N (0.013 ml, 0.090 mmol) at RT. The reaction mixture was stirred at RT for 1 h then diluted with DCM and washed with water. The organic phase was dried over Na$_2$SO$_4$, filtered and evaporated to dryness. The resulting residue was dissolved in DCM (0.5 ml) then TFA (0.023 ml, 0.300 mmol) was added at RT. The reaction mixture was stirred at RT for 30 min then evaporated to dryness. The resulting crude material was purified by reverse phase prep-HPLC (Waters system) to yield the title compound (TFA salt, 11.6 mg, 0.016 mmol, 54%) as a colorless solid. HPLC: $^At_{Ret}$=1.93 min; LC-MS: m/z 604.5 [M+H]$^+$; $^1$H NMR (400 MHz, DMSO-d$_6$): 0.85-0.96 (m, 3H), 1.12-1.24 (m, 4H), 1.49-1.68 (m, 5H), 1.68-1.78 (m, 1H), 2.78-3.02 (m, 4H), 3.13-3.22 (m, 1H), 3.25-3.33 (m, 1H), 3.33-3.46 (m, 1H), 3.62 (d, J=19.7, 1H), 3.78 (s, 3H), 3.81-3.90 (m, 1H), 4.15-4.26 (m, 1H), 4.93-5.02 (m, 1H), 6.02 (br. s., 1H), 6.84 (s, 1H), 6.86-6.89 (m, 1H), 7.12-7.17 (m, 2H), 7.19-7.24 (m, 2H), 7.25-7.34 (m, 4H).

Example 63

7-((R)-sec-Butoxy)-1-(4-chloro-phenyl)-6-methoxy-2-{4-[1-(methyl-piperidin-4-yl-amino)-ethyl]-phenyl}-1,4-dihydro-2H-isoquinolin-3-one

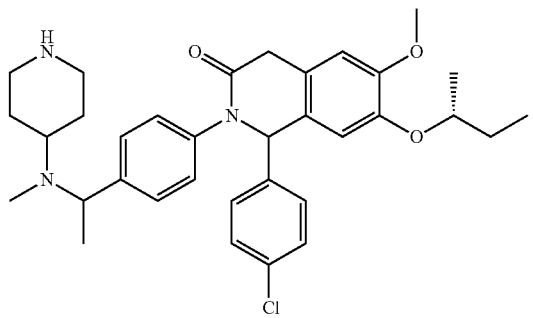 [SMILES: CC[C@@H](C)Oc1cc2c(cc1OC)CC(=O)N(c1ccc(C(C)N(C)C3CCNCC3)cc1)C2c1ccc(Cl)cc1]

To a solution of Intermediate 61.1 (25 mg, 0.038 mmol) in DCM (0.5 ml) were successively added AcOH (0.006 ml, 0.113 mmol), formaldehyde (37% in water, 0.008 ml, 0.113 mmol) and NaBH(OAc)₃ (24.0 mg, 0.113 mmol) at RT. The reaction mixture was stirred at RT for 1 h then diluted with DCM and washed with water. The organic phase was dried over Na₂SO₄, filtered and evaporated to dryness. The resulting yellow foam was dissolved in DCM (0.5 ml) and TFA (0.059 ml, 0.760 mmol) was added at RT. The reaction mixture was stirred for 20 min then evaporated to dryness. The resulting crude material was purified by reverse phase prep-HPLC (Waters system) to yield the title compound (TFA salt, 22 mg, 0.038 mmol, quant.) as a colorless solid. HPLC: $^A t_{Ret}$=1.66 min; LC-MS: m/z 576.5 [M+H]⁺; ¹H NMR (400 MHz, DMSO-d₆): 0.85-0.96 (m, 3H), 1.12-1.30 (m, 4H), 1.47-1.69 (m, 5H), 1.71-1.83 (m, 1H), 1.85-1.98 (m, 1H), 2.04-2.18 (m, 1H), 2.24-2.36 (m, 1H), 2.36-2.46 (m, 2H), 2.60-2.71 (m, 2H), 2.71-2.86 (m, 1H), 2.88-3.06 (m, 1H), 3.06-3.17 (m, 1H), 3.64 (d, J=20.1, 1H), 3.74 (s, 3H), 3.83-3.98 (m, 1H), 4.19-4.32 (m, 1H), 4.61-4.87 (m, 1H), 6.12-6.23 (m, 1H), 6.88 (s, 1H), 7.03-7.13 (m, 1H), 7.28-7.42 (m, 6H), 7.51-7.63 (m, 2H).

Example 64

7-((R)-sec-Butoxy)-1-(4-chloro-phenyl)-2-(4-{1-[(cis-4-dimethylamino-cyclohexyl)-methyl-amino]-ethyl}-phenyl)-6-methoxy-1,4-dihydro-2H-isoquinolin-3-one

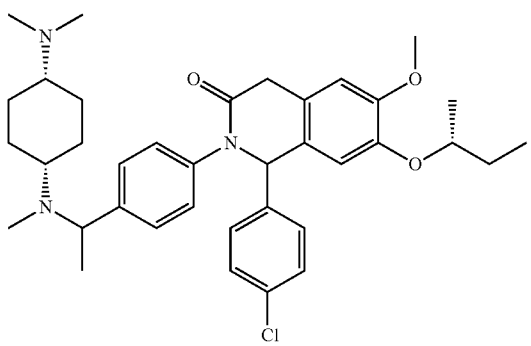 [SMILES: CC[C@@H](C)Oc1cc2c(cc1OC)CC(=O)N(c1ccc(C(C)N(C)[C@H]3CC[C@@H](N(C)C)CC3)cc1)C2c1ccc(Cl)cc1]

The title compound (TFA salt, 17.4 mg, 0.024 mmol, 54%) was obtained as a colorless solid by methylation of Intermediate 64.2 (TFA salt, 30 mg, 0.043 mmol) with formaldehyde (37% in water, 0.013 ml, 0.17 mmol) analogously to Example 63. Purification of the crude material was performed by reverse phase prep-HPLC (Waters system). HPLC: $^A t_{Ret}$=1.71 min; LC-MS: m/z 618.5 [M+H]⁺; ¹H NMR (400 MHz, CD₃OD): 0.87-1.01 (m, 3H, mixture of diastereoisomers), 1.12-1.27 (m, 3H, mixture of diastereoisomers), 1.46-2.44 (m, 13H), 2.57-2.73 (m, 1H), 2.86-2.94 (m, 1H), 2.96 (s, 6H), 3.80 (d, J=20.1, 1H), 3.87 (s, 3H), 4.08 (d, J=20.5, 1H), 4.19-4.28 (m, 1H), 4.68-4.82 (m, 1H), 6.05-6.10 (m, 1H), 6.77-6.82 (m, 1H), 6.90 (s, 1H), 7.19-7.36 (m, 6H), 7.51-7.59 (m, 2H).

Intermediate 64.1: [4-(1-{4-[7-((R)-sec-Butoxy)-1-(4-chloro-phenyl)-6-methoxy-3-oxo-3,4-dihydro-1H-isoquinolin-2-yl]-phenyl}-ethylamino)-cis-cyclohexyl]-carbamic acid tert-butyl ester

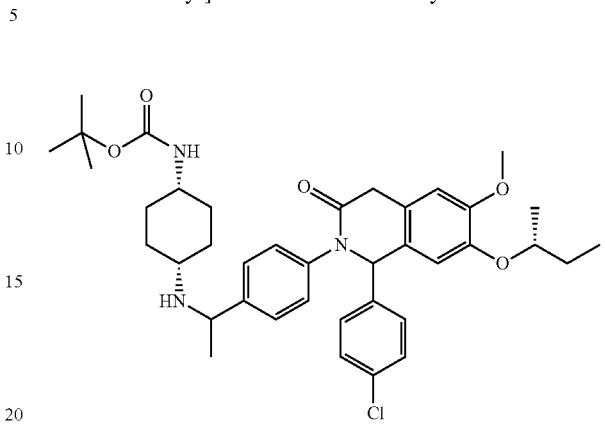

The title compound (137 mg, 0.20 mmol, 97%) was obtained as a yellow resin from Intermediate 55.2 (100 mg, 0.21 mmol) and (4-amino-cyclohexyl)-carbamic acid tert-butyl ester (135 mg, 0.63 mmol) analogously to Intermediate 61.1. Purification of the crude material was performed by Combi-Flash Companion™ (Isco Inc.) column chromatography (SiO₂; gradient elution, [heptane/DCM 1:1]/TBME containing 5% of 7M NH₃ in MeOH 95:5→100% TBME containing 5% of 7M NH₃ in MeOH). TLC: R_F=0.16 (heptane/DCM/TBME containing 5% of 7M NH₃ in MeOH 1:1:2); HPLC: $^A t_{Ret}$=2.20 min; LC-MS: m/z 676.4 [M+H]⁺; ¹H NMR (400 MHz, DMSO-d): 0.82-0.92 (m, 3H), 1.13-1.22 (m, 3H), 1.31-1.70 (m, 22H), 2.28-2.37 (m, 1H), 3.22-3.31 (m, 1H), 3.60 (d, J=19.8, 1H), 3.71-3.80 (m, 4H), 3.85 (dd, J=19.7, 3.3, 1H), 4.19-4.31 (m, 1H), 6.07-6.12 (m, 1H), 6.55-6.62 (m, 1H), 6.86 (s, 1H), 7.06-7.13 (m, 3H), 7.27-7.32 (m, 2H), 7.33-7.40 (m, 4H).

Intermediate 64.2: 2-{4-[1-(cis-4-Amino-cyclohexylamino)-ethyl]-phenyl}-7-((R)-sec-butoxy)-1-(4-chloro-phenyl)-6-methoxy-1,4-dihydro-2H-isoquinolin-3-one

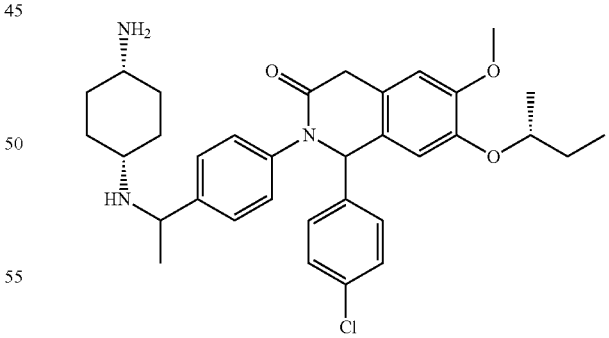

The title compound (TFA salt, 50 mg, 0.072 mmol, 49%) was obtained as a colorless solid by cleavage of the Boc protection of Intermediate 64.1 (100 mg, 0.15 mmol) analogously to Example 61. Purification of the crude material was performed by reverse phase prep-HPLC (Waters system). HPLC: $^A t_{Ret}$=1.68 min; LC-MS: m/z 576.3 [M+H]⁺; ¹H NMR (400 MHz, CD₃OD): 0.89-1.00 (2t, J=7.5, 3H, mixture of diastereoisomers), 1.14-1.25 (2 d, J=6.1, 3H, mixture of diastereoisomers), 1.48-1.75 (m, 5H), 1.76-2.06 (m, 8H), 2.98-3.09 (m, 1H), 3.38-3.47 (m, 1H), 3.79 (d, J=20.5, 1H), 3.86 (s, 3H), 4.07 (d, J=20.5, 1H), 4.17-4.29 (m, 1H), 4.55-4.64 (m, 1H), 6.06 (br. s., 1H), 6.77-6.81 (m, 1H), 6.90 (s, 1H), 7.19-7.25 (m, 2H), 7.26-7.34 (m, 4H), 7.49-7.55 (m, 2H).

Example 65

N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-(cis-4-dimethylamino-cyclohexyl)-acetamide

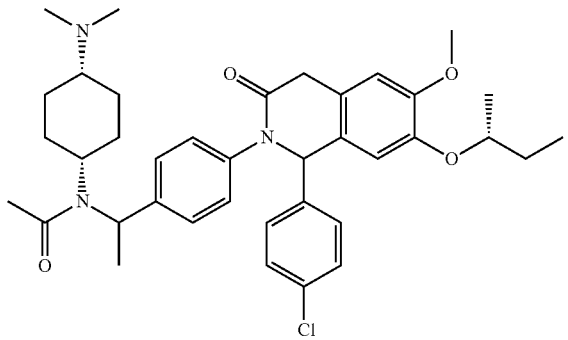 [SMILES: CC[C@@H](C)Oc1cc2c(cc1OC)CC(=O)N(c1ccc(C(C)N(C(C)=O)[C@H]3CC[C@@H](N(C)C)CC3)cc1)C2c1ccc(Cl)cc1]

To a solution of Intermediate 64.1 (35 mg, 0.052 mmol) in DCM (0.5 ml) were successively added acetyl chloride (0.006 ml, 0.078 mmol) and Et$_3$N (0.022 ml, 0.155 mmol) at RT. The reaction mixture was stirred at RT for 1 h, diluted with DCM and washed with water. The organic layer was dried over Na$_2$SO$_4$, filtered and evaporated to dryness. The resulting yellow foam was dissolved in DCM (0.5 ml) and TFA (0.08 ml, 1.0 mmol) was added. The mixture was stirred at RT for 1 h then evaporated to dryness. The resulting brown resin was dissolved in DCM (0.7 ml) and AcOH (0.009 ml, 0.155 mmol), formaldehyde 37% in water (0.012 ml, 0.155 mmol) and NaBH(OAc)$_3$ (32.9 mg, 0.155 mmol) were successively added at RT. The reaction mixture was stirred at RT for 1 h, diluted with DCM and washed with water. The organic layer was dried over Na$_2$SO$_4$, filtered and evaporated to dryness. The resulting crude material was purified by reverse phase prep-HPLC (Waters system) to yield the title compound (TFA salt, 16.8 mg, 0.022 mmol, 42%) as a colorless solid. HPLC: $^At_{Ret}$=1.99 min; LC-MS: m/z 646.5 [M+H]$^+$.

Example 66

2-{4-[1-(trans-4-Amino-cyclohexylamino)-ethyl]-phenyl}-7-((R)-sec-butoxy)-1-(4-chloro-phenyl)-6-methoxy-1,4-dihydro-2H-isoquinolin-3-one

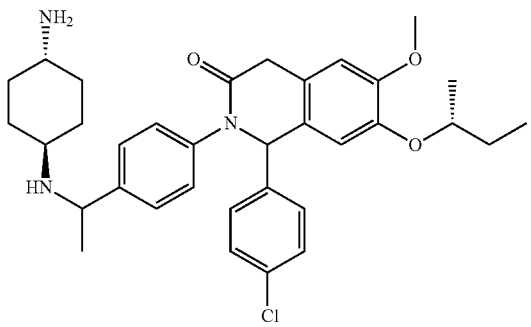 [SMILES: CC[C@@H](C)Oc1cc2c(cc1OC)CC(=O)N(c1ccc(C(C)N[C@H]3CC[C@H](N)CC3)cc1)C2c1ccc(Cl)cc1]

A solution of Intermediate 66.1 (40 mg, 0.056 mmol) in EtOH (1 ml) was evacuated under vacuum and back filled with argon (2×). Ammonium formate (5.3 mg, 0.084 mmol) and Pd/C (3.0 mg, 0.003 mmol) were added at RT and the suspension was vigorously stirred for 1 h. The reaction mixture was filtered over a Celite pad, the catalyst was washed with DCM and the filtrate evaporated to dryness. The resulting crude material was purified by reverse phase prep-HPLC (Waters system) to yield the title compound (TFA salt, 12.6 mg, 0.018 mmol, 32%) as a colorless solid. HPLC: $^At_{Ret}$=1.73 min; LC-MS: m/z 576.4 [M+H]$^+$; $^1$H NMR (400 MHz, CD$_3$OD): 0.88-1.01 (2t, J=7.5, 3H, mixture of diastereoisomers), 1.13-1.27 (2 d, J=6.1, 3H, mixture of diastereoisomers), 1.33-1.78 (m, 9H), 2.09-2.23 (m, 3H), 2.28-2.38 (m, 1H), 2.90-3.03 (m, 1H), 3.07-3.18 (m, 1H), 3.79 (d, J=20.3, 1H), 3.86 (s, 3H), 4.09 (d, J=20.3, 1H), 4.18-4.31 (m, 1H), 4.52-4.63 (m, 1H), 6.05 (s, 1H), 6.77-6.83 (m, 1H), 6.90 (s, 1H), 7.19-7.26 (m, 2H), 7.26-7.35 (m, 4H), 7.48-7.55 (m, 2H).

Intermediate 66.1: [4-(1-{4-[7-((R)-sec-Butoxy)-1-(4-chloro-phenyl)-6-methoxy-3-oxo-3,4-dihydro-1H-isoquinolin-2-yl]-phenyl}-ethylamino)-trans-cyclohexyl]-carbamic acid benzyl ester

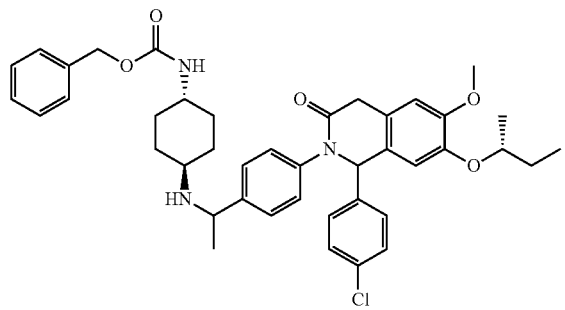 [SMILES: CC[C@@H](C)Oc1cc2c(cc1OC)CC(=O)N(c1ccc(C(C)N[C@H]3CC[C@H](NC(=O)OCc4ccccc4)CC3)cc1)C2c1ccc(Cl)cc1]

The title compound (232 mg, 0.29 mmol, 70%) was obtained as a yellow resin from Intermediate 55.2 (200 mg, 0.42 mmol) and trans-(4-amino-cyclohexyl)-carbamic acid benzyl ester (312 mg, 1.26 mmol) analogously to Intermediate 61.1. Purification of the crude material was performed by Combi-Flash Companion™ (Isco Inc.) column chromatography (SiO$_2$; gradient elution, [heptane/DCM 1:1]/TBME containing 5% of 7M NH$_3$ in MeOH 95:5→100% TBME containing 5% of 7M NH$_3$ in MeOH). TLC: R$_F$=0.10 (heptane/DCM/TBME containing 5% of 7M NH$_3$ in MeOH 1:1:2); HPLC: $^At_{Ret}$=2.24 min; LC-MS: m/z 710.4 [M+H]$^+$;

$^1$H NMR (400 MHz, DMSO-d$_6$): 0.80-0.93 (m, 3H), 1.09-1.20 (m, 3H), 1.43-2.10 (m, 12H), 3.12-3.25 (m, 1H), 3.60 (d, J=19.6, 1H), 3.74 (s, 3H), 3.78-3.90 (m, 2H), 4.17-4.32 (m, 1H), 4.95-5.01 (m, 2H), 6.10 (br. s., 1H), 6.86 (s, 1H), 7.03-7.14 (m, 4H), 7.25-7.41 (m, 11H).

Example 67

7-((R)-sec-Butoxy)-1-(4-chloro-phenyl)-2-{4-[1-(4-dimethylamino-piperidin-1-yl)-ethyl]-phenyl}-6-methoxy-1,4-dihydro-2H-isoquinolin-3-one

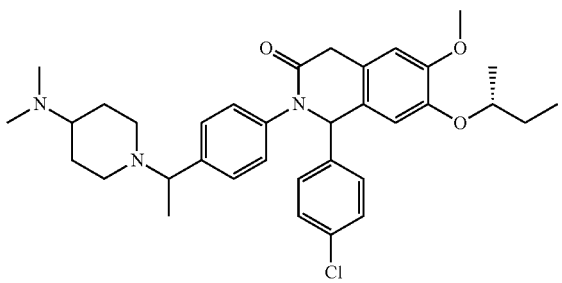 [SMILES: CC[C@@H](C)Oc1cc2c(cc1OC)CC(=O)N(c1ccc(C(C)N3CCC(N(C)C)CC3)cc1)C2c1ccc(Cl)cc1]

To a solution of Intermediate 67.2 (20 mg, 0.030 mmol) in DCM (0.5 ml) were successively added AcOH (0.005 ml, 0.089 mmol), formaldehyde (37% in water, 0.007 ml, 0.089 mmol) and NaBH(OAc)$_3$ (18.81 mg, 0.089 mmol) at RT. The reaction mixture was stirred at RT for 1 h then diluted with DCM and washed with water. The organic phase was dried over Na$_2$SO$_4$, filtered and evaporated to dryness. The resulting crude material was purified by reverse phase prep-HPLC (Waters system) to yield the title compound (TFA salt, 7.5 mg, 0.011 mmol, 36%) as a colorless solid. HPLC: $^A t_{Ret}$=1.70 min; LC-MS: m/z 590.3 [M+H]$^+$; $^1$H NMR (400 MHz, CD$_3$OD): 0.89-1.01 (2t, J=7.5, 3H, mixture of diastereoisomers), 1.14-1.26 (2 d, J=6.1, 3H, mixture of diastereoisomers), 1.49-1.74 (m, 2H), 1.74-1.80 (m, 3H), 1.96-2.17 (m, 2H), 2.28-2.45 (m, 2H), 2.84-3.07 (m, 2H), 2.91 (s, 6H), 3.38-3.48 (m, 1H), 3.51-3.61 (m, 1H), 3.79 (d, J=20.3, 1H), 3.83-3.95 (m, 1H), 3.86 (s, 3H), 4.07 (d, J=20.3, 1H), 4.18-4.31 (m, 1H), 4.48-4.59 (m, 1H), 6.06 (s, 1H), 6.79-6.85 (m, 1H), 6.90 (s, 1H), 7.19-7.26 (m, 2H), 7.27-7.36 (m, 4H), 7.50-7.58 (m, 2H).

Intermediate 67.1: [1-(1-{4-[7-((R)-sec-Butoxy)-1-(4-chloro-phenyl)-6-methoxy-3-oxo-3,4-dihydro-1H-isoquinolin-2-yl]-phenyl}-ethyl)-piperidin-4-yl]-carbamic acid tert-butyl ester

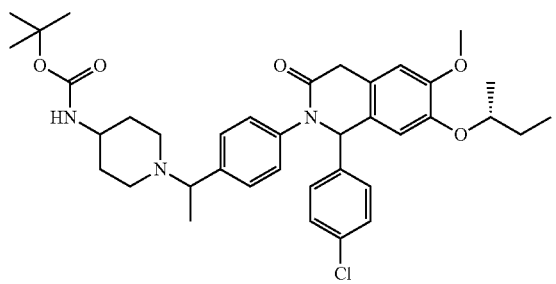 [SMILES: CC[C@@H](C)Oc1cc2c(cc1OC)CC(=O)N(c1ccc(C(C)N3CCC(NC(=O)OC(C)(C)C)CC3)cc1)C2c1ccc(Cl)cc1]

The title compound (230 mg, 0.35 mmol, 83%) was obtained as a yellow resin from Intermediate 55.2 (200 mg, 0.42 mmol) and piperidin-4-yl-carbamic acid tert-butyl ester (251 mg, 1.26 mmol) analogously to Intermediate 61.1. Purification of the crude material was performed by Combi-Flash Companion™ (Isco Inc.) column chromatography (SiO$_2$; gradient elution, [heptane/DCM 1:1]/TBME containing 5% of 7M NH$_3$ in MeOH 95:5→100% TBME containing 5% of 7M NH$_3$ in MeOH). TLC: R$_F$=0.29 (heptane/DCM/TBME containing 5% of 7M NH$_3$ in MeOH 1:1:2); HPLC: $^A t_{Ret}$=2.15 min; LC-MS: m/z 662.4 [M+H]$^+$; $^1$H NMR (400 MHz, DMSO-d$_6$): 0.83-0.96 (m, 3H), 1.13-1.22 (m, 3H), 1.33-1.40 (m, 9H), 1.45-1.96 (m, 8H), 2.26-2.42 (m, 1H), 2.57-2.67 (m, 1H), 2.81-3.00 (m, 2H), 3.06-3.20 (m, 1H), 3.35-3.43 (m, 1H), 3.60 (d, J=19.8, 1H), 3.73 (s, 3H), 3.84 (dd, J=19.7, 3.8, 1H), 4.18-4.34 (m, 1H), 5.70-5.82 (m, 1H), 6.06-6.15 (m, 1H), 6.67-6.78 (m, 1H), 6.86 (s, 1H), 7.06-7.17 (m, 3H), 7.20-7.29 (m, 2H), 7.31-7.42 (m, 4H).

Intermediate 67.2: 2-{4-[1-(4-Amino-piperidin-1-yl)-ethyl]-phenyl}-7-((R)-sec-butoxy)-1-(4-chloro-phenyl)-6-methoxy-1,4-dihydro-2H-isoquinolin-3-one

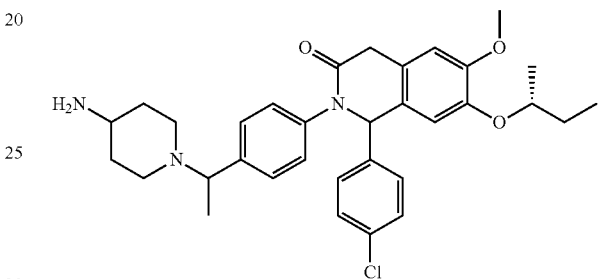

The title compound (TFA salt, 25.3 mg, 0.037 mmol, 59%) was obtained as a colorless solid from Intermediate 67.1 (41.7 mg, 0.063 mmol) by treatment with TFA analogously to Example 61. Purification of the crude material was performed by reverse phase prep-HPLC (Waters system). HPLC: $^A t_{Ret}$=1.70 min; LC-MS: m/z 562.6 [M+H]$^+$; $^1$H NMR (400 MHz, CD$_3$OD): 0.88-1.01 (2t, J=7.5, 3H, mixture of diastereoisomers), 1.13-1.26 (2 d, J=6.1, 3H, mixture of diastereoisomers), 1.51-1.81 (m, 5H), 1.83-2.07 (m, 2H), 2.16-2.34 (m, 2H), 2.80-3.12 (m, 2H), 3.34-3.43 (m, 1H), 3.44-3.53 (m, 1H), 3.79 (d, J=20.3, 1H), 3.79-3.89 (m, 1H), 3.86 (s, 3H), 4.08 (d, J=20.1, 1H), 4.18-4.30 (m, 1H), 4.43-4.59 (m, 1H), 6.06 (s, 1H), 6.77-6.84 (m, 1H), 6.90 (s, 1H), 7.19-7.26 (m, 2H), 7.26-7.35 (m, 4H), 7.48-7.57 (m, 2H).

Example 68

7-((R)-sec-Butoxy)-1-(4-chloro-phenyl)-2-(4-{1-[4-(isopropyl-methyl-amino)-piperidin-1-yl]-ethyl}-phenyl)-6-methoxy-1,4-dihydro-2H-isoquinolin-3-one

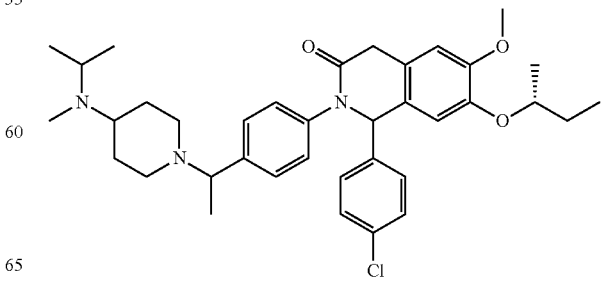

The title compound (TFA salt, 15.3 mg, 0.021 mmol, 43%) was obtained from Intermediate 67.2 (27 mg, 0.048 mmol) after two consecutive reductive amination with acetone and formaldehyde respectively, analogously to Example 53. Purification of the crude material was performed by reverse phase prep-HPLC (Waters system). HPLC: $^A t_{Ret}$=1.71 min; LC-MS: m/z 618.6 [M+H]$^+$; $^1$H NMR (400 MHz, CD$_3$OD): 0.89-1.01 (2t, J=7.5, 3H, mixture of diastereoisomers), 1.15-1.26 (2 d, J=6.1, 3H, mixture of diastereoisomers), 1.29-1.43 (m, 6H), 1.49-1.80 (m, 5H), 1.95-2.20 (m, 2H), 2.23-2.49 (m, 2H), 2.80-3.06 (m, 2H), 3.22-3.37 (m, 3H), 3.45-3.65 (m, 2H), 3.78 (d, J=20.5, 1H), 3.78-3.88 (m, 1H), 3.86 (s, 3H), 4.07 (d, J=20.1, 1 H), 4.20-4.30 (m, 1H), 4.39-4.55 (m, 1H), 6.06 (s, 1H), 6.79-6.85 (m, 1H), 6.90 (s, 1H), 7.20-7.26 (m, 2H), 7.27-7.36 (m, 4H), 7.49-7.58 (m, 2H).

Example 69

N-[1-(1-{4-[7-((R)-sec-Butoxy)-1-(4-chloro-phenyl)-6-methoxy-3-oxo-3,4-dihydro-1H-isoquinolin-2-yl]-phenyl}-ethyl)-piperidin-4-yl]-acetamide

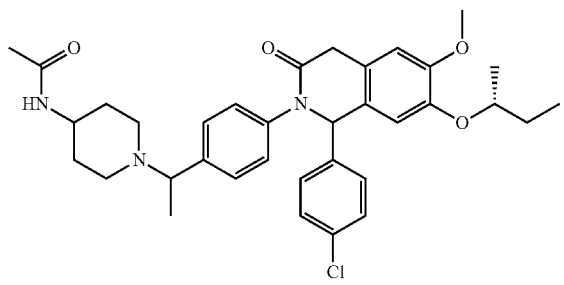 [SMILES: CC[C@@H](C)Oc1cc2c(cc1OC)CC(=O)N(c1ccc(C(C)N3CCC(NC(C)=O)CC3)cc1)C2c1ccc(Cl)cc1]

To a solution of Intermediate 67.2 (24 mg, 0.043 mmol) in MeCN (0.5 ml) were successively added Et$_3$N (0.018 ml, 0.13 mmol) and acetyl chloride (0.005 ml, 0.064 mmol) at RT. The reaction mixture was stirred at RT for 1 h then directly subjected to purification by reverse phase prep-HPLC (Waters system) to yield the title compound (TFA salt, 3.2 mg, 0.004 mmol, 10%) as a colorless solid. HPLC: $^A t_{Ret}$=1.88 min; LC-MS: m/z 604.5 [M+H]$^+$.

Example 70

2-{4-[1-(4-Acetyl-piperazin-1-yl)-ethyl]-phenyl}-7-((R)-sec-butoxy)-1-(4-chloro-phenyl)-6-methoxy-1,4-dihydro-2H-isoquinolin-3-one

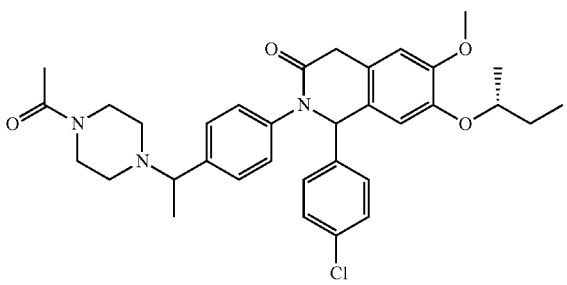 [SMILES: CC[C@@H](C)Oc1cc2c(cc1OC)CC(=O)N(c1ccc(C(C)N3CCN(C(C)=O)CC3)cc1)C2c1ccc(Cl)cc1]

To a solution of Intermediate 70.1 (TFA salt, 15.4 mg, 0.023 mmol) in MeCN (0.5 ml) were successively added Et$_3$N (0.013 ml, 0.093 mmol) and acetyl chloride (0.003 ml, 0.035 mmol) at RT. The reaction mixture was stirred at RT for 1 h then directly subjected to purification by reverse phase prep-HPLC (Waters system) to yield the title compound (TFA salt, 7.6 mg, 0.011 mmol, 46%) as a colorless solid. HPLC: $^A t_{Ret}$=1.90 min; LC-MS: m/z 590.4 [M+H]$^+$; $^1$H NMR (400 MHz, CD$_3$OD): 0.88-1.02 (2t, J=7.5, 3H, mixture of diastereoisomers), 1.12-1.27 (2 d, J=6.1, 3H, mixture of diastereoisomers), 1.48-1.74 (m, 2H), 1.74-1.83 (m, 3H), 2.13 (s, 3H), 2.81-3.40 (m, 8H), 3.79 (d, J=20.3, 1H), 3.86 (s, 3H), 4.07 (d, J=20.3, 1H), 4.18-4.29 (m, 1H), 4.46-4.56 (m, 1H), 6.06 (s, 1H), 6.78-6.83 (m, 1H), 6.90 (s, 1H), 7.19-7.26 (m, 2H), 7.28-7.35 (m, 4H), 7.48-7.54 (m, 2H).

Intermediate 70.1: 7-((R)-sec-Butoxy)-1-(4-chloro-phenyl)-6-methoxy-2-[4-(1-piperazin-1-yl-ethyl)-phenyl]-1,4-dihydro-2H-isoquinolin-3-one

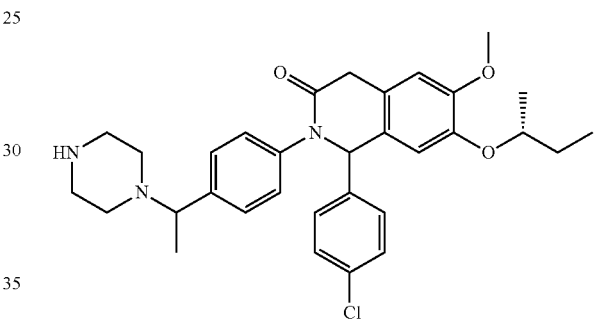

The title compound (TFA salt, 18.9 mg, 0.029 mmol, 45%) was obtained as a colorless solid from Intermediate 55.2 (30 mg, 0.063 mmol) and piperazine-1-carboxylic acid tert-butyl ester (35.1 mg, 0.188 mmol) analogously to Example 61. Purification of the crude material was performed by reverse phase prep-HPLC (Waters system). HPLC: $^A t_{Ret}$=1.71 min; LC-MS: m/z 548.2 [M+H]$^+$; $^1$H NMR (400 MHz, CD$_3$OD): 0.87-1.01 (2t, J=7.5, 3H, mixture of diastereoisomers), 1.13-1.27 (2 d, J=6.1, 3H, mixture of diastereoisomers), 1.46-1.54 (m, 3H), 1.54-1.78 (m, 2H), 2.79-3.06 (m, 4H), 3.24-3.38 (m, 4H), 3.76 (d, J=20.3, 1H), 3.82-3.92 (m, 4H), 4.05 (d, J=20.1, 1H), 4.19-4.30 (m, 1H), 6.01 (s, 1H), 6.80-6.85 (m, 1H), 6.90 (s, 1H), 7.15-7.25 (m, 4H), 7.28-7.34 (m, 2H), 7.39-7.46 (m, 2H).

Example 71

Compounds 71aa to 71ca were obtained from Intermediate 55.2 (or analogues prepared similarly) or Intermediate 58.1 (or analogues prepared similarly) analogously to Example 55 to 70.

| # | Structure | Name/HPLC/MS |
|---|---|---|
| 71aa | 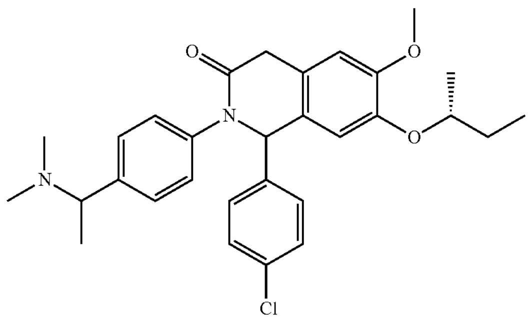 [SMILES: CC[C@@H](C)Oc1cc2c(cc1OC)CC(=O)N(c1ccc(C(C)N(C)C)cc1)C2c1ccc(Cl)cc1] | 7-((R)-sec-Butoxy)-1-(4-chloro-phenyl)-2-[4-(1-dimethylamino-ethyl)-phenyl]-6-methoxy-1,4-dihydro-2H-isoquinolin-3-one.<br>HPLC: $^At_{Ret}$ = 1.97; LC-MS: m/z 507.3 [M + H]$^+$. |
| 71ab | 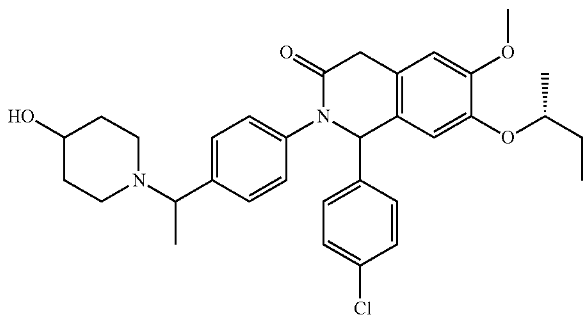 [SMILES: CC[C@@H](C)Oc1cc2c(cc1OC)CC(=O)N(c1ccc(C(C)N3CCC(O)CC3)cc1)C2c1ccc(Cl)cc1] | 7-((R)-sec-Butoxy)-1-(4-chloro-phenyl)-2-{4-[1-(4-hydroxy-piperidin-1-yl)-ethyl]-phenyl}-6-methoxy-1,4-dihydro-2H-isoquinolin-3-one.<br>HPLC: $^At_{Ret}$ = 1.88; LC-MS: m/z 563.3 [M + H]$^+$. |
| 71ac | 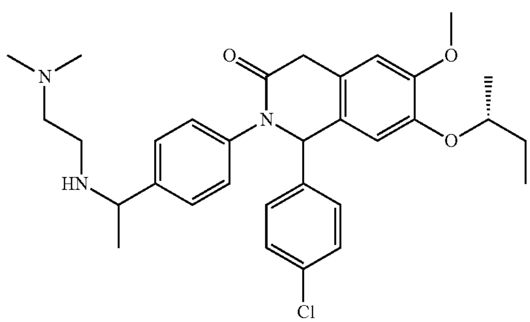 [SMILES: CC[C@@H](C)Oc1cc2c(cc1OC)CC(=O)N(c1ccc(C(C)NCCN(C)C)cc1)C2c1ccc(Cl)cc1] | 7-((R)-sec-Butoxy)-1-(4-chloro-phenyl)-2-{4-[1-(2-dimethylamino-ethylamino)-ethyl]-phenyl}-6-methoxy-1,4-dihydroxy-2H-isoquinolin-3-one.<br>HPLC: $^At_{Ret}$ = 1.72; LC-MS: m/z 550.5 [M + H]$^+$. |
| 71ad | 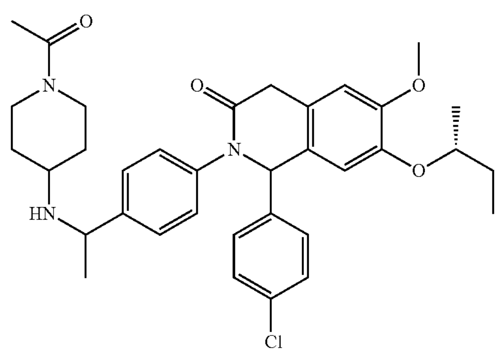 [SMILES: CC[C@@H](C)Oc1cc2c(cc1OC)CC(=O)N(c1ccc(C(C)NC3CCN(C(C)=O)CC3)cc1)C2c1ccc(Cl)cc1] | 2-{4-[1-(1-Acetyl-piperidin-4-ylamino)-ethyl]-phenyl}-7-((R)-sec-butoxy)-1-(4-chloro-phenyl)-6-methoxy-1,4-dihydro-2H-isoquinolin-3-one.<br>HPLC: $^At_{Ret}$ = 1.88; LC-MS: m/z 604.7 [M + H]$^+$. |
| 71ae | 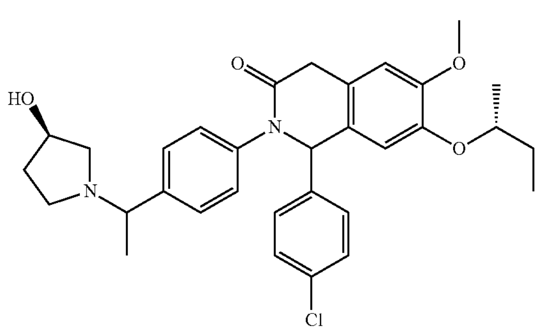 [SMILES: CC[C@@H](C)Oc1cc2c(cc1OC)CC(=O)N(c1ccc(C(C)N3CC[C@@H](O)C3)cc1)C2c1ccc(Cl)cc1] | 7-((R)-sec-Butoxy)-1-(4-chloro-phenyl)-2-{4-[1-((R)-3-hydroxy-pyrrolidin-1-yl)-ethyl]-phenyl}-6-methoxy-1,4-dihydro-2H-isoquinolin-3-one.<br>HPLC: $^At_{Ret}$ = 1.88; LC-MS: m/z 549.5 [M + H]$^+$. |

-continued

| # | Structure | Name/HPLC/MS |
|---|---|---|
| 71af | 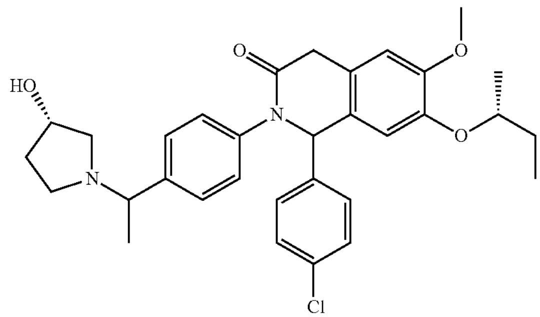 [SMILES: CC[C@@H](C)Oc1cc2c(cc1OC)CC(=O)N(c1ccc(C(C)N3CC[C@H](O)C3)cc1)C2c1ccc(Cl)cc1] | 7-((R)-sec-Butoxy)-1-(4-chloro-phenyl)-2-{4-[1-((S)-3-hydroxy-pyrrolidin-1-yl)-ethyl]-phenyl}-6-methoxy-1,4-dihydro-2H-isoquinolin-3-one.<br>HPLC: $^A t_{Ret}$ = 1.88; LC-MS: m/z 549.4 [M + H]$^+$. |
| 71ag | 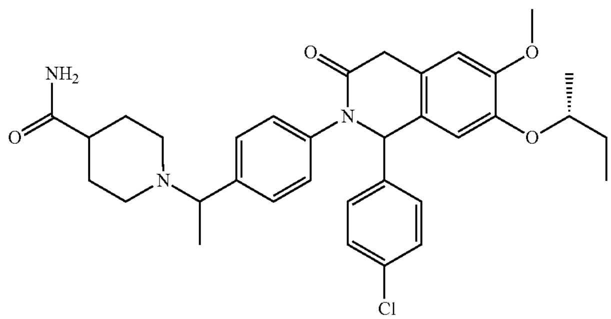 [SMILES: CC[C@@H](C)Oc1cc2c(cc1OC)CC(=O)N(c1ccc(C(C)N3CCC(C(N)=O)CC3)cc1)C2c1ccc(Cl)cc1] | 1-(1-{4-[7-((R)-sec-Butoxy)-1-(4-chloro-phenyl)-6-methoxy-3-oxo-3,4-dihydro-1H-isoquinolin-2-yl]-phenyl}-ethyl)-piperidine-4-carboxylic acid amide.<br>HPLC: $^A t_{Ret}$ = 1.87; LC-MS: m/z 590.4 [M + H]$^+$. |
| 71ah | 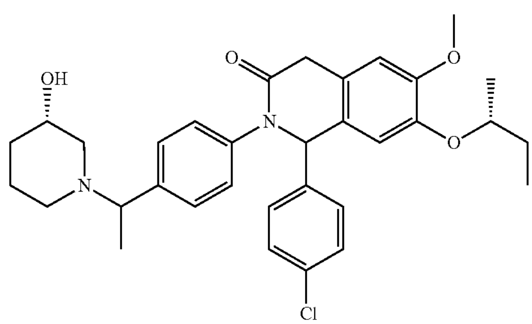 [SMILES: CC[C@@H](C)Oc1cc2c(cc1OC)CC(=O)N(c1ccc(C(C)N3CCC[C@H](O)C3)cc1)C2c1ccc(Cl)cc1] | 7-((R)-sec-Butoxy)-1-(4-chloro-phenyl)-2-{4-[1-((S)-3-hydroxy-piperidin-1-yl)-ethyl]-phenyl}-6-methoxy-1,4-dihydro-2H-isoquinolin-3-one.<br>HPLC: $^A t_{Ret}$ = 1.90; LC-MS: m/z 563.4 [M + H]$^+$. |
| 71ai | 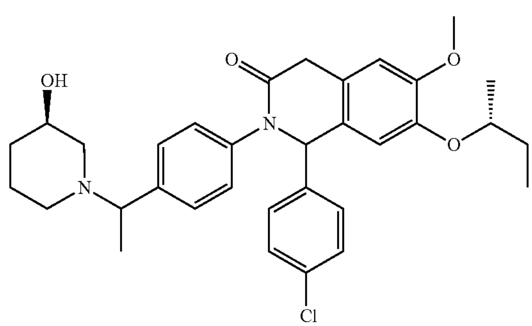 [SMILES: CC[C@@H](C)Oc1cc2c(cc1OC)CC(=O)N(c1ccc(C(C)N3CCC[C@@H](O)C3)cc1)C2c1ccc(Cl)cc1] | 7-((R)-sec-Butoxy)-1-(4-chloro-phenyl)-2-{4-[1-((R)-3-hydroxy-piperidin-1-yl)-ethyl]-phenyl}-6-methoxy-1,4-dihydro-2H-isoquinolin-3-one.<br>HPLC: $^A t_{Ret}$ = 1.91; LC-MS: m/z 563.3 [M + H]$^+$. |
| 71aj | 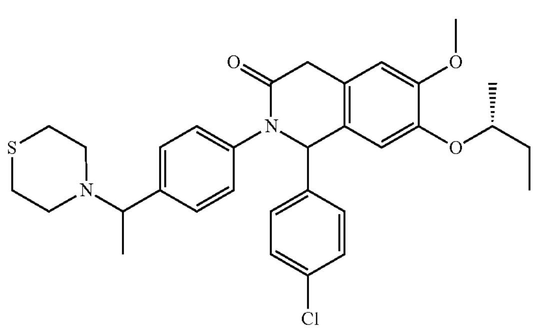 [SMILES: CC[C@@H](C)Oc1cc2c(cc1OC)CC(=O)N(c1ccc(C(C)N3CCSCC3)cc1)C2c1ccc(Cl)cc1] | 7-((R)-sec-Butoxy)-1-(4-chloro-phenyl)-6-methoxy-2-[4-(1-thiomorpholin-4-yl-ethyl)-phenyl]-1,4-dihydro-2H-isoquinolin-3-one.<br>HPLC: $^A t_{Ret}$ = 1.99; LC-MS: m/z 565.3 [M + H]$^+$. |

| # | Structure | Name/HPLC/MS |
|---|---|---|
| 71ak | 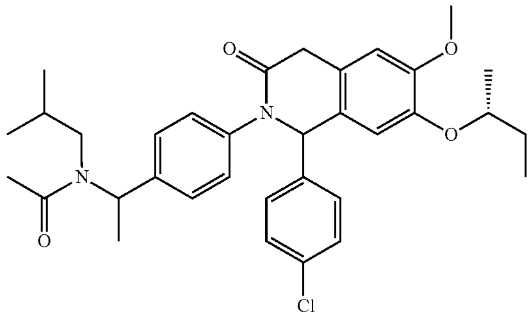 [SMILES: CC[C@@H](C)Oc1cc2c(cc1OC)CC(=O)N(c1ccc(C(C)N(CC(C)C)C(C)=O)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-isobutyl-acetamide.<br>HPLC: $^A t_{Ret}$ = 2.83; LC-MS: m/z 577.3 [M + H]$^+$. |
| 71al | 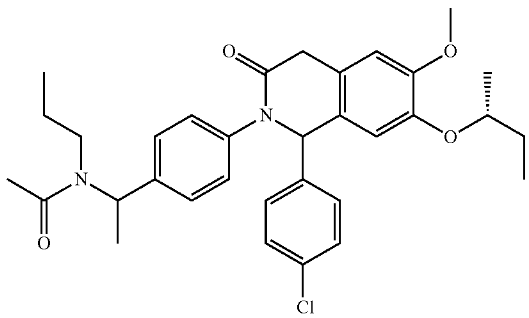 [SMILES: CCCN(C(C)=O)C(C)c1ccc(N2C(=O)Cc3cc(OC)c(O[C@H](C)CC)cc3C2c2ccc(Cl)cc2)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-propyl-acetamide.<br>HPLC: $^A t_{Ret}$ = 2.71; LC-MS: m/z 563.3 [M + H]$^+$. |
| 71am | 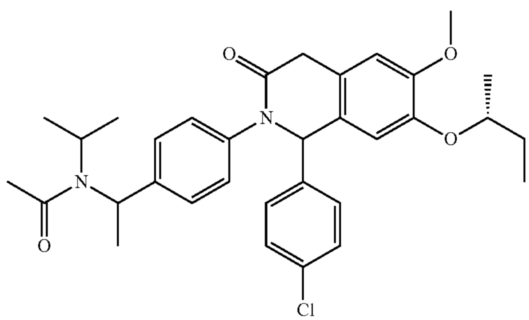 [SMILES: CC[C@@H](C)Oc1cc2c(cc1OC)CC(=O)N(c1ccc(C(C)N(C(C)=O)C(C)C)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-isopropyl-acetamide.<br>HPLC: $^A t_{Ret}$ = 2.71; LC-MS: m/z 563.4 [M + H]$^+$. |
| 71an | 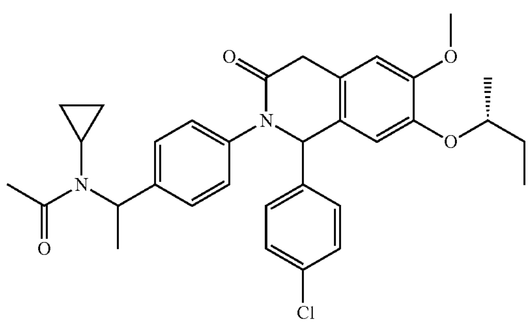 [SMILES: CC[C@@H](C)Oc1cc2c(cc1OC)CC(=O)N(c1ccc(C(C)N(C(C)=O)C3CC3)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-cyclopropyl-acetamide.<br>HPLC: $^A t_{Ret}$ = 2.69; LC-MS: m/z 561.4 [M + H]$^+$. |
| 71ao | 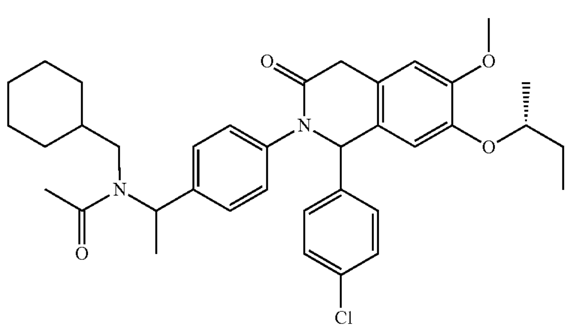 [SMILES: CC[C@@H](C)Oc1cc2c(cc1OC)CC(=O)N(c1ccc(C(C)N(CC3CCCCC3)C(C)=O)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-cyclohexylmethyl-acetamide.<br>HPLC: $^A t_{Ret}$ = 3.13; LC-MS: m/z 617.5 [M + H]$^+$. |

-continued

| # | Structure | Name/HPLC/MS |
|---|---|---|
| 71ap | 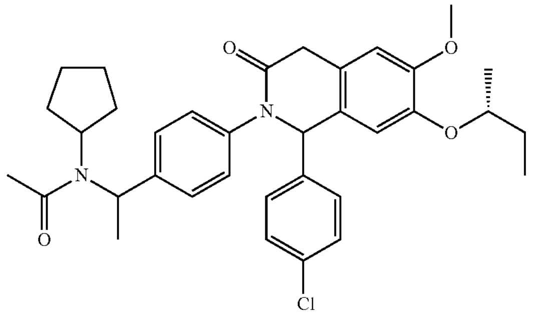 [SMILES: CC[C@@H](C)Oc1cc2c(cc1OC)CC(=O)N(c1ccc(C(C)N(C(C)=O)C3CCCC3)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-cyclopentyl-acetamide.<br>HPLC: $^A t_{Ret}$ = 2.90; LC-MS: m/z 589.4 [M + H]$^+$. |
| 71aq | 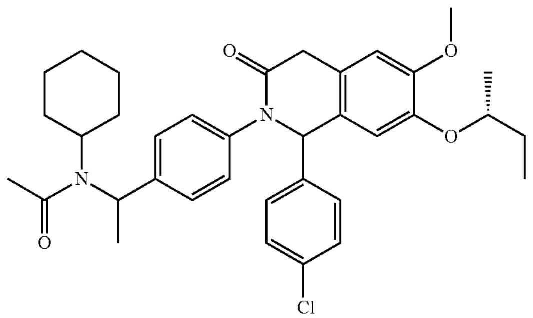 [SMILES: CC[C@@H](C)Oc1cc2c(cc1OC)CC(=O)N(c1ccc(C(C)N(C(C)=O)C3CCCCC3)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-cyclohexyl-acetamide.<br>HPLC: $^A t_{Ret}$ = 3.02; LC-MS: m/z 603.3 [M + H]$^+$. |
| 71ar | 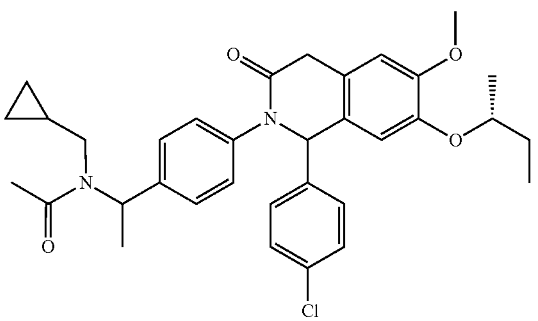 [SMILES: CC[C@@H](C)Oc1cc2c(cc1OC)CC(=O)N(c1ccc(C(C)N(CC3CC3)C(C)=O)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-cyclopropylmethyl-acetamide.<br>HPLC: $^A t_{Ret}$ = 2.75; LC-MS: m/z 575.3 [M + H]$^+$. |
| 71as | 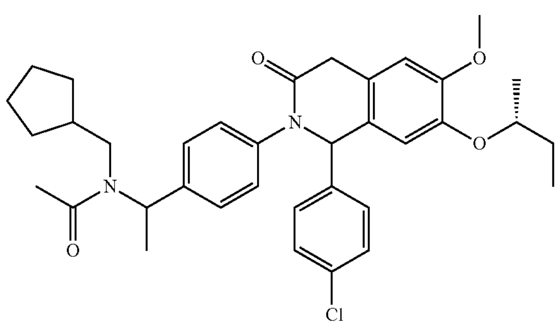 [SMILES: CC[C@@H](C)Oc1cc2c(cc1OC)CC(=O)N(c1ccc(C(C)N(CC3CCCC3)C(C)=O)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-cyclopentylmethyl-acetamide.<br>HPLC: $^A t_{Ret}$ = 3.03; LC-MS: m/z 603.6 [M + H]$^+$. |
| 71at | 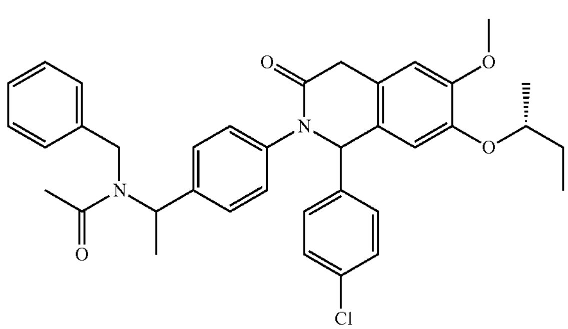 [SMILES: CC[C@@H](C)Oc1cc2c(cc1OC)CC(=O)N(c1ccc(C(C)N(Cc3ccccc3)C(C)=O)cc1)C2c1ccc(Cl)cc1] | N-Benzyl-N-(1-{4-[7-((R)-sec-butoxy)-1-(4-chloro-phenyl)-6-methoxy-3-oxo-3,4-dihydro-1H-isoquinolin-2-yl]-phenyl}-ethyl)-acetamide.<br>HPLC: $^A t_{Ret}$ = 2.87; LC-MS: m/z 611.5 [M + H]$^+$. |

| # | Structure | Name/HPLC/MS |
|---|---|---|
| 71au | 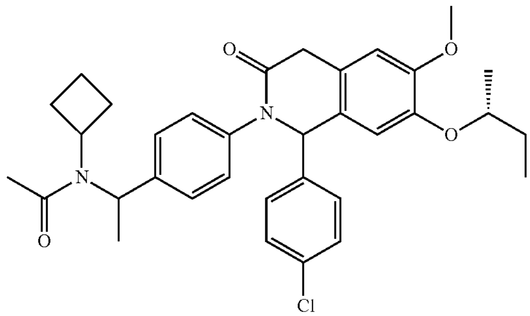 [SMILES: CC[C@@H](C)Oc1cc2c(cc1OC)CC(=O)N(c1ccc(C(C)N(C(C)=O)C3CCC3)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-cyclobutyl-acetamide.<br>HPLC: $^A t_{Ret}$ = 2.81; LC-MS: m/z 575.3 [M + H]$^+$. |
| 71av | 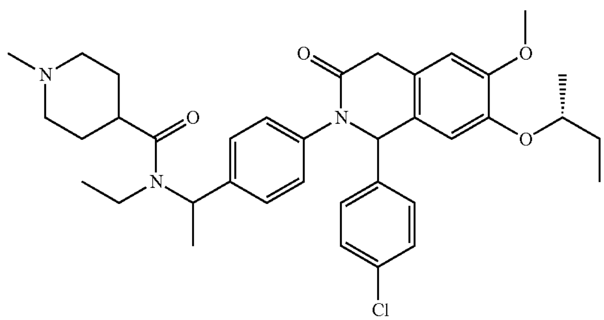 [SMILES: CC[C@@H](C)Oc1cc2c(cc1OC)CC(=O)N(c1ccc(C(C)N(CC)C(=O)C3CCN(C)CC3)cc1)C2c1ccc(Cl)cc1] | 1-Methyl-piperidine-4-carboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A t_{Ret}$ = 2.00; LC-MS: m/z 632.7 [M + H]$^+$. |
| 71aw | 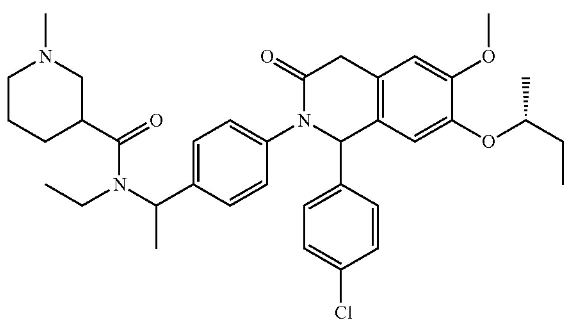 [SMILES: CC[C@@H](C)Oc1cc2c(cc1OC)CC(=O)N(c1ccc(C(C)N(CC)C(=O)C3CCCN(C)C3)cc1)C2c1ccc(Cl)cc1] | 1-Methyl-piperidine-3-carboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A t_{Ret}$ = 2.05; LC-MS: m/z 632.7 [M + H]$^+$. |
| 71ax | 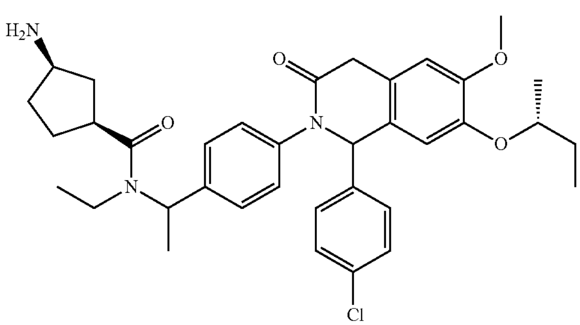 [SMILES: CC[C@@H](C)Oc1cc2c(cc1OC)CC(=O)N(c1ccc(C(C)N(CC)C(=O)[C@H]3CC[C@@H](N)C3)cc1)C2c1ccc(Cl)cc1] | (1S,3R)-3-Amino-cyclopentanecarboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A t_{Ret}$ = 2.08; LC-MS: m/z 618.7 [M + H]$^+$. |
| 71ay | 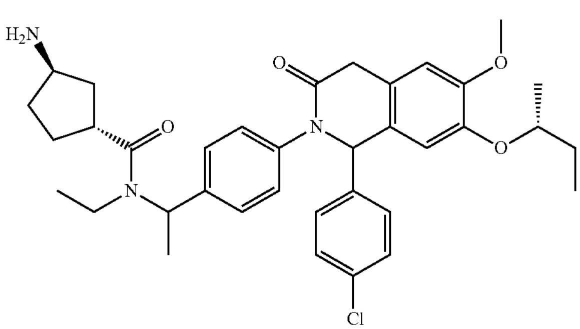 [SMILES: CC[C@@H](C)Oc1cc2c(cc1OC)CC(=O)N(c1ccc(C(C)N(CC)C(=O)[C@@H]3CC[C@@H](N)C3)cc1)C2c1ccc(Cl)cc1] | (1R,3R)-3-Amino-cyclopentanecarboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A t_{Ret}$ = 2.02; LC-MS: m/z 618.7 [M + H]$^+$. |

-continued

| # | Structure | Name/HPLC/MS |
|---|---|---|
| 71az | 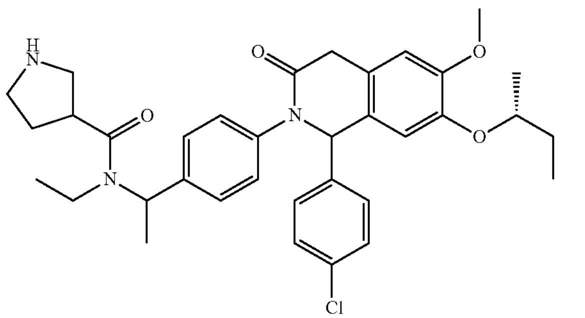 [SMILES: CC[C@@H](C)Oc1cc2c(cc1OC)CC(=O)N(c1ccc(C(C)N(CC)C(=O)C3CCNC3)cc1)C2c1ccc(Cl)cc1] | Pyrrolidine-3-carboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A t_{Ret}$ = 2.01; LC-MS: m/z 604.6 [M + H]$^+$. |
| 71ab | 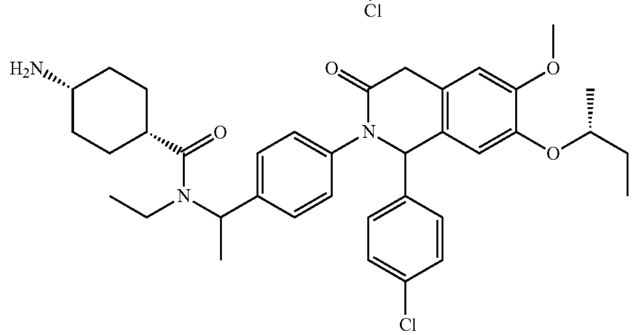 | Cis-4-Amino-cyclohexanecarboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A t_{Ret}$ = 2.08; LC-MS: m/z 632.5 [M + H]$^+$. |
| 71bb | 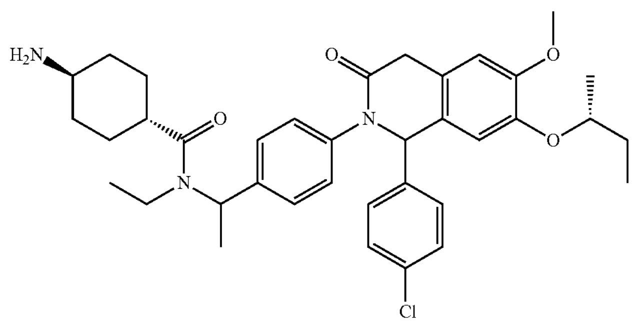 [SMILES: CC[C@@H](C)Oc1cc2c(cc1OC)CC(=O)N(c1ccc(C(C)N(CC)C(=O)[C@H]3CC[C@H](N)CC3)cc1)C2c1ccc(Cl)cc1] | Trans-4-Amino-cyclohexanecarboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A t_{Ret}$ = 2.03; LC-MS: m/z 632.5 [M + H]$^+$. |
| 71bc[(1)] | | Trans-4-Dimethylamino)-cyclohexane-carboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A t_{Ret}$ = 2.07; LC-MS: m/z 660.7 [M + H]$^+$. |
| 71bd | 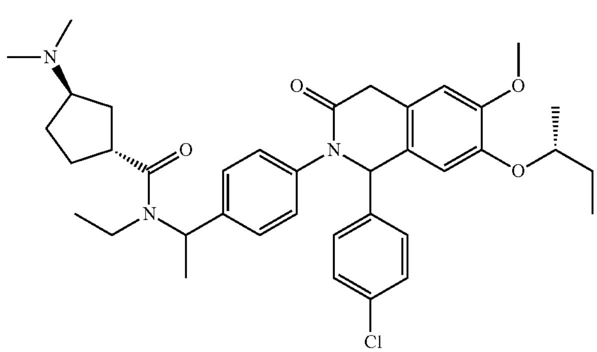 [SMILES: CC[C@@H](C)Oc1cc2c(cc1OC)CC(=O)N(c1ccc(C(C)N(CC)C(=O)[C@@H]3CC[C@@H](N(C)C)C3)cc1)C2c1ccc(Cl)cc1] | (1R,3R)-3-Dimethylamino-cyclopentanecarboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A t_{Ret}$ = 2.05; LC-MS: m/z 645.3 [M + H]$^+$. |

| # | Structure | Name/HPLC/MS |
|---|---|---|
| 71be | 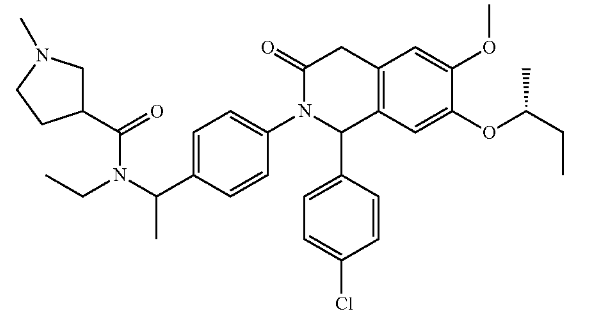 [SMILES: CC[C@@H](C)Oc1cc2c(cc1OC)CC(=O)N(c1ccc(C(C)N(CC)C(=O)C3CCN(C)C3)cc1)C2c1ccc(Cl)cc1] | 1-Methyl-pyrrolidine-3-carboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A$t$_{Ret}$ = 2.04; LC-MS: m/z 618.5 [M + H]$^+$. |
| 71bf | 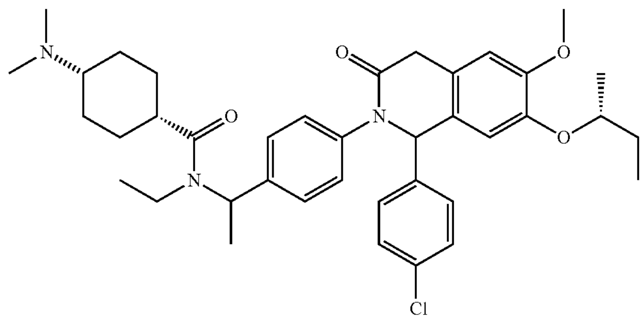 [SMILES: CC[C@@H](C)Oc1cc2c(cc1OC)CC(=O)N(c1ccc(C(C)N(CC)C(=O)[C@H]3CC[C@@H](N(C)C)CC3)cc1)C2c1ccc(Cl)cc1] | Cis-4-Dimethylamino-cyclohexanecarboxylic acid (1-{4-[7-((R)-sec-butoxy)-1-(4-chloro-phenyl)-6-methoxy-3-oxo-3,4-dihydro-1H-isoquinolin-2-yl]-phenyl}-ethyl)-ethylamide.<br>HPLC: $^A$t$_{Ret}$ = 2.12; LC-MS: m/z 660.7 [M + H]$^+$. |
| 71bg | 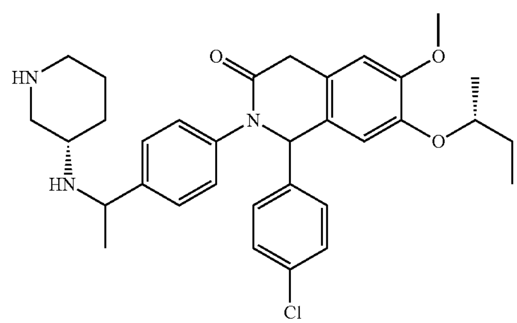 [SMILES: CC[C@@H](C)Oc1cc2c(cc1OC)CC(=O)N(c1ccc(C(C)N[C@H]3CCCNC3)cc1)C2c1ccc(Cl)cc1] | 7-((R)-sec-Butoxy)-1-(4-chloro-phenyl)-6-methoxy-2-{4-[1-((S)-piperidin-3-ylamino)-ethyl]-phenyl}-1,4-dihydro-2H-isoquinolin-3-one.<br>HPLC: $^A$t$_{Ret}$ = 1.70; LC-MS: m/z 562.2 [M + H]$^+$. |
| 71bh | 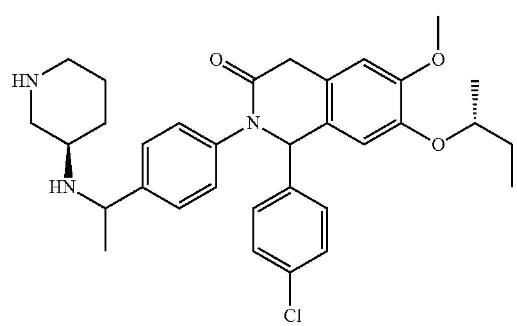 [SMILES: CC[C@@H](C)Oc1cc2c(cc1OC)CC(=O)N(c1ccc(C(C)N[C@@H]3CCCNC3)cc1)C2c1ccc(Cl)cc1] | 7-((R)-sec-Butoxy)-1-(4-chloro-phenyl)-6-methoxy-2-{4-[1-((R)-piperidin-3-ylamino)-ethyl]-phenyl}-1,4-dihydro-2H-isoquinolin-3-one.<br>HPLC: $^A$t$_{Ret}$ = 1.71; LC-MS: m/z 562.3 [M + H]$^+$. |
| 71bi | 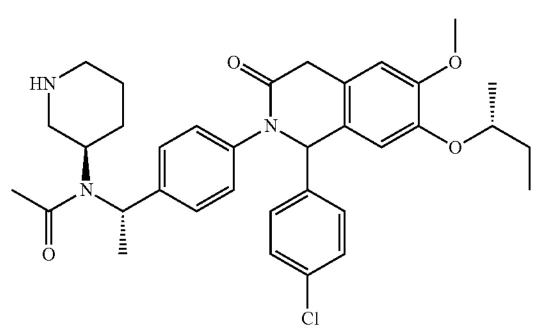 [SMILES: CC[C@@H](C)Oc1cc2c(cc1OC)CC(=O)N(c1ccc([C@H](C)N(C(C)=O)[C@@H]3CCCNC3)cc1)C2c1ccc(Cl)cc1] | N-((S)-1-{4-[7-((R)-sec-Butoxy)-1-(4-chloro-phenyl)-6-methoxy-3-oxo-3,4-dihydro-1H-isoquinolin-2-yl]-phenyl}-ethyl)-N-(R)-piperidin-3-yl-acetamide.<br>HPLC: $^A$t$_{Ret}$ = 1.93; LC-MS: m/z 604.4 [M + H]$^+$. |

-continued

| # | Structure | Name/HPLC/MS |
|---|---|---|
| 71bj | 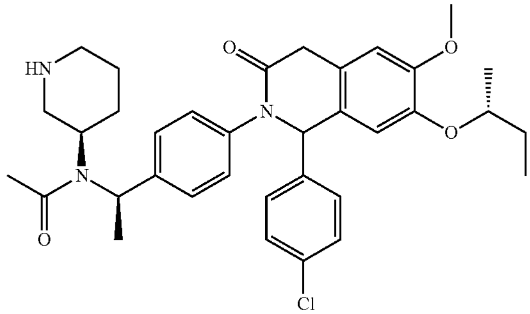 [SMILES: CC[C@@H](C)Oc1cc2c(cc1OC)CC(=O)N(c1ccc([C@@H](C)N(C(C)=O)[C@@H]3CCCNC3)cc1)C2c1ccc(Cl)cc1] | N-((R)-1-{4-[7-((R)-sec-Butoxy)-1-(4-chloro-phenyl)-6-methoxy-3-oxo-3,4-dihydro-1H-isoquinolin-2-yl]-phenyl}-ethyl)-N-(R)-piperidin-3-yl-acetamide. HPLC: $^A t_{Ret}$ = 2.02; LC-MS: m/z 604.3 [M + H]$^+$. |
| 71bk | 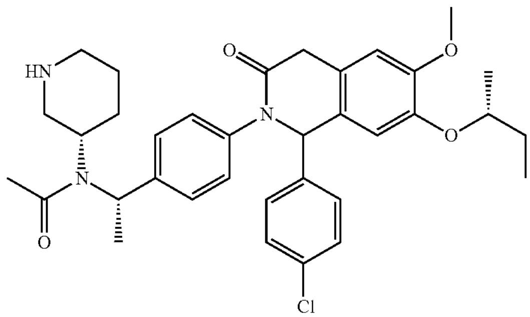 [SMILES: CC[C@@H](C)Oc1cc2c(cc1OC)CC(=O)N(c1ccc([C@H](C)N(C(C)=O)[C@H]3CCCNC3)cc1)C2c1ccc(Cl)cc1] | N-((S)-1-{4-[7-((R)-sec-Butoxy)-1-(4-chloro-phenyl)-6-methoxy-3-oxo-3,4-dihydro-1H-isoquinolin-2-yl]-phenyl}-ethyl)-N-(S)-piperidin-3-yl-acetamide. HPLC: $^A t_{Ret}$ = 2.02; LC-MS: m/z 604.3 [M + H]$^+$. |
| 71bl | 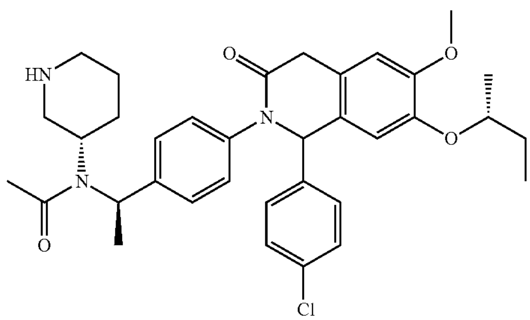 [SMILES: CC[C@@H](C)Oc1cc2c(cc1OC)CC(=O)N(c1ccc([C@@H](C)N(C(C)=O)[C@H]3CCCNC3)cc1)C2c1ccc(Cl)cc1] | N-((R)-1-{4-[7-((R)-sec-Butoxy)-1-(4-chloro-phenyl)-6-methoxy-3-oxo-3,4-dihydro-1H-isoquinolin-2-yl]-phenyl}-ethyl)-N-(S)-piperidin-3-yl-acetamide. HPLC: $^A t_{Ret}$ = 1.92; LC-MS: m/z 604.3 [M + H]$^+$. |
| 71bm | 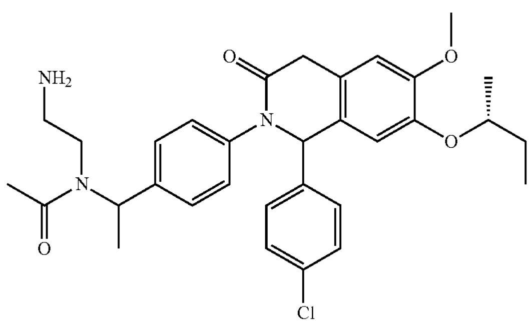 [SMILES: CC[C@@H](C)Oc1cc2c(cc1OC)CC(=O)N(c1ccc(C(C)N(CCN)C(C)=O)cc1)C2c1ccc(Cl)cc1] | N-(2-Amino-ethyl)-N-(1-{4-[7-((R)-sec-butoxy)-1-(4-chloro-phenyl)-6-methoxy-3-oxo-3,4-dihydro-1H-isoquinolin-2-yl]-phenyl}-ethyl)-acetamide. HPLC: $^A t_{Ret}$ = 1.92; LC-MS: m/z 564.5 [M + H]$^+$. |
| 71bn | 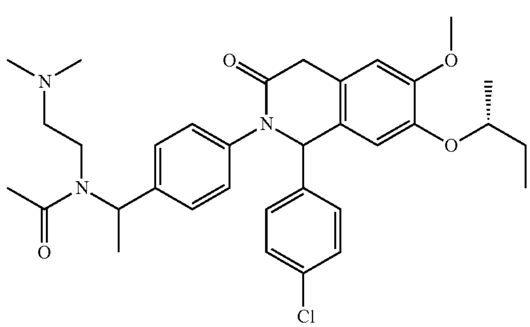 [SMILES: CC[C@@H](C)Oc1cc2c(cc1OC)CC(=O)N(c1ccc(C(C)N(CCN(C)C)C(C)=O)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-(2-dimethylamino)-ethyl)-acetamide. HPLC: $^A t_{Ret}$ = 1.94; LC-MS: m/z 592.4 [M + H]$^+$. |

| # | Structure | Name/HPLC/MS |
|---|---|---|
| 71bo | 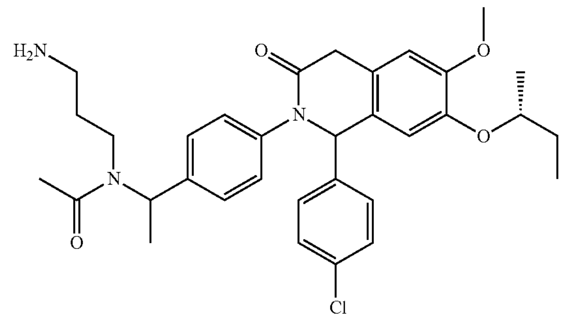 [SMILES: CC[C@@H](C)Oc1cc2c(cc1OC)CC(=O)N(c1ccc(C(C)N(CCCN)C(C)=O)cc1)C2c1ccc(Cl)cc1] | N-(3-Amino-propyl)-N-(1-{4-[7-((R)-sec-butoxy)-1-(4-chloro-phenyl)-6-methoxy-3-oxo-3,4-dihydro-1H-isoquinolin-2-yl]-phenyl}-ethyl)-acetamide.<br>HPLC: $^A t_{Ret}$ = 1.93; LC-MS: m/z 578.4 [M + H]$^+$. |
| 71bp | 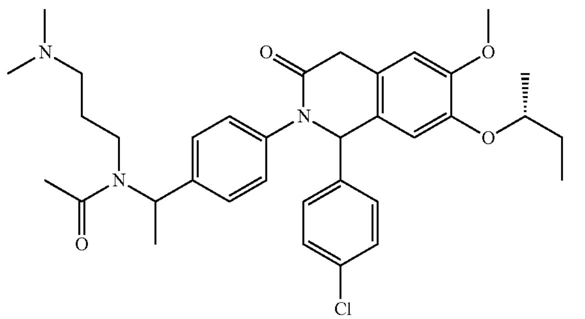 [SMILES: CC[C@@H](C)Oc1cc2c(cc1OC)CC(=O)N(c1ccc(C(C)N(CCCN(C)C)C(C)=O)cc1)C2c1ccc(Cl)cc1] | N-(1-{4-[7-((R)-sec-Butoxy)-1-(4-chloro-phenyl)-6-methoxy-3-oxo-3,4-dihydro-1H-isoquinolin-2-yl]-phenyl}-ethyl)-N-(3-dimethylamino-propyl)-acetamide.<br>HPLC: $^A t_{Ret}$ = 1.96; LC-MS: m/z 606.4 [M + H]$^+$. |
| 71bq | 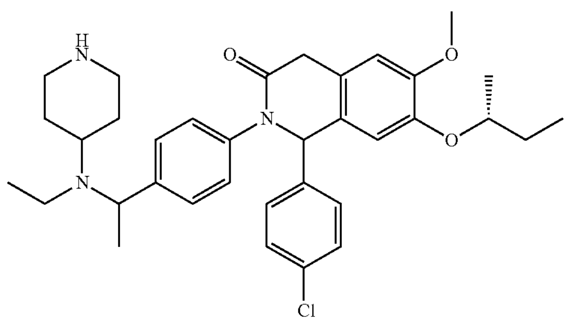 [SMILES: CC[C@@H](C)Oc1cc2c(cc1OC)CC(=O)N(c1ccc(C(C)N(CC)C3CCNCC3)cc1)C2c1ccc(Cl)cc1] | 7-((R)-sec-Butoxy)-1-(4-chloro-phenyl)-2-{4-[1-(ethyl-piperidin-4-yl-amino)-ethyl]-phenyl}-6-methoxy-1,4-dihydro-2H-isoquinolin-3-one.<br>HPLC: $^A t_{Ret}$ = 1.68; LC-MS: m/z 590.5 [M + H]$^+$. |
| 71br | 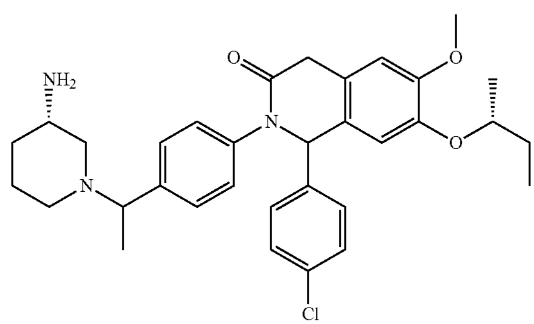 | 2-{4-[1-((S)-3-Amino-piperidin-1-yl)-ethyl]-phenyl}-7-((R)-sec-butoxy)-1-(4-chloro-phenyl)-6-methoxy-1,4-dihydro-2H-isoquinolin-3-one.<br>HPLC: $^A t_{Ret}$ = 1.72; LC-MS: m/z 562.3 [M + H]$^+$. |
| 71bs | 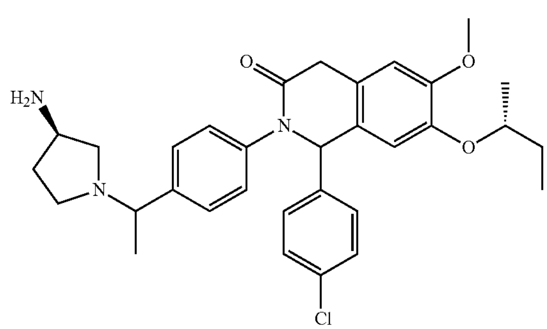 [SMILES: CC[C@@H](C)Oc1cc2c(cc1OC)CC(=O)N(c1ccc(C(C)N3CC[C@@H](N)C3)cc1)C2c1ccc(Cl)cc1] | 2-{4-[1-((R)-3-Amino-pyrrolidin-1-yl)-ethyl]-phenyl}-7-((R)-sec-butoxy)-1-(4-chloro-phenyl)-6-methoxy-1,4-dihydro-2H-isoquinolin-3-one.<br>HPLC: $^A t_{Ret}$ = 1.73; LC-MS: m/z 548.3 [M + H]$^+$. |

| # | Structure | Name/HPLC/MS |
|---|---|---|
| 71bt | 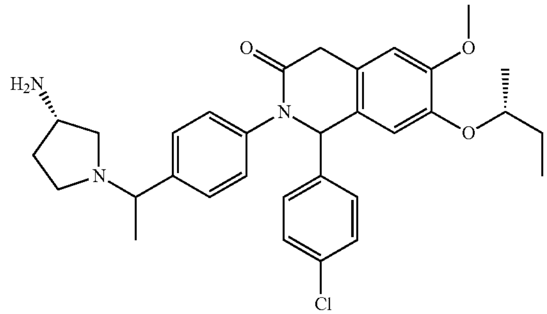 [SMILES: CC[C@@H](C)Oc1cc2c(cc1OC)CC(=O)N(c1ccc(C(C)N3CC[C@H](N)C3)cc1)C2c1ccc(Cl)cc1] | 2-{4-[1-((S)-3-Amino-pyrrolidin-1-yl)-ethyl]-phenyl}-7-((R)-sec-butoxy)-1-(4-chloro-phenyl)-6-methoxy-1,4-dihydro-2H-isoquinolin-3-one.<br>HPLC: $^A t_{Ret}$ = 1.71; LC-MS: m/z 548.3 [M + H]$^+$. |
| 71bu | 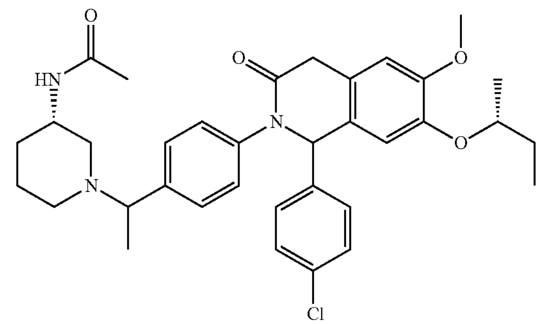 [SMILES: CC[C@@H](C)Oc1cc2c(cc1OC)CC(=O)N(c1ccc(C(C)N3CCC[C@H](NC(C)=O)C3)cc1)C2c1ccc(Cl)cc1] | N-[(S)-1-(1-{4-[7-((R)-sec-Butoxy)-1-(4-chloro-phenyl)-6-methoxy-3-oxo-3,4-dihydro-1H-isoquinolin-2-yl]-phenyl}-ethyl)-piperidin-3-yl]-acetamide.<br>HPLC: $^A t_{Ret}$ = 1.90; LC-MS: m/z 604.3 [M + H]$^+$. |
| 71bv | 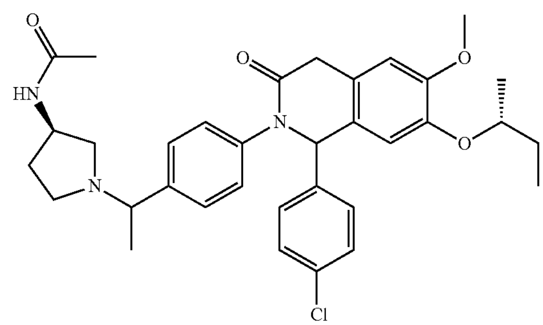 [SMILES: CC[C@@H](C)Oc1cc2c(cc1OC)CC(=O)N(c1ccc(C(C)N3CC[C@@H](NC(C)=O)C3)cc1)C2c1ccc(Cl)cc1] | N-[(R)-1-(1-{4-[7-((R)-sec-Butoxy)-1-(4-chloro-phenyl)-6-methoxy-3-oxo-3,4-dihydro-1H-isoquinolin-2-yl]-phenyl}-ethyl)-pyrrolidin-3-yl]-acetamide.<br>HPLC: $^A t_{Ret}$ = 1.88; LC-MS: m/z 590.3 [M + H]$^+$. |
| 71bw | 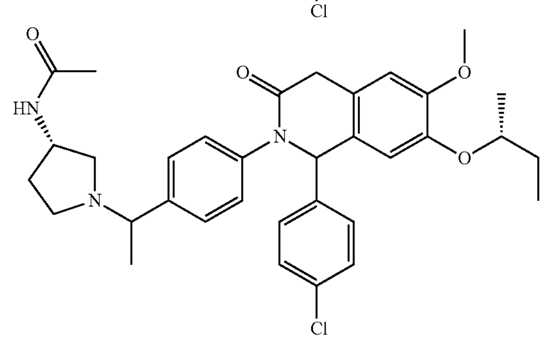 | N-[(S)-1-(1-{4-[7-((R)-sec-Butoxy)-1-(4-chloro-phenyl)-6-methoxy-3-oxo-3,4-dihydro-1H-isoquinolin-2-yl]-phenyl}-ethyl)-pyrrolidin-3-yl]-acetamide.<br>HPLC: $^A t_{Ret}$ = 1.88; LC-MS: m/z 590.3 [M + H]$^+$. |
| 71bx | 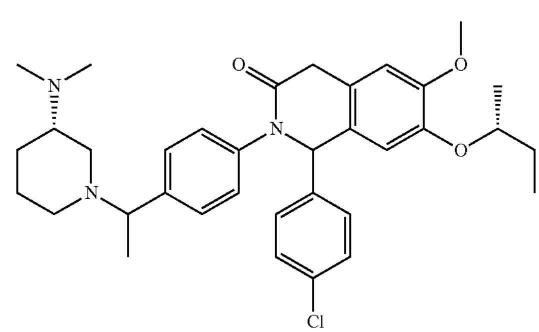 [SMILES: CC[C@@H](C)Oc1cc2c(cc1OC)CC(=O)N(c1ccc(C(C)N3CCC[C@H](N(C)C)C3)cc1)C2c1ccc(Cl)cc1] | 7-((R)-sec-Butoxy-1-(4-chloro-phenyl)-2-{4-[1-((S)-3-dimethylamino-piperidin-1-yl)-ethyl]-phenyl}-6-methoxy-1,4-dihydro-2H-isoquinolin-3-one.<br>HPLC: $^A t_{Ret}$ = 1.74; LC-MS: m/z 590.4 [M + H]$^+$. |

| # | Structure | Name/HPLC/MS |
|---|---|---|
| 71by | 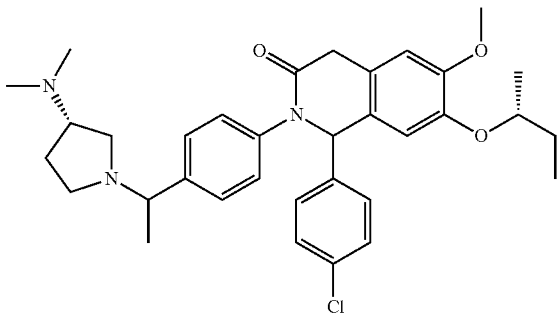 [SMILES: CC[C@@H](C)Oc1cc2c(cc1OC)CC(=O)N(c1ccc(C(C)N3CC[C@H](N(C)C)C3)cc1)C2c1ccc(Cl)cc1] | 7-((R)-sec-Butoxy)-1-(4-chloro-phenyl)-2-{4-[1-((S)-3-dimethylamino-pyrrolidin-1-yl)-ethyl]-phenyl}-6-methoxy-1,4-dihydro-2H-isoquinolin-3-one.<br>HPLC: $^A t_{Ret}$ = 1.77; LC-MS: m/z 576.4 [M + H]$^+$. |
| 71bz | 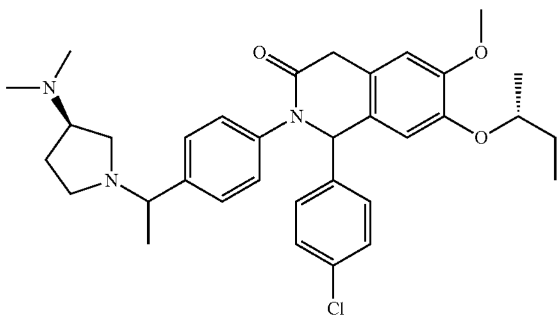 [SMILES: CC[C@@H](C)Oc1cc2c(cc1OC)CC(=O)N(c1ccc(C(C)N3CC[C@@H](N(C)C)C3)cc1)C2c1ccc(Cl)cc1] | 7-((R)-sec-Butoxy)-1-(4-chloro-phenyl)-2-{4-[1-((R)-3-dimethylamino-pyrrolidin-1-yl)-ethyl]-phenyl}-6-methoxy-1,4-dihydro-2H-isoquinolin-3-one.<br>HPLC: $^A t_{Ret}$ = 1.72; LC-MS: m/z 576.5 [M + H]$^+$. |
| 71ca | 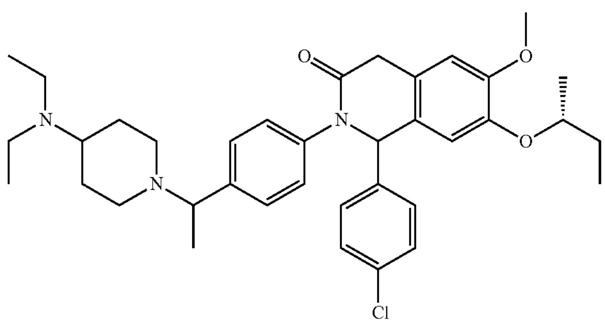 [SMILES: CC[C@@H](C)Oc1cc2c(cc1OC)CC(=O)N(c1ccc(C(C)N3CCC(N(CC)CC)CC3)cc1)C2c1ccc(Cl)cc1] | 7-((R)-sec-Butoxy)-1-(4-chloro-phenyl)-2-{4-[1-(4-diethylamino-piperidin-1-yl)-ethyl]-phenyl}-6-methoxy-1,4-dihydro-2H-isoquinolin-3-one.<br>HPLC: $^A t_{Ret}$ = 1.70; LC-MS: m/z 618.5 [M + H]$^+$. |

(1)The title compound (TFA salt, 7.9 mg, 0.01 mmol, 63%) was obtained as a colorless solid from Example before (TFA salt, 12 mg, 0.016 mmol) analogously to Example 67. Purification of the crude material was performed by reverse phase prep-HPLC (Waters system).

Example 72

7-((R)-sec-Butoxy)-1-(4-chloro-phenyl)-6-methoxy-2-{4-[1-(3-oxo-morpholin-4-yl)-ethyl]-phenyl}-1,4-dihydro-2H-isoquinolin-3-one

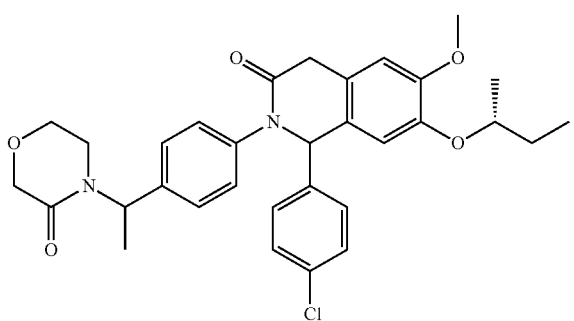 [SMILES: CC[C@@H](C)Oc1cc2c(cc1OC)CC(=O)N(c1ccc(C(C)N3CCOCC3=O)cc1)C2c1ccc(Cl)cc1]

To a solution of Intermediate 72.1 (53 mg, 0.10 mmol) and Et$_3$N (0.042 ml, 0.30 mmol) in DCM (1 ml) was added chloroacetyl chloride (0.020 ml, 0.25 mmol) at RT. The reaction mixture was stirred at RT for 1 h then evaporated to dryness. The resulting residue was dissolved in EtOH (0.5 ml) and NaOH (35% in water, 0.025 ml, 0.22 mmol) was added at RT. The suspension was well stirred for 2 h then diluted with DCM and washed with water. The organic phase was dried over Na$_2$SO$_4$, filtered and evaporated to dryness. The resulting crude material was purified by reverse phase prep-HPLC (Waters system) to yield the title compound (18.9 mg, 0.034 mmol, 33%) as a light yellow solid. HPLC: $^A t_{Ret}$=2.45 min; LC-MS: m/z 563.4 [M+H]$^+$; $^1$H NMR (400 MHz, DMSO-d): 0.83-0.96 (m, 3H), 1.12-1.25 (2 d, J=6.1, 3H, mixture of diastereoisomers), 1.40-1.48 (m, 3H), 1.48-1.72 (m, 2H), 2.75-2.86 (m, 1H), 3.23-3.36 (m, 1H), 3.61 (d, J=19.8, 1H), 3.68-3.93 (m, 5H), 4.10 (s, 2H), 4.18-4.31 (m, 1H), 5.76 (q, J=7.3, 1H), 6.11 (d, J=3.2, 1H), 6.86 (s, 1H), 7.06-7.12 (m, 1H), 7.15-7.21 (m, 2H), 7.24-7.30 (m, 2H), 7.33-7.39 (m, 4H).

Intermediate 72.1: 7-((R)-sec-Butoxy)-1-(4-chloro-phenyl)-2-{4-[1-(2-hydroxy-ethylamino)-ethyl]-phenyl}-6-methoxy-1,4-dihydro-2H-isoquinolin-3-one

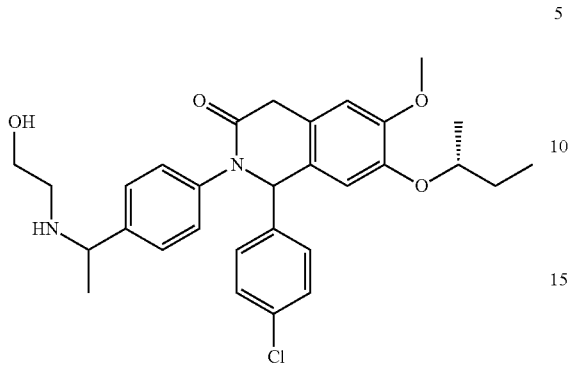

The title compound (139 mg, 0.27 mmol, 63%) was obtained as a yellow solid from Intermediate 55.2 (200 mg, 0.42 mmol) and ethanolamine (0.076 ml, 1.26 mmol) analogously to Intermediate 61.1. Purification of the crude material was performed by Combi-Flash Companion™ (Isco Inc.) column chromatography (SiO$_2$; gradient elution, DCM/MeOH 99.5:0.5→9:1). TLC: R$_F$=0.26 (DCM/MeOH 9:1); HPLC: $^A$t$_{Ret}$=1.88 min; LC-MS: m/z 523.2 [M+H]$^+$; $^1$H NMR (400 MHz, DMSO-d): 0.82-0.97 (m, 3H), 1.11-1.25 (2 d, J=6.1, 3H, mixture of diastereoisomers), 1.45-1.72 (m, 5H), 2.59-2.75 (m, 1H), 2.81-2.97 (m, 1H), 3.53-3.95 (m, 7H), 4.18-4.32 (m, 1H), 4.33-4.46 (m, 1H), 6.16 (br. s., 1H), 6.87 (s, 1H), 7.10 (d, J=6.6, 1H), 7.23-7.42 (m, 6H), 7.44-7.55 (m, 2H), 8.73-8.91 (m, 1H), 8.94-9.10 (m, 1H).

Example 73a (S)-7-((R)-sec-Butoxy)-1-(4-chloro-phenyl)-2-{4-[(trans-4-dimethylamino-cyclohexylmethyl)-methyl-amino]-phenyl}-6-methoxy-1,4-dihydro-2H-isoquinolin-3-one and Example 73b (R)-7-((R)-sec-Butoxy)-1-(4-chloro-phenyl)-2-{4-[(trans-4-dimethylamino-cyclohexylmethyl)-methyl-amino]-phenyl}-6-methoxy-1,4-dihydro-2H-isoquinolin-3-one

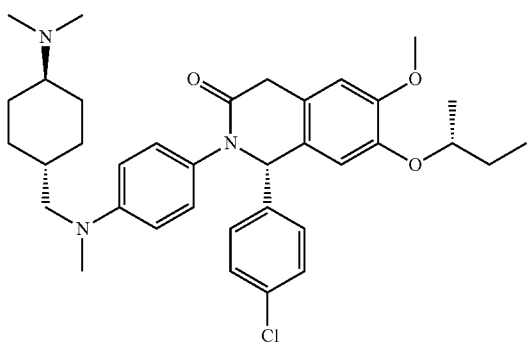

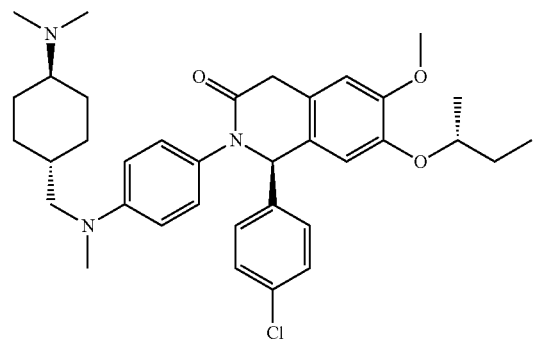

The title examples were obtained by chiral separation of the racemic Example 54bj. The chiral chromatography was performed using a Gilson HPLC system with a Chiralpak AD 500×50 mm, 20 M column, eluting with 40% EtOH+0.1% diethylamine in n-heptane with a flow rate of 60-120 ml/min.

Example 73a

HPLC: $^A$t$_{Ret}$=1.97; LC-MS: m/z 604.6 [M+H]$^+$; $^1$H NMR (500 MHz, DMSO-d): 0.86 (t, J=7.5, 3H), 0.94-1.06 (m, 2H), 1.18 (d, J=6.1, 3H), 1.22-1.34 (m, 2H), 1.43-1.67 (m, 3H), 1.71-1.80 (m, 2H), 1.85-1.94 (m, 2H), 2.54 (br. s., 6H), 2.76-2.90 (m, 1H), 2.87 (s, 3H), 3.11 (d, J=7.0, 2H), 3.56 (d, J=19.8, 1H), 3.72 (s, 3H), 3.88 (d, J=19.8, 1H), 4.17-4.24 (m, 1H), 5.94 (s, 1H), 6.52-6.59 (m, 2H), 6.82 (s, 1H), 6.86-6.91 (m, 2H), 7.01 (s, 1H), 7.34 (s, 4H).

Example 73b

HPLC: $^A$t$_{Ret}$=1.98; LC-MS: m/z 604.6 [M+H]$^+$; $^1$H NMR (500 MHz, DMSO-d$_6$): 0.90 (t, J=7.5, 3H), 0.97-1.07 (m, 2H), 1.11 (d, J=6.0, 3H), 1.30-1.42 (m, 2H), 1.49-1.69 (m, 3H), 1.73-1.82 (m, 2H), 1.91-1.98 (m, 2H), 2.66-2.72 (2 s, 6H), 2.87 (s, 3H), 2.89-2.96 (m, 1H), 3.12 (d, J=7.0, 2H), 3.55 (d, J=19.8, 1H), 3.72 (s, 3H), 3.88 (d, J=19.8, 1H), 4.21-4.29 (m, 1H), 5.93 (s, 1H), 6.53-6.60 (m, 2H), 6.82 (s, 1H), 6.87-6.92 (m, 2H), 7.02 (s, 1H), 7.34 (s, 4H).

Example 74

Compounds 74aa to 74bb were obtained analogously to Example 73 by chiral column chromatography performed on the corresponding racemic mixture.

| # | Structure | Name/HPLC/MS |
|---|---|---|
| 74aa | 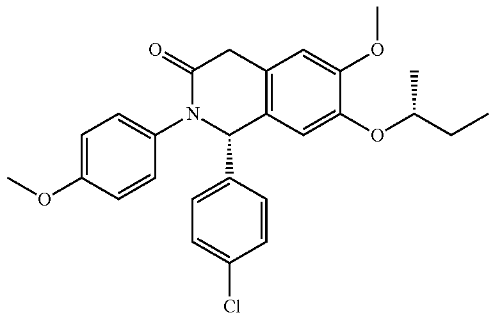 [SMILES: CC[C@@H](C)Oc1cc2c(cc1OC)CC(=O)N(c1ccc(OC)cc1)[C@H]2c1ccc(Cl)cc1] | (S)-7-((R)-sec-Butoxy)-1-(4-chloro-phenyl)-6-methoxy-2-(4-methoxy-phenyl)-1,4-dihydro-2H-isoquinolin-3-one.<br>HPLC: $^Bt_{Ret}$ = 2.78; API-MS: m/z 466.2 [M + H]$^+$. |
| 74ab | 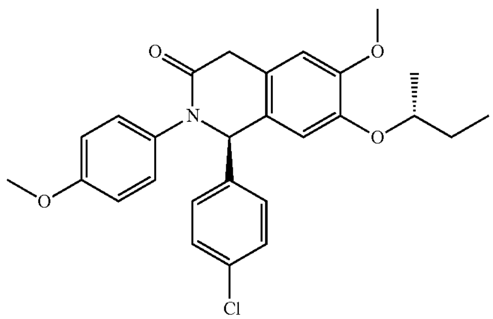 [SMILES: CC[C@@H](C)Oc1cc2c(cc1OC)CC(=O)N(c1ccc(OC)cc1)[C@@H]2c1ccc(Cl)cc1] | (R)-7-((R)-sec-Butoxy)-1-(4-chloro-phenyl)-6-methoxy-2-(4-methoxy-phenyl)-1,4-dihydro-2H-isoquinolin-3-one.<br>HPLC: $^Bt_{Ret}$ = 2.78; API-MS: m/z 466.2 [M + H]$^+$. |
| 74ac | 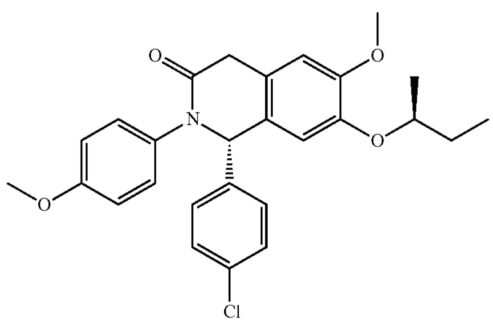 [SMILES: CC[C@H](C)Oc1cc2c(cc1OC)CC(=O)N(c1ccc(OC)cc1)[C@H]2c1ccc(Cl)cc1] | (S)-7-((S)-sec-Butoxy)-1-(4-chloro-phenyl)-6-methoxy-2-(4-methoxy-phenyl)-1,4-dihydro-2H-isoquinolin-3-one.<br>HPLC: $^Bt_{Ret}$ = 2.78; API-MS: m/z 466.2 [M + H]$^+$. |
| 74ad | 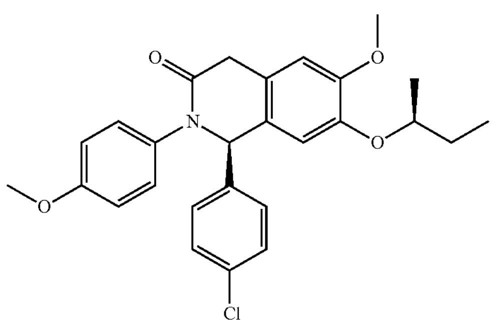 [SMILES: CC[C@H](C)Oc1cc2c(cc1OC)CC(=O)N(c1ccc(OC)cc1)[C@@H]2c1ccc(Cl)cc1] | (R)-7-((S)-sec-Butoxy)-1-(4-chloro-phenyl)-6-methoxy-2-(4-methoxy-phenyl)-1,4-dihydro-2H-isoquinolin-3-one.<br>HPLC: $^Bt_{Ret}$ = 2.78; API-MS: m/z 466.2 [M + H]$^+$. |
| 74ae | 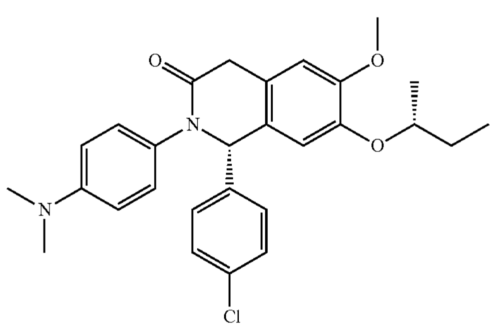 | (S)-7-((R)-sec-Butoxy)-1-(4-chloro-phenyl)-2-(4-dimethylamino-phenyl)-6-methoxy-1,4-dihydro-2H-isoquinolin-3-one.<br>HPLC: $^At_{Ret}$ = 2.03 min; API-MS: m/z 480.6 [M + H]$^+$. |

-continued

| # | Structure | Name/HPLC/MS |
|---|---|---|
| 74af | 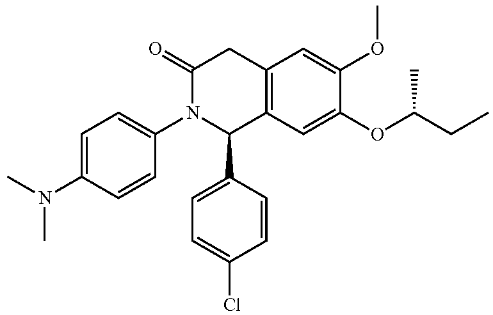 [SMILES: CC[C@@H](C)Oc1cc2c(cc1OC)CC(=O)N(c1ccc(N(C)C)cc1)[C@@H]2c1ccc(Cl)cc1] | (R)-7-((R)-sec-Butoxy)-1-(4-chloro-phenyl)-2-(4-dimethylamino-phenyl)-6-methoxy-1,4-dihydro-2H-isoquinolin-3-one.<br>HPLC: $^{A}t_{Ret}$ = 2.03 min; API-MS: m/z 480.6 [M + H]$^{+}$. |
| 74ag | 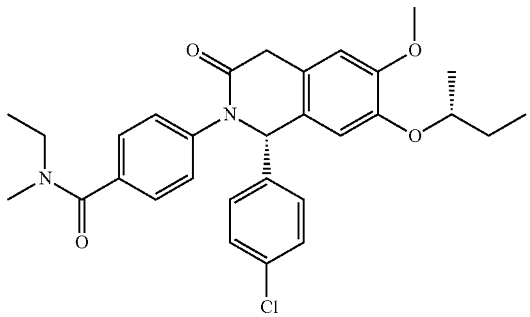 [SMILES: CC[C@@H](C)Oc1cc2c(cc1OC)CC(=O)N(c1ccc(C(=O)N(C)CC)cc1)[C@H]2c1ccc(Cl)cc1] | 4-[(S)-7-((R)-sec-Butoxy)-1-(4-chloro-phenyl)-6-methoxy-3-oxo-3,4-dihydro-1H-isoquinolin-2-yl]-N-ethyl-N-methyl-benzamide.<br>HPLC: $^{A}t_{Ret}$ = 2.47; LC-MS: m/z 521.4 [M + H]$^{+}$. |
| 74ah | 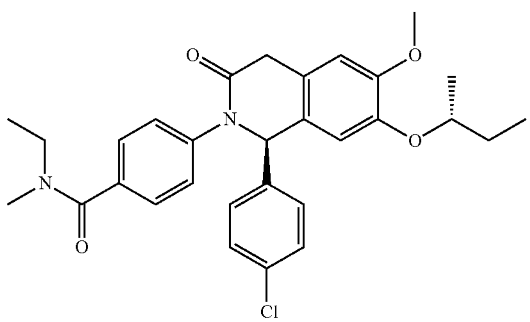 [SMILES: CC[C@@H](C)Oc1cc2c(cc1OC)CC(=O)N(c1ccc(C(=O)N(C)CC)cc1)[C@@H]2c1ccc(Cl)cc1] | 4-[(R)-7-((R)-sec-Butoxy)-1-(4-chloro-phenyl)-6-methoxy-3-oxo-3,4-dihydro-1H-isoquinolin-2-yl]-N-ethyl-N-methyl-benzamide.<br>HPLC: $^{A}t_{Ret}$ = 2.46; LC-MS: m/z 521.3 [M + H]$^{+}$. |
| 74ai | 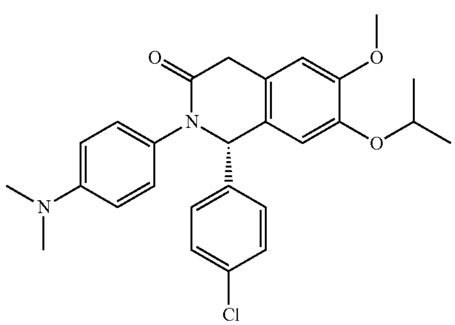 [SMILES: COc1cc2c(cc1OC(C)C)[C@H](c1ccc(Cl)cc1)N(c1ccc(N(C)C)cc1)C(=O)C2] | (S)-1-(4-Chloro-phenyl)-2-(4-dimethylamino-phenyl)-7-isopropoxy-6-methoxy-1,4-dihydro-2H-isoquinolin-3-one.<br>HPLC: $^{A}t_{Ret}$ = 1.87; LC-MS: m/z 465.3 [M + H]$^{+}$. |
| 74aj | 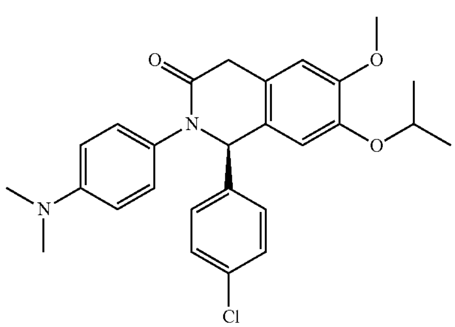 [SMILES: COc1cc2c(cc1OC(C)C)[C@@H](c1ccc(Cl)cc1)N(c1ccc(N(C)C)cc1)C(=O)C2] | (R)-1-(4-Chloro-phenyl)-2-(4-dimethylamino-phenyl)-7-isopropoxy-6-methoxy-1,4-dihydro-2H-isoquinolin-3-one.<br>HPLC: $^{A}t_{Ret}$ = 1.87; LC-MS: m/z 465.3[M + H]$^{+}$. |

-continued

| # | Structure | Name/HPLC/MS |
|---|---|---|
| 74ak | 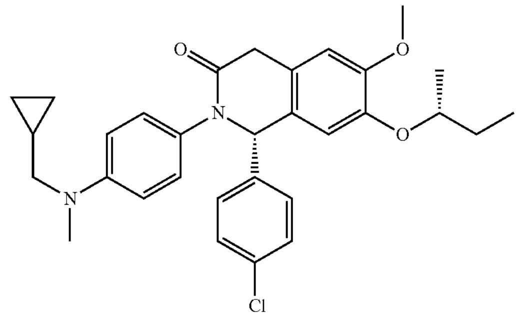 [SMILES: CC[C@@H](C)Oc1cc2c(cc1OC)CC(=O)N(c1ccc(N(C)CC3CC3)cc1)[C@H]2c1ccc(Cl)cc1] | (S)-7-((R)-sec-Butoxy)-1-(4-chloro-phenyl)-2-[4-(cyclopropylmethyl-methyl-amino)-phenyl]-6-methoxy-1,4-dihydro-2H-isoquinolin-3-one.<br>HPLC: $^{A}t_{Ret}$ = 2.09; LC-MS: m/z 519.4 [M + H]$^+$. |
| 74al | 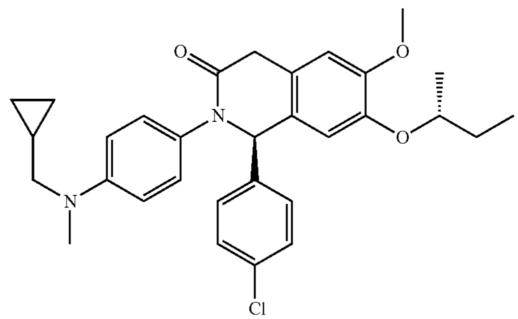 [SMILES: CC[C@@H](C)Oc1cc2c(cc1OC)CC(=O)N(c1ccc(N(C)CC3CC3)cc1)[C@@H]2c1ccc(Cl)cc1] | (R)-7-((R)-sec-Butoxy)-1-(4-chloro-phenyl)-2-[4-(cyclopropylmethyl-methyl-amino)-phenyl]-6-methoxy-1,4-dihydro-2H-isoquinolin-3-one.<br>HPLC: $^{A}t_{Ret}$ = 2.09; LC-MS: m/z 519.4 [M + H]$^+$. |
| 74am | 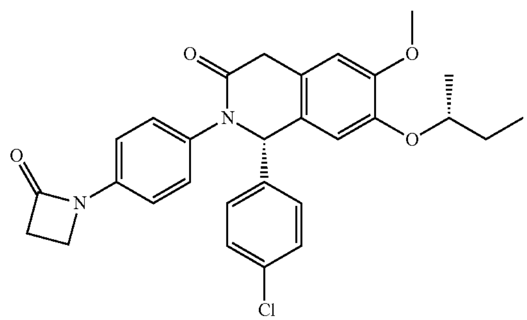 [SMILES: CC[C@@H](C)Oc1cc2c(cc1OC)CC(=O)N(c1ccc(N3CCC3=O)cc1)[C@H]2c1ccc(Cl)cc1] | (S)-7-((R)-sec-Butoxy)-1-(4-chloro-phenyl)-6-methoxy-2-[4-(2-oxo-azetidin-1-yl)-phenyl]-1,4-dihydro-2H-isoquinolin-3-one.<br>HPLC: $^{A}t_{Ret}$ = 2.49; LC-MS: m/z 505.4 [M + H]$^+$. |
| 74an | 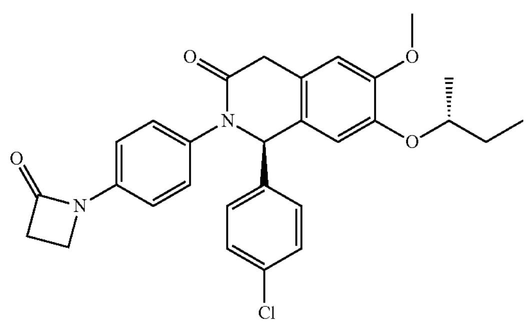 [SMILES: CC[C@@H](C)Oc1cc2c(cc1OC)CC(=O)N(c1ccc(N3CCC3=O)cc1)[C@@H]2c1ccc(Cl)cc1] | (R)-7-((R)-sec-Butoxy)-1-(4-chloro-phenyl)-6-methoxy-2-[4-(2-oxo-azetidin-1-yl)-phenyl]-1,4-dihydro-2H-isoquinolin-3-one.<br>HPLC: $^{A}t_{Ret}$ = 2.49; LC-MS: m/z 505.5 [M + H]$^+$. |
| 74ao | 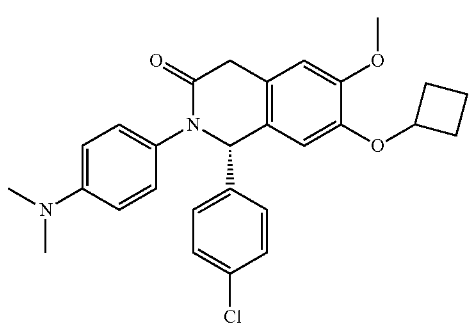 | (S)-1-(4-Chloro-phenyl)-7-cyclobutoxy-2-(4-dimethylamino-phenyl)-6-methoxy-1,4-dihydro-2H-isoquinolin-3-one.<br>HPLC: $^{A}t_{Ret}$ = 1.94; LC-MS: m/z 477.3 [M + H]$^+$. |

| # | Structure | Name/HPLC/MS |
|---|---|---|
| 74ap | 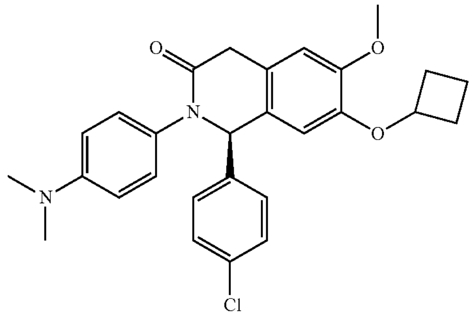 [SMILES: COc1cc2c(cc1OC1CCC1)[C@@H](c1ccc(Cl)cc1)N(c1ccc(N(C)C)cc1)C(=O)C2] | (R)-1-(4-Chloro-phenyl)-7-cyclobutoxy)-2-(4-dimethylamino-phenyl)-6-methoxy-1,4-dihydro-2H-isoquinolin-3-one.<br>HPLC: $^A t_{Ret}$ = 1.94; LC-MS: m/z 477.3 [M + H]$^+$. |
| 74aq | 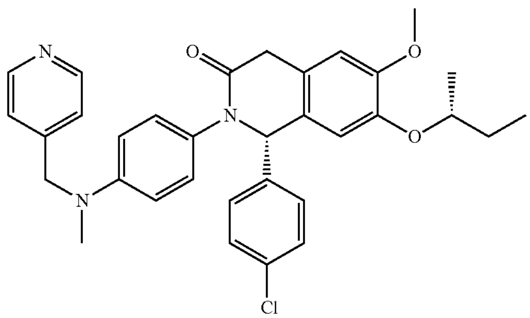 | (S)-7-((R)-sec-Butoxy)-1-(4-chloro-phenyl)-6-methoxy-2-[4-(methyl-pyridin-4-ylmethyl-amino)-phenyl]-1,4-dihydro-2H-isoquinolin-3-one.<br>HPLC: $^A t_{Ret}$ = 2.05; LC-MS: m/z 556.2 [M + H]$^+$. |
| 74ar | 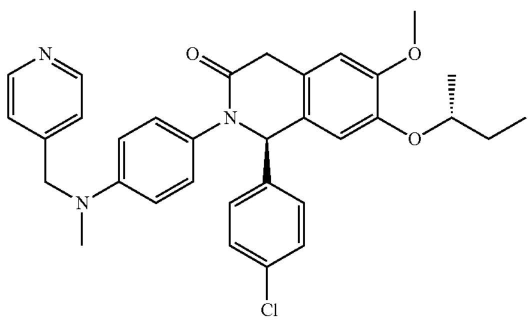 [SMILES: CC[C@@H](C)Oc1cc2c(cc1OC)CC(=O)N(c1ccc(N(C)Cc3ccncc3)cc1)[C@@H]2c1ccc(Cl)cc1] | (R)-7-((R)-sec-Butoxy)-1-(4-chloro-phenyl)-6-methoxy-2-[4-(methyl-pyridin-4-ylmethyl-amino)-phenyl]-1,4-dihydro-2H-isoquinolin-3-one.<br>HPLC: $^A t_{Ret}$ = 2.06; LC-MS: m/z 556.2 [M + H]$^+$. |
| 74as | 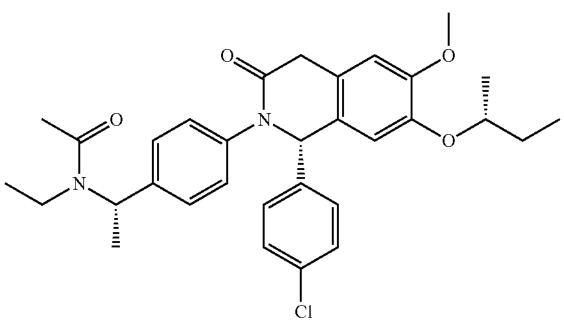 [SMILES: CC[C@@H](C)Oc1cc2c(cc1OC)CC(=O)N(c1ccc([C@H](C)N(CC)C(C)=O)cc1)[C@H]2c1ccc(Cl)cc1] | N-((S)-1-{4-[(S)-7-((R)-sec-Butoxy)-1-(4-chloro-phenyl)-6-methoxy-3-oxo-3,4-dihydro-1H-isoquinolin-2-yl]-phenyl}-ethyl)-N-ethyl-acetamide.<br>HPLC: $^A t_{Ret}$ = 2.57; LC-MS: m/z 549.6 [M + H]$^+$. |
| 74at | 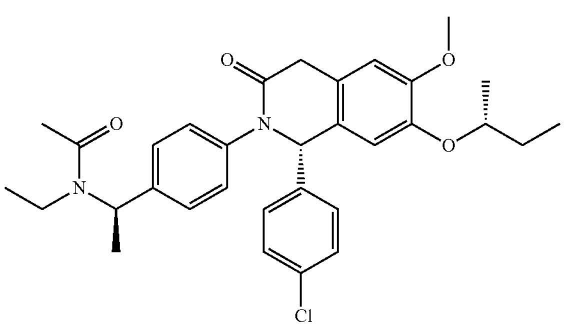 [SMILES: CC[C@@H](C)Oc1cc2c(cc1OC)CC(=O)N(c1ccc([C@@H](C)N(CC)C(C)=O)cc1)[C@H]2c1ccc(Cl)cc1] | N-((R)-1-{4-[(S)-7-((R)-sec-Butoxy)-1-(4-chloro-phenyl)-6-methoxy-3-oxo-3,4-dihydro-1H-isoquinolin-2-yl]-phenyl}-ethyl)-N-ethyl-acetamide.<br>HPLC: $^A t_{Ret}$ = 2.57; LC-MS: m/z 549.4 [M + H]$^+$. |

-continued

| # | Structure | Name/HPLC/MS |
|---|---|---|
| 74au | 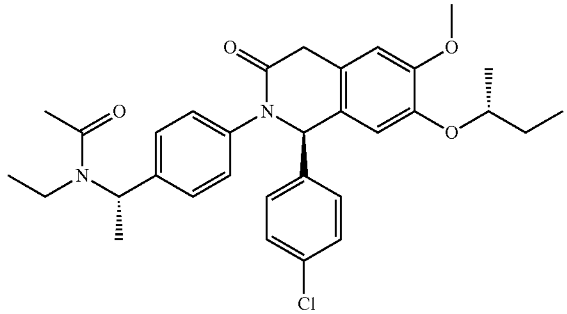 [SMILES: CC[C@@H](C)Oc1cc2c(cc1OC)CC(=O)N(c1ccc([C@H](C)N(CC)C(C)=O)cc1)[C@@H]2c1ccc(Cl)cc1] | N-((S)-1-{4-[(R)-7-((R)-sec-Butoxy)-1-(4-chloro-phenyl)-6-methoxy-3-oxo-3,4-dihydro-1H-isoquinolin-2-yl]-phenyl}-ethyl)-N-ethyl-acetamide.<br>HPLC: $^A t_{Ret}$ = 2.58; LC-MS: m/z 549.5 [M + H]$^+$. |
| 74av | 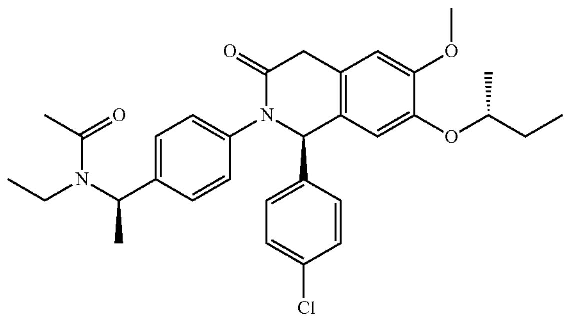 [SMILES: CC[C@@H](C)Oc1cc2c(cc1OC)CC(=O)N(c1ccc([C@@H](C)N(CC)C(C)=O)cc1)[C@@H]2c1ccc(Cl)cc1] | N-((R)-1-{4-[(R)-7-((R)-sec-Butoxy)-1-(4-chloro-phenyl)-6-methoxy-3-oxo-3,4-dihydro-1H-isoquinolin-2-yl]-phenyl}-ethyl)-N-ethyl-acetamide.<br>HPLC: $^A t_{Ret}$ = 2.58; LC-MS: m/z 549.6 [M + H]$^+$. |
| 74aw | 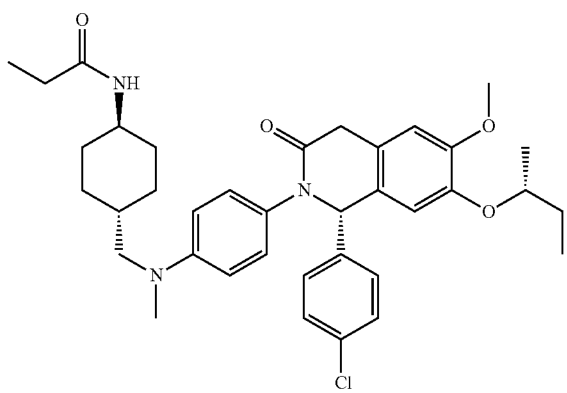 [SMILES: CCC(=O)N[C@H]1CC[C@H](CN(C)c2ccc(N3C(=O)Cc4cc(OC)c(O[C@H](C)CC)cc4[C@@H]3c3ccc(Cl)cc3)cc2)CC1] | N-{4-[({4-[(S)-7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-propionamide.<br>HPLC: $^A t_{Ret}$ = 2.22; LC-MS: m/z 632.6 [M + H]$^+$. |
| 74ax | 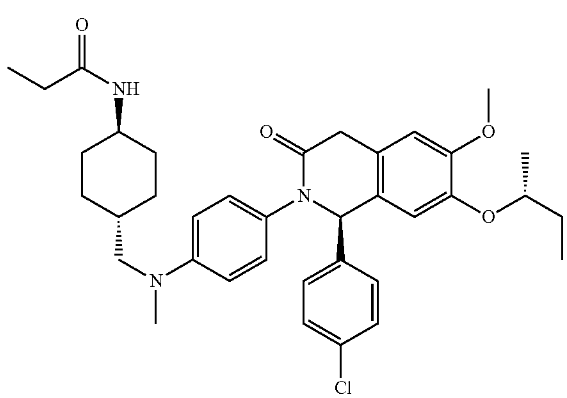 [SMILES: CCC(=O)N[C@H]1CC[C@H](CN(C)c2ccc(N3C(=O)Cc4cc(OC)c(O[C@H](C)CC)cc4[C@H]3c3ccc(Cl)cc3)cc2)CC1] | N-{4-[({4-[(R)-7-((R)-sec-Butoxy)-1-(4-chloro-phenyl)-6-methoxy-3-oxo-3,4-dihydro-1H-isoquinolin-2-yl]-phenyl}-methyl-amino)-methyl]-trans-cyclohexyl}-propionamide.<br>HPLC: $^A t_{Ret}$ = 2.22; LC-MS: m/z 632.7 [M + H]$^+$. |

| # | Structure | Name/HPLC/MS |
|---|---|---|
| 74ay | 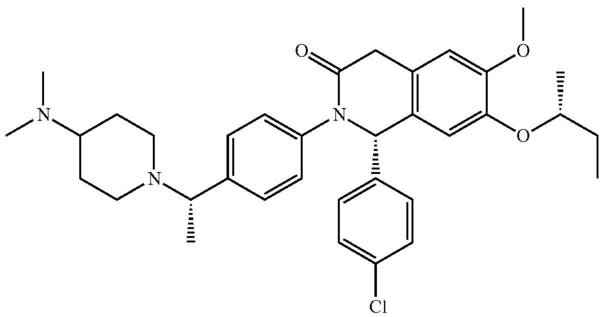 [SMILES: CC[C@@H](C)Oc1cc2c(cc1OC)CC(=O)N(c1ccc([C@H](C)N3CCC(N(C)C)CC3)cc1)[C@H]2c1ccc(Cl)cc1] | (S)-7-((R)-sec-Butoxy)-1-(4-chloro-phenyl)-2-{4-[(S)-1-(4-dimethylamino-piperidin-1-yl)-ethyl]-phenyl}-6-methoxy-1,4-dihydro-2H-isoquinolin-3-one.<br>HPLC: $^At_{Ret}$ = 1.72; LC-MS: m/z 590.7 [M + H]$^+$. |
| 74az | 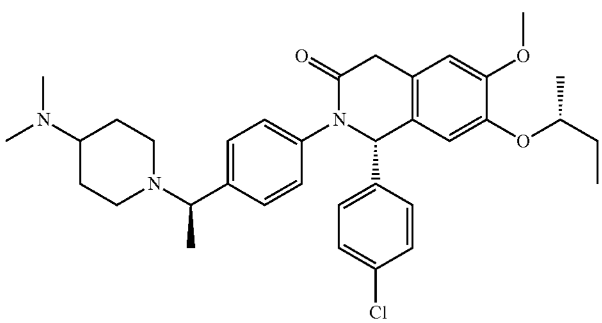 [SMILES: CC[C@@H](C)Oc1cc2c(cc1OC)CC(=O)N(c1ccc([C@@H](C)N3CCC(N(C)C)CC3)cc1)[C@H]2c1ccc(Cl)cc1] | (S)-7-((R)-sec-Butoxy)-1-(4-chloro-phenyl)-2-{4-[(R)-1-(4-dimethylamino-piperidin-1-yl)-ethyl]-phenyl}-6-methoxy-1,4-dihydro-2H-isoquinolin-3-one.<br>HPLC: $^At_{Ret}$ = 1.73; API-MS: m/z 590.7 [M + H]$^+$. |
| 74ba | 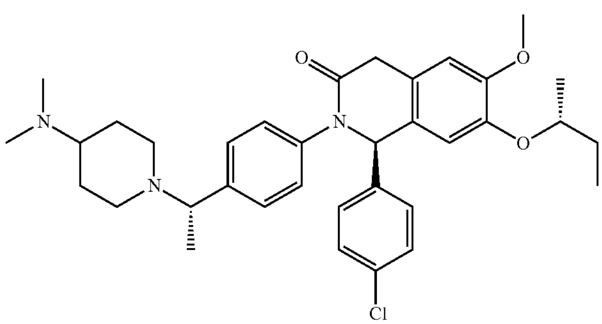 [SMILES: CC[C@@H](C)Oc1cc2c(cc1OC)CC(=O)N(c1ccc([C@H](C)N3CCC(N(C)C)CC3)cc1)[C@@H]2c1ccc(Cl)cc1] | (R)-7-((R)-sec-Butoxy)-1-(4-chloro-phenyl)-2-{4-[(S)-1-(4-dimethylamino-piperidin-1-yl)-ethyl]-phenyl}-6-methoxy-1,4-dihydro-2H-isoquinolin-3-one.<br>HPLC: $^At_{Ret}$ = 1.70; LC-MS: m/z 590.7 [M + H]$^+$. |
| 74bb | 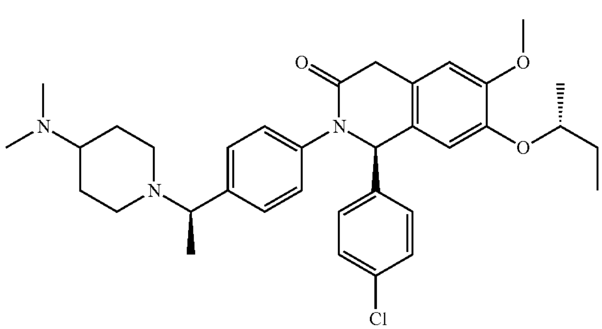 [SMILES: CC[C@@H](C)Oc1cc2c(cc1OC)CC(=O)N(c1ccc([C@@H](C)N3CCC(N(C)C)CC3)cc1)[C@@H]2c1ccc(Cl)cc1] | (R)-7-((R)-sec-Butoxy)-1-(4-chloro-phenyl)-2-{4-[(R)-1-(4-(dimethylamino-piperidin-1-yl)-ethyl]-phenyl}-6-methoxy-1,4-dihydro-2H-isoquinolin-3-one.<br>HPLC: $^At_{Ret}$ = 1.72; LC-MS: m/z 590.7 [M + H]$^+$. |

Example 75

(S)-1-(4-Chloro-phenyl)-2-{4-[(trans-4-dimethylamino-cyclohexylmethyl)-methyl-amino]-phenyl}-7-isopropoxy-6-methoxy-1,4-dihydro-2H-isoquinolin-3-one

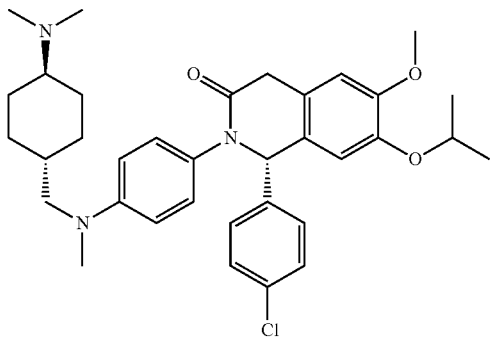 [SMILES: COc1cc2c(cc1OC(C)C)[C@H](c1ccc(Cl)cc1)N(c1ccc(N(C)C[C@H]3CC[C@H](N(C)C)CC3)cc1)C(=O)C2]

A sealable reaction flask was charged with Intermediate 75.6 (30 mg, 0.087 mmol), CuI (3.3 mg, 0.017 mmol), (+/−)-trans-1,2-diaminocyclohexane (0.002 ml, 0.017 mmol) and $K_3PO_4$ (36.8 mg, 0.17 mmol) then evacuated under vacuum and back-filled with argon (3×). A solution of Intermediate 75.8 (48.4 mg, 0.13 mmol) in anhydrous dioxane (0.5 ml) was added, the reaction flask was sealed and the slurry was heated at 110° C. and stirred for 14 h. The reaction mixture was cooled to RT, diluted with DCM and washed with a 2M aqueous $Na_2CO_3$ solution. The organic phase was dried over $Na_2SO_4$, filtered and evaporated. The resulting crude material was purified by reverse phase prep-HPLC (Waters system) to yield the title compound (TFA salt, 25 mg, 0.036 mmol, 40%) as a brownish solid. HPLC: $^At_{Ret}$=1.83 min; LC-MS: m/z 590.7 [M+H]$^+$; $^1$H NMR (400 MHz, DMSO-$d_6$). 0.96-1.10 (m, 2H), 1.19 (d, J=6.1, 3H), 1.24 (d, J=6.1, 3H), 1.30-1.46 (m, 2H), 1.59-1.71 (m, 1H), 1.74-1.86 (m, 2H), 1.90-2.03 (m, 2H), 2.71 (2 s, 6H), 2.89 (s, 3H), 3.03-3.19 (m, 3H), 3.57 (d, J=19.8, 1H), 3.73 (s, 3H), 3.90 (d, J=19.8, 1H), 4.39-4.51 (m, 1H), 5.94 (s, 1H), 6.54-6.63 (m, 2H), 6.84 (s, 1H), 6.87-6.95 (m, 2H), 7.03 (s, 1H), 7.35 (s, 4H), 9.22-9.37 (m, 1H).

Intermediate 75.1:
(4-Isopropoxy-3-methoxy-phenyl)-acetic acid ethyl ester

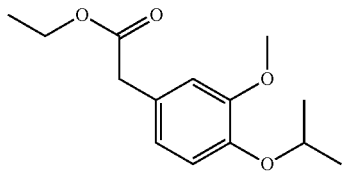 [SMILES: CCOC(=O)Cc1ccc(OC(C)C)c(OC)c1]

A mixture of ethyl (4-hydroxy-3-methoxy-phenyl)-acetic acid ethyl ester (11.22 g, 53.4 mmol) and $K_2CO_3$ (22.13 g, 160 mmol) in DMF (100 ml) was heated at 60° C. 2-Iodopropane (9.06 ml, 91 mmol) was added and the mixture was vigorously stirred at 60° C. for 5 h. The reaction mixture was cooled to RT, diluted with AcOEt and washed with water. The aqueous phase was separated and further extracted with AcOEt. The combined organic fractions were dried over $Na_2SO_4$, filtered and evaporated to dryness. The resulting crude material was purified by Combi-Flash Companion™ (Isco Inc.) column chromatography ($SiO_2$; gradient elution, heptane/AcOEt 98:2-3:1) to yield the title compound (11.94 g, 47.3 mmol, 89%) as a colorless oil. TLC: $R_F$=0.44 (heptane/AcOEt 7:3); HPLC: $^At_{Ret}$=2.14 min; LC-MS: m/z 253.4 [M+H]$^+$; $^1$H NMR (400 MHz, CDCl$_3$): 1.28 (t, J=7.1, 3H), 1.38 (d, J=6.1, 6H), 3.56 (s, 2H), 3.87 (s, 3H), 4.17 (q, J=7.1, 2H), 4.50 (h, J=6.1, 1H), 6.77-6.89 (m, 3H).

Intermediate 75.2:
(2-Formyl-4-isopropoxy-5-methoxy-phenyl)-acetic acid ethyl ester

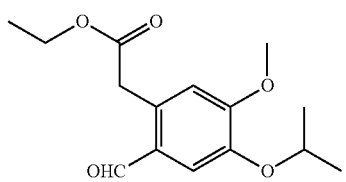 [SMILES: CCOC(=O)Cc1cc(OC)c(OC(C)C)cc1C=O]

To a solution of Intermediate 75.1 (11.94 g, 47.3 mmol) and dichloro-methoxy-methane (8.56 ml, 95 mmol) in DCM (350 ml) was slowly added $SnCl_4$ (1M solution in DCM, 95 ml, 95 mmol) over a 45 min period at 0° C. (ice bath). After the addition, the reaction mixture was further stirred at 0° C. for 45 min then poured into water and extracted with DCM (2×). The organic phase was washed with a 2M aqueous $Na_2CO_3$ solution, then dried over $Na_2SO_4$, filtered and evaporated to dryness. The resulting crude material was purified by Combi-Flash Companion™ (Isco Inc.) column chromatography ($SiO_2$; gradient elution, heptane/AcOEt 95:5→1:1) to yield the title compound (11.13 g, 39.7 mmol, 84%) as a yellow oil which crystallized on standing into an off-white solid. TLC: $R_F$=0.50 (heptane/AcOEt 1:1); HPLC: $^At_{Ret}$=1.93 min; LC-MS: m/z 281.4 [M+H]$^+$; $^1$H NMR (400 MHz, DMSO-d): 1.18 (t, J=7.1, 3H) 1.28 (d, J=6.1, 6H) 3.84 (s, 3H) 4.01 (s, 2H) 4.07 (q, J=7.1, 2H) 4.56-4.68 (m, 1H) 7.03 (s, 1H) 7.45 (s, 1H) 9.93 (s, 1H).

Intermediate 75.3: (4-Isopropoxy-5-methoxy-2-{[(E)-(S)-2-methyl-propane-2-sulfinylimino]-methyl}-phenyl)-acetic acid ethyl ester

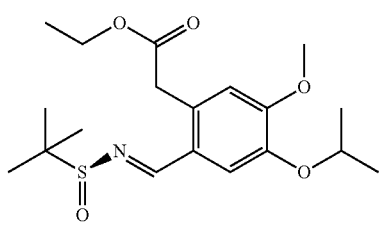 [SMILES: CCOC(=O)Cc1cc(OC)c(OC(C)C)cc1/C=N/[S@@](=O)C(C)(C)C]

To a solution of Intermediate 75.2 (9.14 g, 32.6 mmol) and (S)-(−)-2-methyl-2-propanesulfinamide (5.93 g, 48.9 mmol) in DCM (200 ml) was added Ti(OEt)$_4$ (27.3 ml, 130 mmol) at 0° C. (ice bath). The reaction mixture was heated at reflux, stirred for 5 h then cooled to RT and quenched by the careful addition of water (14.7 ml). The resulting white precipitate was filtered through a Celite pad, the filter cake was washed with DCM and the filtrate then evaporated to dryness. The resulting crude material was purified by Combi-Flash Companion™ (Isco Inc.) column chromatography (SiO$_2$; gradient elution, heptane/AcOEt 95:5→1:1) to yield the title compound (11.07 g, 28.9 mmol, 89%) as a yellow oil. TLC: R$_F$=0.40 (heptane/AcOEt 1:1); HPLC: $^A$t$_{Ret}$=2.35 min; LC-MS: m/z 384.5 [M+H]$^+$; $^1$H NMR (400 MHz, DMSO-d$_6$): 1.17 (t, J=7.1, 3H) 1.15 (s, 9H) 1.27 (d, J=6.1, 6H) 3.83 (s, 3H) 3.94-4.07 (m, 4H) 4.58-4.66 (m, 1H) 7.04 (s, 1H) 7.50 (s, 1H) 8.49 (s, 1H).

Intermediate 75.4:
(4-Chloro-phenyl)-trimethyl-stannane

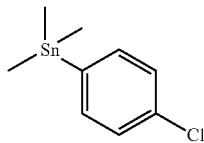

To a 1M solution of trimethyltin chloride in THF (92 ml, 92 mmol) was slowly added a 1M solution of 4-chlorophenyl-magnesium bromide in Et$_2$O (92 ml, 92 mmol) over a 40 min period at −10° C. so that the temperature never exceed 0° C. After the addition, the cooling bath was removed and the resulting suspension was stirred at RT for 1 h. A saturated aqueous solution of NH$_4$Cl (14 ml) was added followed by water until complete dissolution of the precipitate. The mixture was transferred into a separating funnel and extracted with Et$_2$O (3×). The combined organic fractions were dried over Na$_2$SO$_4$, filtered and evaporated to dryness. The resulting crude material was purified by Combi-Flash Companion™ (Isco Inc.) column chromatography (SiO$_2$; isocratic elution with cyclohexane) to yield the title compound (24.47 g, 89 mmol, 97%) as a colorless oil. TLC: R$_F$=0.76 (cyclohexane/AcOEt 95:5); HPLC: $^A$t$_{Ret}$=3.25 min; $^1$H NMR (400 MHz, CDCl$_3$): 0.31 (s, 9H) 7.32-7.36 (m, 2H) 7.41-7.45 (m, 2H).

Intermediate 75.5: {2-[(S)-(4-Chloro-phenyl)-((S)-2-methyl-propane-2-sulfinylamino)-methyl]-4-isopropoxy-5-methoxy-phenyl}-acetic acid ethyl ester

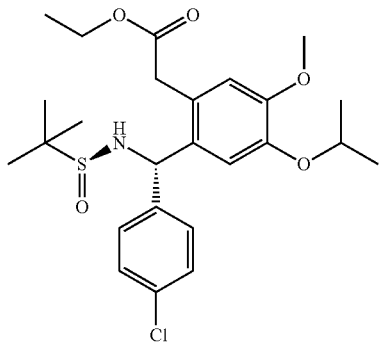 [SMILES: CCOC(=O)Cc1cc(OC)c(OC(C)C)cc1[C@@H](N[S@@](=O)C(C)(C)C)c1ccc(Cl)cc1]

A 250-mL flask was charged with Intermediate 75.3 (10.97 g, 28.6 mmol) and anhydrous THF (50 ml) then evacuated under vacuum and back-filled with argon (3×). Intermediate 75.4 (15.75 g, 57.2 mmol) and bis(acetonitrile)(1,5-cyclooctadiene)rhodium(I)tetrafluoro-borate (1.09 g, 2.86 mmol) were successively added at RT and the resulting orange suspension was heated at 60° C. and stirred for 2 h. Additional bis(acetonitrile)(1,5-cyclooctadiene)rhodium(I)tetrafluoroborate (1.09 g, 2.86 mmol) was added at 60° C. and the mixture was further stirred for 4 h. The reaction mixture was cooled to RT, diluted with AcOEt and washed with water. The organic phase was dried over Na$_2$SO$_4$, filtered and evaporated to dryness. The resulting crude material was purified by Combi-Flash Companion™ (Isco Inc.) column chromatography (SiO$_2$; gradient elution, heptane/AcOEt 95:5→3:7) to yield the title compound (3.96 g, 7.98 mmol, 28%) as a brownish resin. TLC: R$_F$=0.29 (heptane/AcOEt 1:1); HPLC: $^A$t$_{Ret}$=2.70 min; LC-MS: m/z 496.3 [M+H]$^+$; $^1$H NMR (400 MHz, DMSO-d$_6$): 1.10-1.19 (m, 15H), 1.23 (d, J=5.9, 3H), 3.57 (d, J=16.4, 1H), 3.68 (d, J=16.1, 1H), 3.73 (s, 3H), 3.93-4.05 (m, 2H), 4.37-4.45 (m, 1H), 5.62 (d, J=6.1, 1H), 5.82 (d, J=6.1, 1H), 6.82 (s, 1H), 6.94 (s, 1H), 7.25-7.30 (m, 2H), 7.36-7.41 (m, 2H).

Intermediate 75.6: (S)-1-(4-Chloro-phenyl)-7-isopropoxy-6-methoxy-1,4-dihydro-2H-isoquinolin-3-one

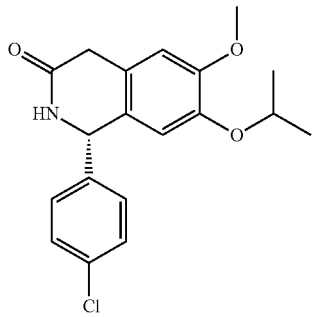

A solution of Intermediate 75.5 (3.96 g, 7.98 mmol) in 1.25M HCl in MeOH (128 ml) was stirred at RT for 30 min. The reaction mixture was evaporated to dryness and the resulting residue was dissolved in MeOH (40 ml). Et$_3$N (5.56 ml, 39.9 mmol) was added at RT then the mixture was stirred for 15 min and evaporated to dryness. The resulting crude material was purified by Combi-Flash Companion™ (Isco Inc.) column chromatography (SiO$_2$; gradient elution, [heptane/DCM 1:1]/TBME 9:1→100% TBME) to yield the title compound (2.51 g, 7.24 mmol, 91%, ee 92%) as an off-white solid. TLC: R$_F$=0.13 (heptane/DCM/TBME 1:1:2); HPLC: $^A$t$_{Ret}$=2.03 min; LC-MS: m/z 346.4 [M+H]$^+$; $^1$H NMR (400 MHz, DMSO-d): 1.16 (d, J=6.1, 3H), 1.21 (d, J=6.1, 3H), 3.36 (d, J=19.8, 1H), 3.51 (d, J=19.8, 1H), 3.72 (s, 3H), 4.40 (spt, J=6.1, 1H), 5.55 (d, J=3.4, 1H), 6.79 (s, 1H), 6.84 (s, 1H), 7.26-7.33 (m, 2H), 7.35-7.42 (m, 2H), 8.49 (d, J=3.9, 1H).

Intermediate 75.7: {4-[(4-Iodo-phenylamino)-methyl]-trans-cyclohexyl}-carbamic acid tert-butyl ester

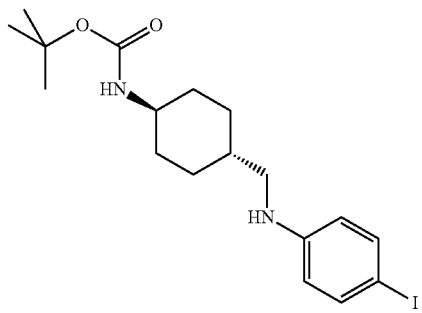 [SMILES: CC(C)(C)OC(=O)N[C@H]1CC[C@H](CNc2ccc(I)cc2)CC1]

To a solution of 4-iodo-phenylamine (1 g, 4.57 mmol) in DCM (25 ml) were successively added AcOH (0.523 ml, 9.13 mmol), (4-formyl-cyclohexyl)-carbamic acid tert-butyl ester (1.14 g, 5.02 mmol) and NaBH(OAc)₃ (1.94 g, 9.13 mmol) at RT. The reaction mixture was stirred at RT for 1 h then diluted with Et₂O and washed successively with a 2M aqueous HCl solution and a 2M aqueous Na₂CO₃ solution. The organic phase was dried over Na₂SO₄, filtered and evaporated to dryness. The resulting crude material was purified by Combi-Flash Companion™ (Isco Inc.) column chromatography (SiO₂; gradient elution, heptane/AcOEt 95:5→1:1) to yield the title compound (1.56 g, 3.62 mmol, 79%) as a colorless solid. TLC: $R_F$=0.72 (heptane/AcOEt 1:1); HPLC: $^At_{Ret}$=2.64 min; LC-MS: m/z 431.4 [M+H]⁺; ¹H NMR (400 MHz, DMSO-d₆): 0.87-1.03 (m, 2H), 1.03-1.17 (m, 2H), 1.32-1.48 (m, 1H), 1.37 (s, 9H), 1.70-1.86 (m, 4H), 2.76-2.86 (m, 2H), 3.08-3.25 (m, 1H), 5.77-5.89 (m, 1H), 6.34-6.46 (m, 2H), 6.59-6.71 (m, 1H), 7.24-7.35 (m, 2H).

Intermediate 75.8: (Trans-4-dimethylamino-cyclohexylmethyl)-(4-iodo-phenyl)-methyl-amine

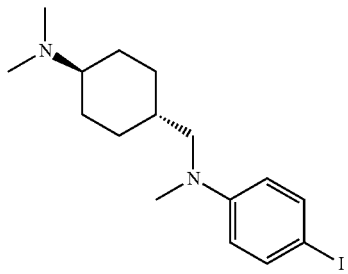 [SMILES: CN(C[C@H]1CC[C@H](N(C)C)CC1)c1ccc(I)cc1]

To a solution of Intermediate 75.7 (200 mg, 0.47 mmol) in DCM (2 ml) was added TFA (1.07 ml, 13.94 mmol) at RT. The reaction mixture was stirred at RT for 45 min then evaporated to dryness. The resulting residue was dissolved in DCM (5 ml) and AcOH (0.221 ml, 3.86 mmol), formaldehyde (37% in water, 0.289 ml, 3.86 mmol) and NaBH(OAc)₃ (818 mg, 3.86 mmol) were successively added at RT. The reaction mixture was stirred at RT for 1 h then diluted with DCM and washed with a 2M aqueous Na₂CO₃ solution (2×). The organic phase was dried over Na₂SO₄, filtered and evaporated to dryness. The resulting crude material was purified by Combi-Flash Companion™ (Isco Inc.) column chromatography (SiO₂; gradient elution, [heptane/DCM 1:1]/TBME containing 5% of 7M NH₃ in MeOH 95:5→100% TBME containing 5% of 7M NH₃ in MeOH) to yield the title compound (141 mg, 0.38 mmol, 83%) as a light yellow oil. TLC: $R_F$=0.32 (heptane/DCM/TBME containing 5% of 7M NH₃ in MeOH 1:1:2); HPLC: $^At_{Ret}$=1.42 min; LC-MS: m/z 373.4 [M+H]⁺; ¹H NMR (400 MHz, DMSO-d₆): 0.89-1.01 (m, 2H), 1.02-1.14 (m, 2H), 1.51-1.63 (m, 1H), 1.63-1.72 (m, 2H), 1.73-1.82 (m, 2H), 2.02-2.11 (m, 1H), 2.13 (s, 6H), 2.87 (s, 3H), 3.12 (d, J=7.1, 2H), 6.46-6.53 (m, 2H), 7.35-7.43 (m, 2H).

Example 76

(S)-1-(4-Chloro-phenyl)-2-{4-[(trans-4-dimethylamino-cyclohexylmethyl)-ethyl-amino]-phenyl}-7-isopropoxy-6-methoxy-1,4-dihydro-2H-isoquinolin-3-one

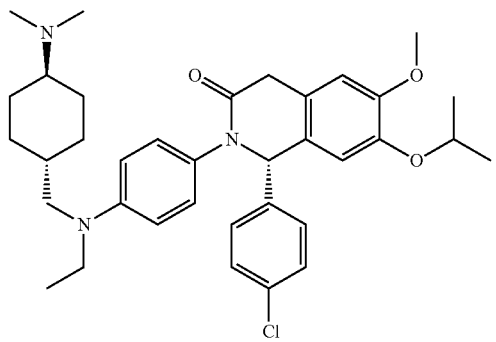 [SMILES: CCN(C[C@H]1CC[C@H](N(C)C)CC1)c1ccc(N2C(=O)Cc3cc(OC)c(OC(C)C)cc3[C@@H]2c2ccc(Cl)cc2)cc1]

The title compound (TFA salt, 18.8 mg, 0.026 mmol, 36%) was obtained as a yellow solid from Intermediate 75.6 (25 mg, 0.072 mmol) and Intermediate 76.3 (41.9 mg, 0.108 mmol) analogously to Example 75. Purification of the crude material was performed by reverse phase prep-HPLC (Waters system). HPLC: $^Bt_{Ret}$=1.75 min; LC-MS: m/z 604.5 [M+H]⁺; ¹H NMR (400 MHz, DMSO-d₆): 0.96-1.11 (m, 5H), 1.20 (d, J=5.9, 3H), 1.24 (d, J=6.1, 3H), 1.30-1.45 (m, 2H), 1.54-1.70 (m, 1H), 1.78-1.89 (m, 2H), 1.92-2.03 (m, 2H), 2.67-2.74 (2 s, 6H), 3.02-3.16 (m, 3H), 3.33 (q, J=6.8, 2H), 3.53-3.60 (m, 1H), 3.73 (s, 3H), 3.88 (d, J=19.8, 1H), 4.40-4.50 (m, 1H), 5.94 (s, 1H), 6.54-6.62 (m, 2H), 6.84 (s, 1H), 6.86-6.93 (m, 2H), 7.06 (s, 1H), 7.33-7.41 (m, 4H).

Intermediate 76.1: (4-{[Ethyl-(4-iodo-phenyl)-amino]-methyl}-trans-cyclohexyl)-carbamic acid tert-butyl ester

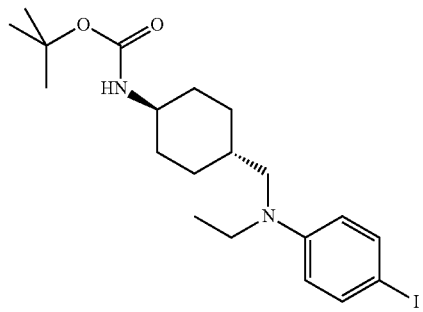 [SMILES: CCN(C[C@H]1CC[C@H](NC(=O)OC(C)(C)C)CC1)c1ccc(I)cc1]

To a suspension of Intermediate 75.7 (100 mg, 0.232 mmol) and K₂CO₃ (64.2 mg, 0.465 mmol) in DMF (1 ml) was added iodoethane (0.192 ml, 2.33 mmol) at RT. The reaction mixture was heated at 60° C., vigorously stirred for 14 h then cooled to RT and poured into water. The mixture was extracted with Et₂O (2×) and the combined organic fractions were dried over Na₂SO₄, filtered and evaporated to dryness to yield the crude title compound (104 mg, 0.23 mmol, quant.) as a brownish solid which was used in the next step without further purification. HPLC: $^Bt_{Ret}$=2.76 min; API-MS: m/z 459.3 [M+H]⁺; ¹H NMR (400 MHz, DMSO-d₆): 0.92-1.14

(m, 7H), 1.37 (s, 9H), 1.45-1.59 (m, 1H), 1.61-1.82 (m, 4H), 3.05 (d, J=7.1, 2H), 3.10-3.24 (m, 1H), 3.31 (q, J=6.8, 2H), 6.44-6.55 (m, 2H), 6.60-6.69 (m, 1H), 7.33-7.42 (m, 2H).

Intermediate 76.2: (Trans-4-dimethylamino-cyclohexylmethyl)-ethyl-(4-iodo-phenyl)-amine

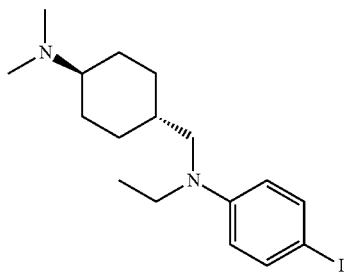 [SMILES: CCN(C[C@H]1CC[C@H](N(C)C)CC1)c1ccc(I)cc1]

The title compound (45 mg, 0.116 mmol, 54%) was obtained as a colorless oil from Intermediate 76.1 (101 mg, 0.22 mmol) analogously to Intermediate 75.8. Purification of the crude material was performed by Combi-Flash Companion™ (Isco Inc.) column chromatography (SiO$_2$; gradient elution, [heptane/DCM 1:1]/TBME containing 5% of 7M NH$_3$ in MeOH 9:1→100% TBME containing 5% of 7M NH$_3$ in MeOH). HPLC: $^B t_{Ret}$=1.30 min; API-MS: m/z 387.3 [M+H]$^+$; $^1$H NMR (400 MHz, DMSO-d): 0.89-1.17 (m, 7H), 1.47-1.65 (m, 1H), 1.67-1.85 (m, 4H), 2.14 (s, 6H), 3.04 (d, J=7.1, 2H), 3.26-3.39 (m, 3H), 6.44-6.52 (m, 2H), 7.32-7.41 (m, 2H).

Example 77

N-{4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexyl}-methanesulfonamide

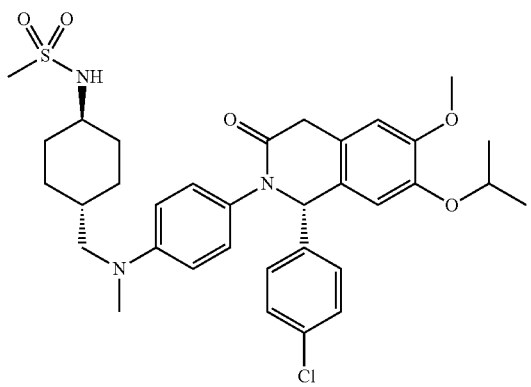 [SMILES: COc1cc2c(cc1OC(C)C)[C@H](c1ccc(Cl)cc1)N(c1ccc(N(C)C[C@H]3CC[C@H](NS(C)(=O)=O)CC3)cc1)C(=O)C2]

To a solution of Intermediate 77.3 (20 mg, 0.036 mmol) in MeCN (0.5 ml) were successively added Et$_3$N (0.015 ml, 0.107 mmol) and methanesulfonyl chloride (8.2 mg, 0.071 mmol) at RT. The reaction mixture was stirred at RT for 1 h then directly subjected to purification by reverse phase prep-HPLC (Waters system) to yield the title compound (TFA salt, 5 mg, 0.007 mmol, 19%) as a reddish solid. HPLC: $^A t_{Ret}$=2.15 min; LC-MS: m/z 640.7 [M+H]$^+$; $^1$H NMR (400 MHz, DMSO-d$_6$): 0.94-1.21 (m, 4H), 1.19 (d, J=5.9, 3H), 1.24 (d, J=6.1, 3H), 1.49-1.61 (m, 1H), 1.61-1.71 (m, 2H), 1.84-1.93 (m, 2H), 2.85-2.90 (m, 6H), 2.96-3.20 (m, 3H), 3.57 (d, J=19.8, 1H), 3.73 (s, 3H), 3.89 (d, J=19.8, 1H), 4.40-4.50 (m, 1H), 5.95 (s, 1H), 6.54-6.62 (m, 2H), 6.84 (s, 1H), 6.87-6.93 (m, 2H), 6.96 (d, J=7.3, 1H), 7.04 (s, 1H), 7.35 (s, 4H).

Intermediate 77.1: (4-{[(4-Iodo-phenyl)-methyl-amino]-methyl}-trans-cyclohexyl)-carbamic acid tert-butyl ester

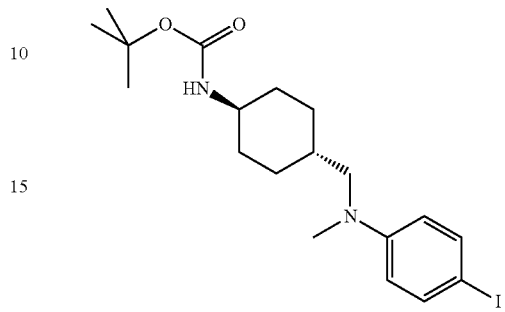

To a solution of Intermediate 75.7 (748 mg, 1.74 mmol) in DCM (15 ml) were successively added AcOH (0.199 ml, 3.48 mmol), formaldehyde (37% in water, 0.259 ml, 3.48 mmol) and NaBH(OAc)$_3$ (737 mg, 3.48 mmol) at RT. The reaction mixture was stirred at RT for 2 h then diluted with DCM and washed with a 2M aqueous Na$_2$CO$_3$ solution (2×). The organic phase was dried over Na$_2$SO$_4$, filtered and evaporated to dryness. The resulting crude material was purified by Combi-Flash Companion™ (Isco Inc.) column chromatography (SiO$_2$; gradient elution, heptane/AcOEt 98:2→7:3) to yield the title compound (584 mg, 1.31 mmol, 76%) as a colorless solid. TLC: R$_F$=0.36 (heptane/AcOEt 3:1); HPLC: $^A t_{Ret}$=2.76 min; LC-MS: m/z 445.4 [M+H]$^+$; $^1$H NMR (400 MHz, DMSO-d$_6$): 0.90-1.13 (m, 4H), 1.36 (s, 9H), 1.48-1.66 (m, 3H), 1.69-1.81 (m, 2H), 2.87 (s, 3H), 3.08-3.21 (m, 1H), 3.12 (d, J=7.1, 2H), 6.45-6.54 (m, 2H), 6.68 (d, J=8.1, 1H), 7.34-7.43 (m, 2H).

Intermediate 77.2: {4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexyl}-carbamic acid tert-butyl ester

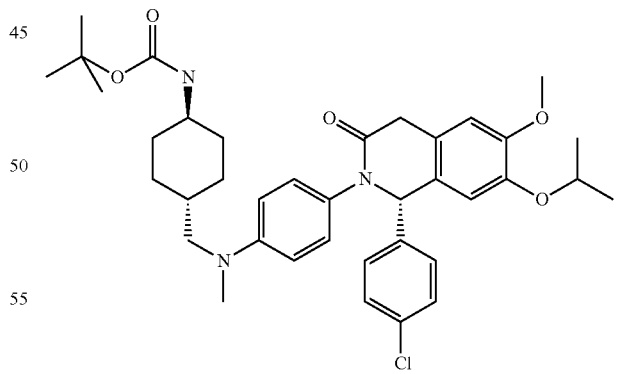

The title compound (1.03 g, 1.56 mmol, 69%) was obtained as a brownish solid from Intermediate 75.6 (780 mg, 2.26 mmol) and Intermediate 77.1 (1.2 g, 2.71 mmol) analogously to Example 75. Purification of the crude material was performed by Combi-Flash Companion™ (Isco Inc.) column chromatography (SiO$_2$; gradient elution, [heptane/DCM 1:1]/TBME 95:5→4:6). HPLC: $^A t_{Ret}$=2.63 min; LC-MS: m/z 662.7 [M+H]$^+$; $^1$H NMR (400 MHz, DMSO-d$_6$): 0.91-1.12 (m, 4H), 1.19 (d, J=6.1, 3H), 1.24 (d, J=6.1, 3H), 1.36 (s, 9H), 1.48-1.60 (m, 1H), 1.59-1.68 (m, 2H), 1.70-1.80 (m, 2H), 2.87 (s, 3H), 3.05-3.21 (m, 3H), 3.57 (d, J=20.1, 1H), 3.73 (s, 3H), 3.89 (d, J=20.1, 1H), 4.40-4.50 (m, 1H), 5.94 (s, 1H), 6.52-6.60 (m, 2H), 6.66 (d, J=7.8, 1H), 6.83 (s, 1H), 6.86-6.93 (m, 2H), 7.04 (s, 1H), 7.35 (s, 4H).

Intermediate 77.3: (S)-2-{4-[(Trans-4-amino-cyclohexylmethyl)-methyl-amino]-phenyl}-1-(4-chlorophenyl)-7-isopropoxy-6-methoxy-1,4-dihydro-2H-isoquinolin-3-one

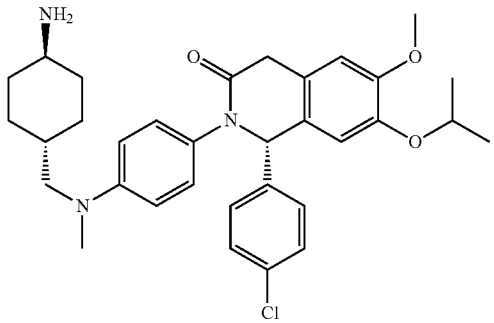 [SMILES: COc1cc2c(cc1OC(C)C)[C@H](c1ccc(Cl)cc1)N(c1ccc(N(C)C[C@H]3CC[C@H](N)CC3)cc1)C(=O)C2]

To a solution of Intermediate 77.2 (270 mg, 0.41 mmol) in DCM (2 ml) was added TFA (0.942 ml, 12.23 mmol) at RT. The reaction mixture was stirred at RT for 30 min then diluted with DCM and washed with a 2M aqueous $Na_2CO_3$ solution (2×). The organic phase was dried over $Na_2SO_4$, filtered and evaporated to dryness to yield the crude title compound (251 mg, 0.41 mmol, quant.) as a brownish solid which was used in the next step without further purification. HPLC: $^At_{Ret}$=1.77 min; LC-MS: m/z 562.6 [M+H]$^+$; $^1$H NMR (400 MHz, DMSO-d): 0.89-1.00 (m, 2H), 1.19 (d, J=5.9, 3H), 1.21-1.33 (m, 5H), 1.51-1.68 (m, 3H), 1.68-1.78 (m, 2H), 2.39-2.47 (m, 1H), 2.87 (s, 3H), 3.06-3.14 (m, 2H), 3.57 (d, J=19.8, 1H), 3.73 (s, 3H), 3.89 (d, J=19.6, 1H), 4.40-4.50 (m, 1H), 5.94 (s, 1H), 6.52-6.60 (m, 2H), 6.84 (s, 1H), 6.86-6.93 (m, 2H), 7.04 (s, 1H), 7.36 (s, 4H).

Example 78

Oxazole-4-carboxylic acid {4-[({4-[(S)-1-(4-chlorophenyl)-7-isopropoxy-6-methoxy-3-oxo-3,4-dihydro-1H-isoquinolin-2-yl]-phenyl}-methyl-amino)-methyl]-trans-cyclohexyl}-amide

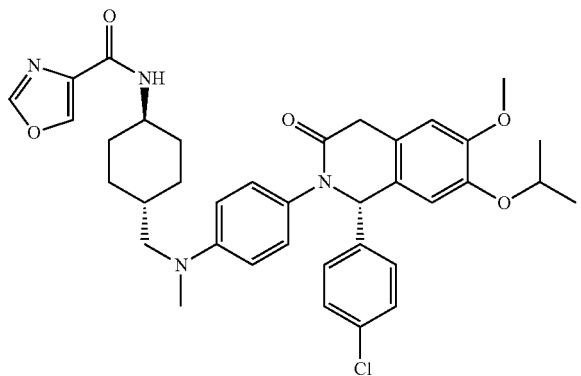 [SMILES: COc1cc2c(cc1OC(C)C)[C@H](c1ccc(Cl)cc1)N(c1ccc(N(C)C[C@H]3CC[C@H](NC(=O)c4cocn4)CC3)cc1)C(=O)C2]

To a solution of Intermediate 77.3 (20 mg, 0.036 mmol) in DMF (0.5 ml) were successively added 4-oxazolecarboxylic acid (4.8 mg, 0.043 mmol), $Et_3N$ (0.010 ml, 0.071 mmol) and HATU (17.6 mg, 0.046 mmol) at RT. The reaction mixture was heated at 50° C. and stirred for 14 h, then cooled to RT and directly subjected to purification by reverse phase prep-HPLC (Waters system) to yield the title compound (TFA salt, 11 mg, 0.014 mmol, 40%) as a reddish solid. HPLC: $^At_{Ret}$=2.14 min; LC-MS: m/z 657.7 [M+H]$^+$; $^1$H NMR (400 MHz, DMSO-d$_6$): 0.99-1.14 (m, 2H), 1.19 (d, J=5.9, 3H), 1.24 (d, J=6.1, 3H), 1.27-1.42 (m, 2H), 1.54-1.66 (m, 1H), 1.65-1.82 (m, 4H), 2.90 (s, 3H), 3.14 (d, J5=6.6, 2H), 3.57 (d, J=19.8, 1H), 3.73 (s, 3H), 3.89 (d, J=19.8, 1H), 4.40-4.50 (m, 1H), 5.96 (s, 1H), 6.56-6.64 (m, 2H), 6.84 (s, 1H), 6.88-6.95 (m, 2H), 7.04 (s, 1H), 7.36 (s, 4H), 7.96 (d, J=8.3, 1H), 8.49 (s, 1H), 8.58 (s, 1H).

Example 79

(S)-1-(4-Chloro-phenyl)-7-isopropoxy-6-methoxy-2-(4-{methyl-[4-(3-oxo-piperazin-1-yl)-trans-cyclohexylmethyl]-amino}-phenyl)-1,4-dihydro-2H-isoquinolin-3-one

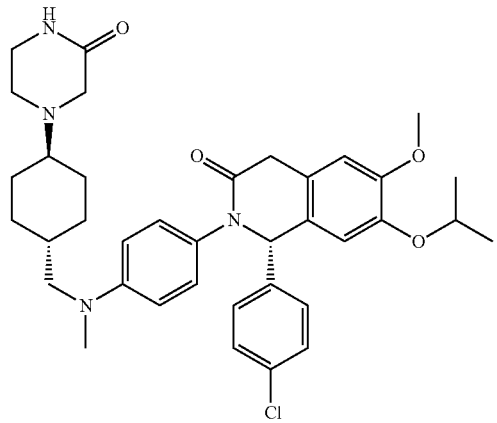 [SMILES: COc1cc2c(cc1OC(C)C)[C@H](c1ccc(Cl)cc1)N(c1ccc(N(C)C[C@H]3CC[C@H](N4CCNC(=O)C4)CC3)cc1)C(=O)C2]

To a solution of Intermediate 79.2 (49 mg, 0.063 mmol) in DCM (0.5 ml) was added TFA (0.097 ml, 1.261 mmol) at RT. The reaction mixture was stirred at RT for 5 h and evaporated to dryness. The resulting residue was dissolved in MeOH (0.5 ml) then $Et_3N$ (0.088 ml, 0.63 mmol) was added and the mixture was stirred at RT for 1 h. The reaction mixture was directly subjected to purification by reverse phase prep-HPLC (Waters system) to yield the title compound (TFA salt, 19.4 mg, 0.026 mmol, 41%) as an off-white solid. HPLC: $^At_{Ret}$=1.76 min; LC-MS: m/z 645.7 [M+H]$^+$; $^1$H NMR (400 MHz, DMSO-d$_6$): 0.90-1.04 (m, 2H), 1.08-1.20 (m, 2H), 1.19 (d, J=6.1, 3H), 1.24 (d, J=6.1, 3H), 1.52-1.66 (m, 1H), 1.66-1.83 (m, 4H), 2.20-2.31 (m, 1H), 2.55-2.63 (m, 2H), 2.88 (s, 3H), 3.00 (s, 2H), 3.04-3.15 (m, 4H), 3.57 (d, J=20.1, 1H), 3.73 (s, 3H), 3.89 (d, J=19.8, 1H), 4.41-4.50 (m, 1H), 5.94 (s, 1H), 6.52-6.60 (m, 2H), 6.83 (s, 1H), 6.86-6.94 (m, 2H), 7.04 (s, 1H), 7.36 (s, 4H), 7.66 (br. s., 1H).

Intermediate 79.1: {4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexylamino}-acetic acid methyl ester

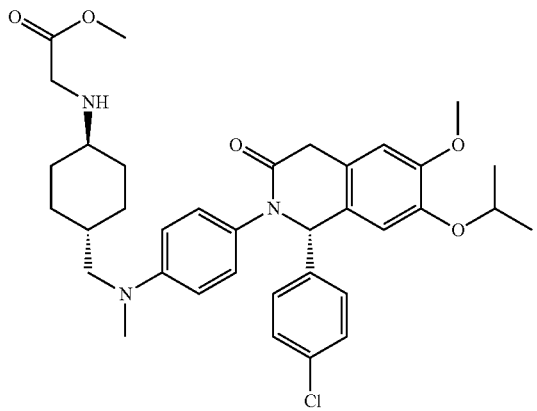 [SMILES: COC(=O)CN[C@H]1CC[C@H](CN(C)c2ccc(N3C(=O)Cc4cc(OC)c(OC(C)C)cc4[C@@H]3c3ccc(Cl)cc3)cc2)CC1]

To a solution of Intermediate 77.3 (100 mg, 0.178 mmol) in DCM (1.5 ml) were successively added Et$_3$N (0.050 ml, 0.356 mmol) and methyl 2-bromoacetate (0.018 ml, 0.196 mmol) at RT. The reaction mixture was stirred at RT for 6 h then additional Et$_3$N (0.050 ml, 0.356 mmol) and methyl 2-bromoacetate (0.018 ml, 0.196 mmol) were added. The mixture was further stirred at RT for 24 h then diluted with DCM and washed with water. The organic phase was dried over Na$_2$SO$_4$, filtered and evaporated. The resulting crude material was purified by Combi-Flash Companion™ (Isco Inc.) column chromatography (SiO$_2$; gradient elution, DCM/[DCM/7M NH$_3$ in MeOH 9:1]95:5→100% DCM/7M NH$_3$ in MeOH 9:1) to yield the title compound (75 mg, 0.118 mmol, 67%) as a yellow resin. TLC: R$_F$=0.68 (DCM/7M NH$_3$ in MeOH 9:1); HPLC: $^At_{Ret}$=1.85 min; LC-MS: m/z 634.7 [M+H]$^+$; $^1$H NMR (400 MHz, DMSO-d$_6$): 0.83-1.01 (m, 4H), 1.19 (d, J=6.1, 3H), 1.24 (d, J=6.1, 3H), 1.51-1.69 (m, 3H), 1.74-1.86 (m, 2H), 2.24-2.36 (m, 1H), 2.87 (s, 3H), 3.06-3.13 (m, 2H), 3.29-3.35 (m, 2H), 3.57 (d, J=19.8, 1H), 3.61 (s, 3H), 3.73 (s, 3H), 3.89 (d, J=19.8, 1H), 4.41-4.49 (m, 1H), 5.92-5.96 (m, 1H), 6.51-6.59 (m, 2H), 6.83 (s, 1H), 6.86-6.92 (m, 2H), 7.04 (s, 1H), 7.35 (s, 4H).

Intermediate 79.2: ((2-tert-Butoxycarbonylamino-ethyl)-{4-[({4-[(S)-1-(4-chloro-phenyl)-7-isopropoxy-6-methoxy-3-oxo-3,4-dihydro-1H-isoquinolin-2-yl]-phenyl}-methyl-amino)-methyl]-trans-cyclohexyl}-amino)-acetic acid methyl ester

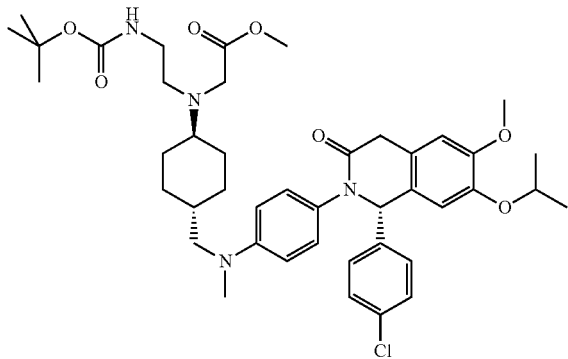 [SMILES: COC(=O)CN(CCNC(=O)OC(C)(C)C)[C@H]1CC[C@H](CN(C)c2ccc(N3C(=O)Cc4cc(OC)c(OC(C)C)cc4[C@@H]3c3ccc(Cl)cc3)cc2)CC1]

To a solution of Intermediate 79.1 (144 mg, 0.227 mmol) in DCM (2 ml) were successively added N-Boc-2-aminoacetaldehyde (72.3 mg, 0.454 mmol), AcOH (0.039 ml, 0.681 mmol) and NaBH(OAc)$_3$ (144 mg, 0.681 mmol) at RT. The suspension was stirred at RT for 1 h then diluted with DCM and washed with a 2M aqueous Na$_2$CO$_3$ solution. The organic phase was dried over Na$_2$SO$_4$, filtered and evaporated. The resulting crude material was purified by reverse phase prep-HPLC (Waters system). Fractions containing pure material were combined and concentrated under vacuum. The resulting aqueous mixture was basified by the addition of Na$_2$CO$_3$ 2M and extracted with AcOEt. The organic layer was washed with brine, dried over Na$_2$SO$_4$, filtered and evaporated to dryness to yield the title compound (142.6 mg, 0.183 mmol, 81%) as a yellow solid. HPLC: $^At_{Ret}$=2.20 min; LC-MS: m/z 777.9 [M+H]$^+$; $^1$H NMR (500 MHz, DMSO-d$_6$): 0.89-0.99 (m, 2H), 1.02-1.12 (m, 2H), 1.17 (d, J=6.0, 3H), 1.22 (d, J=6.0, 3H), 1.35 (s, 9H), 1.49-1.74 (m, 6H), 2.52-2.58 (m, 2H), 2.85 (s, 3H), 2.86-2.93 (m, 2H), 3.05-3.10 (m, 2H), 3.28 (s, H), 3.52-3.59 (m, 1H), 3.57 (s, 3H), 3.71 (s, 3H), 3.87 (d, J=19.8, 1H), 4.39-4.48 (m, 1H), 5.93 (s, 1H), 6.44-6.50 (m, 1H), 6.51-6.58 (m, 2H), 6.82 (s, 1H), 6.85-6.91 (m, 2H), 7.03 (s, 1H), 7.34 (s, 4H).

Example 80

({4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexyl}-methyl-amino)-acetic acid methyl ester

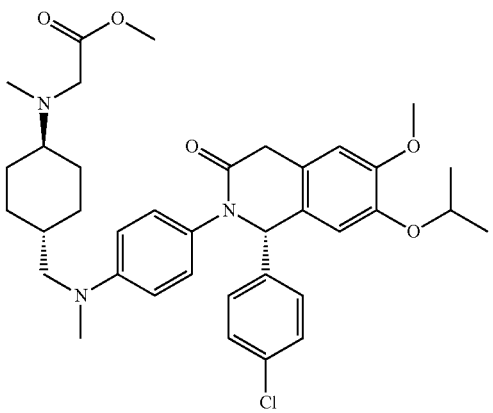 [SMILES: COC(=O)CN(C)[C@H]1CC[C@H](CN(C)c2ccc(N3C(=O)Cc4cc(OC)c(OC(C)C)cc4[C@@H]3c3ccc(Cl)cc3)cc2)CC1]

To a solution of Intermediate 79.1 (22 mg, 0.035 mmol) in DCM (0.5 ml) were successively added AcOH (0.006 ml, 0.10 mmol), formaldehyde (37% in water, 0.008 ml, 0.10 mmol) and NaBH(OAc)$_3$ (22.1 mg, 0.10 mmol) at RT. The reaction mixture was stirred at RT for 3 h then diluted with DCM and washed with a 2M aqueous Na$_2$CO$_3$ solution (2×). The organic phase was dried over Na$_2$SO$_4$, filtered and evaporated to dryness. The resulting crude material was purified by reverse phase prep-HPLC (Waters system) to yield the title compound (TFA salt, 4.6 mg, 0.006 mmol, 17%) as a colorless solid. HPLC: $^At_{Ret}$=1.87 min; LC-MS: m/z 648.7 [M+H]$^+$; $^1$H NMR (400 MHz, DMSO-d$_6$): 0.96-1.11 (m, 2H), 1.19 (d, J=5.9, 3H), 1.24 (d, J=5.9, 3H), 1.36-1.54 (m, 2H), 1.60-1.72 (m, 1H), 1.74-1.84 (m, 2H), 1.92-2.06 (m, 2H), 2.76 (br. s., 3H), 2.89 (s, 3H), 3.10-3.16 (m, 2H), 3.16-3.27 (m, 1H), 3.57 (d, J=20.1, 1H), 3.73 (s, 3H), 3.78 (s, 3H), 3.90 (d, J=20.1, 1H), 4.04-4.15 (m, 1H), 4.25-4.35 (m, 1H), 4.41-4.50 (m, 1H), 5.94 (s, 1H), 6.54-6.62 (m, 2H), 6.84 (s, 1H), 6.87-6.94 (m, 2H), 7.03 (s, 1H), 7.36 (s, 4H).

Example 81

(S)-1-(4-Chloro-phenyl)-7-isopropoxy-6-methoxy-2-{4-[methyl-(trans-4-morpholin-4-yl-cyclohexylmethyl)-amino]-phenyl}-1,4-dihydro-2H-isoquinolin-3-one

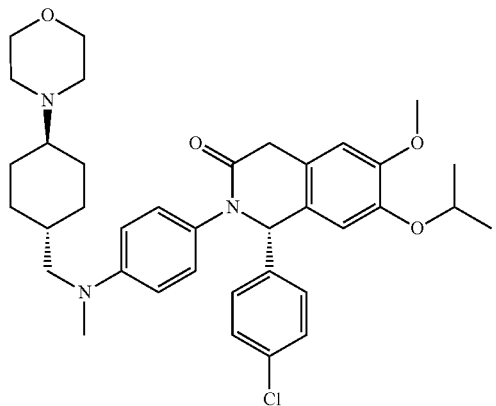 [SMILES: COc1cc2c(cc1OC(C)C)[C@H](c1ccc(Cl)cc1)N(c1ccc(N(C)C[C@H]3CC[C@H](N4CCOCC4)CC3)cc1)C(=O)C2]

To a solution of Intermediate 77.3 (20 mg, 0.036 mmol) in DMF (0.5 ml) were successively added $K_2CO_3$ (24.59 mg, 0.178 mmol) and bis(2-bromoethyl)ether (0.022 ml, 0.178 mmol) at RT. The reaction mixture was stirred at RT for 14 h then diluted with AcOEt and washed with water. The organic phase was dried over $Na_2SO_4$, filtered and evaporated to dryness. The resulting crude material was purified by reverse phase prep-HPLC (Waters system) to yield the title compound (TFA salt, 14.3 mg, 0.019 mmol, 54%) as a reddish solid. HPLC: $^At_{Ret}$=1.86 min; LC-MS: m/z 632.4 [M+H]$^+$; $^1$H NMR (400 MHz, DMSO-d$_6$): 0.96-1.12 (m, 2H), 1.19 (d, J=6.1, 3H), 1.24 (d, J=6.1, 3H), 1.30-1.44 (m, 2H), 1.57-1.72 (m, 1H), 1.75-1.86 (m, 2H), 2.01-2.11 (m, 2H), 2.89 (s, 3H), 3.02-3.19 (m, 5H), 3.32-3.41 (m, 2H), 3.57 (d, J=20.1, 1H), 3.61-3.70 (m, 2H), 3.73 (s, 3H), 3.90 (d, J=20.1, 1H), 3.95-4.03 (m, 2H), 4.40-4.51 (m, 1H), 5.94 (s, 1H), 6.54-6.62 (m, 2H), 6.84 (s, 1H), 6.87-6.94 (m, 2H), 7.03 (s, 1H), 7.36 (s, 4H).

Example 82

1-{4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexyl}-piperazine-2,5-dione

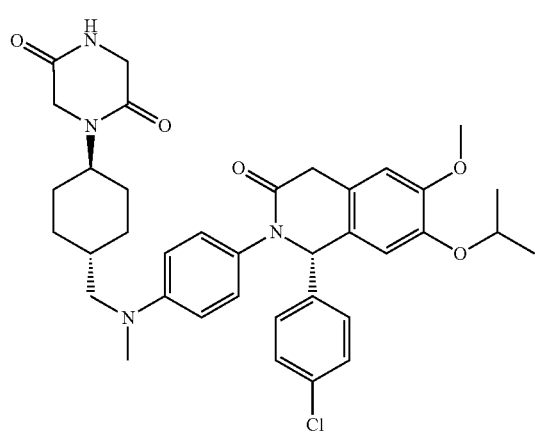 [SMILES: COc1cc2c(cc1OC(C)C)[C@H](c1ccc(Cl)cc1)N(c1ccc(N(C)C[C@H]3CC[C@H](N4CC(=O)NCC4=O)CC3)cc1)C(=O)C2]

To a solution of the crude Intermediate 82.1 (45.1 mg) in DCM (0.5 ml) was added TFA (0.182 ml, 2.36 mmol) at RT. The reaction mixture was stirred at RT for 45 min and evaporated to dryness. The resulting residue was dissolved in MeOH (0.5 ml) then Et$_3$N (0.066 ml, 0.47 mmol) was added and the mixture was stirred at RT for 1 h. The reaction mixture was directly subjected to purification by reverse phase prep-HPLC (Waters system) to yield the title compound (TFA salt, 18 mg, 0.023 mmol, 49% over 2 steps) as a colorless solid. HPLC: $^At_{Ret}$=1.99 min; LC-MS: m/z 659.3 [M+H]$^+$; $^1$H NMR (400 MHz, DMSO-d$_6$): 1.01-1.15 (m, 2H), 1.19 (d, J=5.9, 3H), 1.24 (d, J=6.1, 3H), 1.39-1.56 (m, 4H), 1.57-1.68 (m, 1H), 1.68-1.78 (m, 2H), 2.89 (s, 3H), 3.13 (d, J=6.6, 2H), 3.57 (d, J=20.1, 1H), 3.69-3.78 (m, 7H), 3.90 (d, J=19.8, 2H), 4.09-4.19 (m, 1H), 4.41-4.51 (m, 1H), 5.95 (s, 1H), 6.54-6.64 (m, 2H), 6.84 (s, 1H), 6.87-6.95 (m, 2H), 7.04 (s, 1H), 7.36 (s, 4H), 8.09 (br. s., 1H).

Intermediate 82.1: ((2-tert-Butoxycarbonylamino-acetyl)-{4-[({4-[(S)-1-(4-chloro-phenyl)-7-isopropoxy-6-methoxy-3-oxo-3,4-dihydro-1H-isoquinolin-2-yl]-phenyl}-methyl-amino)-methyl]-trans-cyclohexyl}-amino)-acetic acid methyl ester

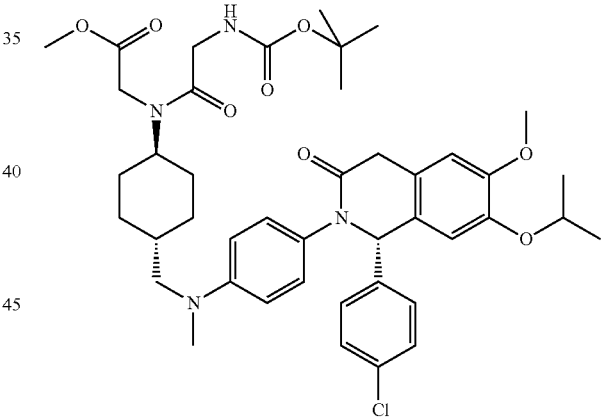

To a solution of Intermediate 79.1 (30 mg, 0.047 mmol) in DMF (0.5 ml) were successively added tert-butoxycarbonylamino-acetic acid (9.12 mg, 0.052 mmol), Et$_3$N (0.013 ml, 0.095 mmol) and HATU (23.38 mg, 0.061 mmol) at RT. The reaction mixture was heated at 50° C. and stirred for 2 h30, then cooled to RT, diluted with Et$_2$O and washed with water (2×). The organic phase was dried over Na$_2$SO$_4$, filtered and evaporated to dryness to yield the crude title compound (45.1 mg) as a yellow resin, which was used in the next step without further purification. HPLC: $^At_{Ret}$=2.67 min; LC-MS: m/z 791.3 [M+H]$^+$.

Example 83

2-(Carbamoylmethyl-{4-[({4-[(S)-1-(4-chloro-phenyl)-7-isopropoxy-6-methoxy-3-oxo-3,4-dihydro-1H-isoquinolin-2-yl]-phenyl}-methyl-amino)-methyl]-trans-cyclohexyl}-amino)-acetamide

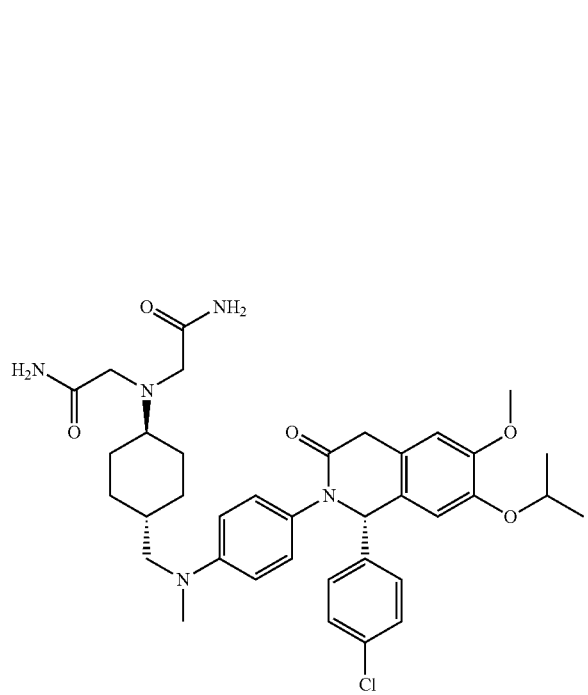 [SMILES: COc1cc2c(cc1OC(C)C)[C@H](c1ccc(Cl)cc1)N(c1ccc(N(C)C[C@H]3CC[C@H](N(CC(N)=O)CC(N)=O)CC3)cc1)C(=O)C2]

A suspension of Intermediate 77.3 (20 mg, 0.036 mmol), 2-bromoacetamide (15.7 mg, 0.114 mmol) and K$_2$CO$_3$ (14.8 mg, 0.107 mmol) in DMF (0.5 ml) was stirred at RT for 14 h, then diluted with DCM and washed with water. The organic phase was dried over Na$_2$SO$_4$, filtered and evaporated to dryness. The resulting crude material was purified by Combi-Flash Companion™ (Isco Inc.) column chromatography (SiO$_2$; gradient elution, DCM/[DCM/7M NH$_3$ in MeOH 9:1] 95:5→100% DCM/7M NH$_3$ in MeOH 9:1) to yield the title compound (17 mg, 0.025 mmol, 71%) as a colorless solid. TLC: R$_F$=0.16 (DCM/7M NH$_3$ in MeOH 9:1); HPLC: $^A$t$_{Ret}$=1.81 min; LC-MS: m/z 676.3 [M+H]$^+$; $^1$H NMR (400 MHz, DMSO-d$_6$): 0.87-1.01 (m, 2H), 1.05-1.16 (m, 2H), 1.19 (d, J=6.1, 3H), 1.24 (d, J=6.1, 3H), 1.50-1.64 (m, 1H), 1.64-1.81 (m, 4H), 2.27-2.38 (m, 1H), 2.86 (s, 3H), 2.97 (s, 4H), 3.05-3.12 (m, 2H), 3.57 (d, J=19.8, 1H), 3.73 (s, 3H), 3.89 (d, J=19.8, 1H), 4.40-4.50 (m, 1H), 5.94 (s, 1H), 6.52-6.59 (m, 2H), 6.83 (s, 1H), 6.85-6.92 (m, 2H), 7.04 (s, 1H), 7.06-7.13 (m, 2H), 7.35 (s, 4H), 7.66-7.73 (m, 2H).

Example 84

(S)-1-(4-Chloro-phenyl)-7-isopropoxy-6-methoxy-2-(4-{methyl-[4-(3-oxo-[1,4]diazepan-1-yl)-trans-cyclohexylmethyl]-amino}-phenyl)-1,4-dihydro-2H-isoquinolin-3-one

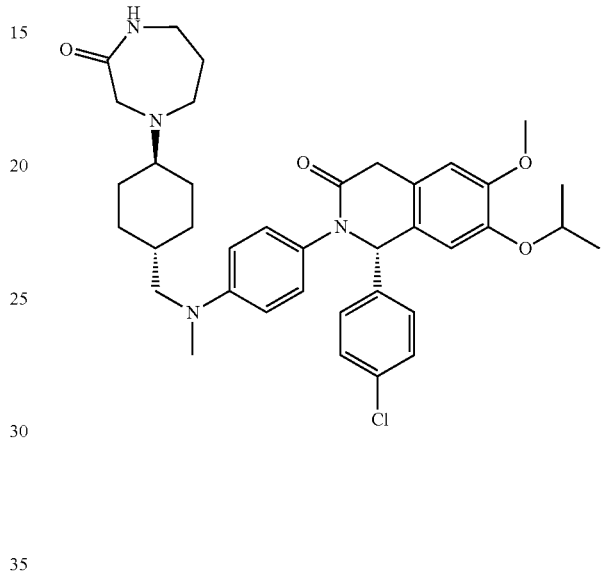

To a solution of the crude Intermediate 84.1 (41.9 mg) in MeOH (0.5 ml) were successively added NH$_4$Cl (22.97 mg, 0.429 mmol) and ammonium formate (6.02 mg, 0.095 mmol). The reaction flask was evacuated under vacuum and flushed with argon (3×) then Pd/C (1.016 mg, 0.01 mmol) was added, the flask was sealed and the reaction mixture was stirred at RT for 2 h. Additional ammonium formate (18.05 mg, 0.286 mmol) was added and the reaction mixture was further stirred at RT for 1 h. The suspension was filtered and the filtrate evaporated to dryness. The resulting residue was dissolved in AcOEt and washed with water. The organic phase was dried over Na$_2$SO$_4$, filtered and evaporated to dryness. The resulting residue was dissolved in MeOH (0.5 ml) then Et$_3$N (0.062 ml, 0.44 mmol) was added and the mixture was stirred at RT for 14 h. The reaction mixture was directly subjected to purification by reverse phase prep-HPLC (Waters system) to yield the title compound (TFA salt, 12.8 mg, 0.017 mmol, 35% from Intermediate 79.1) as a colorless solid. HPLC: $^A$t$_{Ret}$=1.81 min; LC-MS: m/z 659.3 [M+H]$^+$; $^1$H NMR (400 MHz, DMSO-d): 0.97-1.13 (m, 2H), 1.19 (d, J=6.1, 3H), 1.24 (d, J=6.1, 3H), 1.37-1.54 (m, 2H), 1.61-1.74 (m, 1H), 1.74-1.90 (m, 3H), 1.90-2.10 (m, 3H), 2.89 (s, 3H), 3.08-3.15 (m, 2H), 3.16-3.51 (m, 5H), 3.57 (d, J=20.1, 1H), 3.73 (s, 3H), 3.75-3.83 (m, 1H), 3.91 (d, J=19.6, 1H), 4.09-4.21 (m, 1H), 4.40-4.52 (m, 1H), 5.94 (s, 1H), 6.53-6.62 (m, 2H), 6.84 (s, 1H), 6.87-6.95 (m, 2H), 7.03 (s, 1H), 7.36 (s, 4H), 8.30-8.40 (m, 1H).

Intermediate 84.1: ((3-Benzyloxycarbonylamino-propyl)-{4-[({4-[(S)-1-(4-chloro-phenyl)-7-isopropoxy-6-methoxy-3-oxo-3,4-dihydro-1H-isoquinolin-2-yl]-phenyl}-methyl-amino)-methyl]-trans-cyclohexyl}-amino)-acetic acid methyl ester

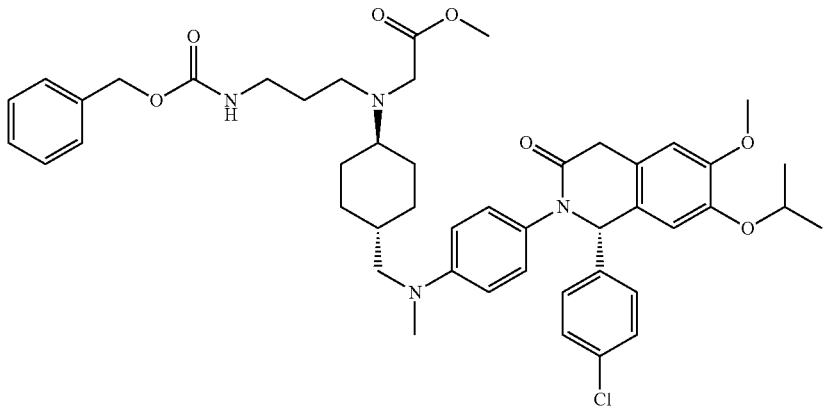 [SMILES: COC(=O)CN(CCCNC(=O)OCc1ccccc1)[C@H]1CC[C@H](CN(C)c2ccc(N3C(=O)Cc4cc(OC)c(OC(C)C)cc4[C@@H]3c3ccc(Cl)cc3)cc2)CC1]

To a solution of Intermediate 79.1 (30 mg, 0.047 mmol) in DCM (0.5 ml) were successively added 3-[(benzyloxycarbonyl)-amino]propionaldehyde (11.76 mg, 0.057 mmol), AcOH (0.005 ml, 0.095 mmol) and NaBH(OAc)₃ (20.05 mg, 0.095 mmol) at RT. The suspension was stirred at RT for 1 h then diluted with DCM and washed with a 2M aqueous Na₂CO₃ solution. The organic phase was dried over Na₂SO₄, filtered and evaporated to dryness to give the crude title compound (41.9 mg) as a yellow resin, which was used in the next step without further purification. HPLC: $^A t_{Ret}$=2.25 min; LC-MS: m/z 825.4 [M+H]⁺.

Example 85

(S)-1-(4-Chloro-phenyl)-7-isopropoxy-6-methoxy-2-(4-{methyl-[4-(4-oxo-imidazolidin-1-yl)-trans-cyclohexylmethyl]-amino}-phenyl)-1,4-dihydro-2H-isoquinolin-3-one

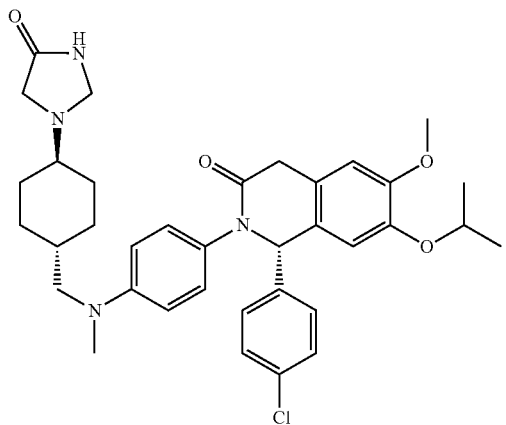 [SMILES: COc1cc2c(cc1OC(C)C)[C@H](c1ccc(Cl)cc1)N(c1ccc(N(C)C[C@H]3CC[C@H](N4CNC(=O)C4)CC3)cc1)C(=O)C2]

A solution of the crude Intermediate 85.1 (135 mg) and formaldehyde (37% in water, 0.156 ml, 2.1 mmol) in EtOH (3 ml) was heated at 80° C. and stirred for 4 h. The reaction mixture was cooled to RT and evaporated to dryness. The resulting residue was heated at 150° C. for 14 h under vacuum then cooled to RT and purified by reverse phase prep-HPLC (Waters system) to yield the title compound (TFA salt, 22.5 mg, 0.030 mmol, 14% from Intermediate 79.1) as a yellow solid. HPLC: $^A t_{Ret}$=1.89 min; LC-MS: m/z 631.2 [M+H]⁺; ¹H NMR (400 MHz, CD₃OD): 1.07-1.18 (m, 2H), 1.20 (d, J=6.1, 3H), 1.26 (d, J=6.1, 3H), 1.33-1.47 (m, 2H), 1.71-1.85 (m, 1H), 1.87-1.96 (m, 2H), 2.10-2.21 (m, 2H), 2.96 (s, 3H), 3.21 (d, J=6.6, 2H), 3.26-3.29 (m, 1H), 3.72 (d, J=20.3, 1H), 3.84 (s, 3H), 3.95 (s, 2H), 4.03 (d, J=20.3, 1H), 4.39-4.49 (m, 1H), 4.80 (s, 2H), 5.87 (s, 1H), 6.64-6.71 (m, 2H), 6.78 (s, 1H), 6.85-6.93 (m, 3H), 7.13-7.20 (m, 2H), 7.25-7.31 (m, 2H).

Intermediate 85.1: 2-{4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexylamino}-acetamide

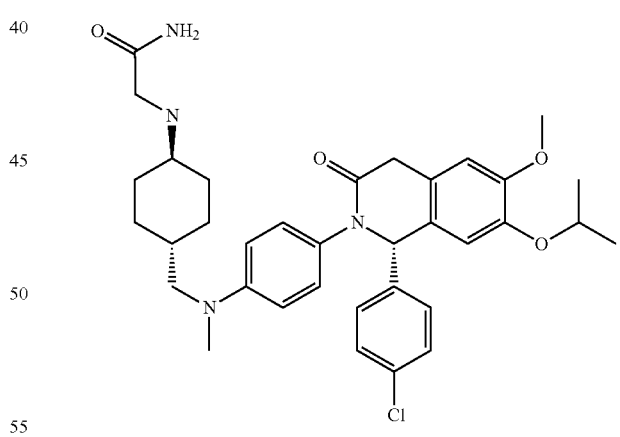

In a sealed reaction flask, a solution of Intermediate 79.1 (134 mg, 0.21 mmol) in a 7M NH₃ solution in MeOH (3.35 ml) was heated at 70° C. and stirred for 14 h. The reaction mixture was cooled to RT and evaporated to dryness to yield the crude title compound (135 mg) as an orange resin, which was used in the next step without further purification. HPLC: $^A t_{Ret}$=1.85 min; LC-MS: m/z 619.3 [M+H]⁺; ¹H NMR (400 MHz, CD₃OD): 0.95-1.14 (m, 4H), 1.21 (d, J=5.9, 3H), 1.26 (d, J=6.1, 3H), 1.64-1.80 (m, 3H), 1.90-1.98 (m, 2H), 2.33-2.44 (m, 1H), 2.93 (s, 3H), 3.12-3.19 (m, 2H), 3.26 (s, 2H), 3.35 (s, 2H), 3.71 (d, J=20.1, 1H), 3.84 (s, 3H), 4.02 (d, J=20.5, 1H), 4.40-4.49 (m, 1H), 5.86 (s, 1H), 6.59-6.65 (m, 2H), 6.79 (s, 1H), 6.82-6.89 (m, 3H), 7.13-7.18 (m, 2H), 7.25-7.31 (m, 2H).

Example 86

Compounds 86a to 86e were obtained analogously to Example 75 by reaction of Intermediate 75.6 (or analogues prepared similarly) with various bromo- or iodo-aryl intermediates prepared analogously to Intermediate 75.8. Compounds 86f and 86 g were obtained analogously to Example 77 and Example 78 by reaction of Intermediate 77.3 (or analogues prepared similarly) with various sulfonyl chlorides, acyl chlorides or carboxylic acids. Compounds 86h and 86i were obtained analogously to Example 81 by reaction of Intermediate 77.3 (or analogues prepared similarly) with various bis-halogenated alkyl analogues.

| # | Structure | Name/HPLC/MS/NMR |
|---|---|---|
| 86a | 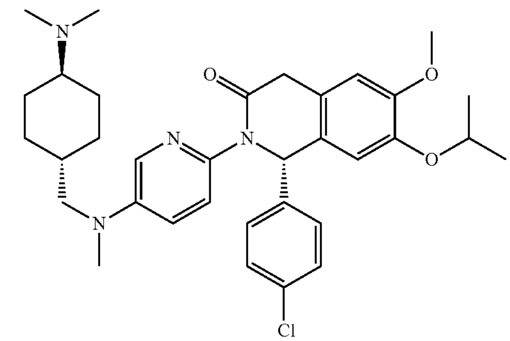 [SMILES: COc1cc2c(cc1OC(C)C)[C@H](c1ccc(Cl)cc1)N(c1ccc(N(C)C[C@H]3CC[C@H](N(C)C)CC3)cn1)C(=O)C2] | (S)-1-(4-Chloro-phenyl)-2-{5-[(trans-4-dimethylamino-cyclohexylmethyl)-methyl-amino]-pyridin-2-yl}-7-isopropoxy-6-methoxy-1,4-dihydro-2H-isoquinolin-3-one.<br>HPLC: $^{A}t_{Ret}$ = 1.83; LC-MS: m/z 591.6 [M + H]$^{+}$. |
| 86b | 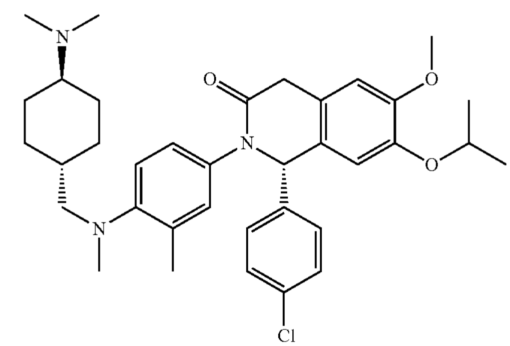 [SMILES: COc1cc2c(cc1OC(C)C)[C@H](c1ccc(Cl)cc1)N(c1ccc(N(C)C[C@H]3CC[C@H](N(C)C)CC3)c(C)c1)C(=O)C2] | (S)-1-(4-Chloro-phenyl)-2-{4-[(trans-4-dimethylamino-cyclohexylmethyl)-methyl-amino]-3-methyl-phenyl}-7-isopropoxy-6-methoxy-1,4-dihydro-2H-isoquinolin-3-one<br>NVP-CEX461-AI-1<br>HPLC: $^{A}t_{Ret}$ = 1.61; LC-MS: m/z 604.7 [M + H]$^{+}$. |
| 86c | 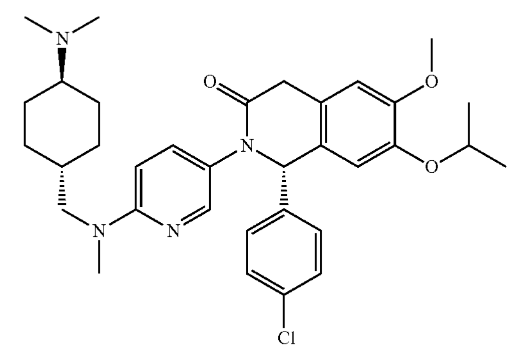 [SMILES: COc1cc2c(cc1OC(C)C)[C@H](c1ccc(Cl)cc1)N(c1ccc(N(C)C[C@H]3CC[C@H](N(C)C)CC3)nc1)C(=O)C2] | (S)-1-(4-Chloro-phenyl)-2-{6-[(trans-4-dimethylamino-cyclohexylmethyl)-methyl-amino]-pyridin-3-yl}-7-isopropoxy-6-methoxy-1,4-dihydro-2H-isoquinolin-3-one.<br>HPLC: $^{A}t_{Ret}$ = 1.56; LC-MS: m/z 591.7 [M + H]$^{+}$. |
| 86d | 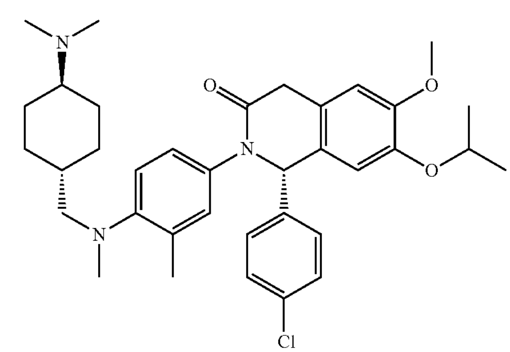 | (S)-1-(4-Chloro-phenyl)-2-{4-[(trans-4-dimethylamino-cyclohexylmethyl)-methyl-amino]-3-fluoro-phenyl}-7-isopropoxy-6-methoxy-1,4-dihydro-2H-isoquinolin-3-one.<br>HPLC: $^{A}t_{Ret}$ = 1.98; LC-MS: m/z 608.7 [M + H]$^{+}$. |

| # | Structure | Name/HPLC/MS/NMR |
|---|---|---|
| 86e | 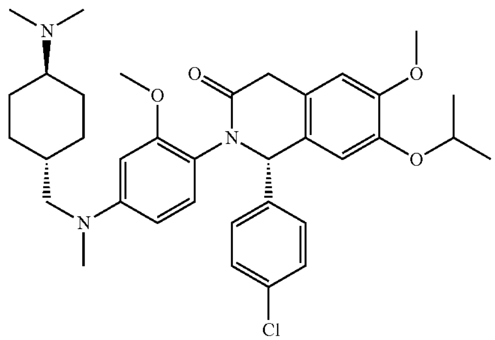 [SMILES: COc1cc2c(cc1OC(C)C)[C@H](c1ccc(Cl)cc1)N(c1ccc(N(C)C[C@H]3CC[C@H](N(C)C)CC3)cc1OC)C(=O)C2] | (S)-1-(4-Chloro-phenyl)-2-{4-[(trans-4-dimethylamino-cyclohexylmethyl)-methyl-amino]-2-methoxy-phenyl}-7-isopropoxy-6-methoxy-1,4-dihydro-2H-isoquinolin-3-one.<br>HPLC: $^A t_{Ret}$ = 1.92; LC-MS: m/z 620.3 [M + H]$^+$. |
| 86f | 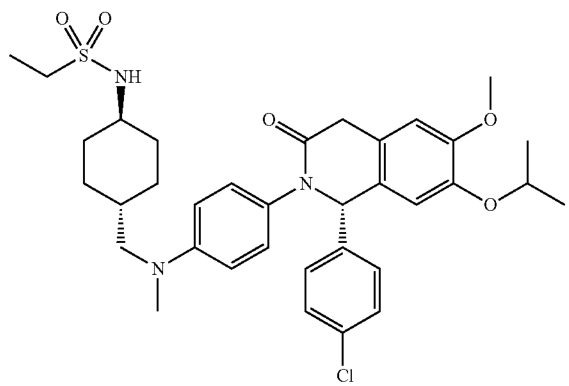 [SMILES: CCS(=O)(=O)N[C@H]1CC[C@H](CN(C)c2ccc(N3C(=O)Cc4cc(OC)c(OC(C)C)cc4[C@@H]3c3ccc(Cl)cc3)cc2)CC1] | Ethanesulfonic acid {4-[({4-[(S)-1-(4-chloro-phenyl)-7-isopropoxy-6-methoxy-3-oxo-3,4-dihydro-1H-isoquinolin-2-yl]-phenyl}-methyl-amino)-methyl]-trans-cyclohexyl}-amide.<br>HPLC: $^A t_{Ret}$ = 2.25; LC-MS: m/z 654.7 [M + H]$^+$. |
| 86g | 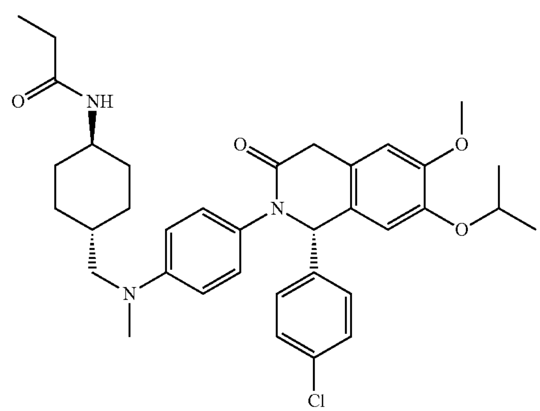 [SMILES: CCC(=O)N[C@H]1CC[C@H](CN(C)c2ccc(N3C(=O)Cc4cc(OC)c(OC(C)C)cc4[C@@H]3c3ccc(Cl)cc3)cc2)CC1] | N-{4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexyl}-propionamide.<br>HPLC: $^A t_{Ret}$ = 2.13; LC-MS: m/z 618.3 [M + H]$^+$. |
| 86h | 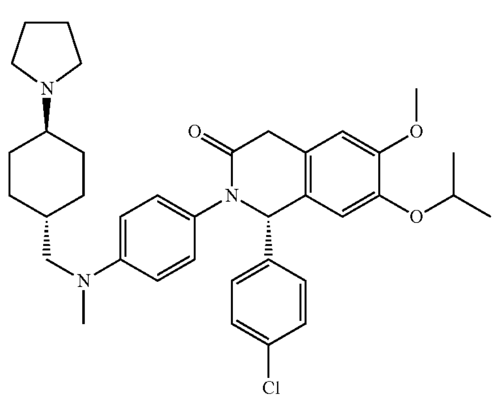 [SMILES: COc1cc2c(cc1OC(C)C)[C@H](c1ccc(Cl)cc1)N(c1ccc(N(C)C[C@H]3CC[C@H](N4CCCC4)CC3)cc1)C(=O)C2] | (S)-1-(4-Chloro-phenyl)-7-isopropoxy-6-methoxy-2-{4-[methyl-(trans-4-pyrrolidin-1-yl-cyclohexylmethyl)-amino]-phenyl}-1,4-dihydro-2H-isoquinolin-3-one.<br>HPLC: $^A t_{Ret}$ = 1.89; LC-MS: m/z 616.4 [M + H]$^+$. |

| # | Structure | Name/HPLC/MS/NMR |
|---|---|---|
| 86i | 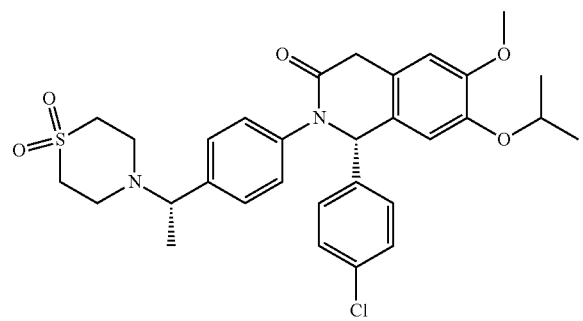 | (S)-1-(4-Chloro-phenyl)-7-isopropoxy-6-methoxy-2-{4-[methyl-(trans-4-piperidin-1-yl-cyclohexylmethyl)-amino]-phenyl}-1,4-dihydro-2H-isoquinolin-3-one. HPLC: $^A t_{Ret}$ = 1.92; LC-MS: m/z 630.4 [M + H]$^+$. |

Example 87

(S)-1-(4-Chloro-phenyl)-2-{4-[(S)-1-(1,1-dioxo-1lambda*6*-thiomorpholin-4-yl)-ethyl]-phenyl}-7-isopropoxy-6-methoxy-1,4-dihydro-2H-isoquinolin-3-one The title compound (TFA salt, 11.9 mg, 0.017 mmol, 20%) was obtained as a light yellow solid from Intermediate 75.6 (30 mg, 0.087 mmol) and Intermediate 87.1 (41.4 mg, 0.13 mmol) analogously to Example 75. Purification of the crude material was performed by reverse phase prep-HPLC (Waters system). HPLC: $^A t_{Ret}$=1.90 min; LC-MS: m/z 583.5 [M+H]$^+$; $^1$H NMR (400 MHz, CD$_3$OD): 1.23 (d, J=5.9, 3H), 1.28 (d, J=6.1, 1H), 1.53 (d, J=6.6, 1H), 3.21 (br. s., 8H), 3.77 (d, J=20.3, 1H), 3.87 (s, 3H), 4.05 (d, J=20.3, 1H), 4.10-4.19 (m, 1H), 4.42-4.52 (spt, J=5.9, 1H), 6.02 (s, 1H), 6.83 (s, 1H), 6.90 (s, 1H), 7.15-7.23 (m, 4H), 7.28-7.34 (m, 2H), 7.41-7.47 (m, 2H).

Intermediate 87.1: 4-[(S)-1-(4-Bromo-phenyl)-ethyl]-thiomorpholine 1,1-dioxide

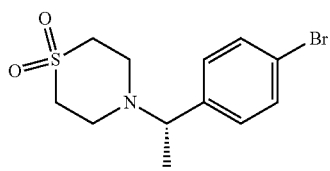 [SMILES: C[C@@H](c1ccc(Br)cc1)N1CCS(=O)(=O)CC1]

A solution of (S)-1-(4-bromophenyl)ethanamine (0.144 ml, 1.0 mmol) and vinylsulfonylethene (0.100 ml, 1.0 mmol) in EtOH (4.0 ml) was heated at 100° C. and stirred for 3 h. The reaction mixture was cooled to RT and evaporated to dryness. The resulting crude material was purified by Combi-Flash Companion™ (Isco Inc.) column chromatography (gradient elution, heptane/AcOEt 95:5 to 4:6) to yield the title compound (256 mg, 0.804 mmol, 80% yield) as a colorless oil which crystallized on standing into a colorless solid. TLC: R$_F$=0.40 (heptane/AcOEt 1:1); HPLC: $^B t_{Ret}$=1.29 min; LC-MS: m/z 320.2 [M+H]$^+$; $^1$H NMR (400 MHz, CDCl$_3$): 1.39 (d, J=6.8, 3H), 2.92-3.09 (m, 8H), 3.76 (q, J=6.8, 1H), 7.19-7.26 (m, 2H), 7.45-7.53 (m, 2H).

Example 88

(S)-2-{4-[(S)-1-(4-Acetyl-piperazin-1-yl)-ethyl]-phenyl}-1-(4-chloro-phenyl)-7-isopropoxy-6-methoxy-1,4-dihydro-2H-isoquinolin-3-one

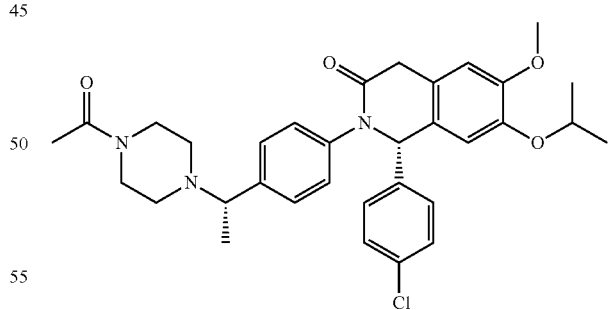

The title compound (TFA salt, 18.3 mg, 0.027 mmol, 26%) was obtained from Intermediate 75.6 (36 mg, 0.104 mmol) and Intermediate 88.3 (48.6 mg, 0.156 mmol) analogously to Example 75. Purification of the crude material was performed by reverse phase prep-HPLC (Waters system). HPLC: $^A t_{Ret}$=1.76 min; LC-MS: m/z 576.5 [M+H]$^+$; $^1$H NMR (400 MHz, DMSO-d$_6$): 1.22 (d, J=6.1, 3H), 1.25 (d, J=5.9, 3H), 1.53-1.68 (m, 3H), 2.01 (br. s., 3H), 2.69-3.20 (m, 4H), 3.56-3.69 (m, 2H), 3.73 (s, 3H), 3.86 (d, J=19.8, 1H), 3.90-4.08 (m, 1H), 4.36-4.61 (m, 3H), 6.17 (s, 1H), 6.87 (s, 1H), 7.13 (s, 1H), 7.30-7.42 (m, 6H), 7.44-7.54 (m, 2H).

Intermediate 88.1: 1-[(S)-1-(4-Bromo-phenyl)-ethyl]-4-(toluene-4-sulfonyl)-piperazine

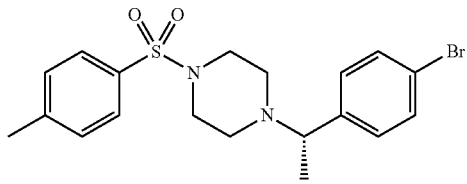 [SMILES: Cc1ccc(S(=O)(=O)N2CCN([C@@H](C)c3ccc(Br)cc3)CC2)cc1]

A mixture of (S)-1-(4-bromophenyl)ethanamine (0.36 ml, 2.50 mmol) and N,N-bis(2-chloroethyl)-4-methylbenzene-sulfonamide (864 mg, 2.62 mmol) in DIPEA (0.873 ml, 5.0 mmol) was heated at 125° C. and stirred for 20 h. The reaction mixture was cooled to RT then diluted into DCM (30 ml) and washed with Na$_2$CO$_3$ 2M in water (40 ml). The aqueous phase was further extracted with DCM (3×20 ml) and the combined organic fractions were dried over Na$_2$SO$_4$, filtered and evaporated to dryness. AcOEt was added in small portions into a hot mixture of the crude in heptane until complete dissolution. The mixture was allowed to cooled to RT during which time precipitation occurred. The mixture was cooled to 0° C. (ice bath) for 30 min then filtered. The solid was washed with heptane, dried under air and finally under high vacuum to yield the title compound (810 mg, 1.91 mmol, 77% yield) as a brownish solid. HPLC: $^A t_{Ret}$=1.66 min; LC-MS: m/z 425.4 [M+H]$^+$; $^1$H NMR (400 MHz, CDCl$_3$): 1.29 (d, J=6.8, 3H), 2.41-2.50 (m, 5H), 2.52-2.61 (m, 2H), 2.93-3.05 (m, 4H), 3.34 (q, J=6.7, 1H), 7.09-7.16 (m, 2H), 7.31-7.37 (m, 2H), 7.39-7.44 (m, 2H), 7.61-7.66 (m, 2H).

Intermediate 88.2: 1-[(S)-1-(4-Bromo-phenyl)-ethyl]-piperazine

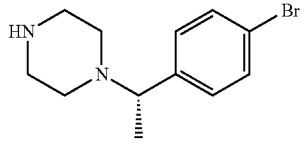

To a solution of Intermediate 88.1 (802 mg, 1.89 mmol) in TFA (1.46 ml, 18.95 mmol) was added H$_2$SO$_4$ (0.707 ml, 13.26 mmol) at RT. The mixture was heated at 75° C. and stirred for 6 h then cooled to RT, diluted with AcOEt and carefully washed with Na$_2$CO$_3$ 2M in water (2×) and brine. The organic layer was dried over Na$_2$SO$_4$, filtered and evaporated to dryness to yield the crude title compound (479.6 mg, 1.728 mmol, 91% yield) as an orange oil which was used in the next step without further purification. HPLC: $^A t_{Ret}$=0.86 min; LC-MS: m/z 269.5 [M+H]$^+$; $^1$H NMR (400 MHz, CDCl$_3$): 1.33 (d, J=6.6, 3H), 2.29-2.39 (m, 2H), 2.40-2.53 (m, 2H), 2.84-2.90 (m, 4H), 3.32 (q, J=6.8, 1 H), 7.18-7.24 (m, 2H), 7.41-7.48 (m, 2H).

Intermediate 88.3: 1-{4-[(S)-1-(4-Bromo-phenyl)-ethyl]-piperazin-1-yl}-ethanone

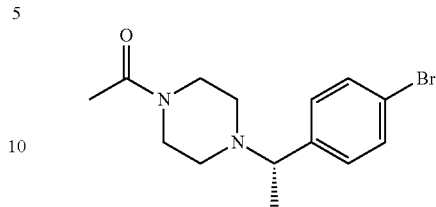

To a solution of Intermediate 88.2 (103 mg, 0.371 mmol) in DCM (1.8 ml) were successively added Et$_3$N (0.155 ml, 1.113 mmol) and acetyl chloride (0.066 ml, 0.928 mmol) at RT. The mixture was stirred at RT for 1 h then diluted into AcOEt (20 ml) and washed with Na$_2$CO$_3$ 2M in water (10 ml). The organic phase was dried over Na$_2$SO$_4$, filtered and evaporated to dryness. The resulting crude material was purified by Combi-Flash Companion™ (Isco Inc.) column chromatography (SiO$_2$; gradient elution, [heptane/DCM 1:1]/TBME containing 5% of 7M NH$_3$ in MeOH 95:5 to 1:1) to yield the title compound (108 mg, 0.347 mmol, 93% yield) as a light yellow oil. HPLC: $^A t_{Ret}$=1.01 min; LC-MS: m/z 311.4 [M+H]$^+$; $^1$H NMR (400 MHz, CDCl$_3$): 1.35 (d, J=6.6, 3H), 2.07 (s, 3H), 2.29-2.54 (m, 4H), 3.37 (q, J=6.8, 1H), 3.43 (t, J=5.1, 2H), 3.52-3.68 (m, 2H), 7.17-7.24 (m, 2H), 7.43-7.49 (m, 2H).

Example 89

(R)-1-(S)-1-{4-[(S)-1-(4-Chloro-phenyl)-7-isopropoxy-6-methoxy-3-oxo-3,4-dihydro-1H-isoquinolin-2-yl]-phenyl}-ethyl)-pyrrolidine-2-carboxylic acid methylamide

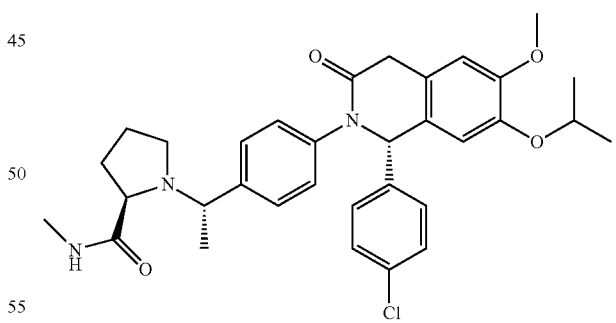

To a solution of Intermediate 89.4 (TFA salt, 8.7 mg, 0.013 mmol) in DMF (0.5 ml) were successively added methylamine (2M in THF, 0.077 ml, 0.155 mmol), Et$_3$N (0.004 ml, 0.031 mmol) and HATU (11.8 mg, 0.031 mmol) at RT. The reaction mixture was heated at 50° C. and stirred for 14 h, then cooled to RT and directly subjected to purification by reverse phase prep-HPLC (Waters system) to yield the title compound (TFA salt, 4.8 mg, 0.007 mmol, 54%) as a colorless solid. HPLC: $^A t_{Ret}$=1.76 min; LC-MS: m/z 576.5 [M+H]$^+$.

Intermediate 89.1: (R)-1-[(S)-1-(4-Bromo-phenyl)-ethyl]-pyrrolidine-2-carboxylic acid methyl ester And Intermediate 89.2: (S)-1-[(S)-1-(4-Bromo-phenyl)-ethyl]-pyrrolidine-2-carboxylic acid methyl ester

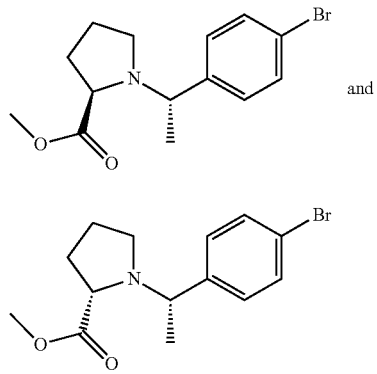

The following procedure was adapted from W. A. J. Starmans, R. W. A. Walgers, L. Thijs, R. de Gelder, J. M. M. Smits, and B. Zwanenburg, Tetrahedron 54 (1998) 4991-5004. To a mixture of methyl 2,5-dibromopentanoate (0.401 ml, 2.56 mmol) and $K_2CO_3$ (706 mg, 5.11 mmol) in MeCN (7 ml) and water (0.7 ml) was added dropwise a solution of (S)-1-(4-bromophenyl)ethanamine (0.405 ml, 2.81 mmol) in MeCN (3.5 ml) at 80° C. After the addition, the reaction mixture was further stirred at 80° C. for 14 h then cooled to RT, diluted into AcOEt (50 ml) and washed with water (40 ml). The aqueous phase was further extracted with AcOEt and the combined organic fractions were dried over $Na_2SO_4$, filtered and evaporated to dryness. The resulting crude material was purified and both diastereoisomers separated by reversed phase prep-HPLC (gradient elution, MeCN/water containing 20 mM ammonium formate). Fractions containing pure material were combined and concentrated under vacuum. The resulting aqueous mixture was basified by the addition of $Na_2CO_3$ 2M and extracted with AcOEt. The organic layer was washed with brine, dried over $Na_2SO_4$, filtered and evaporated to dryness to yield the title compounds as light yellow oils. Intermediate 89.1: 240 mg, 0.77 mmol, 30%; HPLC: $^At_{Ret}$=1.15 min; $^Ct_{Ret}$=4.07 min; LC-MS: m/z 314.4 [M+H]$^+$; $^1$H NMR (400 MHz, CDCl$_3$): 1.38 (d, J=6.6, 3H), 1.76-1.99 (m, 3H), 2.04-2.16 (m, 1H), 2.52 (q, J=8.1, 1H), 3.05-3.13 (m, 1H), 3.47 (dd, J=9.4, 3.5, 1H), 3.51 (s, 3H), 3.66 (q, J=6.6, 1H), 7.21-7.26 (m, 2H), 7.39-7.45 (m, 2H). Intermediate 89.2: 222 mg, 0.71 mmol, 28%; HPLC: $^At_{Ret}$=1.15 min, $^Ct_{Ret}$=5.18 min; LC-MS: m/z 314.4 [M+H]$^+$; $^1$H NMR (400 MHz, CDCl$_3$): 1.36 (d, J=6.8, 3H), 1.73-1.84 (m, 1H), 1.84-1.96 (m, 2H), 2.03-2.14 (m, 1H), 2.54-2.63 (m, 1H), 2.93-3.02 (m, 1H), 3.31 (dd, J=9.2, 4.0, 1H), 3.69 (s, 3H), 3.72 (q, J=6.6, 1 H), 7.17-7.22 (m, 2H), 7.42-7.47 (m, 2H). The configuration of each diastereoisomers was attributed by comparing the $^1$H NMR spectra with published $^1$H NMR data of close analogues (see R. Almansa, D. Guijarro and M. Yus Tetrahedron: Asymmetry 18, 2007, 2828-2840).

Intermediate 89.3: (R)-1-((S)-1-{4-[(S)-1-(4-Chloro-phenyl)-7-isopropoxy-6-methoxy-3-oxo-3,4-dihydro-1H-isoquinolin-2-yl]-phenyl}-ethyl)-pyrrolidine-2-carboxylic acid methyl ester

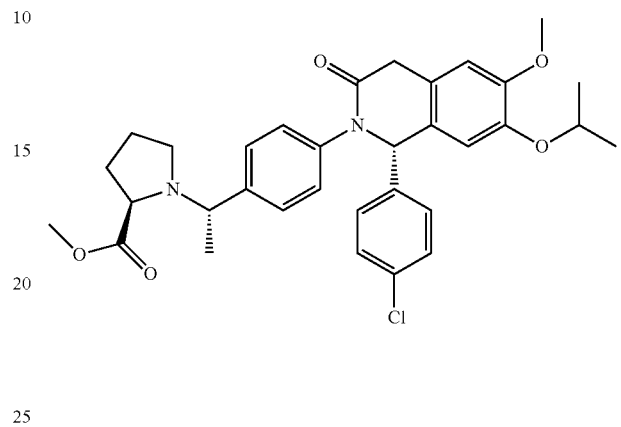

The title compound (TFA salt, 50.3 mg, 0.073 mmol, 36%) was obtained as a yellow solid from Intermediate 75.6 (70 mg, 0.20 mmol) and Intermediate 89.1 (95 mg, 0.30 mmol) analogously to Example 75. Purification of the crude material was performed by reverse phase prep-HPLC (Waters system). HPLC: $^At_{Ret}$=1.85 min; LC-MS: m/z 577.5 [M+H]$^+$.

Intermediate 89.4: (R)-1-((S)-1-{4-[(S)-1-(4-Chloro-phenyl)-7-isopropoxy-6-methoxy-3-oxo-3,4-dihydro-1H-isoquinolin-2-yl]-phenyl}-ethyl)-pyrrolidine-2-carboxylic acid

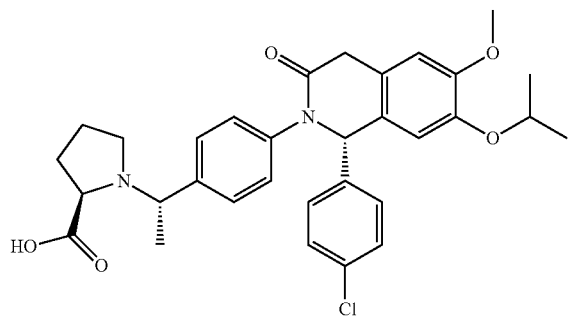 [SMILES: COc1cc2c(cc1OC(C)C)[C@H](c1ccc(Cl)cc1)N(c1ccc([C@H](C)N3CCC[C@@H]3C(=O)O)cc1)C(=O)C2]

A mixture of Intermediate 89.3 (TFA salt, 50.3 mg, 0.073 mmol) and LiOH monohydrate (22 mg, 0.52 mmol) in MeOH (1 ml) and water (0.25 ml) was heated at 60° C. and stirred for 14 h then cooled to RT and directly subjected to purification by reverse phase prep-HPLC (Waters system) to yield the title compound (TFA salt, 12.4 mg, 0.018 mmol, 25%) as an off-white solid. HPLC: $^At_{Ret}$=1.85 min; LC-MS: m/z 563.6 [M+H]$^+$.

Example 90

(S)-1-((S)-1-{4-[(S)-1-(4-Chloro-phenyl)-7-isopropoxy-6-methoxy-3-oxo-3,4-dihydro-1H-isoquinolin-2-yl]-phenyl}-ethyl)-pyrrolidine-2-carboxylic acid methyl ester

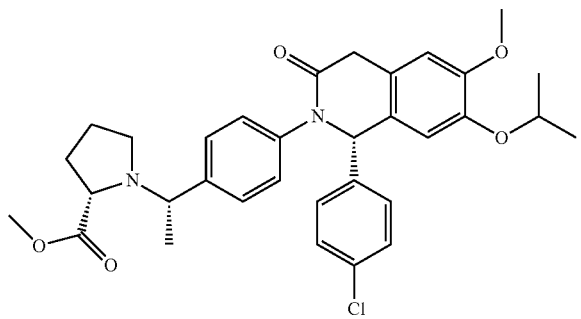 [SMILES: COC(=O)[C@@H]1CCCN1[C@@H](C)c1ccc(N2C(=O)Cc3cc(OC)c(OC(C)C)cc3[C@@H]2c2ccc(Cl)cc2)cc1]

The title compound (TFA salt, 20.5 mg, 0.030 mmol, 34%) was obtained from Intermediate 75.6 (30 mg, 0.087 mmol) and Intermediate 89.2 (40.6 mg, 0.13 mmol) analogously to Example 75. Purification of the crude material was performed by reverse phase prep-HPLC (Waters system). HPLC: $^A t_{Ret}$=1.86 min; LC-MS: m/z 577.6 [M+H]$^+$.

Example 91

Compounds 91a to 91c were obtained analogously to Example 87 and Example 88 by reaction of Intermediate 75.6 with various bromo- or iodo-aryl intermediates prepared analogously to Intermediate 87.1 or Intermediate 88.3.

| # | Structure | Name/HPLC/MS/NMR |
|---|---|---|
| 91a | 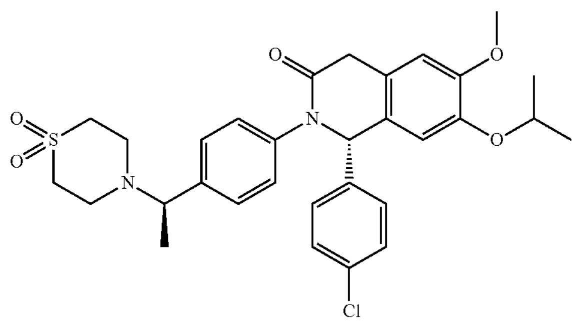 [SMILES: COc1cc2c(cc1OC(C)C)[C@H](c1ccc(Cl)cc1)N(c1ccc([C@@H](C)N3CCS(=O)(=O)CC3)cc1)C(=O)C2] | (S)-1-(4-Chloro-phenyl)-2-{4-[(R)-1-(1,1-dioxo-1lambda*6*-thiomorpholin-4-yl)-ethyl]-phneyl}-7-isopropoxy-6-methoxy-1,4-dihydro-2H-isoquinolin-3-one.<br>HPLC: $^A t_{Ret}$ = 1.91; LC-MS: m/z 583.5 [M + H]$^+$. |
| 91b | 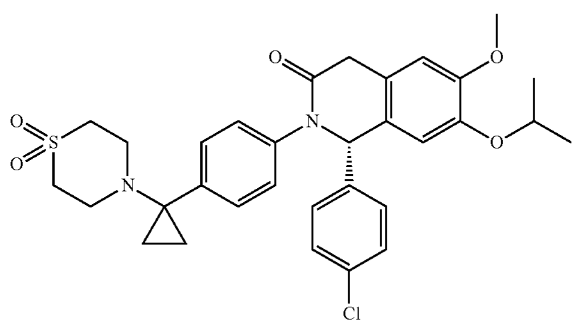 [SMILES: COc1cc2c(cc1OC(C)C)[C@H](c1ccc(Cl)cc1)N(c1ccc(C3(N4CCS(=O)(=O)CC4)CC3)cc1)C(=O)C2] | (S)-1-(4-Chloro-phenyl)-2-{4-[1-(1,1-dioxo-1lambda*6*-thiomorpholin-4-yl)-cyclopropyl]-phenyl}-7-isopropyl-6-methoxy-1,4-dihydro-2H-isoquinolin-3-one.<br>HPLC: $^A t_{Ret}$ = 2.42; LC-MS: m/z 595.6 [M + H]$^+$. |
| 91c | 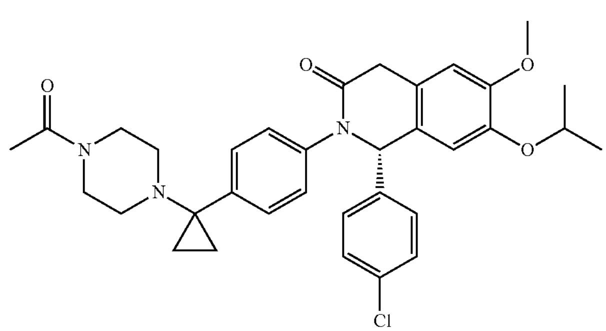 [SMILES: COc1cc2c(cc1OC(C)C)[C@H](c1ccc(Cl)cc1)N(c1ccc(C3(N4CCN(C(C)=O)CC4)CC3)cc1)C(=O)C2] | (S)-2-[4-[1-(4-Acetyl-piperazin-1-yl)-cyclopropyl]-phenyl}-1-(4-chloro-phenyl)-7-isopropoxy-6-methoxy-1,4-dihydro-2H-isoquinolin-3-one.<br>HPLC: $^A t_{Ret}$ = 1.79; LC-MS: m/z 588.6 [M + H]$^+$. |

Example 92

Trans-4-dimethylamino-cyclohexanecarboxylic acid {4-[(S)-1-(4-chloro-phenyl)-7-isopropoxy-6-methoxy-3-oxo-3,4-dihydro-1H-isoquinolin-2-yl]-phenyl}-methylamide

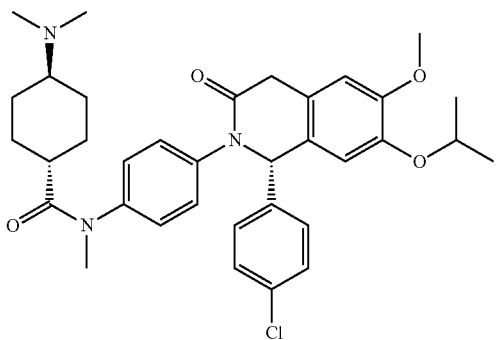 [SMILES: COc1cc2c(cc1OC(C)C)[C@H](c1ccc(Cl)cc1)N(c1ccc(N(C)C(=O)[C@H]3CC[C@H](N(C)C)CC3)cc1)C(=O)C2]

The title compound (TFA salt, 19.4 mg, 0.027 mmol, 19%) was obtained as a light yellow solid from Intermediate 75.6 (50 mg, 0.145 mmol) and Intermediate 92.2 (58.9 mg, 0.174 mmol) analogously to Example 75. Purification of the crude material was performed by reverse phase prep-HPLC (Waters system). HPLC: $^A t_{Ret}$=1.85 min; LC-MS: m/z 604.3 [M+H]$^+$; $^1$H NMR (400 MHz, DMSO-d$_6$): 1.01-1.18 (m, 2H), 1.21 (d, J=6.1, 3H), 1.25 (d, J=6.1, 3H), 1.39-1.57 (m, 2H), 1.70-1.85 (m, 2H), 1.87-2.01 (m, 2H), 2.06-2.22 (m, 1H), 2.61-2.72 (2 s, 6H), 3.02-3.21 (m, 4H), 3.65 (d, J=19.8, 1H), 3.74 (s, 3H), 3.90 (d, J=19.6, 1H), 4.41-4.50 (m, 1H), 6.17 (s, 1H), 6.88 (s, 1H), 7.09 (s, 1H), 7.24-7.42 (m, 8H).

Intermediate 92.1: {4-[(4-Bromo-phenyl)-methyl-carbamoyl]-trans-cyclohexyl}-carbamic acid tert-butyl ester

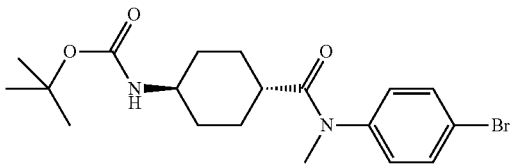 [SMILES: CN(c1ccc(Br)cc1)C(=O)[C@H]1CC[C@H](NC(=O)OC(C)(C)C)CC1]

To a solution of trans-4-(Boc-amino)cyclohexanecarboxylic acid (148 mg, 0.608 mmol) in DMF were successively added 4-bromo-N-methylaniline (0.084 ml, 0.669 mmol), Et$_3$N (0.170 ml, 1.217 mmol) and HATU (278 mg, 0.730 mmol) at RT. The reaction mixture was heated at 80° C. for 6 h then additional HATU (278 mg, 0.730 mmol) was added and the mixture was further stirred at 80° C. for 14 h. The reaction mixture was cooled to RT, diluted with TBME and washed successively with HCl 2M in water and Na$_2$CO$_3$ 2M in water. The organic phase was dried over Na$_2$SO$_4$, filtered and evaporated to dryness. The resulting crude material was purified by reverse phase prep-HPLC (gradient elution, H$_2$O containing 0.1% TFA/MeCN 8:8→2:8) to yield the title compound (97 mg, 0.236 mmol, 39%) as a brownish solid. HPLC: $^A t_{Ret}$=2.38 min; LC-MS: m/z 411.4 [M+H]$^+$; $^1$H NMR (400 MHz, DMSO-d$_6$): 0.73-0.99 (m, 2H), 1.35 (s, 9H), 1.32-1.45 (m, 3H), 1.55-1.76 (m, 4H), 1.86-2.15 (m, 1H), 3.11 (br. s., 3H), 6.56 (br. s., 1H), 7.27-7.35 (m, 2H), 7.61-7.69 (m, 2H).

Intermediate 92.2:
Trans-4-dimethylamino-cyclohexanecarboxylic acid (4-bromo-phenyl)-methyl-amide

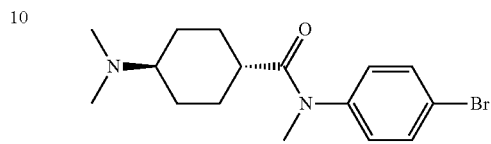

The title compound (65 mg, 0.192 mmol, 82%) was obtained as a yellow resin from Intermediate 92.1 (96 mg, 0.233 mmol) analogously to Intermediate 75.8. Purification of the crude material was performed by Combi-Flash Companion™ (Isco Inc.) column chromatography (SiO$_2$; gradient elution, DCM/[DCM/7M NH$_3$ in MeOH 9:1] 95:5→100% DCM/7M NH$_3$ in MeOH 9:1). TLC: R$_F$=0.40 (DCM/7M NH$_3$ in MeOH 9:1); HPLC: $^A t_{Ret}$=1.23 min; LC-MS: m/z 339.2 [M+H]$^+$; $^1$H NMR (400 MHz, DMSO-d$_6$): 0.70-1.01 (m, 2H), 1.31-1.46 (m, 2H), 1.59-1.78 (m, 4H), 1.94-2.19 (m, 8H), 3.11 (br. s., 3H), 7.22-7.38 (m, 2H), 7.57-7.74 (m, 2H).

Example 93

(S)-1-(4-Chloro-phenyl)-2-{4-[2-(4-dimethylamino-piperidin-1-yl)-1-methyl-ethyl]-phenyl}-7-isopropoxy-6-methoxy-1,4-dihydro-2H-isoquinolin-3-one

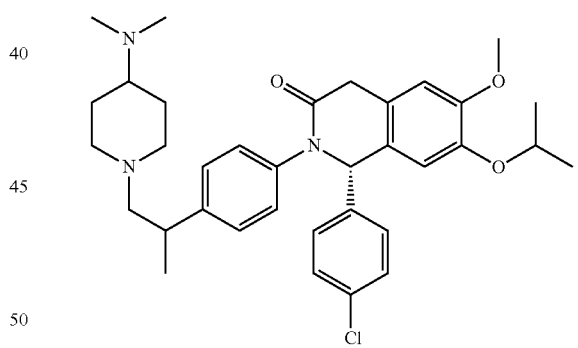

The title compound (25 mg, 0.042 mmol, 27%) was obtained as a colorless solid from Intermediate 75.6 (54 mg, 0.156 mmol) and Intermediate 93.4 (61 mg, 0.187 mmol) analogously to Example 75. Purification of the crude material was performed by reverse phase prep-HPLC (Waters system). The purified compound (TFA salt) was dissolved in MeOH and eluted through a basic ion exchange resin (PL-HCO3 MP SPE from Polymer Laboratories) to remove the TFA salt. HPLC: $^A t_{Ret}$=1.77 min; LC-MS: m/z 590.2 [M+H]$^+$; $^1$H NMR (400 MHz, DMSO-d$_6$): 1.14 (d, J=6.6, 3H), 1.20 (d, J=5.9, 3H), 1.24 (d, J=5.9, 3H), 1.27-1.33 (m, 1H), 1.62-1.70 (m, 2H), 1.74-2.01 (m, 3H), 2.28-2.35 (m, 2H), 2.79-2.95 (m, 4H), 3.60 (d, J=19.8, 1H), 3.73 (s, 3H), 3.83-3.92 (m, 1H), 4.41-4.51 (m, 1H), 6.08 (s, 1H), 6.85 (s, 1H), 7.04-7.12 (m, 3H), 7.16-7.24 (m, 2H), 7.33-7.38 (m, 4H).

Intermediate 93.1 2-(4-Bromo-phenyl)-propionic acid ethyl ester

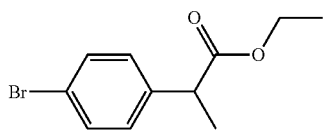

To a solution of ethyl 4-bromophenylacetate (2 g, 8.23 mmol) in anhydrous DMF (20 ml) was carefully added NaH (60% in mineral oil, 0.494 g, 12.34 mmol) at 0° C. (ice bath). The resulting slurry was stirred at 0° C. for 30 min, then MeI (0.643 ml, 10.28 mmol) was added and the reaction mixture was allowed to warm to RT and further stirred for 1 h. A saturated aqueous NH$_4$Cl solution was added to quench the reaction and the mixture was extracted with AcOEt (2×). The combined organic fractions were dried over Na$_2$SO$_4$, filtered and evaporated to dryness. The resulting crude material was purified by Combi-Flash Companion™ (Isco Inc.) column chromatography (SiO$_2$; gradient elution, heptane/AcOEt 99:1 to 8:2) to yield the title compound (777.8 mg, 3.03 mmol, 37% yield) as a colorless oil. TLC: R$_F$=0.64 (heptane/AcOEt 3:1); HPLC: $^A$t$_{Ret}$=2.60 min; $^1$H NMR (400 MHz, DMSO-d$_6$): 1.13 (t, J=7.1, 3H), 1.37 (d, J=7.1, 3H), 3.79 (q, J=7.1, 1H), 3.98-4.12 (m, 2H), 7.22-7.28 (m, 2H), 7.49-7.56 (m, 2H).

Intermediate 93.2 2-(4-Bromo-phenyl)-propionic acid

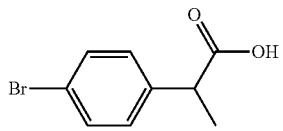

The title compound (263 mg, 1.15 mmol, 98%) was obtained as a yellow solid from Intermediate 93.1 (300 mg, 1.17 mmol) analogously to Intermediate 1.2. The crude material was used in the next step without further purification. HPLC: $^A$t$_{Ret}$=1.90 min; $^1$H NMR (400 MHz, DMSO-d$_6$): 1.34 (d, J=7.1, 3H), 3.69 (q, J=7.1, 1H), 7.21-7.28 (m, 2H), 7.48-7.55 (m, 2H), 12.42 (s, 1H).

Intermediate 93.3 2-(4-Bromo-phenyl)-1-(4-dimethylamino-piperidin-1-yl)-propan-1-one

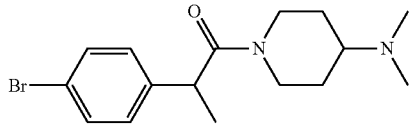 [SMILES: CC(C(=O)N1CCC(N(C)C)CC1)c1ccc(Br)cc1]

The title compound (370 mg, 1.09 mmol, 96%) was obtained as a yellow resin from Intermediate 93.2 (259 mg, 1.13 mmol) and 4-(dimethylamino)-piperidine (174 mg, 1.36 mmol) analogously to Intermediate 92.1. Purification of the crude material was performed by Combi-Flash Companion™ (Isco Inc.) column chromatography (SiO$_2$; gradient elution, DCM/7M NH$_3$ in MeOH 99:1→9:1). TLC: R$_F$=0.49 (DCM/ 7M NH$_3$ in MeOH 9:1); HPLC: $^A$t$_{Ret}$=1.28 min; LC-MS: m/z 339.1 [M+H]$^+$; $^1$H NMR (400 MHz, DMSO-d$_6$): 0.26-1.05 (m, 1H), 1.14-1.37 (m, 4H), 1.38-1.77 (m, 2H), 2.04 (s, 3H), 2.18 (s, 3H), 2.22-2.38 (m, 1H), 2.52-2.59 (m, 1H), 2.61-3.00 (m, 1H), 3.80-3.99 (m, 1H), 4.07-4.19 (m, 1H), 4.30-4.46 (m, 1H), 7.17-7.28 (m, 2H), 7.47-7.56 (m, 2H).

Intermediate 93.4 {1-[2-(4-Bromo-phenyl)-propyl]-piperidin-4-yl}-dimethyl-amine

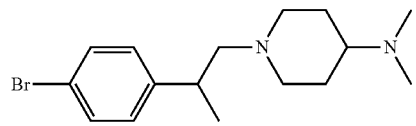 [SMILES: CC(CN1CCC(N(C)C)CC1)c1ccc(Br)cc1]

To a solution of Intermediate 93.3 (221 mg, 0.651 mmol) in anhydrous THF (3 ml) were successively added BH$_3$.THF (1M in THF, 3.26 ml, 3.26 mmol) and a few drops of 4M HCl in dioxane at RT. The reaction mixture was heated at 70° C., stirred for 2 h30 then cooled to RT and carefully quenched by the addition of a 2M aqueous HCl solution (6.5 ml). The mixture was heated at 100° C. and stirred for 30 min, then cooled to RT, diluted with AcOEt and washed with a 2M aqueous Na$_2$CO$_3$ solution (2×). The organic phase was dried over Na$_2$SO$_4$, filtered and evaporated to dryness. The resulting crude material was purified by reverse phase column chromatography (gradient elution, water+0.1% TFA/MeCN+ 0.1% TFA 98:2 to 6:4). Fractions containing the desired compound were collected, basified by the addition of solid Na$_2$CO$_3$ and extracted with AcOEt. The organic layer was dried over Na$_2$SO$_4$, filtered and evaporated to dryness to yield the title compound (127 mg, 0.39 mmol, 60% yield) as a colorless oil which crystallized into a colorless solid on standing. HPLC: $^A$t$_{Ret}$=1.10 min; LC-MS: m/z 325.2 [M+H]$^+$; $^1$H NMR (400 MHz, DMSO-d$_6$): 1.14 (d, J=7.1, 3H), 1.19-1.35 (m, 2H), 1.61-1.70 (m, 2H), 1.76-1.91 (m, 2H), 1.92-2.02 (m, 1H), 2.13 (s, 6H), 2.33 (d, J=7.6, 2H), 2.79-2.88 (m, 2H), 2.92 (q, J=7.1, 1H), 7.15-7.23 (m, 2H), 7.41-7.49 (m, 2H).

Example 94

(S)-1-(4-Chloro-phenyl)-2-{4-[2-(4-dimethylamino-piperidin-1-yl)-1-methyl-2-oxo-ethyl]-phenyl}-7-isopropoxy-6-methoxy-1,4-dihydro-2H-isoquinolin-3-one

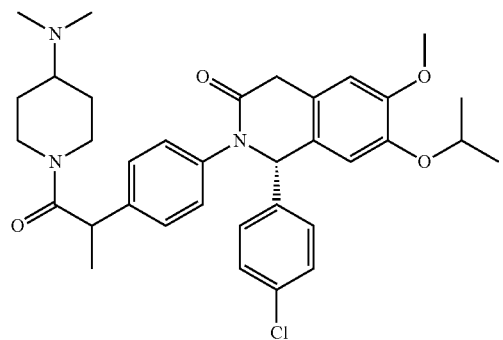 [SMILES: COc1cc2c(cc1OC(C)C)[C@H](c1ccc(Cl)cc1)N(c1ccc(C(C)C(=O)N3CCC(N(C)C)CC3)cc1)C(=O)C2]

The title compound (TFA salt, 11.6 mg, 0.019 mmol, 13%) was obtained as a light yellow solid from Intermediate 75.6 (50 mg, 0.145 mmol) and Intermediate 93.3 (58.9 mg, 0.174 mmol) analogously to Example 75. Purification of the crude material was performed by reverse phase prep-HPLC (Waters system). HPLC: $^At_{Ret}$=1.91 min; LC-MS: m/z 604.3 [M+H]$^+$; $^1$H NMR (400 MHz, DMSO-d$_6$): 1.14-1.32 (m, 10H), 1.37-2.03 (m, 3H), 2.41-2.62 (m, 3H), 2.62-3.04 (m, 4H), 3.25-3.39 (m, 1H), 3.60 (d, J=19.8, 1H), 3.73 (s, 3H), 3.81-3.89 (m, 1H), 3.96-4.20 (m, 2H), 4.40-4.50 (m, 1H), 4.51-4.61 (m, 1H), 6.05-6.12 (m, 1H), 6.86 (s, 1H), 7.03-7.18 (m, 3H), 7.19-7.30 (m, 2H), 7.30-7.42 (m, 4H).

Examples 95, 101, 104, 105, 106, 107, 112, 117, 118, 119, 126, 130, 132, 138, 139, 144, 147, 149, 150, 152, 153, 172, 174, 175, 180, 183, 195, 196, 197, 198, 199, 200, 202, 203, 204, 205, 207, 209, 210, 211, 212, 214, 216, 226, 227, 228 and Intermediates 123.1, 137.1, 163.1, 164.2, 169.1, 176.2, 177.2, 178.1, 192.2, 201.1, 215.2, 219.1 were obtained analogously to Example 75 by reaction of Intermediate 75.6 (or analogues prepared similarly).

Examples 96, 98, 182, 188 and Intermediates 166.2, 185.2, 186.1, 187.2, 189.3 were obtained analogously to Example 1 by reaction of intermediate 96.1 (or analogues

| | Structure | Name/HPLC/MS |
|---|---|---|
| 95 | 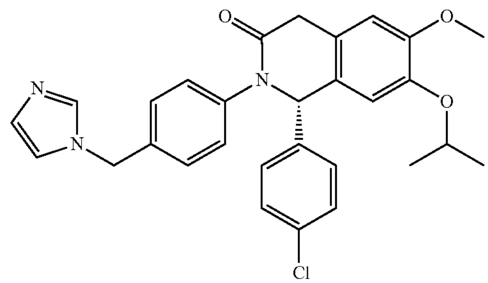 [SMILES: COc1cc2c(cc1OC(C)C)[C@H](c1ccc(Cl)cc1)N(c1ccc(Cn3ccnc3)cc1)C(=O)C2] | (S)-1-(4-Chloro-phenyl)-2-(4-imidazol-1ylmethyl-phenyl)-7-isopropoxy-6-methoxy-1,4-dihydro-2H-isoquinolin-3-one. HPLC: $^Et_{Ret}$ = 4.686; LC-MS: m/z 502.4 [M + H]$^+$. |
| 96 | 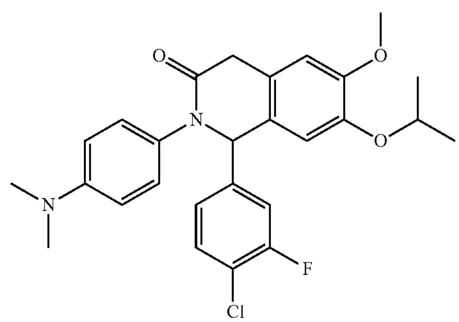 [SMILES: COc1cc2c(cc1OC(C)C)C(c1ccc(Cl)c(F)c1)N(c1ccc(N(C)C)cc1)C(=O)C2] | 1-(4-Chloro-3-fluoro-phenyl)-2-(4-dimethylamino-phenyl)-7-isopropoxy-6-methoxy-1,4-dihydro-2H-isoquinolin-3-one. HPLC: $^Kt_{Ret}$ = 6.166; LC-MS: m/z 483.4 [M + H]$^+$. |
| 98 | 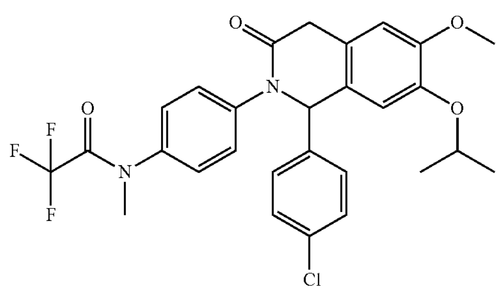 [SMILES: COc1cc2c(cc1OC(C)C)C(c1ccc(Cl)cc1)N(c1ccc(N(C)C(=O)C(F)(F)F)cc1)C(=O)C2] | N-{4-[1-(4-Chloro-phenyl)-7-isopropoxy-6-methoxy-3-oxo-3,4-dihydro-1H-isoquinolin-2-yl]-phenyl}-2,2,2-trifluoro-N-methyl-acetamide. HPLC: $^Kt_{Ret}$ = 7.338; LC-MS: m/z 547.1 [M + H]$^+$. |
| 99 | 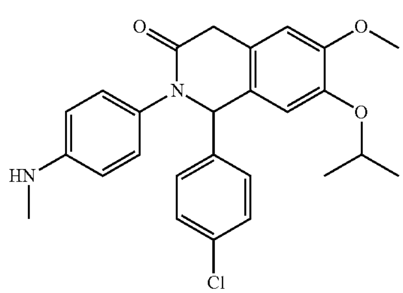 [SMILES: CNc1ccc(N2C(=O)Cc3cc(OC)c(OC(C)C)cc3C2c2ccc(Cl)cc2)cc1] | 1-(4-Chloro-phenyl)-7-isopropoxy-6-methoxy-2-(4-methylamino-phenyl)-1,4-dihydro-2H-isoquinolin-3-one. HPLC: $^Kt_{Ret}$ = 5.878; LC-MS: m/z 451.4 [M + H]$^+$. |

| | Structure | Name/HPLC/MS |
|---|---|---|
| 100 | 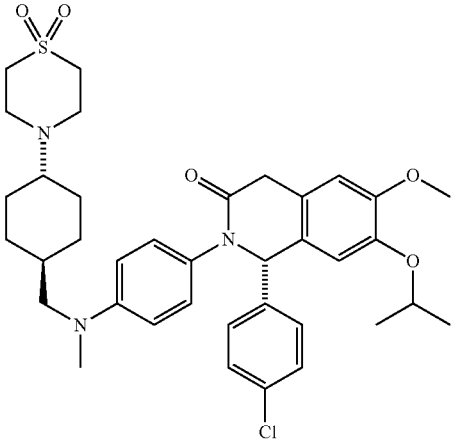 [SMILES: COc1cc2c(cc1OC(C)C)[C@H](c1ccc(Cl)cc1)N(c1ccc(N(C)C[C@H]3CC[C@H](N4CCS(=O)(=O)CC4)CC3)cc1)C(=O)C2] | (S)-1-(4-Chloro-phenyl)-2-(4-{[4-(1,1-dioxo-1lambda*6*-thiomorpholin-4-yl)-trans-cyclohexylmethyl]-methyl-amino}-phenyl)-7-isopropoxy-6-methoxy-1,4-dihydro-2H-isoquinolin-3-one.<br>HPLC: $^At_{Ret}$ = 2.02; LC-MS: m/z 680.2 [M + H]$^+$. |
| 101 | 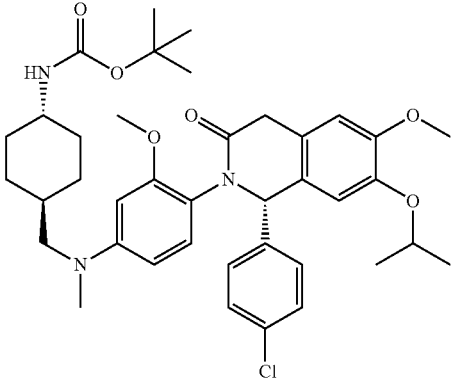 [SMILES: COc1cc2c(cc1OC(C)C)[C@H](c1ccc(Cl)cc1)N(c1ccc(N(C)C[C@H]3CC[C@H](NC(=O)OC(C)(C)C)CC3)cc1OC)C(=O)C2] | {4-[({4-[(S)-1-(4-Chloro-phenyl)-7-isopropoxy-6-methoxy-3-oxo-3,4-dihydro-1H-isoquinolin-2-yl]-3-methoxy-phenyl}-methyl-amino)-methyl]-trans-cyclohexyl}-carbamic acid tert-butyl ester.<br>HPLC: $^At_{Ret}$ = 2.84; LC-MS: m/z 692.2 [M + H]$^+$. |
| 102 | 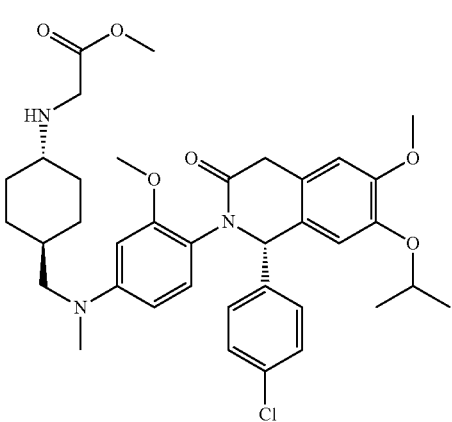 [SMILES: COC(=O)CN[C@H]1CC[C@H](CN(C)c2ccc(N3C(=O)Cc4cc(OC)c(OC(C)C)cc4[C@@H]3c3ccc(Cl)cc3)c(OC)c2)CC1] | {4-[({4-[(S)-1-(4-Chloro-phenyl)-7-isopropoxy-6-methoxy-3-oxo-1,4-dihydro-1H-isoquinolin-2-yl]-3-methoxy-phenyl}-methyl-amino)-methyl]-trans-cyclohexylamino}-acetic acid methyl ester.<br>HPLC: $^At_{Ret}$ = 1.99; LC-MS: m/z 664.3 [M + H]$^+$. |

-continued

| | Structure | Name/HPLC/MS |
|---|---|---|
| 103 | 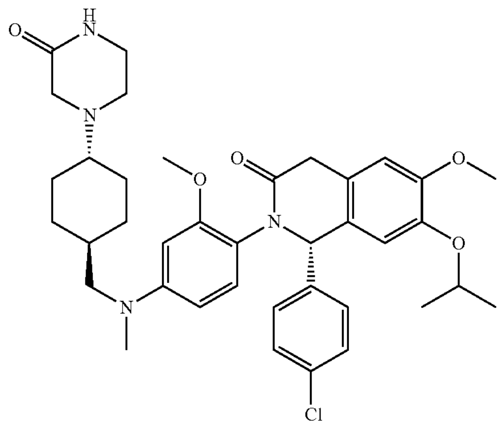 [SMILES: COc1cc2c(cc1OC(C)C)[C@H](c1ccc(Cl)cc1)N(c1ccc(N(C)C[C@H]3CC[C@H](N4CCNC(=O)C4)CC3)cc1OC)C(=O)C2] | (S)-1-(4-Chloro-phenyl)-7-isopropoxy-6-methoxy-2-(2-methoxy-4-{methyl-[4-(3-oxo-piperazin-1-yl)-trans-cyclohexylmethyl]-amino}-phenyl)-1,4-dihydro-2H-isoquinolin-3-one.<br>HPLC: $^A t_{Ret}$ = 1.91; LC-MS: m/z 675.3 [M + H]$^+$. |
| 104 | 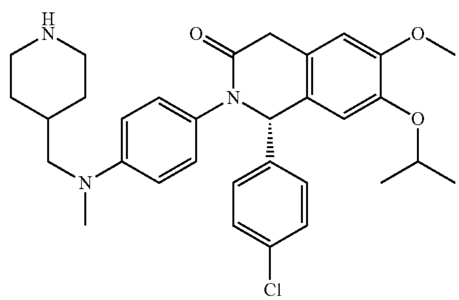 [SMILES: COc1cc2c(cc1OC(C)C)[C@H](c1ccc(Cl)cc1)N(c1ccc(N(C)CC3CCNCC3)cc1)C(=O)C2] | (S)-1-(4-Chloro-phenyl)-7-isopropoxy-6-methoxy-2-[4-(methyl-piperidin-4-ylmethyl-amino)-phenyl]-1,4-dihydro-2H-isoquinolin-3-one.<br>HPLC: $^A t_{Ret}$ = 1.94; LC-MS: m/z 548.2 [M + H]$^+$. |
| 105 | 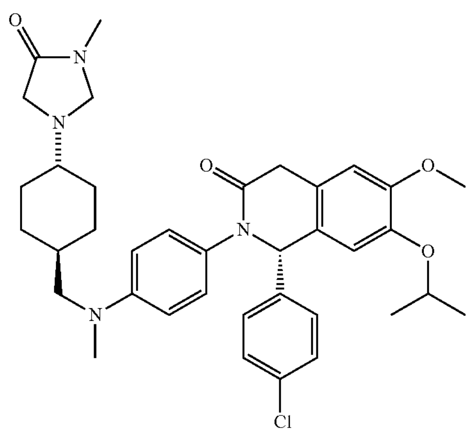 [SMILES: COc1cc2c(cc1OC(C)C)[C@H](c1ccc(Cl)cc1)N(c1ccc(N(C)C[C@H]3CC[C@H](N4CC(=O)N(C)C4)CC3)cc1)C(=O)C2] | (S)-1-(4-Chloro-phenyl)-7-isopropoxy-6-methoxy-2-(4-{methyl-[4-(3-methyl-4-oxo-imidazolidin-1-yl)-trans-cyclohexylmethyl]-amino}-phenyl)-1,4-dihydro-2H-isoquinolin-3-one.<br>HPLC: $^F t_{Ret}$ = 1.164; LC-MS: m/z 645.5 [M + H]$^+$. |
| 106 | 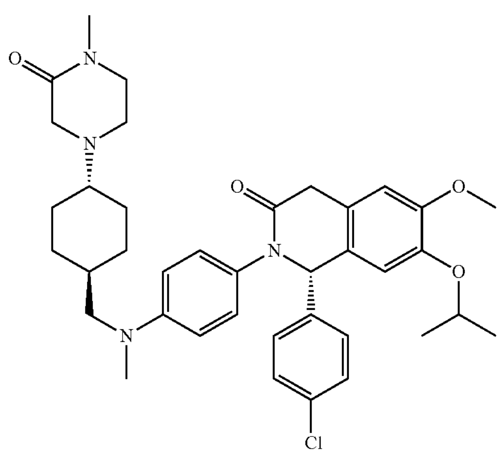 | (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one.<br>HPLC: $^E t_{Ret}$ = 4.57; LC-MS: m/z 659.2 [M + H]$^+$. |

| | Structure | Name/HPLC/MS |
|---|---|---|
| 107 | 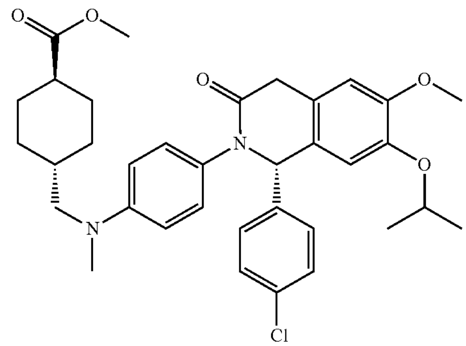 [SMILES: COc1cc2c(cc1OC(C)C)[C@H](c1ccc(Cl)cc1)N(c1ccc(N(C)C[C@H]3CC[C@H](C(=O)OC)CC3)cc1)C(=O)C2] | 4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexanecarboxylic acid methyl ester.<br>HPLC: $^{G}t_{Ret}$ = 7.244; LC-MS: m/z 605.4 [M + H]$^{+}$. |
| 108 | 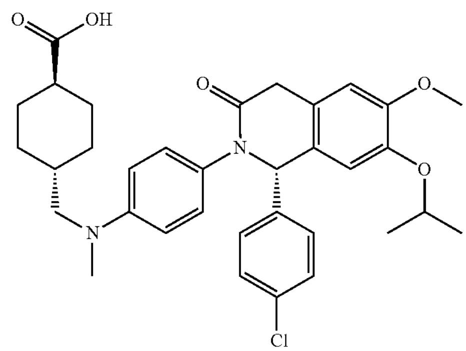 [SMILES: COc1cc2c(cc1OC(C)C)[C@H](c1ccc(Cl)cc1)N(c1ccc(N(C)C[C@H]3CC[C@H](C(=O)O)CC3)cc1)C(=O)C2] | 4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexanecarboxylic acid.<br>HPLC: $^{G}t_{Ret}$ = 6.443; LC-MS: m/z 591.4 [M + H]$^{+}$. |
| 109 | 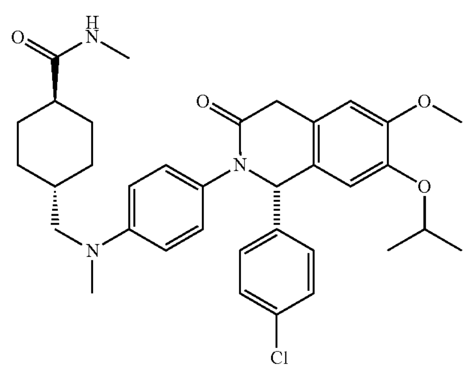 [SMILES: CNC(=O)[C@H]1CC[C@H](CN(C)c2ccc(N3C(=O)Cc4cc(OC)c(OC(C)C)cc4[C@@H]3c3ccc(Cl)cc3)cc2)CC1] | 4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexanecarboxylic acid methylamide.<br>HPLC: $^{A}t_{Ret}$ = 2.12; LC-MS: m/z 604.2 [M + H]$^{+}$. |
| 110 | 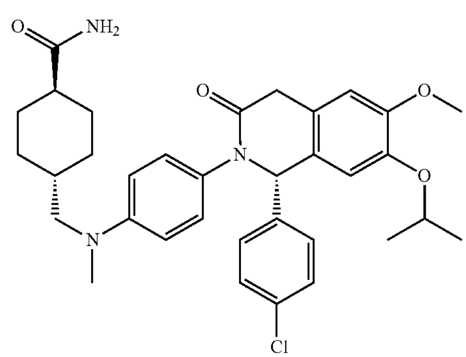 [SMILES: COc1cc2c(cc1OC(C)C)[C@H](c1ccc(Cl)cc1)N(c1ccc(N(C)C[C@H]3CC[C@H](C(N)=O)CC3)cc1)C(=O)C2] | 4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexanecarboxylic acid amide.<br>HPLC: $^{A}t_{Ret}$ = 2.03; LC-MS: m/z 590.2 [M + H]$^{+}$. |

| | Structure | Name/HPLC/MS |
|---|---|---|
| 111 | 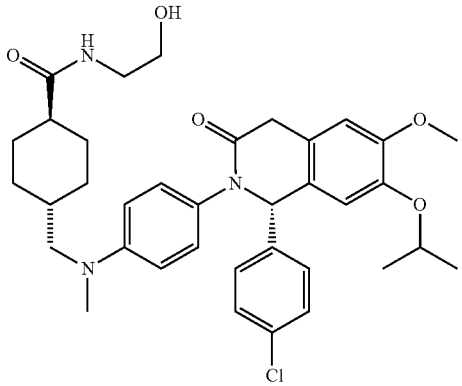 | 4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexane-carboxylic acid (2-hydroxy-ethyl)-amide. HPLC: $^A t_{Ret}$ = 1.98; LC-MS: m/z 634.2 [M + H]$^+$. |
| 112 | 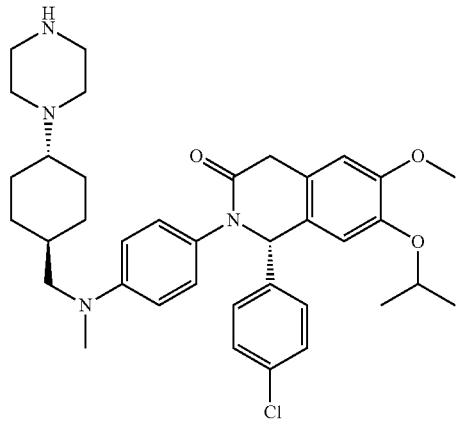 [SMILES: COc1cc2c(cc1OC(C)C)[C@H](c1ccc(Cl)cc1)N(c1ccc(N(C)C[C@H]3CC[C@H](N4CCNCC4)CC3)cc1)C(=O)C2] | (S)-1-(4-Chloro-phenyl)-7-isopropoxy-6-methoxy-2-{4-[methyl-(4-piperazin-1-yl-trans-cyclohexymethyl)-amino]-phenyl}-1,4-dihydro-2H-isoquinolin-3-one. HPLC: $^A t_{Ret}$ = 1.76; LC-MS: m/z 631.3 [M + H]$^+$. |
| 113 | 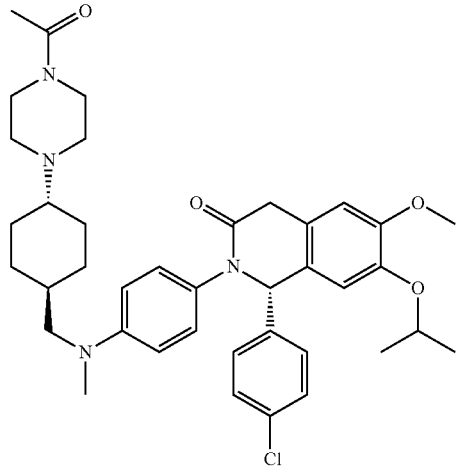 [SMILES: COc1cc2c(cc1OC(C)C)[C@H](c1ccc(Cl)cc1)N(c1ccc(N(C)C[C@H]3CC[C@H](N4CCN(C(C)=O)CC4)CC3)cc1)C(=O)C2] | (S)-2-(4-{[4-(4-Acetyl-piperazin-1-yl)-trans-cyclohexylmethyl]-methyl-amino}-phenyl)-1-(4-chloro-phenyl)-7-isopropoxy-6-methoxy-1,4-dihydro-2H-isoquinolin-3-one. HPLC: $^A t_{Ret}$ = 1.89; LC-MS: m/z 673.3 [M + H]$^+$. |

US 9,051,279 B2

317                                                                                                                                       318

-continued

| | Structure | Name/HPLC/MS |
|---|---|---|
| 114 | 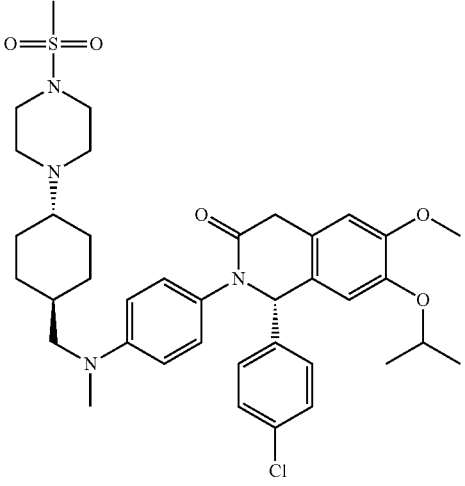 [SMILES: COc1cc2c(cc1OC(C)C)[C@H](c1ccc(Cl)cc1)N(c1ccc(N(C)C[C@H]3CC[C@H](N4CCN(S(C)(=O)=O)CC4)CC3)cc1)C(=O)C2] | (S)-1-(4-Chloro-phenyl)-7-isopropoxy-2-(4-{[4-(4-methanesulfonyl-piperazin-1-yl)-trans-cyclohexylmethyl]-methyl-amino}-phenyl)-6-methoxy-1,4-dihydro-2H-isoquinolin-3-one.<br>HPLC: $^At_{Ret}$ = 1.97; LC-MS: m/z 709.4 [M + H]$^+$. |
| 115 | 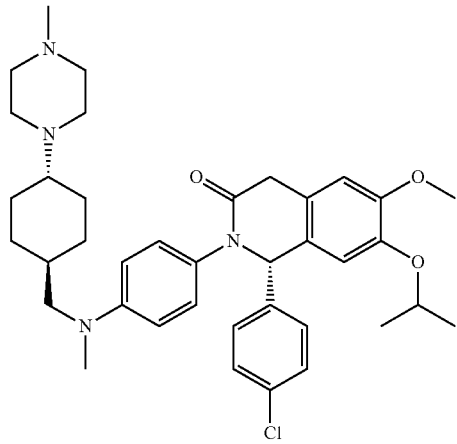 [SMILES: COc1cc2c(cc1OC(C)C)[C@H](c1ccc(Cl)cc1)N(c1ccc(N(C)C[C@H]3CC[C@H](N4CCN(C)CC4)CC3)cc1)C(=O)C2] | (S)-1-(4-Chloro-phenyl)-7-isopropoxy-6-methoxy-2-(4-{methyl-[4-(4-methyl-piperazin-1-yl)-trans-cyclohexylmethyl]-amino}-phenyl)-1,4-dihydro-2H-isoquinolin-3-one.<br>HPLC: $^At_{Ret}$ = 178; LC-MS: m/z 645.5 [M + H]$^+$. |
| 116 | 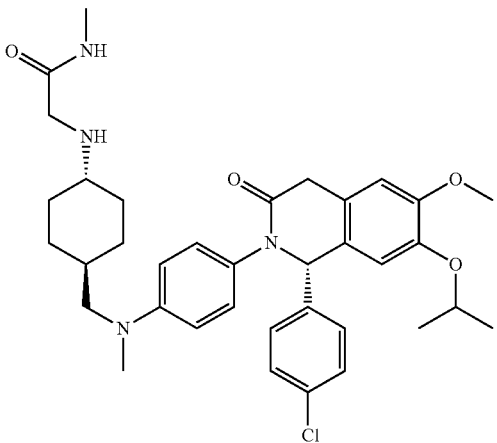 [SMILES: CNC(=O)CN[C@H]1CC[C@H](CN(C)c2ccc(N3C(=O)Cc4cc(OC)c(OC(C)C)cc4[C@@H]3c3ccc(Cl)cc3)cc2)CC1] | 2-{4-[({4-[(S)-1-(4-chloro-phenyl)-7-isopropoxy-6-methoxy-3-oxo-3,4-dihydro-1H-isoquinolin-2-yl]-phenyl}-methyl-amino)-methyl]-trans-cyclohexylamino}-N-methyl-acetamide.<br>HPLC: $^At_{Ret}$ = 1.86; LC-MS: m/z 633.2 [M + H]$^+$. |

| | Structure | Name/HPLC/MS |
|---|---|---|
| 117 | 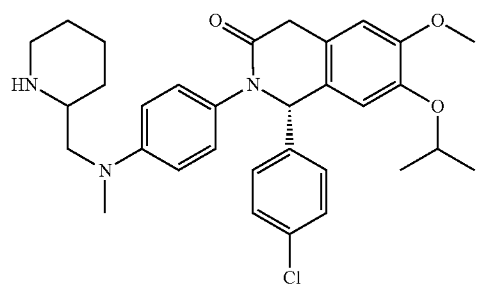 [SMILES: COc1cc2c(cc1OC(C)C)[C@H](c1ccc(Cl)cc1)N(c1ccc(N(C)CC3CCCCN3)cc1)C(=O)C2] | (S)-1-(4-Chloro-phenyl)-7-isopropoxy-6-methoxy-2-[4-(methyl-piperidin-2-ylmethyl-amino)-phenyl]-1,4-dihydro-2H-isoquinolin-3-one.<br>HPLC: $^A t_{Ret}$ = 1.93; LC-MS: m/z 548.4 [M + H]$^+$. |
| 118 | 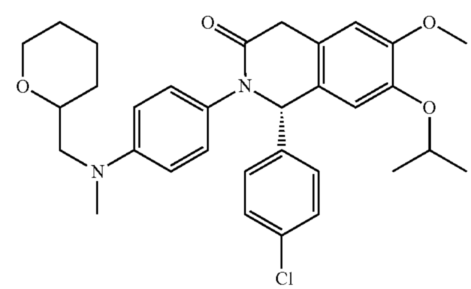 [SMILES: COc1cc2c(cc1OC(C)C)[C@H](c1ccc(Cl)cc1)N(c1ccc(N(C)CC3CCCCO3)cc1)C(=O)C2] | (S)-1-(4-Chloro-phenyl)-7-isopropoxy-6-methoxy-2-{4-[methyl-(tetrahydro-pyran-2-yl-methyl)-amino]-phenyl}-1,4-dihydro-2H-isoquinolin-3-one.<br>HPLC: $^A t_{Ret}$ = 2.41; LC-MS: m/z 549.4 [M + H]$^+$. |
| 119 | 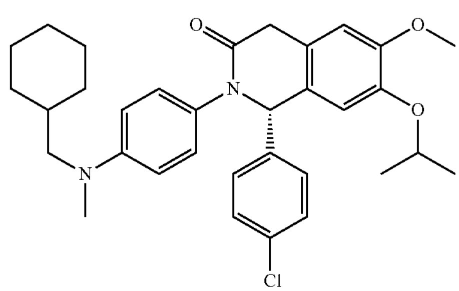 [SMILES: COc1cc2c(cc1OC(C)C)[C@H](c1ccc(Cl)cc1)N(c1ccc(N(C)CC3CCCCC3)cc1)C(=O)C2] | (S)-1-(4-Chloro-phenyl)-2-[4-(cyclohexylmethyl-methyl-amino)-phenyl]-7-isopropoxy-6-6methoxy-1,4-dihydro-2H-isoquinolin-3-one.<br>HPLC: $^A t_{Ret}$ = 2.70; LC-MS: m/z 547.5 [M + H]$^+$. |
| 120 | 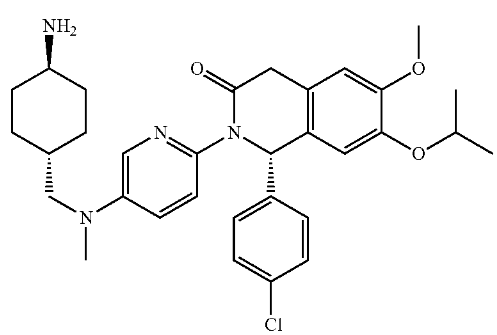 [SMILES: COc1cc2c(cc1OC(C)C)[C@H](c1ccc(Cl)cc1)N(c1ccc(N(C)C[C@H]3CC[C@H](N)CC3)cn1)C(=O)C2] | (S)-2-{5-[(Trans-4-amino-cyclohexylmethyl)-methyl-amino]-pyridin-2-yl}-1-(4-chloro-phenyl)-7-isopropoxy-6-methoxy-1,4-dihydro-2H-isoquinolin-3-one.<br>HPLC: $^F t_{Ret}$ = 0.98; LC-MS: m/z 563.4 [M + H]$^+$. |
| 121 | 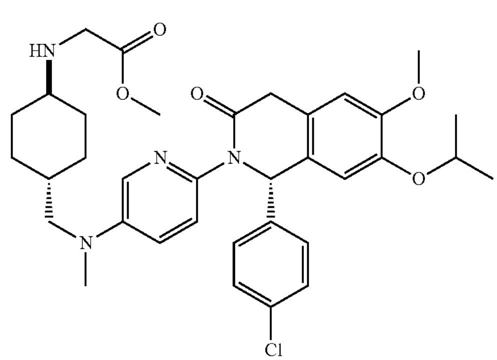 [SMILES: COC(=O)CN[C@H]1CC[C@H](CN(C)c2ccc(N3C(=O)Cc4cc(OC)c(OC(C)C)cc4[C@@H]3c3ccc(Cl)cc3)nc2)CC1] | {4-[({6-[(S)-1-(4-Chloro-phenyl)-7-isopropoxy-6-methoxy-3-oxo-3,4-dihydro-1H-isoquinolin-2-yl]-pyridin-3-yl}-methyl-amino)-methyl]-trans-cyclohexylamino}-acetic acid methyl ester.<br>HPLC: $^F t_{Ret}$ = 1.204; LC-MS: m/z 635.5 [M + H]$^+$. |

| | Structure | Name/HPLC/MS |
|---|---|---|
| 122 | 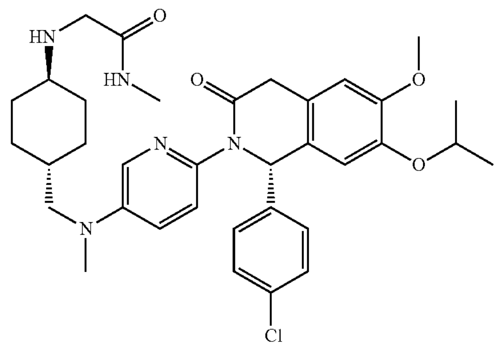 [SMILES: CNC(=O)CN[C@H]1CC[C@H](CN(C)c2ccc(N3C(=O)Cc4cc(OC)c(OC(C)C)cc4[C@@H]3c3ccc(Cl)cc3)nc2)CC1] | 2-{4-[({6-[(S)-1-(4-Chloro-phenyl)-7-isopropoxy-6-methoxy-3-oxo-3,4-dihydro-1H-isoquinolin-2-yl]-pyridin-3-yl}-methyl-amino)-methyl]-trans-cyclohexylamino}-N-methyl-acetamide.<br>HPLC: $^F t_{Ret}$ = 1.080; LC-MS: m/z 634.2 [M + H]$^+$. |
| 123 | 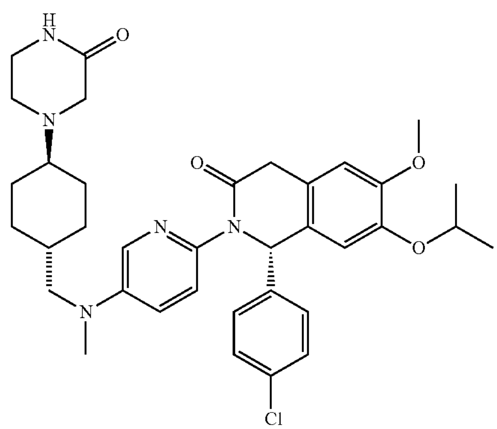 | (S)-1-(4-Chloro-phenyl)-7-isopropoxy-6-methoxy-2-(5-{methyl-[4-(3-oxo-piperazin-1-yl)-trans-cyclohexylmethyl]-amino}-pyridin-2-yl)-1,4-dihydro-2H-isoquinolin-3-one.<br>HPLC: $^F t_{Ret}$ = 1.082; LC-MS: m/z 646.2 [M + H]$^+$. |
| 124 | 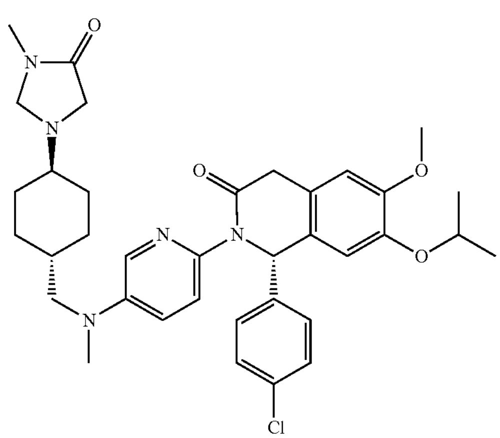 [SMILES: COc1cc2c(cc1OC(C)C)[C@H](c1ccc(Cl)cc1)N(c1ccc(N(C)C[C@H]3CC[C@H](N4CC(=O)N(C)C4)CC3)cn1)C(=O)C2] | (S)-1-(4-Chloro-phenyl)-7-isopropoxy-6-methoxy-2-(5-{methyl-[4-(3-oxo-imidazolidin-1-yl)-trans-cyclohexylmethyl]-amino}-pyridin-2-yl)-1,4-dihydro-2H-isoquinolin-3-one.<br>HPLC: $^F t_{Ret}$ = 1.236; LC-MS: m/z 646.4 [M + H]$^+$. |

-continued

| | Structure | Name/HPLC/MS |
|---|---|---|
| 125 | 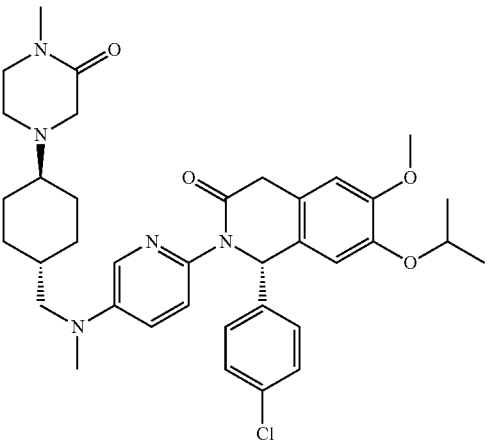 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cn1)C(=O)C2] | (S)-1-(4-Chloro-phenyl)-7-isopropoxy-6-methoxy-2-(5-{methyl-[4-(4-methyl-3-oxo-piperazin-1-yl)-trans-cyclohexylmethyl]-amino}-pyridin-2-yl)-1,4-dihydro-2H-isoquinolin-3-one.<br>HPLC: $^F$t$_{Ret}$ = 1.019; LC-MS: m/z 660.4 [M + H]$^+$. |
| 126 | 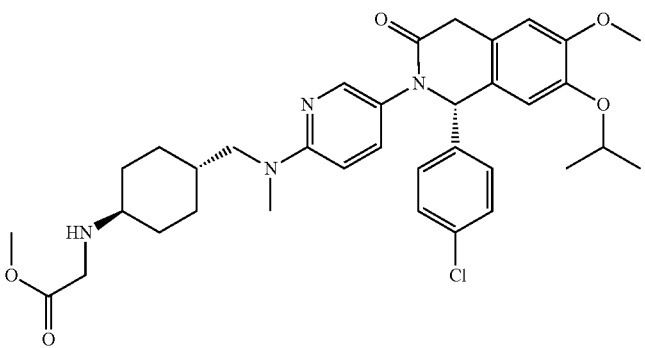 [SMILES: COC(=O)CN[C@H]1CC[C@H](CN(C)c2ccc(N3C(=O)Cc4cc(OC)c(OC(C)C)cc4[C@@H]3c3ccc(Cl)cc3)cn2)CC1] | {4-[({5-[(S)-1-(4-Chloro-phenyl)-7-isopropoxy-6-methoxy-3-oxo-3,4-dihydro-1H-isoquinolin-2-yl]-pyridin-2-yl}-methyl-amino)-methyl]-trans-cyclohexylamino}-acetice acid methyl ester.<br>HPLC: $^G$t$_{Ret}$ = 5.334; LC-MS: m/z 635.4 [M + H]$^+$. |
| 127 | 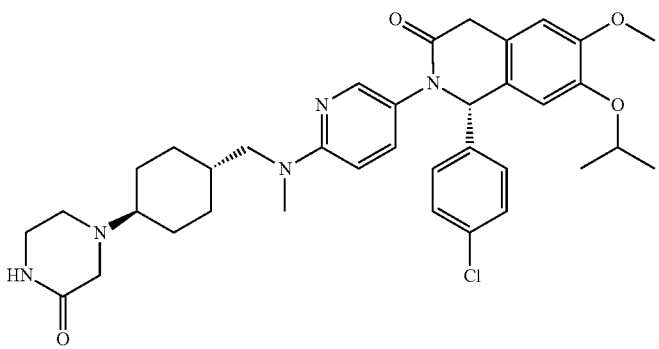 [SMILES: COc1cc2c(cc1OC(C)C)[C@H](c1ccc(Cl)cc1)N(c1ccc(N(C)C[C@H]3CC[C@H](N4CCNC(=O)C4)CC3)nc1)C(=O)C2] | (S)-1-(4-Chloro-phenyl)-7-isopropoxy-6-methoxy-2-(6-{methyl-[4-(3-oxo-piperazin-1-yl)-trans-cyclohexylmethyl]-amino}-pyridin-3-yl)-1,4-dihydro-2H-isoquinolin-3-one.<br>HPLC: $^G$t$_{Ret}$ = 5.162; LC-MS: m/z 646.2 [M + H]$^+$. |
| 128 | 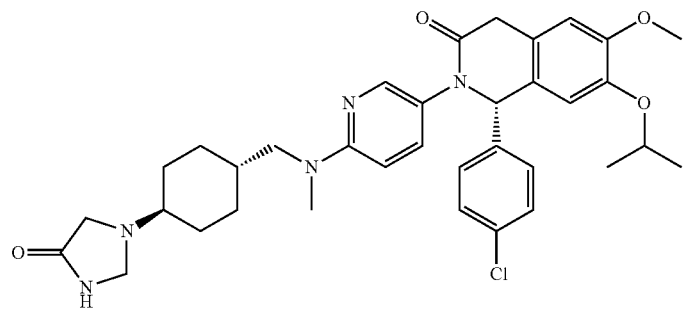 [SMILES: COc1cc2c(cc1OC(C)C)[C@H](c1ccc(Cl)cc1)N(c1ccc(N(C)C[C@H]3CC[C@H](N4CNC(=O)C4)CC3)nc1)C(=O)C2] | (S)-1-(4-Chloro-phenyl)-7-isopropoxy-6-methoxy-2-(6-{methyl-[4-(4-oxo-imidazolidin-1-yl)-trans-cyclohexylmethyl]-amino}-pyridin-3-yl)-1,4-dihydro-2H-isoquinolin-3-one.<br>HPLC: $^G$t$_{Ret}$ = 0.99; LC-MS: m/z 632.2 [M + H]$^+$. |

-continued

| | Structure | Name/HPLC/MS |
|---|---|---|
| 129 | 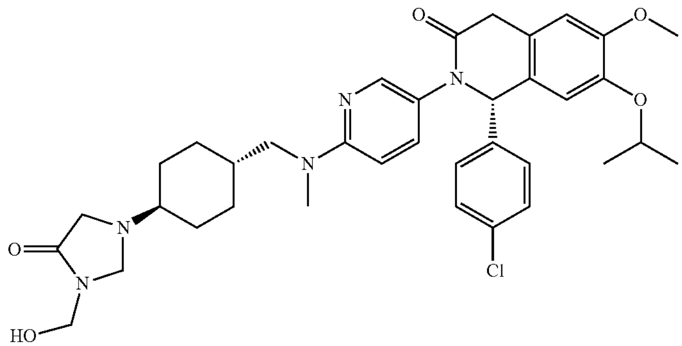 [SMILES: COc1cc2c(cc1OC(C)C)[C@H](c1ccc(Cl)cc1)N(c1ccc(N(C)C[C@H]3CC[C@H](N4CC(=O)N(CO)C4)CC3)nc1)C(=O)C2] | (S)-1-(4-Chloro-phenyl)-2-(6-{[4-(3-hydroxymethyl-4-oxo-imidazolidin-1-yl)-trans-cyclohexylmethyl]-methyl-amino}-pyridin-3-yl)-7-isopropoxy-6-methoxy-1,4-dihydro-2H-isoquinolin-3-one. HPLC: $^G t_{Ret}$ = 1.01; LC-MS: m/z 662.5 [M + H]$^+$. |
| 130 | 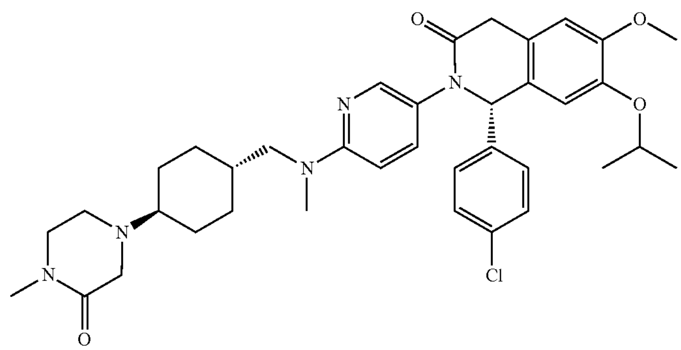 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)nc1)C(=O)C2] | (S)-1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one. HPLC: $^G t_{Ret}$ = 5.252; LC-MS: m/z 660.5 [M + H]$^+$. |
| 131 | 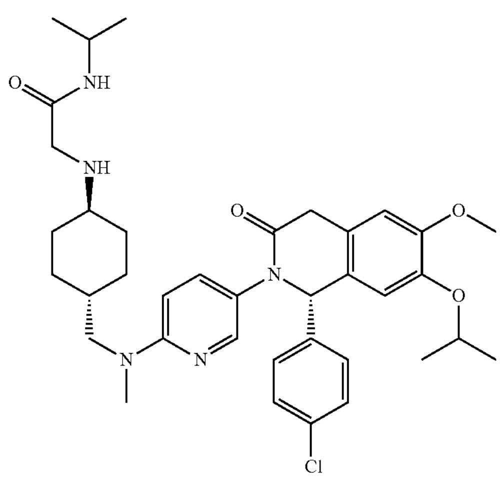 [SMILES: COc1cc2c(cc1OC(C)C)[C@H](c1ccc(Cl)cc1)N(c1ccc(N(C)C[C@H]3CC[C@H](NCC(=O)NC(C)C)CC3)nc1)C(=O)C2] | 2-{4-[({5-[(S)-1-(4-Chloro-phenyl)-7-isopropoxy-6-methoxy-3-oxo-3,4-dihydro-1H-isoquinolin-2-yl]-pyridin-2-yl}-methyl-amino)-methyl]-trans-cyclohexylamino}-N-isopropyl-acetamide. HPLC: $^H t_{Ret}$ = 1.21; LC-MS: m/z 662.3 [M + H]$^+$. |
| 132 | 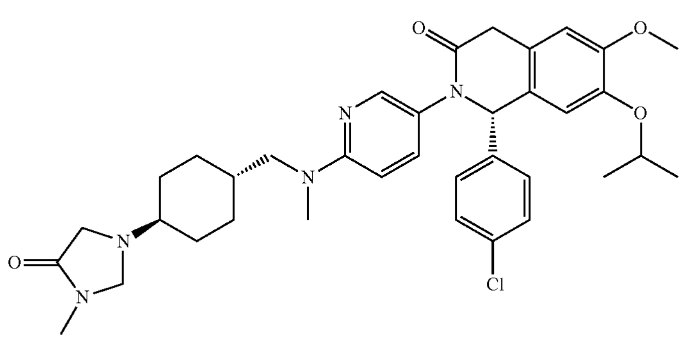 [SMILES: COc1cc2c(cc1OC(C)C)[C@H](c1ccc(Cl)cc1)N(c1ccc(N(C)C[C@H]3CC[C@H](N4CC(=O)N(C)C4)CC3)nc1)C(=O)C2] | (S)-1-(4-Chloro-phenyl)-7-isopropoxy-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one. HPLC: $^G t_{Ret}$ = 5.269; LC-MS: m/z 646.5 [M + H]$^+$. |

-continued

| | Structure | Name/HPLC/MS |
|---|---|---|
| 133 | 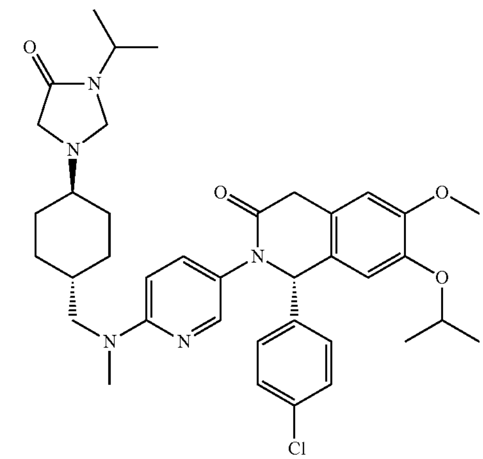 [SMILES: COc1cc2c(cc1OC(C)C)[C@H](c1ccc(Cl)cc1)N(c1ccc(N(C)C[C@H]3CC[C@H](N4CC(=O)N(C(C)C)C4)CC3)nc1)C(=O)C2] | (S)-1-(4-Chloro-phenyl)-7-isopropoxy-2-(6-{[4-(3-isopropyl-4-oxo-imidazolidin-1-yl)-trans-cyclohexylmethyl]-methyl-amino}-pyridin-3-yl)-6-methoxy-1,4-dihydro-2H-isoquinolin-3-one.<br>HPLC: $^H t_{Ret}$ = 1.40; LC-MS: m/z 674.2 [M + H]$^+$. |
| 134 | 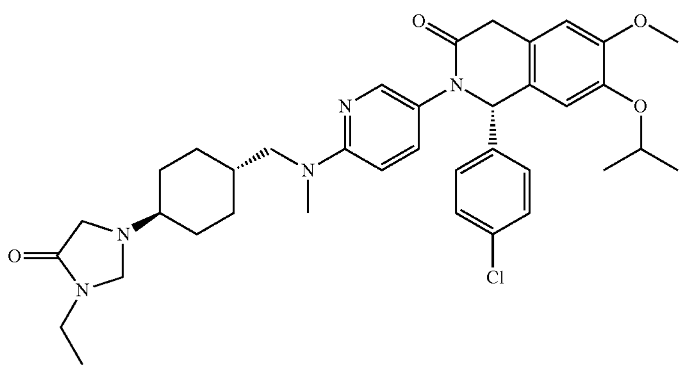 [SMILES: CCN1CN([C@H]2CC[C@H](CN(C)c3ccc(N4C(=O)Cc5cc(OC)c(OC(C)C)cc5[C@@H]4c4ccc(Cl)cc4)cn3)CC2)CC1=O] | (S)-1-(4-Chloro-phenyl)-3-(6-{[4-(3-ethyl-4-oxo-imidazolidin-1-yl)-trans-cyclohexylmethyl]-methyl.amino}-pyridin-3-yl)-7-isopropoxy-6-methoxy-1,4-dihydro-2H-isoquinolin-3-one.<br>HPLC: $^G t_{Ret}$ = 5.343; LC-MS: m/z 660.3 [M + H]$^+$. |
| 135 | 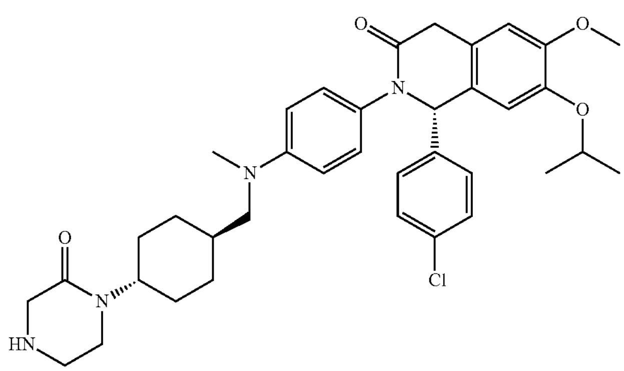 [SMILES: COc1cc2c(cc1OC(C)C)[C@H](c1ccc(Cl)cc1)N(c1ccc(N(C)C[C@H]3CC[C@H](N4CCNCC4=O)CC3)cc1)C(=O)C2] | (S)-1-(4-Chloro-phenyl)-7-isopropoxy-6-methoxy-2-(4-{methyl-[4-(3-oxo-piperazin-1-yl)-trans-cyclohexylmethyl]-amino}-phenyl))-1,4-dihydro-2H-isoquinolin-3-one.<br>HPLC: $^H t_{Ret}$ = 1.54; LC-MS: m/z 646.3 [M + H]$^+$. |
| 136 | 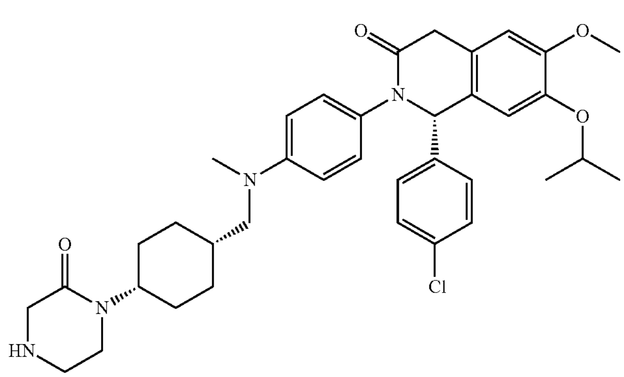 [SMILES: COc1cc2c(cc1OC(C)C)[C@H](c1ccc(Cl)cc1)N(c1ccc(N(C)C[C@H]3CC[C@@H](N4CCNCC4=O)CC3)cc1)C(=O)C2] | (S)-1-(4-Chloro-phenyl)-7-isopropoxy-6-methoxy-2-(4-{methyl-[4-(2-oxo-piperazin-1-yl)-cis-cyclohexylmethyl]-amino}-phenyl)-1,4-dihydro-2H-isoquinolin-3-one.<br>HPLC: $^H t_{Ret}$ = 1.52; LC-MS: m/z 645.3 [M + H]$^+$. |

| | Structure | Name/HPLC/MS |
|---|---|---|
| 137 | 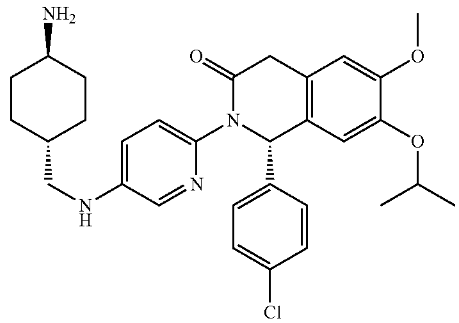 [SMILES: COc1cc2c(cc1OC(C)C)[C@H](c1ccc(Cl)cc1)N(c1ccc(NC[C@H]3CC[C@H](N)CC3)cn1)C(=O)C2] | (S)-2-{5-[(Trans-4-amino-cyclohexylmethyl)-amino]-pyridin-2-yl}-1-(4-chloro-phenyl)-7-isopropoxy-6-methoxy-1,4-dihydro-2H-isoquinolin-3-one.<br>HPLC: $^F t_{Ret}$ = 0.937; LC-MS: m/z 549.4 [M + H]⁺. |
| 138 | 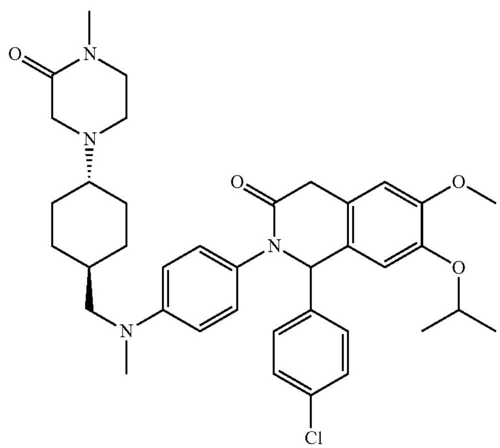 [SMILES: COc1cc2c(cc1OC(C)C)C(c1ccc(Cl)cc1)N(c1ccc(N(C)C[C@H]3CC[C@H](N4CCN(C)C(=O)C4)CC3)cc1)C(=O)C2] | 1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one.<br>HPLC: $^E t_{Ret}$ = 4.737; LC-MS: m/z 659.2 [M + H]⁺. |
| 139 | 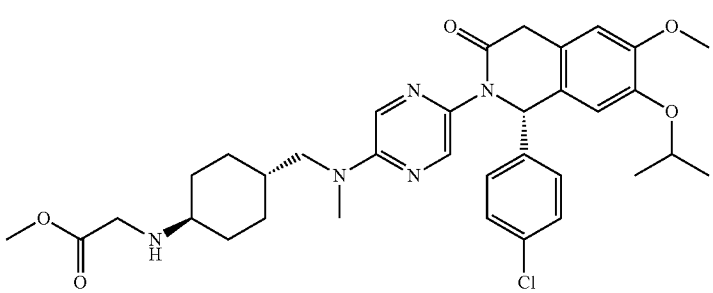 [SMILES: COC(=O)CN[C@H]1CC[C@H](CN(C)c2cnc(N3C(=O)Cc4cc(OC)c(OC(C)C)cc4[C@@H]3c3ccc(Cl)cc3)cn2)CC1] | {4-[({5-[(S)-1-(4-Chloro-phenyl)-7-isopropoxy-6-methoxy-3-oxo-3,4-dihydro-1H-isoquinolin-2-yl]-pyrazin-2-yl}-methyl-amino)-methyl]-trans-cyclohexylamino}-acetic acid methyl ester.<br>HPLC: $^I t_{Ret}$ = 5.36; LC-MS: m/z 636.5 [M + H]⁺. |
| 140 | 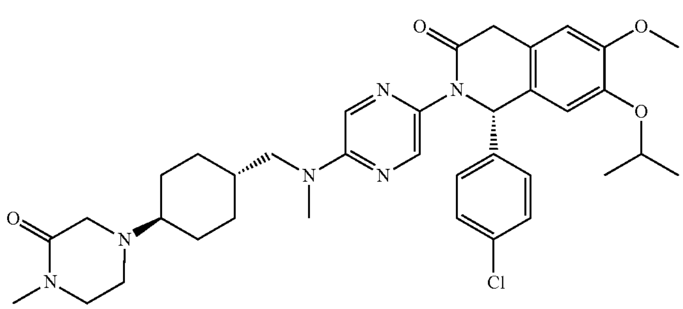 [SMILES: COc1cc2c(cc1OC(C)C)[C@H](c1ccc(Cl)cc1)N(c1cnc(N(C)C[C@H]3CC[C@H](N4CCN(C)C(=O)C4)CC3)cn1)C(=O)C2] | (S)-1-(4-Chloro-phenyl)-7-isopropoxy-6-methoxy-2-(5-methoxy-2-(5-{methyl-[4-(4-methyl-3-oxo-piperazin-1-yl)-trans-cyclohexylmethyl]-amino}-pyrazin-2-yl)-1,4-dihydro-2H-isoquinolin-3-one.<br>HPLC: $^I t_{Ret}$ = 5.167; LC-MS: m/z 661.5 [M + H]⁺. |

| | Structure | Name/HPLC/MS |
|---|---|---|
| 141 | 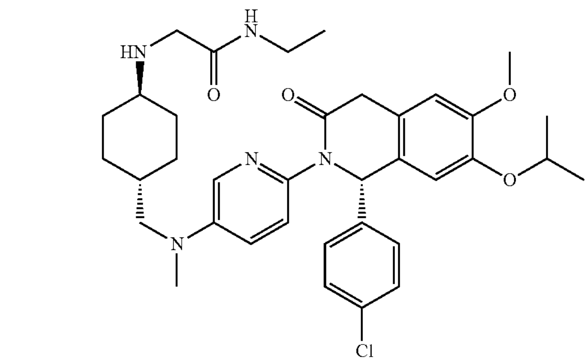 [SMILES: CCNC(=O)CN[C@H]1CC[C@H](CN(C)c2ccc(N3C(=O)Cc4cc(OC)c(OC(C)C)cc4[C@@H]3c3ccc(Cl)cc3)nc2)CC1] | 2-{4-[({6-[(S)-1-(4-Chloro-phenyl)-7-isopropoxy-6-methoxy-3-oxo-3,4-dihydro-1H-isoquinolin-2-yl]-pyridin-3-yl}-methyl-amino)-methyl]-trans-cyclohexylamino}-N-ethyl-acetamide.<br>HPLC: $^F t_{Ret}$ = 1.016; LC-MS: m/z 648.5 [M + H]$^+$. |
| 142 | 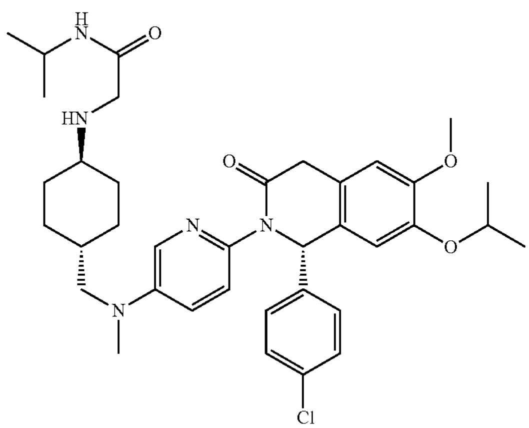 [SMILES: COc1cc2c(cc1OC(C)C)[C@H](c1ccc(Cl)cc1)N(c1ccc(N(C)C[C@H]3CC[C@H](NCC(=O)NC(C)C)CC3)cn1)C(=O)C2] | 2-{4-[({6-[(S)-1-(4-Chloro-phenyl)-7-isopropoxy-6-methoxy-3-oxo-3,4-dihydro-1H-isoquinolin-2-yl]-pyridin-3-yl}-methyl-amino)-methyl]-trans-cyclohexylamino}-N-isopropyl-acetamide.<br>HPLC: $^F t_{Ret}$ = 1.035; LC-MS: m/z 662.5 [M + H]$^+$. |
| 143 | 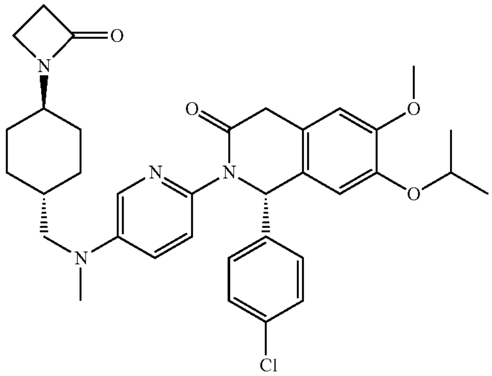 [SMILES: COc1cc2c(cc1OC(C)C)[C@H](c1ccc(Cl)cc1)N(c1ccc(N(C)C[C@H]3CC[C@H](N4CCC4=O)CC3)cn1)C(=O)C2] | (S)-1-(4-Chloro-phenyl)-7-isopropoxy-6-methoxy-2-(5-{methyl-[4-(2-oxo-azetidin-1-yl)-trans-cyclohexyl-methyl]-amino}-pyridin-2-yl)-1,4-dihydro-2H-isoquinolin-3-one.<br>HPLC: $^F t_{Ret}$ = 1.294; LC-MS: m/z 617.4 [M + H]$^+$. |
| 144 | 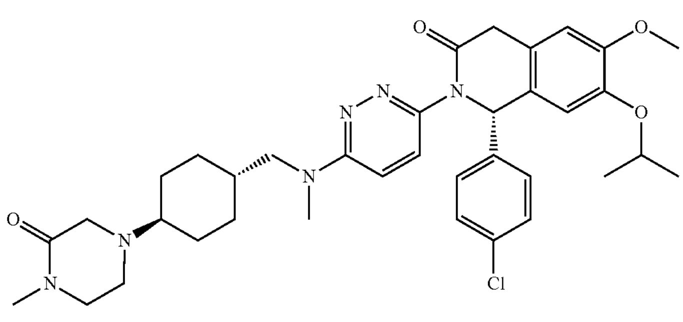 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)nn1)C(=O)C2] | (S)-1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridazin-3-yl)-1,4-dihydro-2H-isoquinolin-3-one.<br>HPLC: $^I t_{Ret}$ = 4.465; LC-MS: m/z 661.5 [M + H]$^+$. |

| | Structure | Name/HPLC/MS |
|---|---|---|
| 145 | 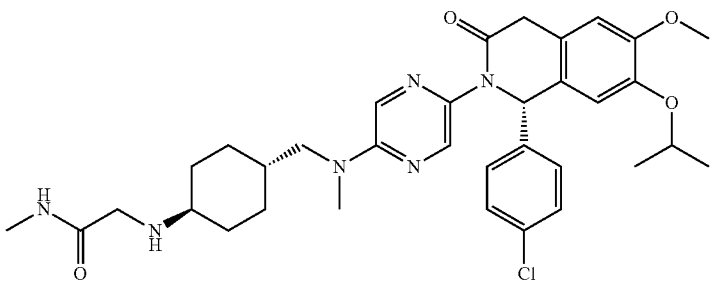 [SMILES: CNC(=O)CN[C@H]1CC[C@H](CN(C)c2cnc(N3C(=O)Cc4cc(OC)c(OC(C)C)cc4[C@@H]3c3ccc(Cl)cc3)cn2)CC1] | 2-{4-[({5-[(S)-1-(4-Chloro-phenyl)-7-isopropoxy-6-methoxy-3-oxo-3,4-dihydro-1H-isoquinolin-2-yl]-pyrazin-2-yl}-methyl-amino)-methyl]-trans-cyclohexyl-amino}-N-methyl-acetamide.<br>HPLC: $^I t_{Ret}$ = 5.14; LC-MS: m/z 635.5 [M + H]$^+$. |
| 146 | 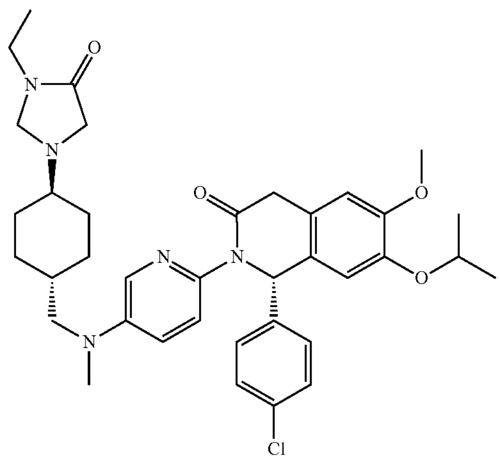 [SMILES: CCN1CN([C@H]2CC[C@H](CN(C)c3ccc(N4C(=O)Cc5cc(OC)c(OC(C)C)cc5[C@@H]4c4ccc(Cl)cc4)nc3)CC2)CC1=O] | (S)-1-(4-Chloro-phenyl)-2-(5-{[4-(3-ethyl-4-oxo-imidazolidin-1-yl)-trans-cyclohexylmethyl]-methyl-amino}-pyridin-2-yl)-7-isopropoxy-6-methoxy-1,4-dihydro-2H-isoquinolin-3-one.<br>HPLC: $^F t_{Ret}$ = 1.132; LC-MS: m/z 660.3 [M + H]$^+$. |
| 147 | 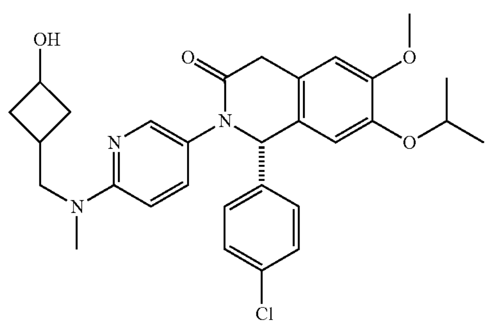 [SMILES: COc1cc2c(cc1OC(C)C)[C@H](c1ccc(Cl)cc1)N(c1ccc(N(C)CC3CC(O)C3)nc1)C(=O)C2] | (S)-1-(4-Chloro-phenyl)-2-{6-[(3-hydroxy-cyclobutylmethyl)-methyl-amino]-pyridin-3-yl}-7-isopropoxy-6-methoxy-1,4-dihydro-2H-isoquinolin-3-one.<br>HPLC: $^F t_{Ret}$ = 0.989; LC-MS: m/z 536.4 [M + H]$^+$. |
| 148 | 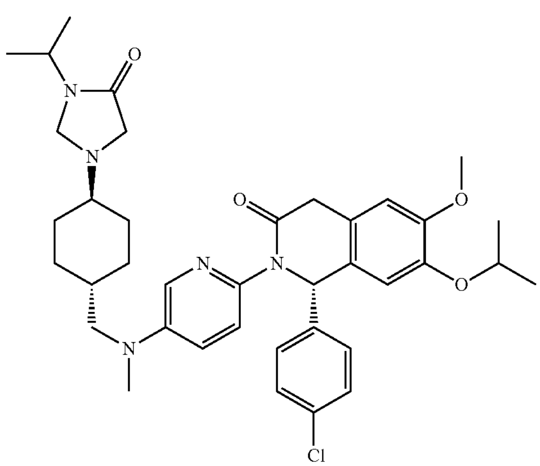 [SMILES: COc1cc2c(cc1OC(C)C)[C@H](c1ccc(Cl)cc1)N(c1ccc(N(C)C[C@H]3CC[C@H](N4CC(=O)N(C(C)C)C4)CC3)cn1)C(=O)C2] | (S)-1-(4-Chloro-phenyl)-7-isopropoxy-2-(5-{[4-(3-isopropyl-4-oxo-imidazolidin-1-yl)-trans cyclohexyl-methyl]-methyl-amino}-pyridin-2-yl)-6-methoxy-1,4-dihydro-2H-isoquinolin-3-one.<br>HPLC: $^F t_{Ret}$ = 1.165; LC-MS: m/z 674.3 [M + H]$^+$. |

-continued

| | Structure | Name/HPLC/MS |
|---|---|---|
| 149 | 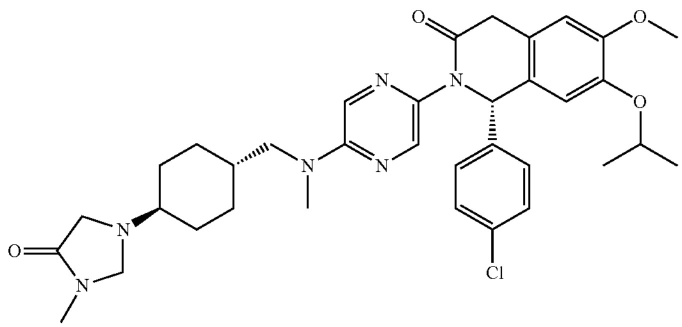 | (S)-1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one. HPLC: $^{t}t_{Ret}$ = 5.202; LC-MS: m/z 647.2 [M + H]$^{+}$. |
| 150 | 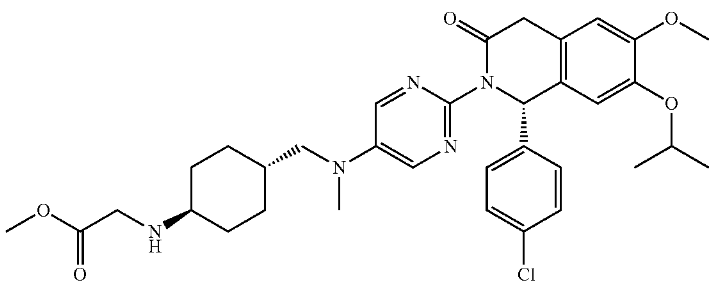 [SMILES: COC(=O)CN[C@H]1CC[C@H](CN(C)c2cnc(N3C(=O)Cc4cc(OC)c(OC(C)C)cc4[C@@H]3c3ccc(Cl)cc3)nc2)CC1] | {4-[({2-[(S)-1-(4-Chloro-phenyl)-7-isopropoxy-6-methoxy-3-oxo-3,4-dihydro-1H-isoquinolin-2-yl]-pyrimidin-5-yl}-methyl-amino)-methyl]-trans-cyclohexylamino}-acetic acid methyl ester. HPLC: $^{t}t_{Ret}$ = 5.07; LC-MS: m/z 636.4 [M + H]$^{+}$. |
| 151 | 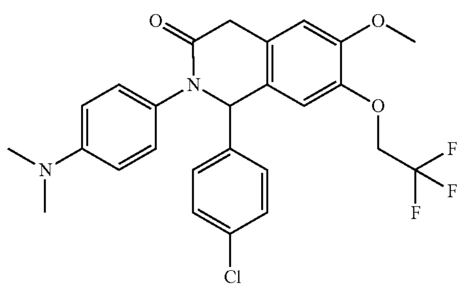 [SMILES: COc1cc2c(cc1OCC(F)(F)F)C(c1ccc(Cl)cc1)N(c1ccc(N(C)C)cc1)C(=O)C2] | 1-(4-Chloro-phenyl)-2-(4-dimethylamino-phenyl)-6-methoxy-7-(2,2,2-trifluoro-ethoxy)-1,4-dihydro-2H-isoquinolin-3-one. HPLC: $^{t}t_{Ret}$ = 6.02; LC-MS: m/z 505.4 [M + H]$^{+}$. |
| 152 | 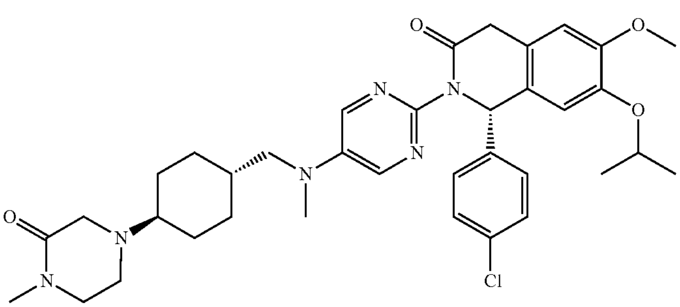 [SMILES: COc1cc2c(cc1OC(C)C)[C@H](c1ccc(Cl)cc1)N(c1ncc(N(C)C[C@H]3CC[C@H](N4CCN(C)C(=O)C4)CC3)cn1)C(=O)C2] | (S)-1-(4-Chloro-phenyl)-7-isopropoxy-6-methoxy-2-(5-{methyl-[4-(4-methyl-3-oxo-ipiperazin-1-yl)-trans-cyclohexylmethyl]-amino}-pyrimidin-2-yl)-1,4-dihydro-2H-isoquinolin-3-one. HPLC: $^{t}t_{Ret}$ = 4.929; LC-MS: m/z 661.5 [M + H]$^{+}$. |
| 153 | 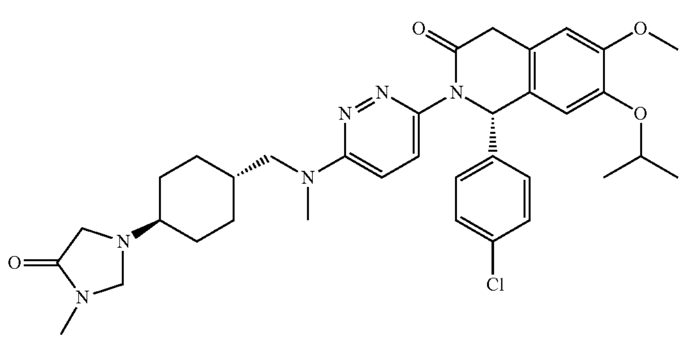 [SMILES: COc1cc2c(cc1OC(C)C)[C@H](c1ccc(Cl)cc1)N(c1ccc(N(C)C[C@H]3CC[C@H](N4CC(=O)N(C)C4)CC3)nn1)C(=O)C2] | (S)-1-(4-Chloro-phenyl)-7-isopropoxy-6-methoxy-2-(6-{methyl-[4-(3-methyl-4-oxo-imidazolidin-1-yl)-trans-cyclohexylmethyl]-amino}-pyridazin-3-yl)-1,4-dihydro-2H-isoquinolin-3-one. HPLC: $^{t}t_{Ret}$ = 4.497; LC-MS: m/z 647 [M + H]$^{+}$. |

| | Structure | Name/HPLC/MS |
|---|---|---|
| 154 | 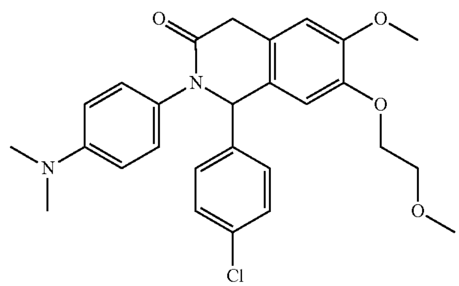 | 1-(4-Chloro-phenyl)-2-(4-dimethylamino-phenyl)-6-methoxy-7-(2-methoxyethoxy)-1,4-dihydro-2H-isoquinolin-3-one. HPLC: $^{J}t_{Ret}$ = 4.577; LC-MS: m/z 481.4 [M + H]$^+$. |
| 155 | 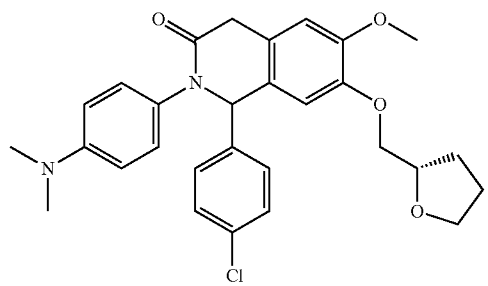 | 1-(4-Chloro-phenyl)-2-(4-dimethylamino-phenyl)-6-methoxy-7-[(S)-1-(tetrahydro-furan-2-yl)-methoxy]-1,4-dihydro-2H-isoquinolin-3-one. HPLC: $^{J}t_{Ret}$ = 4.72; LC-MS: m/z 507.1 [M + H]$^+$. |
| 156 | 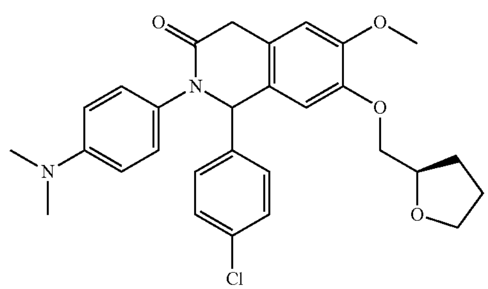 [SMILES: COc1cc2c(cc1OC[C@H]1CCCO1)C(c1ccc(Cl)cc1)N(c1ccc(N(C)C)cc1)C(=O)C2] | 1-(4-Chloro-phenyl)-2-(4-dimethylamino-phenyl)-6-methoxy-7-[(R)-1-(tetrahydro-furan-2-yl)-methoxy]-1,4-dihydro-2H-isoquinolin-3-one. HPLC: $^{J}t_{Ret}$ = 4.737; LC-MS: m/z 507.3 [M + H]$^+$. |
| 157 | 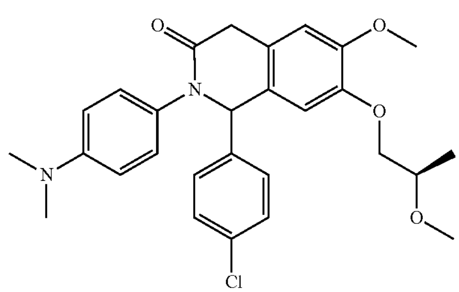 | 1-(4-Chloro-phenyl)-2-(4-dimethylamino-phenyl)-6-methoxy-7-((R)-2-methoxy-propopxy)-1,4-dihydro-2H-isoquinolin-3-one. HPLC: $^{J}t_{Ret}$ = 5.340; LC-MS: m/z 495.3 [M + H]$^+$. |
| 158 | 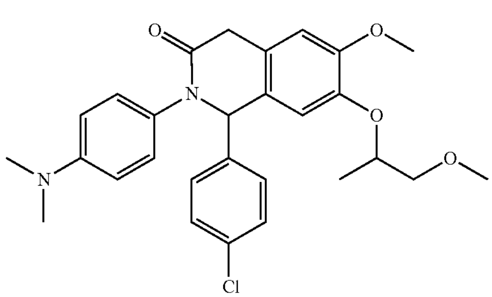 | 1-(4-Chloro-phenyl)-2-(4-dimethylamino-phenyl)-6-methoxy-7-(-2-methoxy-1-methyl-ethoxy))-1,4-dihydro-2H-isoquinolin-3-one. HPLC: $^{J}t_{Ret}$ = 5.11; LC-MS: m/z 495.2 [M + H]$^+$. |

| | Structure | Name/HPLC/MS |
|---|---|---|
| 159 | 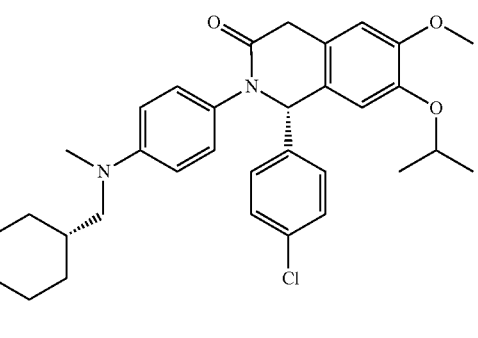 | 4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexane-carboxylic acid (2-hydroxy-2-methyl-propyl)-amide.<br>HPLC: $^{G}t_{Ret}$ = 6.496; LC-MS: m/z 662.5 [M + H]$^+$. |
| 160 | 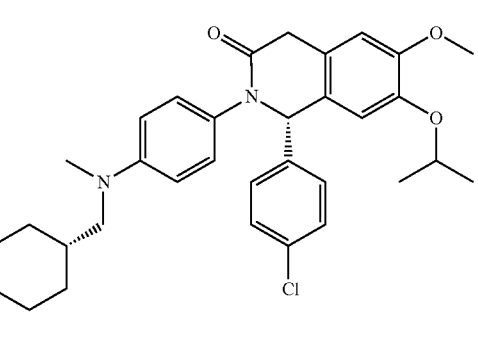 | (4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexane-carboxylic acid ((1R,2S) 2-hydroxy-cyclopentyl)-amide.<br>HPLC: $^{G}t_{Ret}$ = 6.420; LC-MS: m/z 674.6 [M + H]$^+$. |
| 161 | 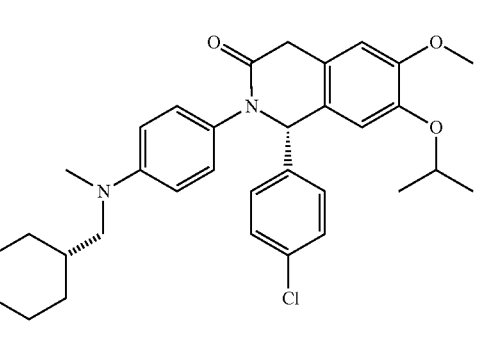 | (4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexane-carboxylic acid ((1R) 2-hydroxy-propyl)-amide.<br>HPLC: $^{G}t_{Ret}$ = 6.305; LC-MS: m/z 648.2 [M + H]$^+$. |
| 162 | 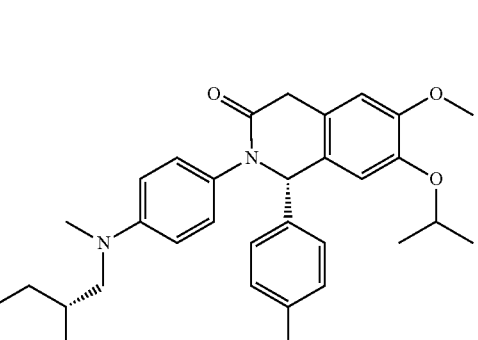 | (4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexanecarboxylic acid ((S) 2-hydroxy-propyl)-amide.<br>HPLC: $^{G}t_{Ret}$ = 6.111; LC-MS: m/z 648.2 [M + H]$^+$. |

-continued

| | Structure | Name/HPLC/MS |
|---|---|---|
| 163 | 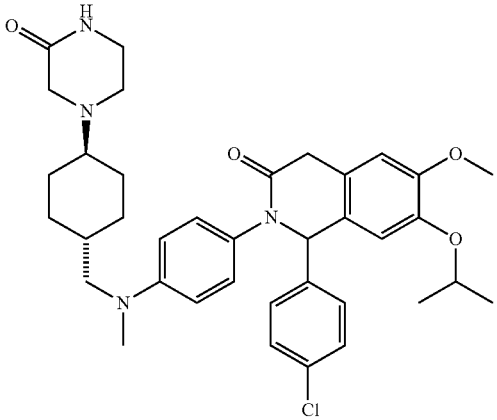 | 1-(4-Chloro-phenyl)-7-isopropoxy-6-methoxy-2-(4-{methyl-[4-(3-oxo-piperazin-1-yl)-trans-cyclohexylmethyl]-amino}-phenyl)-1,4-dihydro-2H-isoquinolin-3-one. HPLC: $^C t_{Ret}$ = 8.718; LC-MS: m/z 645.2 [M + H]$^+$. |
| 164 | 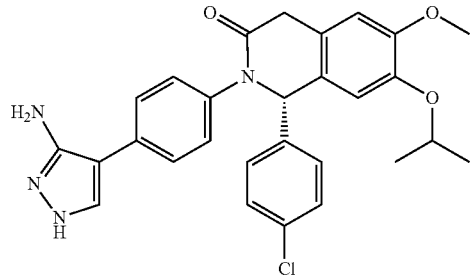 [SMILES: COc1cc2c(cc1OC(C)C)[C@H](c1ccc(Cl)cc1)N(c1ccc(-c3c[nH]nc3N)cc1)C(=O)C2] | (S)-2-[4-(3-Amino-1H-pyrazol-4-yl)-phenyl]-1-(4-chloro-phenyl)-7-isopropoxy-6-methoxy-1,4-dihydro-2H-isoquinolin-3-one. HPLC: $^G t_{Ret}$ = 6.802; LC-MS: m/z 503.4 [M + H]$^+$. |
| 165 | 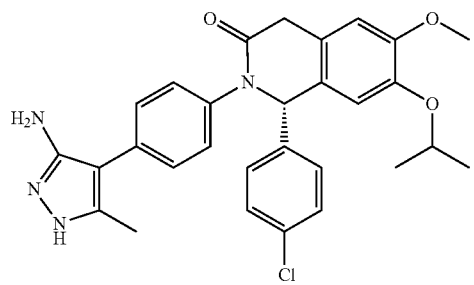 | (S)-2-[4-(3-Amino-5-methyl-1H-pyrazol-4-yl)-phenyl]-1-(4-chloro-phenyl)-7-isopropoxy-6-methoxy-1,4-dihydro-2H-isoquinolin-3-one. HPLC: $^G t_{Ret}$ = 6.662; LC-MS: m/z 517.4 [M + H]$^+$. |
| 166 | 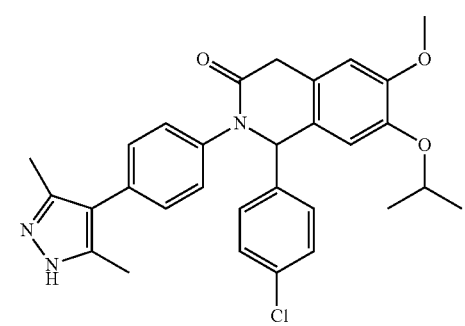 [SMILES: COc1cc2c(cc1OC(C)C)C(c1ccc(Cl)cc1)N(c1ccc(-c3c(C)n[nH]c3C)cc1)C(=O)C2] | 1-(4-Chloro-phenyl)-2-[4-(3,5-dimethyl-1H-pyrazol-4-yl)-phenyl]-7-isopropoxy-6-methoxy-1,4-dihydro-2H-isoquinolin-3-one. HPLC: $^E t_{Ret}$ = 4.823; LC-MS: m/z 516.3 [M + H]$^+$. |
| 167 | 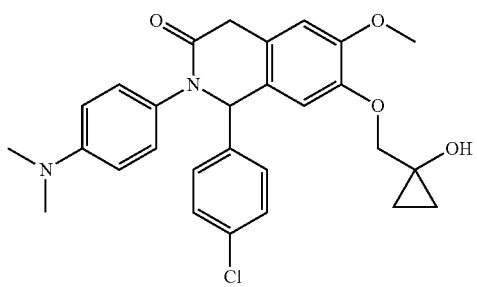 [SMILES: COc1cc2c(cc1OCC1(O)CC1)C(c1ccc(Cl)cc1)N(c1ccc(N(C)C)cc1)C(=O)C2] | 1-(4-Chloro-phenyl)-2-(4-dimethylamino-phenyl)-7-(1-hydroxy-cyclopropylmethoxy))-6-methoxy-1,4-dihydro-2H-isoquinolin-3-one. HPLC: $^J t_{Ret}$ = 4.795; LC-MS: m/z 493.4 [M + H]$^+$. |

| Structure | Name/HPLC/MS |
|---|---|
| 168 | 1-(4-Chloro-phenyl)-2-(4-dimethylamino-phenyl)-6-methoxy-7-(3-methoxy-propoxy)-1,4-dihydro-2H-isoquinolin-3-one.<br>HPLC: $^J t_{Ret}$ = 5.417; LC-MS: m/z 495.4 [M + H]$^+$. |
| 169 | (S)-1-(4-Chloro-phenyl)-7-isopropoxy-6-methoxy-2-{4-[1-(2-oxo-piperazin-1-yl)-ethyl]-phenyl}-1,4-dihydro-2H-isoquinolin-3-one.<br>HPLC: $^F t_{Ret}$ = 0.928; LC-MS: m/z 550.0 [M + H]$^+$. |
| 170 | 1-(4-Chloro-phenyl)-2-(4-dimethylamino-phenyl)-6-methoxy-7-(oxetan-2-ylmethoxy)-1,4-dihydro-2H-isoquinolin-3-one.<br>HPLC: $^J t_{Ret}$ = 4.968; LC-MS: m/z 493.4 [M + H]$^+$. |
| 171 | 1-(4-Chloro-phenyl)-7-(2,2-difluoro-ethoxy)-2-(4-dimethylamino-phenyl)—6-methoxy-1,4-dihydro-2H-isoquinolin-3-one.<br>HPLC: $^J t_{Ret}$ = 5.59; LC-MS: m/z 487.4 [M + H]$^+$. |
| 172 | {4-[({5-[1-(4-Chloro-phenyl)-7-isopropoxy-6-methoxy-3-oxo-3,4-dihydro-1H-isoquinolin-2-yl]-pyrazin-2-yl}-methyl-amino)-methyl]-trans-cyclohexylamino}-acetic acid methylester.<br>HPLC: $^I t_{Ret}$ = 5.31; LC-MS: m/z 636.5 [M + H]$^+$. |

-continued

| | Structure | Name/HPLC/MS |
|---|---|---|
| 173 | 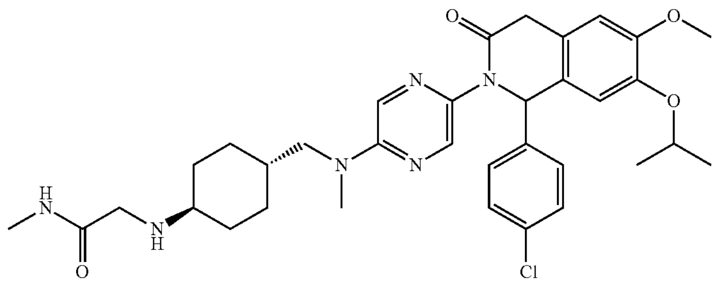 [SMILES: CNC(=O)CN[C@H]1CC[C@H](CN(C)c2cnc(N3C(=O)Cc4cc(OC)c(OC(C)C)cc4C3c3ccc(Cl)cc3)cn2)CC1] | 2-{4-[({5-[1-(4-Chloro-phenyl)-7-isopropoxy-6-methoxy-3-oxo-3,4-dihydro-1H-isoquinolin-2-yl]-pyrazin-2-yl}-methyl-amino)-methyl]-trans-cyclhexylamino}-N-methyl-acetamide.<br>HPLC: $^I t_{Ret}$ = 5.15; LC-MS: m/z 635.6 [M + H]$^+$. |
| 174 | 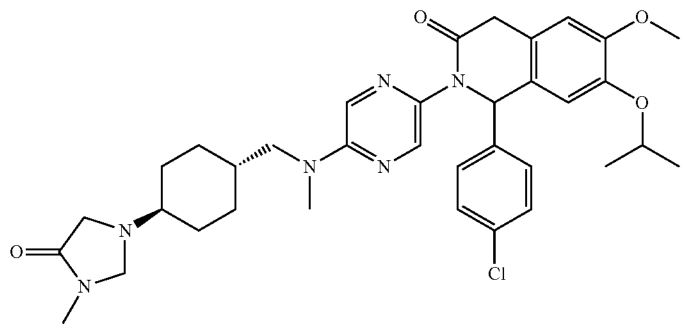 [SMILES: COc1cc2c(cc1OC(C)C)C(c1ccc(Cl)cc1)N(c1cnc(N(C)C[C@H]3CC[C@H](N4CC(=O)N(C)C4)CC3)cn1)C(=O)C2] | 1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one.<br>HPLC: $^I t_{Ret}$ = 5.18; LC-MS: m/z 647.5 [M + H]$^+$. |
| 175 | 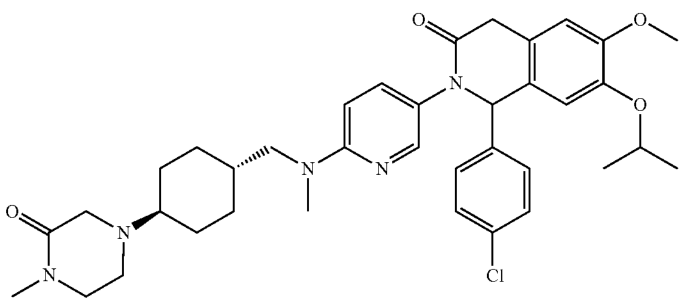 [SMILES: COc1cc2c(cc1OC(C)C)C(c1ccc(Cl)cc1)N(c1ccc(N(C)C[C@H]3CC[C@H](N4CCN(C)C(=O)C4)CC3)nc1)C(=O)C2] | 1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one.<br>HPLC: $^I t_{Ret}$ = 4.41; LC-MS: m/z 660.7 [M + H]$^+$. |
| 176 | 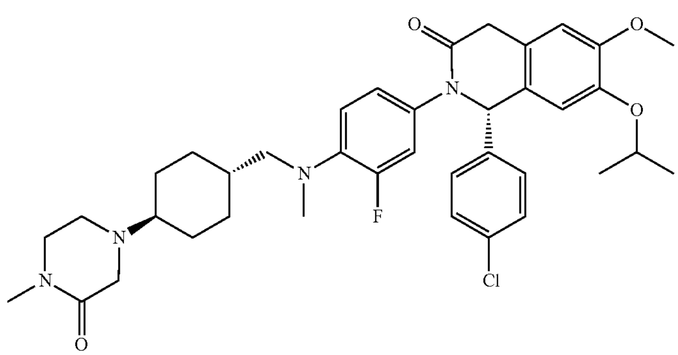 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)c(F)c1)C(=O)C2] | (S)-1-(4-Chloro-phenyl)-2-(3-fluoro-4-{methyl-[4-(4-methyl-3-oxo-piperazin-1-yl)-trans-cyclohexylmethyl]-amino}-phenyl)-7-isopropoxy-6-methoxy-1,4-dihydro-2H-isoquinolin-3-one.<br>HPLC: $^G t_{Ret}$ = 6.588; LC-MS: m/z 677.6 [M + H]$^+$. |
| 177 | 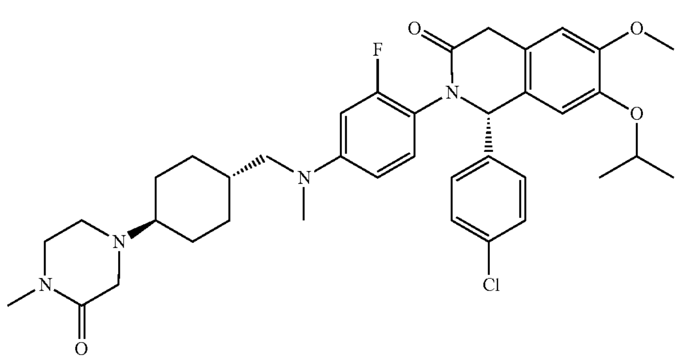 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1F)C(=O)C2] | (S)-1-(4-Chloro-phenyl)-2-(2-fluoro-4-{methyl-[4-(4-methyl-3-oxo-piperazin-1-yl)-trans-cyclohexylmethyl]-amino}-phenyl)-7-isopropoxy-6-methoxy-1,4-dihydro-2H-isoquinolin-3-one.<br>HPLC: $^G t_{Ret}$ = 6.766; LC-MS: m/z 677.7 [M + H]$^+$. |

| | Structure | Name/HPLC/MS |
|---|---|---|
| 178 | 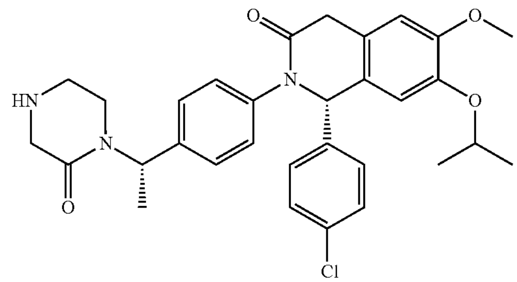 [SMILES: COc1cc2c(cc1OC(C)C)[C@H](c1ccc(Cl)cc1)N(c1ccc([C@H](C)N3CCNCC3=O)cc1)C(=O)C2] | (S)-1-(4-Chloro-phenyl)-7-isopropoxy-6-methoxy-2-{4-[(S)-1-(2-oxo-piperazin-1-yl)-ethyl]-phenyl}-1,4-dihydro-2H-isoquinolin-3-one. HPLC: $^E t_{Ret}$ = 4.449 min; LC-MS: m/z 549.2 [M + H]$^+$. |
| 179 | 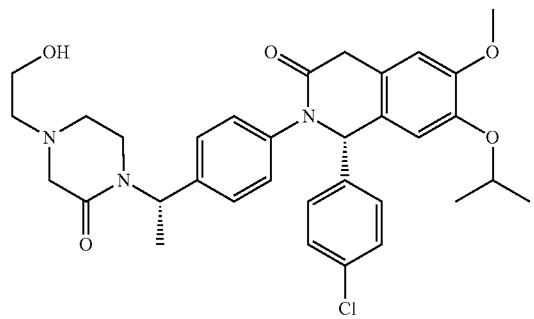 | (S)-1-(4-Chloro-phenyl)-2-(4-{(S)-1-[4-(2-hydroxy-ethyl)-2-oxo-piperazin-1-yl]-ethyl}-phenyl)-7-isopropoxy-6-methoxy-1,4-dihydro-2H-isoquinolin-3-one. HPLC: $^F t_{Ret}$ = 1.080; LC-MS: m/z 634.2 [M + H]$^+$. |
| 180 | 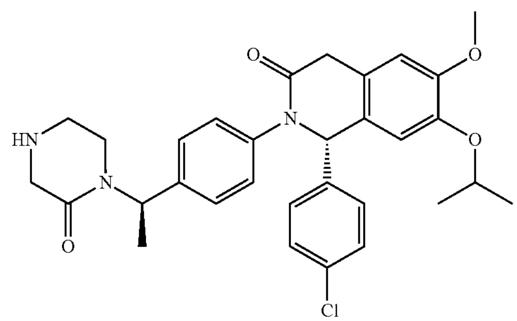 [SMILES: COc1cc2c(cc1OC(C)C)[C@H](c1ccc(Cl)cc1)N(c1ccc([C@@H](C)N3CCNCC3=O)cc1)C(=O)C2] | (S)-1-(4-Chloro-phenyl)-7-isopropoxy-6-methoxy-2-{4-[(R)-1-(2-oxo-piperazin-1-yl)-ethyl]-phenyl}-1,4-dihydro-2H-isoquinolin-3-one. HPLC: $^F t_{Ret}$ = 0.922; LC-MS: m/z 548.5 [M + H]$^+$. |
| 181 | 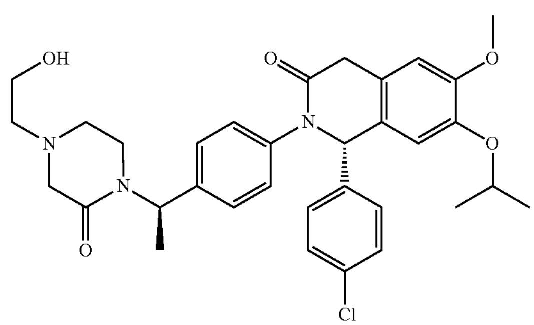 [SMILES: COc1cc2c(cc1OC(C)C)[C@H](c1ccc(Cl)cc1)N(c1ccc([C@@H](C)N3CCN(CCO)CC3=O)cc1)C(=O)C2] | (S)-1-(4-Chloro-phenyl)-2-(4-{(R)-1-[4-(2-hydroxy-ethyl)-2-oxo-piperazin-1-yl]-ethyl}-phenyl)-7-isopropoxy-6-methoxy-1,4-dihydro-2H-isoquinolin-3-one. HPLC: $^F t_{Ret}$ = 0.932; LC-MS: m/z 592.5 [M + H]$^+$. |
| 182 | 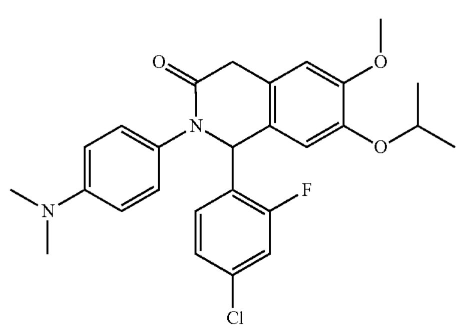 [SMILES: COc1cc2c(cc1OC(C)C)C(c1ccc(Cl)cc1F)N(c1ccc(N(C)C)cc1)C(=O)C2] | 1-(4-Chloro-2-fluoro-phenyl)-2-(4-dimethylamino-phenyl)-7-isopropoxy-6-methoxy-1,4-dihydro-2H-isoquinolin-3-one. HPLC: $^K t_{Ret}$ = 6.178; LC-MS: m/z 483.4 [M + H]$^+$. |

-continued

| | Structure | Name/HPLC/MS |
|---|---|---|
| 183 | 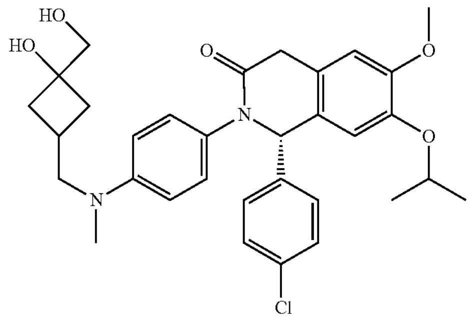 [SMILES: COc1cc2c(cc1OC(C)C)[C@H](c1ccc(Cl)cc1)N(c1ccc(N(C)CC3CC(O)(CO)C3)cc1)C(=O)C2] | (S)-1-(4-chloro-phenyl)-2-{4-[(3-hydroxy-3-hydroxymethyl-cyclobutylmethyl)-methyl-amino}-phenyl)-7-isopropoxy-6-methoxy-1,4-dihydro-2H-isoquinolin-3-one.<br>HPLC: $^F t_{Ret}$ = 1.098; LC-MS: m/z 565.5 [M + H]$^+$. |
| 184 | 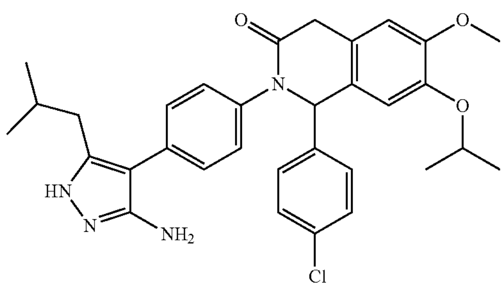 [SMILES: COc1cc2c(cc1OC(C)C)C(c1ccc(Cl)cc1)N(c1ccc(-c3c(N)n[nH]c3CC(C)C)cc1)C(=O)C2] | 2-[4-(3-Amino-5-isobutyl-1H-pyrazol-4-yl)-phenyl]-1-(4-chloro-phenyl)-7-isopropoxy-6-6-methoxy-1,4-dihydro-2H-isoquinolin-3-one.<br>HPLC: $^G t_{Ret}$ = 6.832; LC-MS: m/z 559.5 [M + H]$^+$. |
| 185 | 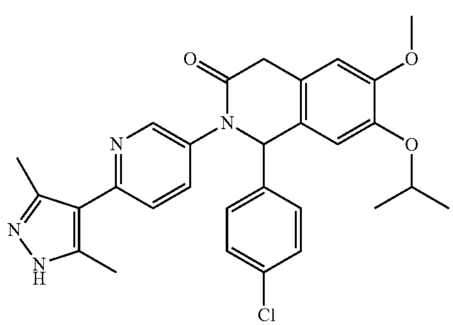 [SMILES: COc1cc2c(cc1OC(C)C)C(c1ccc(Cl)cc1)N(c1ccc(-c3c(C)n[nH]c3C)nc1)C(=O)C2] | 1-(4-Chloro-phenyl)-2-[6-(3,5-dimethyl-1H-pyrazol-4-yl)-pyridin-3-yl]-7-isopropoxy-6-methoxy-1,4-dihydro-2H-isoquinolin-3-one.<br>HPLC: $^E t_{Ret}$ = 4.685; LC-MS: m/z 517.0 [M + H]$^+$. |
| 186 | 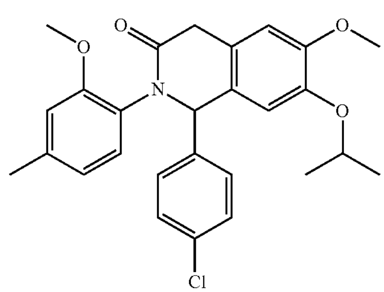 [SMILES: COc1cc2c(cc1OC(C)C)C(c1ccc(Cl)cc1)N(c1ccc(C)cc1OC)C(=O)C2] | 1-(4-Chloro-phenyl)-7-isopropoxy-6-methoxy-2-(2-methoxy-4-methyl-2-phenyl)-1,4-dihydro-2H-isoquinolin-3-one.<br>HPLC: $^L t_{Ret}$ = 5.74; LC-MS: m/z 466.4 [M + H]$^+$. |

-continued

| | Structure | Name/HPLC/MS |
|---|---|---|
| 187 | 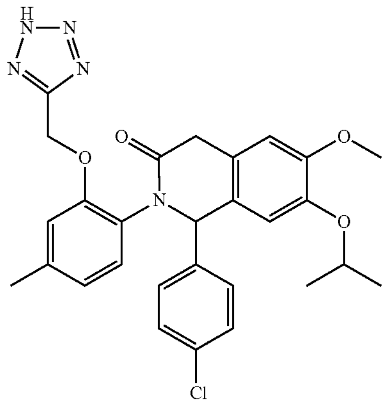 [SMILES: COc1cc2c(cc1OC(C)C)C(c1ccc(Cl)cc1)N(c1ccc(C)cc1OCc1nn[nH]n1)C(=O)C2] | 1-(4-Chloro-phenyl)-7-isopropoxy-6-methoxy-2-[4-methyl-2-(2H-tetrazol-5-ylmethoxy)-phenyl]-1,4-dihydro-2H-isoquinolin-3-one.<br>HPLC: $^L t_{Ret}$ = 5.20; LC-MS: m/z 534.4 [M + H]$^+$. |
| 188 | 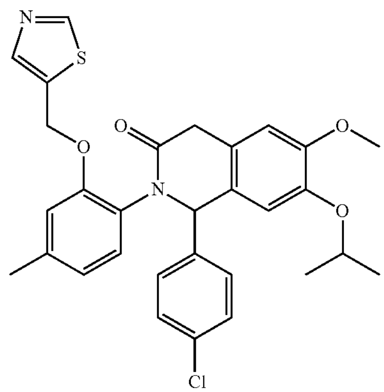 [SMILES: COc1cc2c(cc1OC(C)C)C(c1ccc(Cl)cc1)N(c1ccc(C)cc1OCc1cncs1)C(=O)C2] | 1-(4-Chloro-phenyl)-7-isopropoxy-6-methoxy-2-[4-methyl-2-(thiazol-5-ylmethoxy)-phenyl]-1,4-dihydro-2H-isoquinolin-3-one.<br>HPLC: $^M t_{Ret}$ = 1.23; LC-MS: m/z 549.4 [M + H]$^+$. |
| 189 | 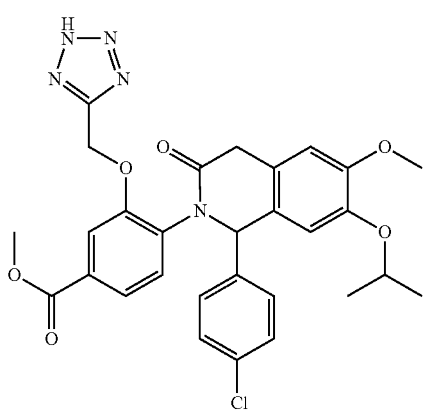 [SMILES: COC(=O)c1ccc(N2C(=O)Cc3cc(OC)c(OC(C)C)cc3C2c2ccc(Cl)cc2)c(OCc2nn[nH]n2)c1] | 4-[1-(4-Chloro-phenyl)-7-isopropoxy-6-methoxy-3-oxo-3,4-dihydro-1H-isoquinolin-2-yl]-3-(2H-tetrazol-5-ylmethoxy)-benzoic acid methyl ester.<br>HPLC: $^M t_{Ret}$ = 1.10; LC-MS: m/z 578.2 [M + H]$^+$. |
| 190 | 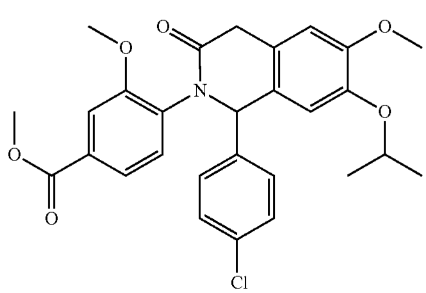 [SMILES: COC(=O)c1ccc(N2C(=O)Cc3cc(OC)c(OC(C)C)cc3C2c2ccc(Cl)cc2)c(OC)c1] | 4-[1-(4-Chloro-phenyl)-7-isopropoxy-6-methoxy-3-oxo-3,4-dihydro-1H-isoquinolin-2-yl]-3-methoxy-benzoic acid methylester.<br>HPLC: $^M t_{Ret}$ = 1.19; LC-MS: m/z 510.3 [M + H]$^+$. |

| | Structure | Name/HPLC/MS |
|---|---|---|
| 191 | 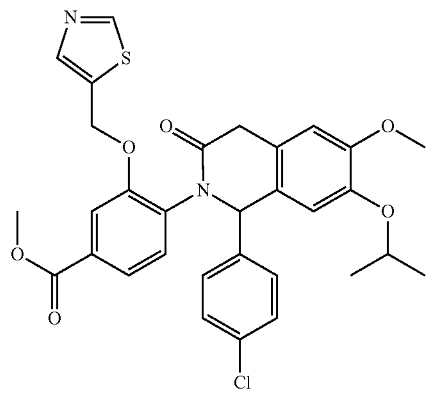 [SMILES: COC(=O)c1ccc(N2C(=O)Cc3cc(OC)c(OC(C)C)cc3C2c2ccc(Cl)cc2)c(OCc2cncs2)c1] | 4-[1-(4-Chloro-phenyl)-7-isopropoxy-6-methoxy-3-oxo-3,4-dihydro-1H-isoquinolin-2-yl]-3-(thiazol-5-ylmethoxy)-benzoic acid methylester.<br>HPLC: $^M t_{Ret}$ = 1.15; LC-MS: m/z 593.3 [M + H]$^+$. |
| 192 | 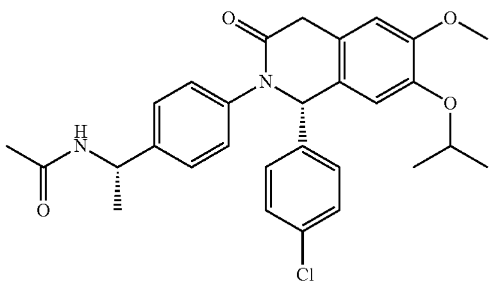 [SMILES: COc1cc2c(cc1OC(C)C)[C@H](c1ccc(Cl)cc1)N(c1ccc([C@H](C)NC(C)=O)cc1)C(=O)C2] | N-((S)-1-{4-[(S)-1-(4-Chloro-phenyl)-7-isopropoxy-6-methoxy-3-oxo-3,4-dihydro-1H-isoquinolin-2-yl]-phenyl}-ethyl)-acetamide.<br>HPLC: $^K t_{Ret}$ = 6.55; LC-MS: m/z 524.5 [M + NH$_3$]$^+$. |
| 193 | 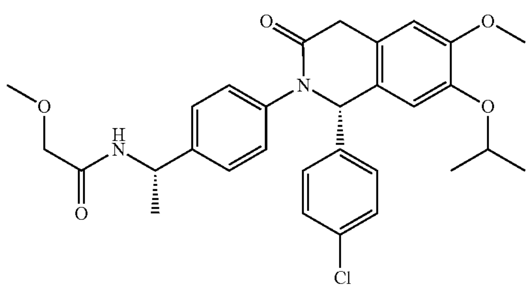 [SMILES: COCC(=O)N[C@@H](C)c1ccc(N2C(=O)Cc3cc(OC)c(OC(C)C)cc3[C@@H]2c2ccc(Cl)cc2)cc1] | N-((S)-1-{4-[(S)-1-(4-Chloro-phenyl)-7-isopropoxy-6-methoxy-3-oxo-3,4-dihydro-1H-isoquinolin-2-yl]-phenyl}-ethyl)-2-methoxy-acetamide.<br>HPLC: $^K t_{Ret}$ = 6.72; LC-MS: m/z 554.5 [M + NH$_3$]$^+$. |
| 194 | 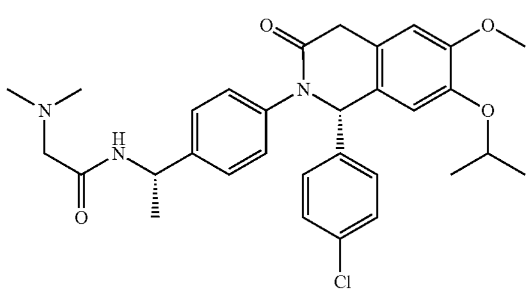 [SMILES: COc1cc2c(cc1OC(C)C)[C@H](c1ccc(Cl)cc1)N(c1ccc([C@H](C)NC(=O)CN(C)C)cc1)C(=O)C2] | N-((S)-1-{4-[(S)-1-(4-Chloro-phenyl)-7-isopropoxy-6-methoxy-3-oxo-3,4-dihydro-1H-isoquinolin-2-yl]-phenyl}-ethyl)-2-dimethylamino-acetamide.<br>HPLC: $^K t_{Ret}$ = 6.15; LC-MS: m/z 550.5 [M + H]$^+$. |
| 195 | 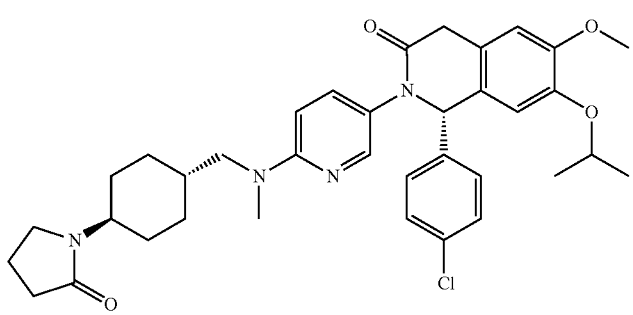 [SMILES: COc1cc2c(cc1OC(C)C)[C@H](c1ccc(Cl)cc1)N(c1ccc(N(C)C[C@H]3CC[C@H](N4CCCC4=O)CC3)nc1)C(=O)C2] | (S)-1-(4-Chloro-phenyl)-7-isopropoxy-6-methoxy-2-(6-{methyl-[4-(2-oxo-pyrrolidin-1-yl)-trans-cyclohexylmethyl]-amino}-pyridin-3-yl)-1,4-dihydro-2H-isoquinolin-3-one.<br>HPLC: $^J t_{Ret}$ = 4.21; LC-MS: m/z 631.6 [M + H]$^+$. |

| | Structure | Name/HPLC/MS |
|---|---|---|
| 196 | 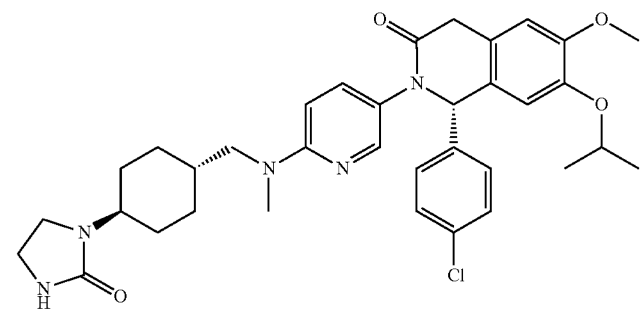 [SMILES: COc1cc2c(cc1OC(C)C)[C@H](c1ccc(Cl)cc1)N(c1ccc(N(C)C[C@H]3CC[C@H](N4CCNC4=O)CC3)nc1)C(=O)C2] | (S)-1-(4-Chloro-phenyl)-7-isopropoxy-6-methoxy-2-(6-{methyl-[4-(2-oxo-imidazolidin-1-yl)-trans-cyclohexylmethyl]-amino}-pyridin-3-yl)-1,4-dihydro-2H-isoquinolin-3-one.<br>HPLC: $^{J}t_{Ret}$ = 4.60; LC-MS: m/z 632.6 [M + H]$^+$. |
| 197 | 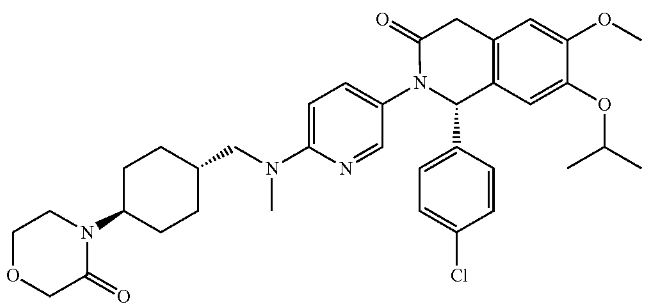 [SMILES: COc1cc2c(cc1OC(C)C)[C@H](c1ccc(Cl)cc1)N(c1ccc(N(C)C[C@H]3CC[C@H](N4CCOCC4=O)CC3)nc1)C(=O)C2] | (S)-1-(4-Chloro-phenyl)-7-isopropoxy-6-methoxy-2-(6-{methyl-[4-(3-oxo-morpholin-4-yl)-trans-cyclohexylmethyl]-amino}-pyridin-3-yl)-1,4-dihydro-2H-isoquinolin-3-one.<br>HPLC: $^{J}t_{Ret}$ = 4.72; LC-MS: m/z 647.6 [M + H]$^+$. |
| 198 | 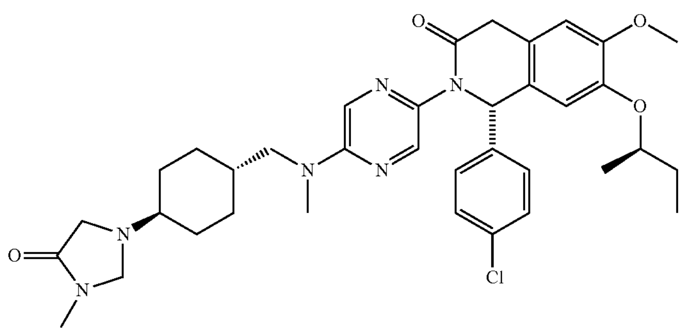 [SMILES: CC[C@@H](C)Oc1cc2c(cc1OC)CC(=O)N(c1cnc(N(C)C[C@H]3CC[C@H](N4CC(=O)N(C)C4)CC3)cn1)[C@H]2c1ccc(Cl)cc1] | (S)-2-((R)-sec-Butoxy)-1-(4-chloro-phenyl)-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one.<br>HPLC: $^{J}t_{Ret}$ = 5.475; LC-MS: m/z 661.6 [M + H]$^+$. |
| 199 | 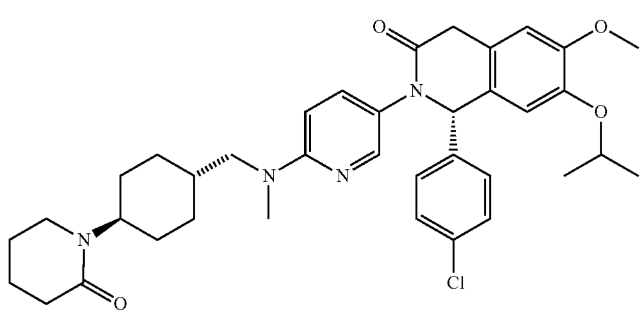 | (S)-1-(4-Chloro-phenyl)-7-isopropoxy-6-methoxy-2-(6-{methyl-[4-(2-oxo-piperidin-1-yl)-trans-cyclohexylmethyl]-amino}-pyridin-3-yl)-1,4-dihydro-2H-isoquinolin-3-one.<br>HPLC: $^{J}t_{Ret}$ = 4.97; LC-MS: m/z 645.6 [M + H]$^+$. |
| 200 | 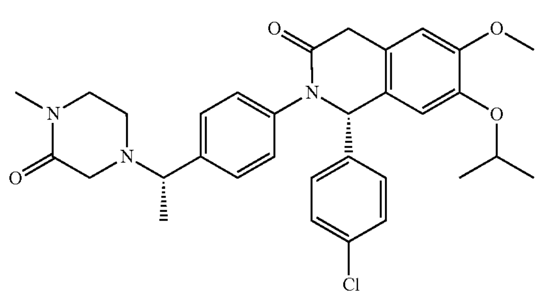 [SMILES: COc1cc2c(cc1OC(C)C)[C@H](c1ccc(Cl)cc1)N(c1ccc([C@H](C)N3CCN(C)C(=O)C3)cc1)C(=O)C2] | (S)-1-(4-Chloro-phenyl)-7-isopropoxy-6-methoxy-2-{4-[(S)-1-(4-methyl-3-oxo-piperazin-1-yl)-ethyl]-phenyl}-1,4-dihydro-2H-isoquinolin-3-one.<br>HPLC: $^{K}t_{Ret}$ = 6.01; LC-MS: m/z 562.5 [M + H]$^+$. |

-continued

| | Structure | Name/HPLC/MS |
|---|---|---|
| 201 | 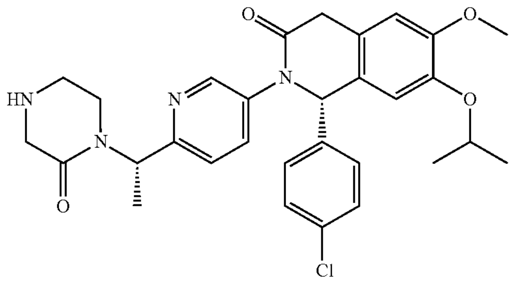 [SMILES: COc1cc2c(cc1OC(C)C)[C@H](c1ccc(Cl)cc1)N(c1ccc([C@H](C)N3CCNCC3=O)nc1)C(=O)C2] | (S)-1-(4-Chloro-phenyl)-7-isopropoxy-6-methoxy-2-{6-[(S)-1-(2-oxo-piperazin-1-yl)-ethyl]-pyridin-3-yl}-1,4-dihydro-2H-isoquinolin-3-one. HPLC: $^E t_{Ret}$ = 4.515; LC-MS: m/z 549.2 [M + H]$^+$. |
| 202 | 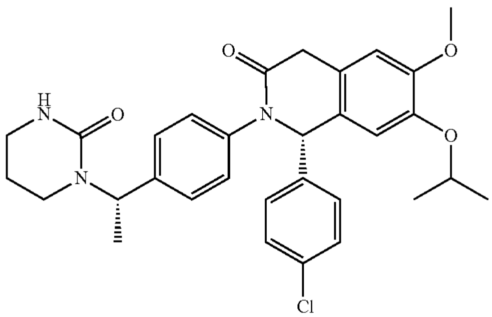 [SMILES: COc1cc2c(cc1OC(C)C)[C@H](c1ccc(Cl)cc1)N(c1ccc([C@H](C)N3CCCNC3=O)cc1)C(=O)C2] | (S)-1-(4-Chloro-phenyl)-7-isopropoxy-6-methoxy-2-{4-[(S)-1-(2-oxo-tetrahydro-pyrimidin-1-yl)-ethyl]-phenyl}-1,4-dihydro-2H-isoquinolin-3-one. HPLC: $^F t_{Ret}$ = 1.178; LC-MS: m/z 565.4 [M + NH$_3$]$^+$. |
| 203 | 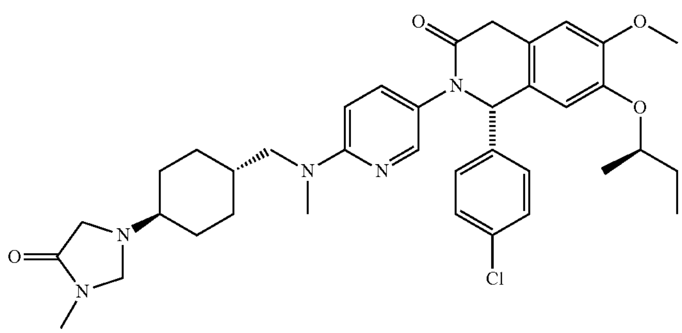 [SMILES: CC[C@@H](C)Oc1cc2c(cc1OC)CC(=O)N(c1ccc(N(C)C[C@H]3CC[C@H](N4CC(=O)N(C)C4)CC3)nc1)[C@H]2c1ccc(Cl)cc1] | (S)-7-((R)-sec-Butoxy)-1-(4-chloro-phenyl)-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one. HPLC: $^I t_{Ret}$ = 4.671; LC-MS: m/z 660.6 [M + H]$^+$. |
| 204 | 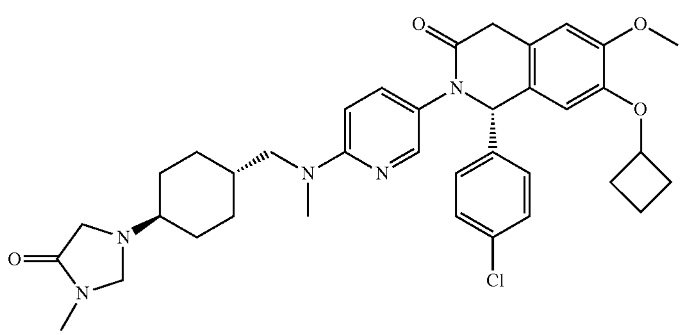 | (S)-1-(4-Chloro-phenyl)-7-cyclobutoxy-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one. HPLC: $^I t_{Ret}$ = 4.52; LC-MS: m/z 658.6 [M + H]$^+$. |
| 205 | 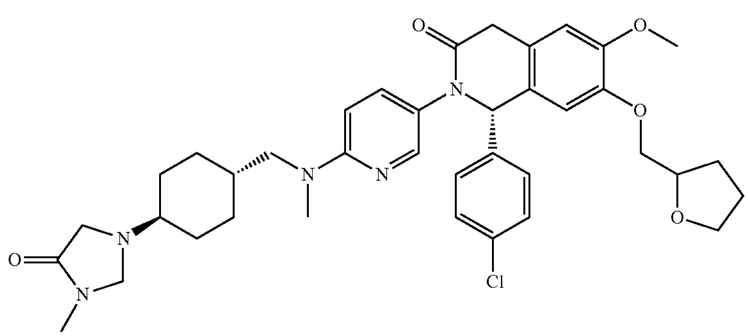 [SMILES: COc1cc2c(cc1OCC1CCCO1)[C@H](c1ccc(Cl)cc1)N(c1ccc(N(C)C[C@H]3CC[C@H](N4CC(=O)N(C)C4)CC3)nc1)C(=O)C2] | (S)-1-(4-Chloro-phenyl)-6-methoxy-2-(6-{methyl-[4-(3-methyl-4-oxo-imidazolidin-1-yl)-trans-cyclohexylmethyl]-amino}-pyridin-3-yl)-7-[(S)-1-(tetrahydro-furan-2-yl)methoxy]-1,4-dihydro-2H-isoquinolin-3-one. HPLC: $^I t_{Ret}$ = 4.26; LC-MS: m/z 688.7 [M + H]$^+$. |

-continued

| | Structure | Name/HPLC/MS |
|---|---|---|
| 206 | 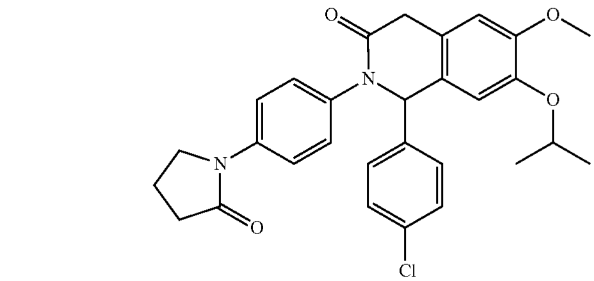 [SMILES: COc1cc2c(cc1OC(C)C)C(c1ccc(Cl)cc1)N(c1ccc(N3CCCC3=O)cc1)C(=O)C2] | 1-(4-Chloro-phenyl)-7-isopropoxy-6-methoxy-2-[4-(2-oxo-pyrrolidin-1-yl)-phenyl]-1,4-dihydro-2H-isoquinolin-3-one.<br>HPLC: $^{K}$t$_{Ret}$ = 6.81; LC-MS: m/z 505.4 [M + H]$^{+}$. |
| 207 | 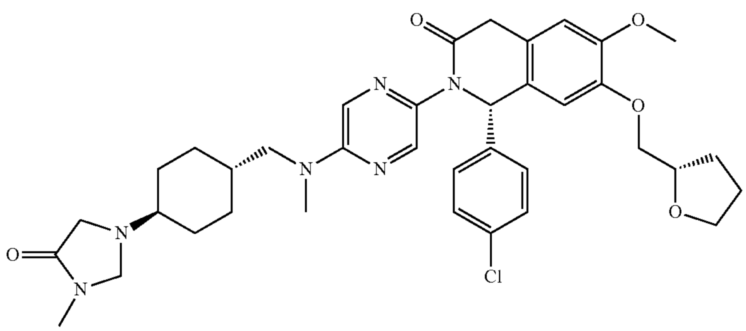 [SMILES: COc1cc2c(cc1OC[C@@H]1CCCO1)[C@H](c1ccc(Cl)cc1)N(c1cnc(N(C)C[C@H]3CC[C@H](N4CC(=O)N(C)C4)CC3)cn1)C(=O)C2] | (S)-1-(4-Chloro-phenyl)-6-methoxy-2-(5-{methyl-[4-(3-methyl-4-oxo-imidazolidin-1-yl)-trans-cyclohexylmethyl]-amino}-pyrazin-2-yl)-7-[(S)-1-(tetrahydro-furan-2-yl)methoxy]-1,4-dihydro-2H-isoquinolin-3-one.<br>HPLC: $^{E}$t$_{Ret}$ = 4.686; LC-MS: m/z 689.7 [M + H]$^{+}$. |
| 208 | 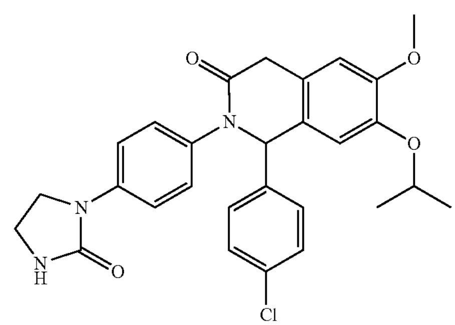 [SMILES: COc1cc2c(cc1OC(C)C)C(c1ccc(Cl)cc1)N(c1ccc(N3CCNC3=O)cc1)C(=O)C2] | 1-(4-Chloro-phenyl)-7-isopropoxy-6-methoxy-2-[4-(2-oxo-imidazolidin-1-yl)-phenyl]-1,4-dihydro-2H-isoquinolin-3-one.<br>HPLC: $^{E}$t$_{Ret}$ = 5.090; LC-MS: m/z 506.0 [M + H]$^{+}$. |
| 209 | 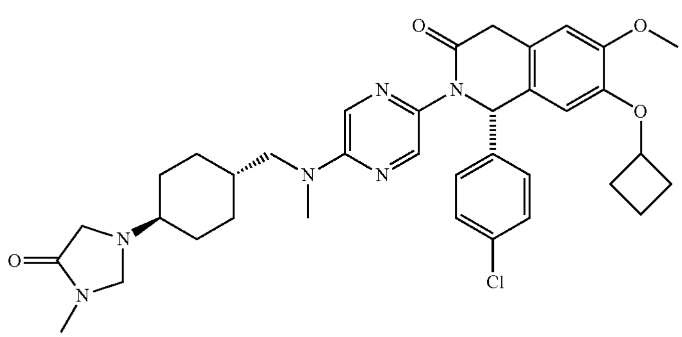 [SMILES: COc1cc2c(cc1OC1CCC1)[C@H](c1ccc(Cl)cc1)N(c1cnc(N(C)C[C@H]3CC[C@H](N4CC(=O)N(C)C4)CC3)cn1)C(=O)C2] | (S)-1-(4-Chloro-phenyl)-7-cyclobutoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one.<br>HPLC: $^{I}$t$_{Ret}$ = 5.31; LC-MS: m/z 659.6 [M + H]$^{+}$. |
| 210 | 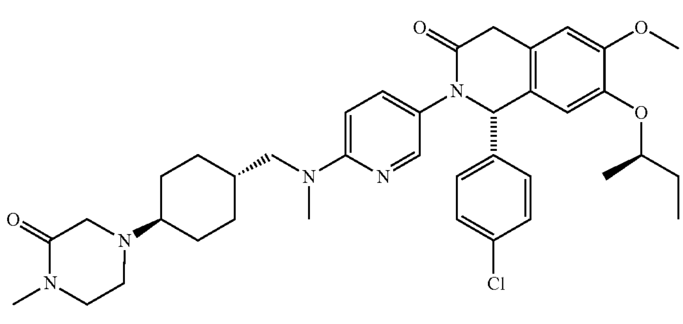 [SMILES: CC[C@@H](C)Oc1cc2c(cc1OC)CC(=O)N(c1ccc(N(C)C[C@H]3CC[C@H](N4CCN(C)C(=O)C4)CC3)nc1)[C@H]2c1ccc(Cl)cc1] | (S)-7-((R)-sec-Butoxy)-1-(4-chloro-phenyl)-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one.<br>HPLC: $^{I}$t$_{Ret}$ = 4.64; LC-MS: m/z 674.7 [M + H]$^{+}$. |

| | Structure | Name/HPLC/MS |
|---|---|---|
| 211 | 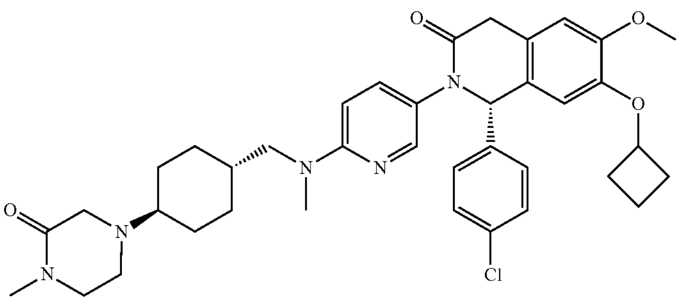 | (S)-1-(4-Chloro-phenyl)-7-cyclobutoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one. HPLC: $^I$t$_{Ret}$ = 4.52; LC-MS: m/z 672.7 [M + H]$^+$. |
| 212 | 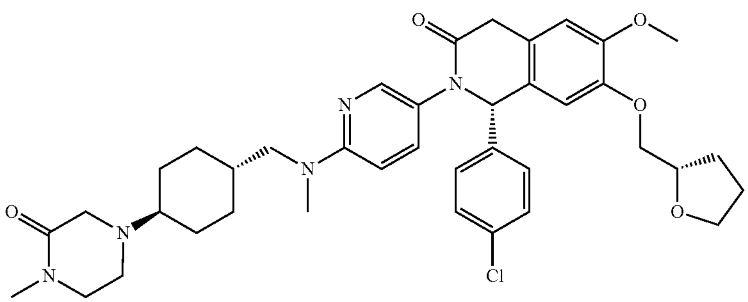 [SMILES: COc1cc2c(cc1OC[C@@H]1CCCO1)[C@H](c1ccc(Cl)cc1)N(c1ccc(N(C)C[C@H]3CC[C@H](N4CCN(C)C(=O)C4)CC3)nc1)C(=O)C2] | (S)-1-(4-Chloro-phenyl)-6-methoxy-2-(6-{methyl-[4-(4-methyl-3-oxo-piperazin-1-yl)-trans-cyclohexylmethyl]-amino}-pyridin-3-yl)-7-[(S)-1-(tetrahydro-furan-2-yl)methoxy]-1,4-dihydro-2H-isoquinolin-3-one. HPLC: $^E$t$_{Ret}$ = 4.10; LC-MS: m/z 702.0 [M + H]$^+$. |
| 213 | 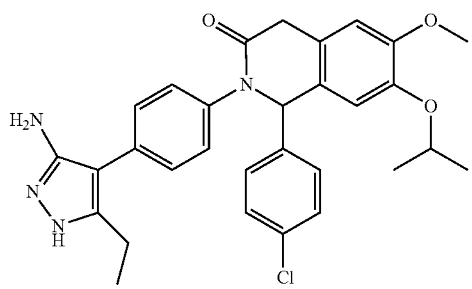 [SMILES: CCc1[nH]nc(N)c1-c1ccc(N2C(=O)Cc3cc(OC)c(OC(C)C)cc3C2c2ccc(Cl)cc2)cc1] | 2-[4-(3-Amino-5-ethyl-1H-pyrazol-4-yl)-phenyl]-1-(4-chloro-phenyl)-7-isopropoxy-6-methoxy-1,4-dihydro-2H-isoquinolin-3-one. HPLC: $^G$t$_{Ret}$ = 7.089; LC-MS: m/z 531.5 [M + H]$^+$. |
| 214 | 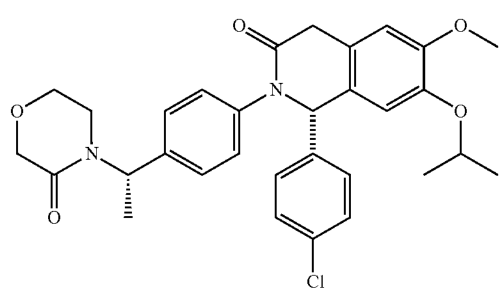 [SMILES: COc1cc2c(cc1OC(C)C)[C@H](c1ccc(Cl)cc1)N(c1ccc([C@H](C)N3CCOCC3=O)cc1)C(=O)C2] | (S)-1-(4-Chloro-phenyl)-7-isopropoxy-6-methoxy-2-{4-[(S)-1-(3-oxo-morphlin-4-yl)-ethyl]-phenyl}-1,4-dihydro-2H-isoquinolin-3-one. HPLC: $^E$t$_{Ret}$ = 5.253; LC-MS: m/z 549 [M + H]$^+$. |
| 216 | 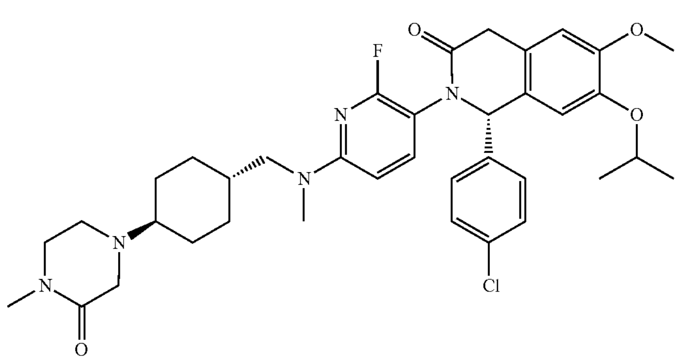 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)nc1F)C(=O)C2] | (S)-1-(4-Chloro-phenyl)-2-(2-fluoro-6-{methyl-[4-(4-methyl-3-oxo-piperazin-1-yl)-trans-cyclohexylmethyl]-amino}-pyridin-3-yl)-7-isopropoxy-6-methoxy-1,4-dihydro-2H-isoquinolin-3-one. HPLC: $^G$t$_{Ret}$ = 6.661; LC-MS: m/z 678.3 [M + H]$^+$. |

| | Structure | Name/HPLC/MS |
|---|---|---|
| 217 | 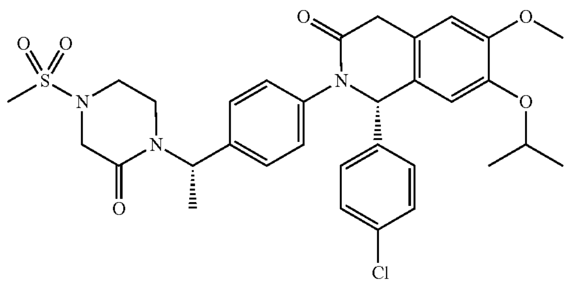 [SMILES: COc1cc2c(cc1OC(C)C)[C@H](c1ccc(Cl)cc1)N(c1ccc([C@H](C)N3CCN(S(C)(=O)=O)CC3=O)cc1)C(=O)C2] | (S)-1-(4-Chloro-phenyl)-7-isopropoxy-2-{4-[(S)-1-(4-methanesulfonyl-2-oxo-piperazin-1-yl)-ethyl]-phenyl}-6-methoxy-1,4-dihydro-2H-isoquinolin-3-one.<br>HPLC: $^{E}t_{Ret}$ = 5.131; LC-MS: m/z 626.2 [M + H]$^+$. |
| 218 | 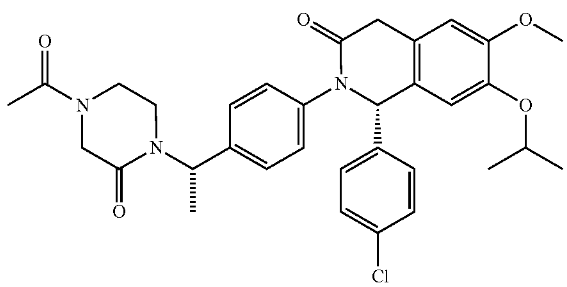 [SMILES: COc1cc2c(cc1OC(C)C)[C@H](c1ccc(Cl)cc1)N(c1ccc([C@H](C)N3CCN(C(C)=O)CC3=O)cc1)C(=O)C2] | (S)-2-{4-[(S)-1-(4-Acetyl-2-oxo-piperazin-1-yl)-ethyl]-phenyl}-1-(4-chloro-phenyl)-7-isopropoxy-6-methoxy-1,4-dihydro-2H-isoquinolin-3-one.<br>HPLC: $^{E}t_{Ret}$ = 5.126; LC-MS: m/z 590.2 [M + H]$^+$. |
| 219 | 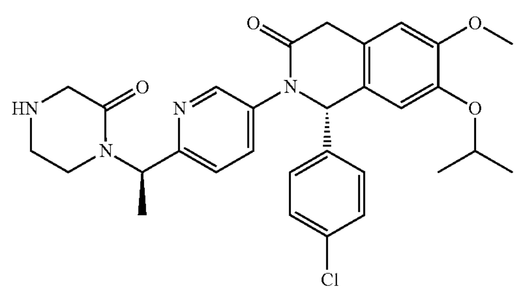 [SMILES: COc1cc2c(cc1OC(C)C)[C@H](c1ccc(Cl)cc1)N(c1ccc([C@@H](C)N3CCNCC3=O)nc1)C(=O)C2] | (S)-1-(4-Chloro-phenyl)-7-isopropoxy-6-methoxy-2-{6-[(R)-1-(2-oxo-piperazin-1-yl)-ethyl]-pyridin-3-yl}-1,4-dihydro-2H-isoquinolin-3-one.<br>HPLC: $^{E}t_{Ret}$ = 4.449; LC-MS: m/z 549.2 [M + H]$^+$. |
| 220 | 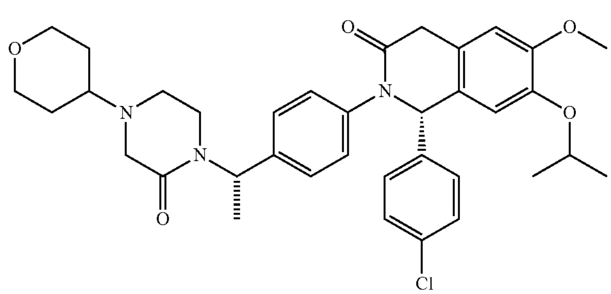 [SMILES: COc1cc2c(cc1OC(C)C)[C@H](c1ccc(Cl)cc1)N(c1ccc([C@H](C)N3CCN(C4CCOCC4)CC3=O)cc1)C(=O)C2] | (S)-1-(4-Chloro-phenyl)-7-isopropoxy-6-methoxy-2-(4-{(S)-1-[2-oxo-4-(tetrahydro-pyran-4-yl)-piperazin-1-yl]-ethyl}-phenyl)-1,4-dihydro-2H-isoquinolin-3-one.<br>HPLC: $^{E}t_{Ret}$ = 4.762; LC-MS: m/z 632.2 [M + H]$^+$. |
| 221 | 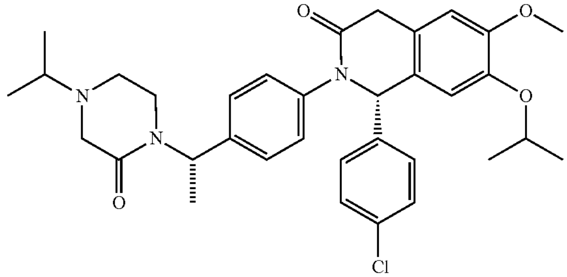 [SMILES: COc1cc2c(cc1OC(C)C)[C@H](c1ccc(Cl)cc1)N(c1ccc([C@H](C)N3CCN(C(C)C)CC3=O)cc1)C(=O)C2] | (S)-1-(4-Chloro-phenyl)-7-isopropoxy-2-{4-[(S)-1-(4-isopropyl-2-oxo-piperazin-1-yl)-ethyl]-phenyl}-6-methoxy-1,4-dihydro-2H-isoquinolin-3-one.<br>HPLC: $^{E}t_{Ret}$ = 4.831; LC-MS: m/z 590.3 [M + H]$^+$. |

-continued

| | Structure | Name/HPLC/MS |
|---|---|---|
| 222 | 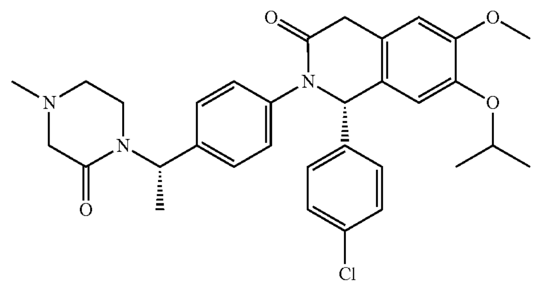 [SMILES: COc1cc2c(cc1OC(C)C)[C@H](c1ccc(Cl)cc1)N(c1ccc([C@H](C)N3CCN(C)CC3=O)cc1)C(=O)C2] | (S)-1-(4-Chloro-phenyl)-7-isopropoxy-6-methoxy-2-{4-[(S)-1-(4-methyl-2-oxo-piperazin-1-yl)-ethyl]-phenyl}-1,4-dihydro-2H-isoquinolin-3-one.<br>HPLC: $^{E}t_{Ret}$ = 4.711; LC-MS: m/z 562.3 [M + H]$^+$. |
| 223 | 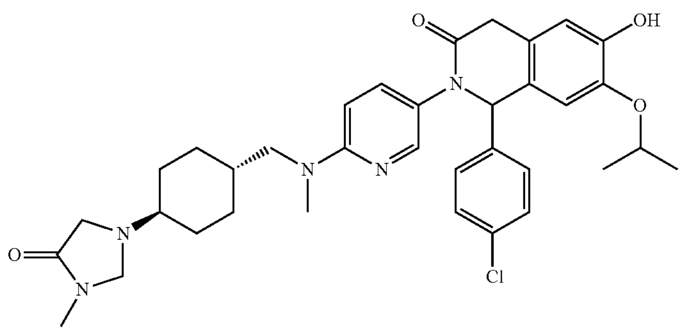 [SMILES: CC(C)Oc1cc2c(cc1O)CC(=O)N(c1ccc(N(C)C[C@H]3CC[C@H](N4CC(=O)N(C)C4)CC3)nc1)C2c1ccc(Cl)cc1] | 1-(4-Chloro-phenyl)-6-hydroxy-7-isopropoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one.<br>HPLC: $^{J}t_{Ret}$ = 3.99; LC-MS: m/z 632.6 [M + H]$^+$. |
| 224 | 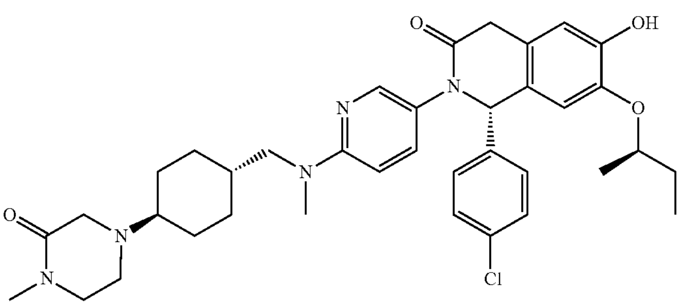 [SMILES: CC[C@@H](C)Oc1cc2c(cc1O)CC(=O)N(c1ccc(N(C)C[C@H]3CC[C@H](N4CCN(C)C(=O)C4)CC3)nc1)[C@H]2c1ccc(Cl)cc1] | (S)-7-((R)-sec-Butoxy)-1-(4-chloro-phenyl)-6-hydroxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one.<br>HPLC: $^{J}t_{Ret}$ = 4.11 min; LC-MS: m/z 660.7 [M + H]$^+$. |
| 225 | 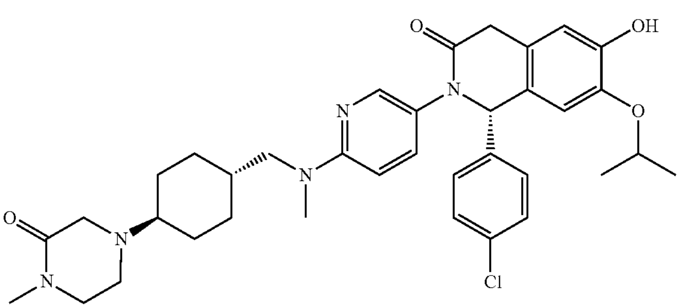 [SMILES: CC(C)Oc1cc2c(cc1O)CC(=O)N(c1ccc(N(C)C[C@H]3CC[C@H](N4CCN(C)C(=O)C4)CC3)nc1)[C@H]2c1ccc(Cl)cc1] | 1-(4-Chloro-phenyl)-6-hydroxy-7-isopropoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one.<br>HPLC: $^{J}t_{Ret}$ = 4.10; LC-MS: m/z 646.6 [M + H]$^+$. |
| 226 | 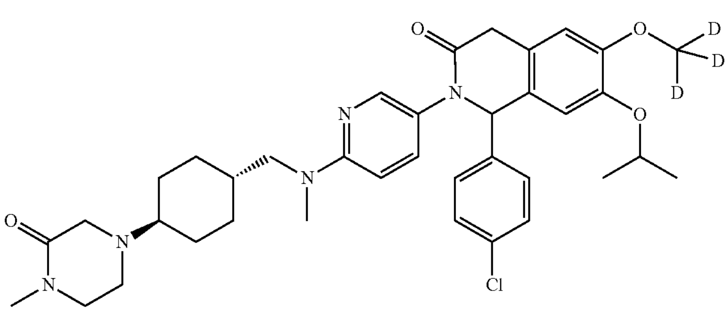 [SMILES: [2H]C([2H])([2H])Oc1cc2c(cc1OC(C)C)C(c1ccc(Cl)cc1)N(c1ccc(N(C)C[C@H]3CC[C@H](N4CCN(C)C(=O)C4)CC3)nc1)C(=O)C2] | 1-(4-Chloro-phenyl)-7-isopropoxy-6-d$_3$-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one.<br>HPLC: $^{J}t_{Ret}$ = 4.38; LC-MS: m/z 663.6 [M + H]$^+$. |

| | Structure | Name/HPLC/MS |
|---|---|---|
| 227 | 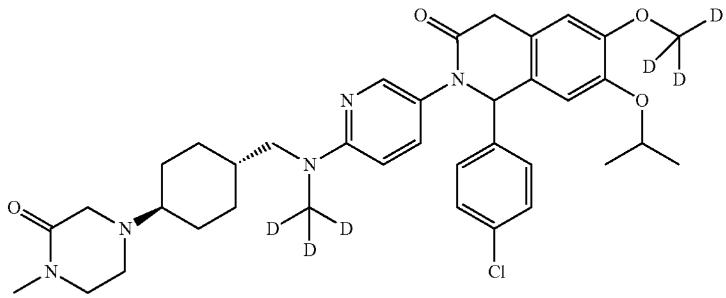 [SMILES: [2H]C([2H])([2H])Oc1cc2c(cc1OC(C)C)C(c1ccc(Cl)cc1)N(c1ccc(N(C[C@H]3CC[C@H](N4CCN(C)C(=O)C4)CC3)C([2H])([2H])[2H])nc1)C(=O)C2] | 1-(4-Chloro-phenyl)-7-isopropoxy-6-d₃-methoxy-2-(6-{d₃-methyl-[4-(4-methyl-3-oxo-piperazin-1-yl)-trans-cyclohexylmethyl]-amino}-pyridin-3-yl)-1,4-dihydro-2H-isoquinolin-3-one. HPLC: $^E t_{Ret}$ = 4.38; LC-MS: m/z 666.6 [M + H]⁺. |
| 228 | 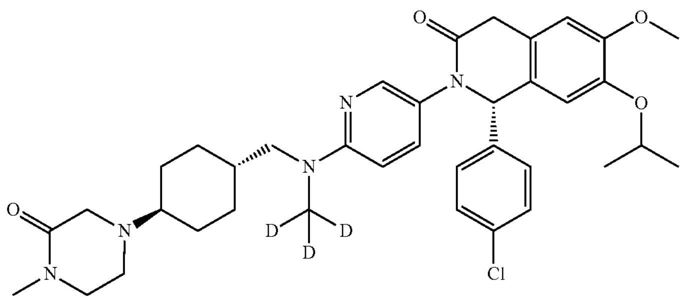 | (S)-1-(4-Chloro-phenyl)-7-isopropoxy-6-methoxy-2-(6-{d₃-methyl-[4-(4-methyl-3-oxo-piperazin-1-yl)-trans-cyclohexylmethyl]-amino}-pyridin-3-yl)-1,4-dihydro-2H-isoquinolin-3-one. HPLC: $^E t_{Ret}$ = 4.38; LC-MS: m/z 663.6 [M + H]⁺. |

Intermediate 95.1: 1-(4-Iodo-benzyl)-1H-imidazole

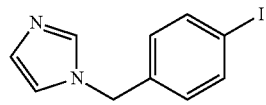 [SMILES: Ic1ccc(Cn2ccnc2)cc1]

To a solution of imidazole (400 mg, 5.88 mmol) and K₂CO₃ (1.22 g, 8.81 mmol) in DMF (19 ml) was added 4-iodobenzyl bromide (1.83 g, 6.17 mol) at RT under protection from light. After stirring for 11.5 h, the reaction mixture was poured into water. The aqueous layer was extracted twice with EtOAc, the combined organic layers were washed with water and brine, dried over Na₂SO₄, filtered and concentrated. The residue was purified by column chromatography to afford the title compound (757 mg, 2.66 mmol, 45%) as a beige solid. HPLC: $^E t_{Ret}$=3.838 min; LC-MS: m/z 285.2 [M+H]⁺.

Intermediate 96.1: (4-Isopropoxy-3-methoxy-phenyl)-acetyl chloride

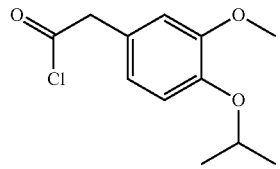 [SMILES: COc1cc(CC(=O)Cl)ccc1OC(C)C]

To a solution of Intermediate 96.2 (1.41 g, 6.29 mmol) in DCM (50 mL) was added 1-chloro-N,N,2-trimethylpropenylamine (1.0 mL, 7.55 mol) at 0° C. After stirring for 0.5 h, the reaction mixture was concentrated in vacuo and the crude product was used without further purification. HPLC: $^E t_{Ret}$=4.772 min (Methyl ester after quenching by MeOH).

Intermediate 96.2: (4-Isopropoxy-3-methoxy-phenyl)-acetic acid

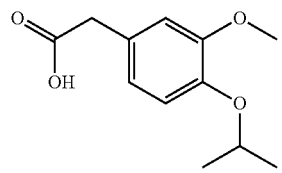 [SMILES: COc1cc(CC(=O)O)ccc1OC(C)C]

The title compound (11.5 g, 78 mmol, 99%) was obtained as a white solid from Intermediate 75.1 (20.0 g, 79 mmol) analogously to Intermediate 1.2. HPLC: $^E t_{Ret}$=4.117 min; LC-MS: m/z 223 [M+H]⁻.

Example 98

N-{4-[1-(4-Chloro-phenyl)-7-isopropoxy-6-methoxy-3-oxo-3,4-dihydro-1H-isoquinolin-2-yl]-phenyl}-2,2,2-trifluoro-N-methyl-acetamide

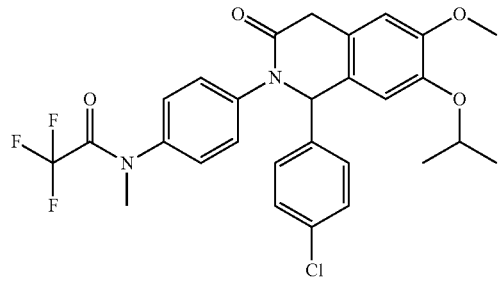 [SMILES: COc1cc2c(cc1OC(C)C)C(c1ccc(Cl)cc1)N(c1ccc(N(C)C(=O)C(F)(F)F)cc1)C(=O)C2]

The title compound (236 mg, 0.43 mmol, 53.1%) was obtained as a white solid from Intermediate 98.1 (410 mg, 0.81 mmol) and 2-iodopropane (0.24 mL, 2.43 mmol) analo gously to Intermediate 138.2. HPLC: $^{K}t_{Ret}$=7.34 min; LC-MS: m/z 547.2 [M+H]⁺.

Intermediate 98.1: N-{4-[1-(4-Chloro-phenyl)-7-hydroxy-6-methoxy-3-oxo-3,4-dihydro-1H-isoquinolin-2-yl]-phenyl}-2,2,2-trifluoro-N-methyl-acetamide

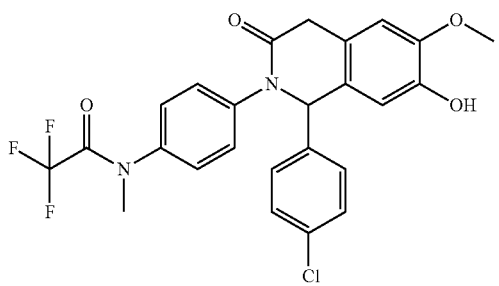 [SMILES: COc1cc2c(cc1O)C(c1ccc(Cl)cc1)N(c1ccc(N(C)C(=O)C(F)(F)F)cc1)C(=O)C2]

The title intermediate (415 mg, 0.82 mmol, 57.8%) was obtained as a white solid from Intermediate 98.2 (629 mg, 1.84 mmol) and Intermediate 187.3 (723 mg, 1.42 mmol) analogously to Example 1. The 4-methoxyphenylmethyl group was cleaved in-situ under the reaction conditions. HPLC: $^{K}t_{Ret}$=6.478 min; LC-MS: m/z 505.1 [M+H]⁺.

Intermediate 98.2: N-(4-{[1-(4-Chloro-phenyl)-meth-(E)-ylidene]-amino}-phenyl)-2,2,2-trifluoro-N-methyl-acetamide

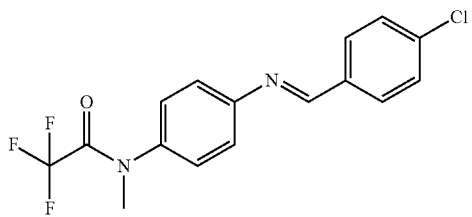 [SMILES: CN(C(=O)C(F)(F)F)c1ccc(/N=C/c2ccc(Cl)cc2)cc1]

The title compound (0.73 g, 2.16 mmol, 47.1%) was obtained as a white solid from Intermediate 98.3 (1.0 g, 4.58 mmol) and 4-chloro-benzaldehyde (0.71 g, 5.04 mmol) analogously to Intermediate 1.4. ¹H NMR (600 MHz, DMSO-d₆) 3.30 (s, 3H) 7.35 (d, 2H) 7.49 (d, 2H) 7.61 (d, 2H) 7.96 (d, 2H) 8.67 (s, 1H).

Intermediate 98.3: N-(4-Amino-phenyl)-2,2,2-trifluoro-N-methyl-acetamide

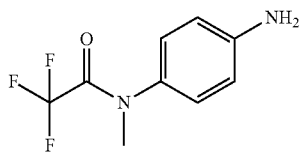

The title intermediate (2.67 g, 12.2 mmol, 100%) was obtained as a solid from Intermediate 98.4 (3.0 g, 12.1 mmol) analogously to Intermediate 43.2. HPLC: $^{K}t_{Ret}$=0.73 min; LC-MS: m/z 219.3 [M+H]⁺.

Intermediate 98.4: 2,2,2-Trifluoro-N-methyl-N-(4-nitro-phenyl)-acetamide

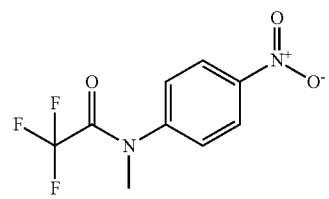 [SMILES: CN(C(=O)C(F)(F)F)c1ccc([N+](=O)[O-])cc1]

The title intermediate (11.8 g, 12.2 mmol, 100%) was obtained as a solid from N-methyl-4-nitroaniline (8.5 g, 54.2 mmol) and trifluoroacetic anhydride (11.4 mL, 81 mmol) analogously to Intermediate 43.1. HPLC: $^{K}t_{Ret}$=1.90 min; LC-MS: m/z 249.4 [M+H]⁺.

Example 100

(S)-1-(4-Chloro-phenyl)-2-(4-{[4-(1,1-dioxo-1 lambda*6*-thiomorpholin-4-yl)-trans-cyclohexylmethyl]-methyl-amino}-phenyl)-7-isopropoxy-6-methoxy-1,4-dihydro-2H-isoquinolin-3-one

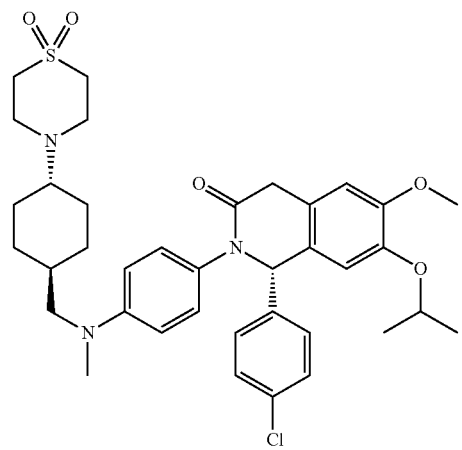 [SMILES: COc1cc2c(cc1OC(C)C)[C@H](c1ccc(Cl)cc1)N(c1ccc(N(C)C[C@H]3CC[C@H](N4CCS(=O)(=O)CC4)CC3)cc1)C(=O)C2]

The title intermediate (25 mg, 0.031 mmol, 59%) was obtained as a white solid from Intermediate 77.3 (30 mg, 0.053 mmol) and divinylsulfone (6.3 mg, 0.053 mmol) analogously to Intermediate 87.1. HPLC: $^{A}t_{Ret}$=2.02 min; LC-MS: m/z 680.2 [M+H]⁺.

Intermediate 101.1: (4-{[(4-Bromo-3-methoxy-phenyl)-methyl-amino]-methyl}-trans-cyclohexyl)-carbamic acid tert-butyl ester

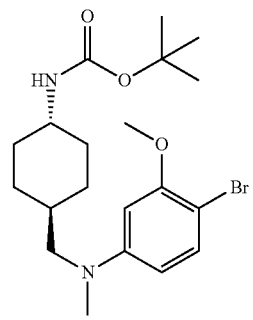 [SMILES: COc1cc(N(C)C[C@H]2CC[C@H](NC(=O)OC(C)(C)C)CC2)ccc1Br]

The title intermediate (266 mg, 0.62 mmol, 49%) was obtained as a white solid from Intermediate 101.2 (695 mg, 1.86 mmol) and 37% water solution of formaldehyde (0.38 mL, 5.08 mmol) analogously to Intermediate 77.1. HPLC: $^{A}t_{Ret}$=2.67 min; LC-MS: m/z 427.1 [M+H]⁺.

Intermediate 101.2: {4-[(4-Bromo-3-methoxy-phenylamino)-methyl]-trans-cyclohexyl}-carbamic acid tert-butyl ester

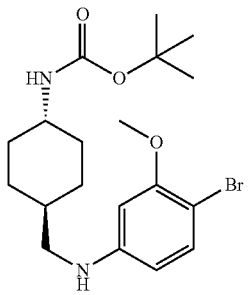 [SMILES: COc1cc(NC[C@H]2CC[C@H](NC(=O)OC(C)(C)C)CC2)ccc1Br]

The title intermediate (526 mg, 1.27 mmol, 86%) was obtained as a grey solid from (4-formyl-cyclohexyl)-carbamic acid tert-butyl ester (371 mg, 1.63 mmol) and 4-bromo-3-methoxyaniline (300 mg, 1.48 mmol) analogously to Intermediate 75.7. HPLC: $^At_{Ret}$=2.60 min; LC-MS: m/z 413.1 [M+H]$^+$.

Intermediate 102.1: (S)-2-{4-[(Trans-4-amino-cyclohexylmethyl)-methyl-amino]-2-methoxy-phenyl}-1-(4-chloro-phenyl)-7-isopropoxy-6-methoxy-1,4-dihydro-2H-isoquinolin-3-one

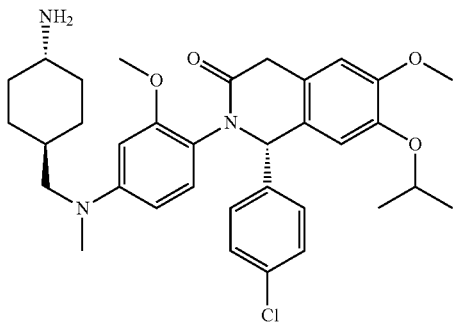 [SMILES: COc1cc2c(cc1OC(C)C)[C@H](c1ccc(Cl)cc1)N(c1ccc(N(C)C[C@H]3CC[C@H](N)CC3)cc1OC)C(=O)C2]

The title intermediate (40.9 mg, 0.058 mmol, 100%) was obtained as a orange resin from Example 101 (40 mg, 0.58 mmol) analogously to Example 51. HPLC: $^At_{Ret}$=1.90 min; LC-MS: m/z 592.2 [M+H]$^+$.

Intermediate 103.1: ((2-tert-Butoxycarbonylamino-ethyl)-{4-[({4-[(S)-1-(4-chloro-phenyl)-7-isopropoxy-6-methoxy-3-oxo-3,4-dihydro-1H-isoquinolin-2-yl]-3-methoxy-phenyl}-methyl-amino)-methyl]-trans-cyclohexyl}-amino)-acetic acid methyl ester

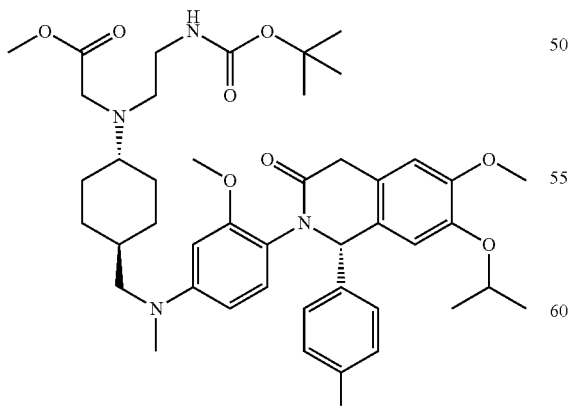

The title intermediate (37 mg, 0.038 mmol, quantitative) was obtained as a yellow solid from Example 102 (25 mg, 0.038 mmol) and N-Boc-2-aminoacetaldehyde (9 mg, 0.056 mmol) analogously to Intermediate 79.2. HPLC: $^At_{Ret}$=2.31 min; LC-MS: m/z 807.4[M+H]$^+$.

Intermediate 104.1: (4-Iodo-phenyl)-methyl-piperidin-4-ylmethyl-amine

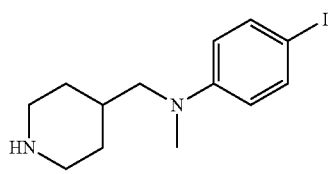 [SMILES: CN(CC1CCNCC1)c1ccc(I)cc1]

The title intermediate (94 mg, 0.28 mmol, 61.2%) was obtained as a yellow resin from Intermediate 104.2 (200 mg, 0.46 mmol) analogously to Example 51. HPLC: $^At_{Ret}$=1.50 min; LC-MS: m/z 331.1 [M+H]$^+$.

Intermediate 104.2: 4-{[(4-Iodo-phenyl)-methyl-amino]-methyl}-piperidine-1-carboxylic acid tert-butyl ester

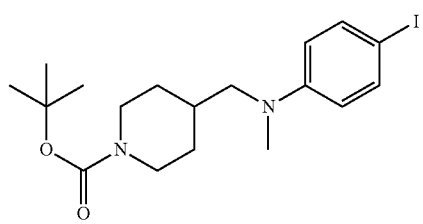 [SMILES: CN(CC1CCN(C(=O)OC(C)(C)C)CC1)c1ccc(I)cc1]

The title intermediate (3.27 g, 7.60 mmol, 83%) was obtained as a brown oil from Intermediate 104.3 (4.27 g, 9.13 mmol) and 37% water solution of formaldehyde (1.36 mL, 18.2 mmol) analogously to Intermediate 77.1. HPLC: $^At_{Ret}$=3.19 min; LC-MS: m/z 431 [M+H]$^+$.

Intermediate 104.3: 4-[(4-Iodo-phenylamino)-methyl]-piperidine-1-carboxylic acid tert-butyl ester

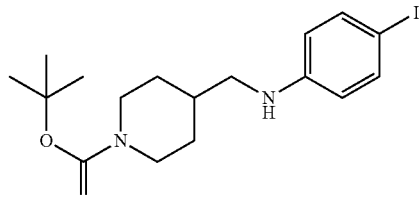

The title intermediate (4.27 g, 9.13 mmol, 100%) was obtained as a violet solid from 4-formyl-piperidine-1-carboxylic acid tert-butyl ester (2.73 g, 12.8 mmol) and 4-iodoaniline (2.0 g, 9.13 mmol) analogously to Intermediate 75.7. HPLC: $^At_{Ret}$=2.97 min; LC-MS: m/z 361.1 [M+HCOOH]$^+$.

Example 105

(S)-1-(4-Chloro-phenyl)-7-isopropoxy-6-methoxy-2-(4-{methyl-[4-(3-methyl-4-oxo-imidazolidin-1-yl)-trans-cyclohexylmethyl]-amino}-phenyl)-1,4-dihydro-2H-isoquinolin-3-one

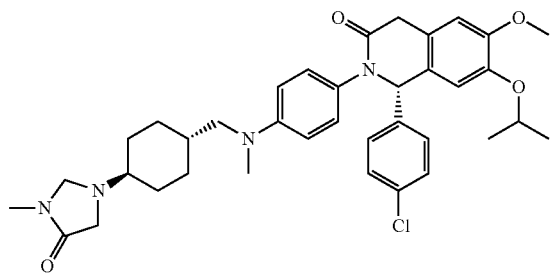 [SMILES: COc1cc2c(cc1OC(C)C)[C@H](c1ccc(Cl)cc1)N(c1ccc(N(C)C[C@H]3CC[C@H](N4CC(=O)N(C)C4)CC3)cc1)C(=O)C2]

The title compound (104 mg, 0.16 mmol, 19.4%) was obtained as a yellow solid from Intermediate 75.6 (287 mg, 0.83 mmol) and Intermediate 105.1 (372 mg, 0.87 mmol) analogously to Example 75. HPLC: $^F t_{Ret}$=1.164 min; LC-MS: m/z 645.5 [M+H]$^+$; $^1$H NMR (400 MHz, DMSO-d$_6$) 0.85-1.09 (m, 4H) 1.19 (dd, J=19.55, 5.86 Hz, 6H) 1.49-1.87 (m, 5H) 2.08-2.25 (m, 1H) 2.70 (s, 3H) 2.85 (s, 3H) 3.09 (s, 4H) 3.55 (d, J=19.94 Hz, 1H) 3.71 (s, 3H) 3.87 (d, J=19.55 Hz, 1H) 4.02 (s, 2H) 4.33-4.49 (m, 1H) 5.92 (s, 1H) 6.54 (d, J=8.99 Hz, 2H) 6.80 (s, 1H) 6.87 (d, J=8.99 Hz, 2H) 7.02 (s, 1H) 7.33 (s, 4H).

Intermediate 105.1: 1-(4-{[(4-Iodo-phenyl)-methyl-amino]-methyl}-trans-cyclohexyl)-3-methyl-imidazolidin-4-one

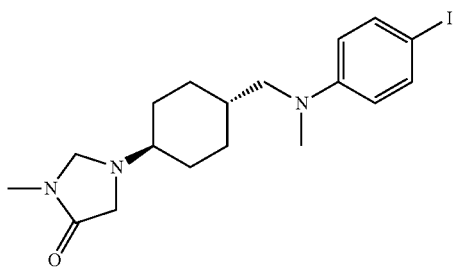 [SMILES: CN1CN([C@H]2CC[C@H](CN(C)c3ccc(I)cc3)CC2)CC1=O]

A mixture of Intermediate 105.2 (535 mg, 1.29 mmol) and 37% aqueous solution of formaldehyde (0.96 mL, 12.9 mmol) in EtOH (20 mL) was sealed and heated at 80° C. for 20 h. The reaction mixture was concentrated in vacuo, then the resulting yellow oil was directly purified by column chromatography to afford the title compound (553 mg, 1.29 mmol, 100%) as a beige solid. HPLC: $^F t_{Ret}$=1.088 min; LC-MS: m/z 428.1 [M+H]$^+$.

Intermediate 105.2: 2-(4-{[(4-Iodo-phenyl)-methyl-amino]-methyl}-trans-cyclohexylamino)-N-methyl-acetamide

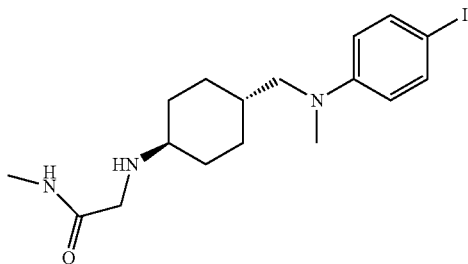 [SMILES: CNC(=O)CN[C@H]1CC[C@H](CN(C)c2ccc(I)cc2)CC1]

A mixture of Intermediate 105.3 (700 mg, 1.68 mmol) and 33% EtOH solution of MeNH$_2$ (2.1 mL, 168 mmol) was sealed and heated at 80° C. for 24 h. The reaction mixture was concentrated in vacuo, then the resulting yellow oil was directly purified by column chromatography to afford the title compound (535 mg, 1.29 mmol, 77%) as a beige solid. HPLC: $^F t_{Ret}$=0.982 min; LC-MS: m/z 416.2 [M+H]$^+$.

Intermediate 105.3: (4-{[(4-Iodo-phenyl)-methyl-amino]-methyl}-trans-cyclohexylamino)-acetic acid methyl ester

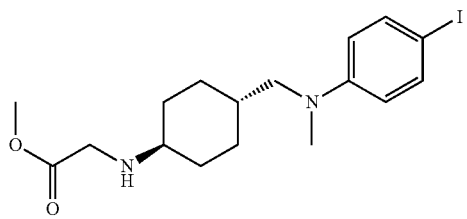 [SMILES: COC(=O)CN[C@H]1CC[C@H](CN(C)c2ccc(I)cc2)CC1]

To a solution of Intermediate 105.4 (16.9 g, 49.2 mmol) in DMF (300 mL) was successively added potassium carbonate (14.3 g, 103 mmol) and methyl 2-bromoacetate (4.77 mL, 51.7 mmol) at −10° C. The suspension was stirred for 4.5 h at −10° C. to 10° C. The reaction mixture was diluted with EtOAc, the organic phase was washed with water and brine, and dried over Na$_2$SO$_4$, filtered and evaporated to dryness. Purification of the residue by normal phase column chromatography, eluting with 100% DCM to 100% EtOAc, gave the title compound as brown oil (9.45 g, 21.6 mmol, 43.8%). HPLC: $^E t_{Ret}$=4.22 min; LC-MS: m/z 417.0 [M+H]$^+$.

Intermediate 105.4: (Trans-4-amino-cyclohexylmethyl)-(4-iodo-phenyl)-methyl-amine

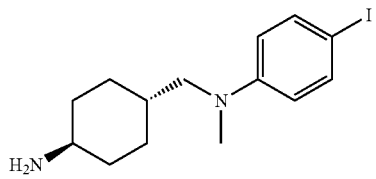

To a solution of Intermediate 77.1 (21.9 g, 49.5 mmol) in DCM (300 mL) was added drop wise TFA (114 mL, 1484 mmol) at 0° C. The reaction mixture was stirred for 30 min at RT, then concentrated in vacuo. The residue was diluted with EtOAc, and adjusted to pH 9 at 0° C. by addition of 2M NaOH. The phases were separated and water layer was extracted with EtOAc. The organic layer was washed with water and brine, dried over Na$_2$SO$_4$, and filtered. Concentration in vacuo gave the title compound as grey solid (16.9 g, 47.8 mmol, 97%). HPLC: $^E t_{Ret}$=3.92 min; LC-MS: m/z 345.1 [M+H]$^+$.

Example 106

(S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one

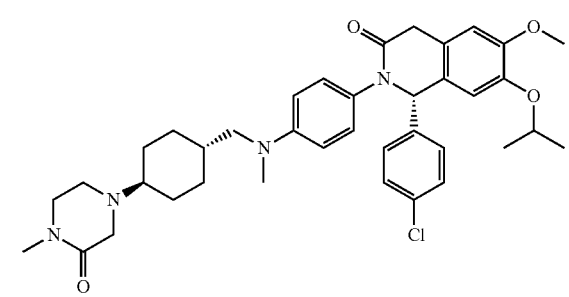 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2]

A sealable reaction flask was charged with potassium phosphate (4.44 g, 20.29 mmol), evacuated and heated for 15 min at 170° C. The reaction flask was back-filled with argon at RT and Intermediate 75.6 (3.64 g, 10.15 mmol), Intermediate 106.1 (5.48 g, 12.18 mmol), dioxan (75 mL) and (+/−)-trans-1,2-diaminocyclohexane (0.37 mL, 3.04 mmol) were added subsequently. The reaction flask was carefully evacuated under vacuum (2×) and backfilled with argon (2×) and copper (I) iodide (0.586 g, 3.04 mmol) were added. The reaction mixture was stirred for 22.5 h at 95° C. The mixture was extracted between EtOAc (3×) and water (3×). The organic phases were washed with brine and dried over $Na_2SO_4$, filtered and evaporated to dryness. Purification of the residue by normal phase column chromatography, eluting with 100% EtOAc to 20% MeOH/EtOAc followed by reverse phase prep-HPLC afforded the TFA salt which was extracted between EtOAc (2×) and 1M aqueous $NaHCO_3$ (1×). The organic phases were washed with brine and dried over $Na_2SO_4$, filtered and evaporated to dryness gave the title compound as white solid (1.59 g, 2.41 mmol, 23.8%): HPLC: $^E t_{Ret}$=4.57 min; LC-MS: m/z 659.2 [M+H]$^+$; $^1$H NMR (400 MHz, DMSO-d$_6$) 0.88-1.01 (m, 2H) 1.05-1.14 (m, 2H) 1.16 (d, J=5.86 Hz, 3H) 1.21 (d, J=6.25 Hz, 3H) 1.48-1.62 (m, 1H) 1.73 (dd, 4H) 2.14-2.27 (m, 1H) 2.65 (t, J=5.47 Hz, 2H) 2.76 (s, 3H) 2.85 (s, 3H) 3.02 (s, 2H) 3.06-3.20 (m, 4H) 3.54 (d, 1H) 3.71 (s, 3H) 3.87 (d, J=19.53 Hz, 1H) 4.39-4.47 (m, 1H) 5.92 (s, 1H) 6.54 (d, 2H) 6.81 (s, 1H) 6.87 (d, 2H) 7.02 (s, 1H) 7.33 (s, 4H).

Intermediate 106.1: 4-(4-{[(4-Iodo-phenyl)-methyl-amino]-methyl}-trans-cyclohexyl)-1-methyl-piperazin-2-one

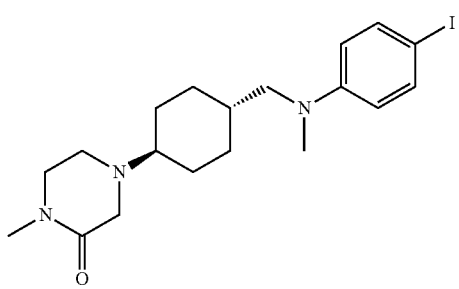 [SMILES: CN1CCN([C@H]2CC[C@H](CN(C)c3ccc(I)cc3)CC2)CC1=O]

To a solution of Intermediate 106.2 (13.3 g, 20.9 mmol) in dioxane (52.3 mL) was added 4M dioxane solution of HCl (105 mL, 418 mmol) at 0° C. The reaction mixture was stirred at RT for 0.5 h. The solution was concentrated and the residue was dissolved in MeOH (157 mL), triethylamine (27.3 ml, 196 mmol) was added drop wise at 0° C. and the mixture was stirred for 1 h at RT. The reaction mixture was concentrated and the residue extracted between EtOAc (2×) and 1M aqueous $NaHCO_3$ (1×). The organic phases were washed with brine and dried over $Mg_2SO_4$, filtered and evaporated to dryness. The cure material was suspended in $Et_2O$ (50 mL), and after stirring and sonication during 30 min, it was filtered on paper, washed with $Et_2O$ (50 mL) and dryness under high vacuum to give a white powder (8.11 g, 18.0 mmol, 86%). HPLC: $^E t_{Ret}$=4.035 min; LC-MS: m/z 442.1 [M+H]$^+$; $^1$H NMR (400 MHz, DMSO-d$_6$) 0.84-1.02 (m, 2H) 1.02-1.12 (m, 2H) 1.52-1.60 (m, 1H) 1.60-1.84 (m, 4H) 2.16-2.27 (m, 1H) 2.65 (t, J=5.47 Hz, 2H) 2.76 (s, 3H) 2.85 (s, 3H) 3.02 (s, 2H) 3.10 (d, J=7.03 Hz, 2H) 3.14-3.20 (m, 2H) 6.47 (d, 2H) 7.37 (d, 2H).

Intermediate 106.2: [[2-(tert-Butoxycarbonyl-methyl-amino)-ethyl]-(4-{[(4-iodo-phenyl)-methyl-amino]-methyl}-trans-cyclohexyl)-amino]-acetic acid methyl ester

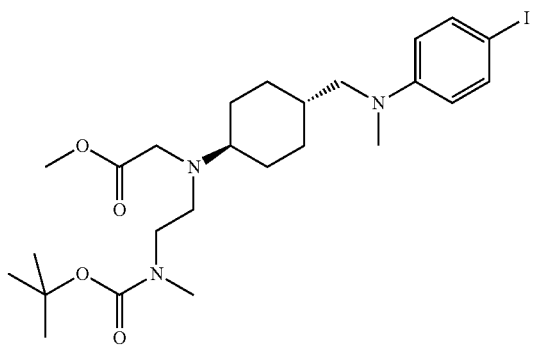 [SMILES: COC(=O)CN(CCN(C)C(=O)OC(C)(C)C)[C@H]1CC[C@H](CN(C)c2ccc(I)cc2)CC1]

To a suspension of Intermediate 105.3 (9.45 g, 21.6 mmol), methyl-(2-oxo-ethyl)-carbamic acid tert-butyl ester (4.11 g, 23.7 mmol) and AcOH (3.7 mL, 64.7 mmol) in DCM (108 mL) was added potion wise NaBH(OAc)$_3$ (13.7 g, 64.7 mmol) at 0° C. After stirring for 1 h at RT, the reaction mixture was added carefully saturated aqueous $NaHCO_3$ to pH 8 followed by extraction with DCM (2×). The organic phases were dried over $Mg_2SO_4$, filtered and evaporated, which gave the crude title intermediate (13.3 g, 20.9 mmol, 97% with 90% purity). This material was used for the next step without further purifications. HPLC: $^E t_{Ret}$=5.32 min; LC-MS: m/z 574.3 [M+H]$^+$.

Example 107

4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexanecarboxylic acid methyl ester

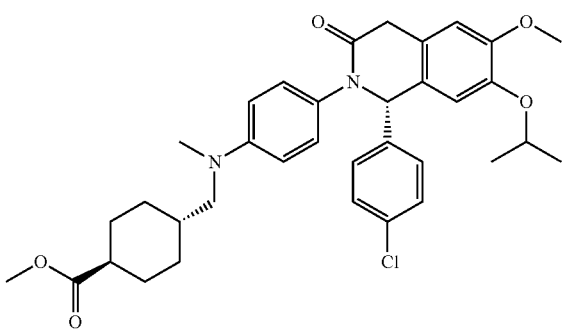 [SMILES: COc1cc2c(cc1OC(C)C)[C@H](c1ccc(Cl)cc1)N(c1ccc(N(C)C[C@H]3CC[C@H](C(=O)OC)CC3)cc1)C(=O)C2]

The title compound (244 mg, 0.40 mmol, 25.8%) was obtained as a white solid from Intermediate 75.6 (540 mg, 1.56 mmol) and Intermediate 107.1 (665 mg, 1.71 mmol) analogously to Example 75. HPLC: $^G t_{Ret}$=7.244 min; LC-MS: m/z 605.4 [M+H]$^+$.

377

Intermediate 107.1: 4-{[(4-Iodo-phenyl)-methyl-amino]-methyl}-trans-cyclohexanecarboxylic acid methyl ester

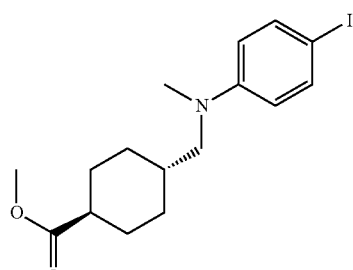

The title intermediate (700 mg, 1.81 mmol, 97%) was obtained as a white solid from Intermediate 107.2 (695 mg, 1.86 mmol) and 37% water solution of formaldehyde (306 mg, 3.72 mmol) analogously to Intermediate 77.1. HPLC: $^G t_{Ret}$=8.063 min; LC-MS: m/z 388.2 [M+H]$^+$.

Intermediate 107.2: 4-[(4-Iodo-phenylamino)-methyl]-trans-cyclohexanecarboxylic acid methyl ester

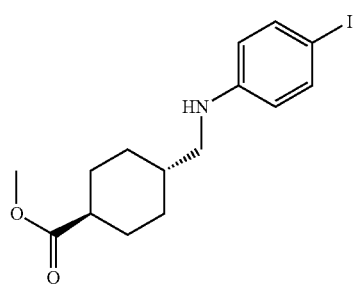 [SMILES: COC(=O)[C@H]1CC[C@H](CNc2ccc(I)cc2)CC1]

The title intermediate (700 mg, 1.87 mmol, 40%) was obtained as a white solid from 4-formyl-cyclohexanecarboxylic acid methyl ester (800 mg, 4.7 mmol) and 4-iodoaniline (601 mg, 2.74 mmol) analogously to Intermediate 75.7. HPLC: $^G t_{Ret}$=7.874 min; LC-MS: m/z 374.2 [M+H]$^+$.
4-Formyl-cyclohexanecarboxylic acid methyl ester was prepared by the following method. To a solution of trans-4-hydroxymethyl-cyclohexanecarboxylic acid methyl ester (which is reported in Synthesis Comm. (1982) page 42-43) (861 mg, 5.0 mmol) and Et$_3$N (2.1 mL, 15.0 mmol) in DCM (16 mL) was slowly added a solution of pyridine sulfur trioxide (2.39 g, 15 mmol) in DMSO (10 mL) at 0° C. (ice bath). After 70 min stirring, it was then diluted into DCM and washed with water. The organic layer was dried over Na$_2$SO$_4$, filtered and evaporated to dryness. This crude material (0.8 g, 4.7 mmol) was used for the next step without further purification.

378

Example 108

4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexanecarboxylic acid The title compound (81 mg, 0.124 mmol, 100%) was obtained as a white solid from Example 107 (75 mg, 0.124 mmol) analogously to Intermediate 26.1. HPLC: $^G t_{Ret}$=6.497 min; LC-MS: m/z 591.2 [M+H]$^+$.

Intermediate 112.1: (4-Iodo-phenyl)-methyl-(4-piperazin-1-yl-trans-cyclohexylmethyl)-amine The title intermediate (351 mg, 0.85 mmol, 74.1%) was obtained as a white solid from Intermediate 112.2 (650 mg, 1.14 mmol) and analogously to Intermediate 88.2. HPLC: $^A t_{Ret}$=1.32 min; LC-MS: m/z 414.1[M+H]$^+$.

Intermediate 112.2: (4-Iodo-phenyl)-methyl-{4-[4-(toluene-4-sulfonyl)-piperazin-1-yl]-trans-cyclohexylmethyl}-amine The title intermediate (654 mg, 1.15 mmol, 54.2%) was obtained as a white solid from Intermediate 105.4 (0.73 g, 2.12 mmol) and N,N-bis(2-chloroethyl)-4-methylbenzene-sulfonamide (0.73 g, 2.23 mmol) analogously to Intermediate 88.1. HPLC: $^A t_{Ret}$=2.07 min; LC-MS: m/z 568.0 [M+H]$^+$.

Example 116

2-{4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexy-lamino}-N-methyl-acetamide

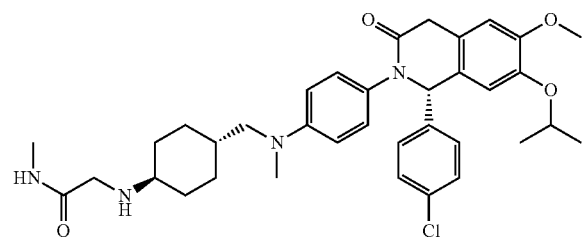 [SMILES: CNC(=O)CN[C@H]1CC[C@H](CN(C)c2ccc(N3C(=O)Cc4cc(OC)c(OC(C)C)cc4[C@@H]3c3ccc(Cl)cc3)cc2)CC1]

The title compound (94.9 mg, 0.15 mmol, 95%) was obtained as a yellow solid from Intermediate 79.1 (100 mg, 0.158 mmol) analogously to Intermediate 105.2. HPLC: $^A t_{Ret}$=1.86 min; LC-MS: m/z 633.2 [M+H]$^+$.

Intermediate 117.1:
(4-Iodo-phenyl)-methyl-piperidin-2-ylmethyl-amine

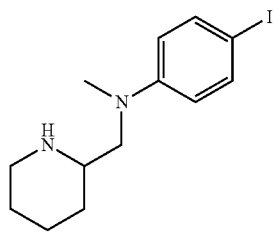 [SMILES: CN(CC1CCCCN1)c1ccc(I)cc1]

The title intermediate (200 mg, 0.61 mmol, 89%) was obtained as a brown resin from Intermediate 117.2 (308 mg, 0.68 mmol) analogously to Example 51. HPLC: $^A t_{Ret}$=1.49 min; LC-MS: m/z 331.2 [M+H]$^+$.

Intermediate 117.2: 2-{[(4-Iodo-phenyl)-methyl-amino]-methyl}-piperidine-1-carboxylic acid tert-butyl ester

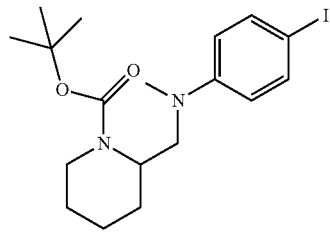 [SMILES: CN(CC1CCCCN1C(=O)OC(C)(C)C)c1ccc(I)cc1]

The title intermediate (310 mg, 0.68 mmol, 100%) was obtained as a violet solid from 2-formyl-piperidine-1-carboxylic acid tert-butyl ester (213 mg, 0.72 mmol) and 4-iodoaniline (150 mg, 0.68 mmol) analogously to Intermediate 75.7, and successively methylation was performed analo gously to Intermediate 77.1. HPLC: $^A t_{Ret}$=3.23 min; LC-MS: m/z 431.2 [M+H]$^+$.

Intermediate 118.1: (4-Iodo-phenyl)-methyl-(tetrahydro-pyran-2-ylmethyl)-amine

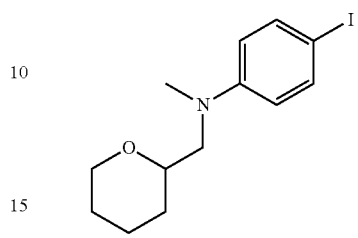

The title intermediate (143 mg, 0.43 mmol, 78%) was obtained as light brown oil from Intermediate 118.2 (175 mg, 0.55 mmol) and 37% water solution of formaldehyde (0.12 mL, 1.65 mmol) analogously to Intermediate 77.1. HPLC: $^A t_{Ret}$=2.48 min; LC-MS: m/z 332.2 [M+H]$^+$.

Intermediate 118.2: (4-Iodo-phenyl)-(tetrahydro-pyran-2-ylmethyl)-amine

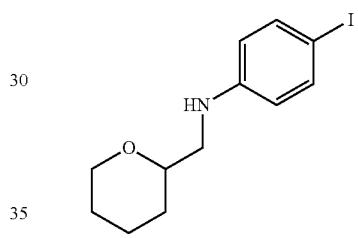

The title intermediate (177 mg, 0.56 mmol, 13%) was obtained as a brown solid from 2H-pyran-2-carboxaldehyde (490 mg, 4.29 mmol) and 4-iodoaniline (940 mg, 4.29 mmol) analogously to Intermediate 75.7. HPLC: $^A t_{Ret}$=2.44 min; LC-MS: m/z 318.2 [M+H]$^+$.

Intermediate 119.1:
Cyclohexylmethyl-(4-iodo-phenyl)-methyl-amine

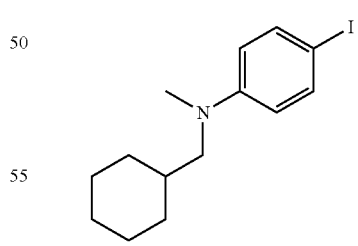

The title intermediate (195 mg, 0.59 mmol, 86%) was obtained as a colorless oil from cyclohexanecarbaldehyde (81 mg, 0.72 mmol) and 4-iodoaniline (150 mg, 0.68 mmol) analogously to Intermediate 75.7, and successively methylation was performed analogously to Intermediate 77.1. HPLC: $^A t_{Ret}$=3.26 min; LC-MS: m/z 330.2 [M+H]$^+$.

Example 120

(S)-2-{5-[(Trans-4-amino-cyclohexylmethyl)-methyl-amino]-pyridin-2-yl}-1-(4-chloro-phenyl)-7-isopropoxy-6-methoxy-1,4-dihydro-2H-isoquinolin-3-one

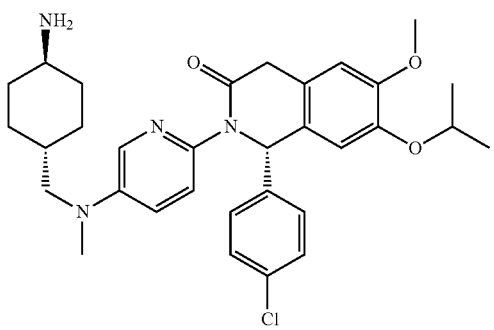 [SMILES: COc1cc2c(cc1OC(C)C)[C@H](c1ccc(Cl)cc1)N(c1ccc(N(C)C[C@H]3CC[C@H](N)CC3)cn1)C(=O)C2]

The title compound (334 mg, 0.593 mmol, 78%) was obtained as a yellow foam from Intermediate 120.1 (504 mg, 0.760 mmol) analogously to Example 51: HPLC: $^F t_{Ret}$=0.98; LC-MS: m/z 563.4 [M+H]$^+$.

Intermediate 120.1: {4-[({6-[(S)-1-(4-Chloro-phenyl)-7-isopropoxy-6-methoxy-3-oxo-3,4-dihydro-1H-isoquinolin-2-yl]-pyridin-3-yl}-methyl-amino)-methyl]-trans-cyclohexyl}-carbamic acid tert-butyl ester

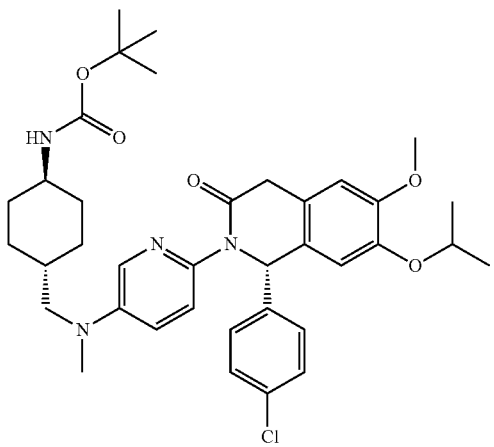 [SMILES: COc1cc2c(cc1OC(C)C)[C@H](c1ccc(Cl)cc1)N(c1ccc(N(C)C[C@H]3CC[C@H](NC(=O)OC(C)(C)C)CC3)cn1)C(=O)C2]

The title intermediate (151 mg, 0.228 mmol, 79%) was obtained as a brown solid from Intermediate 120.2 (176 mg, 0.347 mmol) and Intermediate 75.6 (100 mg, 0.289 mmol) analogously to Example 75. HPLC: $^F t_{Ret}$=1.563; LC-MS: m/z 663.5 [M+H]$^+$.

Intermediate 120.2: (4-{[(6-Iodo-pyridin-3-yl)-methyl-amino]-methyl}-trans-cyclohexyl)-carbamic acid tert-butyl ester

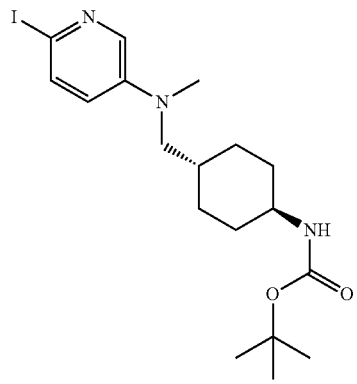 [SMILES: CN(C[C@H]1CC[C@H](NC(=O)OC(C)(C)C)CC1)c1ccc(I)nc1]

The title intermediate (1.0 g, 2.24 mmol, 64%) was obtained as a solid from Intermediate 120.3 (1.5 g, 3.48 mmol) and formaldehyde (37% in water, 0.326 mL, 4.35 mmol) analogously to Intermediate 77.1. HPLC: $^F t_{Ret}$=1.446; LC-MS: m/z 446.2 [M+H]$^+$.

Intermediate 120.3: {4-[(6-Iodo-pyridin-3-ylamino)-methyl]-trans-cyclohexyl}-carbamic acid tert-butyl ester

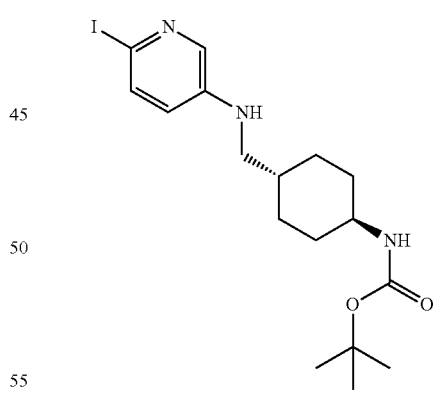

The title intermediate (1.95 g, 4.52 mmol, 99%) was obtained as a slight pink solid from trans-(4-formylcyclohexyl) carbamic acid tert-butyl ester (1.136 g, 5 mmol) and 6-Iodo-pyridin-3-ylamine (1 g, 4.55 mmol) analogously to Intermediate 75.7. HPLC: $^F t_{Ret}$=1.289; LC-MS: m/z 432.1 [M+H]$^+$.

Example 121

{4-[({6-[(S)-1-(4-Chloro-phenyl)-7-isopropoxy-6-methoxy-3-oxo-3,4-dihydro-1H-isoquinolin-2-yl]-pyridin-3-yl}-methyl-amino)-methyl]-trans-cyclohexylamino}-acetic acid methyl ester

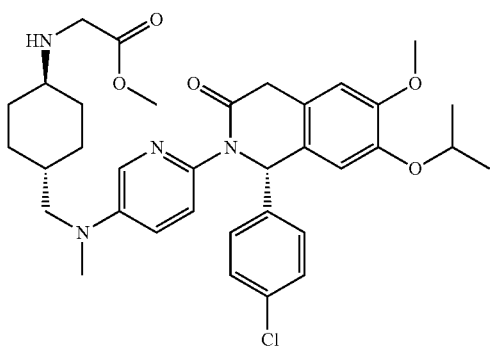 [SMILES: COC(=O)CN[C@H]1CC[C@H](CN(C)c2ccc(N3C(=O)Cc4cc(OC)c(OC(C)C)cc4[C@@H]3c3ccc(Cl)cc3)nc2)CC1]

The title compound (140 mg, 0.221 mmol, 45%) was obtained as a yellow foam from Example 120 (275 mg, 0.487 mmol) analogously to Intermediate 79.1. HPLC: $^{F}t_{Ret}$=1.204; LC-MS: m/z 635.5 [M+H]$^+$.

Example 122

2-{4-[({6-[(S)-1-(4-Chloro-phenyl)-7-isopropoxy-6-methoxy-3-oxo-3,4-dihydro-1H-isoquinolin-2-yl]-pyridin-3-yl}-methyl-amino)-methyl]-trans-cyclohexylamino}-N-methyl-acetamide

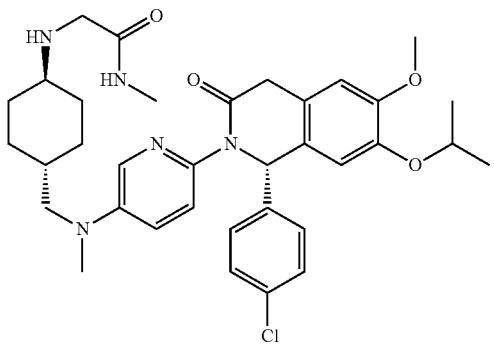 [SMILES: CNC(=O)CN[C@H]1CC[C@H](CN(C)c2ccc(N3C(=O)Cc4cc(OC)c(OC(C)C)cc4[C@@H]3c3ccc(Cl)cc3)nc2)CC1]

The mixture of Example 121 (65 mg, 0.102 mmol) and a solution of methylamine (33% in EtOH, 1.2 mL, 10.23 mmol) was heated for 15 h at 90° C. The mixture was concentrated under vacuum and the precipitate collected by filtration. The residue was purified by Combi-Flash Companion™ (Isco Inc.) column chromatography (SiO$_2$; gradient elution, DCM/[DCM/EtOH 9:1] 1:0→3:7) yielding the title compound as a yellow solid (40 mg, 0.064 mmol, 63%). HPLC: $^{F}t_{Ret}$=1.080; LC-MS: m/z 634.2 [M+H]$^+$.

Example 123

(S)-1-(4-Chloro-phenyl)-7-isopropoxy-6-methoxy-2-(5-{methyl-[4-(3-oxo-piperazin-1-yl)-trans-cyclohexylmethyl]-amino}-pyridin-2-yl)-1,4-dihydro-2H-isoquinolin-3-one

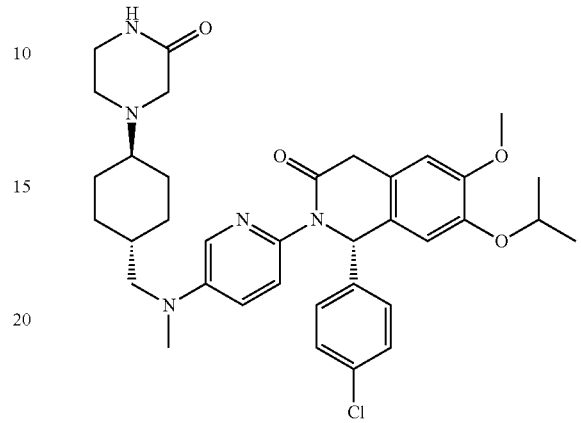

To a solution of Intermediate 123.1 (44 mg, 0.045 mmol) in MeOH (1 mL) was added HCl (4M in dioxane, 0.564 mL, 2.256 mmol) at RT. The reaction mixture was stirred at RT for 2 h and evaporated to dryness. The resulting residue was dissolved in MeOH (1 mL) then Et$_3$N (0.094 mL, 0.677 mmol) was added and the mixture was stirred at RT for 1.5 h. After evaporation to dryness, the residue was purified by Combi-Flash Companion™ (Isco Inc.) column chromatography (SiO$_2$; gradient elution, DCM/[DCM/EtOH/NH3 aq. 90:9:1] 1:0→1:9) yielding the title compound as a yellow solid (17 mg, 0.027 mmol, 60%). HPLC: $^{F}t_{Ret}$=1.082; LC-MS: m/z 646.2 [M+H]$^+$.

Intermediate 123.1: ((2-tert-Butoxycarbonylamino-ethyl)-{4-[({6-[(S)-1-(4-chloro-phenyl)-7-isopropoxy-6-methoxy-3-oxo-3,4-dihydro-1H-isoquinolin-2-yl]-pyridin-3-yl}-methyl-amino)-methyl]-trans-cyclohexyl}-amino)-acetic acid methyl ester

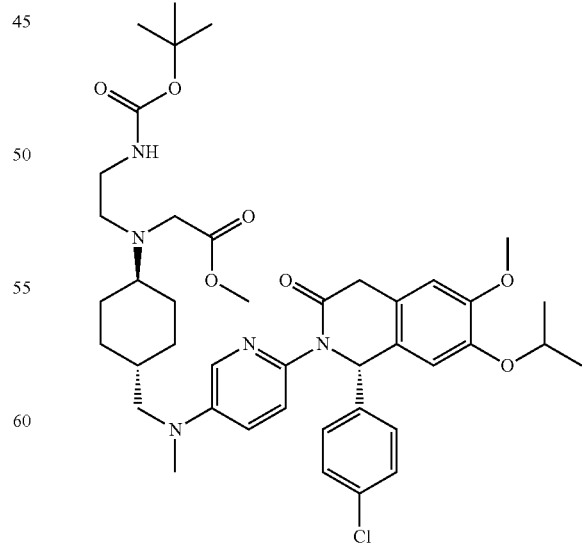

The title intermediate (44 mg, 0.045 mmol, quantitative) was obtained as a yellow solid from Example 121 (30 mg, 0.048 mmol) analogously to Intermediate 79.2. HPLC: $^F t_{Ret}$=1.444; LC-MS: m/z 778.6 [M+H]$^+$.

Example 124

(S)-1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyridin-2-yl)-1,4-dihydro-2H-isoquinolin-3-one

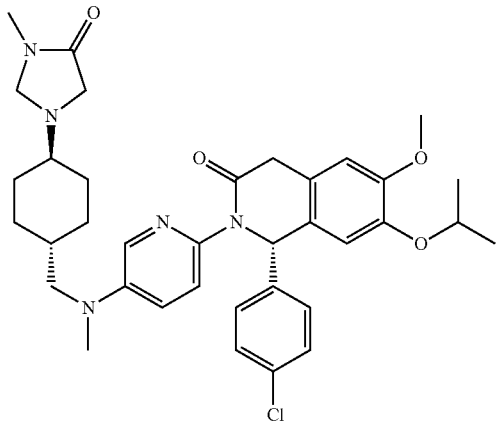 [SMILES: COc1cc2c(cc1OC(C)C)[C@H](c1ccc(Cl)cc1)N(c1ccc(N(C)C[C@H]3CC[C@H](N4CC(=O)N(C)C4)CC3)cn1)C(=O)C2]

The mixture of Example 122 (38 mg, 0.061 mmol) and formaldehyde (0.046 ml, 37% solution, 10 eq, 0.612 mmol) was heated for 15 h in EtOH (1 mL) at 80° C. The reaction mixture was concentrated to dryness and the residue was purified by Combi-Flash Companion™ (Isco Inc.) column chromatography (SiO$_2$; gradient elution, DCM/[DCM/MeOH 9:1] 1:0→0:1) yielding the title compound as a colorless solid (31 mg, 0.048 mmol, 79%). HPLC: $^F t_{Ret}$=1.236; LC-MS: m/z 646.4 [M+H]$^+$.

Example 125

(S)-1-(4-Chloro-phenyl)-7-isopropoxy-6-methoxy-2-(5-{methyl-[4-(4-methyl-3-oxo-piperazin-1-yl)-trans-cyclohexylmethyl]-amino}-pyridin-2-yl)-1,4-dihydro-2H-isoquinolin-3-one

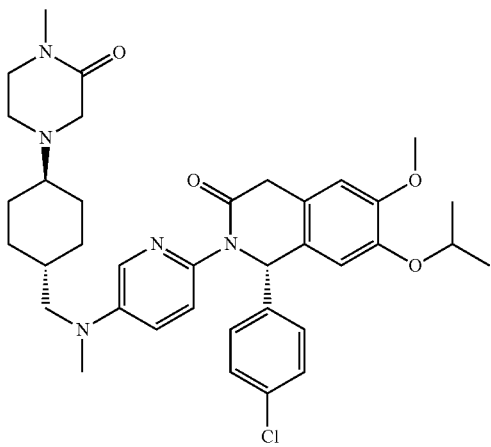 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cn1)C(=O)C2]

The title compound (140 mg, 0.221 mmol, 45%) was obtained as a yellow foam from Intermediate 125.1 (275 mg, 0.487 mmol) analogously to Example 123. HPLC: $^F t_{Ret}$=1.019; LC-MS: m/z 660.4 [M+H]$^+$.

Intermediate 125.1: ([2-(tert-Butoxycarbonyl-methyl-amino)-ethyl]-{4-[({6-[(S)-1-(4-chloro-phenyl)-7-isopropoxy-6-methoxy-3-oxo-3,4-dihydro-1H-isoquinolin-2-yl]-pyridin-3-yl}-methyl-amino)-methyl]-trans-cyclohexyl}-amino)-acetic acid methyl ester

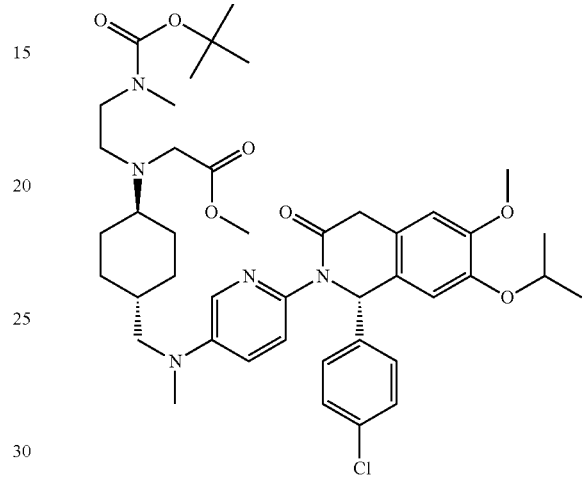

The title intermediate (84 mg, 0.107 mmol, 90%) was obtained as a yellow solid from Example 121 (75 mg, 0.118 mmol) and N-Boc-(methylamino)acetaldehyde (24.54 mg, 0.142 mmol) analogously to Intermediate 79.2. HPLC: $^F t_{Ret}$=1.256; LC-MS: m/z 792.2 [M+H]$^+$.

Example 126

{4-[({5-[(S)-1-(4-Chloro-phenyl)-7-isopropoxy-6-methoxy-3-oxo-3,4-dihydro-1H-isoquinolin-2-yl]-pyridin-2-yl}-methyl-amino)-methyl]-trans-cyclohexylamino}-acetic acid methyl ester

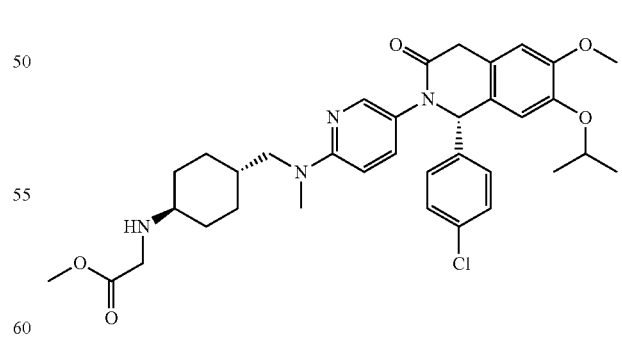

The title compound (250 mg, 0.39 mmol, 29%) was obtained as a white solid from Intermediate 75.6 (470 mg, 1.36 mmol) and Intermediate 130.3 (680 mg, 1.63 mmol) analogously to Example 75. HPLC: $^G t_{Ret}$=5.334 min; LC-MS: m/z 635.4 [M+H]$^+$.

Intermediate 127.1: ((2-tert-Butoxycarbonylamino-ethyl)-{4-[({5-[(S)-1-(4-chloro-phenyl)-7-isopropoxy-6-methoxy-3-oxo-3,4-dihydro-1H-isoquinolin-2-yl]-pyridin-2-yl}-methyl-amino)-methyl]-trans-cyclohexyl}-amino)-acetic acid methyl ester

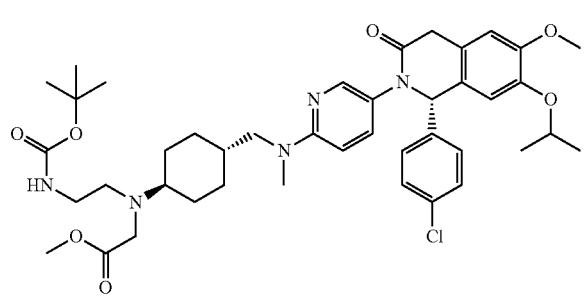 [SMILES: COC(=O)CN(CCNC(=O)OC(C)(C)C)[C@H]1CC[C@H](CN(C)c2ccc(N3C(=O)Cc4cc(OC)c(OC(C)C)cc4[C@@H]3c3ccc(Cl)cc3)cn2)CC1]

The title intermediate (24.6 mg, 0.032 mmol, 41.8%) was obtained as a white solid from Example 126 (48 mg, 0.076 mmol) and N-Boc-2-aminoacetaldehyde (25.3 mg, 0.151 mmol) analogously to Intermediate 79.2. HPLC: $^{G}t_{Ret}$=5.832 min; LC-MS: m/z 778.6 [M+H]$^+$.

Example 128

(S)-1-(4-Chloro-phenyl)-7-isopropoxy-6-methoxy-2-(6-{methyl-[4-(4-oxo-imidazolidin-1-yl)-trans-cyclohexylmethyl]-amino}-pyridin-3-yl)-1,4-dihydro-2H-isoquinolin-3-one

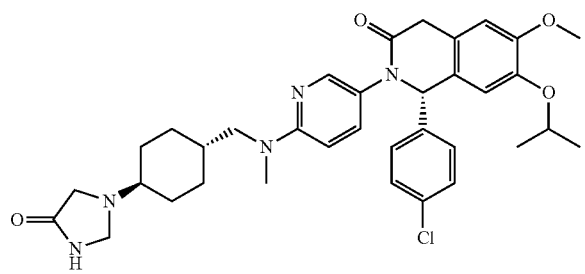 [SMILES: COc1cc2c(cc1OC(C)C)[C@H](c1ccc(Cl)cc1)N(c1ccc(N(C)C[C@H]3CC[C@H](N4CNC(=O)C4)CC3)nc1)C(=O)C2]

A mixture of Intermediate 128.1 (153 mg, 0.23 mmol) and 37% aqueous solution of formaldehyde (0.17 mL, 2.32 mmol) in EtOH (5 mL) was sealed in a vial and heated for 3.5 h at 80° C. The reaction mixture was concentrated in vacuo and the resulting brownish oil was purified by column chromatography respectively preparative thin layer chromatography to afford the title compound (5 mg, 7.12 mmol, 3%) as a colorless resin. HPLC: $^{G}t_{Ret}$=0.99; LC-MS: m/z 632.2 [M+H]$^+$. Additionally, Intermediate 129 (44.5 mg, 0.067 mmol, 29%) was identified as a side product and isolated from the crude reaction mixture. HPLC: $^{G}t_{Ret}$=1.01; LC-MS: m/z 662.5 [M+H]$^+$.

Intermediate 128.1: 2-{4-[({5-[(S)-1-(4-Chloro-phenyl)-7-isopropoxy-6-methoxy-3-oxo-3,4-dihydro-1H-isoquinolin-2-yl]-pyridin-2-yl}-methyl-amino)-methyl]-trans-cyclohexylamino}-acetamide

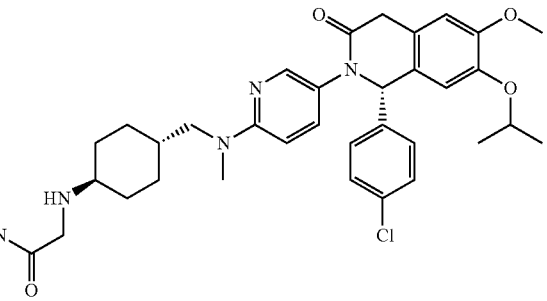

The title intermediate (154 mg, 0.23 mmol, 100%) was obtained as a white solid from Example 126 (149 mg, 0.23 mmol) analogously to Intermediate 85.1. HPLC: $^{G}t_{Ret}$=5.177 min; LC-MS: m/z 620.2 [M+H]$^+$.

Example 130

(S)-1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one

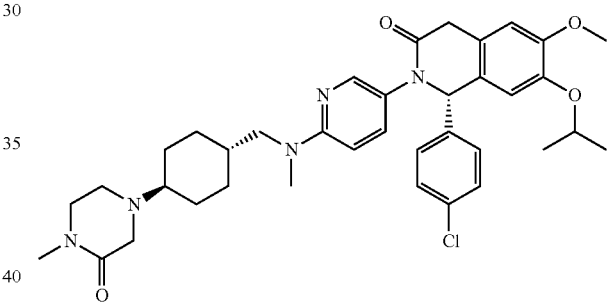

A sealable reaction flask was charged with potassium phosphate (2.94 g, 13.45 mmol), evacuated and heated for 1 h at 100° C. The reaction flask was back-filled with argon at RT and Intermediate 75.6 (2.35 g, 6.73 mmol), Intermediate 130.1 (3.01 g, 6.73 mmol), dioxan (45 mL) and (+/−)-trans-1,2-diaminocyclohexane (0.167 mL, 1.345 mmol) were added subsequently. The reaction flask was carefully evacuated under vacuum (2×) and backfilled with argon (2×) and copper (I) iodide (0.256 g, 1.345 mmol) were added. The reaction mixture was stirred 17 h at 95° C. The mixture was extracted between EtOAc (3×) and water (3×). The organic phases were washed with brine and dried over Na$_2$SO$_4$, filtered and evaporated to dryness. Purification of the residue by normal phase column chromatography, eluting with DCM-MeOH-aq. 30% NH$_4$OH (200:10:1) followed by reverse phase prep-HPLC afforded the TFA salt which was extracted between EtOAc (2×) and 1M aqueous NaHCO$_3$ (1×). The organic phases were washed with brine and dried over Na$_2$SO$_4$, filtered and evaporated to dryness. The residue was crystallized (EtOAc) to afford the title compound as white crystals (1.84 g, 41%). HPLC: $^{D}t_{Ret}$=0.98 min; LC-MS: m/z 660.7 [M+H]$^+$; $^1$H NMR (600 MHz, DMSO-d$_6$) 0.95 (q, J=11.77 Hz, 2H), 1.11 (t, J=11.81 Hz, 2H), 1.17 (d, J=5.85 Hz, 3H), 1.23 (d, J=5.85 Hz, 3H), 1.55-1.64 m, 1H), 1.64-1.82 (m, 4H), 2.23 (t, J=11.30 Hz, 1H), 2.67 (t, J=4.74 Hz, 2H), 2.78 (s, 3H), 2.95 (s, 3H), 3.04 (s, 2H), 3.18 (t, J=4.84 Hz, 2H), 3.23-3.30 (m, 2H), 3.61 (d, J=19.98 Hz, 1H), 3.73 (s, 3H), 3.96 (d, J=19.98 Hz, 1H), 4.34-4.50 (m, 1H), 5.96 (s, 1H), 6.52 (d, J=9.08 Hz, 1H), 6.84 (s, 1H), 6.95 (s, 1H), 7.21 (d, J=8.88 Hz, 1H), 7.36 (s, 4H), 7.77 (s, 1H).

Intermediate 130.1: 4-(4-{[(5-Iodo-pyridin-2-yl)-methyl-amino]-methyl}-trans-cyclohexyl)-1-methyl-piperazin-2-one

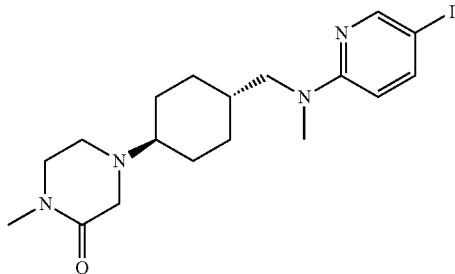 [SMILES: CN1CCN([C@H]2CC[C@H](CN(C)c3ccc(I)cn3)CC2)CC1=O]

To a solution of Intermediate 130.2 (7.90 g, 13.06 mmol) in DCM (130 mL) was added TFA (30.2 mL, 392 mmol) at 0° C. The reaction mixture was stirred at RT for 2.5 h. The solution was concentrated and the residue extracted between EtOAc (2×) and 1M aqueous NaHCO₃ (1×). The organic phases were washed with brine and dried over Na₂SO₄, filtered and evaporated to dryness. The residue was dissolved in MeOH (130 mL) at 0° C., triethylamin (27.3 mL, 196 mmol) was added and the mixture was stirred for 30 min at RT. The reaction mixture was concentrated and the residue extracted between EtOAc (2×) and 1M aqueous NaHCO₃ (1×). The organic phases were washed with brine and dried over Na₂SO₄, filtered and evaporated to dryness. Purification of the residue by normal phase column chromatography, eluting with DCM-MeOH (20:1), crystallization (diisopropylether), gave the title compound as beige crystals (4.90 g, 10.97 mmol, 84%). HPLC: $^D t_{Ret}$=0.75 min; LC-MS: m/z 443.3 [M+H]$^+$; $^1$H NMR (400 MHz, DMSO-d₆): 0.89-1.00 (m, 2H), 1.04-1.13 (m, 2H), 1.55-1.68 (m, 3H), 1.71-1.80 (m, 2H), 2.16-2.26 (m, 1H), 2.61-2.68 (m, 2H), 2.76 (s, 3H), 2.92 (s, 3H), 3.02 (s, 2H), 3.13-3.19 (m, 2H), 3.27-3.31 (m, 2H), 6.47 (d, 1H), 7.65 (d, 1H), 8.15 (s, 1H).

Intermediate 130.2: [[2-(tert-Butoxycarbonyl-methyl-amino)-ethyl]-(4-{[(5-iodo-pyridin-2-yl)-methyl-amino]-methyl}-trans-cyclohexyl)-amino]-acetic acid methyl ester

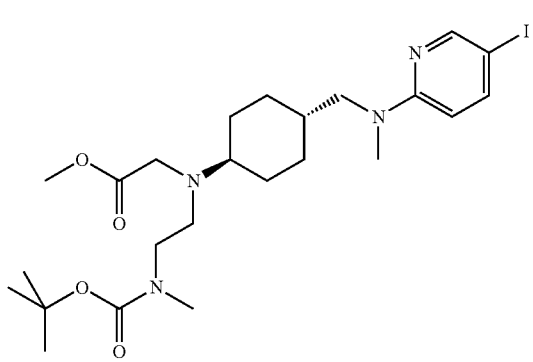 [SMILES: COC(=O)CN(CCN(C)C(=O)OC(C)(C)C)[C@H]1CC[C@H](CN(C)c2ccc(I)cn2)CC1]

To a solution of Intermediate 130.3 (5.80 g, 0.227 mmol), AcOH (1.57 mL, 27.5 mmol) in DCM (250 mL) was added a solution of methyl-(2-oxo-ethyl)-carbamic acid tert-butyl ester (2.86 g, 16.5 mmol) in DCM (25 mL) at 0° C. The mixture was stirred for 20 min at 0° C. After addition of NaBH(OAc)₃ (5.83 g, 27.5 mmol), the cooling bath was removed and the suspension was stirred for 1 h at RT. To the reaction mixture was added carefully 1M aqueous NaHCO₃ (250 mL) followed by extraction with DCM (2×). The organic phases were dried over Na₂SO₄, filtered and evaporated. Purification of the residue by normal phase column chromatography, eluting with DCM-MeOH (98:2), gave the title compound as beige oil (7.95 g, 13.15 mmol, 96%). HPLC: $^D t_{Ret}$=1.14 min; LC-MS: m/z 575.0 [M+H]$^+$.

Intermediate 130.3: (4-{[(5-Iodo-pyridin-2-yl)-methyl-amino]-methyl}-trans-cyclohexylamino)-acetic acid methyl ester

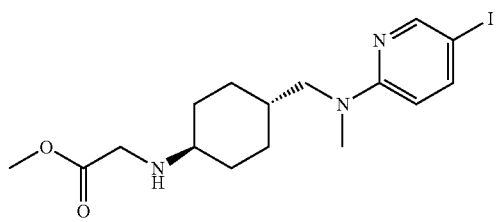 [SMILES: COC(=O)CN[C@H]1CC[C@H](CN(C)c2ccc(I)cn2)CC1]

To a solution of Intermediate 130.4 (6.28 g, 18 mmol) in DMF (180 mL) were successively added potassium carbonate (7.46 g, 54 mmol) and methyl 2-bromoacetate (1.75 mL, 18.9 mmol) at −10° C. The suspension was stirred for 17 h at −10° C. to RT. The reaction mixture was concentrated and the residue extracted between EtOAc (2×) and water (2×). The organic phases were washed with brine and dried over Na₂SO₄, filtered and evaporated to dryness. Purification of the residue by normal phase column chromatography, eluting with DCM-MeOH-aq. 30% NH₄OH (200:10:1), gave the title compound as beige oil (5.84 g, 13.86 mmol, 77%). HPLC: $^D t_{Ret}$=0.78 min; LC-MS: m/z 417.9 [M+H]$^+$.

Intermediate 130.4: (Trans-4-amino-cyclohexylmethyl)-(5-iodo-pyridin-2-yl)-methyl-amine

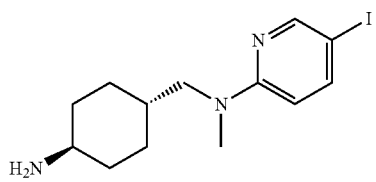 [SMILES: CN(C[C@H]1CC[C@H](N)CC1)c1ccc(I)cn1]

To a solution of Intermediate 130.5 (26.5 g, 58.9 mmol) in DCM (295 mL) was added TFA (136 mL) at 0° C. The reaction mixture was stirred for 30 min at 0° C. and an additional 1 h at RT. The solution was concentrated, extracted between 4M aqueous NaOH (300 mL) and DCM (4×). The organic phases were dried over Na₂SO₄, filtered and evaporated to dryness. Purification of the residue by normal phase column chromatography, eluting with DCM-MeOH-aq. 30% NH4OH (60:10:1), gave the title compound as beige crystals (20.0 g, 57.4 mmol, 97%). HPLC: $^D t_{Ret}$=0.68 min; LC-MS: m/z 346.3 [M+H]$^+$.

Intermediate 130.5: (4-{[(5-Iodo-pyridin-2-yl)-methyl-amino]-methyl}-trans-cyclohexyl)-carbamic acid tert-butyl ester

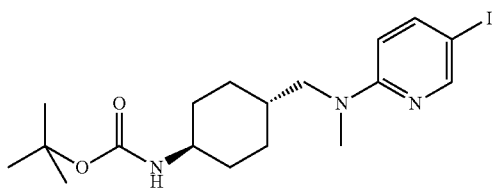 [SMILES: CN(C[C@H]1CC[C@H](NC(=O)OC(C)(C)C)CC1)c1ccc(I)cn1]

The mixture of Intermediate 130.6 (22.4 g, 92 mmol), 2-fluoro-5-iodopyridine (21.4 g, 96 mmol), potassium carbonate (25.3 g, 183 mmol) and DMSO (305 mL) was stirred for 21 h at 80° C. The reaction mixture was concentrated in vacuo and the residue extracted between EtOAc (2×) and 1M aqueous NaHCO$_3$ (1×). The organic phases were washed with brine and dried over Na$_2$SO$_4$, filtered and evaporated to dryness. The residue was crystallized (TBME) to give the title compound as beige crystals (26.7 g, 59.4 mmol, 65%). HPLC: $^D$t$_{Ret}$=1.40 min; LC-MS: m/z 446.4 [M+H]$^+$.

Intermediate 130.6: (Trans-4-methylaminomethyl-cyclohexyl)-carbamic acid tert-butyl ester

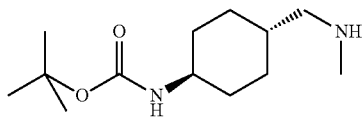 [SMILES: CNC[C@H]1CC[C@H](NC(=O)OC(C)(C)C)CC1]

To a stirred solution of trans-(4-formyl-cyclohexyl)-carbamic acid tert-butyl (50 g, 218 mmol) and MeOH (2.2 L) was added HCl salt of CH$_3$NH$_2$ (15.75 g) at RT. The mixture was stirred for 30 min at RT and then cooled to 5° C. Addition of NaBH(OAc)$_3$ (72.9 g, 327 mmol) in portions during 45 min at 5° C. The reaction mixture was stirred for 1 h at 5° C. and then carefully quenched with 1M aqueous NaHCO$_3$ (300 mL) and 2M NaOH. The resulting suspension was filtered over Hyflo, washed with MeOH and the filtrate was concentrated. The residue was extracted between EtOAc (2×) and 1M aqueous NaHCO$_3$ (1×). The organic phases were washed with brine and dried over Na$_2$SO$_4$, filtered and evaporated to dryness. Purification of the residue by normal phase column chromatography, eluting with DCM-MeOH-aq. 30% NH$_4$OH (40:10:1), gave the title compound as white crystals (22.5 g, 92 mmol, 42%). TLC: R$_f$=0.33; LC-MS: m/z 243.1 [M+H]$^+$.

Example 131

2-{4-[({5-[(S)-1-(4-Chloro-phenyl)-7-isopropoxy-6-methoxy-3-oxo-3,4-dihydro-1H-isoquinolin-2-yl]-pyridin-2-yl}-methyl-amino)-methyl]-trans-cyclohexylamino}-N-isopropyl-acetamide

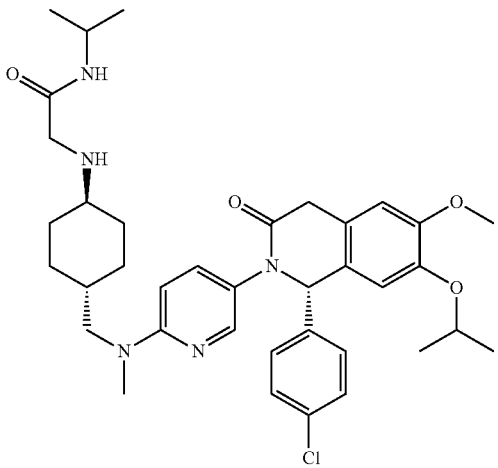 [SMILES: COc1cc2c(cc1OC(C)C)[C@H](c1ccc(Cl)cc1)N(c1ccc(N(C)C[C@H]3CC[C@H](NCC(=O)NC(C)C)CC3)nc1)C(=O)C2]

The mixture of Example 126 (253 mg, 0.398 mmol) and isopropylamine (3.41 ml, 3.41 mmol) was heated for 1.5 h in methanol (3 mL) in the microwave at 120° C. The mixture was concentrated to dryness and the residue was purified by normal phase column chromatography (eluting with n-heptane-ethyl acetate), yielding the title compound as a beige solid (80 mg, 0.121 mmol, 99%). HPLC: $^H$t$_{Ret}$=1.21 min; LC-MS: m/z 662.3 [M+H]$^+$.

Example 132

(S)-1-(4-Chloro-phenyl)-7-isopropoxy-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one

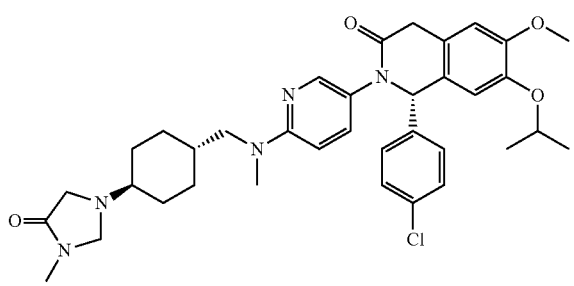 [SMILES: COc1cc2c(cc1OC(C)C)[C@H](c1ccc(Cl)cc1)N(c1ccc(N(C)C[C@H]3CC[C@H](N4CC(=O)N(C)C4)CC3)nc1)C(=O)C2]

The title compound (6.36 g, 9.74 mmol, 57%) was obtained as slightly yellow crystals from Intermediate 75.6 (100 mg, 0.289 mmol) and Intermediate 132.1 (124 mg, 0.289), analogously to Example 130. HPLC: $^D$t$_{Ret}$=1.07 min; LC-MS: m/z 646.6 [M+H]$^+$; $^1$H NMR (400 MHz, DMSO-d$_6$) 0.87-1.09 (m, 4H), 1.15 (d, J=5.87 Hz, 3H), 1.20 (d, J=5.87 Hz, 3H), 1.51-1.85 (m, 5H), 2.06-2.24 (m, 1H), 2.69 (s, 3H), 2.93 (s, 3H), 3.08 (s, 2H), 3.27 (s, 2H), 3.56 (d, 1H), 3.71 (d, J=1.17 Hz, 3H), 3.93 (d, J=19.94 Hz, 1H), 4.01 (s, 2H), 4.27-4.47 (m, 1H), 5.93 (s, 1H), 6.50 (d, J=9.38 Hz, 1H), 6.81 (s, 1H), 6.92 (s, 1H), 7.13-7.24 (m, 1H), 7.33 (d, J=1.17 Hz, 4H), 7.74 (d, J=1.96 Hz, 1H).

Intermediate 132.1: 1-(4-{[(5-Iodo-pyridin-2-yl)-methyl-amino]-methyl}-trans-cyclohexyl)-3-methyl-imidazolidin-4-one

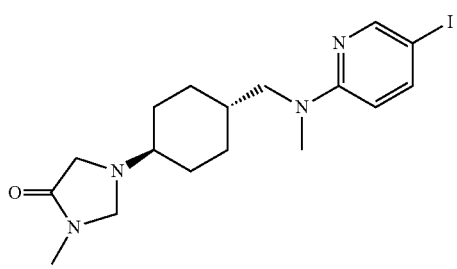 [SMILES: CN1CN([C@H]2CC[C@H](CN(C)c3ccc(I)cn3)CC2)CC1=O]

To the solution of intermediate 132.2 (13.0 g, 29.7 mmol and EtOH (99 mL) was added 37% aqueous solution of formaldehyde (22.09 ml, 297 mmol). The reaction mixture was stirred for 16 h at 80° C. The mixture was concentrated to dryness and the residue was purified by normal phase column chromatography, eluting with DCM-MeOH-aq. 30% NH$_4$OH (200:20:1), gave the title compound after crystallization (diisopropyl ether-hexane) as white crystals (12.1 g, 28.0 mmol, 94%). HPLC: $^D$t$_{Ret}$=0.94 min; LC-MS: m/z 429.3 [M+H]$^+$; $^1$H NMR (400 MHz, DMSO-d$_6$): 0.82-1.06 (m, 4H), 1.60 (m, 3H), 1.79 (m, 2H), 2.15 (m, 1H), 2.69 (s, 3H), 2.93 (s, 3H), 3.08 (s, 2H), 3.27-3.31 (m, 2H), 4.01 (s, 2H), 6.49 (d, 1H), 7.65 (d, 1H), 8.15 (s, 1H).

Intermediate 132.2: 2-(4-{[(5-Iodo-pyridin-2-yl)-methyl-amino]-methyl}-trans-cyclohexyl-amino)-N-methyl-acetamide

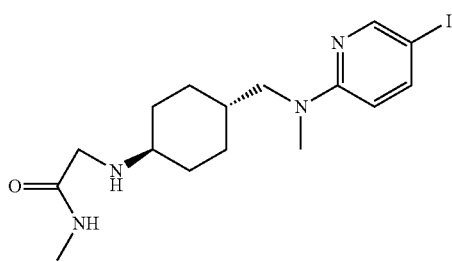 [SMILES: CNC(=O)CN[C@H]1CC[C@H](CN(C)c2ccc(I)cn2)CC1]

The mixture of intermediate 130.3 (12.9 g, 30.6 mmol) and methylamine (33% in EtOH) (191 mL, 1.53 mol) was stirred 16 hours at 80° C. The mixture was concentrated to dryness and the residue was purified by normal phase column chromatography, eluting with DCM-MeOH-aq. 30% NH$_4$OH (200:20:1), gave the title compound as a beige oil (13.0 g, 29.7 mmol, 97%). HPLC: $^D$t$_{Ret}$=0.68 min; LC-MS: m/z 417.3 [M+H]$^+$.

Example 133

(S)-1-(4-Chloro-phenyl)-7-isopropoxy-2-(6-{[4-(3-isopropyl-4-oxo-imidazolidin-1-yl)-trans-cyclohexylmethyl]-methyl-amino}-pyridin-3-yl)-6-methoxy-1,4-dihydro-2H-isoquinolin-3-one

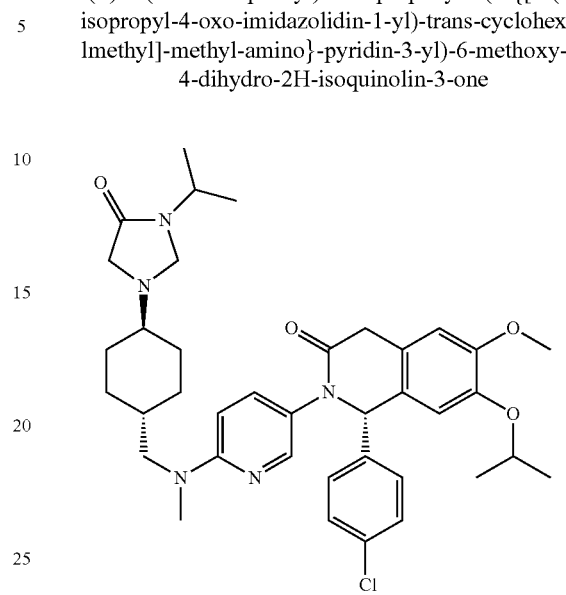

The mixture of Example 131 (80 mg, 0.121 mmol) and formaldehyde (0.090 mL, 37% solution, 10 eq., 1.208 mmol) was heated for 5 h in 2-propanol (4 mL) at 85° C. The mixture was concentrated to dryness and the residue was purified by reversed phase column chromatography. The fractions containing the product were pooled and worked up (addition of NaHCO$_3$), yielding the title compound as an off-white solid (46 mg, 0.068 mmol, >98%). HPLC: $^H$t$_{Ret}$=1.40 min; LC-MS: m/z 674.2 [M+H]$^+$.

Intermediate 134.1: 2-{4-[({5-[(S)-1-(4-Chloro-phenyl)-7-isopropoxy-6-methoxy-3-oxo-3,4-dihydro-1H-isoquinolin-2-yl]-pyridin-2-yl}-methyl-amino)-methyl]-trans-cyclohexylamino}-N-ethyl-acetamide

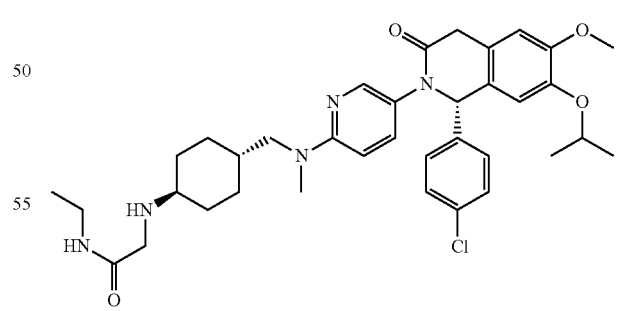

The title intermediate (120 mg, 0.178 mmol, 52%) was obtained as a white solid from Example 126 (217 mg, 0.34 mmol) and ethylamine analogously to Intermediate 85.1. HPLC: $^G$t$_{Ret}$=5.521 min; LC-MS: m/z 648.3 [M+H]$^+$.

Example 135

(S)-1-(4-Chloro-phenyl)-7-isopropoxy-6-methoxy-2-(4-{methyl-[4-(2-oxo-piperazin-1-yl)-trans-cyclohexylmethyl]-amino}-phenyl)-1,4-dihydro-2H-isoquinolin-3-one

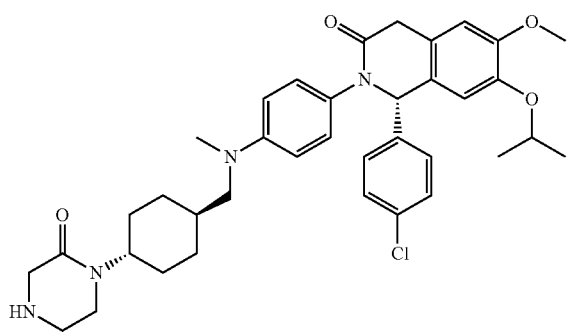 [SMILES: COc1cc2c(cc1OC(C)C)[C@H](c1ccc(Cl)cc1)N(c1ccc(N(C)C[C@H]3CC[C@H](N4CCNCC4=O)CC3)cc1)C(=O)C2]

The mixture of Intermediate 135.1 (110 mg, 0.148 mmol) and 4 N HCl in dioxane (0.738 mL, 2.95 mmol, 20 eq.) was stirred at room temperature in dioxane (3 mL) for 3 h. The mixture was concentrated to dryness and the residue was purified by reversed phase column chromatography (prepHPLC). The fractions containing the product were pooled and worked up (addition of NaHCO$_3$, removal of acetonitrile and extraction with DCM), yielding the title compound as a white solid (24.2 mg, 0.038 mmol, >99%). HPLC: $^H$t$_{Ret}$=1.54 min; LC-MS: m/z 646.3 [M+H]$^+$.

Intermediate 135.1: 4-{4-[({4-[(S)-1-(4-Chloro-phenyl)-7-isopropoxy-6-methoxy-3-oxo-3,4-dihydro-1H-isoquinolin-2-yl]-phenyl}-methyl-amino)-methyl]-trans-cyclohexyl}-3-oxo-piperazine-1-carboxylic acid tert-butyl ester

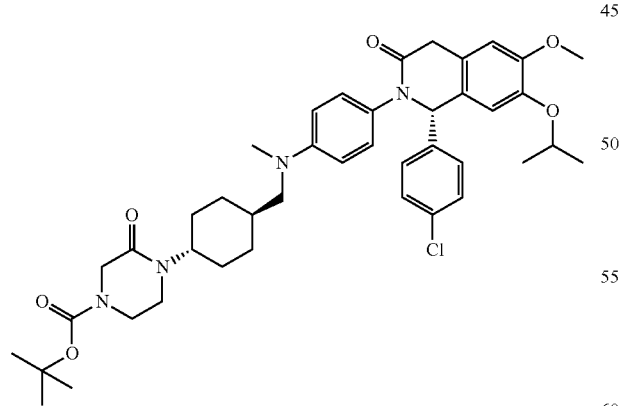

The title intermediate (110 mg, 0.148 mmol, 24.3%) was obtained as a white solid from Intermediate 75.6 (210 mg, 0.607 mmol) and Intermediate 135.2 (352 mg, 0.668 mmol) analogously to Example 75. HPLC: $^M$t$_{Ret}$=1.18 min; LC-MS: m/z 745.4 [M+H]$^+$.

Intermediate 135.2: 4-(4-{[(4-Iodo-phenyl)-methyl-amino]-methyl}-trans-cyclohexyl)-3-oxo-piperazine-1-carboxylic acid tert-butyl ester

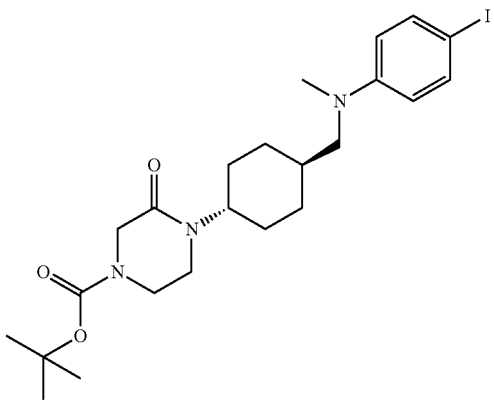 [SMILES: CN(C[C@H]1CC[C@H](N2CCN(C(=O)OC(C)(C)C)CC2=O)CC1)c1ccc(I)cc1]

To a solution of Intermediate 135.3 (0.51 g, 0.904 mmol) in DMF (15 mL) was added potassium tert-butoxide (0.230 g, 1.990 mmol) and the reaction was heated at 80° C. for 5 h. The reaction was diluted with toluene and the organic phase was washed with aq. NaHCO$_3$ solution and brine. The organic phase was dried over Na$_2$SO$_4$, filtered and concentrated in vacuo to obtain side products. The aqueous phase were pooled and extracted with DCM to obtain the crude title product. The product was purified by automated normal phase column chromatography (eluting with n-heptane-ethyl acetate), yielding the title compound as a brownish oil (350 mg, 0.66 mmol, 99%). HPLC: $^M$t$_{Ret}$=1.40 min; LC-MS: m/z 528.1 [M+H]$^+$.

Intermediate 135.3: {2-[(2-Chloro-acetyl)-(4-{[(4-iodo-phenyl)-methyl-amino]-methyl}-trans-cyclohexyl)-amino]-ethyl}-carbamic acid tert-butyl ester

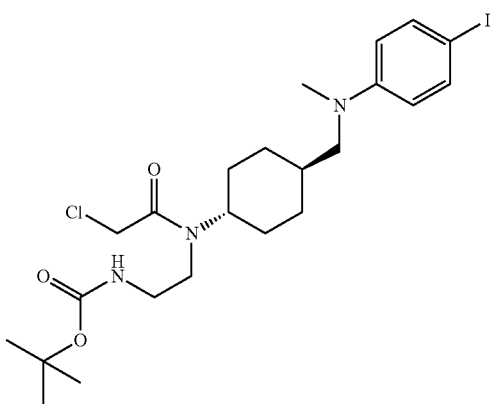 [SMILES: CN(C[C@H]1CC[C@H](N(CCNC(=O)OC(C)(C)C)C(=O)CCl)CC1)c1ccc(I)cc1]

A solution of Intermediate 135.4 (0.50 g, 1.026 mmol) in DCM (20 mL) was immersed in an ice-bath. After 5 min, DIPEA (0.537 mL, 3.08 mmol) was added, then followed by chloracetyl chloride (0.099 mL, 1.231 mmol) were added slowly. The reaction was allowed to warm to RT and after 1 h, the starting material was gone. The reaction mixture was diluted with ethyl acetate and washed with aqueous NaHCO$_3$ solution and brine. The crude product was purified by automated normal phase column chromatography (eluting with n-heptane-ethyl acetate), yielding the title compound as a brownish solid (0.51 g, 0.904 mmol). HPLC: $^M$t$_{Ret}$=1.42 min; LC-MS: m/z 564.1 [M+H]$^+$.

397

Intermediate 135.4: [2-(4-{[(4-Iodo-phenyl)-methyl-amino]-methyl}-trans-cyclohexyl-amino)-ethyl]-carbamic acid tert-butyl ester

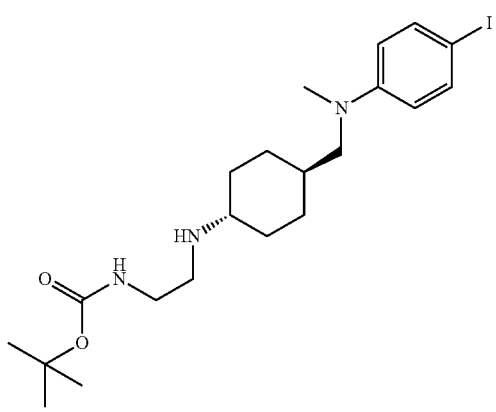 [SMILES: CN(C[C@H]1CC[C@H](NCCNC(=O)OC(C)(C)C)CC1)c1ccc(I)cc1]

The title intermediate 135.4 (0.50 g, 1.026 mmol) was obtained as a colorless oil from Intermediate 105.4 (1.54 g, 3.58 mmol) and N-Boc-2-aminoacetaldehyde (1.139 g, 7.16 mmol) analogously to Example 52. HPLC: $^{M}t_{Ret}$=0.98 min; LC-MS: m/z 488.2 [M+H]$^{+}$.

Example 136

(S)-1-(4-Chloro-phenyl)-7-isopropoxy-6-methoxy-2-(4-{methyl-[4-(2-oxo-piperazin-1-yl)-cis-cyclohexylmethyl]-amino}-phenyl)-1,4-dihydro-2H-isoquinolin-3-one

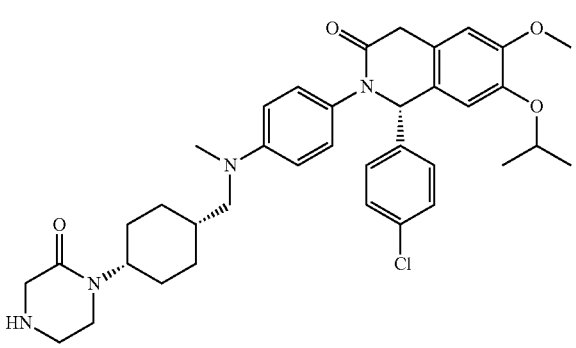 [SMILES: COc1cc2c(cc1OC(C)C)[C@H](c1ccc(Cl)cc1)N(c1ccc(N(C)C[C@H]3CC[C@@H](N4CCNCC4=O)CC3)cc1)C(=O)C2]

The mixture of intermediate 135.1 (110 mg, 0.148 mmol) and 4 N HCl in dioxane (0.738 mL, 2.95 mmol, 20 eq.) was stirred at room temperature in dioxane (3 ml) for 3 h. The mixture was concentrated to dryness and the residue was purified by reversed phase column chromatography (prepH-PLC). The fractions containing the product were pooled and worked up (addition of NaHCO$_3$, removal of acetonitrile and extraction with DCM), yielding the title compound as a white solid (12.3 mg, 0.019 mmol, >99%). HPLC: $^{H}t_{Ret}$=1.52 min; LC-MS: m/z 646.3 [M+H]$^{+}$.

Example 137

(S)-2-{5-[(Trans-4-amino-cyclohexylmethyl)-amino]-pyridin-2-yl}-1-(4-chloro-phenyl)-7-isopropoxy-6-methoxy-1,4-dihydro-2H-isoquinolin-3-one

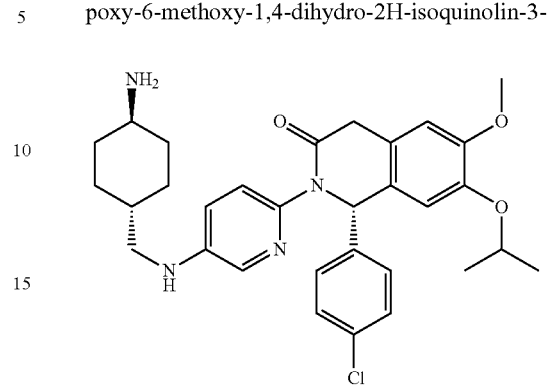

The title compound (111 mg, 0.203 mmol, quantitative) was obtained as a brown solid from Intermediate 137.1 (132 mg, 0.203 mmol) analogously to Example 77.3. HPLC: $^{F}t_{Ret}$=1.937; LC-MS: m/z 549.4 [M+H]$^{+}$.

Intermediate 137.1: [4-({6-[(S)-1-(4-Chloro-phenyl)-7-isopropoxy-6-methoxy-3-oxo-3,4-dihydro-1H-isoquinolin-2-yl]-pyridin-3-ylamino}-methyl)-trans-cyclohexyl]-carbamic acid tert-butyl ester

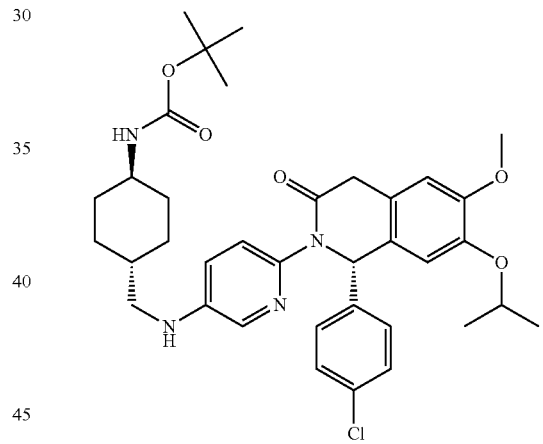

The title intermediate (132 mg, 0.203 mmol, 28%) was obtained as a brown solid from Intermediate 120.1 (367 mg, 0.850 mmol) and Intermediate 75.6 (250 mg, 0.708 mmol) analogously to Example 75. HPLC: $^{F}t_{Ret}$=1.455; LC-MS: m/z 649.3 [M+H]$^{+}$.

Intermediate 138.1: 1-(4-Chloro-phenyl)-7-isopropoxy-6-methoxy-1,4-dihydro-2H-isoquinolin-3-one

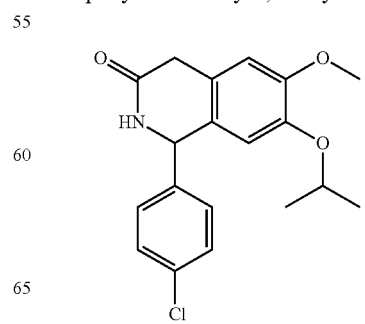

To a solution of Intermediate 138.2 (150 g, 329 mmol) in DMF (650 mL) was successively added cesium carbonate (125 g, 658 mmol) and 2-iodopropane (100 mL, 988 mmol), then the reaction mixture was heated at 55° C. for 3 h. The reaction mixture was slowly poured into the stirred 2 L of iced water. Resulting mixture was extracted with 3 L of EtOAc two times, then washed with 1 L of water 2 times and 0.5 L of brine. Concentration in vacuo gave crude solid, which was stirred in 100 mL of EtOAc at RT, then filtration and dry up gave the title intermediate (97.2 g, 281 mmol, 85%). HPLC: $^E t_{Ret}$=4.99 min; LC-MS: m/z 346.2 [M+H]$^+$; $^1$H NMR (400 MHz, DMSO-d$_6$) 1.16 (dd, J=18.94, 6.05 Hz, 6H), 3.28-3.54 (m, 2H), 3.70 (s, 3H), 4.32-4.47 (m, 1H), 5.53 (d, J=3.90 Hz, 1H), 6.77 (s, 1H), 6.83 (s, 1H), 7.28 (d, 2H), 7.36 (d, 2H), 8.49 (d, J=3.90 Hz, 1H).

Intermediate 138.2: 1-(4-Chloro-phenyl)-7-hydroxy-6-methoxy-1,4-dihydro-2H-isoquinolin-3-one

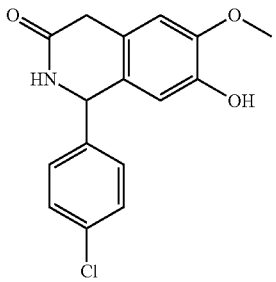 [SMILES: COc1cc2c(cc1O)C(c1ccc(Cl)cc1)NC(=O)C2]

To a suspension of 4-hydroxy-3-methoxyphenylacetonitrile (150 g, 0.919 mol) in phosphoric acid 85% (877 mL, 15.000 mol) was added 4-chlorobenzaldehyde (168 g, 1.195 mol), then the reaction mixture was heated at 120° C. for 2 h. After cooling to 90° C., the reaction mixture was slowly poured into the stirred 4 L of iced water. Resulting suspension was stirred at RT for 2 h, then filtered and washed with 500 mL of water 4 times. Crude and wet material was stirred in acetonitrile (1 L) at RT for 1 h, then filtration and dry up gave the title intermediate (163.6 g, 0.539 mol, 58.6%). HPLC: $^E t_{Ret}$=4.20 min; LC-MS: m/z 304.0 [M+H]$^+$; $^1$H NMR (400 MHz, DMSO-d$_6$) 3.25-3.53 (m, 2H), 3.72 (s, 3H), 5.47 (d, J=3.12 Hz, 1H), 6.53 (s, 1H), 6.72 (s, 1H), 7.24 (d, 2H), 7.37 (d, 2H), 8.42 (d, J=3.51 Hz, 1H), 8.86 (br. s., 1H).

Example 139

{4-[({5-[(S)-1-(4-Chloro-phenyl)-7-isopropoxy-6-methoxy-3-oxo-3,4-dihydro-1H-isoquinolin-2-yl]-pyrazin-2-yl}-methyl-amino)-methyl]-trans-cyclohexylamino}-acetic acid methyl ester

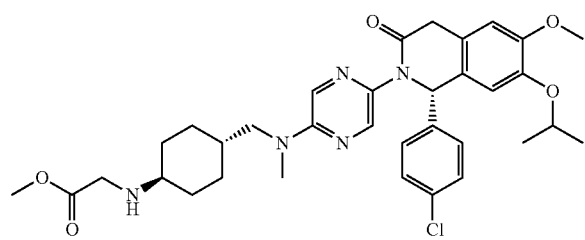 [SMILES: COC(=O)CN[C@H]1CC[C@H](CN(C)c2cnc(N3C(=O)Cc4cc(OC)c(OC(C)C)cc4[C@@H]3c3ccc(Cl)cc3)cn2)CC1]

The title compound (300 mg, 0.467 mmol, 41%) was obtained as a yellow foam from intermediate 139.1 (400 mg, 1.145 mmol) and intermediate 75.6 (472 mg, 1.26 mmol) analogously to Example 75: HPLC: $^D t_{Ret}$=1.40 min; LC-MS: m/z 446.4 [M+H]$^+$.

Intermediate 139.1: (4-{[(5-Bromo-pyrazin-2-yl)-methyl-amino]-methyl}-trans-cyclohexyl-amino)-acetic acid methyl ester

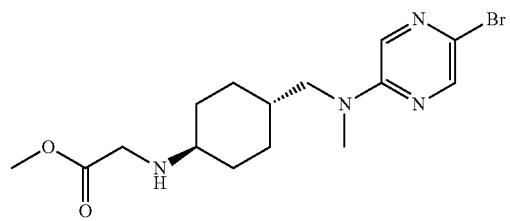 [SMILES: COC(=O)CN[C@H]1CC[C@H](CN(C)c2cnc(Br)cn2)CC1]

The title intermediate (570 mg, 1.52 mmol, 54%) was obtained as a beige crystals from intermediate 139.2 (850 mg, 2.81 mmol) analogously to intermediate 130.3. HPLC: $^D t_{Ret}$=0.68 min; LC-MS: m/z 371/373 [M]$^+$.

Intermediate 139.2: (Trans-4-amino-cyclohexylmethyl)-(5-bromo-pyrazin-2-yl)-methyl-amine

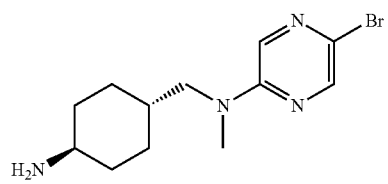 [SMILES: CN(C[C@H]1CC[C@H](N)CC1)c1cnc(Br)cn1]

The title intermediate (17.0 g, 55.7 mmol, 99%) was obtained as slightly yellow crystals from intermediate 139.3 (22.5 g, 55.8 mmol) analogously to Intermediate 130.4. HPLC: $^D t_{Ret}$=0.64 min; LC-MS: m/z 299/301 [M]$^+$.

Intermediate 139.3: (4-{[(5-Bromo-pyrazin-2-yl)-methyl-amino]-methyl}-trans-cyclohexyl)-carbamic acid tert-butyl ester

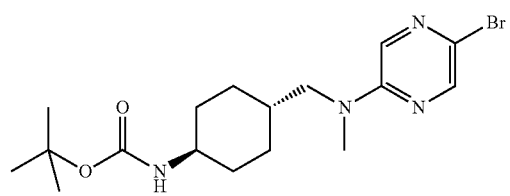 [SMILES: CN(C[C@H]1CC[C@H](NC(=O)OC(C)(C)C)CC1)c1cnc(Br)cn1]

To the stirred mixture of Intermediate 139.4 (16.6 g, 42.7 mmol), acetonitrile (2 L) and aqueous formaldehyde 37% (318 mL) was added NaCNBH$_4$ (5.36 g, 85 mmol) at 10° C. Slowly addition of 4M HCl adjusted the pH from 8.4 to 2.3. The reaction mixture was stirred for 4 h at 10-16° C., while holding the pH at 2.3 (addition of 4M HCl). Addition of a second portion of NaCNBH$_4$ (5.36 g, 85 mmol) and adjusting the pH from 6.9 to 2.3 (addition of 4M HCl). The reaction mixture was stirred an additional 1 h at 16° C., while holding the pH at 2.3 (addition of 4M HCl) and then concentrated. The residue was extracted between water and DCM (2×). The organic phases were washed with brine and dried over Na$_2$SO$_4$, filtered and evaporated to dryness. Purification of the residue by normal phase column chromatography, eluting with EtOAc-heptane (1:2), gave the title compound, after crystallization (TBME) as white crystals (13.53 g, 33.9 mmol, 79%). HPLC: $^Dt_{Ret}$=1.30 min; LC-MS: m/z 399/401 [M]⁺.

Intermediate 139.4: {4-[(5-Bromo-pyrazin-2-ylamino)-methyl]-trans-cyclohexyl}-carbamic acid tert-butyl ester

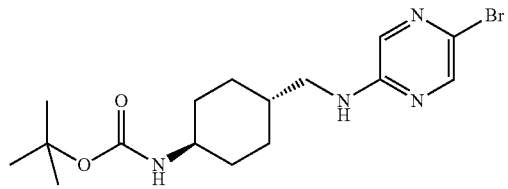

To a stirred solution of trans-(4-formyl-cyclohexyl)-carbamic acid tert-butyl (30 g, 132 mmol), 2-amino-5-bromopyrazine (20.67 g, 119 mmol) and DCM (650 mL) was added NaBH(OAc)₃ (42.0 g, 198 mmol) and AcOH (22.67 mL, 396 mmol) at 20° C. (slightly exothermic). The reaction mixture was stirred for 18 h at RT. The reaction mixture was carefully quenched by slow addition of 1M aqueous NaHCO₃ (1 L). After 1 h stirring at RT, the organic phase was separated and the aqueous phase was extracted with additional DCM (600 mL). The combined organic phases were washed with brine and dried over Na₂SO₄, filtered and evaporated to dryness. Purification of the residue by normal phase column chromatography, eluting with EtOAc-heptane (1:1), gave the title compound, after crystallization (TBME) as slightly yellow crystals (24.3 g, 62.4 mmol, 47%). HPLC: $^Dt_{Ret}$=1.30 min; LC-MS: m/z 385/387 [M]⁺]⁺.

Example 140

(S)-1-(4-Chloro-phenyl)-7-isopropoxy-6-methoxy-2-(5-methoxy-2-(5-{methyl-[4-(4-methyl-3-oxo-piperazin-1-yl)-trans-cyclohexylmethyl]-amino}-pyrazin-2-yl)-1,4-dihydro-2H-isoquinolin-3-one

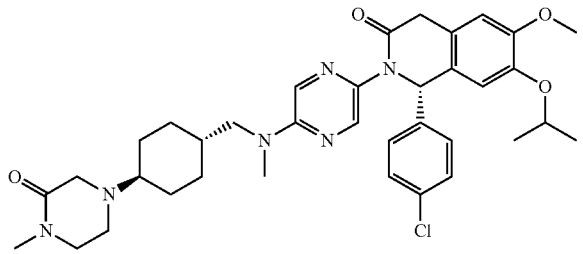 [SMILES: COc1cc2c(cc1OC(C)C)[C@H](c1ccc(Cl)cc1)N(c1cnc(N(C)C[C@H]3CC[C@H](N4CCN(C)C(=O)C4)CC3)cn1)C(=O)C2]

To a solution of Intermediate 140.1 (175 mg, 0.213 mmol) in dioxane (2.13 mL) was added 4M HCl (dioxane) (2.66 mL, 10.64 mmol) at 0° C. The reaction mixture was stirred at RT for 1.5 h. The solution was concentrated and residue was dissolved in MeOH (2.13 mL) at 0° C., triethylamine (0.445 mL, 3.19 mmol) was added and the mixture was stirred for 1 h at RT. The reaction mixture was extracted between EtOAc (2×) and 1M aqueous NaHCO₃ (1×). The organic phases were washed with brine and dried over Na₂SO₄, filtered and evaporated to dryness. Purification of the residue by normal phase column chromatography, eluting with DCM-MeOH (20:1), gave the title compound as slightly yellow foam (118 mg, 0.177 mmol, 83%). HPLC: $^Dt_{Ret}$=0.97 min; LC-MS: m/z 661.5 [M+H]⁺.

Intermediate 140.1: ([2-(tert-Butoxycarbonyl-methyl-amino)-ethyl]-{4-[({5-[(S)-1-(4-chloro-phenyl)-7-isopropoxy-6-methoxy-3-oxo-3,4-dihydro-1H-isoquinolin-2-yl]-pyrazin-2-yl}-methyl-amino)-methyl]-trans-cyclohexyl}-amino)-acetic acid methyl ester

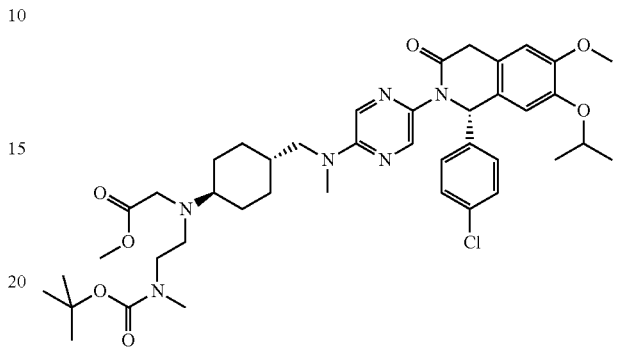

The title intermediate (180 mg, 0.219 mmol, 91%) was obtained as slightly yellow foam from Example 139 (154 mg, 0.240 mmol) and methyl-(2-oxo-ethyl)-carbamic acid tert-butyl ester (49.8 mg, 0.288 mmol), analogously to Intermediate 130.2. HPLC: $^Dt_{Ret}$=1.36 min; LC-MS: m/z 793.6 [M+H]⁺.

Example 141

2-{4-[({6-[(S)-1-(4-Chloro-phenyl)-7-isopropoxy-6-methoxy-3-oxo-3,4-dihydro-1H-isoquinolin-2-yl]-pyridin-3-yl}-methyl-amino)-methyl]-trans-cyclohexylamino}-N-ethyl-acetamide

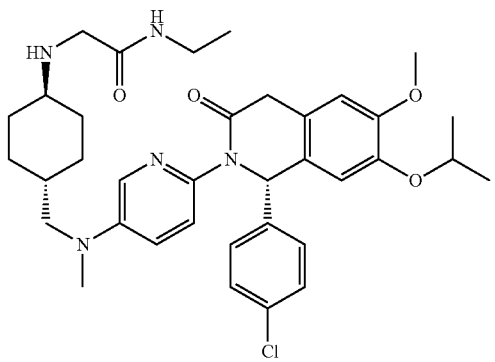 [SMILES: CCNC(=O)CN[C@H]1CC[C@H](CN(C)c2ccc(N3C(=O)Cc4cc(OC)c(OC(C)C)cc4[C@@H]3c3ccc(Cl)cc3)nc2)CC1]

The title compound (73 mg, 0.113 mmol, 63%) was obtained as a yellow foam from Example 120 (100 mg, 0.178 mmol) and 2-bromo-N-ethylacetamide (43 mg, 0.249 mmol) analogously to Intermediate 79.1. HPLC: $^Ft_{Ret}$=1.016; LC-MS: m/z 648.5 [M+H]⁺.

Example 142

2-{4-[({6-[(S)-1-(4-Chloro-phenyl)-7-isopropoxy-6-methoxy-3-oxo-3,4-dihydro-1H-isoquinolin-2-yl]-pyridin-3-yl}-methyl-amino)-methyl]-trans-cyclohexylamino}-N-isopropyl-acetamide

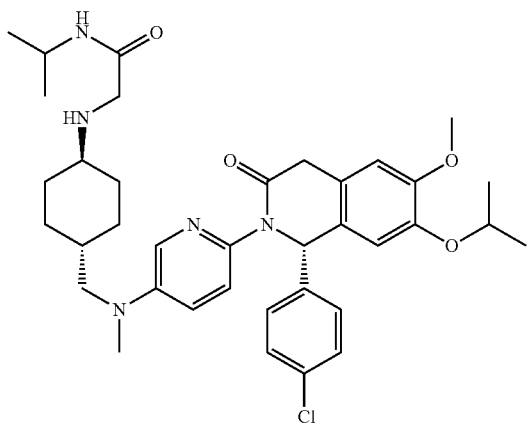 [SMILES: COc1cc2c(cc1OC(C)C)[C@H](c1ccc(Cl)cc1)N(c1ccc(N(C)C[C@H]3CC[C@H](NCC(=O)NC(C)C)CC3)cn1)C(=O)C2]

The title compound (75 mg, 0.113 mmol, 64%) was obtained as a yellow foam from Example 120 (100 mg, 0.178 mmol) and 2-bromo-N-isopropylacetamide (42 mg, 0.231 mmol) analogously to Intermediate 79.1. HPLC: $^F t_{Ret}$=1.035; LC-MS: m/z 662.5 [M+H]$^+$

Example 143

(S)-1-(4-Chloro-phenyl)-7-isopropoxy-6-methoxy-2-(5-{methyl-[4-(2-oxo-azetidin-1-yl)-trans-cyclohexylmethyl]-amino}-pyridin-2-yl)-1,4-dihydro-2H-isoquinolin-3-one

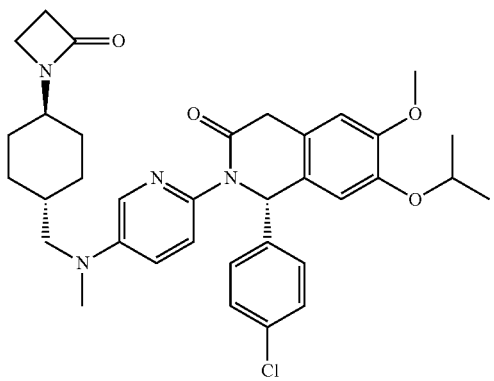 [SMILES: COc1cc2c(cc1OC(C)C)[C@H](c1ccc(Cl)cc1)N(c1ccc(N(C)C[C@H]3CC[C@H](N4CCC4=O)CC3)cn1)C(=O)C2]

To a solution of Example 120 (125 mg, 0.222 mmol) in DCM (3 ml) were successively added DMAP (1.356 mg, 0.0011 mmol), Et$_3$N (0.093 mL, 0.666 mmol) and 3-chloro propionyl chloride (31 mg, 0.244 mmol) at 0° C. The ice bath was then removed and the yellow solution stirred for 1 h. The mixture was then poured onto DCM and washed with saturated NaHCO$_3$. After separation, the organic phase was washed with H$_2$O and the aqueous phase re-extracted with DCM. The combined extracts were washed once with saturated brine, dried over Na$_2$SO$_4$, filtered and concentrated to dryness. The residue was then dissolved in DCM (5 mL) and NaH (60% in mineral oil, 13.62 mg, 0.341 mmol) was added. The reaction mixture was then stirred at RT for 15 h. The reaction mixture was then quenched with water, poured into water and extracted with DCM. The organic phase was washed with saturated brine, dried over Na$_2$SO$_4$, filtered and concentrated to dryness. The crude residue was purified by Combi-Flash Companion™ (Isco Inc.) column chromatography (SiO$_2$; gradient elution, DCM/[DCM/EtOH 9:1] 1:0→0:1) yielding the title compound as a yellow foam (102 mg, 0.165 mmol, 97%). HPLC: $^F t_{Ret}$=1.294; LC-MS: m/z 617.4 [M+H]$^+$.

Example 144

(S)-1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridazin-3-yl)-1,4-dihydro-2H-isoquinolin-3-one

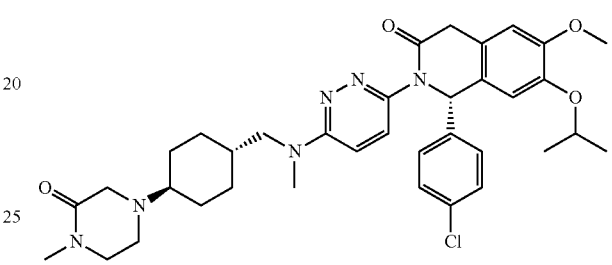

The title compound (13 mg, 0.019 mmol, 11%) was obtained as slightly yellow foam from Intermediate 75.6 (61 mg, 0.175 mmol) and Intermediate 144.1 (77 mg, 0.192 mmol), analogously to Example 130. HPLC: $^D t_{Ret}$=0.93 min; LC-MS: m/z 661.5 [M+H]$^+$.

Intermediate 144.1: 4-(4-{[(6-Bromo-pyridazin-3-yl)-methyl-amino]-methyl}-trans-cyclohexyl)-1-methyl-piperazin-2-one

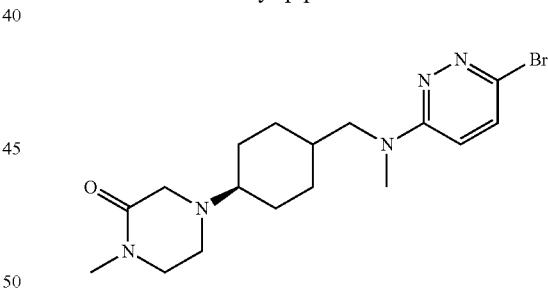

To a solution of Intermediate 144.2 (335 mg, 0.628 mmol) in dioxane (6.28 mL) was added 4M HCl (dioxane) (7.84 mL, 31.4 mmol) at RT. The reaction mixture was stirred at RT for 0.5 h. The solution was concentrated and the residue was dissolved in MeOH (6.28 mL) at 0° C., triethylamine (1.31 mL, 9.41 mmol) was added and the mixture was stirred for 50 min at RT. The reaction mixture was extracted between EtOAc (2×) and 1M aqueous NaHCO$_3$ (1×). The organic phases were washed with brine and dried over Na$_2$SO$_4$, filtered and evaporated to dryness. Purification of the residue by normal phase column chromatography, eluting with DCM-MeOH (10:1), gave the title compound as beige crystals (230 mg, 0.575 mmol, 92%). HPLC: $^D t_{Ret}$=0.54 min; LC-MS: m/z 396/398 [M]$^+$; $^1$H NMR (400 MHz, DMSO-d$_6$): 0.90-1.02 (m, 2H), 1.07-1.17 (m, 2H), 1.65 (m, 3H), 1.78 (m, 2H), 2.23 (m, 1H), 2.66 (m, 2H), 2.77 (s, 3H), 3.03 (m, 5H), 3.17 (m, 2H), 3.36 (m, 2H), 7.04 (d, 1H), 7.49 (d, 1H).

Intermediate 144.2: {(4-{[(6-Bromo-pyridazin-3-yl)-methyl-amino]-methyl}-trans-cyclohexyl)-[2-(tert-butoxycarbonyl-methyl-amino)-ethyl]-amino}-acetic acid methyl ester

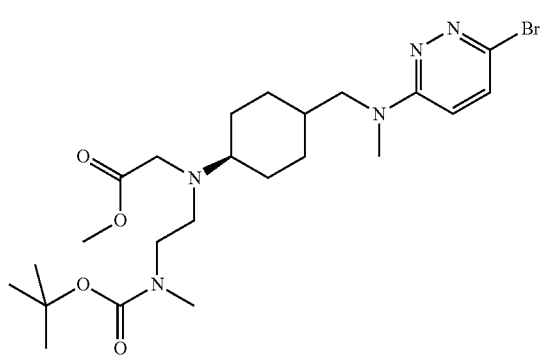

The title intermediate (342 mg, 0.641 mmol, 96%) was obtained as a beige oil from Intermediate 144.3 (250 mg, 0.667 mmol) analogously to Intermediate 130.2. HPLC: $^D t_{Ret}$=0.96 min; LC-MS: m/z 528/530 [M]$^+$.

Intermediate 144.3: (4-{[(6-Bromo-pyridazin-3-yl)-methyl-amino]-methyl}-trans-cyclohexyl-amino)-acetic acid methyl ester

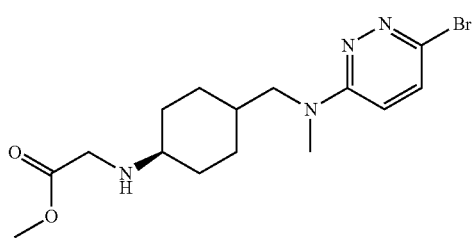

The title intermediate (500 mg, 1.33 mmol, 50%) was obtained as beige crystals from Intermediate 144.4 (800 mg, 2.65 mmol) analogously to Intermediate 130.3. HPLC: $^D t_{Ret}$=0.57 min; LC-MS: m/z 3711373 [M]$^+$.

Intermediate 144.4: (Trans-4-amino-cyclohexylmethyl)-(6-bromo-pyridazin-3-yl)-methyl-amine

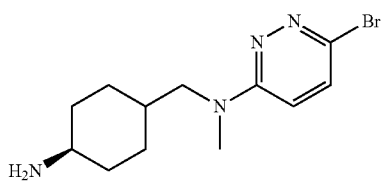

The title intermediate (800 mg, 2.65 mmol, 96%) was obtained as a beige foam from Intermediate 144.5 (1.15 g, 2.76 mmol) analogously to Intermediate 130.4. HPLC: $^D t_{Ret}$=0.52 min; LC-MS: m/z 299/301 [M]$^+$.

Intermediate 144.5: (4-{[(6-Bromo-pyridazin-3-yl)-methyl-amino]-methyl}-trans-cyclohexyl)-carbamic acid tert-butyl ester

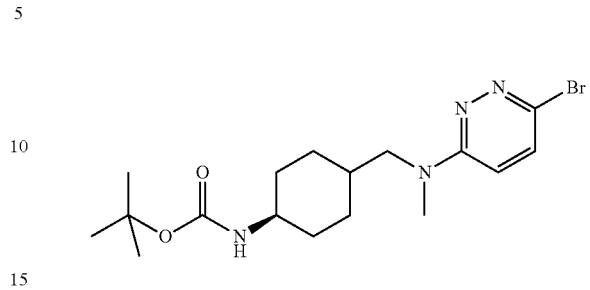

The title intermediate (1.208 g, 2.90 mmol, 40%) was obtained as slightly yellow crystals from Intermediate 144.6 (2.80 g, 7.27 mmol) analogously to Intermediate 139.3. HPLC: $^D t_{Ret}$=1.10 min; LC-MS: m/z 399/401 [M]$^+$.

Intermediate 144.6: {4-[(6-Bromo-pyridazin-3-ylamino)-methyl]-trans-cyclohexyl}-carbamic acid tert-butyl ester

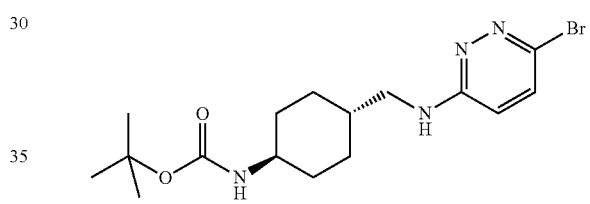

The title intermediate (2.0 g, 5.19 mmol, 32%) was obtained as white crystals from trans-(4-formyl-cyclohexyl)-carbamic acid tert-butyl ester (3.63 g, 15.97 mmol) and 6-bromo-pyridazin-3-ylamine (2.58 g, 14.37 mmol), analogously to Intermediate 139.4. HPLC: $^D t_{Ret}$=1.00 min; LC-MS: m/z 385/387 [M]$^+$.

Example 145

2-{4-[({5-[(S)-1-(4-Chloro-phenyl)-7-isopropoxy-6-methoxy-3-oxo-3,4-dihydro-1H-isoquinolin-2-yl]-pyrazin-2-yl}-methyl-amino)-methyl]-trans-cyclohexylamino}-N-methyl-acetamide

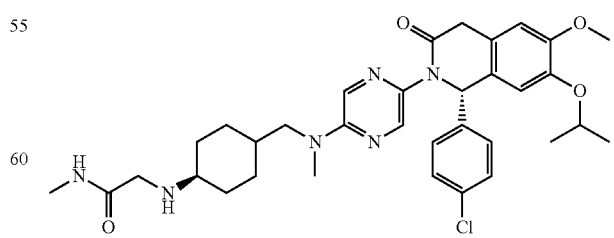

The title compound (115 mg, 0.154 mmol, 85%) was obtained as slightly orange foam from Example 139 (116 mg, 0.181 mmol), analogously to Intermediate 132.2. HPLC: $^D t_{Ret}$=0.93 min; LC-MS: m/z 635.5 [M+H]$^+$.

Example 146

(S)-1-(4-Chloro-phenyl)-2-(5-{[4-(3-ethyl-4-oxo-imidazolidin-1-yl)-trans-cyclohexylmethyl]-methyl-amino}-pyridin-2-yl)-7-isopropoxy-6-methoxy-1,4-dihydro-2H-isoquinolin-3-one

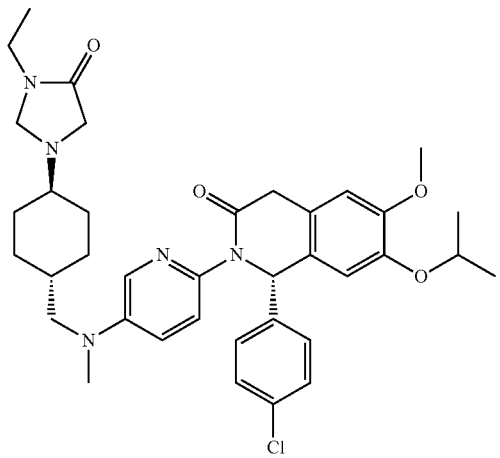 [SMILES: CCN1CN([C@H]2CC[C@H](CN(C)c3ccc(N4C(=O)Cc5cc(OC)c(OC(C)C)cc5[C@@H]4c4ccc(Cl)cc4)nc3)CC2)CC1=O]

The mixture of Example 141 (63 mg, 0.097 mmol) and formaldehyde (0.074 mL, 37% solution, 10 eq., 0.612 mmol) in EtOH (3 mL) was heated for 48 h at 60° C. The mixture was concentrated to dryness and the residue was purified by Combi-Flash Companion™ (Isco Inc.) column chromatography (SiO₂; gradient elution, DCM/[DCM/MeOH 9:1] 1:0→1:1) yielding the title compound as a yellow solid (64 mg, 0.097 mmol, 100%), HPLC: $^F t_{Ret}$=1.132; LC-MS: m/z 660.3 [M+H]⁺.

Example 147

(S)-1-(4-Chloro-phenyl)-2-{6-[(3-hydroxy-cyclobutylmethyl)-methyl-amino]-pyridin-3-yl}-7-isopropoxy-6-methoxy-1,4-dihydro-2H-isoquinolin-3-one

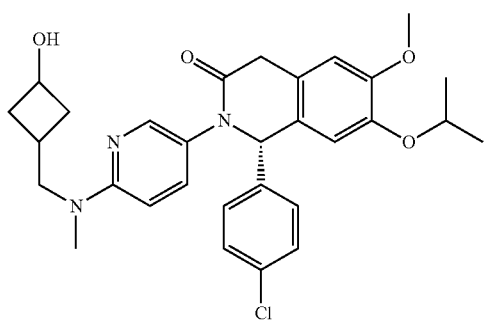 [SMILES: COc1cc2c(cc1OC(C)C)[C@H](c1ccc(Cl)cc1)N(c1ccc(N(C)CC3CC(O)C3)nc1)C(=O)C2]

The title compound (4 mg, 0.007 mmol, 7%) was obtained as a yellow solid from Intermediate 147.2 (65 mg, 0.104 mmol) and Intermediate 75.6 (36 mg, 0.104 mmol) analogously to Example 75. HPLC: $^F t_{Ret}$=0.989; LC-MS: m/z 536.4 [M+H]⁺.

Intermediate 147.2: 4-Nitro-benzoic acid 3-{[(5-iodo-pyridin-2-yl)-methyl-amino]-methyl}-cyclobutyl ester

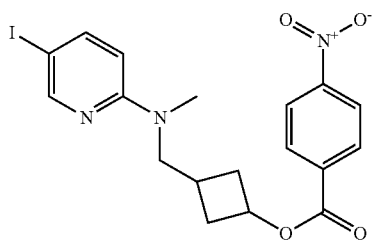 [SMILES: CN(CC1CC(OC(=O)c2ccc([N+](=O)[O-])cc2)C1)c1ccc(I)cn1]

To a solution of Intermediate 147.3 (311 mg, 0.590 mmol) in 3-ethyl-pentan-3-ol (3 mL) was added to 2-bromo-5-iodopyridine (184 mg, 0.649 mmol) and Et₃N (0.247 mL, 1.769 mmol). The yellow suspension was irradiated in a microwave to 150° C. for 8 h. After cooling, the mixture was poured onto EtOAc and water. After phase separation, the aqueous phase was re-extracted twice with EtOH. The combined organic extracts were washed with H₂O, saturated brine, dried over Na₂SO₄, filtered and evaporated to dryness. The resulting crude material was purified by Combi-Flash Companion™ (Isco Inc.) column chromatography (SiO₂; gradient elution, DCM/[DCM/EtOH 9:1] 1:0→0:1)) to yield the title compound (66 mg, 0.104 mmol, 17%), HPLC: $^F t_{Ret}$=1.454; LC-MS: m/z 468.2 [M+H]⁺.

Intermediate 147.3: 4-Nitro-benzoic acid 3-methylaminomethyl-cyclobutyl ester

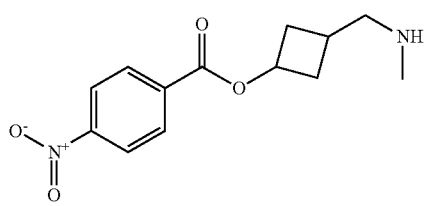 [SMILES: CNCC1CC(OC(=O)c2ccc([N+](=O)[O-])cc2)C1]

To a solution of Intermediate 147.4 (1.811 g, 6.32 mmol) in a mixture of DCM (50 mL) and MeOH (5 mL) was added Et₃N (1.321 mL, 9.48 mmol) at RT. To the resulting suspension were successively added at RT AcOH (1.266 mL, 22.11 mmol), formaldehyde (37% in water, 0.941 mL, 12.64 mmol) and NaBH(OAc)₃ (2.82 g, 12.64 mmol). The reaction mixture was stirred at RT for 1 h then diluted with DCM and washed with a 2M aqueous Na₂CO₃ solution (2×). The organic phase was dried over Na₂SO₄, filtered and evaporated to dryness. The resulting crude material was purified by Combi-Flash Companion™ (Isco Inc.) column chromatography (SiO₂; gradient elution, DCM/[DCM/EtOH 1/NH3 aq. 90:9:1] 1:0→0:1)) to yield the title compound (311 mg, 0.590 mmol, 9%) as a light yellow oil, HPLC: $^F t_{Ret}$=0.683; LC-MS: m/z 265.2 [M+H]⁺.

Intermediate 147.4: 4-Nitro-benzoic acid 3-aminomethyl-cyclobutyl ester HCl salt

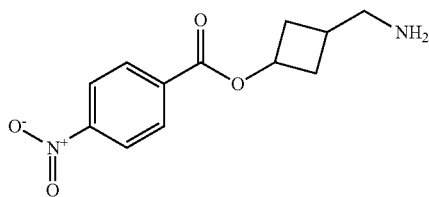 [SMILES: NCC1CC(OC(=O)c2ccc([N+](=O)[O-])cc2)C1]

To a solution of Intermediate 147.5 (5.15 g, 11.76 mmol) in Et$_2$O (150 mL) was added a solution of HCl (1M in Et$_2$O, 47 mL, 47 mmol). The reaction mixture was stirred at RT for 24 h. The precipitate was collected by filtration and the cake washed with Et$_2$O, dried under vacuum, yielding the title intermediate as a colorless solid (2.906 g, 10.14 mmol, 86%), HPLC: $^Ft_{Ret}$=0.885; LC-MS: m/z 251.2 [M]$^+$.

Intermediate 147.5: 4-Nitro-benzoic acid 3-(tert-butoxycarbonylamino-methyl)-cyclobutyl ester

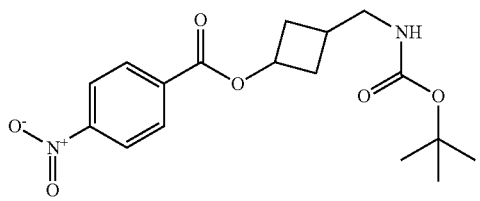 [SMILES: CC(C)(C)OC(=O)NCC1CC(OC(=O)c2ccc([N+](=O)[O-])cc2)C1]

To an ice-cooled solution of (3-Hydroxy-cyclobutylmethyl)-carbamic acid tert-butyl ester (6.98 g, 34.7 mmol), 4-nitrobenzoic acid (11.59 g, 69.4 mmol) and triphenylphosphine (18.19 g, 69.4 mmol) in THF (1 L) was added a solution of DIAD (14.76 g, 69.4 mmol) in THF (10 mL). After removal of the ice bath, the mixture was stirred at RT for 15 h. The mixture was concentrated to dryness and the oily residue was purified normal phase column chromatography (elution with DCM) yielding the title intermediate as a yellow solid (9.89 g, 22.58 mmol, 65%), HPLC: $^Ft_{Ret}$=1.354; LC-MS: m/z 368.3 [M+NH4]$^+$.

Example 148

(S)-1-(4-Chloro-phenyl)-7-isopropoxy-2-(5-{[4-(3-isopropyl-4-oxo-imidazolidin-1-yl)-trans-cyclohexylmethyl]-methyl-amino}-pyridin-2-yl)-6-methoxy-1,4-dihydro-2H-isoquinolin-3-one

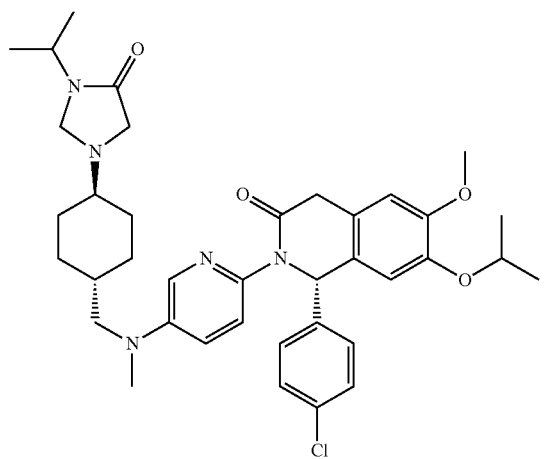 [SMILES: COc1cc2c(cc1OC(C)C)[C@H](c1ccc(Cl)cc1)N(c1ccc(N(C)C[C@H]3CC[C@H](N4CC(=O)N(C(C)C)C4)CC3)cn1)C(=O)C2]

The title compound (68 mg, 0.101 mmol, 89%) was obtained as a yellow foam from Example 142 (75 mg, 0.113 mmol) analogously to Example 146. HPLC: $^Ft_{Ret}$=1.165; LC-MS: m/z 674.3 [M+H]$^+$.

Example 149

(S)-1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one

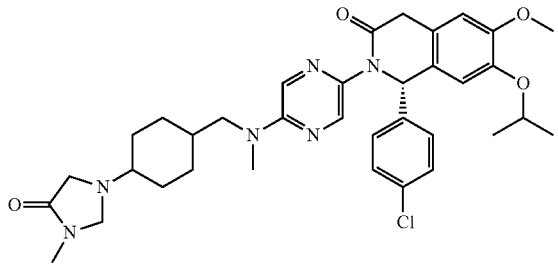 [SMILES: COc1cc2c(cc1OC(C)C)[C@H](c1ccc(Cl)cc1)N(c1cnc(N(C)CC3CCC(N4CC(=O)N(C)C4)CC3)cn1)C(=O)C2]

The title compound (1.23 g, 1.88 mmol, 33%) was obtained as slightly whit crystals from Intermediate 75.6 (2.00 g, 5.73 mmol) and Intermediate 149.1 (2.21 g, 5.73 mmol), analogously to Example 130. HPLC: $^Dt_{Ret}$=1.15 min; LC-MS: m/z 647.6 [M+H]$^+$; $^1$H NMR (600 MHz, DMSO-d$_6$) 0.93-1.12 (m, 4H), 1.23 (dd, J=16.35, 6.05 Hz, 6H), 1.64 (d, J=10.90 Hz, 3H), 1.81 (d, J=10.90 Hz, 2H), 2.18 (t, J=10.29 Hz, 1H), 2.71 (s, 3H), 3.02 (s, 3H), 3.11 (s, 2H), 3.35-3.42 (m, 2H), 3.60 (d, J=19.38 Hz, 1H), 3.73 (s, 3H), 3.81 (d, J=19.38 Hz, 1H), 4.04 (s, 2H), 4.52 (quin, J=6.05 Hz, 1H), 6.40 (s, 1H), 6.87 (s, 1H), 7.20 (s, 1H), 7.34 (s, 4H), 7.91 (s, 1H), 8.17 (s, 1H).

Intermediate 149.1: 1-(4-{[(5-Bromo-pyrazin-2-yl)-methyl-amino]-methyl}-trans-cyclohexyl)-3-methyl-imidazolidin-4-one

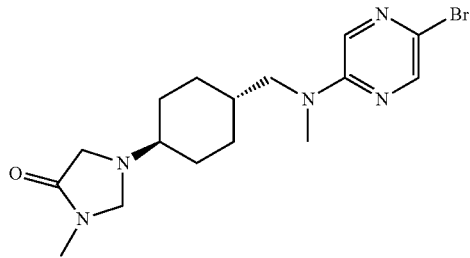 [SMILES: CN1CN([C@H]2CC[C@H](CN(C)c3cnc(Br)cn3)CC2)CC1=O]

The title intermediate (10.4 g, 26.9 mmol, 96%) was obtained as beige crystals from Intermediate 149.2 (10.5 g, 28.1 mmol), analogously to Intermediate 132.1. HPLC: $^Dt_{Ret}$=0.85 min; LC-MS: m/z 382/384 [M]$^+$.

Intermediate 149.2: 2-(4-{[(5-Bromo-pyrazin-2-yl)-methyl-amino]-methyl}-trans-cyclohexyl-amino)-N-methyl-acetamide

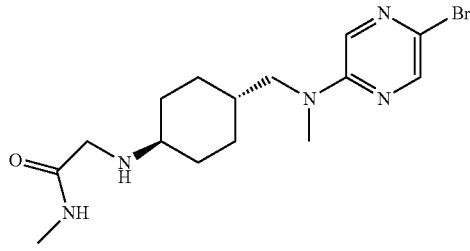 [SMILES: CNC(=O)CN[C@H]1CC[C@H](CN(C)c2cnc(Br)cn2)CC1]

The title intermediate (10.7 g, 28.6 mmol, 93%) was obtained as white crystals from Intermediate 139.1 (12.0 g, 30.7 mmol), analogously to Intermediate 132.2. HPLC: $^D t_{Ret}$=0.71 min; LC-MS: m/z 370/372 [M]$^+$.

Example 150

{4-[({2-[(S)-1-(4-Chloro-phenyl)-7-isopropoxy-6-methoxy-3-oxo-3,4-dihydro-1H-isoquinolin-2-yl]-pyrimidin-5-yl}-methyl-amino)-methyl]-trans-cyclohexylamino}-acetic acid methyl ester

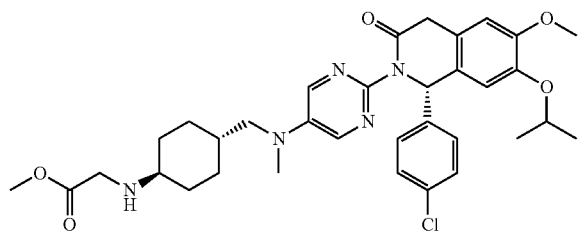 [SMILES: COC(=O)CN[C@H]1CC[C@H](CN(C)c2cnc(N3C(=O)Cc4cc(OC)c(OC(C)C)cc4[C@@H]3c3ccc(Cl)cc3)nc2)CC1]

The title compound (68 mg, 0.104 mmol, 30%) was obtained as a slightly yellow foam from Intermediate 75.6 (120 mg, 0.344 mmol) and Intermediate 150.1 (142 mg, 0.378 mmol), analogously to Example 130. HPLC: $^D t_{Ret}$=0.93 min; LC-MS: m/z 636.4 [M+H]$^+$.

Intermediate 150.1: (4-{[(2-Bromo-pyrimidin-5-yl)-methyl-amino]-methyl}-trans-cyclohexyl-amino)-acetic acid methyl ester

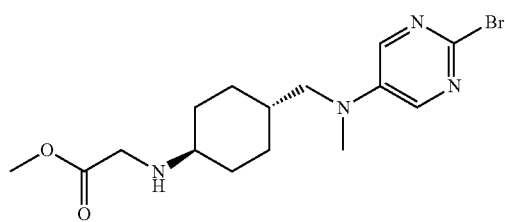 [SMILES: COC(=O)CN[C@H]1CC[C@H](CN(C)c2cnc(Br)nc2)CC1]

The title intermediate (540 mg, 1.44 mmol, 54%) was obtained as white crystals from Intermediate 150.2 (830 mg, 2.64 mmol) analogously to Intermediate 130.3. HPLC: $^D t_{Ret}$=0.55 min; LC-MS: m/z 371/373 [M]$^+$.

Intermediate 150.2: (Trans-4-amino-cyclohexylmethyl)-(2-bromo-pyrimidin-5-yl)-methyl-amine

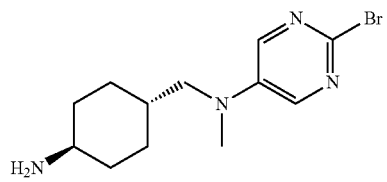 [SMILES: CN(C[C@H]1CC[C@H](N)CC1)c1cnc(Br)nc1]

The title intermediate (830 mg, 2.64 mmol, 97%) was obtained as white foam from Intermediate 150.3 (1.10 g, 2.73 mmol) analogously to Intermediate 130.4. HPLC: $^D t_{Ret}$=0.54 min; LC-MS: m/z 299/301 [M]$^+$.

Intermediate 150.3: (4-{[(2-Bromo-pyrimidin-5-yl)-methyl-amino]-methyl}-trans-cyclohexyl)-carbamic acid tert-butyl ester

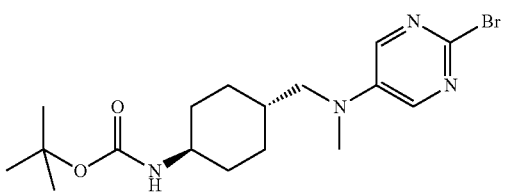 [SMILES: CN(C[C@H]1CC[C@H](NC(=O)OC(C)(C)C)CC1)c1cnc(Br)nc1]

The title intermediate (820 mg, 2.03 mmol, 81%) was obtained as slightly yellow crystals from Intermediate 150.4 (1.0 g, 2.52 mmol) analogously to Intermediate 139.3. HPLC: $^D t_{Ret}$=1.14 min; LC-MS: m/z 399/401 [M]$^+$.

Intermediate 150.4: {4-[(2-Bromo-pyrimidin-5-ylamino)-methyl]-trans-cyclohexyl}-carbamic acid tert-butyl ester

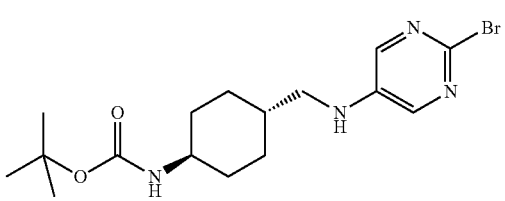 [SMILES: CC(C)(C)OC(=O)N[C@H]1CC[C@H](CNc2cnc(Br)nc2)CC1]

The title intermediate (2.71 g, 6.82 mmol, 49%) was obtained as white crystals from trans-(4-formyl-cyclohexyl)-carbamic acid tert-butyl ester (3.19 g, 14.03 mmol) and 2-bromo-pyrimidin-5-ylamine (2.20 g, 12.63 mmol), analogously to Intermediate 139.4. HPLC: $^D t_{Ret}$=1.08 min; LC-MS: m/z 385/387 [M]$^+$.

Example 151

1-(4-Chloro-phenyl)-2-(4-dimethylamino-phenyl)-6-methoxy-7-(2,2,2-trifluoro-ethoxy)-1,4-dihydro-2H-isoquinolin-3-one

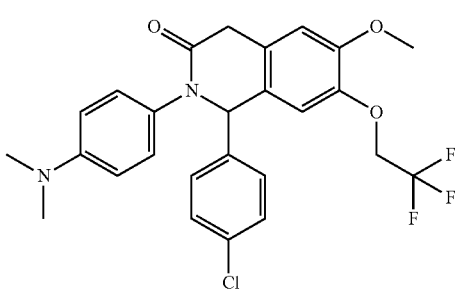 [SMILES: COc1cc2c(cc1OCC(F)(F)F)C(c1ccc(Cl)cc1)N(c1ccc(N(C)C)cc1)C(=O)C2]

To the solution of Intermediate 26.3 (100 mg, 0.236 mmol) and DMF (2.0 mL) was added toluene-4-sulfonic acid 2,2,2-trifluoro-ethyl ester (72.1 mg, 0.284 mmol) and potassium carbonate (65.4 mg, 0.473 mmol). The mixture was stirred for 15 min at 140° C. The reaction mixture was extracted between DCM (2×) and 1M aqueous NaHCO$_3$ (1×). The organic phases were dried over Na$_2$SO$_4$, filtered and evaporated to dryness. Purification of the residue by normal phase column chromatography, eluting with EtOAc-heptane, gave the title compound as a beige foam (42 mg, 0.083 mmol, 35%). HPLC: $^J t_{Ret}$=6.02 min; LC-MS: m/z 505.4 [M+H]$^+$.

Example 152

(S)-1-(4-Chloro-phenyl)-7-isopropoxy-6-methoxy-2-(5-{methyl-[4-(4-methyl-3-oxo-piperazin-1-yl)-trans-cyclohexylmethyl]-amino}-pyrimidin-2-yl)-1,4-dihydro-2H-isoquinolin-3-one

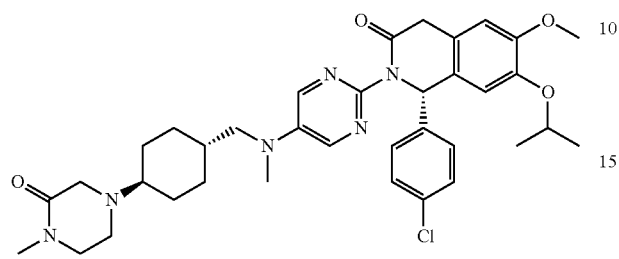

The title compound (7.0 mg, 0.010 mmol, 4.5%) was obtained as a slightly orange foam from Intermediate 75.6 (80 mg, 0.229 mmol) and Intermediate 152.1 (90 mg, 0.252 mmol), analogously to Example 130. HPLC: $^D t_{Ret}$=0.91 min; LC-MS: m/z 661.5 [M+H]$^+$.

Intermediate 152.1: 4-(4-{[(2-Chloro-pyrimidin-5-yl)-methyl-amino]-methyl}-trans-cyclohexyl)-1-methyl-piperazin-2-one

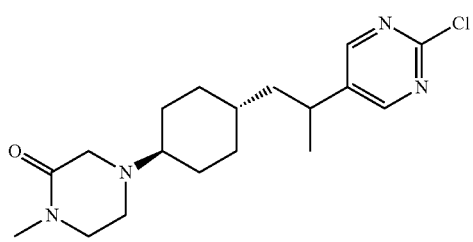 [SMILES: CC(C[C@H]1CC[C@H](N2CCN(C)C(=O)C2)CC1)c1cnc(Cl)nc1]

The title intermediate (99 mg, 0.278 mmol, 85%) was obtained as slightly yellow crystals from Intermediate 152.2 (175 mg, 0.328 mmol) analogously to Intermediate 144.1. HPLC: $^D t_{Ret}$=0.54 min; LC-MS: m/z 352.3 [M+H]$^+$.

Intermediate 152.2: {(4-{[(2-Bromo-pyrimidin-5-yl)-methyl-amino]-methyl}-trans-cyclohexyl)-[2-(tert-butoxycarbonyl-methyl-amino)-ethyl]-amino}-acetic acid methyl ester

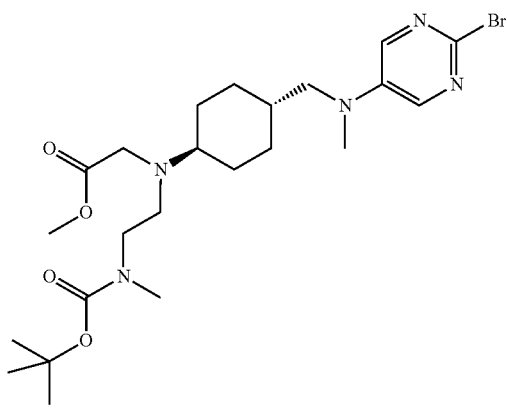 [SMILES: COC(=O)CN(CCN(C)C(=O)OC(C)(C)C)[C@H]1CC[C@H](CN(C)c2cnc(Br)nc2)CC1]

The title intermediate (180 mg, 0.337 mmol, 84%) was obtained as a beige oil from Intermediate 150.1 (150 mg, 0.40 mmol) analogously to Intermediate 130.2. HPLC: $^D t_{Ret}$=1.01 min; LC-MS: m/z 528/530 [M]$^+$.

Example 153

(S)-1-(4-Chloro-phenyl)-7-isopropoxy-6-methoxy-2-(6-{methyl-[4-(3-methyl-4-oxo-imidazolidin-1-yl)-trans-cyclohexylmethyl]-amino}-pyridazin-3-yl)-1,4-dihydro-2H-isoquinolin-3-one

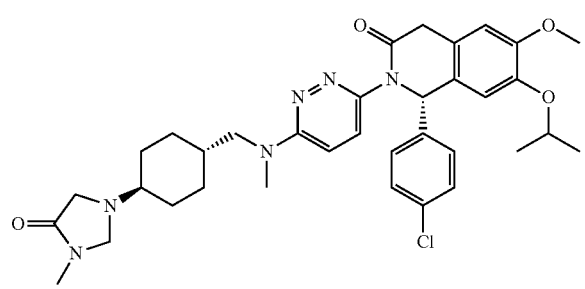 [SMILES: COc1cc2c(cc1OC(C)C)[C@H](c1ccc(Cl)cc1)N(c1ccc(N(C)C[C@H]3CC[C@H](N4CC(=O)N(C)C4)CC3)nn1)C(=O)C2]

The title compound (2.0 mg, 0.010 mmol, 1.7%) was obtained as a slightly yellow foam from Intermediate 75.6 (60 mg, 0.172 mmol) and Intermediate 153.1 (77 mg, 0.189 mmol), analogously to Example 130. HPLC: $^D t_{Ret}$=1.06 min; LC-MS: m/z 647.2 [M+H]$^+$.

Intermediate 153.1: 1-(4-{[(6-Bromo-pyridazin-3-yl)-methyl-amino]-methyl}-trans-cyclohexyl)-3-methyl-imidazolidin-4-one

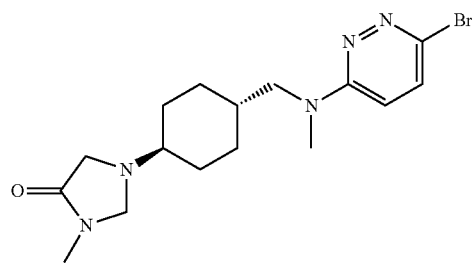 [SMILES: CN1CN([C@H]2CC[C@H](CN(C)c3ccc(Br)nn3)CC2)CC1=O]

The title intermediate (192 mg, 0.497 mmol, 94%) was obtained as white crystals from Intermediate 153.2 (195 mg, 0.527 mmol) analogously to Intermediate 132.1. HPLC: $^D t_{Ret}$=0.65 min; LC-MS: m/z 382/384 [M]$^+$.

Intermediate 153.2: 2-(4-{[(6-Bromo-pyridazin-3-yl)-methyl-amino]-methyl}-trans-cyclohexyl-amino)-N-methyl-acetamide

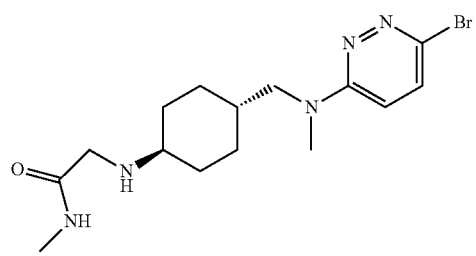 [SMILES: CNC(=O)CN[C@H]1CC[C@H](CN(C)c2ccc(Br)nn2)CC1]

The title intermediate (200 mg, 0.513 mmol, 96%) was obtained as a beige foam from Intermediate 144.3 (200 mg, 0.533 mmol) analogously to Intermediate 132.2. HPLC: $^Dt_{Ret}$=0.49 min; LC-MS: m/z 370/372 [M]$^+$.

Example 154

1-(4-Chloro-phenyl)-2-(4-dimethylamino-phenyl)-6-methoxy-7-(2-methyoxyethoxy)-1,4-dihydro-2H-isoquinolin-3-one

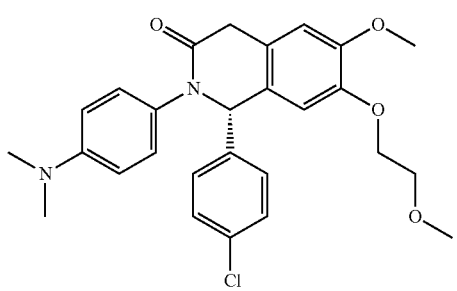

To the solution of Intermediate 26.3 (60 mg, 0.137 mmol) and DMF (0.27 mL) was added 2-bromoethyl methyl ether (20.9 mg, 0.150 mmol) and potassium carbonate (28.4 mg, 0.205 mmol). The mixture was stirred for 90 min at 100° C. The reaction mixture was extracted between EtOAc (2×) and water-brine 9:1 (1×). The organic phases were washed with brine and dried over Na$_2$SO$_4$, filtered and evaporated to dryness. Purification of the residue by normal phase column chromatography, eluting with EtOAc-heptane (1:4), gave the title compound as a beige foam (20 mg, 0.041 mmol, 30%). HPLC: $^Dt_{Ret}$=1.13 min; LC-MS: m/z 481.4 [M+H]$^+$.

Example 155

1-(4-Chloro-phenyl)-2-(4-dimethylamino-phenyl)-6-methoxy-7-[(S)-1-(tetrahydro-furan-2-yl)-methoxy]-1,4-dihydro-2H-isoquinolin-3-one

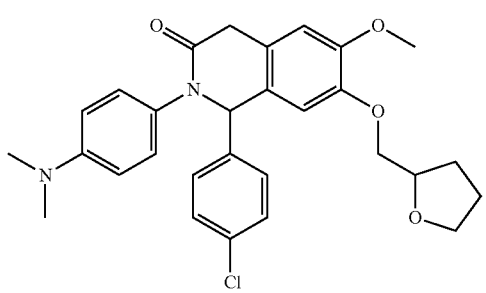 [SMILES: COc1cc2c(cc1OCC1CCCO1)C(c1ccc(Cl)cc1)N(c1ccc(N(C)C)cc1)C(=O)C2]

The title compound (23 mg, 0.045 mmol, 39%) was obtained as a beige foam from Intermediate 26.3 (50 mg, 0.114 mmol) and (S)-tetrahydrofurfuryl alcohol (17.8 mg, 0.171 mmol), analogously to Example 156. HPLC: $^Dt_{Ret}$=1.18 min; LC-MS: m/z 507.1 [M+H]$^+$.

Example 156

1-(4-Chloro-phenyl)-2-(4-dimethylamino-phenyl)-6-methoxy-7-[(R)-1-(tetrahydro-furan-2-yl)methoxy-1,4-dihydro-2H-isoquinolin-3-one

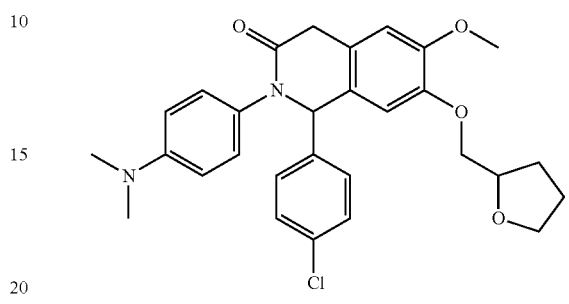

To the solution of Intermediate 26.3 (50 mg, 0.114 mmol) in THF (0.57 mL) was added subsequently (R)-tetrahydrofurfuryl alcohol (17.8 mg, 0.171 mmol), triphenylphosphine (48.8 mg, 0.182 mmol) and di-isopropylazodicarboxylate (34.3 mg, 0.160 mmol) at 0° C. The mixture was stirred for 22 h at RT. The reaction mixture was extracted between EtOAc (2×) and 1M aqueous NaHCO$_3$ (1×). The organic phases were washed with brine and dried over Na$_2$SO$_4$, filtered and evaporated to dryness. Purification of the residue by normal phase column chromatography, eluting with DCM-EtOAc (2:1→1:1), gave the title compound as a beige foam (21 mg, 0.041 mmol, 36%). HPLC: $^Dt_{Ret}$=1.18 min; LC-MS: m/z 507.3 [M+H]$^+$.

Example 157

1-(4-Chloro-phenyl)-2-(4-dimethylamino-phenyl)-6-methoxy-7-((R)-2-methoxy-propopxy)-1,4-dihydro-2H-isoquinolin-3-one

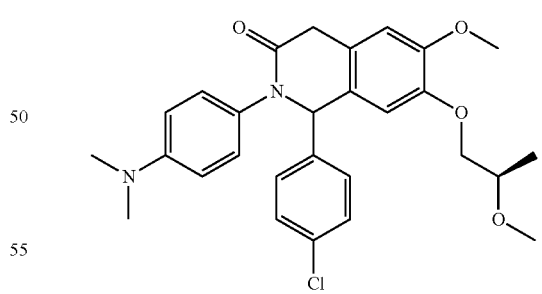

To the solution of Intermediate 26.3 (40 mg, 0.095 mmol) in DCM (2.0 mL) was added subsequently (S)-(+)-2-methoxypropanol (12.8 mg, 0.142 mmol), di-tert-butylazo-dicarboxylate (32.7 mg, 0.142 mmol) and triphenylphosphine (34.7 mg, 0.132 mmol) at 0° C. The mixture was stirred for 18 h at RT. The reaction mixture then directly subjected to purification by reverse phase prep-HPLC (Waters system gave the title compound as a beige foam (10 mg, 0.020 mmol, 21%). HPLC: $^Jt_{Ret}$=5.340; LC-MS: m/z 495.3 [M+H]$^+$.

Example 158

1-(4-Chloro-phenyl)-2-(4-dimethylamino-phenyl)-6-methoxy-7-(-2-methoxy-1-methyl-ethoxy))-1,4-dihydro-2H-isoquinolin-3-one

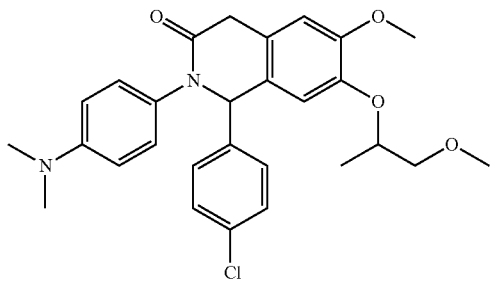

The title compound (38 mg, 0.077 mmol, 65%) was obtained as a beige foam from Intermediate 26.3 (50 mg, 0.118 mmol) and 1-methoxy-2-propanol, analogously to Example 157. HPLC: $^J t_{Ret}$=5.11; LC-MS: m/z 495.2 [M+H]$^+$.

Example 163

1-(4-Chloro-phenyl)-7-isopropoxy-6-methoxy-2-(4-{methyl-[4-(3-oxo-piperazin-1-yl)-trans-cyclohexyl-methyl]-amino}-phenyl)-1,4-dihydro-2H-isoquinolin-3-one

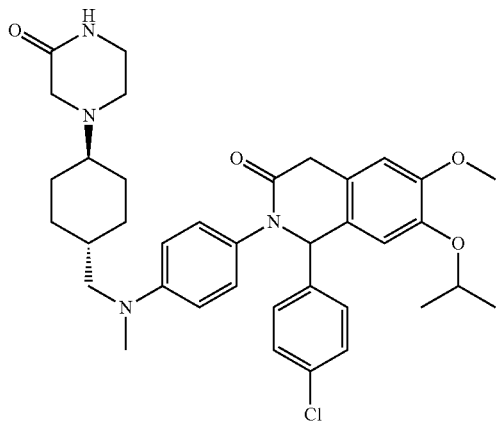

The title compound (25 mg, 0.039 mmol, 42%) was obtained as a white solid from Intermediate 163.1 (74 mg, 0.093 mmol) analogously to Example 79. HPLC: $^C t_{Ret}$=8.718 min; LC-MS: m/z 645.2 [M+H]$^+$.

Intermediate 163.1: ((2-tert-Butoxycarbonylamino-ethyl)-{4-[({4-[1-(4-chloro-phenyl)-7-isopropoxy-6-methoxy-3-oxo-3,4-dihydro-1H-isoquinolin-2-yl]-phenyl}-methyl-amino)-methyl]-trans-cyclohexyl}-amino)-acetic acid methyl ester

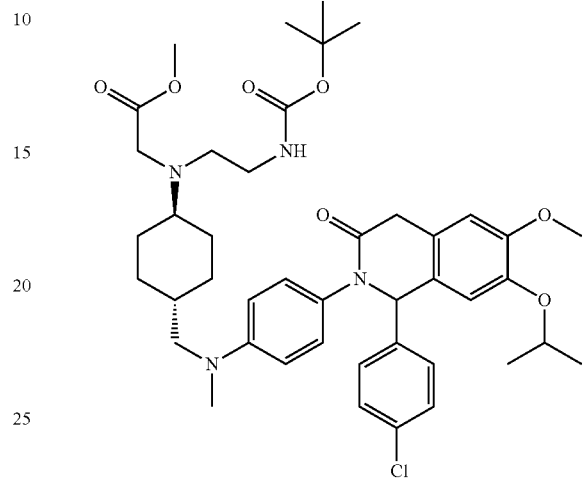

The title intermediate (110 mg, 0.148 mmol, 24.3%) was obtained as an off-white solid from Intermediate 138.1 (200 mg, 0.578 mmol) and Intermediate 106.2 (388 mg, 0.694 mmol) analogously to Example 75. HPLC: $^M t_{Ret}$=2.00 min; LC-MS: m/z 777.2 [M+H]$^+$.

Example 164

(S)-2-[4-(3-Amino-1H-pyrazol-4-yl)-phenyl]-1-(4-chloro-phenyl)-7-isopropoxy-6-methoxy-1,4-dihydro-2H-isoquinolin-3-one

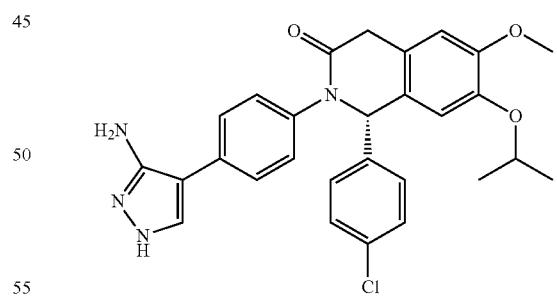

A mixture of Intermediate 164.1 (193 mg, 0.318 mmol), hydrazine hydrate (0.08 mL, 1.59 mmol) and acetic acid (0.09 mL, 1.59 mmol) in toluene (1.0 mL) was heated at reflux for 16 h. The reaction mixture was poured into the stirred iced water. The aqueous layer was extracted twice with EtOAc, the combined organic layers were washed with water and brine, dried (Na$_2$SO$_4$), filtered and concentrated. The residue was purified by column chromatography to afford the title compound (23 mg, 0.044 mmol, 14%) as a white solid. HPLC: $^G t_{Ret}$=6.802 min; LC-MS: m/z 503.4 [M+H]$^+$.

Intermediate 164.1: (Z)-2-{4-[(S)-1-(4-Chloro-phenyl)-7-isopropoxy-6-methoxy-3-oxo-3,4-dihydro-1H-isoquinolin-2-yl]-phenyl}-3-dimethylamino-acrylonitrile

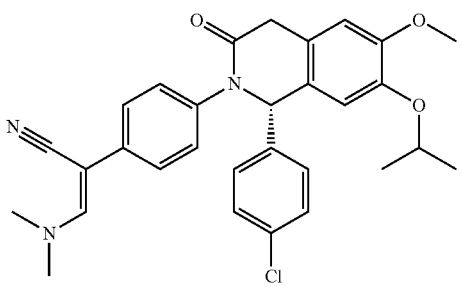 [SMILES: COc1cc2c(cc1OC(C)C)[C@H](c1ccc(Cl)cc1)N(c1ccc(/C(C#N)=C/N(C)C)cc1)C(=O)C2]

A mixture of Intermediate 164.2 (150 mg, 0.32 mmol) and dimethylformamide dimethylacetal (0.09 mL, 0.65 mmol) in toluene (0.5 mL) was heated at reflux for 4 h. The reaction mixture was concentrated in vacuo, which gave the title intermediate (198 mg, 0.32 mmol, 100%). It was used for the next step without further purification. HPLC: $^{G}t_{Ret}$=7.413 min; LC-MS: m/z 516.4 [M+H]$^{+}$.

Intermediate 164.2: {4-[(S)-1-(4-Chloro-phenyl)-7-isopropoxy-6-methoxy-3-oxo-3,4-dihydro-1H-isoquinolin-2-yl]-phenyl}-acetonitrile

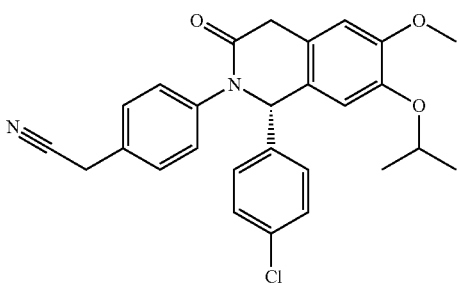 [SMILES: COc1cc2c(cc1OC(C)C)[C@H](c1ccc(Cl)cc1)N(c1ccc(CC#N)cc1)C(=O)C2]

The title intermediate (147 mg, 0.32 mmol, 44.1%) was obtained as a white solid from Intermediate 75.6 (250 mg, 0.72 mmol) and (4-Iodo-phenyl)-acetonitrile (193 mg, 0.79 mmol) analogously to Example 75. HPLC: $^{G}t_{Ret}$=9.082 min; LC-MS: m/z 461.1 [M+H]$^{+}$.

Intermediate 165.1: (Z)-2-{4-[(S)-1-(4-Chloro-phenyl)-7-isopropoxy-6-methoxy-3-oxo-3,4-dihydro-1H-isoquinolin-2-yl]-phenyl}-3-dimethylamino-but-2-enenitrile

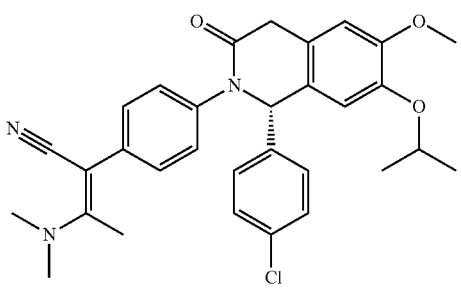

A mixture of Intermediate 164.2 (150 mg, 0.32 mmol) and N,N-dimethylacetamide dimethylacetal (0.10 mL, 0.65 mmol) in toluene (0.5 mL) was stirred for 4 h under reflux. The reaction mixture was concentrated in vacuo, which gave the title intermediate (187 mg, 0.32 mmol, 98%). It was used for the next step without further purification. HPLC: $^{G}t_{Ret}$=7.614 min; LC-MS: m/z 530.5 [M+H]$^{+}$.

Intermediate 166.1: 4-{4-[1-(4-Chloro-phenyl)-7-isopropoxy-6-methoxy-3-oxo-3,4-dihydro-1H-isoquinolin-2-yl]-phenyl}-3,5-dimethyl-pyrazole-1-carboxylic acid tert-butyl ester

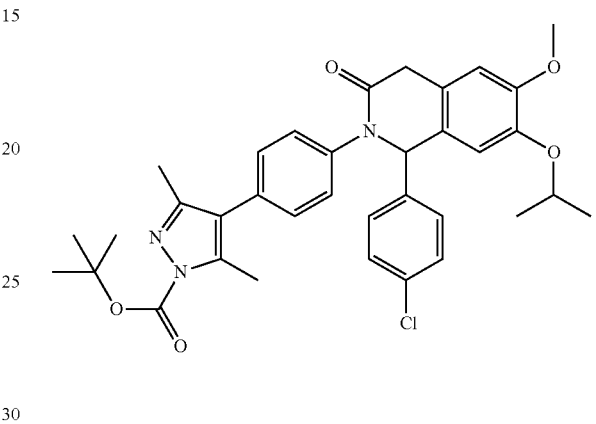

The title intermediate (297 mg, 0.48 mmol, 38%) was obtained as a orange solid from Intermediate 166.2 (700 mg, 1.27 mmol) and 3,5-Dimethyl-4-(4,4,5,5-tetramethyl-[1,3,2]dioxaborolan-2-yl)-pyrazole-1-carboxylic acid tert-butyl ester (453 mg, 1.40 mmol) analogously to Example 36. $^{1}$H NMR (400 MHz, DMSO-d$_{6}$) 1.21 (dd, 6H), 1.55 (s, 9H), 2.11 (s, 3H), 2.36 (s, 3H), 3.62 (d, J=19.92 Hz, 1H), 3.71 (s, 3H), 3.84 (d, J=19.92 Hz, 1H), 4.40-4.49 (m, 1H), 6.16 (s, 1H), 6.85 (s, 1H), 7.14 (s, 1H), 7.26 (dd, 4H), 7.38 (s, 4H).

Intermediate 166.2: 1-(4-Chloro-phenyl)-2-(4-iodo-phenyl)-7-isopropoxy-6-methoxy-1,4-dihydro-2H-isoquinolin-3-one

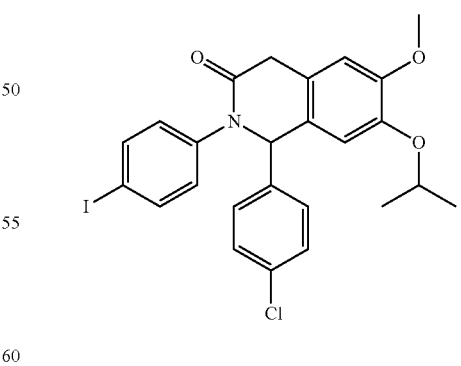

The title intermediate (1.97 g, 3.52 mmol, 56%) was obtained as a white solid from Intermediate 34.1 (2.15 g, 6.29 mmol) and Intermediate 96.1 (1.53 g, 6.29 mmol) analogously to Example 1. HPLC: $^{E}t_{Ret}$=5.925 min; LC-MS: m/z 548.2 [M+H]$^{+}$.

Example 167

1-(4-Chloro-phenyl)-2-(4-dimethylamino-phenyl)-7-(1-hydroxy-cyclo-propylmethoxy))-6-methoxy-1,4-dihydro-2H-isoquinolin-3-one

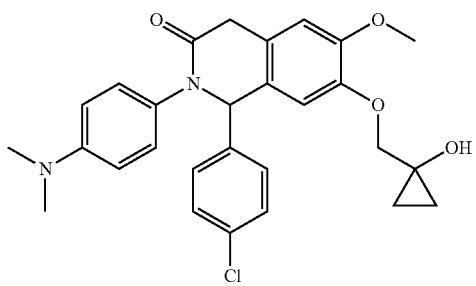 [SMILES: COc1cc2c(cc1OCC1(O)CC1)C(c1ccc(Cl)cc1)N(c1ccc(N(C)C)cc1)C(=O)C2]

The title compound (31 mg, 0.063 mmol, 66%) was obtained as a beige foam from Intermediate 26.3 (40 mg, 0.095 mmol) and [1-(tetrahydro-pyran-2-yloxy)-cyclo-prpyl]-methanol (24.4 mg, 0.142 mmol), analogously to Example 157. HPLC: $^{J}t_{Ret}$=4.795; LC-MS: m/z 493.4 [M+H]$^{+}$.

Example 168

1-(4-Chloro-phenyl)-2-(4-dimethylamino-phenyl)-6-methoxy-7-(3-methoxy-propoxy)-1,4-dihydro-2H-isoquinolin-3-one

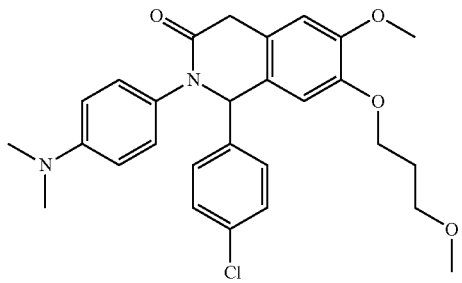

The title compound (15 mg, 0.031 mmol, 32%) was obtained as a beige foam from Intermediate 26.3 (40 mg, 0.095 mmol) and 1-bromo-3-methoxypropane (15.9 mg, 0.104 mmol), analogously to Example 154. HPLC: $^{J}t_{Ret}$=5.417; LC-MS: m/z 495.4 [M+H]$^{+}$.

Example 169

(S)-1-(4-Chloro-phenyl)-7-isopropoxy-6-methoxy-2-{4-[1-(2-oxo-piperazin-1-yl)-ethyl]-phenyl}-1,4-dihydro-2H-isoquinolin-3-one

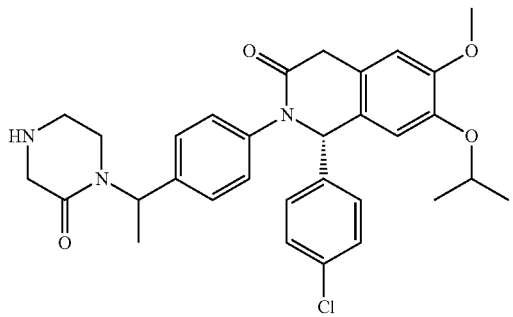 [SMILES: COc1cc2c(cc1OC(C)C)[C@H](c1ccc(Cl)cc1)N(c1ccc(C(C)N3CCNCC3=O)cc1)C(=O)C2]

The title compound (10 mg, 0.018 mmol, 34%) was obtained as a colorless solid from Intermediate 169.1 (50 mg, 0.0.054 mmol) analogously to Example 77.3. HPLC: $^{F}t_{Ret}$=0.928; LC-MS: m/z 550.0 [M+H]$^{+}$.

Intermediate 169.1: 4-(1-{4-[(S)-1-(4-Chloro-phenyl)-7-isopropoxy-6-methoxy-3-oxo-3,4-dihydro-1H-isoquinolin-2-yl]-phenyl}-ethyl)-3-oxo-piperazine-1-carboxylic acid tert-butyl ester

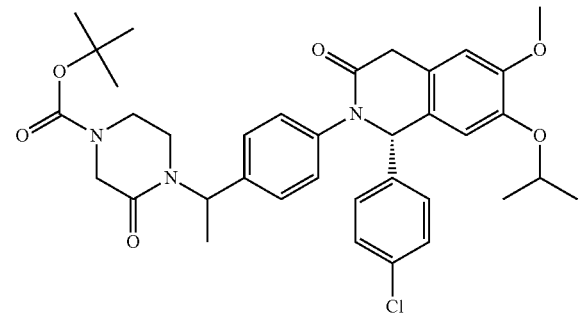 [SMILES: COc1cc2c(cc1OC(C)C)[C@H](c1ccc(Cl)cc1)N(c1ccc(C(C)N3CCN(C(=O)OC(C)(C)C)CC3=O)cc1)C(=O)C2]

The title intermediate (50 mg, 0.054 mmol, 31%) was obtained as a brown solid from Intermediate 169.2 (90 mg, 0.209 mmol) and Intermediate 75.6 (60 mg, 0.174 mmol) analogously to Example 75. HPLC: $^{F}t_{Ret}$=1.352.

Intermediate 169.2: 4-[1-(4-Iodo-phenyl)-ethyl]-3-oxo-piperazine-1-carboxylic acid tert-butyl ester

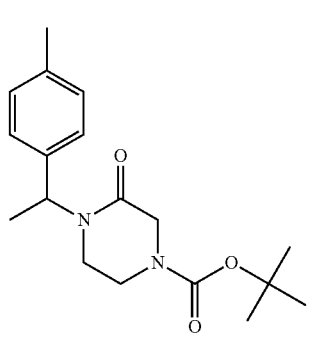 [SMILES: Cc1ccc(C(C)N2CCN(C(=O)OC(C)(C)C)CC2=O)cc1]

To a solution of Boc-3-oxopiperazine (67 mg, 0.328 mmol) in DMF (3 mL) was added NaH (60% in mineral oil, 13 mg, 0.328 mmol). After cooling to 0° C., 1-(1-Bromo-ethyl)-4-iodo-benzene (100 mg, 0.273 mmol) was added. The ice bath was removed and the mixture stirred at RT for 2 h and then partitioned between EtOAc and a solution of NH$_4$Cl. After separation, the aqueous phase was re-extracted twice with DCM and the combined organic extracts were washed with H$_2$O, saturated brine, dried over Na$_2$SO$_4$, filtered and evaporated to dryness. The resulting crude material was purified by Combi-Flash Companion™ (Isco Inc.) column chromatography (SiO$_2$; gradient elution, DCM/EtOAc] 1:0→0:1)) to yield the title intermediate (90 mg, 0.188 mmol, 68%) as a colorless solid. HPLC: $^{F}t_{Ret}$=1.276.

Example 170

1-(4-Chloro-phenyl)-2-(4-dimethylamino-phenyl)-6-methoxy-7-(oxetan-2-ylmethoxy)-1,4-dihydro-2H-isoquinolin-3-one

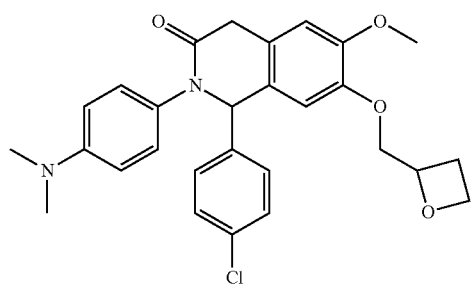 [SMILES: COc1cc2c(cc1OCC1CCO1)C(c1ccc(Cl)cc1)N(c1ccc(N(C)C)cc1)C(=O)C2]

The title compound (10 mg, 0.02 mmol, 28%) was obtained as a beige foam from Intermediate 26.3 (30 mg, 0.071 mmol) and oxetan-2-yl-methanol (7.5 mg, 0.085 mmol), analogously to Example 157. HPLC: $^{J}t_{Ret}$=4.968; LC-MS: m/z 493.4 [M+H]$^{+}$.

Example 171

1-(4-Chloro-phenyl)-7-(2,2-difluoro-ethoxy)-2-(4-dimethylamino-phenyl)-6-methoxy-1,4-dihydro-2H-isoquinolin-3-one

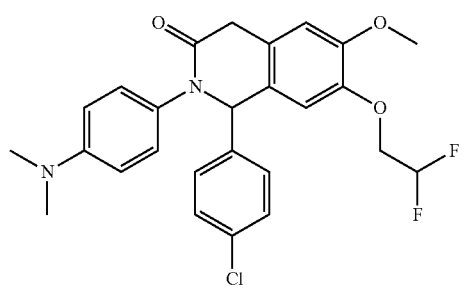 [SMILES: COc1cc2c(cc1OCC(F)F)C(c1ccc(Cl)cc1)N(c1ccc(N(C)C)cc1)C(=O)C2]

To the solution of Intermediate 26.3 (30 mg, 0.071 mmol) and DMF (1.0 mL) was added 1,1-difluoro-2-iodo-ethane (20.4 mg, 0.106 mmol) and potassium carbonate (29.4 mg, 0.213 mmol). The mixture was stirred for 18 h at 50° C. The reaction mixture was extracted between EtOAc (2×) and water-brine 9:1 (1×). The organic phases were washed with brine and dried over Na$_2$SO$_4$, filtered and evaporated to dryness. The residue was subjected to purification by reverse phase prep-HPLC (Waters system gave the title compound as a beige foam (12 mg, 0.024 mmol, 34%). HPLC: $^{J}t_{Ret}$=5.59; LC-MS: m/z 487.4 [M+H]$^{+}$.

Example 172

{4-[({5-[1-(4-Chloro-phenyl)-7-isopropoxy-6-methoxy-3-oxo-3,4-dihydro-1H-isoquinolin-2-yl]-pyrazin-2-yl}-methyl-amino)-methyl]-trans-cyclohexylamino}-acetic acid methyl ester

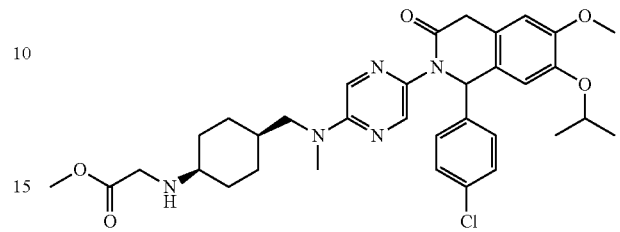

The title compound (73 mg, 0.101 mmol, 31%) was obtained as a orange foam from Intermediate 138.1 (115 mg, 0.329 mmol) and Intermediate 139.1 (142 mg, 0.362 mmol), analogously to Example 130. HPLC: $^{D}t_{Ret}$=1.00 min; LC-MS: m/z 636.5 [M+H]$^{+}$.

Example 173

2-{4-[({5-[1-(4-Chloro-phenyl)-7-isopropoxy-6-methoxy-3-oxo-3,4-dihydro-1H-isoquinolin-2-yl]-pyrazin-2-yl}-methyl-amino)-methyl]-trans-cyclohexylamino}-N-methyl-acetamide

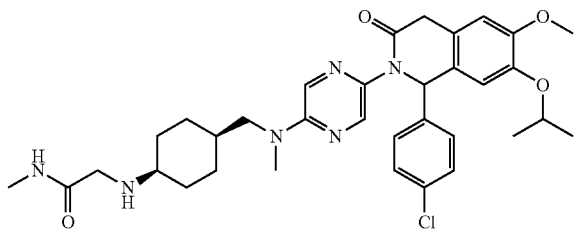 [SMILES: CNC(=O)CN[C@H]1CC[C@@H](CN(C)c2cnc(N3C(=O)Cc4cc(OC)c(OC(C)C)cc4C3c3ccc(Cl)cc3)cn2)CC1]

The title compound (37 mg, 0.058 mmol, 59%) was obtained as a yellow foam from Example 172 (70 mg, 0.097 mmol), analogously to Example 132.2. HPLC: $^{D}t_{Ret}$=0.97 min; LC-MS: m/z 635.6 [M+H]$^{+}$.

Example 174

1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one

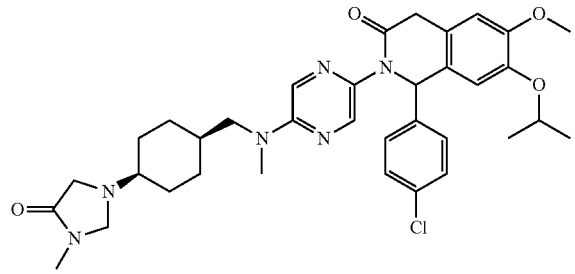 [SMILES: COc1cc2c(cc1OC(C)C)C(c1ccc(Cl)cc1)N(c1cnc(N(C)C[C@H]3CC[C@@H](N4CC(=O)N(C)C4)CC3)cn1)C(=O)C2]

The title compound (29 mg, 0.044 mmol, 79%) was obtained as a yellow foam from Example 173 (36 mg, 0.056 mmol), analogously to Example 132.1. HPLC: $^{D}t_{Ret}$=0.97 min; LC-MS: m/z 635.6 [M+H]$^{+}$.

Example 175

1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one

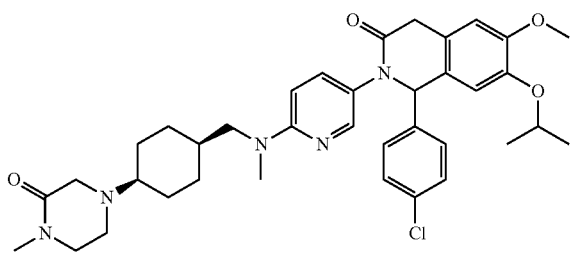 [SMILES: COc1cc2c(cc1OC(C)C)C(c1ccc(Cl)cc1)N(c1ccc(N(C)C[C@H]3CC[C@@H](N4CCN(C)C(=O)C4)CC3)nc1)C(=O)C2]

The title compound (29 mg, 0.044 mmol, 79%) was obtained as a yellow foam from Intermediate 138.1 (35 mg, 0.100 mmol) and Intermediate 130.1 (50 mg, 0.100 mmol), analogously to Example 130. HPLC: $^{D}t_{Ret}$=0.97 min; LC-MS: m/z 660.7 [M+H]J.

Intermediate 176.1: ([2-(tert-Butoxycarbonyl-methyl-amino)-ethyl]-{4-[({4-[(S)-1-(4-chloro-phenyl)-7-isopropoxy-6-methoxy-3-oxo-3,4-dihydro-1H-isoquinolin-2-yl]-2-fluoro-phenyl}-methyl-amino)-methyl]-trans-cyclohexyl}-amino)-acetic acid methyl ester

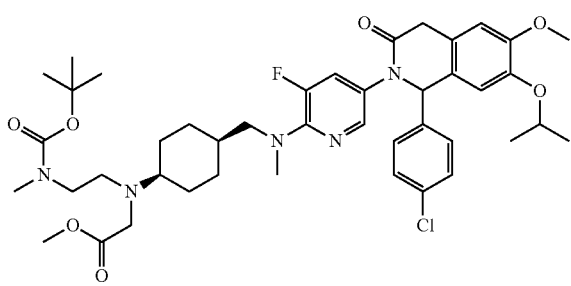 [SMILES: COC(=O)CN(CCN(C)C(=O)OC(C)(C)C)[C@H]1CC[C@@H](CN(C)c2ncc(N3C(=O)Cc4cc(OC)c(OC(C)C)cc4C3c3ccc(Cl)cc3)cc2F)CC1]

The title intermediate (48 mg, 0.059 mmol, 63%) was obtained as a white solid from Intermediate 176.2 (68 mg, 0.094 mmol) and Methyl-(2-oxo-ethyl)-carbamic acid tert-butyl ester (21.1 mg, 0.12 mmol) analogously to Intermediate 79.2. HPLC: $^{G}t_{Ret}$=7.877 min; LC-MS: m/z 809.8 [M+H]$^+$.

Intermediate 176.2: {4-[({4-[(S)-1-(4-Chloro-phenyl)-7-isopropoxy-6-methoxy-3-oxo-3,4-dihydro-1H-isoquinolin-2-yl]-2-fluoro-phenyl}-methyl-amino)-methyl]-trans-cyclohexylamino}-acetic acid methyl ester

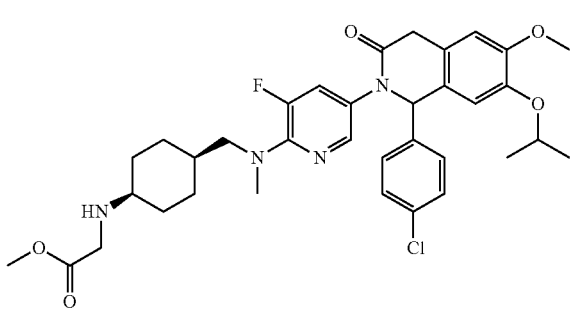 [SMILES: COC(=O)CN[C@H]1CC[C@@H](CN(C)c2ncc(N3C(=O)Cc4cc(OC)c(OC(C)C)cc4C3c3ccc(Cl)cc3)cc2F)CC1]

The title intermediate (361 mg, 0.52 mmol, 38.3%) was obtained as a white solid from Intermediate 75.6 (470 mg, 1.36 mmol) and Intermediate 176.3 (721 mg, 1.49 mmol) analogously to Example 75. HPLC: $^{G}t_{Ret}$=6.786 min; LC-MS: m/z 652.5 [M+H]$^+$.

Intermediate 176.3: (4-{[(2-Fluoro-4-iodo-phenyl)-methyl-amino]-methyl}-trans-cyclohexyl-amino)-acetic acid methyl ester

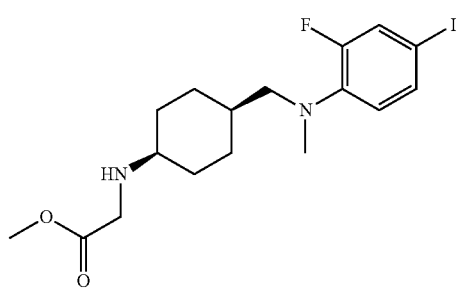 [SMILES: COC(=O)CN[C@H]1CC[C@@H](CN(C)c2ccc(I)cc2F)CC1]

The title intermediate (3.06 g, 6.34 mmol, 70.9%) was obtained as a white solid from Intermediate 176.4 (3.6 g, 8.94 mmol) and methyl-2-bromoacetate (0.95 mL, 10.3 mmol) analogously to Intermediate 79.1. HPLC: $^{G}t_{Ret}$=6.556 min; LC-MS: m/z 435.3 [M+H]$^+$.

Intermediate 176.4: (Trans-4-amino-cyclohexylmethyl)-(2-fluoro-4-iodo-phenyl)-methyl-amine

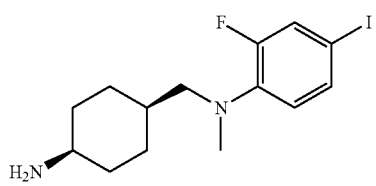 [SMILES: CN(C[C@H]1CC[C@@H](N)CC1)c1ccc(I)cc1F]

The title intermediate (3.62 g, 8.99 mmol, 94%) was obtained as a white solid from Intermediate 176.5 (4.9 g, 9.54 mmol) analogously to Intermediate 77.3. HPLC: $^{G}t_{Ret}$=5.992 min; LC-MS: m/z 362.8 [M+H]$^+$.

Intermediate 176.5: (4-{[(2-Fluoro-4-iodo-phenyl)-methyl-amino]-methyl}-trans-cyclohexyl)-carbamic acid tert-butyl ester

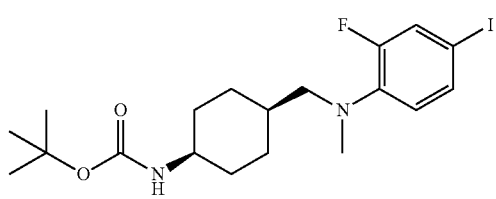 [SMILES: CN(C[C@H]1CC[C@@H](NC(=O)OC(C)(C)C)CC1)c1ccc(I)cc1F]

The title intermediate (4.9 g, 9.54 mmol, 91%) was obtained as a white solid from Intermediate 176.6 (4.7 g, 10.4 mmol) and 37% water solution of formaldehyde (1.56 mL, 20.9 mmol) analogously to Intermediate 77.1. HPLC: $^{G}t_{Ret}$=8.720 min; LC-MS: m/z 463.3 [M+H]$^+$.

Intermediate 176.6: {4-[(2-Fluoro-4-iodo-phenylamino)-methyl]-trans-cyclohexyl}-carbamic acid tert-butyl ester

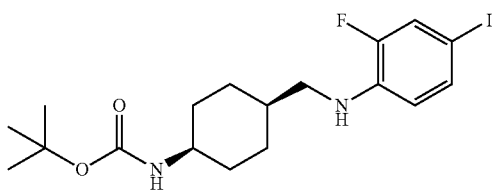 [SMILES: CC(C)(C)OC(=O)N[C@H]1CC[C@@H](CNc2ccc(I)cc2F)CC1]

The title intermediate (4.8 g, 10.7 mmol, 97%) was obtained as a white solid from trans-(4-formyl-cyclohexyl)-carbamic acid tert-butyl ester (3.0 g, 13.2 mmol) and 2-fluoro-4-iodoaniline (2.66 g, 11 mmol) analogously to Intermediate 75.7. HPLC: $^{G}t_{Ret}$=8.586 min; LC-MS: m/z 393.2 [M-BOC+HCOOH]$^+$.

Intermediate 177.1: ([2-(tert-Butoxycarbonyl-methyl-amino)-ethyl]-{4-[({4-[(S)-1-(4-chloro-phenyl)-7-isopropoxy-6-methoxy-3-oxo-3,4-dihydro-1H-isoquinolin-2-yl]-3-fluoro-phenyl}-methyl-amino)-methyl]-trans-cyclohexyl}-amino)-acetic acid methyl ester

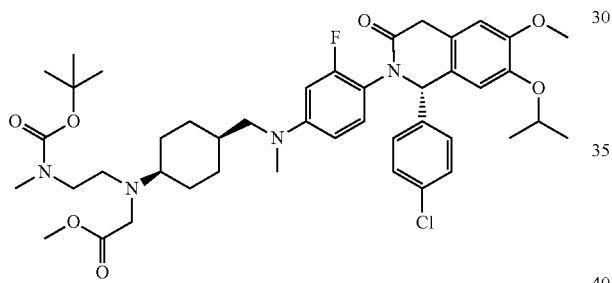

The title intermediate (48 mg, 0.059 mmol, 63.2%) was obtained as a white solid from Intermediate 177.2 (68 mg, 0.094 mmol) and Methyl-(2-oxo-ethyl)-carbamic acid tert-butyl ester (21.1 mg, 0.12 mmol) analogously to Intermediate 79.2. HPLC: $^{G}t_{Ret}$=7.854 min; LC-MS: m/z 809.8 [M+H]$^+$.

Intermediate 177.2: {4-[({4-[(S)-1-(4-Chloro-phenyl)-7-isopropoxy-6-methoxy-3-oxo-3,4-dihydro-1H-isoquinolin-2-yl]-3-fluoro-phenyl}-methyl-amino)-methyl]-trans-cyclohexyl-amino}-acetic acid methyl ester

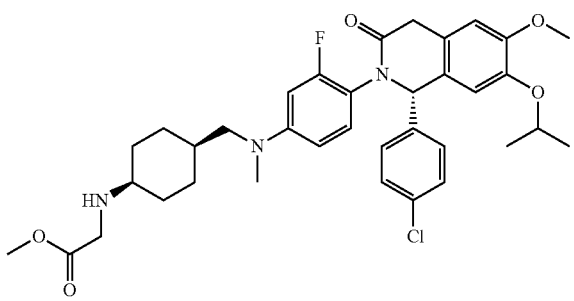 [SMILES: COC(=O)CN[C@H]1CC[C@@H](CN(C)c2ccc(N3C(=O)Cc4cc(OC)c(OC(C)C)cc4[C@@H]3c3ccc(Cl)cc3)c(F)c2)CC1]

The title intermediate (70 mg, 0.097 mmol, 11.3%) was obtained as a white solid from Intermediate 75.6 (295 mg, 0.85 mmol) and Intermediate 177.3 (364 mg, 0.94 mmol) analogously to Example 75. HPLC: $^{G}t_{Ret}$=6.997 min; LC-MS: m/z 652.7 [M+H]$^+$.

Intermediate 177.3: (4-{[(4-Bromo-3-fluoro-phenyl)-methyl-amino]-methyl}-trans-cyclohexyl-amino)-acetic acid methyl ester

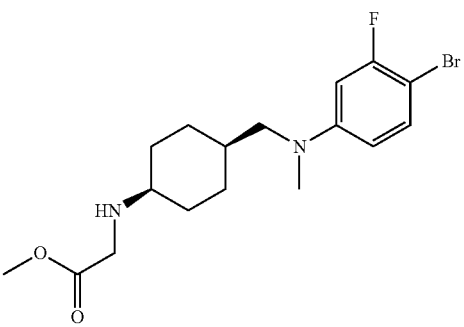 [SMILES: COC(=O)CN[C@H]1CC[C@@H](CN(C)c2ccc(Br)c(F)c2)CC1]

The title intermediate (360 mg, 0.93 mmol, 21.6%) was obtained as a white solid from Intermediate 177.4 (1.36 g, 4.31 mmol) and methyl-2-bromoacetate (0.42 mL, 4.53 mmol) analogously to Intermediate 79.1. HPLC: $^{G}t_{Ret}$=6.333 min; LC-MS: m/z 387.3 [M+H]$^+$.

Intermediate 177.4: (Trans-4-amino-cyclohexylmethyl)-(4-bromo-3-fluoro-phenyl)-methyl-amine

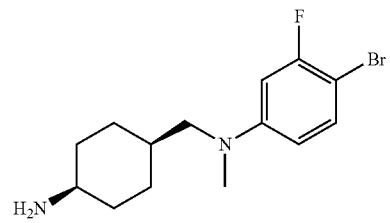 [SMILES: CN(C[C@H]1CC[C@@H](N)CC1)c1ccc(Br)c(F)c1]

The title intermediate (1.36 g, 4.31 mmol, 74.7%) was obtained as a white solid from Intermediate 177.5 (2.4 g, 5.78 mmol) analogously to Intermediate 77.3. HPLC: $^{G}t_{Ret}$=6.245 min; LC-MS: m/z 317.2 [M+H]$^+$.

Intermediate 177.5: (4-{[(4-Bromo-3-fluoro-phenyl)-methyl-amino]-methyl}-trans-cyclohexyl)-carbamic acid tert-butyl ester

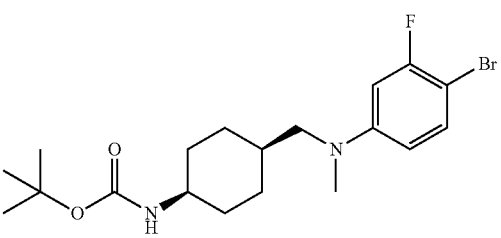

The title intermediate (2.42 g, 5.83 mmol, 75%) was obtained as a white solid from Intermediate 177.6 (3.1 g, 7.72 mmol) and 37% water solution of formaldehyde (1.15 mL, 15.4 mmol) analogously to Intermediate 77.1. HPLC: $^G t_{Ret}$=8.689 min; LC-MS: m/z 417.3 [M+H]⁺.

Intermediate 177.6: {4-[(4-Bromo-3-fluoro-phenylamino)-methyl]-trans-cyclohexyl}-carbamic acid tert-butyl ester

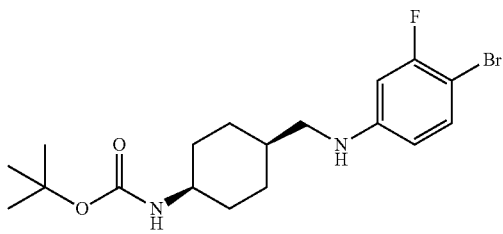

The title intermediate (3.1 g, 7.7 mmol, 77%) was obtained as a white solid from trans-(4-formyl-cyclohexyl)-carbamic acid tert-butyl ester (2.73 g, 12.0 mmol) and 4-bromo-3-fluoro-aniline (1.90 g, 10.0 mmol) analogously to Intermediate 75.7. HPLC: $^G t_{Ret}$=8.221 min; LC-MS: m/z 401.3 [M+H]⁺.

Example 178

(S)-1-(4-Chloro-phenyl)-7-isopropoxy-6-methoxy-2-{4-[(S)-1-(2-oxo-piperazin-1-yl)-ethyl]-phenyl}-1,4-dihydro-2H-isoquinolin-3-one

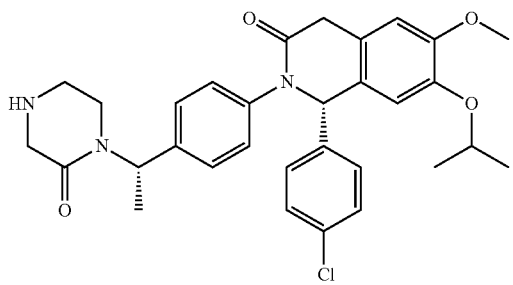 [SMILES: COc1cc2c(cc1OC(C)C)[C@H](c1ccc(Cl)cc1)N(c1ccc([C@H](C)N3CCNCC3=O)cc1)C(=O)C2]

The title compound (665 mg, 1.19 mmol, 85%) was obtained as a yellow solid from Intermediate 178.1 (910 mg, 1.40 mmol) analogously to Example 51. HPLC: $^E t_{Ret}$=4.449 min; LC-MS: m/z 549.2 [M+H]⁺.

Intermediate 178.1: 4-((S)-1-{4-[(S)-1-(4-Chloro-phenyl)-7-isopropoxy-6-methoxy-3-oxo-3,4-dihydro-1H-isoquinolin-2-yl]-phenyl}-ethyl)-3-oxo-piperazine-1-carboxylic acid tert-butyl ester

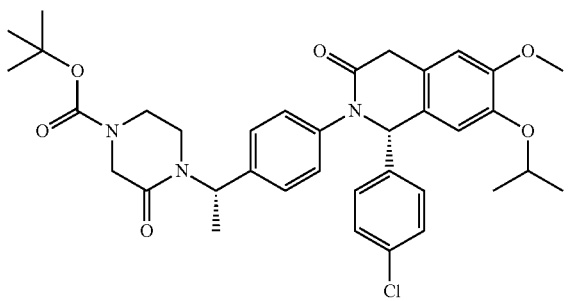 [SMILES: COc1cc2c(cc1OC(C)C)[C@H](c1ccc(Cl)cc1)N(c1ccc([C@H](C)N3CCN(C(=O)OC(C)(C)C)CC3=O)cc1)C(=O)C2]

The title intermediate (910 mg, 1.4 mmol, 26%) was obtained as a yellow solid from Intermediate 75.6 (1.87 g, 5.41 mmol) and Intermediate 178.2 (2.39 g, 5.57 mmol) analogously to Example 75. HPLC: $^E t_{Ret}$=5.677 min; LC-MS: m/z 648.2 [M+H]⁺.

Intermediate 178.2: 4-[(S)-1-(4-Iodo-phenyl)-ethyl]-3-oxo-piperazine-1-carboxylic acid tert-butyl ester

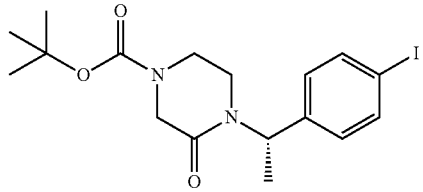 [SMILES: C[C@@H](c1ccc(I)cc1)N1CCN(C(=O)OC(C)(C)C)CC1=O]

To a solution of Intermediate 178.3 (3.58 g, 7.67 mmol) in THF (27.1 mL) was added 60% NaH (0.32 g, 8.05 mmol) at 0° C. under an argon atmosphere. The reaction mixture was stirred for 2 h at RT. The reaction mixture was quenched with water at 0° C. and extracted with EtOAc. The organic phase was washed with a saturated aqueous solution of NaHCO₃, dried (Na₂SO₄), filtered and concentrated. The residue was purified by column chromatography to afford the title compound (3.29 g, 7.49 mmol, 98%) as a beige solid. HPLC: $^E t_{Ret}$=5.516 min; LC-MS: m/z 431.1 [M+H]⁺.

Intermediate 178.3: (2-{(2-Chloro-acetyl)-[(S)-1-(4-iodo-phenyl)-ethyl]-amino}-ethyl)-carbamic acid tert-butyl ester

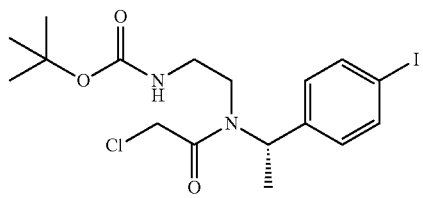 [SMILES: C[C@@H](c1ccc(I)cc1)N(CCNC(=O)OC(C)(C)C)C(=O)CCl]

To a solution of Intermediate 178.4 (4.0 g, 10.25 mmol), Et₃N (4.26 mL, 30.7 mmol) and DMAP (25 mg, 0.20 mmol) in DCM (27.1 mL) was added drop wise chloroacetyl chloride (0.86 mL, 10.7 mmol) at 0° C. under an argon atmosphere. The reaction mixture was stirred for 5 h at RT. The reaction mixture was quenched with water at 0° C. and extracted with EtOAc. The organic phase was washed with a saturated aqueous solution of NaHCO₃, dried (Na₂SO₄), filtered and concentrated. The residue was purified by column chromatography to afford the title compound (3.59 g, 7.69 mmol, 75%) as a white solid. HPLC: $^E t_{Ret}$=5.461 min; LC-MS: m/z 466.8 [M+H]⁺.

Intermediate 178.4: {2-[(S)-1-(4-Iodo-phenyl)-ethylamino]-ethyl}-carbamic acid tert-butyl ester

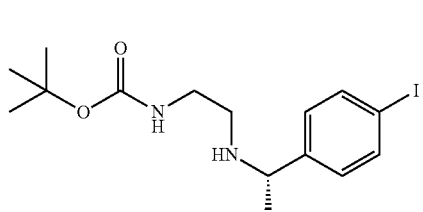

A suspension of Intermediate 178.5 (5.45 g, 22.0 mmol), (2-Bromo-ethyl)-carbamic acid tert-butyl ester (6.43 g, 28.7 mmol), K₂CO₃ (6.1 g, 44.1 mmol) and KI (0.18 g, 1.1 mmol) in tert-BuOH (25 mL) was heated at 60° C. under an argon atmosphere during two overnight. The reaction mixture was allowed to cool down and diluted with iso-PrOH. The mixture was filtered and the filter cake washed with iso-PrOH. The filtrate was evaporated and partitioned between EtOAc and saturated NaHCO$_3$ aqueous solution. The aqueous layer was extracted twice with EtOAc. The combined organic layers were washed with brine, dried over MgSO$_4$, filtered and evaporated to give a brown solid, which was purified by column chromatography to afford the title compound (4.0 g, 10.25 mmol, 46.5%) as an white solid. HPLC: $^E t_{Ret}$=4.489 min; LC-MS: m/z 390.93 [M+H]$^+$.

Intermediate 178.5:
(S)-1-(4-Iodo-phenyl)-ethylamine

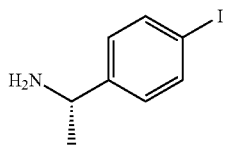

Intermediate 178.5 (13.7 g, 55.4 mmol, 76%) was synthesized from (S)-1-phenyl-ethylamine by following the reported methods in Journal of Medicinal Chemistry, 2001, 44, pp 21. HPLC: $^E t_{Ret}$=3.639 min; LC-MS: m/z 247.8 [M+H]$^+$.

Example 179

(S)-1-(4-Chloro-phenyl)-2-(4-{(S)-1-[4-(2-hydroxy-ethyl)-2-oxo-piperazin-1-yl]-ethyl}-phenyl)-7-iso-propoxy-6-methoxy-1,4-dihydro-2H-isoquinolin-3-one

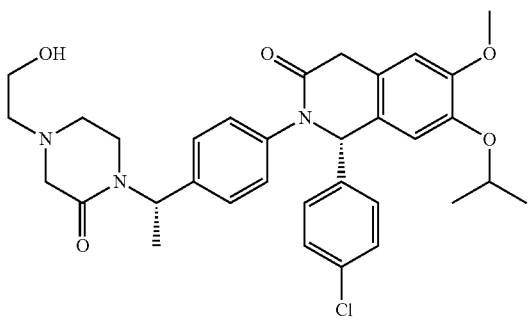 [SMILES: COc1cc2c(cc1OC(C)C)[C@H](c1ccc(Cl)cc1)N(c1ccc([C@H](C)N3CCN(CCO)CC3=O)cc1)C(=O)C2]

To a solution of Example 178 (30 mg, 0.055 mmol) in EtOH (0.8 mL) was successively added Et$_3$N (18.97 µl, 0.137 mmol) and 2-bromoethanol (5.41 µl, 0.077 mmol). The mixture was irradiated to 105° C. for 12 h. After cooling, the mixture was evaporated to dryness. The residue was directly purified by Combi-Flash Companion™ (Isco Inc.) column chromatography (SiO$_2$; gradient elution, DCM/[DCM/EtOH/NH$_3$ aq 90: 9:1] 1:0→0:1)) to yield the title compound (17 mg, 0.029 mmol, 53%) as a pale yellow foam. HPLC: $^F t_{Ret}$=0.936; LC-MS: m/z 592.5 [M+H]$^+$.

Example 180

(S)-1-(4-Chloro-phenyl)-7-isopropoxy-6-methoxy-2-{4-[(R)-1-(2-oxo-piperazin-1-yl)-ethyl]-phenyl}-1,4-dihydro-2H-isoquinolin-3-one

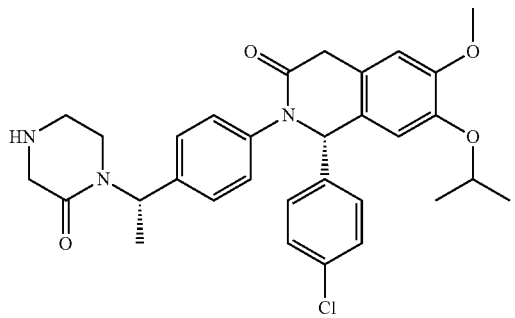 [SMILES: COc1cc2c(cc1OC(C)C)[C@H](c1ccc(Cl)cc1)N(c1ccc([C@H](C)N3CCNCC3=O)cc1)C(=O)C2]

The title compound (75 mg, 0.138 mmol, 64%) was obtained as a pale yellow foam analogously to Example 178, starting from R-(+)-1-(4-bromophenyl)ethylamine. HPLC: $^F t_{Ret}$=0.922; LC-MS: m/z 548.5 [M+H]$^+$.

Example 181

(S)-1-(4-Chloro-phenyl)-2-(4-{(R)-1-[4-(2-hydroxy-ethyl)-2-oxo-piperazin-1-yl]-ethyl}-phenyl)-7-iso-propoxy-6-methoxy-1,4-dihydro-2H-isoquinolin-3-one

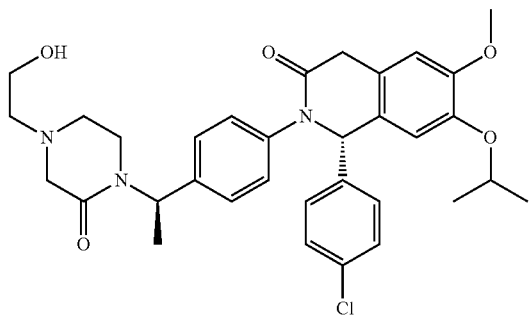 [SMILES: COc1cc2c(cc1OC(C)C)[C@H](c1ccc(Cl)cc1)N(c1ccc([C@@H](C)N3CCN(CCO)CC3=O)cc1)C(=O)C2]

The title compound (25.5 mg, 0.043 mmol, 52.5%) was obtained from Example 180 as a yellow solid analogously to Example 179. HPLC: $^F t_{Ret}$=0.932; LC-MS: m/z 592.5 [M+H]$^+$.

Example 183

(S)-1-(4-Chloro-phenyl)-2-{4-[(3-hydroxy-3-hydroxymethyl-cyclobutyl-methyl)-methyl-amino]-phenyl}-7-isopropoxy-6-methoxy-1,4-dihydro-2H-isoquinolin-3-one

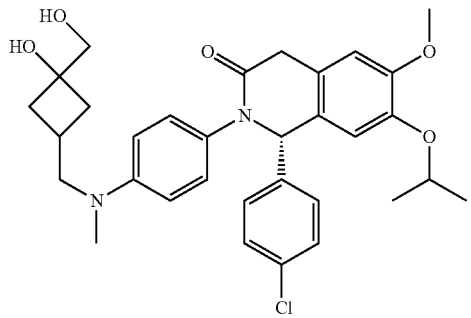 [SMILES: COc1cc2c(cc1OC(C)C)[C@H](c1ccc(Cl)cc1)N(c1ccc(N(C)CC3CC(O)(CO)C3)cc1)C(=O)C2]

The title compound (39 mg, 0.07 mmol, 16%) was obtained as a pale yellow foam from Intermediate 183.1 (200 mg, 0.434 mmol) and Intermediate 75.6 (150 mg, 0.434 mmol) analogously to Example 75. HPLC: $^F t_{Ret}$=1.098; LC-MS: m/z 565.5 [M+H]$^+$.

Intermediate 183.1: 3-{[(4-Bromo-phenyl)-methyl-amino]-methyl}-1-hydroxymethyl-cyclobutanol

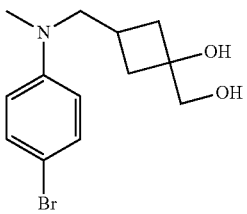 [SMILES: CN(CC1CC(O)(CO)C1)c1ccc(Br)cc1]

To a solution of Intermediate 183.2 (561 mg, 1.785 mmol) in THF (15 mL) was added drop wise at RT borane-methyl sulfide complex (0.802 ml, 8.03 mmol). The mixture was then heated at 45° C. for 5 h. After cooling to RT, the suspension was diluted with THF and quenched at 0° C. with MeOH. The solvent were removed by evaporation and the residue was diluted with EtOH (5 mL) and 1M NaOH (10 mL) and heated to reflux for 2 h. After cooling to RT and filtration, the filtrate was concentrated and the residue partitioned between H$_2$O and EtOAC. After separation, the aqueous phase was re-extracted twice with EtOAc. The combined organic extracts were washed with saturated brine, dried over Na$_2$SO$_4$, filtered and evaporated to dryness. The resulting crude material was purified by Combi-Flash Companion™ (Isco Inc.) column chromatography (SiO$_2$; gradient elution, DCM/[DCM/EtOH/NH$_3$ aq 90:9:1] 1:0→0:1)) to yield the title intermediate (467 mg, 1.558 mmol, 87%) as a cis/trans mixture of pale beige crystalline solid, HPLC: $^F t_{Ret}$=0.854/0.871; LC-MS: m/z 300.2 [M+H]$^+$ Intermediate 183.2:
3-Hydroxy-3-hydroxymethyl-cyclobutanecarboxylic acid (4-bromo-phenyl)-methyl-amide

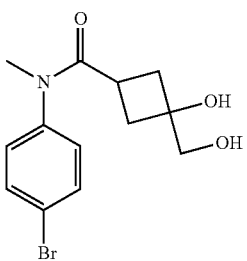 [SMILES: CN(C(=O)C1CC(O)(CO)C1)c1ccc(Br)cc1]

To a suspension of AD-Mix-Alpha (2.748 g, 1.963 mmol) in a mixture of tBuOH (10 mL) and H$_2$O (10 mL) was added at 5° C. Intermediate 183.3 (500 mg, 1.785 mmol) as a concentrated tBuOH solution. The cooling bath was removed and the mixture stirred at RT for 1 h then filtered. The filtrate was concentrated under vacuum and the remaining aqueous phase extracted four times with DCM. The combined organic extracts were washed with saturated brine, dried over Na$_2$SO$_4$, filtered and evaporated to dryness to yield the title intermediate as an oil (586 mg, 1.865 mmol). HPLC: $^F t_{Ret}$=0.797; LC-MS: m/z 314.2 [M+H]$^+$.

Intermediate 183.3:
3-Methylene-cyclobutanecarboxylic acid (4-bromo-phenyl)-methyl-amide

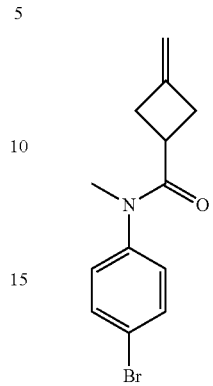

To a solution of Intermediate 183.4 (1.748 g, 15.59 mmol) in DCM (30 mL) was successively added at 0° C., three drops of DMF and oxalyl chloride (1.433 ml, 16.37 mmol). The ice bath was removed and the mixture stirred for 2 h at RT. Volatiles were evaporated, the pale yellow oil dried under vacuum and then dissolved in DCM. To this solution was added at 0° C., a solution of 4-bromo-N-methylaniline (2.90 g, 15.59 mmol), Et$_3$N (6.48 mL, 46.8 mmol) and DMAP (1.904 g, 15.59 mmol) in DCM (30 mL). After addition, the ice bath was removed and the mixture stirred at RT for 1 h. The reaction mixture was then quenched with H$_2$O and NaHCO$_3$, and partitioned between DCM and H$_2$O. After separation, the aqueous phase was re-extracted twice with DCM and the combined organic extracts were washed with saturated brine, dried over Na$_2$SO$_4$, filtered and evaporated to dryness. The resulting crude material was purified by Combi-Flash Companion™ (Isco Inc.) column chromatography (SiO$_2$; gradient elution, DCM/[DCM/EtOH 9:1] 1:0→1:1)) to yield the title intermediate (3.36 g, 12.02 mmol, 77%) as a pale yellow oil. HPLC: $^F t_{Ret}$=1.232; LC-MS: m/z 280.2 [M+H]$^+$.

Intermediate 183.4:
3-Methylene-cyclobutanecarboxylic acid

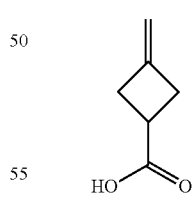

3-methylenecyclobutanecarbonitrile (5 g, 53.7 mmol) was added to a solution of NaOH (15.33 g, 383 mmol) in H$_2$O (51 mL). The biphasic mixture was heated to reflux for 3 h. After cooling to RT, the mixture was acidified by addition of 32% HCl and saturated with NaCl. The aqueous phase was extracted six time with DCM. The combined organic extracts were washed with saturated brine, dried over Na$_2$SO$_4$, filtered and evaporated to dryness to yield the title intermediate (6.01 g, 53.6 mmol, 100%) as an oil. HPLC: $^F t_{Ret}$=0.673; LC-MS: m/z 111.1 [M−H].

Intermediate 184.1: 2-{4-[(S)-1-(4-Chloro-phenyl)-7-isopropoxy-6-methoxy-3-oxo-3,4-dihydro-1H-isoquinolin-2-yl]-phenyl}-5-methyl-3-oxo-hexanenitrile

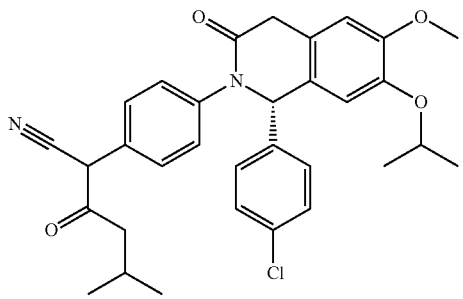 [SMILES: COc1cc2c(cc1OC(C)C)[C@H](c1ccc(Cl)cc1)N(c1ccc(C(C#N)C(=O)CC(C)C)cc1)C(=O)C2]

To a mixture of Intermediate 164.2 (102 mg, 0.22 mmol) and isovaleryl chloride (0.12 mL, 0.98 mmol) in DMF (2.0 mL) was added 60% of NaH in mineral oil (11 mg, 0.275 mmol) at 0° C. (ice bath). The resulting mixture was stirred at RT for 1 h, AcOH was carefully added to quench the reaction and the mixture was extracted with AcOEt (2×). The combined organic fractions were dried over $Na_2SO_4$, filtered and evaporated to dryness. The resulting crude material was purified by column chromatography to yield the title intermediate (120 mg, 0.22 mmol, 100%). HPLC: $^G t_{Ret}$=8.00 min; LC-MS: m/z 545.43 $[M+H]^+$.

Intermediate 185.1: 4-{5-[1-(4-Chloro-phenyl)-7-isopropoxy-6-methoxy-3-oxo-3,4-dihydro-1H-isoquinolin-2-yl]-pyridin-2-yl}-3,5-dimethyl-pyrazole-1-carboxylic acid tert-butyl ester

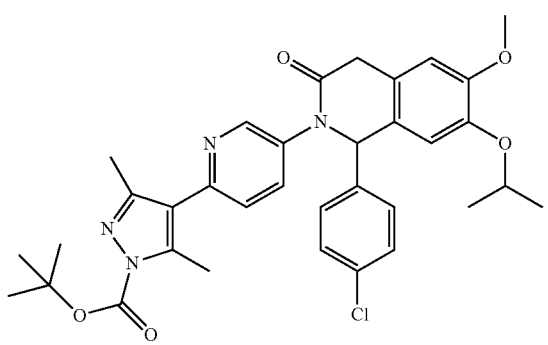 [SMILES: COc1cc2c(cc1OC(C)C)C(c1ccc(Cl)cc1)N(c1ccc(-c3c(C)nn(C(=O)OC(C)(C)C)c3C)nc1)C(=O)C2]

The title intermediate (233 mg, 0.38 mmol, 63%) was obtained as a yellow solid from Intermediate 185.2 (300 mg, 0.60 mmol) and 3,5-Dimethyl-4-(4,4,5,5-tetramethyl-[1,3,2]dioxaborolan-2-yl)-pyrazole-1-carboxylic acid tert-butyl ester (212 mg, 0.66 mmol) analogously to Example 36. LC-MS: m/z 617.0 $[M+H]^+$; $^1$H NMR (400 MHz, DMSO-$d_6$) 1.18-1.30 (m, 6H), 1.58 (s, 9H), 2.24 (s, 3H), 2.73 (s, 3H), 3.71 (s, 1H), 3.74 (s, 3H), 3.92 (s, 1H), 4.40-4.50 (m, 1H), 6.25 (s, 1H), 6.89 (s, 1H), 7.06 (s, 1H), 7.39 (s, 3H), 7.48 (d, J=8.59 Hz, 1H), 7.70 (d, J=11.32 Hz, 1H), 7.95 (s, 1H), 8.51 (d, J=3.51 Hz, 1H).

Intermediate 185.2: 2-(6-Bromo-pyridin-3-yl)-1-(4-chloro-phenyl)-7-isopropoxy-6-methoxy-1,4-dihydro-2H-isoquinolin-3-one

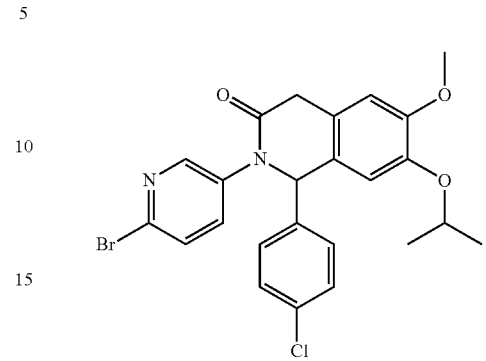

The title intermediate (607 mg, 1.21 mmol, 18.5%) was obtained as a white solid from Intermediate 185.3 (1.93 g, 6.53 mmol) and Intermediate 96.1 (1.95 g, 8.00 mmol) analogously to Example 1. HPLC: $^E t_{Ret}$=5.526 min; LC-MS: m/z 502.7 $[M+H]^+$.

Intermediate 185.3: (6-Bromo-pyridin-3-yl)-[1-(4-chloro-phenyl)-meth-(E)-ylidene]-amine

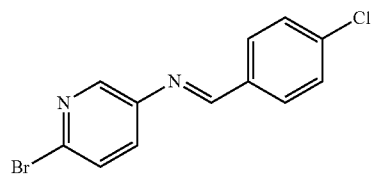 [SMILES: Clc1ccc(/C=N/c2ccc(Br)nc2)cc1]

The title compound (1.93 g, 6.53 mmol, 83%) was obtained as a orange solid from 6-Bromo-pyridin-3-ylamine (1.36 g, 7.89 mmol) and 4-chloro-benzaldehyde (1.38 g, 9.86 mmol) analogously to Intermediate 1.4. $^1$H NMR (400 MHz, DMSO-$d_6$) 7.61 (d, 2H), 7.69 (d, 2H), 7.95 (d, 2H), 8.30-8.35 (m, 1H), 8.71 (s, 1H).

Example 186

1-(4-Chloro-phenyl)-7-isopropoxy-6-methoxy-2-(2-methoxy-4-methyl-phenyl)-1,4-dihydro-2H-isoquinolin-3-one

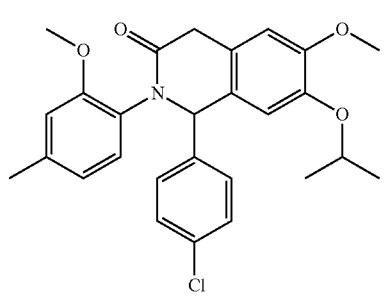 [SMILES: COc1cc2c(cc1OC(C)C)C(c1ccc(Cl)cc1)N(c1ccc(C)cc1OC)C(=O)C2]

A mixture of Intermediate 186.1 (33 mg, 0.078 mmol), 2-iodopropane (0.023 mL, 0.234 mmol) and $Cs_2CO_3$ (50.7 mg, 0.156 mmol) in DMF (0.5 mL) was stirred for 1 h at 50° C. The reaction mixture was allowed to cool to RT, quenched by addition of a saturated aqueous solution of $NaHCO_3$ and extracted with AcOEt. The organic phase was washed with a saturated aqueous solution of NaHCO$_3$, dried (Na$_2$SO$_4$), filtered and concentrated. The residue was purified by column chromatography (SiO$_2$; DCM/MeOH 99:1) to afford 33 mg of the title compound as a white solid. TLC: R$_F$=0.88 (DCM/MeOH 9:1); HPLC: $^L$t$_{Ret}$=5.74 min; LC-MS: m/z 466.4 [M+H]$^+$; $^1$H NMR (400 MHz, DMSO-d$_6$): 1.06-1.25 (m, 6H) 2.25 (s, 3H) 2.41-2.52 (m, 6H) 3.54 (d, 1H) 3.92 (d, 1H) 4.31-4.50 (m, 1H) 5.69 (br, 1H) 6.46-6.97 (m, 5H) 7.29 (br, 4H).

Intermediate 186.1: 1-(4-Chloro-phenyl)-7-hydroxy-6-methoxy-2-(2-methoxy-4-methyl-phenyl)-1,4-dihydro-2H-isoquinolin-3-one

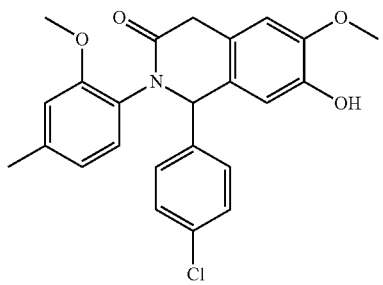

To solution of Intermediate 187.3 (375 mg, 0.818 mmol) in DCM (10 mL) was added a solution of Intermediate 186.2 (276 mg, 1.06 mmol) in DCM (5 mL) at 0° C. and under an argon atmosphere. The reaction mixture was stirred for 1 h at RT and cooled to 0° C. Trifluoromethane sulfonic acid (0.291 mL, 3.27 mmol) was added. The resulting mixture was stirred 1 h at 0° C., quenched by addition of a saturated aqueous solution of NaHCO$_3$ and extracted with DCM. The organic phase was washed with a saturated aqueous solution of NaHCO$_3$, dried (Na$_2$SO$_4$), filtered and concentrated. The residue was purified by column chromatography (SiO$_2$; DCM/MeOH 100:0→98:2) followed by trituration in AcOEt to afford 35 mg of the title compound as a white solid. TLC: R$_F$=0.71 (DCM/MeOH 9:1); HPLC: $^L$t$_{Ret}$=4.77 min; LC-MS: m/z 424.3 [M+H]$^+$.

Intermediate 186.2: [1-(4-Chloro-phenyl)-meth-(E)-ylidene]-(2-methoxy-4-methyl-phenyl)-amine

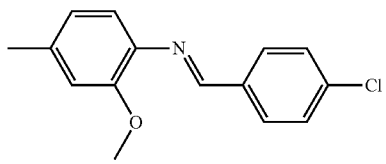 [SMILES: COc1cc(C)ccc1/N=C/c1ccc(Cl)cc1]

A mixture of Intermediate 186.3 (1.57 g, 11.4 mmol), and 4-chlorobenzaldehyde (1.63 g, 11.4 mmol) and acetic acid (0.66 mL, 11.4 mmol) was stirred for 18 h at 85° C., allowed to cool to RT and concentrated to afford 3.25 g of the title compound as an brown oil which was used as a crude material. $^1$H NMR (400 MHz, DMSO-d) 2.32 (s, 3H), 3.78 (s, 3H), 6.77 (d, J=7.82 Hz, 1H), 6.90 (s, 1H), 6.97 (d, J=7.82 Hz, 1H), 7.57 (d, J=8.60 Hz, 2H), 7.91 (d, J=8.60 Hz, 2H), 8.54 (s, 1H).

Intermediate 186.3: 2-Methoxy-4-methyl-phenylamine

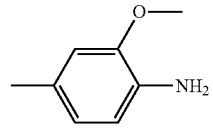

A mixture of 5-methyl-2-nitroanisole (2 g, 12 mmol) and Raney nickel (2.2 g) in MeOH/THF (120 mL, 3:1 v/v) was shaken for 20 h at RT and under 0.1 bar of H$_2$. The reaction mixture was filtered through a pad of celite and the filtrate was concentrated to afford 1.57 g of the title compound as colorless oil. HPLC: $^L$t$_{Ret}$=1.44 min; LC-MS: m/z 138.1 [M+H]$^+$.

Example 187

1-(4-Chloro-phenyl)-7-isopropoxy-6-methoxy-2-[4-methyl-2-(2H-tetrazol-5-ylmethoxy)-phenyl]-1,4-dihydro-2H-isoquinolin-3-one

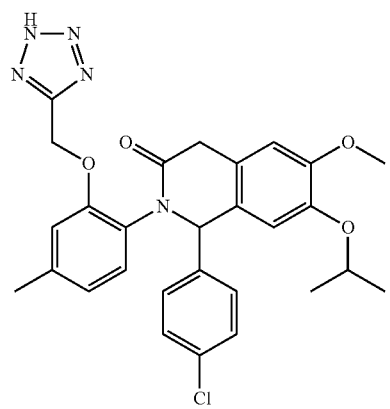 [SMILES: COc1cc2c(cc1OC(C)C)C(c1ccc(Cl)cc1)N(c1ccc(C)cc1OCc1nn[nH]n1)C(=O)C2]

A mixture of Intermediate 187.1 (500 mg, 1.02 mmol), sodium azide (199 mg, 3.06 mmol) and ammonium chloride (163 mg, 3.06 mmol) in DMF (4 mL) was stirred for 3 h at 100° C., allowed to cool to RT, quenched by addition of a saturated aqueous solution of NaCl and extracted with AcOEt. The organic phase was washed with a saturated aqueous solution of NaCl, dried (Na$_2$SO$_4$), filtered and concentrated. The residue was purified by column chromatography (SiO$_2$; DCM/MeOH 99:1→94:6) to afford 257 mg of the title compound as a yellow solid. TLC: R$_F$=0.32 (DCM/MeOH 9:1); HPLC: $^L$t$_{Ret}$=5.20 min; LC-MS: m/z 534.4 [M+H]$^+$; $^1$H NMR (400 MHz, DMSO-d6): 1.04-1.23 (m, 6H) 2.24 (s, 3H) 3.53 (d, 1H) 3.69 (s, 3H) 3.91 (d, 1H) 4.29-4.43 (m, 1H) 5.42 (br, 2H) 5.83 (br, 1H) 6.59-6.86 (m, 4H) 7.07 (br, 1H) 7.18-7.37 (m, 4H).

Intermediate 187.1: {2-[1-(4-Chloro-phenyl)-7-iso-propoxy-6-methoxy-3-oxo-3,4-dihydro-1H-iso-quinolin-2-yl]-5-methyl-phenoxy}-acetonitrile

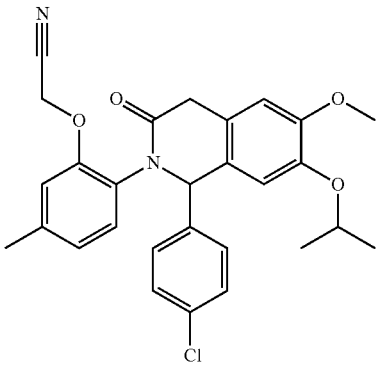 [SMILES: COc1cc2c(cc1OC(C)C)C(c1ccc(Cl)cc1)N(c1ccc(C)cc1OCC#N)C(=O)C2]

A mixture of Intermediate 187.2 (1.1 g, 2.52 mmol), 2-iodopropane (0.75 mL, 7.55 mmol) and $Cs_2CO_3$ (1.6 g, 5.03 mmol) in DMF (20 mL) was stirred for 2 h at 50° C. under an argon atmosphere. The reaction mixture was allowed to cool to RT, quenched by addition of a saturated aqueous solution of $NaHCO_3$ and extracted with AcOEt. The organic phase was washed with a saturated aqueous solution of $NaHCO_3$, dried ($Na_2SO_4$), filtered and concentrated. The residue was purified by column chromatography ($SiO_2$; DCM/MeOH 100:0→98:2) to afford 1.1 g of the title compound as a white solid. TLC: $R_F$=0.81 (DCM/MeOH 9:1); HPLC: $^L t_{Ret}$=5.45 min; LC-MS: m/z 491.4 $[M+H]^+$.

Intermediate 187.2: {2-[1-(4-Chloro-phenyl)-7-hydroxy-6-methoxy-3-oxo-3,4-dihydro-1H-isoquinolin-2-yl]-5-methyl-phenoxy}-acetonitrile

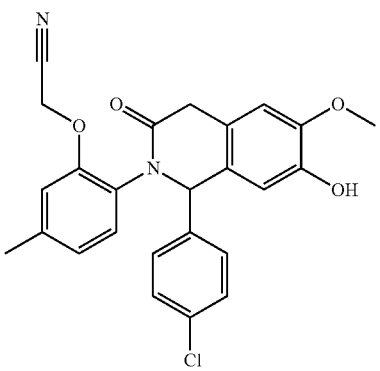

To solution of Intermediate 187.3 (2.3 g, 7.27 mmol) in DCM (50 mL) was added a solution of Intermediate 187.7 (2.7 g, 9.45 mmol) in DCM (5 mL) at 0° C. and under an argon atmosphere. The reaction mixture was stirred for 1 h at RT and cooled to 0° C. Trifluoromethane sulfonic acid (2.6 mL, 29.1 mmol) was added. The resulting mixture was stirred 1 h at 0° C., quenched by addition of a saturated aqueous solution of $NaHCO_3$ and extracted with DCM. The organic phase was washed with a saturated aqueous solution of $NaHCO_3$, dried ($Na_2SO_4$), filtered and concentrated. The residue was purified by column chromatography ($SiO_2$; DCM/MeOH 100:0→98:2) followed by trituration in AcOEt to afford 1.2 g of the title compound as a white solid. TLC: $R_F$=0.57 (DCM/MeOH 9:1); HPLC: $^L t_{Ret}$=4.57 min; LC-MS: m/z 449.3 $[M+H]^+$.

Intermediate 187.3: [3-Methoxy-4-(4-methoxy-benzyloxy)-phenyl]-acetyl chloride

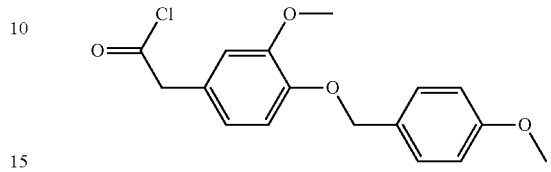

To a cold (0° C.) solution of Intermediate 187.4 (2.2 g, 7.26 mmol) in DCM (50 mL) was added 1-chloro-N,N,2-trimethyl-1-propenyl-amine (1.2 mL, 8.71 mmol), under an argon atmosphere. The reaction mixture was stirred for 30 min at 0° C. and concentrated to afford 3 g of the title compound as a colorless oil which was immediately used. HPLC: $^L t_{Ret}$=5.04 min (Methyl ester after quenching by MeOH).

Intermediate 187.4: [3-Methoxy-4-(4-methoxy-benzyloxy)-phenyl]-acetic acid

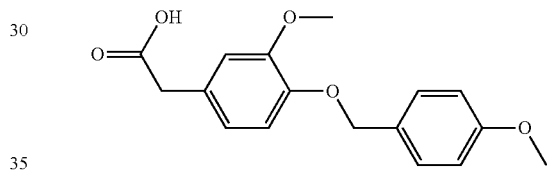

To a stirred solution of Intermediate 187.5 (8.5 g, 25.6 mmol) in THF (50 mL) was added LiOH (2.2 g, 51.3 mmol) in $H_2O$ (25 mL). The reaction mixture was stirred for 16 h at RT, concentrated, diluted with $H_2O$ (50 mL) and acidified to pH 1. The resulting precipitate was collected by filtration to provide 7.1 g of the title compound as a white solid. HPLC: $^L t_{Ret}$=4.26 min; LC-MS: m/z 320.3 $[M+18]^+$.

Intermediate 187.5: [3-Methoxy-4-(4-methoxy-benzyloxy)-phenyl]-acetic acid ethyl ester

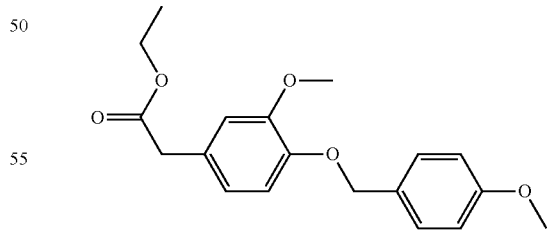

A mixture of Intermediate 187.6 (5.6 g, 26.7 mmol), 4-methoxybenzyl chloride (4.4 mL, 32.1 mmol) and $K_2CO_3$ (4.8 g, 34.8 mmol) in DMF (40 mL) was stirred for 30 min at 100° C., allowed to cool to RT, quenched by addition of a saturated aqueous solution of $NaHCO_3$ and extracted with DCM. The organic phase was washed with a saturated aqueous solution of $NaHCO_3$, dried ($Na_2SO_4$), filtered and concentrated. The residue was purified by column chromatography ($SiO_2$; gradient elution, hexane/AcOEt 95:5→75:25) to yield 8.5 g of the title compound as a white solid. TLC: $R_F$=0.76 (hexane/AcOEt 1:1). HPLC: $^Lt_{Ret}$=5.32 min; $^1$H NMR (400 MHz, DMSO-d$_6$) 1.16 (t, J=7.04 Hz, 3H), 3.54 (s, 2H), 3.71 (s, 3H), 3.73 (s, 3H), 4.05 (q, J=7.30 Hz, 2H), 4.94 (s, 2H), 6.72 (dd, J=8.21, 1.96 Hz, 1H), 6.86 (d, J=1.96 Hz, 1H), 6.89-6.98 (m, 3H), 7.34 (d, J=8.60 Hz, 2H).

Intermediate 187.6:
(4-Hydroxy-3-methoxy-phenyl)-acetic acid ethyl ester

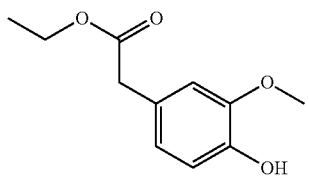

A mixture of homovanillic acid (5 g, 27.4 mmol) and H$_2$SO$_4$ (96%, 1.46 mL, 27.4 mmol) in EtOH (100 mL) was stirred for 1 h at 85° C., allowed to cool to RT and concentrated. The residue was diluted in H$_2$O and extracted with DCM. The organic phase was washed with H$_2$O, dried (Na$_2$SO$_4$), filtered and concentrated to afford 5.8 g of the title compounds as a yellow oil. LC-MS: m/z 211.2 [M+H]$^+$.

Intermediate 187.7: (2-{[1-(4-Chloro-phenyl)-meth-(E)-ylidene]-amino}-5-methyl-phenoxy)-acetonitrile

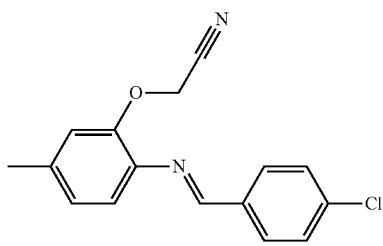 [SMILES: Cc1ccc(/N=C/c2ccc(Cl)cc2)c(OCC#N)c1]

A mixture of Intermediate 187.8 (1.5 g, 9.25 mmol) and 4-chlorobenzaldehyde (1.3 g, 9.25 mmol) in EtOH (20 mL) was stirred for 18 h at 85° C., allowed to cool to RT and concentrated to afford 2.7 g of the title compound as a red oil which was used as a crude material. $^1$H NMR (400 MHz, DMSO-d$_6$) 2.32 (s, 3H), 5.18 (s, 2H), 6.93 (d, J=7.82 Hz, 1H), 7.02 (s, 1H), 7.08 (d, J=7.82 Hz, 1H), 7.57 (dd, 2H), 7.92 (dd, 2H), 8.55 (s, 1H).

Intermediate 187.8:
(2-Amino-5-methyl-phenoxy)-acetonitrile

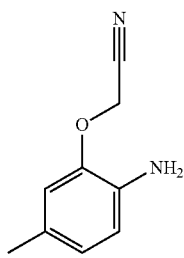

A mixture of Intermediate 187.9 (6.3 g, 22.5 mmol) and TFA (17.3 mL, 225 mmol) in DCM (50 mL) was stirred for 1 h at RT, quenched by addition of a saturated aqueous solution of NaHCO$_3$ and extracted with DCM. The organic phase was washed with a saturated aqueous solution of NaHCO$_3$, dried (Na$_2$SO$_4$), filtered and concentrated. The residue was purified by column chromatography (SiO$_2$; hexane/AcOEt 95:5→80:20) to yield 1.5 g of the title compound as an orange solid. TLC: $R_F$=0.6 (hexane/AcOEt 1:1); HPLC: $^Lt_{Ret}$=1.43 min; LC-MS: m/z 163.1 [M+H]$^+$.

Intermediate 187.9:
(2-Cyanomethoxy-4-methyl-phenyl)-carbamic acid tert-butyl ester

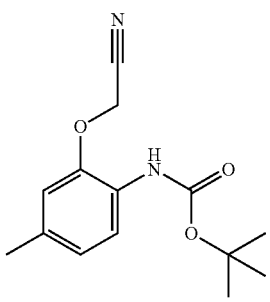 [SMILES: Cc1ccc(NC(=O)OC(C)(C)C)c(OCC#N)c1]

A mixture of Intermediate 187.10 (5 g, 22.4 mmol), K$_2$CO$_3$ (9.3 g, 67.2 mmol) and bromoacetonitrile (2.2 mL, 33.6 mmol) in DMF (50 mL) was stirred for 1 h at RT, quenched by addition of a saturated aqueous solution of NaHCO$_3$ and extracted with AcOEt. The organic phase was washed with a saturated aqueous solution of NaHCO$_3$, dried (Na$_2$SO$_4$), filtered and concentrated to afford 6.3 g of the title compound as a black oil which was used as a crude material. HPLC: $^Lt_{Ret}$=5.21 min; LC-MS: m/z 261.3 [M−H]$^-$.

Intermediate 187.10:
(2-Hydroxy-4-methyl-phenyl)-carbamic acid tert-butyl ester

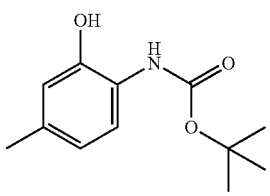 [SMILES: Cc1ccc(NC(=O)OC(C)(C)C)c(O)c1]

To a stirred solution of 6-amino-m-cresol (5 g, 40.6 mmol) in DCM (100 mL) was added di-tert-butyl carbonate (9.4 ml, 40.6 mmol), under an argon atmosphere. The resulting mixture was stirred for 18 h at RT, quenched by addition of a saturated aqueous solution of NaHCO$_3$ and extracted with DCM. The organic phase was washed with a saturated aqueous solution of NaHCO$_3$, dried (Na$_2$SO$_4$), filtered and concentrated to afford 9.1 g of the title compound as a black oil which was used as a crude material. HPLC: $^Lt_{Ret}$=4.86 min; LC-MS: m/z 224.3 [M+H]$^+$.

Example 188

1-(4-Chloro-phenyl)-7-isopropoxy-6-methoxy-2-[4-methyl-2-(thiazol-5-yl methoxy)-phenyl]-1,4-dihydro-2H-isoquinolin-3-one

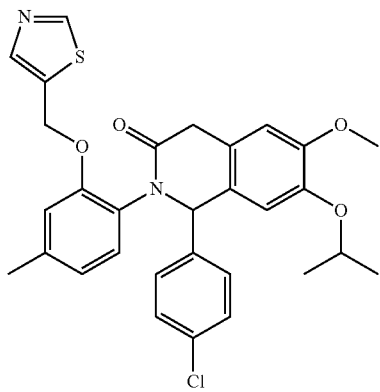 [SMILES: COc1cc2c(cc1OC(C)C)C(c1ccc(Cl)cc1)N(c1ccc(C)cc1OCc1cncs1)C(=O)C2]

To solution of Intermediate 187.3 (773 mg, 2.23 mmol) in DCM (10 mL) was added a solution of Intermediate 188.1 (841 mg, 2.452 mmol) in DCM (5 mL) and under an argon atmosphere. The reaction mixture was stirred for 1 h at RT and cooled to 0° C. Trifluoromethane sulfonic acid (0.291 mL, 3.27 mmol) was added. The resulting mixture was stirred 10 min at 0° C., quenched by addition of a saturated aqueous solution of NaHCO$_3$ and extracted with DCM. The organic phase was washed with a saturated aqueous solution of NaHCO$_3$, dried (Na$_2$SO$_4$), filtered and concentrated. The residue was purified by column chromatography (SiO$_2$; gradient elution, DCM/MeOH 100:0→98:2) followed by trituration in AcOEt to afford 400 mg of the title compound as a white solid. TLC: R$_F$=0.42 (DCM/MeOH 9:1); LC-MS: m/z 549.4 [M+H]$^+$; $^1$H NMR (400 MHz, DMSO-d6): 1.00-1.32 (m, 6H) 2.26 (s, 3H) 3.54 (d, 1H) 3.71 (s, 3H) 3.84-4.00 (m, 1H) 4.28-4.45 (m, 1H) 5.12-5.49 (m, 2H) 5.63 (br, 1H) 6.47-6.87 (m, 4H) 6.95-7.45 (m, 5H) 7.83 (s, 1H) 9.00 (br, 1H).

Intermediate 188.1: [1-(4-Chloro-phenyl)-meth-(E)-ylidene]-[4-methyl-2-(thiazol-5-yl-methoxy-phenyl)-amine

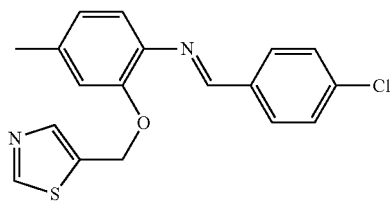 [SMILES: Cc1ccc(/N=C/c2ccc(Cl)cc2)c(OCc2cncs2)c1]

A mixture of Intermediate 188.2 (815 mg, 3.70 mmol), and 4-chlorobenzaldehyde (472 mg, 3.70 mmol) and acetic acid (0.21 ml, 3.70 mmol) was stirred for 18 h at 85° C., allowed to cool to RT and concentrated to afford 1.39 g of the title compound as a black oil which was used as a crude material. $^1$H NMR (400 MHz, DMSO-d$_6$) 1.00-1.32 (m, 6H), 2.26 (s, 3H), 3.54 (d, 1H), 3.71 (s, 3H), 3.84-4.00 (m, 1H), 4.28-4.45 (m, 1H), 5.12-5.49 (m, 2H), 5.63 (br, 1H), 6.47-6.87 (m, 4H), 6.95-7.45 (m, 5H), 7.83 (s, 1H), 9.00 (br, 1H).

Intermediate 188.2: 4-Methyl-2-(thiazol-5-ylmethoxy)-phenylamine

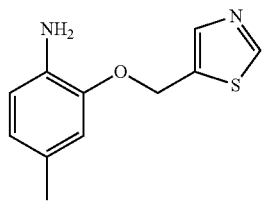

A mixture of Intermediate 188.3 (935 mg, 3.74 mmol) and Raney nickel (400 mg) in MeOH/THF (40 mL, 3:1 v/v) was shaken for 27.5 h at RT, under 0.1 bar of H$_2$. The reaction mixture was filtered through a pad of celite and the filtrate was concentrated. The residue was purified by column chromatography (SiO$_2$; DCM/MeOH 100:0→98:2) to afford 815 mg of the title compound as a red oil. TLC: R$_F$=0.6 (DCM/MeOH 9:1); HPLC: $^L$t$_{Ret}$=1.76 min; LC-MS: m/z 221.2 [M+H]$^+$.

Intermediate 188.3: 5-(5-Methyl-2-nitro-phenoxymethyl)-thiazole

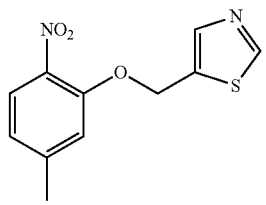 [SMILES: Cc1ccc([N+](=O)[O-])c(OCc2cncs2)c1]

To a solution of 5-(hydroxymethyl)-1,3-thiazole (1 g, 8.68 mmol) in DMF (15 mL) was added NaH (0.413 g, 9.47 mmol) under an argon atmosphere. The reaction mixture was stirred for 20 min at 0° C. 3-Fluoro-4-nitrotoluene (1.2 g, 7.89 mmol) was added. The resulting mixture was stirred for 1 h at RT, quenched by addition of a saturated aqueous solution of NaHCO$_3$ and extracted with AcOEt. The organic phase was washed with a saturated aqueous solution of NaHCO$_3$, dried (Na$_2$SO$_4$), filtered and concentrated. The residue was purified by column chromatography (SiO$_2$; hexane/AcOEt 60:40→40:60) to afford 936 mg of the title compound as an orange solid. TLC: R$_F$=0.35 (hexane/AcOEt 1:1); HPLC: $^L$t$_{Ret}$=4.26 min; LC-MS: m/z 251.2 [M+H]$^+$.

Example 189

4-[1-(4-Chloro-phenyl)-7-isopropoxy-6-methoxy-3-oxo-3,4-dihydro-1H-isoquinolin-2-yl]-3-(2H-tetrazol-5-ylmethoxy)-benzoic acid methyl ester

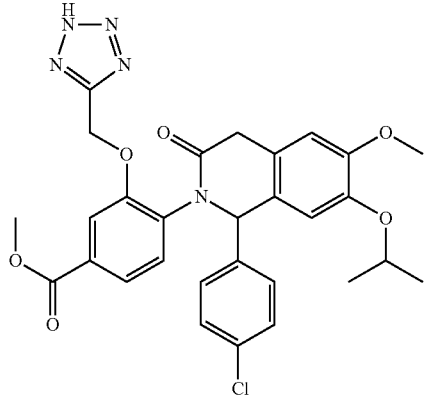 [SMILES: COC(=O)c1ccc(N2C(=O)Cc3cc(OC)c(OC(C)C)cc3C2c2ccc(Cl)cc2)c(OCc2nn[nH]n2)c1]

The title compound (132.4 mg, 0.208 mmol) was obtained as an off-white solid from Intermediate 189.1 (398 mg, 0.744 mmol) analogously to Example 187. HPLC: $^M t_{Ret}$=1.10 min; LC-MS: m/z 578.2 [M+H]$^+$; $^1$H NMR (400 MHz, DMSO-d$_6$): 1.14 (d, J=5.85 Hz, 3H) 1.20 (d, J=5.85 Hz, 3H) 3.57-3.63 (m, 1H) 3.73 (s, 3H) 3.85 (s, 3H) 3.96 (d, J=19.98 Hz, 1H) 4.38 (dt, J=11.96, 6.03 Hz, 1H) 5.35-5.72 (m, 2H) 5.95 (br. s., 1H) 6.73 (s, 1H) 6.83 (s, 1H) 6.89-7.20 (m, 1H) 7.20-7.39 (m, 4H) 7.54 (br. s., 1H) 7.80 (br. s., 1H) 16.76 (br. s., 1H).

Intermediate 189.1: 4-[1-(4-Chloro-phenyl)-7-isopropoxy-6-methoxy-3-oxo-3,4-dihydro-1H-isoquinolin-2-yl]-3-cyanomethoxy-benzoic acid methyl ester

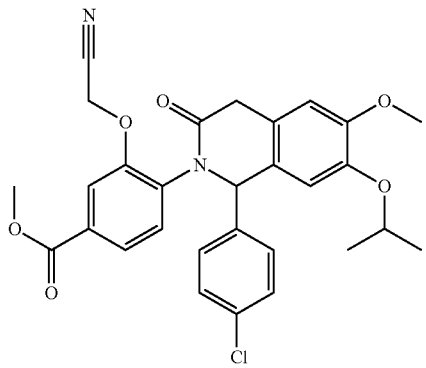 [SMILES: COC(=O)c1ccc(N2C(=O)Cc3cc(OC)c(OC(C)C)cc3C2c2ccc(Cl)cc2)c(OCC#N)c1]

The title intermediate (298.9 mg, 0.559 mmol) was obtained as an off-white solid from Intermediate 189.2 (398 mg, 0.744 mmol) analogously to intermediate 187.9. HPLC: $^M t_{Ret}$=1.17 min; LC-MS: m/z 535 [M+H]$^+$.

Intermediate 189.2: 4-[1-(4-Chloro-phenyl)-7-isopropoxy-6-methoxy-3-oxo-3,4-dihydro-1H-isoquinolin-2-yl]-3-hydroxy-benzoic acid methyl ester

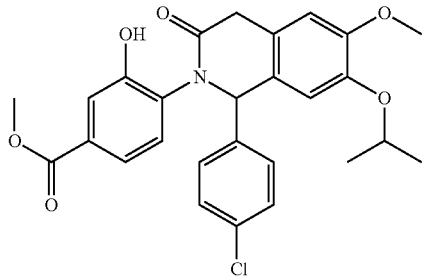 [SMILES: COC(=O)c1ccc(N2C(=O)Cc3cc(OC)c(OC(C)C)cc3C2c2ccc(Cl)cc2)c(O)c1]

The title intermediate (296 mg, 0.597 mmol) was obtained as an off-white solid from Intermediate 189.3 (331 mg, 0.0.542 mmol) using a 1M TBAF solution in THF and the reaction was stirred for 45 minutes at room temperature. After workup, the title compound was obtained as a yellow solid. HPLC: $^M t_{Ret}$=1.13 min; LC-MS: m/z 496 [M+H]$^+$; $^1$H NMR (400 MHz, DMSO-d6): 1.09-1.26 (m, 6H) 3.54-3.65 (m, 1H) 3.74 (s, 3H) 3.81 (s, 3H) 3.94-4.02 (m, 1H) 4.37-4.50 (m, 1H) 5.88 (s, 2H) 6.81-6.96 (m, 2H) 7.22-7.39 (m, 4H) 7.46-7.56 (m, 3H).

Intermediate 189.3: 3-(tert-Butyl-dimethyl-silanyloxy)-4-[1-(4-chloro-phenyl)-7-isopropoxy-6-methoxy-3-oxo-3,4-dihydro-1H-isoquinolin-2-yl]-benzoic acid methyl ester

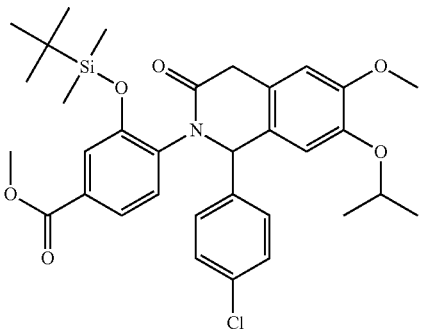 [SMILES: COC(=O)c1ccc(N2C(=O)Cc3cc(OC)c(OC(C)C)cc3C2c2ccc(Cl)cc2)c(O[Si](C)(C)C(C)(C)C)c1]

The title intermediate (331 mg, 0.542 mmol) was obtained as a white solid from Intermediate 96.2 (555 mg, 2.475 mmol) and Intermediate 189.4 (1.0 g, 2.475 mmol) analogously to intermediate 187.2. HPLC: $^M t_{Ret}$=1.47 min; LC-MS: m/z 610 [M+H]$^+$; $^1$H NMR (400 MHz, DMSO-d6): −0.17-0.25 (m, 6H) 0.60-0.93 (m, 9H) 1.06-1.27 (m, 6H) 3.51-3.66 (m, 1H) 3.69-3.77 (m, 3H) 3.82 (d, J=12.92 Hz, 3H) 3.92-4.13 (m, 1H) 4.34-4.50 (m, 1H) 5.66-5.95 (m, 1H) 6.79-7.02 (m, 2H) 7.20-7.61 (m, 7H).

Intermediate 189.4: 3-(tert-Butyl-dimethyl-silanyloxy)-4-{[1-(4-chloro-phenyl)-meth-(E)-ylidene]-amino}-benzoic acid methyl ester

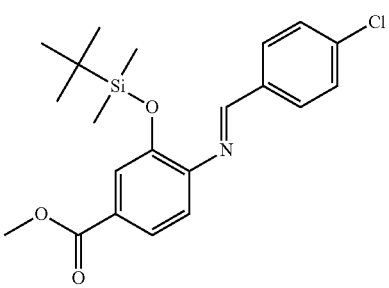 [SMILES: COC(=O)c1ccc(/N=C/c2ccc(Cl)cc2)c(O[Si](C)(C)C(C)(C)C)c1]

The title intermediate (4.75 g, 9.99 mmol) was obtained as a brown solid from Intermediate 189.5 (3.37 g, 11.63 mmol) using TBDMS chloride (1.753 g, 11.63 mmol), triethylamine (3.24 mL, 23.26 mmol), DMAP (142 mg, 1.163 mmol) in 116 mL DCM stirring at room temperature for 15 h. $^1$H NMR (400 MHz, DMSO-d6): 0.14 (s, 6H) 0.92 (s, 9H) 3.84 (s, 3H) 7.18 (d, J=8.20 Hz, 1H) 7.43 (d, J=1.56 Hz, 1H) 7.63 (d, J=8.59 Hz, 3H) 7.96 (d, J=8.20 Hz, 2H) 8.58 (s, 1H).

Intermediate 189.5: 4-{[1-(4-Chloro-phenyl)-meth-(E)-ylidene]-amino}-3-hydroxy-benzoic acid methyl ester

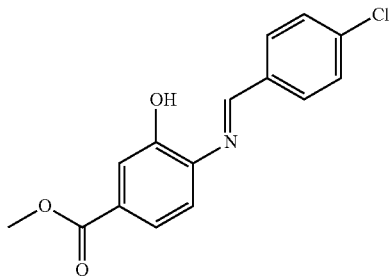 [SMILES: COC(=O)c1ccc(/N=C/c2ccc(Cl)cc2)c(O)c1]

The title intermediate (3.37 g, 11.63 mmol) was obtained as an off-white solid from chloro benzaldehyde (1.682 g, 11.96 mmol) and methyl 4-amino-3hydroxybenzoate (2.0 g, 11.96 mmol) analogously to intermediate 187.7. $^1$H NMR (400 MHz, DMSO-d6): 3.83 (s, 3H) 7.22 (d, J=8.20 Hz, 1H) 7.36-7.54 (m, 2H) 7.61 (d, J=8.59 Hz, 2H) 8.04 (d, J=8.59 Hz, 2H) 8.70 (s, 1H) 9.59 (s, 1H).

Example 190

4-[1-(4-Chloro-phenyl)-7-isopropoxy-6-methoxy-3-oxo-3,4-dihydro-1H-isoquinolin-2-yl]-3-methoxy-benzoic acid methyl ester

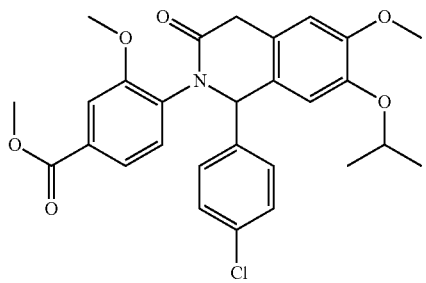 [SMILES: COC(=O)c1ccc(N2C(=O)Cc3cc(OC)c(OC(C)C)cc3C2c2ccc(Cl)cc2)c(OC)c1]

The title compound was obtained by reaction of Intermediate 189.2 (200 mg, 0.403 mmol) with iodomethane (86 mg, 0.605 mmol) in the presence of potassium carbonate (167 mg, 1.21 mmol) in 4 mL DMF at 100° C. for 30 min. The reaction mixture was diluted with ethyl acetate and washed with aqueous NaHCO$_3$ solution and brine. The crude product was purified by automated normal phase column chromatography (eluting with n-heptane-ethyl acetate), yielding the title compound as a brownish solid (0.51 g, 0.904 mmol). HPLC: $^M t_{Ret}$=1.19 min; LC-MS: m/z 510.3 [M+H]$^+$. $^1$H NMR (400 MHz, DMSO-d$_6$): 1.14 (d, J=5.85 Hz, 3H) 1.22 (d, J=5.85 Hz, 3H) 3.61 (d, J=19.98 Hz, 1H) 3.66-3.93 (m, 9H) 3.99 (d, J=19.98 Hz, 1H) 4.36-4.48 (m, 1H) 5.83 (br. s., 1H) 6.86 (s, 2H) 6.92-7.69 (m, 7H).

Example 191

4-[1-(4-Chloro-phenyl)-7-isopropoxy-6-methoxy-3-oxo-3,4-dihydro-1H-isoquinolin-2-yl]-3-(thiazol-5-ylmethoxy)-benzoic acid methyl ester

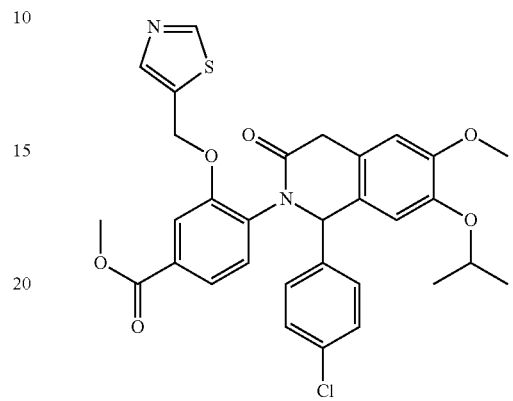

The title compound was obtained by reaction of Intermediate 189.2 (400 mg, 0.807 mmol) with 5-(hydroxymethyl)-1,3,thiazole (139 mg, 1.210 mmol) in the presence of di-tert-butylazodicarboxylate (279 mg, 1.21 mmol) and triphenylphosphine in 8 mL dry DCM at room temperature for 19 h. The reaction mixture was concentrated in vacuo and the crude product was purified by automated normal phase column chromatography (eluting with n-heptane-ethyl acetate), yielding the title compound as a colorless oil (0.375 g, 0.518 mmol). HPLC: $^M t_{Ret}$=1.15 min; LC-MS: m/z 593.3 [M+H]$^+$. $^1$H NMR (400 MHz, DMSO-d6): 1.15 (d, J=5.85 Hz, 3H) 1.21 (d, J=6.06 Hz, 3H) 3.58-3.64 (m, 1H) 3.74 (s, 3H) 3.86 (s, 3H) 3.89-4.06 (m, 1H) 4.34-4.44 (m, 1H) 5.47 (br. s., 2H) 5.80 (br. s., 1H) 6.80 (s, 1H) 6.86 (s, 1H) 7.26 (br. s., 4H) 7.42-7.83 (m, 3H) 7.87 (s, 1H) 9.04 (br. s., 1H).

Intermediate 192.1: (S)-2-[4-((S)-1-Amino-ethyl)-phenyl]-1-(4-chloro-phenyl)-7-isopropoxy-6-methoxy-1,4-dihydro-2H-isoquinolin-3-one

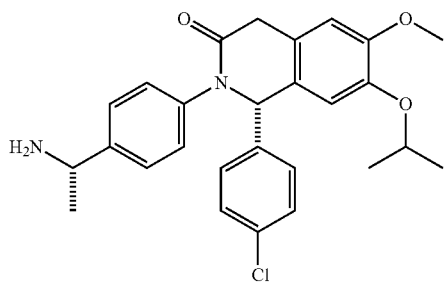 [SMILES: COc1cc2c(cc1OC(C)C)[C@H](c1ccc(Cl)cc1)N(c1ccc([C@H](C)N)cc1)C(=O)C2]

The title compound (1.28 g, 2.75 mmol, 100%) was obtained as a solid from Intermediate 192.2 (1.55 g, 2.74 mmol) analogously to Example 51. HPLC: $^K t_{Ret}$=5.99 min; LC-MS: m/z 465.4 [M+H]$^+$.

Intermediate 192.2: ((S)-1-{4-[(S)-1-(4-Chloro-phenyl)-7-isopropoxy-6-methoxy-3-oxo-3,4-dihydro-1H-isoquinolin-2-yl]-phenyl}-ethyl)-carbamic acid tert-butyl ester

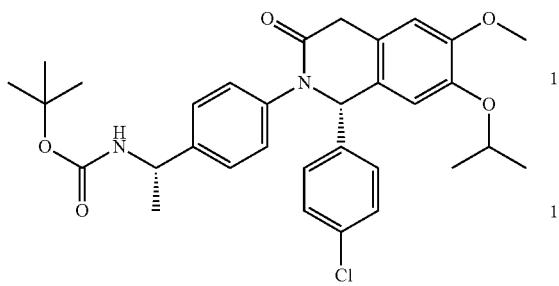

The title intermediate (1.61 g, 2.85 mmol, 49.3%) was obtained as a white solid from Intermediate 75.6 (2.0 g, 5.78 mmol) and Intermediate 192.3 (2.0 g, 5.78 mmol) analogously to Example 75. HPLC: $^{K}t_{Ret}$=7.55 min; LC-MS: m/z 582.5 [M+NH4]$^{+}$.

Intermediate 192.3: [(S)-1-(4-Iodo-phenyl)-ethyl]-carbamic acid tert-butyl ester

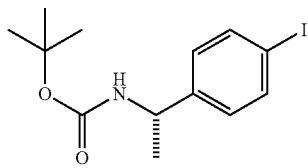 [SMILES: C[C@H](NC(=O)OC(C)(C)C)c1ccc(I)cc1]

To a mixture of Intermediate 178.5 (5.0 g, 20.2 mmol) and Et$_3$N (5.64 mL, 40.5 mmol) in DCM (35 mL) was added di-tert-butyl dicarbonate (5.3 g, 24.3 mmol). After stirring for 1 h at RT, it was quenched by addition of a saturated aqueous solution of NH$_4$Cl and extracted with DCM. The organic phase was washed with a saturated aqueous solution of NaHCO$_3$, dried (Na$_2$SO$_4$), filtered and concentrated. The residue was purified by column chromatography (SiO$_2$; hexane/AcOEt 90:10) to yield (6.27 g, 18.1 mmol, 89%) of the title compound as a white solid. HPLC: $^{K}t_{Ret}$=7.35 min; LC-MS: m/z 365.2 [M+NH4]$^{+}$.

Example 195

(S)-1-(4-Chloro-phenyl)-7-isopropoxy-6-methoxy-2-(6-{methyl-[4-(2-oxo-pyrrolidin-1-yl)-trans-cyclohexylmethyl]-amino}-pyridin-3-yl)-1,4-dihydro-2H-isoquinolin-3-one

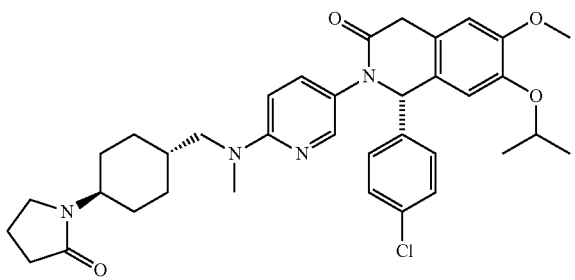 [SMILES: COc1cc2c(cc1OC(C)C)[C@H](c1ccc(Cl)cc1)N(c1ccc(N(C)C[C@H]3CC[C@H](N4CCCC4=O)CC3)nc1)C(=O)C2]

The title compound (28 mg, 0.044 mmol, 15%) was obtained as a yellow foam from Intermediate 75.6 (100 mg, 0.289 mmol) and Intermediate 195.1 (120 mg, 0.289 mmol), analogously to Example 130. HPLC: $^{D}t_{Ret}$=1.05 min; LC-MS: m/z 631.5 [M+H]$^{+}$.

Intermediate 195.1: 1-(4-{[(5-Iodo-pyridin-2-yl)-methyl-amino]-methyl}-trans-cyclohexyl)-pyrrolidin-2-one

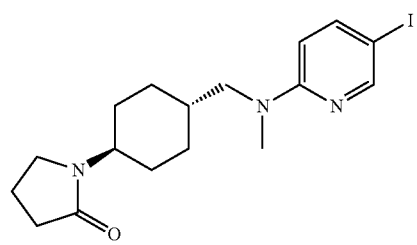 [SMILES: CN(C[C@H]1CC[C@H](N2CCCC2=O)CC1)c1ccc(I)cn1]

To the mixture of Intermediate 195.2 (1.31 g, 2.91 mmol), potassium carbonate (9.26 g, 67.0 mmol) and acetone (150 mL) was added potassium iodide (1.015 g, 6.12 mmol). The mixture was stirred for 48 h at reflux temperature. The reaction mixture was concentrated and the residue was extracted between EtOAc (2×) and 1M aqueous NaHCO$_3$ (1×). The organic phases were washed with brine and dried over Na$_2$SO$_4$, filtered and evaporated to dryness. The residue was crystallized (iPrOH) to afford the title compound as beige crystals (769 mg, 1.71 mmol, 59%). HPLC: $^{J}t_{Ret}$=2.95 min; LC-MS: m/z 414.3 [M+H]$^{+}$.

Intermediate 195.2: 4-Chloro-N-(4-{[(5-iodo-pyridin-2-yl)-methyl-amino]-methyl}-trans-cyclohexyl)-butyramide

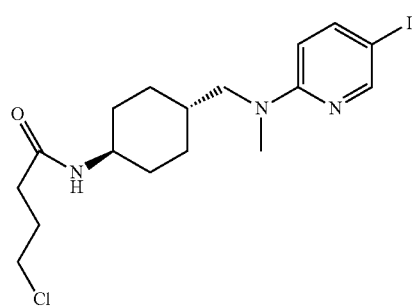 [SMILES: CN(C[C@H]1CC[C@H](NC(=O)CCCCl)CC1)c1ccc(I)cn1]

To the stirred solution of Intermediate 130.4 (1.0 g, 2.90 mmol), triethylamine (0.803 mL, 5.79 mmol) and chloroform (30 mL) was added drop wise 4-chloro-butyryl chloride. The mixture was stirred for 1 h at RT. The reaction mixture was extracted between DCM (2×) and 1M aqueous NaHCO$_3$ (1×). The organic phases were washed with brine and dried over Na$_2$SO$_4$, filtered and evaporated to dryness. The residue was crystallized (DCM-hexane) to afford the title compound as beige crystals (1.30 g, 2.90 mmol, 99%). HPLC: $^{J}t_{Ret}$=4.26 min; LC-MS: m/z 450.3 [M+H]$^{+}$.

Example 196

(S)-1-(4-Chloro-phenyl)-7-isopropoxy-6-methoxy-2-(6-{methyl-[4-(2-oxo-imidazolidin-1-yl)-trans-cyclohexylmethyl]-amino}-pyridin-3-yl)-1,4-dihydro-2H-isoquinolin-3-one

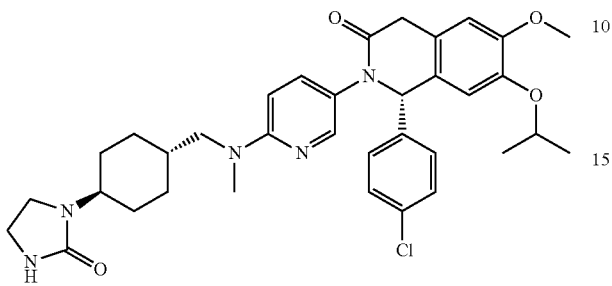

The title compound (61 mg, 0.096 mmol, 33%) was obtained as a yellow foam from Intermediate 75.6 (100 mg, 0.289 mmol) and Intermediate 196.1 (120 mg, 0.289 mmol), analogously to Example 130. HPLC: $^{D}t_{Ret}$=1.12 min; LC-MS: m/z 632.6 [M+H]$^+$.

Intermediate 196.1: 1-(4-{[(5-Iodo-pyridin-2-yl)-methyl-amino]-methyl}-trans-cyclohexyl)-imidazolidin-2-one

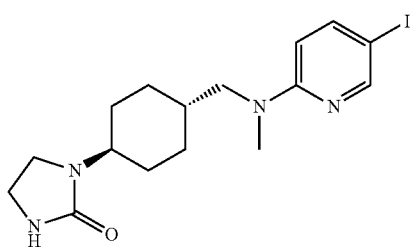 [SMILES: CN(C[C@H]1CC[C@H](N2CCNC2=O)CC1)c1ccc(I)cn1]

To the solution of Intermediate 196.2 (295 mg, 0.76 mmol) and THF (30 mL) was added CDI (123 mg, 0.76 mmol). The mixture was stirred for 1 h at reflux temperature. The reaction mixture was extracted between EtOAc (2×) and 1M aqueous NaHCO$_3$ (1×). The organic phases were washed with brine and dried over Na$_2$SO$_4$, filtered and evaporated to dryness. The residue was crystallized (EtOAc) to afford the title compound as beige crystals (204 mg, 0.492 mmol, 64%). HPLC: $^{J}t_{Ret}$=3.71 min; LC-MS: m/z 415.3 [M+H]$^+$.

Intermediate 196.2: N*1*-(4-{[(5-Iodo-pyridin-2-yl)-methyl-amino]-methyl}-trans-cyclohexyl)-ethane-1,2-diamine

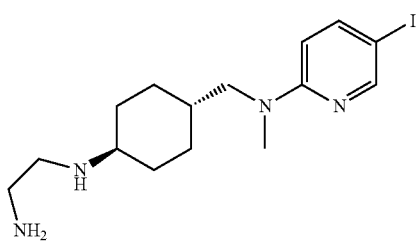 [SMILES: CN(C[C@H]1CC[C@H](NCCN)CC1)c1ccc(I)cn1]

To the solution of Intermediate 196.3 (390 mg, 0.80 mmol) and DCM (20 mL) was added TFA (1.23 mL, 15.8 mmol). The mixture was stirred for 2 h at RT. The reaction mixture was extracted between DCM (2×) and 1M aqueous NaHCO$_3$ (1×). The organic phases were washed with brine and dried over Na$_2$SO$_4$, filtered and evaporated to dryness, gave the title compound as a slightly yellow oil (298 mg, 767 mmol, 96%). HPLC: $^{J}t_{Ret}$=1.90 min; LC-MS: m/z 389.3 [M+H]$^+$.

Intermediate 196.3: [2-(4-{[(5-Iodo-pyridin-2-yl)-methyl-amino]-methyl}-trans-cyclohexyl-amino)-ethyl]-carbamic acid tert-butyl ester

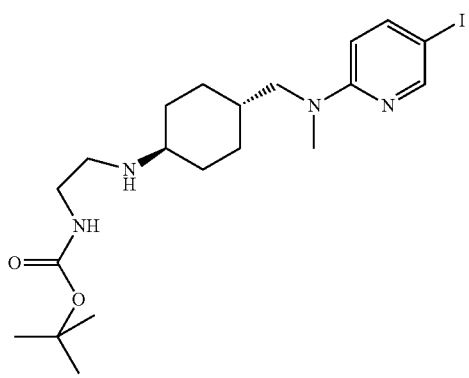 [SMILES: CN(C[C@H]1CC[C@H](NCCNC(=O)OC(C)(C)C)CC1)c1ccc(I)cn1]

To a solution of Intermediate 130.4 (800 mg, 2.317 mmol), (2-oxo-ethyl)-carbamic acid tert-butyl ester (406 mg, 2.55 mmol) in MeOH (50 mL) was added NaBH$_4$CN (218 mg, 3.48 mmol) at RT. The mixture was stirred for 18 h at RT. To the reaction mixture was concentrated and to the residue was added 1M aqueous NaHCO$_3$ followed by extraction with EtOAc (2×). The organic phases were dried over Na$_2$SO$_4$, filtered and evaporated. Purification of the residue by normal phase column chromatography, eluting with DCM-MeOH-aq. 30% NH$_4$OH (200:20:1), gave the title compound as slightly yellow oil (398 mg, 0.815 mmol, 35%). HPLC: $^{J}t_{Ret}$=3.64.

Example 197

(S)-1-(4-Chloro-phenyl)-7-isopropoxy-6-methoxy-2-(6-{methyl-[4-(3-oxo-morpholin-4-yl)-trans-cyclohexylmethyl]-amino}-pyridin-3-yl)-1,4-dihydro-2H-isoquinolin-3-one

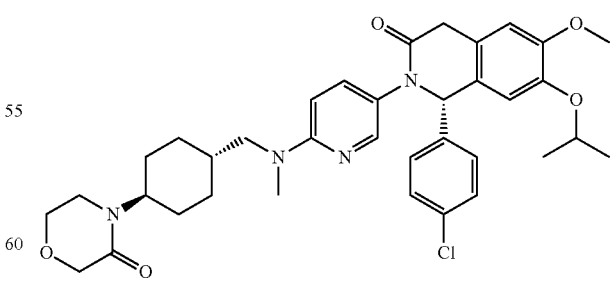

The title compound (74 mg, 0.113 mmol, 39%) was obtained as a yellow foam from Intermediate 75.6 (100 mg, 0.289 mmol) and Intermediate 197.1 (124 mg, 0.289), analogously to Example 130. HPLC: $^{J}t_{Ret}$=1.15 min; LC-MS: m/z 647.5 [M+H]$^+$.

Intermediate 197.1: 4-(4-{[(5-Iodo-pyridin-2-yl)-methyl-amino]-methyl}-trans-cyclohexyl)-morpholin-3-one

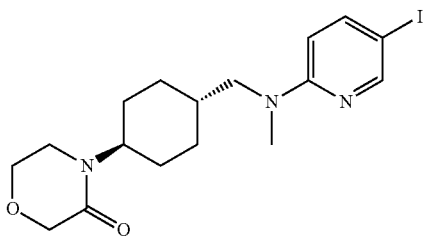 [SMILES: CN(C[C@H]1CC[C@H](N2CCOCC2=O)CC1)c1ccc(I)cn1]

To the stirred solution of Intermediate 197.2 (670 mg, 1.439 mmol) and THF (100 mL) was added NaH (54.5 mg, 2.158 mmol) at 0° C. The mixture was stirred for 3 h at 0° C. The reaction mixture was extracted between EtOAc (2×) and 1M aqueous $NaHCO_3$ (1×). The organic phases were washed with brine and dried over $Na_2SO_4$, filtered and evaporated to dryness. The residue was purified by normal phase column chromatography, eluting with EtOAc-hexane (3:1), afforded the title compound after crystallization (DCM-hexane) as slightly yellow crystals (254 mg, 0.592 mmol, 41%). HPLC: $^Jt_{Ret}$=3.66 min; LC-MS: m/z 430.2 $[M+H]^+$.

Intermediate 197.2: 2-(2-Chloro-ethoxy)-N-(4-{[(5-iodo-pyridin-2-yl)-methyl-amino]-methyl}-trans-cyclohexyl)-acetamide

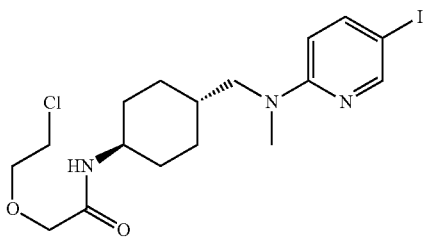 [SMILES: CN(C[C@H]1CC[C@H](NC(=O)COCCCl)CC1)c1ccc(I)cn1]

The title intermediate (670 mg, 1.424 mmol, 98%) was obtained as a slightly yellow oil from Intermediate 130.4 (500 mg, 1.448 mmol) and (2-chloro-ethoxy)-acetyl chloride (227 mg, 1.448 mmol) analogously to Intermediate 195.2. HPLC: $^Jt_{Ret}$=4.40 min; LC-MS: m/z 466.3 $[M+H]^+$.

Example 198

(S)-7-((R)-sec-Butoxy)-1-(4-chloro-phenyl)-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one

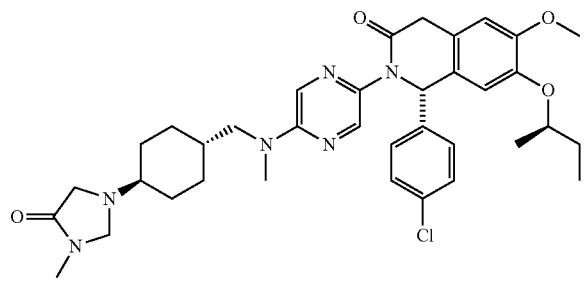 [SMILES: CC[C@@H](C)Oc1cc2c(cc1OC)CC(=O)N(c1cnc(N(C)C[C@H]3CC[C@H](N4CC(=O)N(C)C4)CC3)cn1)[C@H]2c1ccc(Cl)cc1]

The title compound (96 mg, 0.144 mmol, 36%) was obtained as a yellow foam from Intermediate 198.1 (146 mg, 0.400 mmol) and Intermediate 149.1 (50 mg, 0.100 mmol), analogously to Example 130. HPLC: $^Dt_{Ret}$=1.21 min; LC-MS: m/z 661.7 $[M+H]^+$.

Intermediate 198.1: (S)-7-((R)-sec-Butoxy)-1-(4-chloro-phenyl)-6-methoxy-1,4-dihydro-2H-isoquinolin-3-one

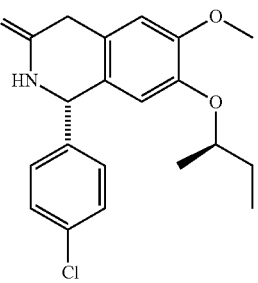

To the solution of Intermediate 198.2 (1.30 g, 4.19 mmol) in THF (42 mL) was added subsequently (S)-butan-2-ol (0.466 g, 6.29 mmol), di-tert-butylazodicarboxylate (1.93 g, 8.39 mmol) and triphenylphosphine (polymer bound 3 mmol/g resin) (2.79 mg, 8.39 mmol) at 0° C. The mixture was stirred for 75 min at RT. The reaction was filtered, washed with EtOAc and the filtrate concentrated. The residue was extracted between EtOAc (3×) and 1M aqueous $NaHCO_3$ (1×). The organic phases were washed with brine and dried over $Na_2SO_4$, filtered and evaporated to dryness. Purification of the residue by normal phase column chromatography, eluting with DCM-MeOH (98:2→95:5), gave the title compound after crystallization (TBME) as white crystals (628 mg, 1.728 mmol, 41%). HPLC: $^Dt_{Ret}$=1.06 min; LC-MS: m/z 360.1 $[M+H]^+$; $]^+$; $^1H$ NMR (400 MHz, DMSO-$d_6$): 0.82 (t, 3H), 1.13 (d, 3H), 1.46 (m, 1H), 1.52 (m, 1H), 3.30-3.35 (d, 1H), 3.46-3.51 (d, 1H), 3.69 (s, 3H), 4.16 (m, 1H), 5.52 (m, 1H), 6.76 (s, 1H), 6.80 (s, 1H), 7.32 (q, 4H), 8.48 (d, 1H).

Intermediate 198.2: (S)-1-(4-Chloro-phenyl)-7-hydroxy-6-methoxy-1,4-dihydro-2H-isoquinolin-3-one

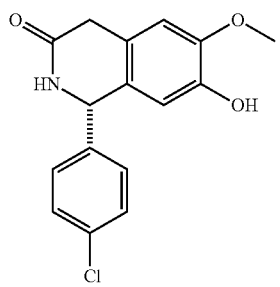

The mixture of Intermediate 75.6 (5.0 g, 14.46 mmol) and ortho-phosphoric acid 85% (48.7 mL, 723 mmol) was stirred for 1.5 h at 100° C. The reaction mixture was cooled to RT, poured (carefully) on 1M aqueous $NaHCO_3$ (500 mL), pH 7.0, and extracted with EtOAc (3×) The organic phases were washed with brine and dried over $Na_2SO_4$, filtered and evaporated to dryness. Purification of the residue by normal phase column chromatography, eluting with DCM, gave the title compound as yellow foam (4.40 g, 14.20 mmol, 98%). HPLC: $^Dt_{Ret}$=0.78 min; LC-MS: m/z 304.2 $[M+H]^+$; $^1H$ NMR (400 MHz, DMSO-d): 3.27-3.34 (d, 1H), 3.44-3.49 (d, 1H), 3.71 (s, 3H), 5.46 (bs, 1H), 6.53 (s, 1H), 6.72 (s, 1H), 7.32 (q, 4H), 8.41 (s, 1H), 8.85 (s, 1H).

Example 199

(S)-1-(4-Chloro-phenyl)-7-isopropoxy-6-methoxy-2-(6-{methyl-[4-(2-oxo-piperidin-1-yl)-trans-cyclohexylmethyl]-amino}-pyridin-3-yl)-1,4-dihydro-2H-isoquinolin-3-one

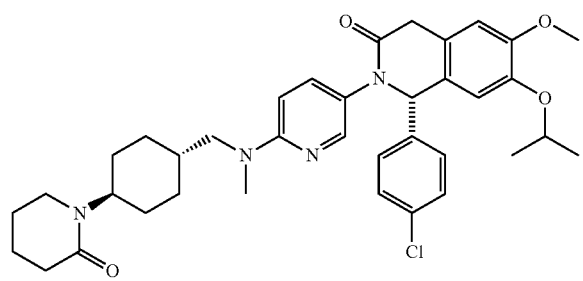 [SMILES: COc1cc2c(cc1OC(C)C)[C@H](c1ccc(Cl)cc1)N(c1ccc(N(C)C[C@H]3CC[C@H](N4CCCCC4=O)CC3)nc1)C(=O)C2]

The title compound (29 mg, 0.045 mmol, 15%) was obtained as a yellow foam from Intermediate 75.6 (100 mg, 0.289 mmol) and Intermediate 199.1 (124 mg, 0.289), analogously to Example 130. HPLC: $^D t_{Ret}$=1.23 min; LC-MS: m/z 645.6 [M+H]$^+$.

Intermediate 199.1: 1-(4-{[(5-Iodo-pyridin-2-yl)-methyl-amino]-methyl}-trans-cyclohexyl)-piperidin-2-one

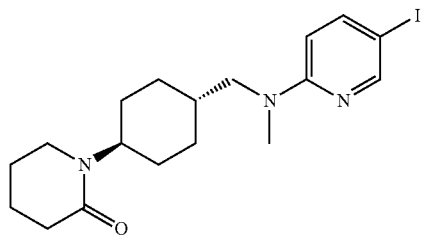 [SMILES: CN(C[C@H]1CC[C@H](N2CCCCC2=O)CC1)c1ccc(I)cn1]

The title intermediate (412 mg, 0.964 mmol, 66%) was obtained as a slightly yellow foam from Intermediate 199.2 (680 mg, 1.466 mmol), analogously to Intermediate 197.1. HPLC: $^J t_{Ret}$=4.34 min; LC-MS: m/z 428.2 [M+H]$^+$.

Intermediate 199.2: 5-Chloro-pentanoic acid (4-{[(5-iodo-pyridin-2-yl)-methyl-amino]-methyl}-trans-cyclohexyl)-amide

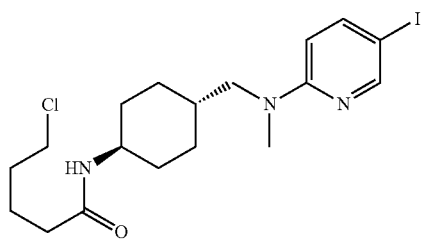 [SMILES: CN(C[C@H]1CC[C@H](NC(=O)CCCCCl)CC1)c1ccc(I)cn1]

The title intermediate (680 mg, 1.437 mmol, 99%) was obtained as a slightly yellow solid from Intermediate 130.4 (500 mg, 1.448 mmol) and 5-chloro-pentanoyl chloride (225 mg, 1.448 mmol) analogously to Intermediate 195.2. HPLC: $^J t_{Ret}$=4.45 min; LC-MS: m/z 464.4 [M+H]$^+$.

Intermediate 200.1: 4-[(S)-1-(4-Iodo-phenyl)-ethyl]-1-methyl-piperazin-2-one

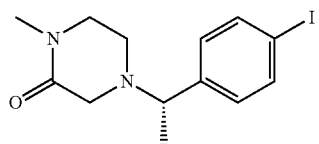

The title intermediate (1.16 g, 3.38 mmol, 75%) was obtained as a white solid from Intermediate 200.2 (1.9 g, 3.99 mmol) analogously to Example 79. HPLC: $^K t_{Ret}$=4.71 min; LC-MS: m/z 345.2 [M+NH]$^+$.

Intermediate 200.2: {[2-(tert-Butoxycarbonyl-methyl-amino)-ethyl]-[(S)-1-(4-iodo-phenyl)-ethyl]-amino}-acetic acid methyl ester

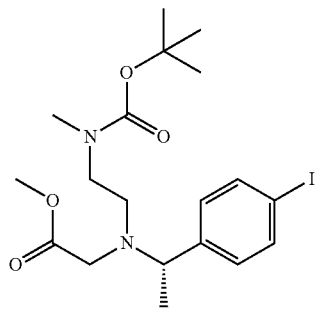 [SMILES: COC(=O)CN(CCN(C)C(=O)OC(C)(C)C)[C@@H](C)c1ccc(I)cc1]

The title intermediate (1.9 g, 3.99 mmol, 85%) was obtained as a white solid from Intermediate 200.3 (1.49 g, 4.67 mmol) analogously to Intermediate 79.2. HPLC: $^K t_{Ret}$=6.37 min; LC-MS: m/z 477.4 [M+NH]$^+$.

Intermediate 200.3: [(S)-1-(4-Iodo-phenyl)-ethylamino]-acetic acid methyl ester

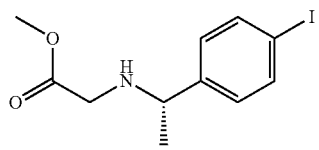

The title intermediate (1.5 g, 4.7 mmol, 74.4%) was obtained as a white solid from Intermediate 178.5 (1.56 g, 6.31 mmol) analogously to Intermediate 79.1. HPLC: $^K t_{Ret}$=4.80 min; LC-MS: m/z 320.2 [M+NH]$^+$.

Intermediate 201.1: 4-((S)-1-{5-[(S)-1-(4-Chloro-phenyl)-7-isopropoxy-6-methoxy-3-oxo-3,4-dihy-dro-1H-isoquinolin-2-yl]-pyridin-2-yl}-ethyl)-3-oxo-piperazine-1-carboxylic acid tert-butyl ester

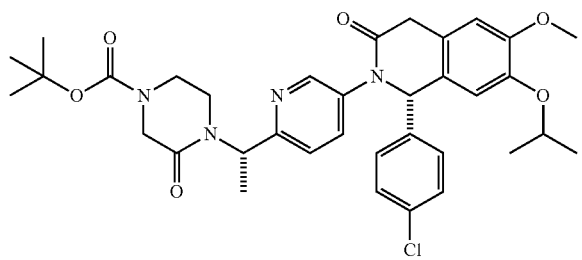 [SMILES: COc1cc2c(cc1OC(C)C)[C@H](c1ccc(Cl)cc1)N(c1ccc([C@H](C)N3CCN(C(=O)OC(C)(C)C)CC3=O)nc1)C(=O)C2]

The title intermediate (106 mg, 0.16 mmol, 20.7%) was obtained as a beige solid from Intermediate 75.6 (286 mg, 0.82 mmol) and Intermediate 201.2 (312 mg, 0.79 mmol) analogously to Example 75. HPLC: $^E t_{Ret}$=5.465 min; LC-MS: m/z 649.2 [M+H]$^+$.

Intermediate 201.2: 4-[(S)-1-(5-Bromo-pyridin-2-yl)-ethyl]-3-oxo-piperazine-1-carboxylic acid tert-butyl ester

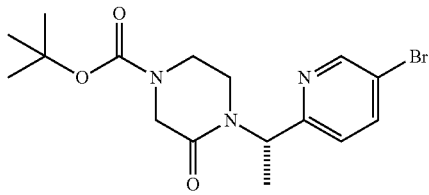 [SMILES: C[C@@H](c1ccc(Br)cn1)N1CCN(C(=O)OC(C)(C)C)CC1=O]

The title intermediate (1.0 g, 2.6 mmol, 88%) was obtained as a white solid from Intermediate 201.3 (1.43 g, 2.96 mmol) analogously to Intermediate 178.2. HPLC: $^E t_{Ret}$=5.029 min; LC-MS: m/z 386.0 [M+H]$^+$.

Intermediate 201.3: {2-[[(S)-1-(5-Bromo-pyridin-2-yl)-ethyl]-(2-chloro-acetyl)-amino]-ethyl}-carbamic acid tert-butyl ester

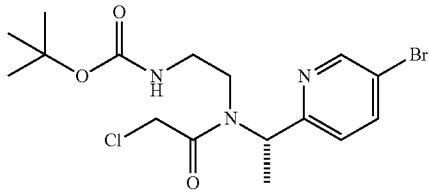 [SMILES: C[C@@H](c1ccc(Br)cn1)N(CCNC(=O)OC(C)(C)C)C(=O)CCl]

The title intermediate (1.43 g, 3.4 mmol, 72.2%) was obtained from Intermediate 201.4 (1.62 g, 4.71 mmol) and chloroacetyl chloride (0.4 mL, 4.99 mmol) analogously to Intermediate 178.3. HPLC: $^E t_{Ret}$=5.025 min; LC-MS: m/z 422.1 [M+H]$^+$.

Intermediate 201.4: {2-[(S)-1-(5-Bromo-pyridin-2-yl)-ethylamino]-ethyl}-carbamic acid tert-butyl ester

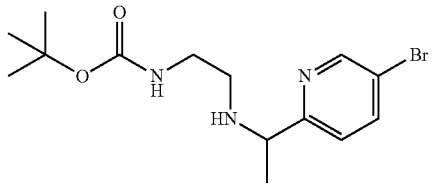 [SMILES: CC(NCCNC(=O)OC(C)(C)C)c1ccc(Br)cn1]

The title intermediate (1.69 g, 4.91 mmol, 68.1%) was obtained as a yellow solid from Intermediate 201.5 (1.45 g, 7.21 mmol) and (2-Bromo-ethyl)-carbamic acid tert-butyl ester (2.1 g, 9.38 mmol) analogously to Intermediate 178.4. HPLC: $^E t_{Ret}$=4.171 min; LC-MS: m/z 346.0 [M+H]$^+$.

Intermediate 201.5: (S)-1-(5-Bromo-pyridin-2-yl)-ethylamine

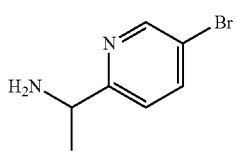

Intermediate 201.6 (345 mg, 1.13 mmol) was dissolved in MeOH (5 mL). Then a solution of 4M HCl in dioxane (1.9 mL, 7.81 mmol) was added drop wise at 0° C. for 5 min. The reaction mixture was warmed up at RT. After 1 h stirring, solvent was evaporated to give a white solid which was washed with Et$_2$O and filtered under azote flow to give a white powder (293 mg, 1.05 mmol, 93%). HPLC: $^E t_{Ret}$=3.025 min; LC-MS: m/z 202.9 [M+H]$^+$.

Intermediate 201.6: 2-Methyl-propane-2-sulfinic acid [(S)-1-(5-bromo-pyridin-2-yl)-ethyl]-amide

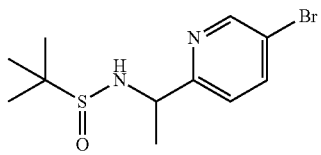 [SMILES: CC(NS(=O)C(C)(C)C)c1ccc(Br)cn1]

To a solution of Intermediate 201.7 (3.67 g, 12.68 mmol) in DCM (72 mL) was added drop wise 3M of Et$_2$O solution of methylmagnesium bromide (8.5 mL, 25.4 mmol) at −60° C. The reaction mixture became intense orange coloured, and then was warmed up to −50° C. for 30 min. Then the reaction mixture was warmed up slowly to 0° C. and the temperature was maintained at 0° C. with an ice bath for 3 h. The reaction mixture was slowly poured into vigorously stirring cold saturated solution of NH$_4$Cl (100 mL). The organic layer was separated and the aqueous layer was extracted twice with DCM. The combined organic layers were dried over MgSO4, filtered and evaporated to give a beige powder. The crude material was pre-absorbed onto SiO$_2$ and submitted to SiO$_2$ column chromatography (elution with a gradient AcOEt/hexane from 40:60 to 100:0). First eluting was collected and evaporated gave the title intermediate (2.88 g, 9.25 mol, 72.9%). HPLC: $^E t_{Ret}$=4.654 min; LC-MS: m/z 307.0 [M+H]$^+$.

Intermediate 201.7: 2-Methyl-propane-2-sulfinic acid 1-(5-bromo-pyridin-2-yl)-meth-(E)-ylideneamide

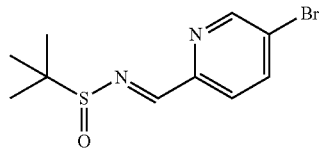

To a solution of 5-bromo-2-formyl-pyridine (3.0 g, 16.1 mmol) in dry THF (95 mL), (S)-tert-butylsulfinamide (2.05 g, 16.9 mmol) was added at RT under argon. Then titanium tetra-isopropoxyide (7 mL, 33.9 mmol) was added drop wise. The reaction mixture was stirred at 73° C. (external temperature) for 2.5 h, and was allowed to cool down. The reaction mixture was slowly poured into a vigorously stirring mixture of ca. 200 mL of brine and ice. The slurry was filtered and washed with DCM. The organic layer was separated and the aqueous layer was extracted twice with DCM. The combined organic layers were washed with brine, dried over MgSO4, filtered, evaporated to give a brown solid. The product was triturated in cold ether and successive filtered solids were combined to give the title intermediate (3.66 g, 12.4 mmol, 77%). HPLC: $^E t_{Ret}$=4.987 min; LC-MS: m/z 291.0 [M+H]$^+$.

Example 202

(S)-1-(4-Chloro-phenyl)-7-isopropoxy-6-methoxy-2-{4-[(S)-1-(2-oxo-tetrahydro-pyrimidin-1-yl)-ethyl]-phenyl}-1,4-dihydro-2H-isoquinolin-3-one

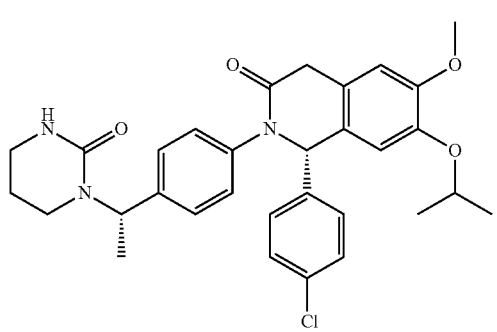 [SMILES: COc1cc2c(cc1OC(C)C)[C@H](c1ccc(Cl)cc1)N(c1ccc([C@H](C)N3CCCNC3=O)cc1)C(=O)C2]

The title compound (22 mg, 0.04 mmol, 13%) was obtained as a pale yellow solid from Intermediate 202.1 (86 mg, 0.304 mmol) and Intermediate 75.6 (100 mg, 0.289 mmol) analogously to Example 75. HPLC $^F t_{Ret}$=1.178; LC-MS: m/z 565.4 [M+NH$_4$]$^+$.

Intermediate 202.1: 1-[(S)-1-(4-Bromo-phenyl)-ethyl]-tetrahydro-pyrimidin-2-one

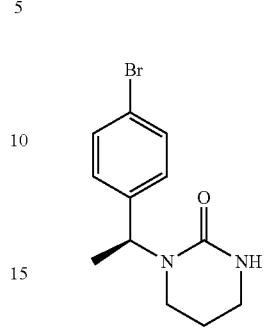

To a solution of S-(−)-1-(4-bromophenyl)ethylamine (1.06 g, 5.3 mmol) in THF (10 mL) was added drop wise at R$_T$ 3-chloropropylisocyanate (0.546 mL, 5.3 mmol). After 1 h, NaH (60% in mineral oil, 0.223 g, 5.57 mmol) was added and the resulting suspension was stirred at RT for 15 h. The reaction was quenched with H$_2$O and NaHCO$_3$ and THF was removed by evaporation. The residue was partioned between DCM and H$_2$O. After separation, the aqueous phase was re-extracted three times with DCM, the combined organic extracts were washed with H$_2$O, saturated brine, dried over Na$_2$SO$_4$, filtered and evaporated to dryness. The resulting crude material was purified by Combi-Flash Companion™ (Isco Inc.) column chromatography (SiO$_2$; gradient elution, DCM/[DCM/EtOH 9:1] 1:0→3:7)) to yield the title intermediate (1.39 g, 4.92 mmol, 93%) as colorless crystals. HPLC: $^F t_{Ret}$=0.992; LC-MS: m/z 283.2 [M+H]$^+$.

Example 203

(S)-7-((R)-sec-Butoxy)-1-(4-chloro-phenyl)-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one

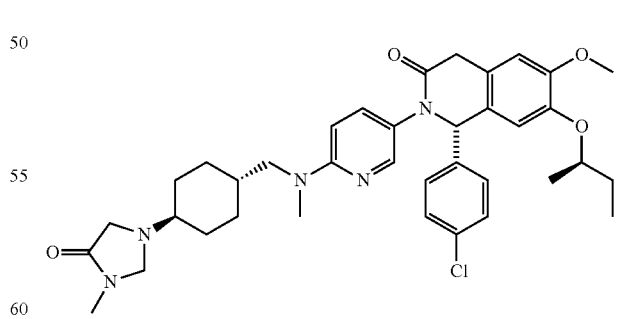

The title compound (100 mg, 0.150 mmol, 41%) was obtained as slightly yellow crystals from Intermediate 198.1 (135 mg, 0.367 mmol) and Intermediate 132.1 (159 mg, 0.367 mmol) analogously to Example 130. HPLC: $^D t_{Ret}$=1.15 min; LC-MS: m/z 660.6 [M+H]$^+$.

Example 204

(S)-1-(4-Chloro-phenyl)-7-cyclobutoxy-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one

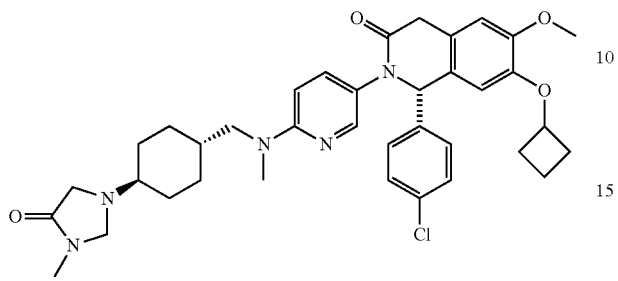

The title compound (184 mg, 0.277 mmol, 52%) was obtained as beige crystals from Intermediate 204.1 (190 mg, 0.526 mmol) and Intermediate 132.1 (227 mg, 0.526 mmol) analogously to Example 130. HPLC: $^Dt_{Ret}$=1.11 min; LC-MS: m/z 658.6 [M+H]$^+$.

Intermediate 204.1: (S)-1-(4-Chloro-phenyl)-7-cyclobutoxy-6-methoxy-1,4-dihydro-2H-isoquinolin-3-one

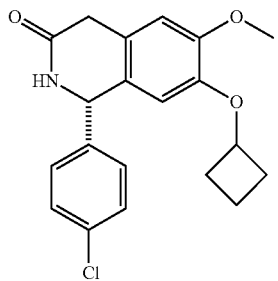 [SMILES: COc1cc2c(cc1OC1CCC1)[C@H](c1ccc(Cl)cc1)NC(=O)C2]

The title intermediate (555 mg, 1.536 mmol, 32%) was obtained as white crystals from Intermediate 198.2 (1.50 g, 4.84 mmol) and cyclobutanol (0.529 g, 0.726 mmol) analogously to Intermediate 198.1. HPLC: $^Dt_{Ret}$=1.05 min; LC-MS: m/z 358.3 [M+H]$^+$.

Example 205

(S)-1-(4-Chloro-phenyl)-6-methoxy-2-(6-{methyl-[4-(3-methyl-4-oxo-imidazolidin-1-yl)-trans-cyclohexylmethyl]-amino}-pyridin-3-yl)-7-[(S)-1-(tetrahydro-furan-2-yl)methoxy]-1,4-dihydro-2H-isoquinolin-3-one

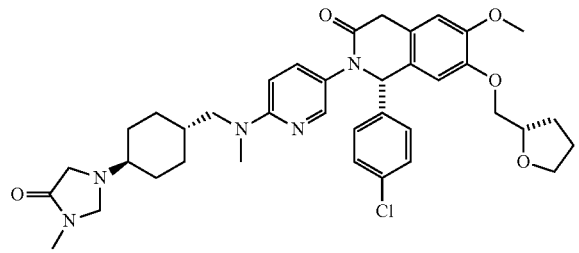

The title compound (110 mg, 0.158 mmol, 41%) was obtained as yellow crystals from Intermediate 205.1 (150 mg, 0.383 mmol) and Intermediate 132.1 (166 mg, 0.383 mmol) analogously to Example 130. HPLC: $^Dt_{Ret}$=1.01 min; LC-MS: m/z 688.7 [M+H]$^+$.

Intermediate 205.1: (S)-1-(4-Chloro-phenyl)-6-methoxy-7-[(S)-1-(tetrahydro-furan-2-yl)methoxy]-1,4-dihydro-2H-isoquinolin-3-one

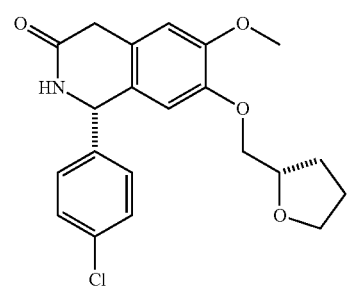

The title intermediate (132 mg, 0.340 mmol, 34%) was obtained as white crystals from Intermediate 198.2 (310 mg, 1.00 mmol) and (S)-(tetrahydrofuran-2-yl)-methanol (155 mg, 1.50 mmol), analogously to Intermediate 198.1. HPLC: $^Dt_{Ret}$=0.96 min; LC-MS: m/z 388.3 [M+H]$^+$.

Example 206

1-(4-Chloro-phenyl)-7-isopropoxy-6-methoxy-2-[4-(2-oxo-pyrrolidin-1-yl)-phenyl]-1,4-dihydro-2H-isoquinolin-3-one

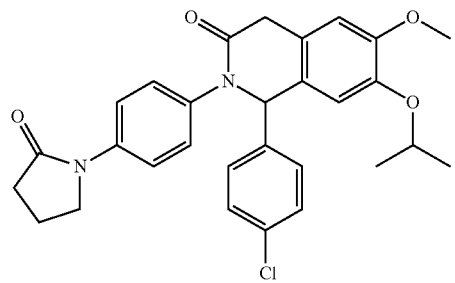 [SMILES: COc1cc2c(cc1OC(C)C)C(c1ccc(Cl)cc1)N(c1ccc(N3CCCC3=O)cc1)C(=O)C2]

A suspension of Intermediate 166.2 (150 mg, 0.274 mmol), 2-pyrrolidinone (25.9 mg, 0.30 mmol), Cu(I)I (2.61 mg, 0.014 mmol), glycine (4.11 mg, 0.055 mmol) and tripotassium phosphate (145 mg, 0.685 mmol) in THF (1.5 mL) was heated at 70° C. for 17 h. The reaction mixture was diluted with EtOAc, washed with saturated aqueous solution of NaHCO$_3$ and brine. The combined organic layers were dried over Na$_2$SO$_4$, filtered and evaporated to dryness. The resulting crude material was purified by Combi-Flash Companion™ (Isco Inc.) column chromatography (SiO$_2$; gradient elution AcOEt/DCM=7:3) to yield the title compound (26 mg, 0.051 mmol, 18.8%). HPLC: $^Kt_{Ret}$=6.81 min; LC-MS: m/z 505.4 [M+H]$^+$.

Example 207

(S)-1-(4-Chloro-phenyl)-6-methoxy-2-(5-{methyl-[4-(3-methyl-4-oxo-imidazolidin-1-yl)-trans-cyclohexylmethyl]-amino}-pyrazin-2-yl)-7-[(R)-1-(tetrahydro-furan-2-yl)methoxy]-1,4-dihydro-2H-isoquinolin-3-one

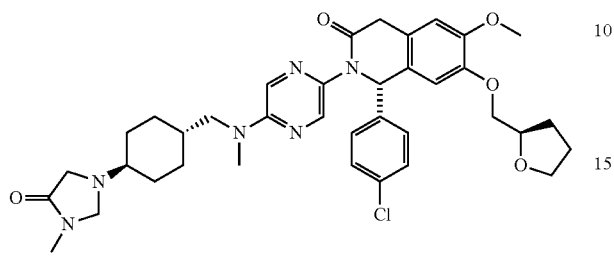

The title compound (48 mg, 0.07 mmol, 9.0%) was obtained as slightly yellow foam from Intermediate 205.1 (300 mg, 0.77 mmol) and Intermediate 149.1 (296 mg, 0.77 mmol) analogously to Example 130. HPLC: $^{E}t_{Ret}$=4.686 min; LC-MS: m/z 689.7 [M+H]$^{+}$.

Example 208

1-(4-Chloro-phenyl)-7-isopropoxy-6-methoxy-2-[4-(2-oxo-imidazolidin-1-yl)-phenyl]-1,4-dihydro-2H-isoquinolin-3-one

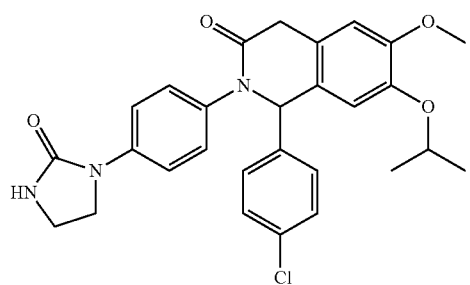 [SMILES: COc1cc2c(cc1OC(C)C)C(c1ccc(Cl)cc1)N(c1ccc(N3CCNC3=O)cc1)C(=O)C2]

The title compound (7.8 mg, 0.015 mmol, 2.5%) was obtained as a white solid from Intermediate 166.2 (340 mg, 0.621 mmol) and Imidazolidin-2-one (107 mg, 1.24 mmol) by the reported method in Synthesis, 2008, 9, pp 1359-1366. HPLC: $^{E}t_{Ret}$=5.090 min; LC-MS: m/z 506.0 [M+H]$^{+}$.

Example 209

(S)-1-(4-Chloro-phenyl)-7-cyclobutoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one

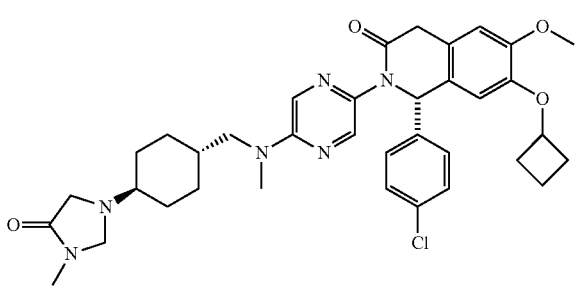

The title compound (126 mg, 0.189 mmol, 38%) was obtained as a yellow foam from Intermediate 204.1 (181 mg, 0.50 mmol) and Intermediate 149.1 (193 mg, 0.50 mmol), analogously to Example 130. HPLC: $^{D}t_{Ret}$=1.16 min; LC-MS: m/z 659.6 [M+H]$^{+}$.

Example 210

(S)-7-((R)-sec-Butoxy)-1-(4-chloro-phenyl)-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one

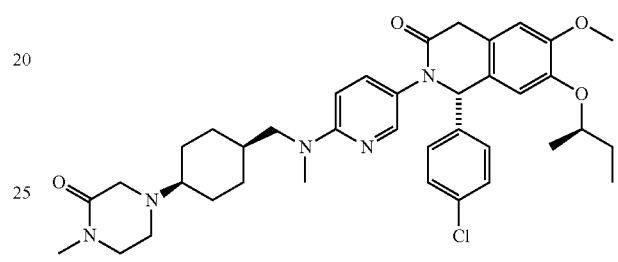

The title compound (176 mg, 0.258 mmol, 47%) was obtained as slightly yellow crystals from Intermediate 198.1 (200 mg, 0.55 mmol) and Intermediate 130.1 (246 mg, 0.55 mmol), analogously to Example 130. HPLC: $^{D}t_{Ret}$=1.05 min; LC-MS: m/z 674.6 [M+H]$^{+}$.

Example 211

(S)-1-(4-Chloro-phenyl)-7-cyclobutoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one

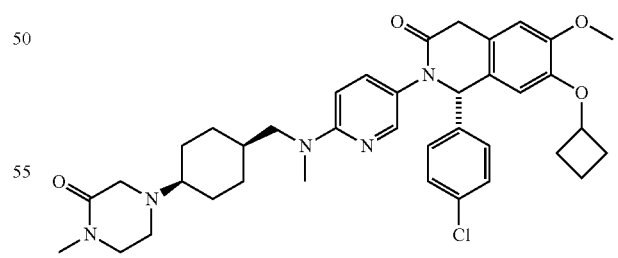

The title compound (137 mg, 0.202 mmol, 48%) was obtained as slightly yellow crystals from Intermediate 204.1 (150 mg, 0.415 mmol) and Intermediate 130.1 (187 mg, 0.415 mmol), analogously to Example 130. HPLC: $^{D}t_{Ret}$=0.99 min; LC-MS: m/z 672.7 [M+H]$^{+}$.

Example 212

(S)-1-(4-Chloro-phenyl)-6-methoxy-2-(6-{methyl-[4-(4-methyl-3-oxo-piperazin-1-yl)-trans-cyclohexylmethyl]-amino}-pyridin-3-yl)-7-[(R)-1-(tetrahydro-furan-2-yl)methoxy]-1,4-dihydro-2H-isoquinolin-3-one

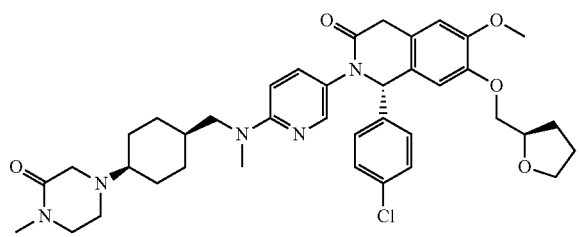 [SMILES: COc1cc2c(cc1OC[C@H]1CCCO1)[C@H](c1ccc(Cl)cc1)N(c1ccc(N(C)C[C@H]3CC[C@@H](N4CCN(C)C(=O)C4)CC3)nc1)C(=O)C2]

The title compound (17.1 mg, 0.024 mmol, 3.2%) was obtained as slightly yellow foam from Intermediate 205.1 (300 mg, 0.77 mmol) and Intermediate 130.1 (342 mg, 0.77 mmol) analogously to Example 130. HPLC: $^{E}t_{Ret}$=4.10 min; LC-MS: m/z 702.0 [M+H]$^+$.

Intermediate 213.1: 2-{4-[(S)-1-(4-Chloro-phenyl)-7-isopropoxy-6-methoxy-3-oxo-3,4-dihydro-1H-isoquinolin-2-yl]-phenyl}-3-oxo-pentanenitrile

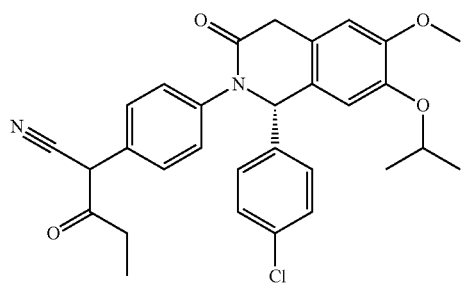 [SMILES: CCC(=O)C(C#N)c1ccc(N2C(=O)Cc3cc(OC)c(OC(C)C)cc3[C@@H]2c2ccc(Cl)cc2)cc1]

To a mixture of Intermediate 164.2 (138 mg, 0.30 mmol) and ethylpropionate (0.14 mL, 1.2 mmol) in THF (0.8 mL) was added 1M THF solution of LiHMDS at 0° C. (ice bath). The resulting mixture was stirred at 0° C. for 30 min, a 0.25M HCl aqueous solution was added to quench the reaction and the mixture was extracted with AcOEt (2×). The combined organic fractions were dried over Na$_2$SO$_4$, filtered and evaporated to dryness. The resulting crude material was purified by Combi-Flash Companion™ (Isco Inc.) column chromatography (SiO$_2$; gradient elution AcOEt/DCM.) to yield the title intermediate (100 mg, 0.17 mmol, 58% yield). HPLC: $^{G}t_{Ret}$=7.619 min; LC-MS: m/z 517.4 [M+H]$^+$.

Intermediate 214.1: 4-[(S)-1-(4-Iodo-phenyl)-ethyl]-morpholin-3-one

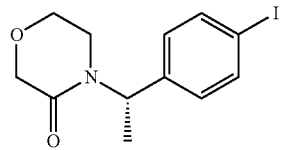 [SMILES: C[C@@H](c1ccc(I)cc1)N1CCOCC1=O]

The title intermediate (239 mg, 0.70 mmol, 81%) was obtained as a white solid from Intermediate 214.2 (320 mg, 0.87 mmol) analogously to Intermediate 178.2. HPLC: $^{E}t_{Ret}$=5.620 min; LC-MS: m/z 331.82 [M+H].

Intermediate 214.2: 2-(2-Chloro-ethoxy)-N—[(S)-1-(4-iodo-phenyl)-ethyl]-acetamide

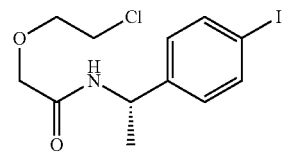 [SMILES: C[C@H](NC(=O)COCCCl)c1ccc(I)cc1]

To a solution of (2-chloro-ethoxy)-acetyl chloride (206 mg, 1.31 mmol) (which was made by the reported method in Heterocycles, vol 74, pp 437-445) in THF (5 mL) was added Intermediate 178.5 (216 mg, 0.87 mmol) and Et$_3$N (0.48 mL, 3.5 mmol). After stirring for over night at RT, it was quenched by addition of a saturated aqueous solution of NaHCO$_3$ and extracted with EtOAc. The organic phase was washed with a saturated aqueous solution of NaHCO$_3$, dried (Na$_2$SO$_4$), filtered and concentrated. The residue was purified by column chromatography to yield (320 mg, 0.87 mmol, 100%) of the title compound as a beige oil. HPLC: $^{E}t_{Ret}$=5.088 min; LC-MS: m/z 367.8 [M+H]$^+$.

Intermediate 216.1: 4-(4-{[(5-Bromo-6-fluoro-pyridin-2-yl)-methyl-amino]-methyl}-trans-cyclohexyl)-1-methyl-piperazin-2-one

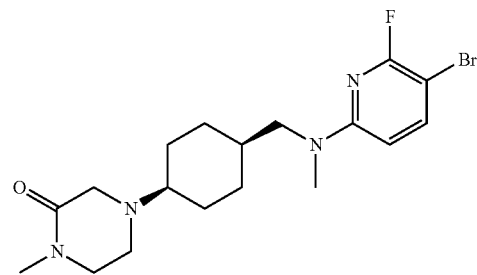 [SMILES: CN1CCN([C@H]2CC[C@@H](CN(C)c3ccc(Br)c(F)n3)CC2)CC1=O]

The title intermediate (701 mg, 1.70 mmol, 99%) was obtained as a white solid from Intermediate 216.2 (950 mg, 1.71 mmol) analogously to Example 79. HPLC: $^{G}t_{Ret}$=5.876 min; LC-MS: m/z 415.3 [M+H]$^+$.

Intermediate 216.2: {(4-{[(5-Bromo-6-fluoro-pyridin-2-yl)-methyl-amino]-methyl}-trans-cyclohexyl)-[2-(tert-butoxycarbonyl-methyl-amino)-ethyl]-amino}-acetic acid methyl ester

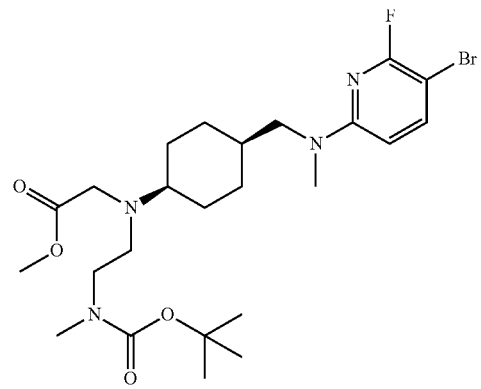 [SMILES: COC(=O)CN(CCN(C)C(=O)OC(C)(C)C)[C@H]1CC[C@@H](CN(C)c2ccc(Br)c(F)n2)CC1]

The title intermediate (956 mg, 1.75 mmol, 91%) was obtained as a white solid from Intermediate 216.3 (750 mg, 1.93 mmol) and Methyl-(2-oxo-ethyl)-carbamic acid tert-butyl ester (502 mg, 2.90 mmol) analogously to Intermediate 79.2. HPLC: $^{G}t_{Ret}$=7.363 min; LC-MS: m/z 547.2 [M+H]$^{+}$.

Intermediate 216.3: (4-{[(5-Bromo-6-fluoro-pyridin-2-yl)-methyl-amino]-methyl}-trans-cyclohexylamino)-acetic acid methyl ester

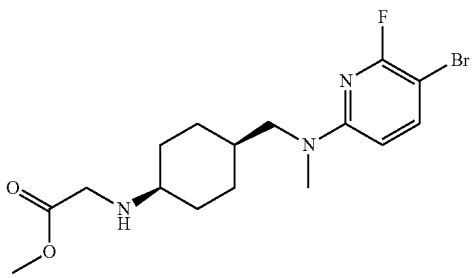 [SMILES: COC(=O)CN[C@H]1CC[C@@H](CN(C)c2ccc(Br)c(F)n2)CC1]

The title intermediate (2.99 g, 7.7 mmol, 84%) was obtained as a white solid from Intermediate 216.4 (3.55 g, 9.12 mmol) and methyl-2-bromoacetate (0.88 mL, 9.58 mmol) analogously to Intermediate 79.1. HPLC: $^{G}t_{Ret}$=6.097 min; LC-MS: m/z 390.3 [M+H]$^{+}$.

Intermediate 216.4: (Trans-4-amino-cyclohexylmethyl)-(5-bromo-6-fluoro-pyridin-2-yl)-methyl-amine

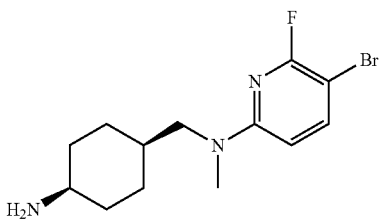 [SMILES: CN(C[C@H]1CC[C@@H](N)CC1)c1ccc(Br)c(F)n1]

The title intermediate (3.59 g, 9.23 mmol, 83%) was obtained as a white solid from Intermediate 216.5 (4.62 mg, 11.1 mmol) analogously to Intermediate 77.3. HPLC: $^{G}t_{Ret}$=5.835 min; LC-MS: m/z 316.3 [M+H]$^{+}$.

Intermediate 216.5: (4-{[(5-Bromo-6-fluoro-pyridin-2-yl)-methyl-amino]-methyl}-trans-cyclohexyl)-carbamic acid tert-butyl ester

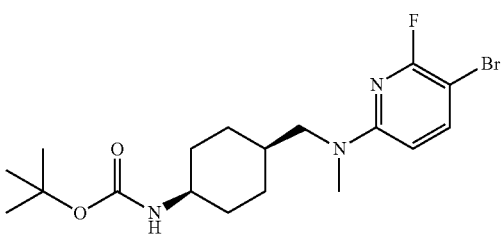 [SMILES: CN(C[C@H]1CC[C@@H](NC(=O)OC(C)(C)C)CC1)c1ccc(Br)c(F)n1]

The title intermediate (3.82 g, 9.18 mmol, 56.8%) was obtained as a white solid from Intermediate 216.6 (6.5 g, 16.1 mmol) and 37% water solution of formaldehyde (122 mL, 1616 mmol) analogously to Intermediate 77.1. HPLC: $^{G}t_{Ret}$=8.299 min; LC-MS: m/z 416.3 [M+H]$^{+}$.

Intermediate 216.6: {4-[(5-Bromo-6-fluoro-pyridin-2-ylamino)-methyl]-trans-cyclohexyl}-carbamic acid tert-butyl ester

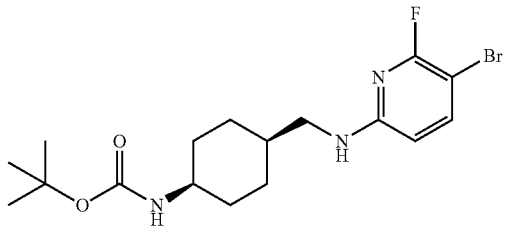 [SMILES: CC(C)(C)OC(=O)N[C@H]1CC[C@@H](CNc2ccc(Br)c(F)n2)CC1]

The title intermediate (6.56 g, 16.3 mmol, 72.4%) was obtained as a white solid from (4-formyl-cyclohexyl)-carbamic acid tert-butyl ester (5.63 g, 24.7 mmol) and 5-bromo-6-fluoro-pyridin-2-ylamine (4.3 g, 22.5 mmol) analogously to Intermediate 75.7. HPLC: $^{G}t_{Ret}$=7.827 min; LC-MS: m/z 402.3 [M+H]$^{+}$.

Intermediate 219.1: 4-((R)-1-{5-[(S)-1-(4-Chlorophenyl)-7-isopropoxy-6-methoxy-3-oxo-3,4-dihydro-1H-isoquinolin-2-yl]-pyridin-2-yl}-ethyl)-3-oxo-piperazine-1-carboxylic acid tert-butyl ester

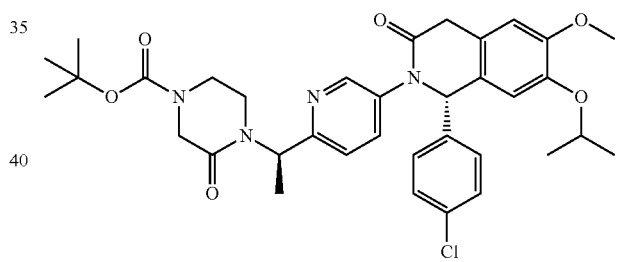

The title intermediate (100 mg, 0.154 mmol, 8.2%) was obtained as a white solid from Intermediate 75.6 (671 mg, 1.94 mmol) and Intermediate 219.2 (724 mg, 1.88 mmol) analogously to Example 75. HPLC: $^{E}t_{Ret}$=5.473 min; LC-MS: m/z 649.2 [M+H]$^{+}$.

Intermediate 219.2: 4-[(R)-1-(5-Bromo-pyridin-2-yl)-ethyl]-3-oxo-piperazine-1-carboxylic acid tert-butyl ester

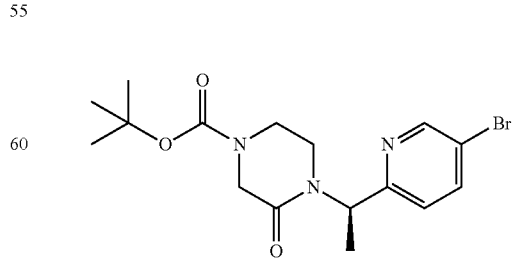

The title intermediate (764 mg, 1.97 mmol, 99%) was obtained as a brown solid from Intermediate 219.3 (837 mg, 1.99 mmol) analogously to Intermediate 178.2. HPLC: $^E t_{Ret}$=5.031 min; LC-MS: m/z 385.9 [M+H]⁺.

Intermediate 219.3: {2-[[(R)-1-(5-Bromo-pyridin-2-yl)-ethyl]-(2-chloro-acetyl)-amino]-ethyl}-carbamic acid tert-butyl ester

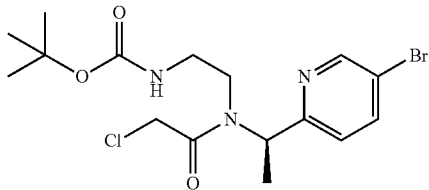 [SMILES: C[C@H](c1ccc(Br)cn1)N(CCNC(=O)OC(C)(C)C)C(=O)CCl]

The title intermediate (837 mg, 1.99 mmol, 80%) was obtained from Intermediate 219.4 (858 mg, 2.49 mmol) and chloroacetyl chloride (0.21 mL, 2.62 mmol) analogously to Intermediate 178.3. HPLC: $^E t_{Ret}$=3.024 min; LC-MS: m/z 421.9 [M+H]⁺.

Intermediate 219.4: {2-[(R)-1-(5-Bromo-pyridin-2-yl)-ethylamino]-ethyl}-carbamic acid tert-butyl ester

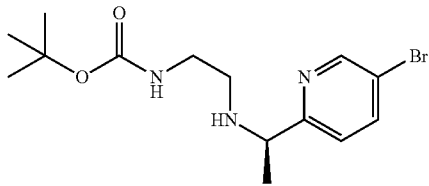 [SMILES: C[C@@H](NCCNC(=O)OC(C)(C)C)c1ccc(Br)cn1]

The title intermediate (868 mg, 2.52 mmol, 73.2%) was obtained as an orange solid from Intermediate 219.5 (693 mg, 3.45 mmol) and (2-Bromo-ethyl)-carbamic acid tert-butyl ester (1.0 g, 4.48 mmol) analogously to Intermediate 178.4. HPLC: $^E t_{Ret}$=4.085 min; LC-MS: m/z 346.1 [M+H]⁺.

Intermediate 219.4: (R)-1-(5-Bromo-pyridin-2-yl)-ethylamine

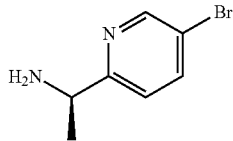

The title intermediate (1.03 g, 3.72 mmol, 92%) was obtained as a white solid from Intermediate 219.5 (1.24 g, 4.06 mmol) analogously to Intermediate 201.5. HPLC: $^E t_{Ret}$=3.024 min; LC-MS: m/z 202.9 [M+H]⁺.

Intermediate 219.5: 2-Methyl-propane-2-sulfinic acid [(R)-1-(5-bromo-pyridin-2-yl)-ethyl]-amide

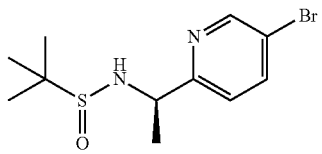 [SMILES: C[C@@H](NS(=O)C(C)(C)C)c1ccc(Br)cn1]

The title intermediate (1.24 g, 4.06 mmol, 54.6%) was obtained as a white solid from Intermediate 219.6 (2.15 g, 7.43 mmol) analogously to Intermediate 201.6. HPLC: $^E t_{Ret}$=4.624 min; LC-MS: m/z 306.83 [M+H]⁺.

Intermediate 219.6: 2-Methyl-propane-2-sulfinic acid [(R)-1-(5-bromo-pyridin-2-yl)-ethyl]-amide

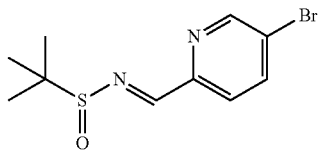

The title intermediate (2.15 g, 7.43 mmol, 46.1%) was obtained as a white solid from 5-bromo-2-formyl-pyridine (3.0 g, 16.1 mmol) and (R)-tert-butylsulfinamide (2.05 g, 16.9 mmol) analogously to Intermediate 201.7. HPLC: $^E t_{Ret}$=5.029 min; LC-MS: m/z 290.74 [M+H]⁺.

Example 223

1-(4-Chloro-phenyl)-6-hydroxy-7-isopropoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one

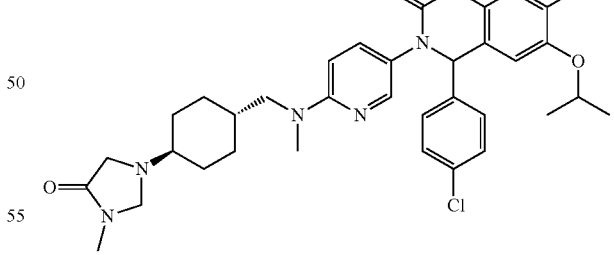

To the stirred mixture of Example 132 (100 mg, 0.155 mmol) and DMF (2.0 mL) was subsequently added sodium hydride (15.6 mg, 0.650 mmol). After stirring 15 min at RT, butane-1-thiol (0.055 mL, 0.511 mmol) was added drop wise at RT and the resulting reaction mixture immediately heated (oil bath; 160° C.) for 15 min. The resulting crude material was purified by reverse phase prep-HPLC (Waters system) to yield the racemic title compound as slightly yellow foam (42 mg, 0.066 mmol, 43%). HPLC: $^J t_{Ret}$=3.99 min; LC-MS: m/z 632.6 [M+H]⁺.

Example 224

7-((R)-sec-Butoxy)-1-(4-chloro-phenyl)-6-hydroxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one

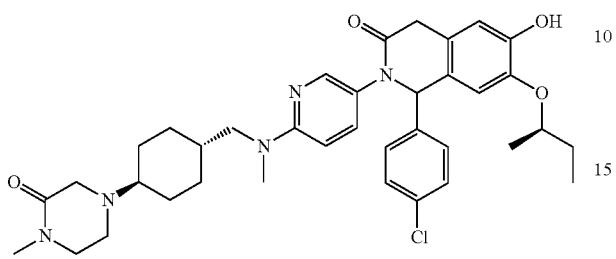

The title compound (45 mg, 0.067 mmol, 45%) was obtained as slightly yellow foam from Example 210 (100 mg, 0.148 mmol), analogously to Example 223. HPLC: $^Jt_{Ret}$=4.11 min; LC-MS: m/z 660.7 [M+H]$^+$.

Example 225

1-(4-Chloro-phenyl)-6-hydroxy-7-isopropoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one

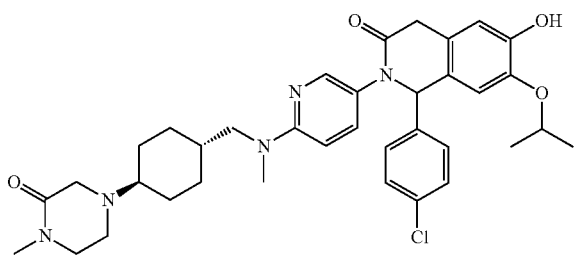 [SMILES: CC(C)Oc1cc2c(cc1O)CC(=O)N(c1ccc(N(C)C[C@H]3CC[C@H](N4CCN(C)C(=O)C4)CC3)nc1)C2c1ccc(Cl)cc1]

The title compound (33 mg, 0.051 mmol, 48%) was obtained as beige foam from Example 130 (70 mg, 0.105 mmol), analogously to Example 223. HPLC: $^Dt_{Ret}$=0.93 min; LC-MS: m/z 646.6 [M+H]$^+$.

Example 226

1-(4-Chloro-phenyl)-7-isopropoxy-6-d$_3$-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one

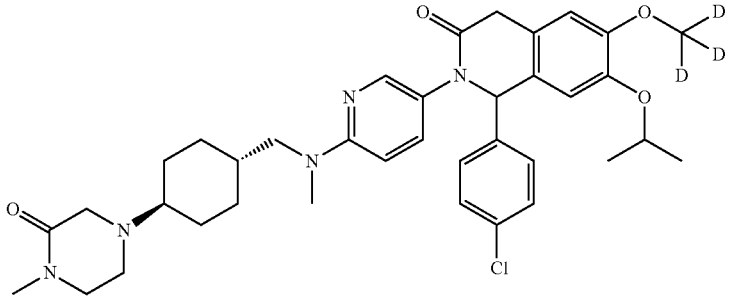 [SMILES: [2H]C([2H])([2H])Oc1cc2c(cc1OC(C)C)C(c1ccc(Cl)cc1)N(c1ccc(N(C)C[C@H]3CC[C@H](N4CCN(C)C(=O)C4)CC3)nc1)C(=O)C2]

The title compound (57 mg, 0.085 mmol, 7.4%) was obtained as a yellow foam from Intermediate 226.1 (400 mg, 1.147 mmol) and Intermediate 130.1 (507 mg, 1.147 mmol), analogously to Example 130. HPLC: $^Dt_{Ret}$=0.99 min; LC-MS: m/z 663.6 [M+H]$^+$; $^1$H NMR (600 MHz, DMSO-d$_6$) 0.89-1.13 (m, 4H) 1.17 (d, J=6.05 Hz, 3H) 1.22 (d, J=5.85 Hz, 3H) 1.56-1.64 (m, 1H) 1.63-1.82 (m, 4H) 2.18-2.27 (m, 1H) 2.66 (t, J=5.35 Hz, 2H) 2.78 (s, 3H) 2.95 (s, 3H) 3.04 (s, 2H) 3.18 (t, J=5.25 Hz, 2H) 3.26-3.33 (m, 2H) 3.55-4.01 (m, 2H) 4.38-4.46 (m, 1H) 5.95 (s, 1H) 6.51 (d, J=8.88 Hz, 1H) 6.83 (s, 1H) 6.95 (s, 1H) 7.20 (dd, J=9.08, 2.62 Hz, 1H) 7.35 (s, 4H) 7.76 (d, J=2.42 Hz, 1H).

Intermediate 226.1: 1-(4-Chloro-phenyl)-7-isopropoxy-6-d$_3$-methoxy-1,4-dihydro-2H-isoquinolin-3-one

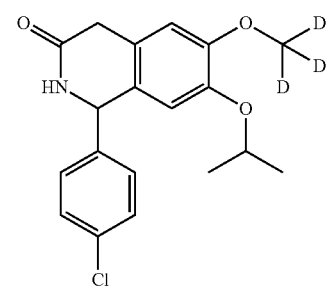 [SMILES: [2H]C([2H])([2H])Oc1cc2c(cc1OC(C)C)C(c1ccc(Cl)cc1)NC(=O)C2]

To the solution of Intermediate 226.2 (1.50 g, 4.52 mmol) and DMF (4.0 mL) was added potassium carbonate (1.25 g, 9.04 mmol) and Iodomethane-d3 (1.41 mL, 22.6 mmol). The suspension was stirred for 2 h at 60° C. The reaction mixture was extracted between EtOAc (3×) and 1M aqueous NaHCO$_3$ (1×). The organic phases were washed with brine and dried over Na$_2$SO$_4$, filtered and evaporated to dryness. Purification of the residue by normal phase column chromatography, eluting with EtOAc-hexane, gave the title compound after crystallization (DCM-hexane) as white crystals (1.10 g, 3.09 mmol, 68%): HPLC: $^Jt_{Ret}$=5.02 min; LC-MS: m/z 349.3 [M+H]$^+$.

Intermediate 226.2: 1-(4-Chloro-phenyl)-6-hydroxy-7-isopropoxy-1,4-dihydro-2H-isoquinolin-3-one

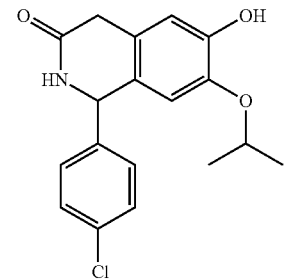 [SMILES: CC(C)Oc1cc2c(cc1O)CC(=O)NC2c1ccc(Cl)cc1]

The title intermediate (4.20 g, 12.15 mmol, 70%) was obtained as yellow foam from Intermediate 138.1 (6.0 g, 17.35 mmol), analogously to Example 223. HPLC: $^{J}t_{Ret}$=4.72 min; LC-MS: m/z 332.3 [M+H]$^{+}$.

Example 227

1-(4-Chloro-phenyl)-7-isopropoxy-6-d$_3$-methoxy-2-(6-{d$_3$-methyl-[4-(4-methyl-3-oxo-piperazin-1-yl)-trans-cyclohexylmethyl]-amino}-pyridin-3-yl)-1,4-dihydro-2H-isoquinolin-3-one

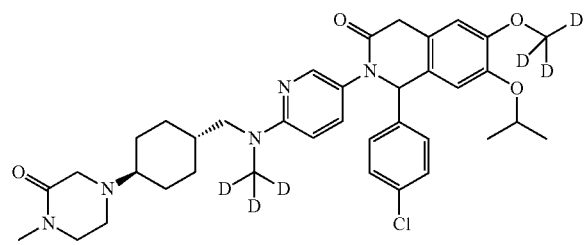 [SMILES: [2H]C([2H])([2H])Oc1cc2c(cc1OC(C)C)C(c1ccc(Cl)cc1)N(c1ccc(N(C[C@H]3CC[C@H](N4CCN(C)C(=O)C4)CC3)C([2H])([2H])[2H])nc1)C(=O)C2]

The title compound (180 mg, 0.267 mmol, 47%) was obtained as slightly yellow crystals from Intermediate 226.1 (200 mg, 0.562 mmol) and Intermediate 227.1 (253 mg, 0.562 mmol), analogously to Example 130. HPLC: $^{D}t_{Ret}$=0.99 min; LC-MS: m/z 666.6 [M+H]$^{+}$; $^{1}$H NMR (600 MHz, DMSO-d$_6$) 0.95 (q, J=11.50 Hz, 2H), 1.03-1.14 (m, 2H), 1.17 (d, J=6.05 Hz, 3H), 1.22 (d, J=6.05 Hz, 3H), 1.54-1.62 (m, 1H), 1.63-1.83 (m, 4H), 2.23 (t, J=11.40 Hz, 1H), 2.66 (t, J=5.15 Hz, 2H), 2.78 (s, 3H), 3.04 (s, 2H), 3.18 (t, J=5.25 Hz, 2H), 3.20-3.29 (m, 2H), 3.60 (d, 1H), 3.96 (d, J=19.98 Hz, 1H), 4.35-4.47 (m, J=5.99, 5.99, 5.99, 5.99, 5.99, 5.75 Hz, 1H), 5.95 (s, 1H), 6.51 (d, J=9.08 Hz, 1H), 6.83 (s, 1H), 6.95 (s, 1H), 7.20 (dd, J=9.08, 2.62 Hz, 1H), 7.35 (s, 4H), 7.76 (d, J=2.42 Hz, 1H).

Intermediate 227.1: 4-(4-{[(5-Iodo-pyridin-2-yl)-d$_3$-methyl-amino]-methyl}-trans-cyclohexyl)-1-methyl-piperazin-2-one

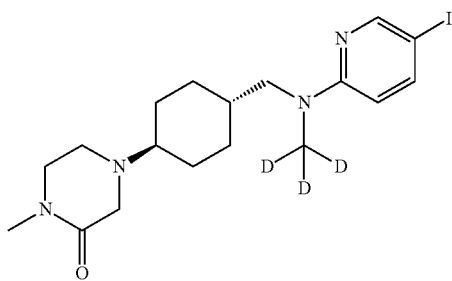 [SMILES: [2H]C([2H])([2H])N(C[C@H]1CC[C@H](N2CCN(C)C(=O)C2)CC1)c1ccc(I)cn1]

The title intermediate (4.51 g, 10.03 mmol, 85%) was obtained as beige crystals from Intermediate 227.2 (7.55 g, 11.77 mmol), analogously to Example 130.1. HPLC: $^{D}t_{Ret}$=0.77 min; LC-MS: m/z 446.3 [M+H]$^{+}$.

Intermediate 227.2: [[2-(tert-Butoxycarbonyl-methyl-amino)-ethyl]-(4-{[(5-iodo-pyridin-2-yl)-d$_3$-methyl-amino]-methyl}-trans-cyclohexyl)-amino]-acetic acid methyl ester

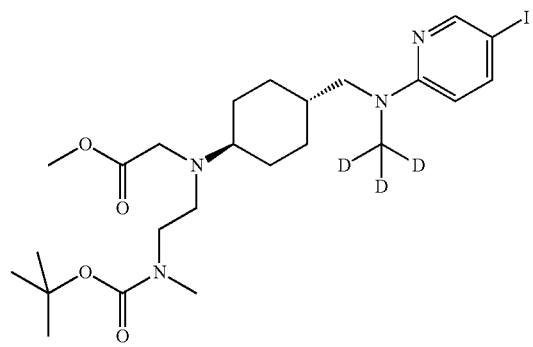 [SMILES: [2H]C([2H])([2H])N(C[C@H]1CC[C@H](N(CCN(C)C(=O)OC(C)(C)C)CC(=O)OC)CC1)c1ccc(I)cn1]

The title intermediate (7.65 g, 11.92 mmol, 96%) was obtained as a colorless oil from Intermediate 227.3 (5.80 g, 12.42 mmol), analogously to Example 130.2. HPLC: $^{D}t_{Ret}$=1.12 min; LC-MS: m/z 578.1 [M+H]$^{+}$.

Intermediate 227.3: (4-{[(5-Iodo-pyridin-2-yl)-d$_3$-methyl-amino]-methyl}-trans-cyclohexyl-amino)-acetic acid methyl ester

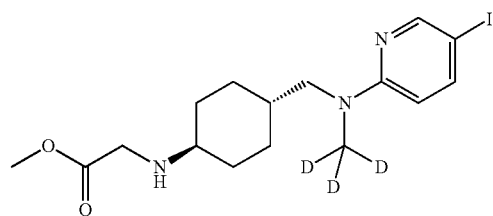 [SMILES: [2H]C([2H])([2H])N(C[C@H]1CC[C@H](NCC(=O)OC)CC1)c1ccc(I)cn1]

The title intermediate (5.90 g, 12.63 mmol, 90%) was obtained as a beige oil from Intermediate 227.4 (6.10 g, 17.34 mmol), analogously to Example 130.3. HPLC: $^{D}t_{Ret}$=0.69 min; LC-MS: m/z 420.9 [M+H]$^{+}$.

Intermediate 227.4: (Trans-4-amino-cyclohexylmethyl)-(5-iodo-pyridin-2-yl)-d$_3$-methyl-amine

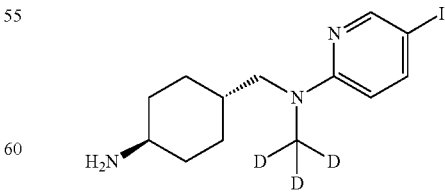

The title intermediate (6.22 g, 17.68 mmol, 94%) was obtained as a beige crystals from Intermediate 227.5 (8.50 g, 18.77 mmol), analogously to Example 130.4. HPLC: $^{D}t_{Ret}$=0.66 min; LC-MS: m/z 349.0 [M+H]$^{+}$.

Intermediate 227.5: (4-{[(5-Iodo-pyridin-2-yl)-d₃-methyl-amino]-methyl}-trans-cyclohexyl)-carbamic acid tert-butyl ester

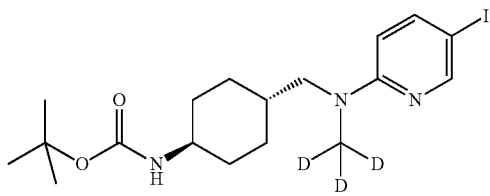 [SMILES: [2H]C([2H])([2H])N(C[C@H]1CC[C@H](NC(=O)OC(C)(C)C)CC1)c1ccc(I)cn1]

The title intermediate (8.60 g, 18.99 mmol, 56%) was obtained as a beige crystals from Intermediate 227.6 (8.40 g, 33.9 mmol), analogously to Example 130.5. HPLC: $^D t_{Ret}$=1.41 min; LC-MS: m/z 449.3 [M+H]⁺.

Intermediate 227.6: (Trans-4-d₃-methylaminomethyl-cyclohexyl)-carbamic acid tert-butyl ester

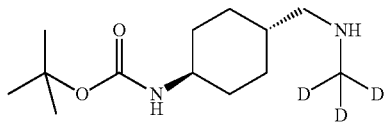 [SMILES: [2H]C([2H])([2H])NC[C@H]1CC[C@H](NC(=O)OC(C)(C)C)CC1]

The title intermediate (8.50 g, 34.3 mmol, 51%) was obtained as a beige crystals from trans-(4-formyl-cyclohexyl)-carbamic acid tert-butyl (15.5 g, 67.5 mmol) and HCl salt of CD₃NH₂ (5.05 g, 70.9 mmol) analogously to Example 130.6. MS: m/z 245.38 [M+H]⁺; ¹H NMR (400 MHz, DMSO-d₆): 0.85-1.16 (m, 4H), 1.33-1.54 (m, 2H), 1.35 (s, 9H), 1.75 (d, 4H), 2.58 (d, 2H), 3.12 (m, 1H), 6.69 (d, 1H).

Example 228

(S)-1-(4-Chloro-phenyl)-7-isopropoxy-6-methoxy-2-(6-{d3-methyl-[4-(4-methyl-3-oxo-piperazin-1-yl)-trans-cyclohexylmethyl]-amino}-pyridin-3-yl)-1,4-dihydro-2H-isoquinolin-3-one

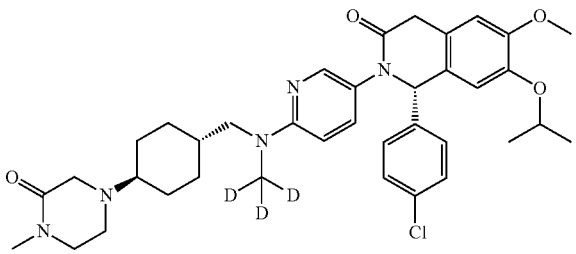 [SMILES: [2H]C([2H])([2H])N(C[C@H]1CC[C@H](N2CCN(C)C(=O)C2)CC1)c1ccc(N2C(=O)Cc3cc(OC)c(OC(C)C)cc3[C@@H]2c2ccc(Cl)cc2)cn1]

The title compound (244 mg, 0.364 mmol, 42%) was obtained as white crystals from Intermediate 75.6 (300 mg, 0.859 mmol) and Intermediate 227.1 (386 mg, 0.859 mmol), analogously to Example 130. HPLC: $^D t_{Ret}$=1.00 min; LC-MS: m/z 663.6 [M+H]⁺; ¹H NMR (600 MHz, DMSO-d₆) 0.95 (q, J=11.64 Hz, 2H), 1.05-1.15 (m, 2H), 1.17 (d, J=6.05 Hz, 3H), 1.22 (d, J=6.05 Hz, 3H), 1.54-1.63 (m, 1H), 1.63-1.81 (m, 4H), 2.23 (t, J=11.20 Hz, 1H), 2.66 (t, J=5.15 Hz, 2H), 2.78 (s, 3H), 3.04 (s, 2H), 3.18 (t, J=5.25 Hz, 2H), 3.21-3.31 (m, 2H), 3.60 (d, 1H), 3.72 (s, 3H), 3.96 (d, 1H), 4.35-4.47 (m, 1H), 5.95 (s, 1H), 6.51 (d, J=9.08 Hz, 1H), 6.83 (s, 1H), 6.95 (s, 1H), 7.20 (dd, J=9.08, 2.42 Hz, 1H), 7.35 (s, 4H), 7.76 (d, J=2.42 Hz, 1H).

In another embodiment of the invention there is provided a compound as exemplified herein.

Other related reference compounds are:
1-(2-Chloro-phenyl)-6,7-diethoxy-2-(4-methoxy-phenyl)-1,4-dihydro-2H-isoquinolin-3-one,
6,7-Diethoxy-1-(2-fluoro-phenyl)-2-(4-methoxy-phenyl)-1,4-dihydro-2H-isoquinolin-3-one
6,7-Diethoxy-2-(4-methoxy-phenyl)-1-o-tolyl-1,4-dihydro-2H-isoquinolin-3-one
6,7-Diethoxy-2-(4-methoxy-phenyl)-1-(2-methoxy-phenyl)-1,4-dihydro-2H-isoquinolin-3-one
6,7-Diethoxy-1-(3-fluoro-phenyl)-2-(4-methoxy-phenyl)-1,4-dihydro-2H-isoquinolin-3-one
6,7-Diethoxy-2-(4-methoxy-phenyl)-1-m-tolyl-1,4-dihydro-2H-isoquinolin-3-one, and
6,7-Diethoxy-2-(4-methoxy-phenyl)-1-(3-methoxy-phenyl)-1,4-dihydro-2H-isoquinolin-3-one.

TABLE 2

Hdm2 and Hdm4 inhibitory activity of representative compounds of the present invention.

| Example | IC₅₀ (μM) of p53-Hdm2 inhibition (TR-FRET) Assay | IC₅₀ (μM) of p53-Hdm4 inhibition (TR-FRET) Assay |
| --- | --- | --- |
| 1 | 0.1159 | 90.18 |
| 3 | 44.9235 | nd |
| 4 | 71.1878 | nd |
| 5 | 50.6536 | nd |
| 6 | 5.505 | 57.73 |
| 7 | 70.2577 | nd |
| 8 | 0.7232 | nd |
| 9 | 5.6602 | nd |
| 10 | 16.7589 | nd |
| 12 | 0.8843 | 60.64 |
| 13 | 1.6775 | nd |
| 14 | 0.3889 | 65.67 |
| 16 | 1.3095 | nd |
| 17 | 0.9706 | 45.89 |
| 18 | 0.6247 | nd |
| 20 | 10.2885 | nd |
| 21 | 25.2904 | nd |
| 22 | 0.2458 | 51.15 |
| 23 | 1.3811 | nd |
| 24 | 0.4242 | 41.7 |
| 25 | 0.1346 | nd |
| 26 | 0.1153 | 62.61 |
| 28 | 0.0818 | 60.15 |
| 29 | 0.3316 | 38.39 |
| 30 | 0.1585 | 23.72 |
| 31 | 0.1538 | 11.38 |
| 32 | 0.1201 | 8.13 |
| 34 | 0.5927 | nd |
| 35 | 0.8769 | nd |
| 36 | 1.383 | 82.03 |
| 38 | 0.1904 | 17.46 |
| 39 | 16.203 | nd |
| 41 | 0.4105 | 41.37 |
| 42 | 0.0084 | 19.32 |
| 43 | 0.6072 | nd |
| 44 | 1.4681 | nd |
| 45 | 0.0047 | 6.01 |
| 46 | 0.0091 | 10.4 |
| 47 | 0.0035 | 4.06 |
| 48 | 0.006 | 8.01 |
| 49 | 0.0107 | nd |
| 50 | 0.0123 | 24.51 |
| 51 | 0.0037 | 4.04 |
| 52 | 0.0058 | 4.54 |
| 53 | 0.0023 | 2.3 |
| 55 | 0.1898 | 63.71 |
| 56 | 0.0471 | 26.74 |
| 57 | 0.0724 | 32.78 |
| 59 | 0.0512 | 29.06 |
| 60 | 0.0472 | 30.11 |
| 61 | 0.0426 | 30.79 |
| 62 | 0.1142 | 77.38 |
| 63 | 0.2599 | 91.98 |

TABLE 2-continued

Hdm2 and Hdm4 inhibitory activity of representative compounds of the present invention.

| Example | IC$_{50}$ (µM) of p53-Hdm2 inhibition (TR-FRET) Assay | IC$_{50}$ (µM) of p53-Hdm4 inhibition (TR-FRET) Assay |
|---|---|---|
| 64 | 0.2026 | 64.38 |
| 65 | 0.0693 | 43.66 |
| 66 | 0.106 | 67.48 |
| 67 | 0.0152 | 16.72 |
| 68 | 0.022 | 18.15 |
| 69 | 0.1119 | 41.62 |
| 70 | 0.0152 | 11.21 |
| 72 | 0.0269 | 17.86 |
| 73a | 0.0019 | 2.88 |
| 73b | 0.7875 | 52.51 |
| 75 | 0.0025 | 2.24 |
| 76 | 0.0027 | 2.89 |
| 77 | 0.0036 | 9.87 |
| 78 | 0.0049 | 22.75 |
| 79 | 0.0016 | 1.66 |
| 80 | 0.0029 | 2.8 |
| 81 | 0.0033 | 2.31 |
| 82 | 0.0063 | 7.05 |
| 83 | 0.0018 | 3.01 |
| 84 | 0.0014 | 1.84 |
| 87 | 0.0333 | 27.9 |
| 88 | 0.0349 | 24.89 |
| 89 | 0.0142 | 9 |
| 90 | 0.2167 | nd |
| 92 | 0.7191 | nd |
| 93 | 0.0215 | 12.5 |
| 94 | 0.0983 | 34.46 |
| 95 | 0.104 | 38.04 |
| 103 | 0.002 | 1.70 |
| 105 | 0.0018 | 2.03 |
| 106 | 0.0008 | 2.10 |
| 113 | 0.0014 | 1.73 |
| 122 | 0.0077 | 8.34 |
| 123 | 0.0047 | 6.83 |
| 124 | 0.0057 | nd |
| 125 | 0.007 | 8.12 |
| 130 | 0.0017 | 1.63 |
| 134 | 0.0041 | 5.09 |
| 140 | 0.0043 | 3.75 |
| 148 | 0.0012 | 2.15 |
| 149 | 0.0043 | 4.13 |
| 178 | 0.0071 | 8.58 |
| 192 | 0.521 | n.d |
| 204 | 0.0021 | 1.36 |
| 205 | 0.0038 | 1.56 |
| 218 | 0.033 | 36.5 | nd = not determined.

In another embodiment of the invention there is provided a crystalline form I of the sulphate salt of the compound of Example 106, ((S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one), and a process to make said crystalline form. The disclosed crystalline sulphate salt form I provides a significant improvement in processing properties compared to the free base amorphous form, and provides improvements in solubility and stability.

Process to Make the Crystalline Form I of the Sulphate Salt of the Compound of Example 106:

A: Slurry Method
Solvent: isopentyl alcohol
(1) About 5 mg of drug substance was first dissolved in 100 µl IPA.
(2) 364 µl 0.025N sulphuric acid was added to the solution very slowly, allowing slow precipitation during the stirring at 60° C.
(3) The suspension was stirred at room temperature overnight.
(4) The supernatant was removed by centrifugation.
(5) The solid product was dried under vacuum oven at 40° C. overnight and investigated by XRPD (X-ray powder diffraction). The process was scaled up, and scale-up samples were further characterized using XRPD. Crystalline form I was obtained.

The X-ray diffraction data were collected at room temperature using a Bruker AXS GMBH D8 Discover powder X-ray diffractometer (Cu Kα radiation) fitted with an automatic sample changer, a theta-theta goniometer, automatic beam divergence slits, a secondary monochromator and a scintillation counter. Samples were prepared for analysis by gently pressing the compound in one glass filter. The sample was rotated while being irradiated with Copper Kα1 X-rays (wavelength=1.54184 Ångstroms) with the x-ray tube operated at 40 kV/40 mA. The analyses were performed with the goniometer running in continuous mode set for a 120 second count per 0.02 degree step over a two theta range of 5 degree to 45 degree. The peaks obtained were aligned against the silicon reference standard.

Instrument Name: X-Ray Diffractometer
Model: D8 Discover
Manufacturer: Bruker AXS GMBH
Wavelength: 1.54184 A (Cu)
Generator setting: 40.00 KV, 40.00 mA
Monochromator
Detector: HI-STAR
Frame Size: 1024 pixels, 107.79 mm
Experiment Method:
2-Theta start: 5.0 degree
2-Theta end: 45.0 degree
Pixel overlap: 20%
Integration stepsize: 0.02 degree
Scan time: 120 seconds
Temperature: Room Temperature

TABLE A

XRPD data of Example 106 sulphate salt crystalline form I (A: slurry method)

| Angle 2-Theta ° | d value Angstrom | Intensity % % |
|---|---|---|
| 17.1 | 5.20 | 126 |
| 18.7 | 4.74 | 103 |
| 20.4 | 4.35 | 89.2 |
| 21.4 | 4.14 | 93.5 |
| 22.9 | 3.89 | 183 |
| 23.5 | 3.78 | 111 |
| 24.1 | 3.68 | 132 |
| 28.3 | 3.15 | 88.9 |

B: Anti-Solvent Method
Solvents: isopropyl alcohol
(1) About 5 mg of drug substance was first dissolved in 91 µl 0.025N sulfuric acid IPA.
(2) Anti-solvent methyl tert-butyl ether was added to precipitate the compound during the stirring at 55-60° C.
(3) The suspension was stirred at 55-60° C. overnight.
(4) By centrifugation, the supernatant was removed.
(5) The solid product was dried in the vacuum oven at 40° C. overnight and investigated by XRPD. The process was scaled up. Scale-up samples were further characterized using XRPD. Crystalline form I was obtained.

TABLE B

XRPD data of Example 106 sulphate salt crystalline form I
(B: Anti-solvent method)

| Angle 2-Theta ° | d value Angstrom | Intensity % % |
|---|---|---|
| 13.5 | 6.56 | 89.1 |
| 16.6 | 5.35 | 117 |
| 16.9 | 5.24 | 226 |
| 18.8 | 4.73 | 114 |
| 19.8 | 4.48 | 167 |
| 21.3 | 4.17 | 117 |
| 22.7 | 3.92 | 270 |
| 23.9 | 3.72 | 172 |
| 24.9 | 3.57 | 180 | error +/− 0.2°.

It will be appreciated by the skilled crystallographer that the relative intensities of the various peaks reported in the Tables and Figures may vary due to a number of factors such as the orientation effects of the crystals in the X-ray beam, and the purity of the material being analysed. The peak positions may also shift for variations in sample weight but will remain substantially the same.

The sulphate salt formed is believed to be the bisulphate salt.

An another embodiment of the invention there is provided a crystalline form I of (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one sulphate salt having a powder X ray diffraction pattern using Cu Kα radiation which includes the following peaks:
Angle 2-Theta °: 18.8, 21.3 and 22.7, error+/−0.2°.

FURTHER EMBODIMENTS

Figure 1:
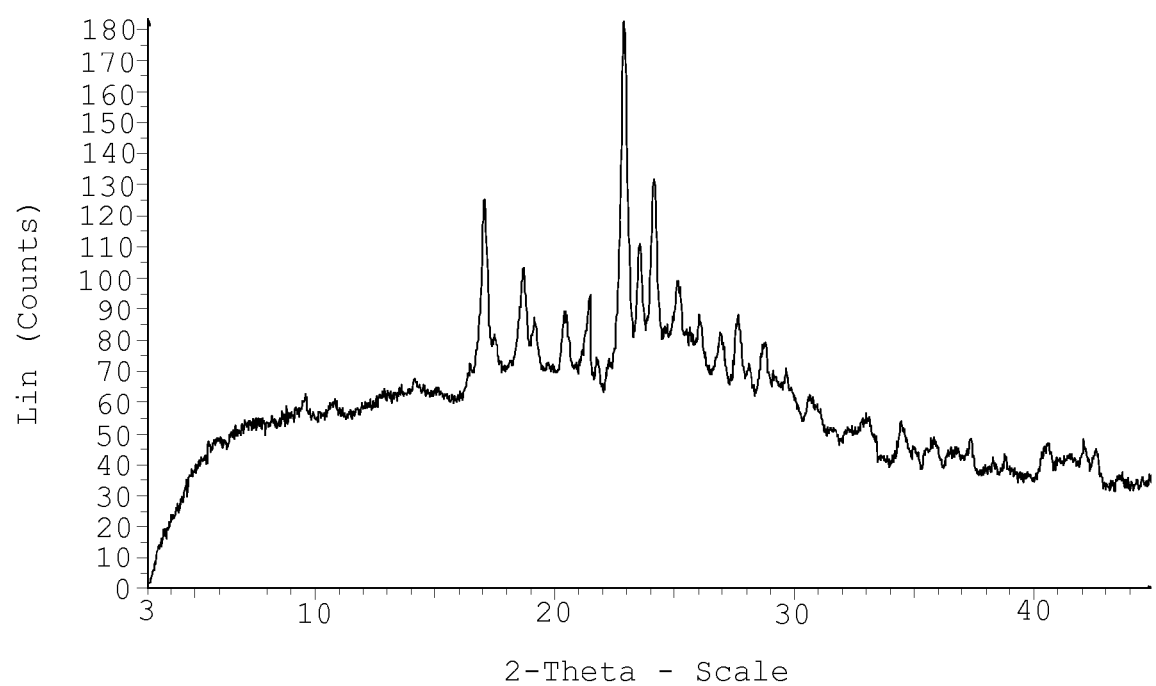
FIG. 1 discloses the X-ray powder diffraction data for Example 106 sulphate salt crystalline form I, as obtained using the slurry method.
Figure 2:
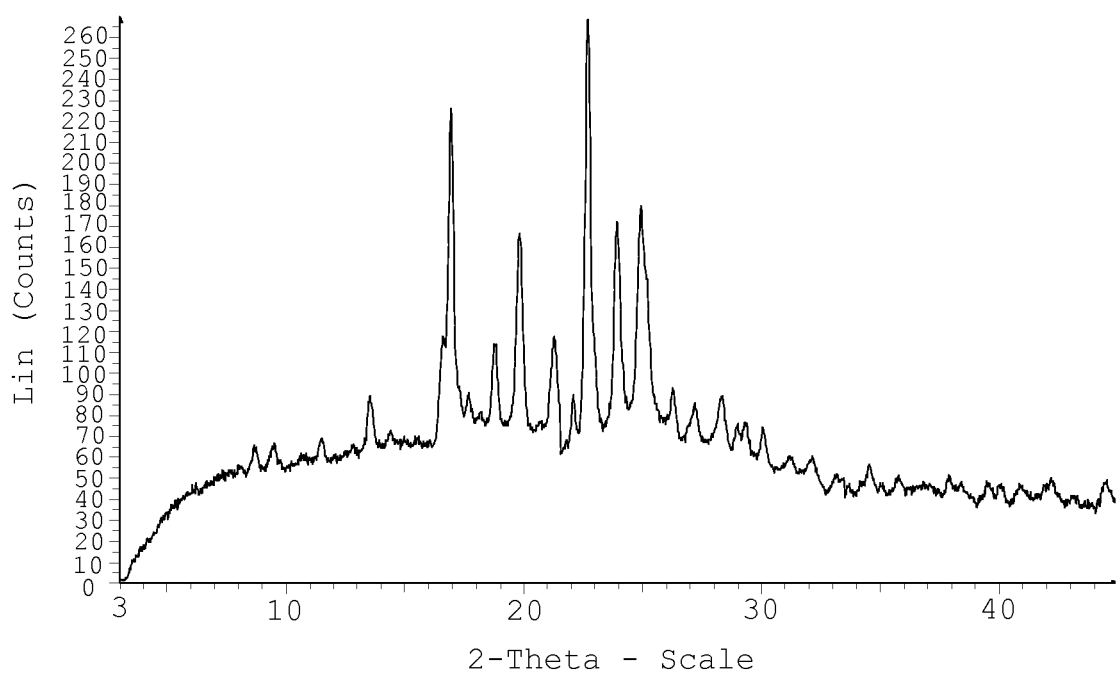
FIG. 2 discloses the X-ray powder diffraction data for Example 106 sulphate salt crystalline form I, as obtained using the anti-solvent method.

1. A substituted nitrogen containing bicyclic heterocycle of the formula (I) and/or tautomers and/or N-oxides and/or pharmaceutically acceptable salts thereof,

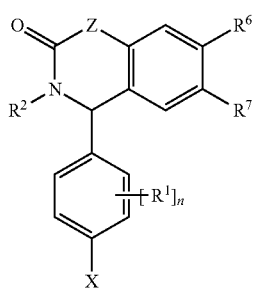

[I]

wherein
Z is $CH_2$ or N—$R^4$;
X is halogen;
$R^4$ is selected from the group consisting of
H—
$C_1$-$C_7$-alkyl-;
$R^6$ is independently selected from the group consisting of
H—
R'O—
$(R')_2$N—;
$R^7$ is independently selected from the group consisting of
R'O—
$(R')_2$N—;
R' is selected from the group consisting of
H—
$C_1$-$C_7$-alkyl-
$C_1$-$C_7$-alkenyl-
halo-$C_1$-$C_7$-alkyl-
halo-$C_1$-$C_7$-alkenyl-
$C_3$-$C_{12}$-cycloalkyl-
heterocyclyl-
aryl-
hydroxy-$C_1$-$C_7$-alkyl-
$C_1$-$C_7$-alkoxy-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
$C_3$-$C_{12}$-cycloalkyl-$C_1$-$C_7$-alkyl-
heterocyclyl-$C_1$-$C_7$-alkyl-
aryl-$C_1$-$C_7$-alkyl-
$C_1$-$C_7$-alkyl-carbonyl-
halo-$C_1$-$C_7$-alkyl-carbonyl-
hydroxy-$C_1$-$C_7$-alkyl-carbonyl-
$C_1$-$C_7$-alkoxy-$C_1$-$C_7$-alkyl-carbonyl-
amino-$C_1$-$C_7$-alkyl-carbonyl-
N—$C_1$-$C_7$-alkyl-amino-$C_1$-$C_7$-alkyl-carbonyl-
N,N-di-$C_1$-$C_7$-alkyl-amino-$C_1$-$C_7$-alkyl-carbonyl-
$C_3$-$C_{12}$-cycloalkyl-carbonyl-
heterocyclyl-$C_1$-$C_7$-alkyl-carbonyl-
aryl-$C_1$-$C_7$-alkyl-carbonyl-
$C_3$-$C_{12}$-cycloalkyl-$C_1$-$C_7$-alkyl-carbonyl-
heterocyclyl-carbonyl-
aryl-carbonyl-
$C_1$-$C_7$-alkyl-carbonyl-$C_1$-$C_7$-alkyl-
halo-$C_1$-$C_7$-alkyl-carbonyl-$C_1$-$C_7$-alkyl-
hydroxy-$C_1$-$C_7$-alkyl-carbonyl-$C_1$-$C_7$-alkyl-
$C_1$-$C_7$-alkoxy-$C_1$-$C_7$-alkyl-carbonyl-$C_1$-$C_7$-alkyl-
amino-$C_1$-$C_7$-alkyl-carbonyl-$C_1$-$C_7$-alkyl-
N—$C_1$-$C_7$-alkyl-amino-$C_1$-$C_7$-alkyl-carbonyl-$C_1$-$C_7$-alkyl-
N,N-di-$C_1$-$C_7$-alkyl-amino-$C_1$-$C_7$-alkyl-carbonyl-$C_1$-$C_7$-alkyl-
$C_3$-$C_{12}$-cycloalkyl-carbonyl-$C_1$-$C_7$-alkyl-
heterocyclyl-carbonyl-$C_1$-$C_7$-alkyl-
aryl-carbonyl-$C_1$-$C_7$-alkyl-
carbonyl-$C_1$-$C_7$-alkyl-
hydroxy-carbonyl-$C_1$-$C_7$-alkyl-
$C_1$-$C_7$-alkoxy-carbonyl-$C_1$-$C_7$-alkyl-
amino-carbonyl-$C_1$-$C_7$-alkyl-
N—$C_1$-$C_7$-alkyl-amino-carbonyl-$C_1$-$C_7$-alkyl-
N,N-di-$C_1$-$C_7$-alkyl-amino-carbonyl-$C_1$-$C_7$-alkyl-
$C_3$-$C_{12}$-cycloalkyl-carbonyl-$C_1$-$C_7$-alkyl-
heterocyclyl-carbonyl-$C_1$-$C_7$-alkyl-
aryl-carbonyl-$C_1$-$C_7$-alkyl-
$C_1$-$C_7$-alkyl-carbonyl-amino-$C_1$-$C_7$-alkyl-
$C_1$-$C_7$-alkyl-carbonyl-N—$C_1$-$C_7$-alkyl-amino-$C_1$-$C_7$-alkyl-
halo-$C_1$-$C_7$-alkyl-carbonyl-amino-$C_1$-$C_7$-alkyl-
halo-$C_1$-$C_7$-alkyl-carbonyl-N—$C_1$-$C_7$-alkyl-amino-$C_1$-$C_7$-alkyl-
wherein aryl, heterocyclyl and $C_3$-$C_{12}$-cycloalkyl are unsubstituted or substituted by 1-4 substituents selected from $C_1$-$C_7$-alkyl, halo-$C_1$-$C_7$-alkyl, halogen, hydroxy, $C_1$-$C_7$-alkoxy, amino, nitro or cyano;

$R^1$ is selected from the group consisting of
halogen-
cyano-
nitro-
$C_1$-$C_7$-alkyl-
$C_1$-$C_7$-alkenyl-
halo-$C_1$-$C_7$-alkyl-
hydroxy-
$C_1$-$C_7$-alkoxy-
amino-
N—$C_1$-$C_7$-alkyl-amino-
N,N-di-$C_1$-$C_7$-alkyl-amino-
hydroxy-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
$C_1$-$C_7$-alkyl-carbonyl-amino-$C_1$-$C_7$-alkyl-
$C_1$-$C_7$-alkyl-carbonyl-N—$C_1$-$C_7$-alkyl-amino-$C_1$-$C_7$-alkyl-;
n is 0 to 2;
$R^2$ is selected from
  (A) phenyl, 2-pyridyl or 3-pyridyl
    substituted in para-position by
    $(R^3)_2$N—Y—
      wherein Y is absent (a bond) or
      $(R^3)_2$N—Y— is selected from

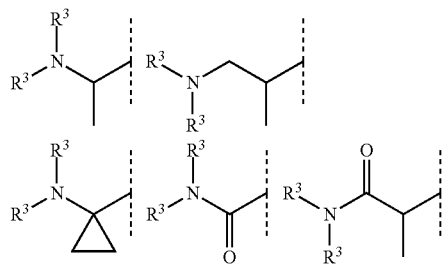

and optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy-
hydroxy-$C_1$-$C_7$-alkyl-;
or
  (B) phenyl, 2-pyridyl or 3-pyridyl
    substituted in para-position by a substituent selected from
    cyano-
    halogen-
    nitro-
    $C_1$-$C_7$-alkyl-
    halo-$C_1$-$C_7$-alkyl-
    hydroxy-$C_1$-$C_7$-alkyl-
    hydroxy-carbonyl-
    $C_1$-$C_7$-alkoxy-carbonyl-
    $C_1$-$C_7$-alkyl-carbonyl-
    $C_1$-$C_7$-alkoxy-
    (C-bound)-heterocyclyl-
      wherein (C-bound)-heterocyclyl is unsubstituted or substituted by 1-4 substituents selected from $C_1$-$C_7$-alkyl, halo-$C_1$-$C_7$-alkyl, halogen, hydroxy, $C_1$-$C_7$-alkoxy, amino, nitro or cyano;
and optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy-
hydroxy-$C_1$-$C_7$-alkyl-;
or
  (C) phenyl,
    substituted in ortho-position by
    $R^3$O—
    and substituted in para- or meta-position by a substituent selected from methyl or chloro;
or
  (D) (C-bound)-heterocycle selected from

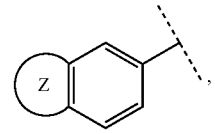

wherein Z is a 4-6 membered heterocyclic ring, annulated to phenyl in para and meta position, containing 1-3 heteroatoms selected from N, O or S,
which is optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy-
hydroxy-$C_1$-$C_7$-alkyl-;
wherein $R^3$ is independently selected from
H—
$C_1$-$C_7$-alkyl-
$C_3$-$C_{12}$-cycloalkyl-
$(R^5)_2$N—$C_3$-$C_{12}$-cycloalkyl-
$(R^5)_2$N—$C_1$-$C_7$-alkyl-
$(R^5)_2$N—$C_3$-$C_{12}$-cycloalkyl-$C_1$-$C_7$-alkyl-
$(R^5)_2$N—$C_3$-$C_{12}$-cycloalkyl-carbonyl-
$R^5$O—$C_3$-$C_{12}$-cycloalkyl-
$R^5$O—$C_1$-$C_7$-alkyl-
$R^5$O—$C_3$-$C_{12}$-cycloalkyl-$C_1$-$C_7$-alkyl-
$R^5$O—$C_3$-$C_{12}$-cycloalkyl-carbonyl-
$(R^5)_2$N-carbonyl-$C_1$-$C_7$-alkyl-
$R^5$O-carbonyl-$C_1$-$C_7$-alkyl-
aryl-$C_1$-$C_7$-alkyl-
heterocyclyl-$C_1$-$C_7$-alkyl-
$C_1$-$C_7$-alkyl-carbonyl-
heterocyclyl-carbonyl-
aryl-carbonyl-
$C_3$-$C_{12}$-cycloalkyl-carbonyl-
$C_3$-$C_{12}$-cycloalkyl-$C_1$-$C_7$-alkyl-
heterocyclyl-
aryl-
  wherein aryl, heterocyclyl and $C_3$-$C_{12}$-cycloalkyl are unsubstituted or substituted by 1-4 substituents selected from
halogen-
$C_1$-$C_7$-alkyl-
halo-$C_1$-$C_7$-alkyl- $C_1$-$C_7$-alkyl-carbonyl-
$C_3$-$C_{12}$-cycloalkyl-carbonyl-
$C_1$-$C_7$-alkyl-sulfonyl-
amino-sulfonyl-
N—$C_1$-$C_7$-alkyl-amino-sulfonyl-
N,N-di-$C_1$-$C_7$-alkyl-amino-sulfonyl-
amino-carbonyl-
N—$C_1$-$C_7$-alkyl-amino-carbonyl-
N,N-di-$C_1$-$C_7$-alkyl-amino-carbonyl-
oxo=
or
two $R^3$, together with the N to which they are attached my form a 3-9 membered heterocyclic ring, optionally containing 1-4 additional heteroatoms selected from N, O or S, said heterocyclic ring is unsubstituted or substituted by 1-3 substituents selected from:
halogen-
$C_1$-$C_7$-alkyl-
halo-$C_1$-$C_7$-alkyl-
oxo=
hydroxy-
$C_1$-$C_7$-alkoxy-
amino-
N—$C_1$-$C_1$-alkyl-amino-
N,N-di-$C_1$-$C_7$-alkyl-amino-
hydroxy-carbonyl-
$C_1$-$C_7$-alkoxy-carbonyl-
amino-carbonyl-
N—$C_1$-$C_7$-alkyl-amino-carbonyl-
N,N-di-$C_1$-$C_7$-alkyl-amino-carbonyl-
$C_1$-$C_7$-alkyl-carbonyl-
$C_1$-$C_7$-alkyl-carbonyl-amino-
$C_1$-$C_7$-alkyl-carbonyl-N—$C_1$-$C_7$-alkyl-amino-;
and
$R^5$ is independently selected from:
H—
$C_1$-$C_7$-alkyl-
$C_1$-$C_7$-alkoxy-carbonyl-$C_1$-$C_1$-alkyl-
amino-carbonyl-$C_1$-$C_7$-alkyl-
N—$C_1$-$C_7$-alkyl-amino-carbonyl-$C_1$-$C_7$-alkyl-
N,N-di-$C_1$-$C_7$-alkyl-amino-carbonyl-$C_1$-$C_7$-alkyl-
$C_1$-$C_7$-alkyl-sulfonyl-
amino-sulfonyl-
N—$C_1$-$C_7$-alkyl-amino-sulfonyl-
N,N-di-$C_1$-$C_7$-alkyl-amino-sulfonyl-
amino-carbonyl-
N—$C_1$-$C_7$-alkyl-amino-carbonyl-
N,N-di-$C_1$-$C_7$-alkyl-amino-carbonyl-
$C_3$-$C_{12}$-cycloalkyl-carbonyl-
$C_1$-$C_7$-alkoxy-carbonyl-amino-$C_1$-$C_7$-alkyl-
$C_1$-$C_7$-alkoxy-carbonyl-N—$C_1$-$C_7$-alkyl-amino-$C_1$-$C_7$-alkyl-
$C_1$-$C_7$-alkoxy-carbonyl-
or
two $R^5$, together with the N to which they are attached my form a 3-9 membered heterocyclic ring, optionally containing 1-4 additional heteroatoms selected from N, O or S, said heterocyclic ring is unsubstituted or substituted by 1-3 substituent selected from $C_1$-$C_7$-alkyl-
oxo=;
with the proviso that if Z is $CH_2$, n is 0 and $R^2$ is selected from
para-$C_1$-$C_3$-alkyl-phenyl-
para-(halo-$C_1$-$C_3$-alkyl)-phenyl-
para-$C_1$-$C_3$-alkoxy-phenyl-
para-halo-phenyl-
para-nitro-phenyl-
para-($C_1$-$C_3$-alkoxy-carbonyl)-phenyl-
para-(hydroxy-carbonyl)-phenyl-
wherein the phenyl is optionally substituted by 1-2 additional substituents,
then $R^6$ and $R^7$ are not both ethoxy or methoxy.

2. A compound according to embodiment 1, wherein $R^2$ is selected from
phenyl, 2-pyridyl or 3-pyridyl
substituted in para-position by
$(R^3)_2N$—Y—
wherein Y is absent (a bond) or
$(R^3)_2N$—Y— is selected from

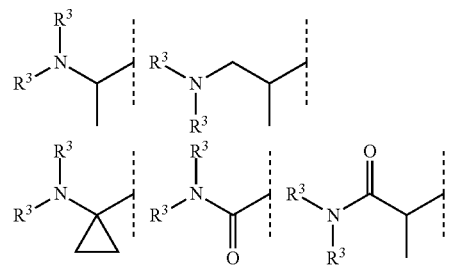

and optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy-
hydroxy-$C_1$-$C_7$-alkyl.

3. A compound according to embodiment 2, wherein Z is $CH_2$.

4. A compound according to anyone of embodiments 2 to 3, wherein
$R^6$ is selected from
R'O—
and
$R^7$ is selected from
R'O—;
or
$R^6$ is selected from
H—
and
$R^7$ is selected from
$(R')_2N$—.

5. A compound according to anyone of embodiments 2 to 4, wherein
R' is selected from the group consisting of
H—
$C_1$-$C_4$-alkyl-
$C_1$-$C_4$-alkenyl-
halo-$C_1$-$C_4$-alkyl-
$C_3$-$C_{12}$-cycloalkyl-
$C_3$-$C_{12}$-cycloalkyl-$C_1$-$C_{12}$-alkyl-
wherein aryl, heterocyclyl and $C_3$-$C_{12}$-cycloalkyl are unsubstituted or substituted by 1-2 substituents selected from $C_1$-$C_4$-alkyl, halo-$C_1$-$C_4$-alkyl, halogen, hydroxy, $C_1$-$C_4$-alkoxy, amino, nitro or cyano.

6. A compound according to anyone of embodiments 2 to 5, wherein n is 0.

7. A compound according to any one of embodiments 2 to 6, wherein
R$^3$ is independently selected from
H—
C$_1$-C$_7$-alkyl-
C$_3$-C$_{12}$-cycloalkyl-
(R$^5$)$_2$N—C$_3$-C$_{12}$-cycloalkyl-
(R$^5$)$_2$N—C$_1$-C$_7$-alkyl-
(R$^5$)$_2$N—C$_3$-C$_{12}$-cycloalkyl-C$_1$-C$_7$-alkyl-
(R$^5$)$_2$N—C$_3$-C$_{12}$-cycloalkyl-carbonyl-
R$^5$O—C$_1$-C$_7$-alkyl-
(R$^5$)$_2$N-carbonyl-C$_1$-C$_7$-alkyl-
R$^5$O-carbonyl-C$_1$-C$_7$-alkyl-
aryl-C$_1$-C$_7$-alkyl-
heterocyclyl-C$_1$-C$_7$-alkyl-
C$_1$-C$_7$-alkyl-carbonyl-
heterocyclyl-carbonyl-
C$_3$-C$_{12}$-cycloalkyl-C$_1$-C$_7$-alkyl-
heterocyclyl-
wherein aryl, heterocyclyl and C$_3$-C$_{12}$-cycloalkyl are unsubstituted or substituted by 1-4 substituents selected from
halo-
C$_1$-C$_7$-alkyl-
halo-C$_1$-C$_7$-alkyl-
C$_1$-C$_7$-alkyl-carbonyl-
C$_3$-C$_{12}$-cycloalkyl-carbonyl-
C$_1$-C$_7$-alkyl-sulfonyl-
N,N-di-C$_1$-C$_7$-alkyl-amino-carbonyl-
oxo=
or
two R$^3$, together with the N to which they are attached my form a 3-9 membered heterocyclic ring, optionally containing 1-4 additional heteroatoms selected from N, O or S, said heterocyclic ring is unsubstituted or substituted by 1-3 substituents selected from:
C$_1$-C$_7$-alkyl-
oxo=
hydroxy-
amino-
N,N-di-C$_1$-C$_7$-alkyl-amino-
hydroxy-carbonyl-
C$_1$-C$_7$-alkoxy-carbonyl-
amino-carbonyl-
N—C$_1$-C$_7$-alkyl-amino-carbonyl-
C$_1$-C$_7$-alkyl-carbonyl-
C$_1$-C$_7$-alkyl-carbonyl-amino-;
and
R$^5$ is independently selected from:
H—
C$_1$-C$_7$-alkyl-
C$_1$-C$_7$-alkoxy-carbonyl-C$_1$-C$_7$-alkyl-
amino-carbonyl-C$_1$-C$_7$-alkyl-
C$_1$-C$_7$-alkyl-sulfonyl-
N,N-di-C$_1$-C$_7$-alkyl-amino-carbonyl-
C$_1$-C$_7$-alkoxy-carbonyl-amino-C$_1$-C$_7$-alkyl-
C$_1$-C$_7$-alkoxy-carbonyl-
or
two R$^5$, together with the N to which they are attached my form a 3-9 membered heterocyclic ring, optionally containing 1-4 additional heteroatoms selected from N, O or S, said heterocyclic ring is unsubstituted or substituted by 1-3 substituent selected from C$_1$-C$_7$-alkyl-
oxo=.

8. A compound according to any one of embodiments 2 to 7, wherein
R$^3$ is independently selected from
H—
C$_1$-C$_4$-alkyl-
C$_3$-C$_{12}$-cycloalkyl-
(R$^5$)$_2$N—C$_3$-C$_7$-cycloalkyl-
(R$^5$)$_2$N—C$_1$-C$_7$-alkyl-
(R$^5$)$_2$N—C$_3$-C$_7$-cycloalkyl-C$_1$-C$_2$-alkyl-
(R$^5$)$_2$N—C$_3$-C$_7$-cycloalkyl-carbonyl-
aryl-C$_1$-C$_2$-alkyl-
heterocyclyl-C$_1$-C$_2$-alkyl-
C$_1$-C$_4$-alkyl-carbonyl-
heterocyclyl-carbonyl-
C$_3$-C$_7$-cycloalkyl-C$_1$-C$_2$-alkyl-
heterocyclyl-
wherein aryl, heterocyclyl and C$_3$-C$_{12}$-cycloalkyl are unsubstituted or substituted by 1-2 substituents selected from
halo-
C$_1$-C$_4$-alkyl-
halo-C$_1$-C$_4$-alkyl-
C$_1$-C$_4$-alkyl-carbonyl-
C$_3$-C$_7$-cycloalkyl-carbonyl-
C$_1$-C$_4$-alkyl-sulfonyl-
N,N-di-C$_1$-C$_4$-alkyl-amino-carbonyl-
oxo=
or
two R$^3$, together with the N to which they are attached my form a 4-7 membered heterocyclic ring, optionally containing 1-2 additional heteroatoms selected from N, O or S, said heterocyclic ring is unsubstituted or substituted by 1-2 substituents selected from:
C$_1$-C$_4$-alkyl-
oxo=
hydroxy-
amino-
N,N-di-C$_1$-C$_4$-alkyl-amino-
hydroxy-carbonyl-
C$_1$-C$_4$-alkoxy-carbonyl-
amino-carbonyl-
N—C$_1$-C$_4$-alkyl-amino-carbonyl-
C$_1$-C$_4$-alkyl-carbonyl-
C$_1$-C$_4$-alkyl-carbonyl-amino-;
and
R$^5$ is independently selected from:
H—
C$_1$-C$_4$-alkyl-
C$_1$-C$_4$-alkoxy-carbonyl-C$_1$-C$_2$-alkyl-
amino-carbonyl-C$_1$-C$_2$-alkyl-
C$_1$-C$_4$-alkyl-sulfonyl-
N,N-di-C$_1$-C$_4$-alkyl-amino-carbonyl-
C$_1$-C$_4$-alkoxy-carbonyl-amino-C$_1$-C$_2$-alkyl-
C$_1$-C$_4$-alkoxy-carbonyl-
or
two R$^5$, together with the N to which they are attached my form a 4-7 membered heterocyclic ring, optionally containing 1-4 additional heteroatoms selected from N, O or S, said heterocyclic ring is unsubstituted or substituted by 1-2 substituent selected from:
C$_1$-C$_4$-alkyl-
oxo=.

9. A compound of formula (I) or pharmaceutically acceptable salt and/or solvate thereof,

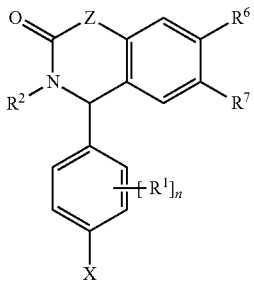

wherein
Z is $CH_2$ or $N-R^4$;
X is halogen;
$R^4$ is selected from the group consisting of
H—
$C_1$-$C_4$-alkyl-;
$R^6$ is independently selected from the group consisting of
H—
R'O—
$(R')_2N$—;
$R^7$ is independently selected from the group consisting of
R'O—
$(R')_2N$—;
each R' is independently selected from the group consisting of
H—
$C_1$-$C_6$-alkyl-
$C_1$-$C_6$-alkenyl-
halo-$C_1$-$C_4$-alkyl-
halo-$C_1$-$C_4$-alkenyl-
$C_3$-$C_7$-cycloalkyl-
heterocyclyl-
aryl-
hydroxy-$C_1$-$C_4$-alkyl-
$C_1$-$C_4$-alkoxy-$C_1$-$C_4$-alkyl-
amino-$C_1$-$C_4$-alkyl-
N—$C_1$-$C_4$-alkyl-amino-$C_1$-$C_4$-alkyl-
N,N-di-$C_1$-$C_4$-alkyl-amino-$C_1$-$C_4$-alkyl-
$C_3$-$C_7$-cycloalkyl-$C_1$-$C_4$-alkyl-
heterocyclyl-$C_1$-$C_4$-alkyl-
aryl-$C_1$-$C_4$-alkyl-
$C_1$-$C_4$-alkyl-carbonyl-
halo-$C_1$-$C_4$-alkyl-carbonyl-
hydroxy-$C_1$-$C_4$-alkyl-carbonyl-
$C_1$-$C_4$-alkoxy-$C_1$-$C_4$-alkyl-carbonyl-
amino-$C_1$-$C_4$-alkyl-carbonyl-
N—$C_1$-$C_4$-alkyl-amino-$C_1$-$C_4$-alkyl-carbonyl-
N,N-di-$C_1$-$C_4$-alkyl-amino-$C_1$-$C_4$-alkyl-carbonyl-
$C_3$-$C_7$-cycloalkyl-carbonyl-
heterocyclyl-$C_1$-$C_4$-alkyl-carbonyl-
aryl-$C_1$-$C_4$-alkyl-carbonyl-
$C_3$-$C_7$-cycloalkyl-$C_1$-$C_4$-alkyl-carbonyl-
heterocyclyl-carbonyl-
aryl-carbonyl-
$C_1$-$C_4$-alkyl-carbonyl-$C_1$-$C_4$-alkyl-
halo-$C_1$-$C_4$-alkyl-carbonyl-$C_1$-$C_4$-alkyl-
hydroxy-$C_1$-$C_4$-alkyl-carbonyl-$C_1$-$C_4$-alkyl-
$C_1$-$C_4$-alkoxy-$C_1$-$C_4$-alkyl-carbonyl-$C_1$-$C_4$-alkyl-
amino-$C_1$-$C_4$-alkyl-carbonyl-$C_1$-$C_4$-alkyl-
N—$C_1$-$C_4$-alkyl-amino-$C_1$-$C_4$-alkyl-carbonyl-$C_1$-$C_4$-alkyl-
N,N-di-$C_1$-$C_4$-alkyl-amino-$C_1$-$C_4$-alkyl-carbonyl-$C_1$-$C_4$-alkyl-
$C_3$-$C_7$-cycloalkyl-carbonyl-$C_1$-$C_4$-alkyl-
heterocyclyl-carbonyl-$C_1$-$C_4$-alkyl-
aryl-carbonyl-$C_1$-$C_4$-alkyl-
carbonyl-$C_1$-$C_4$-alkyl-
hydroxy-carbonyl-$C_1$-$C_4$-alkyl-
$C_1$-$C_4$-alkoxy-carbonyl-$C_1$-$C_4$-alkyl-
amino-carbonyl-$C_1$-$C_4$-alkyl-
N—$C_1$-$C_4$-alkyl-amino-carbonyl-$C_1$-$C_4$-alkyl-
N,N-di-$C_1$-$C_4$-alkyl-amino-carbonyl-$C_1$-$C_4$-alkyl-
$C_3$-$C_7$-cycloalkyl-carbonyl-$C_1$-$C_4$-alkyl-
heterocyclyl-carbonyl-$C_1$-$C_4$-alkyl-
aryl-carbonyl-$C_1$-$C_4$-alkyl-
$C_1$-$C_4$-alkyl-carbonyl-amino-$C_1$-$C_4$-alkyl-
$C_1$-$C_4$-alkyl-carbonyl-N—$C_1$-$C_4$-alkyl-amino-$C_1$-$C_4$-alkyl-
halo-$C_1$-$C_4$-alkyl-carbonyl-amino-$C_1$-$C_4$-alkyl-
halo-$C_1$-$C_4$-alkyl-carbonyl-N—$C_1$-$C_4$-alkyl-amino-$C_1$-$C_4$-alkyl-
wherein aryl, heterocyclyl and $C_3$-$C_7$-cycloalkyl are unsubstituted or substituted by 1-4 substituents selected from $C_1$-$C_4$-alkyl, halo-$C_1$-$C_4$-alkyl, halogen, hydroxy, $C_1$-$C_4$-alkoxy, amino, nitro or cyano;
each $R^1$ is independently selected from the group consisting of
halogen-
cyano-
nitro-
$C_1$-$C_4$-alkyl-
$C_1$-$C_4$-alkenyl-
halo-$C_1$-$C_4$-alkyl-
hydroxy-
$C_1$-$C_4$-alkoxy-
amino-
N—$C_1$-$C_4$-alkyl-amino-
N,N-di-$C_1$-$C_4$-alkyl-amino-
amino-carbonyl-amino-
N—$C_1$-$C_4$-alkyl-amino-carbonyl-amino-
N,N-di-$C_1$-$C_4$-alkyl-amino-carbonyl-amino-
$C_1$-$C_4$ alkyl-carbonyl-amino-
amino-carbonyl-
N—$C_1$-$C_4$-alkyl-amino-carbonyl-
N,N-di-$C_1$-$C_4$-alkyl-amino-carbonyl-
hydroxy-$C_1$-$C_4$-alkyl-
amino-$C_1$-$C_4$-alkyl-
N—$C_1$-$C_4$-alkyl-amino-$C_1$-$C_4$-alkyl-
N,N-di-$C_1$-$C_4$-alkyl-amino-$C_1$-$C_4$-alkyl-
$C_1$-$C_4$-alkyl-carbonyl-amino-$C_1$-$C_4$-alkyl-
$C_1$-$C_4$-alkyl-carbonyl-N—$C_1$-$C_4$-alkyl-amino-$C_1$-$C_4$-alkyl-;
n is 0, 1 or 2;
$R^2$ is selected from
(A) phenyl, 2-pyridyl or 3-pyridyl
substituted in para-position by
$(R^3)_2N$—Y—
wherein Y is absent (a bond) or
$(R^3)_2N$—Y— is selected from

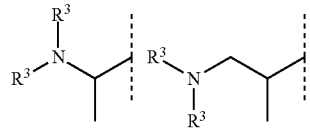

-continued

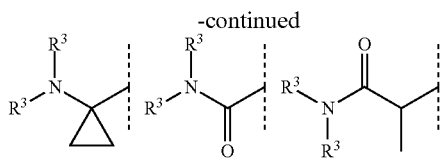

and optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
hydroxy-$C_1$-$C_4$-alkyl-;
or
(B) phenyl, 2-pyridyl or 3-pyridyl
substituted in para-position by a substituent selected from
cyano-
halogen-
nitro-
$C_1$-$C_4$-alkyl-
halo-$C_1$-$C_4$-alkyl-
hydroxy-$C_1$-$C_4$-alkyl-
hydroxy-carbonyl-
$C_1$-$C_4$-alkoxy-carbonyl-
$C_1$-$C_4$-alkyl-carbonyl-
$C_1$-$C_4$-alkoxy-
(C-bound)-heterocyclyl-
wherein (C-bound)-heterocyclyl is unsubstituted or substituted by 1-4 substituents selected from $C_1$-$C_4$-alkyl, halo-$C_1$-$C_4$-alkyl, halogen, hydroxy, $C_1$-$C_4$-alkoxy, amino, nitro or cyano;
and optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
(C-bound or N-bound)heterocyclyl-$C_1$-$C_4$-alkyl-
hydroxy-$C_1$-$C_4$-alkyl-;
or
(C) phenyl,
substituted in ortho-position by
$R^3O$—
and substituted in para- or meta-position by a substituent selected from methyl, chloro, $C_1$-$C_4$-alkyl-carbonyl- or $C_1$-$C_4$-alkoxy-carbonyl-;
(D) (C-bound)-heterocycle selected from

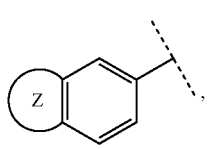

wherein Z is a 4-6 membered heterocyclic ring, annulated to phenyl in para and meta position, containing 1-3 heteroatoms selected from N, O or S,
which is optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
hydroxy-$C_1$-$C_4$-alkyl-;
(E) pyrazin-2-yl (relative to the isoquinolinone or quinazolinone), substituted at the 5 position by:

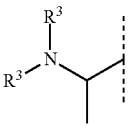

(F) pyridazin-3-yl (relative to the isoquinolinone or quinazolinone), substituted at the 6 position by:

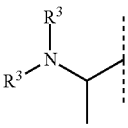

or
(G) pyrimidin-2-yl (relative to the isoquinolinone or quinazolinone), substituted at the 5 position by:

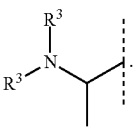

wherein each $R^3$ is independently selected from
H—
$C_1$-$C_4$-alkyl-
hydroxy-$C_1$-$C_4$-alkyl-
$C_3$-$C_7$-cycloalkyl-
$C_1$-$C_4$-alkoxy-$C_1$-$C_4$-alkyl-carbonyl-
amino-$C_1$-$C_4$-alkyl-carbonyl
N—$C_1$-$C_4$-alkyl-amino-$C_1$-$C_4$-alkyl-carbonyl
N,N-di $C_1$-$C_4$-alkyl-amino-$C_1$-$C_4$-alkyl-carbonyl
$(R^5)_2$N—$C_3$-$C_7$-cycloalkyl-
$(R^5)_2$N—$C_1$-$C_4$-alkyl-
$(R^5)_2$N—$C_3$-$C_7$-cycloalkyl-$C_1$-$C_4$-alkyl-
$(R^5)_2$N—$C_3$-$C_7$-cycloalkyl-carbonyl-
$R^5O$—$C_3$-$C_7$-cycloalkyl-
$R^5O$—$C_1$-$C_4$-alkyl-
$R^5O$—$C_3$-$C_7$-cycloalkyl-$C_1$-$C_4$-alkyl-
$R^5O$—($C_1$-$C_4$-alkyl)-$C_3$-$C_7$-cycloalkyl-$C_1$-$C_4$-alkyl-
$R^5O$-(hydroxy-$C_1$-$C_4$-alkyl)-$C_3$-$C_7$-cycloalkyl-$C_1$-$C_4$-alkyl-
$(R^5)_2$N—CO—$C_3$-$C_7$-cycloalkyl-$C_1$-$C_4$-alkyl-
$C_1$-$C_4$-alkoxycarbonyl-$C_3$-$C_7$-cycloalkyl-$C_1$-$C_4$-alkyl-
hydroxycarbonyl-$C_3$-$C_7$-cycloalkyl-$C_1$-$C_4$-alkyl-
amino-carbonyl-$C_3$-$C_7$-cycloalkyl-$C_1$-$C_4$-alkyl-
$R^5O$—$C_3$-$C_7$-cycloalkyl-carbonyl-
$(R^5)_2$N-carbonyl-$C_1$-$C_4$-alkyl-
$R^5O$-carbonyl-$C_1$-$C_4$-alkyl-
aryl-$C_1$-$C_4$-alkyl-
heterocyclyl-$C_1$-$C_4$-alkyl- C$_1$-C$_4$-alkyl-carbonyl-
halo-C$_1$-C$_4$-alkyl-carbonyl-
heterocyclyl-carbonyl-
aryl-carbonyl-
C$_3$-C$_7$-cycloalkyl-carbonyl-
C$_3$-C$_7$-cycloalkyl-C$_1$-C$_4$-alkyl-
heterocyclyl-
aryl-
  wherein aryl, heterocyclyl and C$_3$-C$_7$-cycloalkyl are unsubstituted or substituted by 1-4 substituents selected from
  halogen-
  C$_1$-C$_4$-alkyl-
  halo-C$_1$-C$_4$-alkyl-
  C$_1$-C$_4$-alkyl-carbonyl-
  C$_3$-C$_7$-cycloalkyl-carbonyl-
  C$_1$-C$_4$-alkyl-sulfonyl-
  amino-sulfonyl-
  N—C$_1$-C$_4$-alkyl-amino-sulfonyl-
  N,N-di-C$_1$-C$_4$-alkyl-amino-sulfonyl-
  amino-carbonyl-
  N—C$_1$-C$_4$-alkyl-amino-carbonyl-
  N,N-di-C$_1$-C$_4$-alkyl-amino-carbonyl-
  oxo=
or
two R$^3$, together with the N to which they are attached my form a 3, 4, 5, 6 or 7 membered heterocyclic ring, optionally containing 1, 2, 3 or 4 additional N heteroatoms and optionally containing a O atom and/or a S atom, said heterocyclic ring being unsubstituted or substituted by 1, 2 or 3 substituents selected from:
halogen-
hydroxy-C$_1$-C$_4$-alkyl-
C$_1$-C$_4$-alkyl-
halo-C$_1$-C$_4$-alkyl-
oxo=
hydroxy-
C$_1$-C$_4$-alkoxy-
amino-
N—C$_1$-C$_4$-alkyl-amino-
N,N-di-C$_1$-C$_4$-alkyl-amino-
hydroxy-carbonyl-
C$_1$-C$_4$-alkoxy-carbonyl-
amino-carbonyl-
N—C$_1$-C$_4$-alkyl-amino-carbonyl-
N,N-di-C$_1$-C$_4$-alkyl-amino-carbonyl-
C$_1$-C$_4$-alkyl-carbonyl-
C$_1$-C$_4$-alkyl-sulphonyl-
heterocyclyl-
C$_1$-C$_4$-alkyl-carbonyl-amino-
C$_1$-C$_4$-alkyl-carbonyl-N—C$_1$-C$_4$-alkyl-amino-;
and
each R$^5$ is independently selected from:
H—
C$_1$-C$_4$-alkyl-
hydroxy-C$_1$-C$_4$-alkyl-
C$_1$-C$_4$-alkyl-carbonyl-
C$_1$-C$_4$-alkoxy-carbonyl-C$_1$-C$_4$-alkyl-
amino-carbonyl-C$_1$-C$_4$-alkyl-
N—C$_1$-C$_4$-alkyl-amino-carbonyl-C$_1$-C$_4$-alkyl-
N,N-di-C$_1$-C$_4$-alkyl-amino-carbonyl-C$_1$-C$_4$-alkyl-
C$_1$-C$_4$-alkyl-sulfonyl-
amino-sulfonyl-
N—C$_1$-C$_4$-alkyl-amino-sulfonyl-
N,N-di-C$_1$-C$_4$-alkyl-amino-sulfonyl-
heterocyclyl-carbonyl-
amino-carbonyl-
N—C$_1$-C$_4$-alkyl-amino-carbonyl-
N,N-di-C$_1$-C$_4$-alkyl-amino-carbonyl-
C$_3$-C$_7$-cycloalkyl-carbonyl-
C$_1$-C$_4$-alkoxy-carbonyl-amino-C$_1$-C$_4$-alkyl-
C$_1$-C$_4$-alkoxy-carbonyl-N—C$_1$-C$_4$-alkyl-amino-C$_1$-C$_4$-alkyl-
C$_1$-C$_4$-alkoxy-carbonyl-
C$_3$-C$_7$-cycloalkyl-
hydroxy-C$_3$-C$_7$-cycloalkyl-
or
two R$^5$, together with the N to which they are attached may form a 3, 4, 5, 6 or 7 membered heterocyclic ring, optionally containing 1, 2, 3 or 4 additional N heteroatoms and/or optionally containing a O atom and/or a S atom, said heterocyclic ring being unsubstituted or substituted by from 1, 2 or 3 substituents independently selected from
C$_1$-C$_4$-alkyl-
oxo=,
C$_1$-C$_4$-alkyl-carbonyl,
C$_1$-C$_4$-alkyl-sulphonyl,
hydroxy-C$_1$-C$_4$-alkyl;
with the proviso that if Z is CH$_2$, n is 0 or 1, so that when n is 1 then R$^1$ is ortho-chloro, and R$^2$ is selected from
para-C$_1$-C$_3$-alkyl-phenyl-
para-(halo-C$_1$-C$_3$-alkyl)-phenyl-
para-C$_1$-C$_3$-alkoxy-phenyl-
para-halo-phenyl-
para-nitro-phenyl-
para-(C$_1$-C$_3$-alkoxy-carbonyl)-phenyl-
para-(hydroxy-carbonyl)-phenyl-
wherein the phenyl is optionally substituted by 1-2 additional substituents, said substituents being independently selected from halo and methyl, then R$^6$ and R$^7$ are not both ethoxy or methoxy.

10. A compound of formula (I) as described in embodiment 9, wherein
R$^6$ is selected from H, hydroxy, methoxy, ethoxy, propoxy (isopropoxy or n-propoxy), butoxy (preferably isobutoxy), morpholin-4-ylethoxy, aminoethoxy, 4-methylpiperazin-1-ylcarbonylmethoxy, dimethylaminoethoxy, dimethylaminopropoxy, hydroxyethoxy, hydroxypropoxy, dimethylaminocarbonylmethoxy, methylaminocarbonylmethoxy and d$_3$ methoxy, and preferably R$^6$ is methoxy;
R$^7$ is selected from methoxy, ethoxy, butoxy (including isobutoxy, sec-butoxy, (R)-sec-butoxy, (S)-sec-butoxy), propoxy (including isopropoxy, n-propoxy), cyclopropylmethoxy, cyclopentyloxy, morpholinyl-4-ylpropoxy, 3-hydroxypropoxy, 3-dimethylaminopropoxy, 1-ethylpropoxy, 3-aminopropoxy, cyclobutoxy, 1-methylbutoxy, 1,2-dimethylpropoxy, 3-amino-1-methyl-propoxy, cyclohexyloxy, benzyloxy, cyclohexylmethoxy, cyclobutylmethoxy, cyclopentylmethoxy, 2-methoxy-1-methyl-ethoxy (including in particular (R) 2-methoxy-1-methyl-ethoxy), 1,3-dimethylbut-3-enyloxy, 1-methyl-but-3-enyloxy, pyridin-4-ylmethoxy, trifluoromethoxy, methoxyethoxy, (R) tetrahydrofuran-2-ylmethoxy, (S) tetrahydrofuran-2-ylmethoxy, (R)-2-methoxy-propoxy, 2-methoxy-1-methyl-ethoxy, 1-hydroxycyclopropylmethoxy, 3-methoxy-propoxy, oxetan-2-ylmethoxy, 2,2-difluoro-ethoxy, isopropylamino, ethylcarbonylamino, isopropyl-propyl-amino, (dimethylaminoethyl)-isopropyl-amino, (methylcarbonylaminoethyl)isopropylamino, isobutylamino, cyclopentylmethylamino, 1-ethyl-propyl-amino, cyclohexylamino, butylamino (including sec-butylamino), cyclobutylamino, cyclopentylamino, propylamino, ethylamino, benzylamino, cyclopropylmethylamino, cyclohexylmethylamino, methylcarbonylamino, isopropylcarbonylamino, (methylcarbonyl)isopropylamino, (ethylcarbonyl)isopropylamino, (isopropyl)methyl-amino and (isopropyl)ethyl-amino, and preferably $R^7$ is isopropoxy;

n is 0 or 1;

$R^1$ is selected from hydrogen, fluoro, chloro, methyl, methoxy, bromo, nitro, amino, amino-carbonyl-amino-, methylaminocarbonylamino-, methylaminocarbonyl-, methylcarbonylamino-, ethylaminocarbonylamino-, ethylcarbonylamino-, (ethyl)methylamino-, dimethylamino-, aminocarbonyl-, hydroxymethyl-, aminomethyl-, methylcarbonylaminomethyl-, methylaminomethyl;

$R^2$ is selected from:

(A) i phenyl substituted by:
4-dimethylamino-, 4-methylamino-, 4-morpholin-4-yl-, 4-pyrrolidin-1-yl-, 4-dimethylamino-2-methoxy, 2-methoxy-4-methyl-, 2-methoxy-4-morpholin-4-yl-, 4-dimethylamino-2-methoxy-, 4-dimethylamino-2-methyl-, 4-(N-methyl-N-pyridin-4-ylmethyl-amino)-, 4-(2-oxo-pyrrolidin-1-yl)-, 4-pyrazol-1-yl-, 4-methylcarbonylamino-, 4-(2-oxo-azetidin-1-yl)-, 4-(N-methyl-N-ethyl-amino)carbonyl-, 4-(piperidine-1-carbonyl)-, 4-methylaminocarbonyl, 4-diethylaminocarbonyl-, 4-dimethylaminocarbonyl, 4-(pyrrolidine-1-carbonyl)-, 4-aminocarbonyl-, 4-(N-methyl-N-pyridin-4-yl-aminocarbonyl)-, 4-(N-pyridin-4-yl-aminocarbonyl)-, 4-(N-pyridin-3-yl-aminocarbonyl)-, 4-hydroxymethyl, 4-N-methylcarbonyl-N-methyl-amino-, 4-(N-methylcarbonyl-N-cyclopentylmethyl-amino)-, 4-(N-methyl-N-piperidin-3-yl-methyl-amino)-, 4-[methyl-(1-methyl-piperidin-3-ylmethyl)-amino]-, 4-(N-methyl-N-piperidin-4-ylmethyl-amino)-, 4-[(1-Acetyl-piperidin-4-ylmethyl)-methyl-amino]-, 4-[(1-methanesulfonyl-piperidin-4-ylmethyl)-methyl-amino]-, 4-[(4-Amino-cyclohexylmethyl)-methyl-amino]-, 4-[(4-ethylamino-cyclohexylmethyl)-methyl-amino]-, 4-{[4-(ethyl-methyl-amino)-cyclohexylmethyl]-methyl-amino}-,4-diethylamino, 4-(N-cyclopentylmethyl-N-methyl-amino)-, 4-(N-isopropyl-N-methyl-amino)-, 4-(N-cyclopentyl-N-methyl-amino)-, 4-(N-cyclohexyl-N-methyl-amino)-, 4-(N-sec-butyl-N-methyl-amino)-, 4-(N-cyclopropylmethyl-N-methyl-amino)-, 4-(N-cyclohexylmethyl-N-methyl-amino)-, 4-(N-isobutyl-N-methyl-amino)-, 4-(N-Benzyl-N-methyl-amino)-, 4-(N-ethyl-N-methyl-amino)-, 4-ethylamino-, 4-dipropylamino-, 4-(N-cyclobutyl-N-methyl-amino)-, 4-[(2-fluoro-benzyl)-methyl-amino]-, 4-[(2,3-difluoro-benzyl)-methyl-amino]-, 4-[methyl-(3-trifluoromethyl-benzyl)-amino]-, 4-[methyl-(4-trifluoromethyl-benzyl)-amino]-, 4-[(3-fluoro-benzyl)-methyl-amino]-, 4-(N-methyl-N-pyridin-3-ylmethyl-amino)-, 4-[(4-fluoro-benzyl)-methyl-amino]-, 4-[(3,4-difluoro-benzyl)-methyl-amino]-, 4-[(pyridin-4-ylmethyl)-amino]-, 4-(N-cyclopropylmethyl-N-pyridin-4-ylmethyl-amino)-, 4-(N-ethyl-N-pyridin-4-ylmethyl-amino)-, 4-[(2-morpholin-4-yl-ethyl)-pyridin-4-ylmethyl-amino]-, 4-(N-methyl-N-pyrimidin-4-ylmethyl-amino)-, 4-[(3-fluoro-pyridin-4-ylmethyl)-methyl-amino]-, 4-(N-methyl-N-thiophen-3-ylmethyl-amino)-, 4-[methyl-(3-methyl-3H-imidazol-4-ylmethyl)-amino]-, 4-(N-furan-3-ylmethyl-N-methyl-amino)-, 4-[methyl-(2-morpholin-4-yl-ethyl)-amino]-, 4-[methyl-(1-methyl-piperidin-4-ylmethyl)-amino]-, 4-[methyl-(4-propylamino-cyclohexylmethyl)-amino]-, 4-[(4-dimethylamino-cyclohexylmethyl)-methyl-amino]-, 4-[(4-amino-cyclohexylmethyl)-methyl-amino]-, 4-[(4-dimethylamino-cyclohexylmethyl)-ethyl-amino]-, 4-[methyl-(4-pyrrolidin-1-yl-cyclohexylmethyl)-amino]-, 4-[methyl-(4-piperidin-1-yl-cyclohexylmethyl)-amino]-, [4-(methyl-piperidin-4-ylmethyl-amino)-, 4-{methyl-[4-(3-methyl-4-oxo-imidazolidin-1-yl)-cyclohexylmethyl]-amino}-, 4-(3-amino-1H-pyrazol-4-yl)-, 4-(3-Amino-5-methyl-1H-pyrazol-4-yl)-, 4-(3,5-dimethyl-1H-pyrazol-4-yl)-, 4-(1-pyrrolidin-1-yl-ethyl)-, 4-(1-morpholin-4-yl-ethyl)-, 4-(1-hydroxy-ethyl)-, 4-[1-(piperidin-4-ylamino)-ethyl]-, 4-[1-(N-piperidin-4-yl-N-methylcarbonyl-amino)-ethyl]-, 4-[1-(N-methyl-N-piperidin-4-yl-amino)-ethyl]-, 4-{1-[(4-dimethylamino-cyclohexyl)-methyl-amino]-ethyl}-, 4-[1-(4-amino-cyclohexylamino)-ethyl]-, 4-[1-(4-dimethylamino-piperidin-1-yl)-ethyl]-, 4-{1-[4-(isopropyl-methyl-amino)-piperidin-1-yl]-ethyl}-, 4-(1-dimethylamino-ethyl)-, 4-[1-(4-hydroxy-piperidin-1-yl)-ethyl]-, 4-[1-(2-dimethylamino-ethylamino)-ethyl]-, 4-[1-((R)-3-hydroxy-pyrrolidin-1-yl)-ethyl]-, 4-[1-((S)-3-hydroxy-pyrrolidin-1-yl)-ethyl]-, 4-[1-((S)-3-hydroxy-piperidin-1-yl)-ethyl]-, 4-[1-((R)-3-hydroxy-piperidin-1-yl)-ethyl]-, 4-(1-thiomorpholin-4-yl-ethyl)-, 4-(1-N-isobutyl-N-methylcarbonyl-amino-ethyl)-, 4-(1-N-propyl-N-methylcarbonyl-amino-ethyl)-, 4-(1-N-isopropyl-N-methylcarbonyl-amino-ethyl)-, 4-(1-N-cyclopropyl-N-methylcarbonyl-amino-ethyl)-, 4-(1-N-cyclohexylmethyl-N-methylcarbonyl-amino-ethyl)-, 4-(1-N-cyclopentyl-N-methylcarbonyl-amino-ethyl)-, 4-(1-N-cyclohexyl-N-methylcarbonyl-amino-ethyl)-, 4-(1-N-cyclopropylmethyl-N-methylcarbonyl-amino-ethyl)-, 4-(1-N-cyclopentylmethyl-N-methylcarbonyl-amino-ethyl)-, 4-(1-N-benzyl-N-methylcarbonyl-amino-ethyl)-, 4-(1-N-cyclobutyl-N-methylcarbonyl-amino-ethyl)-, 4-(1-N-pyrrolidine-3-carbonyl-N-ethyl-amino-ethyl)-, 4-(1-N-cis-4-amino-cyclohexanecarbonyl-N-ethyl-amino-ethyl)-, 4-(1-N-trans-4-amino-cyclohexanecarbonyl-N-ethyl-amino-ethyl)-, 4-(1-N-4-dimethylamino-cyclohexanecarbonyl-N-ethyl-amino-ethyl)-, 4-(1-N-4-dimethylamino-cyclopentanecarbonyl-N-ethyl-amino-ethyl)-, 4-(1-N-1-methyl-pyrrolidine-3-yl-carbonyl-N-ethyl-amino-ethyl)-, 4-(1-N-4-dimethylamino-cyclohexanecarbonyl-N-ethyl-amino-ethyl)-, 4-[1-(piperidin-3-ylamino)-ethyl]-, 4-(1-N-(2-aminoethyl)-N-methylcarbonyl-amino-ethyl)-, 4-(1-N-(2-dimethylaminoethyl)-N-methylcarbonyl-amino-ethyl)-, 4-(1-N-(3-aminopropyl)-N-methylcarbonyl-amino-ethyl)-, 4-(1-N-(3-dimethylaminopropyl)-N-methylcarbonyl-amino-ethyl)-, 4-[1-(N-ethyl-N-piperidin-4-yl-amino)-ethyl]-, 4-[1-(3-Amino-piperidin-1-yl)-ethyl]-, 4-[1-((R)-3-Amino-pyrrolidin-1-yl)-ethyl]-, 4-[1-((S)-3-Amino-pyrrolidin-1-yl)-ethyl]-, 4-[1-(3-dimethylamino-pyrrolidin-1-yl)-ethyl]-, [1-(4-diethylamino-piperidin-1-yl)-ethyl]-, 4-[1-(3-oxo-morpholin-4-yl)-ethyl]-, 4-[(4-dimethylamino-cyclohexylmethyl)-methyl-amino]-, 4-(N-methyl-N-ethyl-amino-carbonyl)-, 4-(N-cyclopropylmethyl-N-methyl-amino)-, 4-(2-oxo-azetidin-1-yl)-, 4-(1-N-methylcarbonyl-N-ethyl-amino-ethyl)-, 4-(morpholin-4-yl-cyclohexylmethyl)-amino]-, 4-(morpholin-4-yl-cyclohexylmethyl)-methyl-amino]-, 4-[(4-dimethylamino-cyclohexylmethyl)-methyl-amino]-3-methyl-, 4-[(4-dimethylamino-cyclohexylmethyl)-methyl-amino]-3-fluoro-, 4-[(4-dimethylamino-cyclohexylmethyl)-methylamino]-2-methoxy-, 4-[1-(4-Acetyl-piperazin-1-yl)-ethyl]-, 4-[1-(4-dimethylamino-piperidin-1-yl)-ethyl]-, 4-[(-4-dimethylamino-cyclohexylmethyl)-methyl-amino]-, 4-[(-4-dimethylamino-cyclohexylmethyl)-ethyl-amino]-, 4-[2-(4-dimethylamino-piperidin-1-yl)-1-methyl-ethyl]-, 4-[2-(4-dimethylamino-piperidin-1-yl)-1-methyl-2-oxo-ethyl]-, 4-imidazol-1ylmethyl-, 4-(N-trifluoromethyl-carbonyl-N-methyl-amino)-, 4-[1-(2-oxo-piperazin-1-yl)-ethyl]-, 4-(2-hydroxy-ethyl)-2-oxo-piperazin-1-yl]-ethyl}-, 4-[1-(methyl-carbonylamino)-ethyl]-, 4-[1-(methoxymethylcarbonylamino)-ethyl]-, 4-[1-(dimethylamino-methyl-carbonylamino)-ethyl]-, 4-(2-oxo-pyrrolidin-1-yl)-, 4-(2-oxo-imidazolidin-1-yl)- or 4-(3-amino-5-ethyl-1H-pyrazol-4-yl)-, or R² is selected from phenyl substituted by:

2-fluoro or 3-fluoro and substituted in the para position (relative to the isoquinolinone or quinazolinone), by:

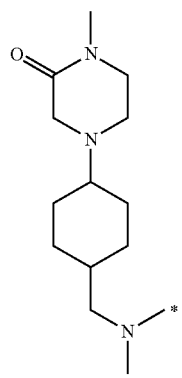 [SMILES: CN(C)CC1CCC(N2CCN(C)C(=O)C2)CC1]

or R² is selected from phenyl substituted in the ortho position (relative to the isoquinolinone or quinazolinone), by methoxy and substituted in the para position (relative to the isoquinolinone or quinazolinone), by:

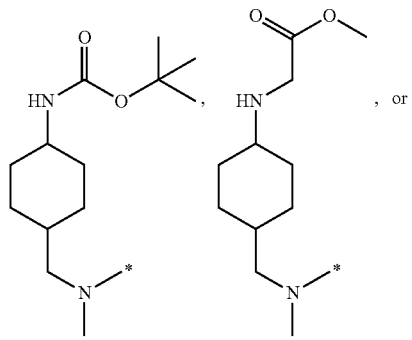

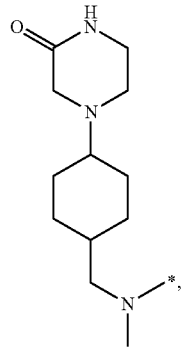

or R² is phenyl substituted in the para position (relative to the isoquinolinone or quinazolinone), by:

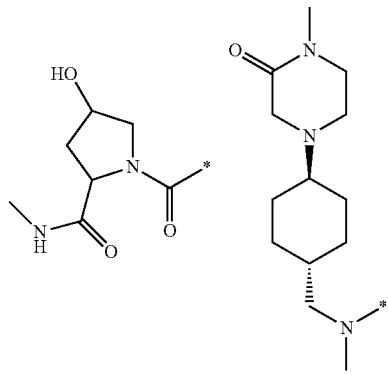

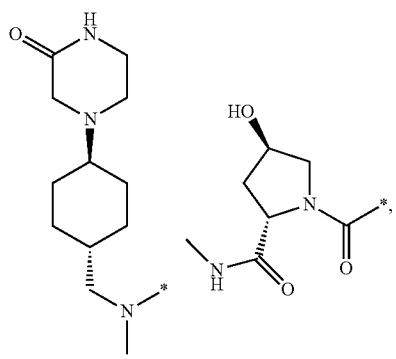

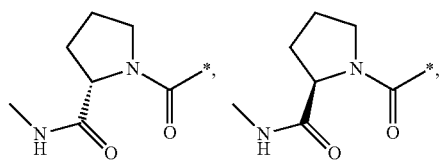

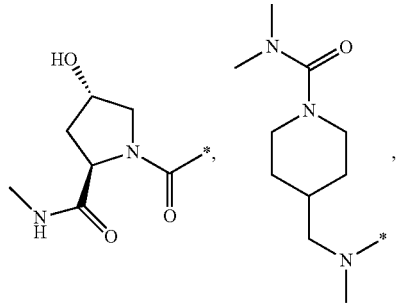

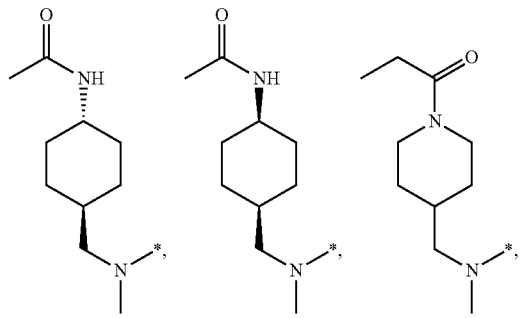

497
-continued
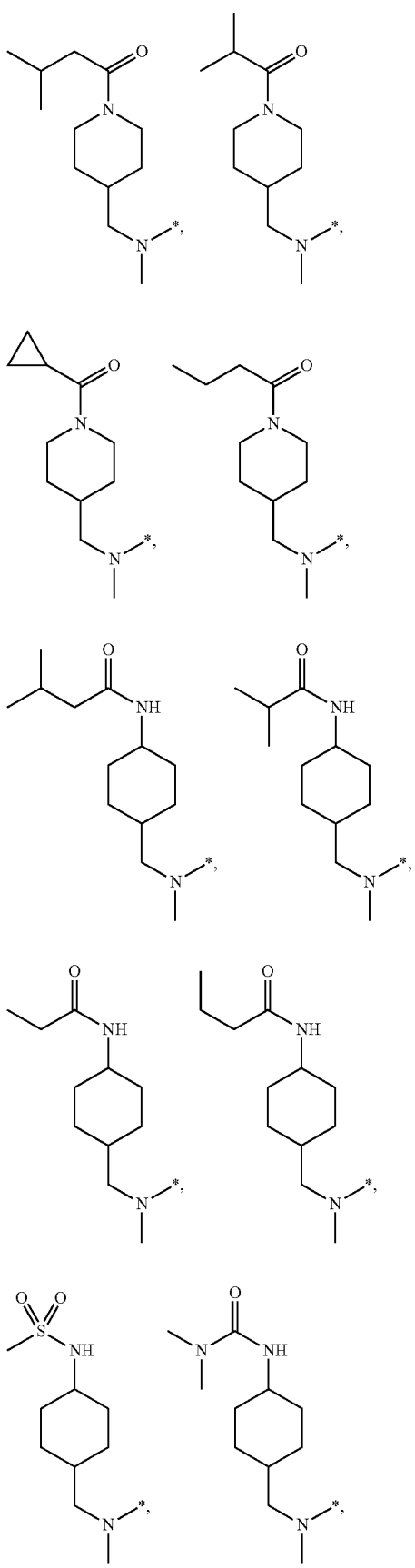
498
-continued
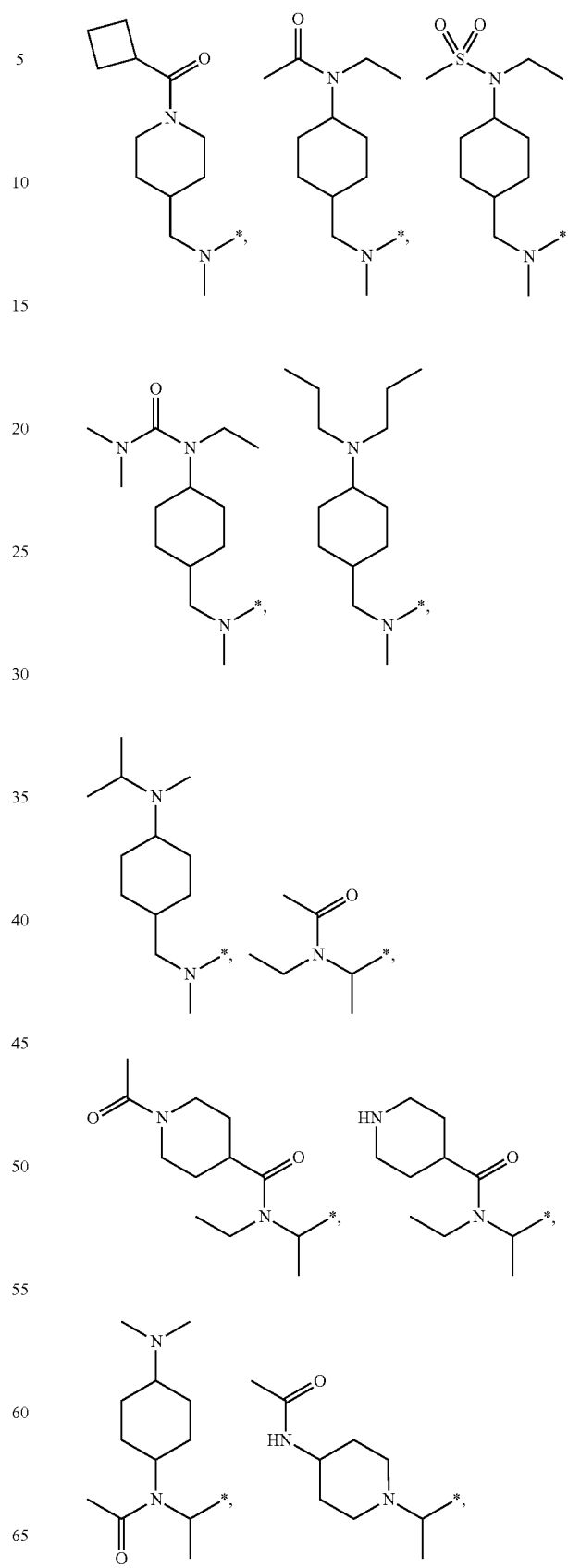

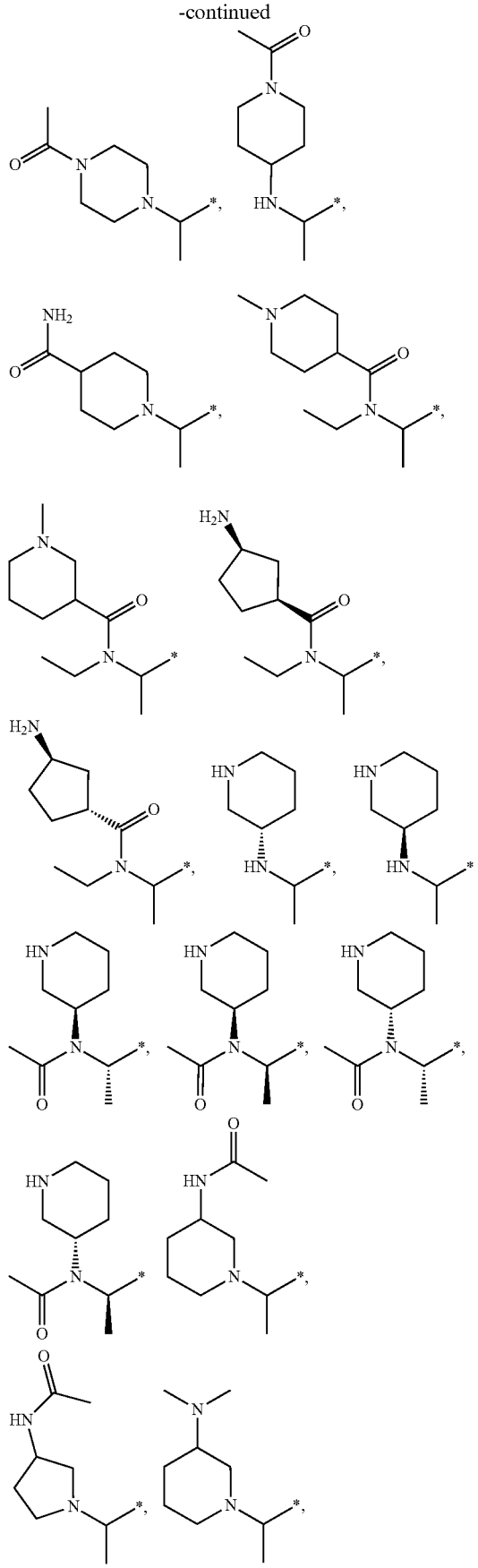
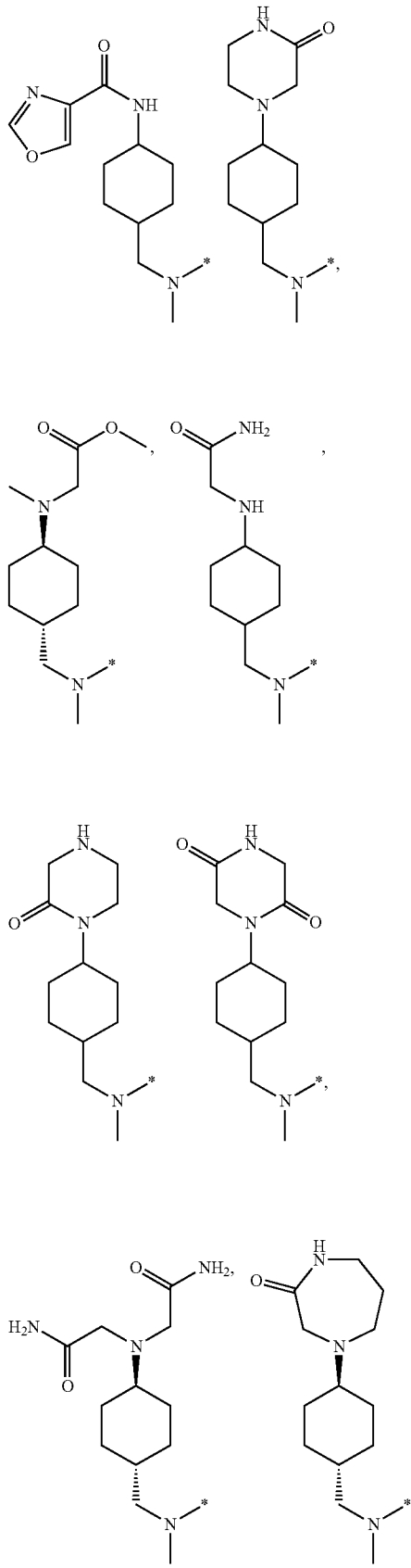

501
-continued
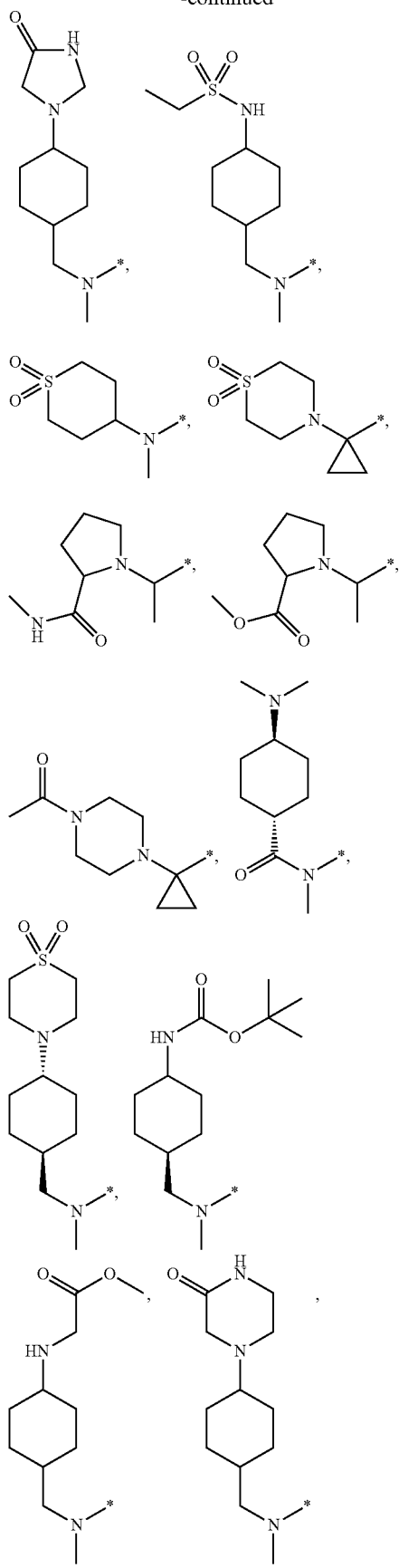
502
-continued
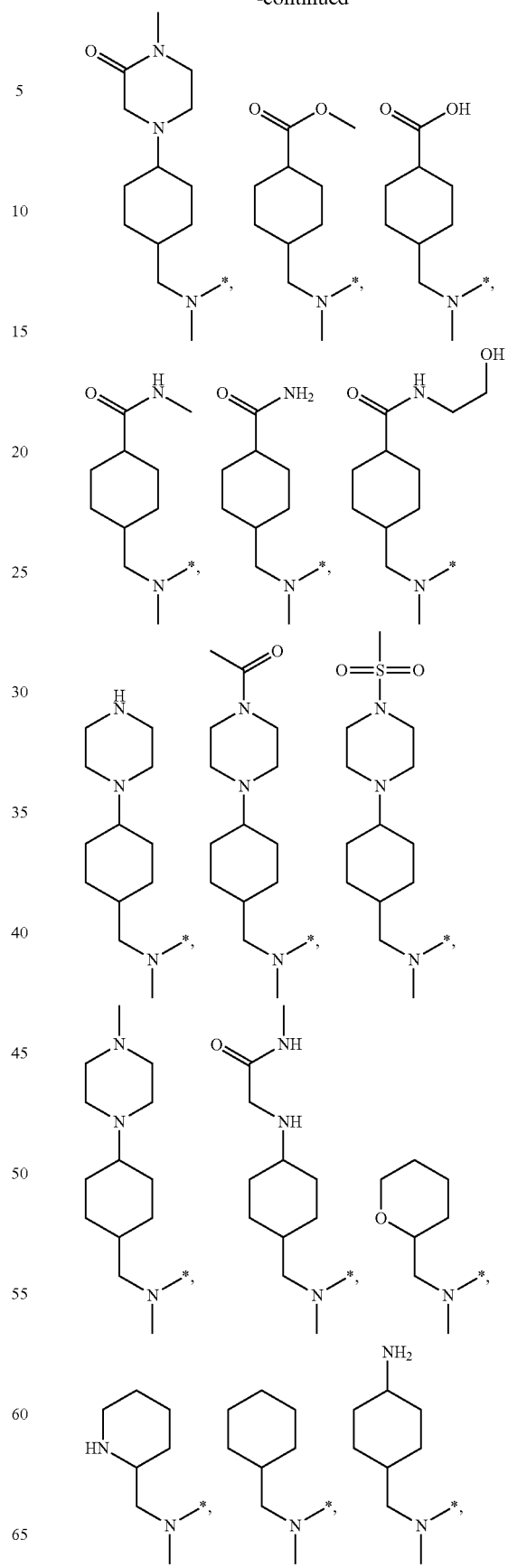

503
-continued
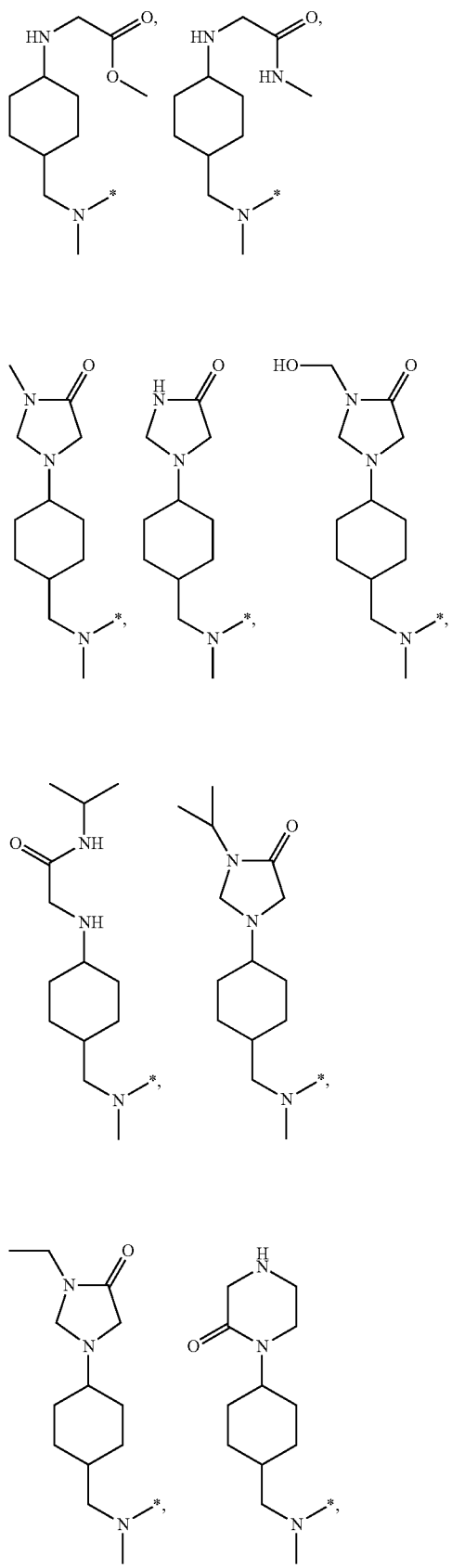
504
-continued
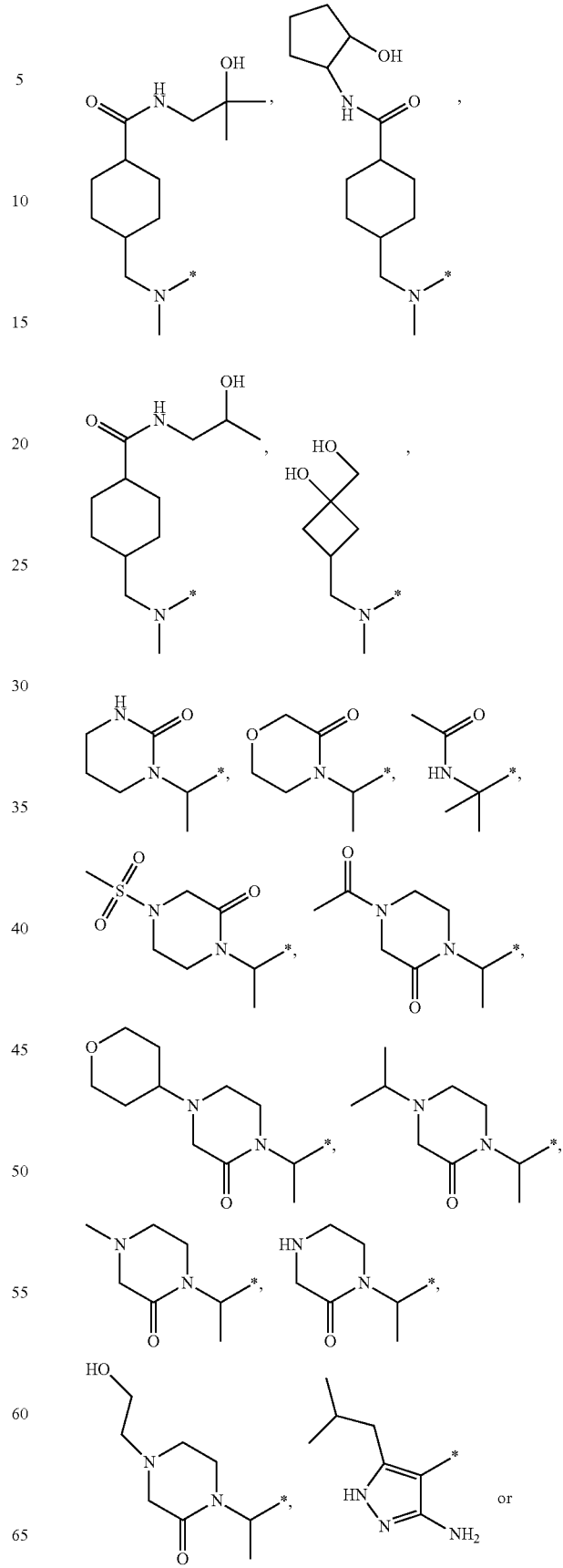

505
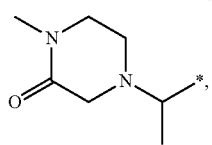
preferably
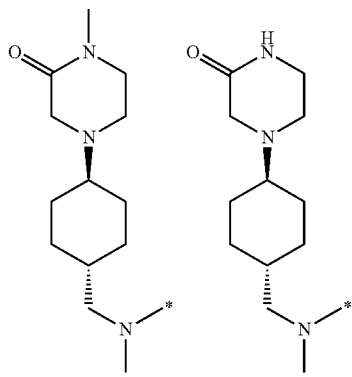
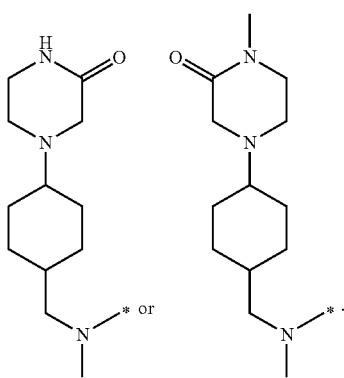
(A) ii or R² is 2-pyridyl (relative to the isoquinolinone or quinazolinone), substituted by: 5-[(4-dimethylamino-cyclohexylmethyl)-methyl-amino]-, 5-[(4-amino-cyclohexylmethyl)amino]-,
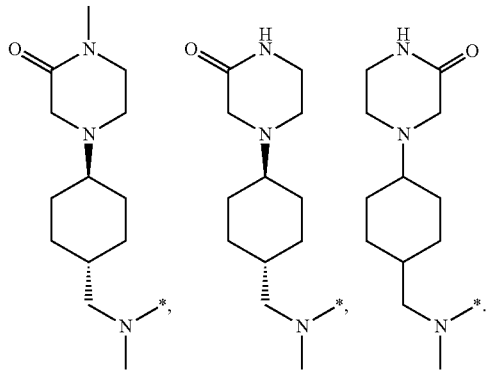
506
-continued
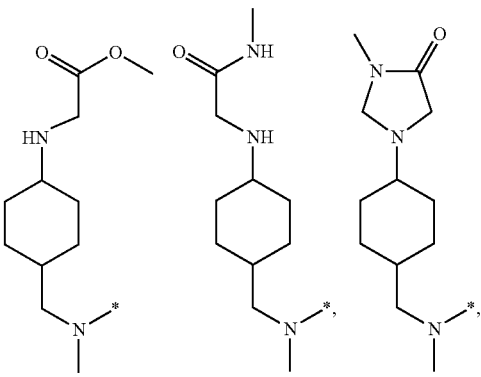
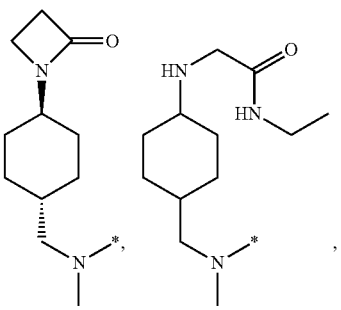
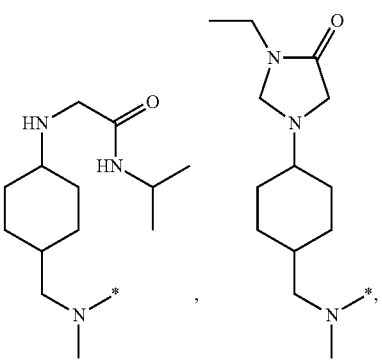
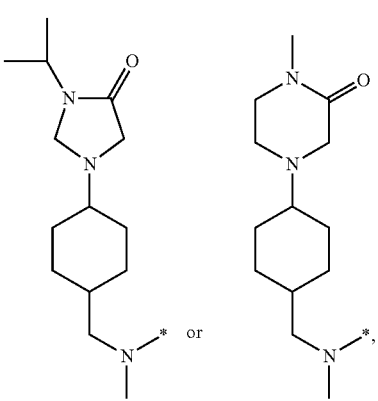

preferably

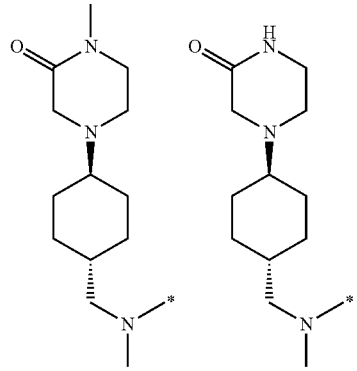

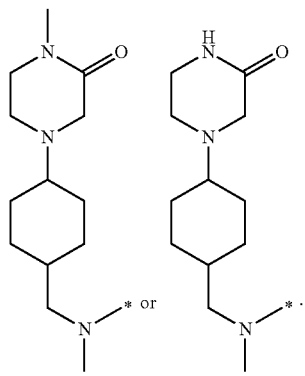

(A) iii or R² is 3-pyridyl (relative to the isoquinolinone or quinazolinone), substituted by: 6-[(4-dimethylamino-cyclohexylmethyl)-methyl-amino]- or 6-[(3-hydroxy-cyclobutylmethyl)-methyl-amino]-, or R² is 3-pyridyl (relative to the isoquinolinone or quinazolinone), substituted in the 6 position by: 6-{methyl-[4-(2-oxo-pyrrolidin-1-yl)-cyclohexylmethyl]-amino}-, 6-{methyl-[4-(2-oxo-imidazolidin-1-yl)-cyclohexylmethyl]-amino}-,

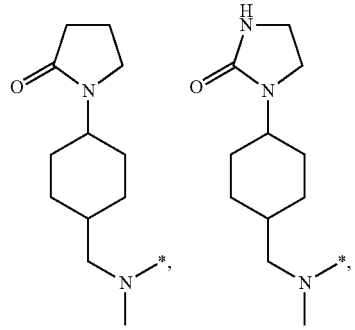

-continued

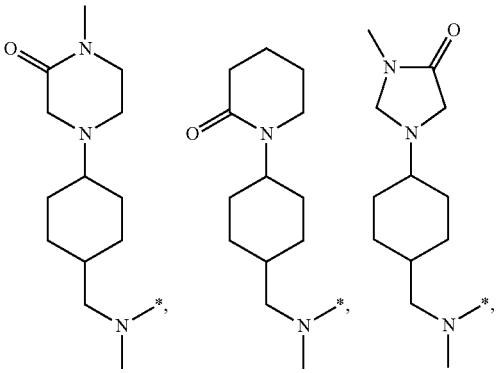

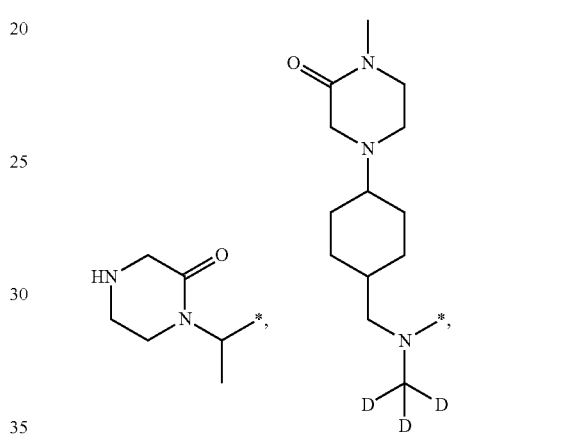

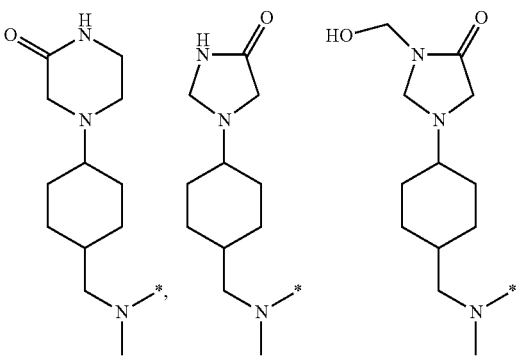

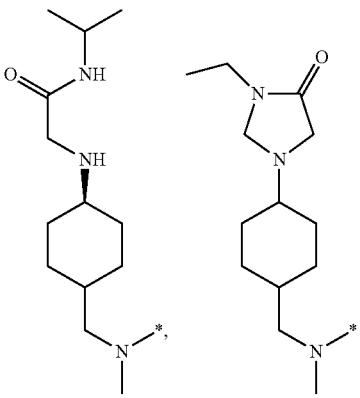

-continued

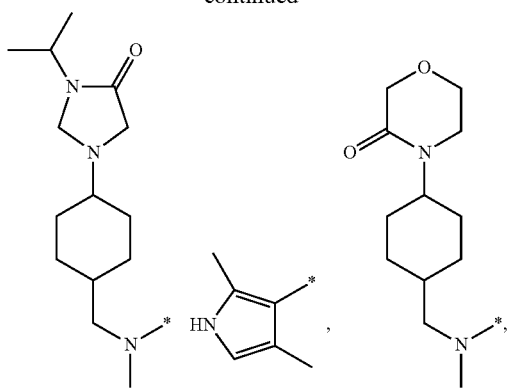

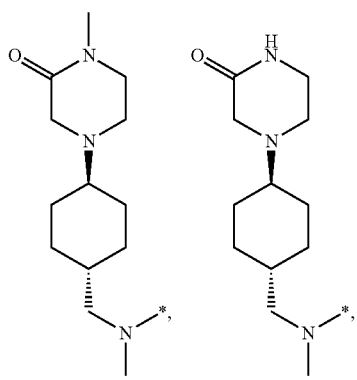

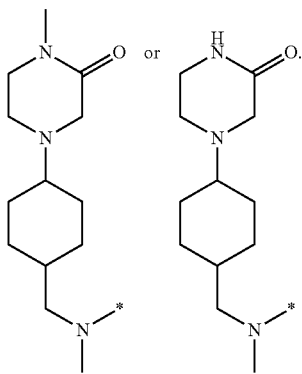

preferably

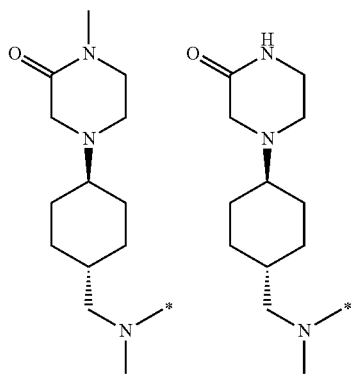

-continued

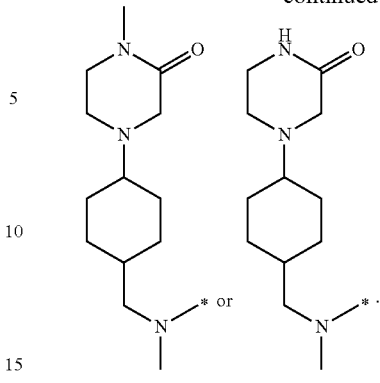

or R² is 3-pyridyl (relative to the isoquinolinone or quinazolinone), substituted by:

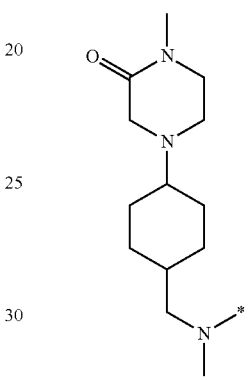

(B) i or R² is phenyl substituted by:
4-methoxy, 4-cyano, 3,4-dimethyl, 2,4-dimethyl, 4-methoxy-2-methyl-, 2-chloro-4-methyl-, 2,4-dimethoxy-, 3,4-dichloro-, 4-methyl-, 3,4-dimethoxy, 2-methoxy-4-methyl-, 4-(1H-pyrazol-4-yl)-, 4-(3,5-dimethyl-1H-pyrazol-4-yl)-,

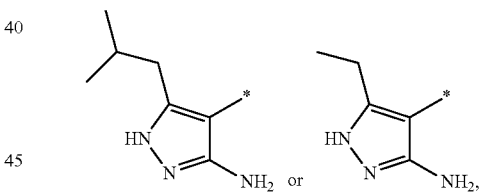

(B) ii or R² is 2-pyridyl (relative to the isoquinolinone or quinazolinone), substituted by 4-methyl,
(B) iii or R² is 3-pyridyl (relative to the isoquinolinone or quinazolinone), substituted by 4-methyl,
(C) or R² is phenyl substituted by:
4-methyl-2-(3-morpholin-4-yl-propoxy)-, 4-methyl-2-hydroxycarbonylmethoxy-, 2-methoxy-5-methyl-, 4-methyl-2-(2H-tetrazol-5-ylmethoxy)-, 4-methyl-2-(thiazol-5-ylmethoxy)-, 4-methoxycarbonyl-2-tetrazol-5-ylmethoxy, 4-methoxycarbonyl-2 methoxy, 4-methoxycarbonyl-2-thiazol-5-ylmethoxy)-, 4-methyl-2-(2-morpholin-4-yl-ethoxy), 2-(3-dimethylamino-propoxy)-4-methyl-, 4-methyl-2-[2-(4-methyl-piperazin-1-yl)-ethoxy]-, 4-methyl-2-[3-(4-methyl-piperazin-1-yl)-propoxy]-, 2-methoxycarbonylmethoxy-5-chloro-, 2-hydroxycarbonylmethoxy-5-chloro-, 5-chloro-2-(2-dimethylamino-ethoxy)-, 5-chloro-2-(3-morpholin-4-yl-propoxy)-, 5-chloro-2-(2-morpholin-4-yl-ethoxy)-, 5-chloro-2-(3-dimethylamino-propoxy)-, 5-chloro-2-(3-hydroxy-propoxy)- or 5-chloro-2-(2-hydroxy-ethoxy)-, (D) or R² is (C-bound)-heterocycle selected from benzofuran-5-yl and 1-methyl-1H-indazol-5-yl,
(E) or R² is pyrazin-2-yl (relative to the isoquinolinone or quinazolinone), substituted at the 5 position by:

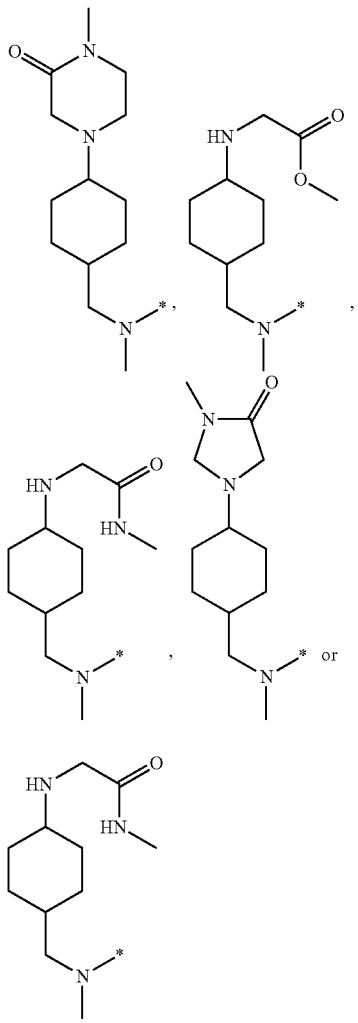

(F) or R² is pyridazin-3-yl (relative to the isoquinolinone or quinazolinone), substituted at the 6 position by:

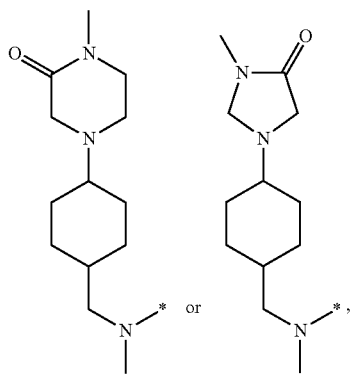 [SMILES: *N(C)CC1CCC(N2CCN(C)C(=O)C2)CC1 ; "or" ; *N(C)CC1CCC(N2CC(=O)N(C)C2)CC1 ; ","]

(G) or R² is pyrimidin-2-yl (relative to the isoquinolinone or quinazolinone), substituted at the 5 position by:

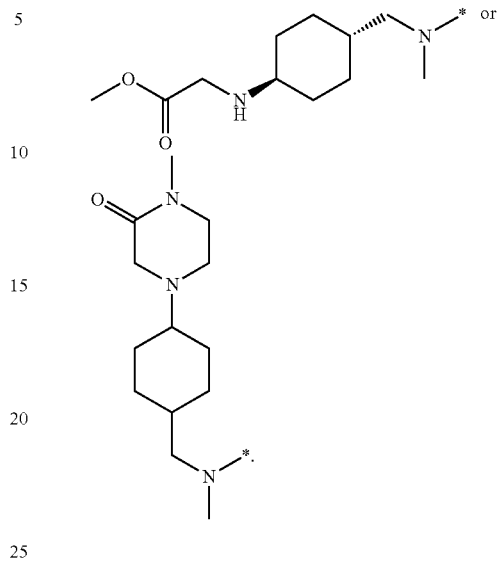

The invention claimed is:
1. A compound of formula (I), or pharmaceutically acceptable salt thereof,

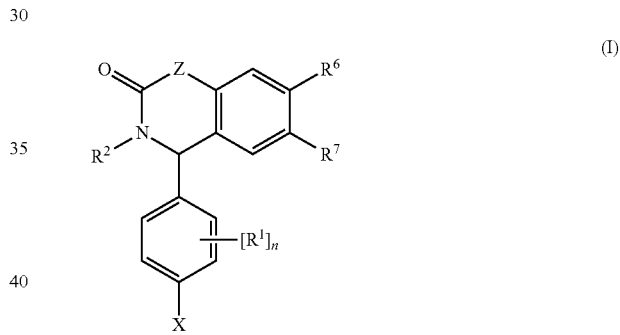

wherein
Z is N—R⁴;
X is halogen;
R⁴ is selected from the group consisting of
H—
$C_1$-$C_7$-alkyl-;
R⁶ is independently selected from the group consisting of
H—
R'O—
(R')₂N—;
R⁷ is independently selected from the group consisting of
R'O—
(R')₂N—;
each R' is independently selected from the group consisting of
H—
$C_1$-$C_7$-alkyl-
$C_1$-$C_7$-alkenyl-
halo-$C_1$-$C_7$-alkyl-
halo-$C_1$-$C_7$-alkenyl-
$C_3$-$C_{12}$-cycloalkyl-
heterocyclyl-
aryl-
hydroxy-$C_1$-$C_7$-alkyl- $C_1$-$C_7$-alkoxy-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
$C_3$-$C_{12}$-cycloalkyl-$C_1$-$C_7$-alkyl-
heterocyclyl-$C_1$-$C_7$-alkyl-
aryl-$C_1$-$C_7$-alkyl-
$C_1$-$C_7$-alkyl-carbonyl-
halo-$C_1$-$C_7$-alkyl-carbonyl-
hydroxy-$C_1$-$C_7$-alkyl-carbonyl-
$C_1$-$C_7$-alkoxy-$C_1$-$C_7$-alkyl-carbonyl-
amino-$C_1$-$C_7$-alkyl-carbonyl-
N—$C_1$-$C_7$-alkyl-amino-$C_1$-$C_7$-alkyl-carbonyl-
N,N-di-$C_1$-$C_7$-alkyl-amino-$C_1$-$C_7$-alkyl-carbonyl-
$C_3$-$C_{12}$-cycloalkyl-carbonyl-
heterocyclyl-$C_1$-$C_7$-alkyl-carbonyl-
aryl-$C_1$-$C_7$-alkyl-carbonyl-
$C_3$-$C_{12}$-cycloalkyl-$C_1$-$C_7$-alkyl-carbonyl-
heterocyclyl-carbonyl-
aryl-carbonyl-
$C_1$-$C_7$-alkyl-carbonyl-$C_1$-$C_7$-alkyl-
halo-$C_1$-$C_7$-alkyl-carbonyl-$C_1$-$C_7$-alkyl-
hydroxy-$C_1$-$C_7$-alkyl-carbonyl-$C_1$-$C_7$-alkyl-
$C_1$-$C_7$-alkoxy-$C_1$-$C_7$-alkyl-carbonyl-$C_1$-$C_7$-alkyl-
amino-$C_1$-$C_7$-alkyl-carbonyl-$C_1$-$C_7$-alkyl-
N—$C_1$-$C_7$-alkyl-amino-$C_1$-$C_7$-alkyl-carbonyl-$C_1$-$C_7$-alkyl-
N,N-di-$C_1$-$C_7$-alkyl-amino-$C_1$-$C_7$-alkyl-carbonyl-$C_1$-$C_7$-alkyl-
$C_3$-$C_{12}$-cycloalkyl-carbonyl-$C_1$-$C_7$-alkyl-
heterocyclyl-carbonyl-$C_1$-$C_7$-alkyl-
aryl-carbonyl-$C_1$-$C_7$-alkyl-
carbonyl-$C_1$-$C_7$-alkyl-
hydroxy-carbonyl-$C_1$-$C_7$-alkyl-
$C_1$-$C_7$-alkoxy-carbonyl-$C_1$-$C_7$-alkyl-
amino-carbonyl-$C_1$-$C_7$-alkyl-
N—$C_1$-$C_7$-alkyl-amino-carbonyl-$C_1$-$C_7$-alkyl-
N,N-di-$C_1$-$C_7$-alkyl-amino-carbonyl-$C_1$-$C_7$-alkyl-
$C_3$-$C_{12}$-cycloalkyl-carbonyl-$C_1$-$C_7$-alkyl-
heterocyclyl-carbonyl-$C_1$-$C_7$-alkyl-
aryl-carbonyl-$C_1$-$C_7$-alkyl-
$C_1$-$C_7$-alkyl-carbonyl-amino-$C_1$-$C_7$-alkyl-
$C_1$-$C_7$-alkyl-carbonyl-N—$C_1$-$C_7$-alkyl-amino-$C_1$-$C_7$-alkyl-
halo-$C_1$-$C_7$-alkyl-carbonyl-amino-$C_1$-$C_7$-alkyl-
halo-$C_1$-$C_7$-alkyl-carbonyl-N—$C_1$-$C_7$-alkyl-amino-$C_1$-$C_7$-alkyl-
wherein aryl, heterocyclyl and $C_3$-$C_{12}$-cycloalkyl are unsubstituted or substituted by 1-4 substituents selected from $C_1$-$C_7$-alkyl, halo-$C_1$-$C_7$-alkyl, halogen, hydroxy, $C_1$-$C_7$-alkoxy, amino, nitro or cyano;
each $R^1$ is independently selected from the group consisting of
halogen-
cyano-
nitro-
$C_1$-$C_7$-alkyl-
$C_1$-$C_7$-alkenyl-
halo-$C_1$-$C_7$-alkyl-
hydroxy-
$C_1$-$C_7$-alkoxy-
amino-
N—$C_1$-$C_7$-alkyl-amino-
N,N-di-$C_1$-$C_7$-alkyl-amino-
amino-carbonyl-amino-
N—$C_1$-$C_7$-alkyl-amino-carbonyl-amino-
N,N-di-$C_1$-$C_7$-alkyl-amino-carbonyl-amino-
$C_1$-$C_7$-alkyl-carbonyl-amino-
amino-carbonyl-
N—$C_1$-$C_7$-alkyl-amino-carbonyl-
N,N-di-$C_1$-$C_7$-alkyl-amino-carbonyl-
hydroxy-$C_1$-$C_7$-alkyl-
amino-$C_1$-$C_7$-alkyl-
N—$C_1$-$C_7$-alkyl-amino-$C_1$-$C_7$-alkyl-
N,N-di-$C_1$-$C_7$-alkyl-amino-$C_1$-$C_7$-alkyl-
$C_1$-$C_7$-alkyl-carbonyl-amino-$C_1$-$C_7$-alkyl-
$C_1$-$C_7$-alkyl-carbonyl-N—$C_1$-$C_7$-alkyl-amino-$C_1$-$C_7$-alkyl-;
n is 0 to 2;
$R^2$ is selected from
(A) phenyl, 2-pyridyl and 3-pyridyl
substituted in the para-position relative to the isoquinolinone or quinazolinone, by $(R^3)_2$N—Y—
wherein Y is absent (a bond) or
$(R^3)_2$N—Y— is selected from

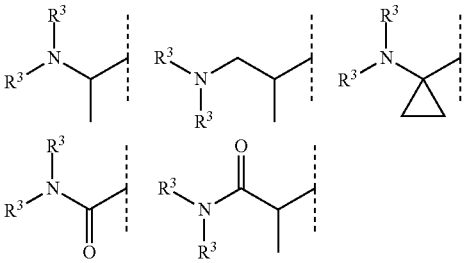

and wherein said phenyl, 2-pyridyl or 3-pyridyl is optionally substituted by 1-2 additional substituents selected from
halogen-
cyano-
$C_1$-$C_7$-alkyl-
halo-$C_1$-$C_7$-alkyl-
hydroxy-
$C_1$-$C_7$-alkoxy- and
hydroxy-$C_1$-$C_7$-alkyl-;
or
(B) phenyl, 2-pyridyl or 3-pyridyl
substituted in para-position relative to the isoquinolinone or quinazolinone by a substituent selected from
cyano-
halogen-
nitro-
$C_1$-$C_7$-alkyl-
halo-$C_1$-$C_7$-alkyl-
hydroxy-$C_1$-$C_7$-alkyl-
hydroxy-carbonyl-
$C_1$-$C_7$-alkoxy-carbonyl-
$C_1$-$C_7$-alkyl-carbonyl-
$C_1$-$C_7$-alkoxy-
(C-bound)-heterocyclyl-
wherein (C-bound)-heterocyclyl is unsubstituted or substituted by 1-4 substituents selected from $C_1$-$C_7$-alkyl, halo-$C_1$-$C_7$-alkyl, halogen, hydroxy, $C_1$-$C_7$-alkoxy, amino, nitro or cyano;
and optionally substituted by 1-2 additional substituents selected from halogen-
cyano-
$C_1$-$C_7$-alkyl-
halo-$C_1$-$C_7$-alkylhydroxy-
C$_1$-C$_7$-alkoxy-
(C-bound or N-bound)heterocyclyl-C$_1$-C$_4$-alkyl-
hydroxy-C$_1$-C$_7$-alkyl-;
Or
(C) phenyl,
  substituted in ortho-position relative to the isoquinolinone or quinazolinone by R$^3$O—
    and substituted in para- or meta-position by a substituent selected from methyl, chloro, C$_1$-C$_7$-alkyl-carbonyl- or C$_1$-C$_7$-alkoxy-carbonyl-;
(D) (C-bound)-heterocycle selected from

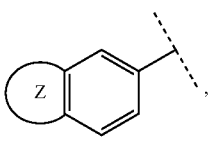

, wherein Z is a 4-6 membered heterocyclic ring, annulated to phenyl in para and meta position, containing 1-3 heteroatoms selected from N, O or S,
which is optionally substituted by 1-2 additional substituents selected from
halogen-
cyano-
C$_1$-C$_7$-alkyl-
halo-C$_1$-C$_7$-alkyl-
hydroxy-
C$_1$-C$_7$-alkoxy-
hydroxy-C$_1$-C$_7$-alkyl-;
(E) pyrazin-2-yl,
substituted at the 5 position by:

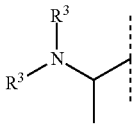

(F) pyridazin-3-yl, substituted at the 6 position by:

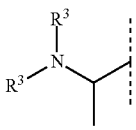

Or
(G) pyrimidin-2-yl, substituted at the 5 position by:

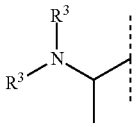

wherein each R$^3$ is independently selected from
H—
C$_1$-C$_7$-alkyl-
hydroxy-C$_1$-C$_7$-alkyl-
C$_3$-C$_{12}$-cycloalkyl-
C$_1$-C$_7$-alkoxy-C$_1$-C$_7$-alkyl-carbonyl-
amino-C$_1$-C$_7$-alkyl-carbonyl
N—C$_1$-C$_7$-alkyl-amino-C$_1$-C$_7$-alkyl-carbonyl
N, N-di C$_1$-C$_7$-alkyl-amino-C$_1$-C$_7$-alkyl-carbonyl
(R$^5$)$_2$N—C$_3$-C$_{12}$-cycloalkyl-
(R$^5$)$_2$N—C$_1$-C$_7$-alkyl-
(R$^5$)$_2$N—C$_3$-C$_{12}$-cycloalkyl-C$_1$-C$_7$-alkyl-
(R$^5$)$_2$N—C$_3$-C$_{12}$-cycloalkyl-carbonyl-
R$^5$O—C$_3$-C$_{12}$-cycloalkyl-
R$^5$O—C$_1$-C$_7$-alkyl-
R$^5$O—C$_3$-C$_{12}$-cycloalkyl-C$_1$-C$_7$-alkyl-
R$^5$O—(C$_1$-C$_7$-alkyl)-C$_3$-C$_{12}$-cycloalkyl-C$_1$-C$_7$-alkyl-
R$^5$O-(hydroxy-C$_1$-C$_7$-alkyl)-C$_3$-C$_{12}$-cycloalkyl-C$_1$-C$_7$-alkyl-
(R$^5$)$_2$N—CO—C$_3$-C$_{12}$-cycloalkyl-C$_1$-C$_7$-alkyl-
C$_1$-C$_7$-alkoxycarbonyl-C$_3$-C$_{12}$-cycloalkyl-C$_1$-C$_7$-alkyl-
hydroxycarbonyl-C$_3$-C$_{12}$-cycloalkyl-C$_1$-C$_7$-alkyl-
amino-carbonyl-C$_3$-C$_{12}$-cycloalkyl-C$_1$-C$_7$-alkyl-
R$^5$O—C$_3$-C$_{12}$-cycloalkyl-carbonyl-
(R$^5$)$_2$N-carbonyl-C$_1$-C$_7$-alkyl-
R$^5$O-carbonyl-C$_1$-C$_7$-alkyl-
aryl-C$_1$-C$_7$-alkyl-
heterocyclyl-C$_1$-C$_7$-alkyl-
C$_1$-C$_7$-alkyl-carbonyl-
halo-C$_1$-C$_7$-alkyl-carbonyl-
heterocyclyl-carbonyl-
aryl-carbonyl-
C$_3$-C$_{12}$-cycloalkyl-carbonyl-
C$_3$-C$_{12}$-cycloalkyl-C$_1$-C$_7$-alkyl-
heterocyclyl-
aryl-
  wherein aryl, heterocyclyl and C$_3$-C$_{12}$-cycloalkyl are unsubstituted or substituted by 1-4 substituents selected from
  halogen-
  C$_1$-C$_7$-alkyl-
  halo-C$_1$-C$_7$-alkyl-
  C$_1$-C$_7$-alkyl-carbonyl-
  C$_3$-C$_{12}$-cycloalkyl-carbonyl-
  C$_1$-C$_7$-alkyl-sulfonyl-
  amino-sulfonyl-
  N—C$_1$-C$_7$-alkyl-amino-sulfonyl-
  N,N-di-C$_1$-C$_7$-alkyl-amino-sulfonyl-
  amino-carbonyl-
  N—C$_1$-C$_7$-alkyl-amino-carbonyl-
  N,N-di-C$_1$-C$_7$-alkyl-amino-carbonyl-
  oxo=
or
two R$^3$, together with the N to which they are attached my form a 3-9 membered heterocyclic ring, optionally containing 1-4 additional heteroatoms selected from N, O or S, said heterocyclic ring is unsubstituted or substituted by 1-3 substituents selected from:
halogen-
hydroxy-C$_1$-C$_7$-alkyl-
C$_1$-C$_7$-alkyl-
halo-C$_1$-C$_7$-alkyl-
oxo=
hydroxy-
C$_1$-C$_7$-alkoxy-
amino-
N—C$_1$-C$_7$-alkyl-amino-
N,N-di-C$_1$-C$_7$-alkyl-amino-
hydroxy-carbonyl-
C$_1$-C$_7$-alkoxy-carbonyl-
amino-carbonyl-
N—C$_1$-C$_7$-alkyl-amino-carbonyl-
N,N-di-C$_1$-C$_7$-alkyl-amino-carbonyl-
C$_1$-C$_7$-alkyl-carbonyl-
C$_1$-C$_7$-alkyl-sulphonyl-
heterocyclyl-
C$_1$-C$_7$-alkyl-carbonyl-amino- $C_1$-$C_7$-alkyl-carbonyl-N—$C_1$-$C_7$-alkyl-amino-;
and
each $R^5$ is independently selected from:
H—
$C_1$-$C_7$-alkyl-
hydroxy-$C_1$-$C_7$-alkyl-
$C_1$-$C_7$-alkyl-carbonyl-
$C_1$-$C_7$-alkoxy-carbonyl-$C_1$-$C_7$-alkyl-
amino-carbonyl-$C_1$-$C_7$-alkyl-
N—$C_1$-$C_7$-alkyl-amino-carbonyl-$C_1$-$C_7$-alkyl-
N,N-di-$C_1$-$C_7$-alkyl-amino-carbonyl-$C_1$-$C_7$-alkyl-
$C_1$-$C_7$-alkyl-sulfonyl-
amino-sulfonyl-
N—$C_1$-$C_7$-alkyl-amino-sulfonyl-
N,N-di-$C_1$-$C_7$-alkyl-amino-sulfonyl-
heterocyclyl-carbonyl-amino-carbonyl-N—
$C_1$-$C_7$-alkyl-amino-carbonyl-
N,N-di-$C_1$-$C_7$-alkyl-amino-carbonyl-
$C_3$-$C_{12}$-cycloalkyl-carbonyl-
$C_1$-$C_7$-alkoxy-carbonyl-amino-$C_1$-$C_7$-alkyl-
$C_1$-$C_7$-alkoxy-carbonyl-N—$C_1$-$C_7$-alkyl-amino-$C_1$-$C_7$-alkyl-
$C_1$-$C_7$-alkoxy-carbonyl-
$C_3$-$C_{12}$-cycloalkyl-
hydroxy-$C_3$-$C_{12}$-cycloalkyl-
or
two $R^5$, together with the N to which they are attached my form a 3-9 membered heterocyclic ring, optionally containing from 1-4 additional heteroatoms selected from N, O or S, said heterocyclic ring is unsubstituted or substituted by from 1 to 3 substituents selected from
$C_1$-$C_7$-alkyl-
oxo=,
$C_1$-$C_7$-alkyl-carbonyl,
$C_1$-$C_7$-alkyl-sulphonyl,
hydroxy-$C_1$-$C_7$-alkyl;
with the proviso that if Z is $CH_2$, n is 0 or 1, and when present, $R^1$ is ortho-chloro, and $R^2$ is selected from
para-$C_1$-$C_3$-alkyl-phenyl-
para-(halo-$C_1$-$C_3$-alkyl)-phenyl-
para-$C_1$-$C_3$-alkoxy-phenyl-
para-halo-phenyl-
para-nitro-phenyl-
para-($C_1$-$C_3$-alkoxy-carbonyl)-phenyl-
para-(hydroxy-carbonyl)-phenyl-
wherein the phenyl is optionally substituted by 1-2 additional substituents, said
substituents being independently selected from halo and methyl,
then $R^6$ and $R^7$ are not both ethoxy or methoxy,
aryl means phenyl or naphthyl,
and
heterocyclyl means an unsaturated, saturated, or partially saturated ring or ring system comprising 3, 4, 5, 6, 7, 8, 9, 10, 11 or 12 ring atoms, and containing at least one heteroatom selected from N, O and S, where the N and S can also optionally be oxidized, and wherein, unless otherwise stated, the heterocyclic group can be attached at a heteroatom or a carbon atom.

2. A compound of formula (I), or pharmaceutically acceptable salt thereof, as claimed in claim 1, wherein X is chloro.

3. A compound of formula (I), or pharmaceutically acceptable salt thereof, according to claim 1, wherein each R' is independently selected from
H—
$C_1$-$C_6$-alkyl-
heterocyclyl-$C_1$-$C_4$-alkyl-
amino-$C_1$-$C_4$-alkyl-
N—$C_1$-$C_4$-alkyl-amino-$C_1$-$C_4$-alkyl-
N,N-di-$C_1$-$C_4$-alkyl-amino-$C_1$-$C_4$-alkyl-
heterocyclyl-carbonyl-$C_1$-$C_4$-alkyl-
hydroxy-$C_1$-$C_4$-alkyl-
amino-carbonyl-$C_1$-$C_4$-alkyl-
N—$C_1$-$C_4$-alkyl-amino-carbonyl-$C_1$-$C_4$-alkyl-
N,N-di-$C_1$-$C_4$-alkyl-amino-carbonyl-$C_1$-$C_4$-alkyl-
$d_3$ methoxy,
$C_3$-$C_7$-cycloalkyl-$C_1$-$C_4$-alkyl-
$C_3$-$C_7$-cycloalkyl-
aryl-$C_1$-$C_4$-alkyl-
$C_1$-$C_4$-alkoxy-$C_1$-$C_4$-alkyl-
$C_1$-$C_6$-alkenyl-
halo-$C_1$-$C_4$-alkyl-
halo-$C_1$-$C_4$-alkenyl-
$C_1$-$C_4$-alkyl-carbonyl-
$C_1$-$C_4$-alkyl-carbonyl-amino-$C_1$-$C_4$-alkyl-
aryl-$C_1$-$C_4$-alkyl-
heterocyclyl- and
aryl-
wherein said $C_3$-$C_7$-cycloalkyl (including the $C_3$-$C_7$-cycloalkyl substituent within $C_3$-$C_7$-cycloalkyl-$C_1$-$C_4$-alkyl-), is optionally substituted by hydroxy or methyl, and wherein aryl (including within aryl-$C_1$-$C_4$-alkyl-), and heterocyclyl (including within heterocyclyl-$C_1$-$C_4$-alkyl- and heterocyclyl-carbonyl-$C_1$-$C_4$-alkyl-), is optionally substituted by 1 or 2 $C_1$-$C_4$-alkyl substituents.

4. A compound of formula (I), or pharmaceutically acceptable salt thereof, as claimed in claim 1, wherein $R^6$ is R'O—.

5. A compound of formula (I), or pharmaceutically acceptable salt thereof, as claimed in claim 1, wherein $R^7$ is R'O—.

6. A compound of formula (I), or pharmaceutically acceptable salt thereof, as claimed in claim 1, wherein $R^2$ is selected from:
(A) phenyl, 2-pyridyl or 3-pyridyl
substituted in para-position relative to the isoquinolinone or quinazolinone by
$(R^3)_2N$—Y—
wherein Y is absent (a bond) or
$(R^3)_2N$—Y— is selected from

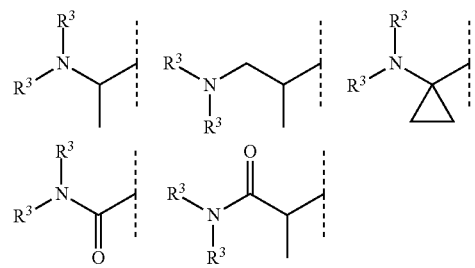

and wherein said phenyl, 2-pyridyl or 3-pyridyl are optionally substituted by 1-2 additional substituents selected from
halogen-
cyano-
$C_1$-$C_4$-alkyl-
halo-$C_1$-$C_4$-alkyl-
hydroxy-
$C_1$-$C_4$-alkoxy-
hydroxy-$C_1$-$C_4$-alkyl-.

7. A compound of formula (I), or pharmaceutically acceptable salt thereof, as claimed in claim 6, wherein $R^2$ is selected from:
(A) phenyl, 2-pyridyl or 3-pyridyl,
substituted in para-position relative to the isoquinolinone or quinazolinone by $(R^3)_2N$—Y—, wherein Y is absent (a bond), and
wherein the phenyl, 2-pyridyl or 3-pyridyl are not further substituted.

8. A compound of formula (I), or a pharmaceutically acceptable salt thereof, as claimed in claim 1, wherein each $R^3$ is independently selected from:
C$_1$-C$_4$-alkyl-
C$_3$-C$_7$-cycloalkyl-C$_1$-C$_4$-alkyl-
heterocyclyl-C$_1$-C$_4$-alkyl-
aryl-C$_1$-C$_4$-alkyl-
(R$^5$)$_2$N—C$_3$-C$_7$-cycloalkyl-
(R$^5$)$_2$N—C$_3$-C$_7$-cycloalkyl-C$_1$-C$_4$-alkyl-
(R$^5$)$_2$N—CO—C$_3$-C$_7$-cycloalkyl-C$_1$-C$_4$-alkyl-
aryl-
heterocyclyl-
C$_3$-C$_7$-cycloalkyl-
wherein aryl, heterocyclyl and C$_3$-C$_7$-cycloalkyl are unsubstituted or substituted by 1-4 substituents selected from
halogen-
C$_1$-C$_4$-alkyl-
halo-C$_1$-C$_4$-alkyl-
C$_1$-C$_4$-alkyl-carbonyl-
C$_3$-C$_7$-cycloalkyl-carbonyl-
C$_1$-C$_4$-alkyl-sulfonyl-
amino-sulfonyl-
N—C$_1$-C$_4$-alkyl-amino-sulfonyl-
N,N-di-C$_1$-C$_4$-alkyl-amino-sulfonyl-
amino-carbonyl-
N—C$_1$-C$_4$-alkyl-amino-carbonyl-
N,N-di-C$_1$-C$_4$-alkyl-amino-carbonyl- and
oxo=.

9. A compound of formula (I), or a pharmaceutically acceptable salt thereof, as claimed in claim 1, wherein $R^2$ is selected from (A) phenyl, 2-pyridyl or 3-pyridyl, substituted in para-position by (R$^3$)$_2$N—Y—, wherein Y is absent, and wherein one $R^3$ is C$_1$-C$_4$-alkyl-, and the other $R^3$ is (R$^5$)$_2$N-cyclohexyl-C$_1$-C$_2$-alkyl-, and wherein the two $R^5$, together with the N to which they are attached form a 6 membered heterocyclic ring, optionally containing 1 additional N heteroatom and/or optionally containing an O atom and/or a S atom, said heterocyclic ring being unsubstituted or substituted by 1 or 2 substituents independently selected from
C$_1$-C$_4$-alkyl-,
oxo=,
C$_1$-C$_4$-alkyl-carbonyl,
C$_1$-C$_4$-alkyl-sulphonyl, and
hydroxy-C$_1$-C$_4$-alkyl.

10. A compound of formula (I), or a pharmaceutically acceptable salt thereof, as claimed in claim 1, wherein when two $R^3$ substituents are present, and they do not join to form a ring, at least one $R^3$ substituent is C$_1$-C$_4$-alkyl-.

11. A compound of claim 1, or a pharmaceutically acceptable salt thereof, selected from:

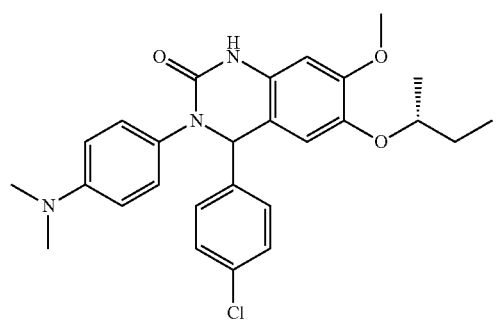

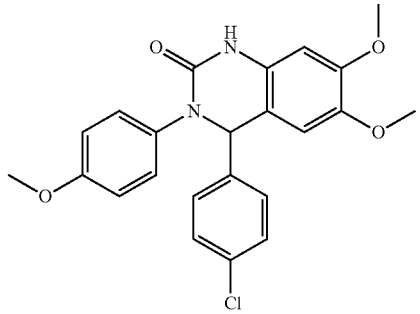

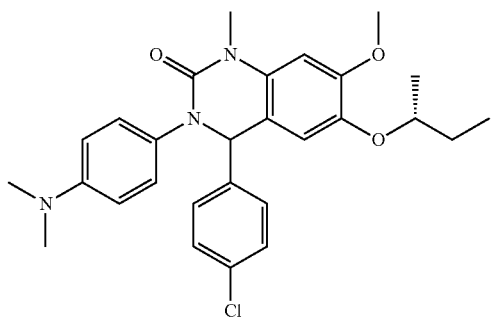

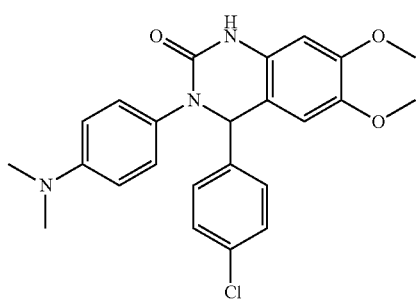

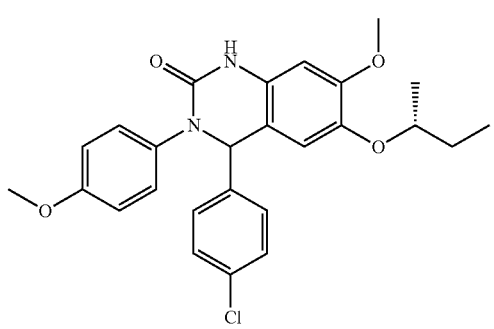

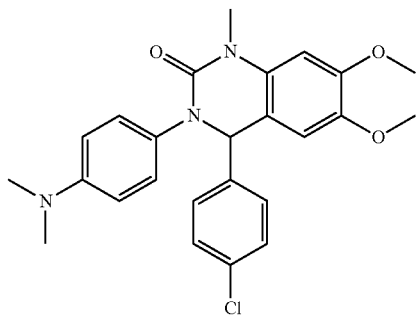

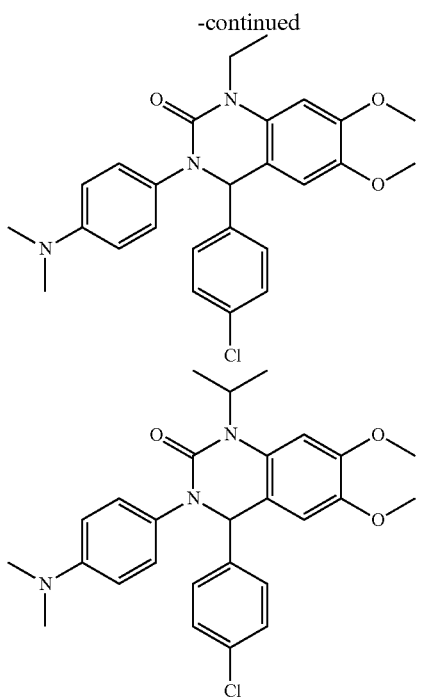

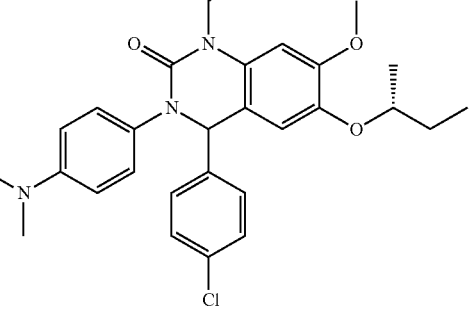

12. A compound of claim 1, in combination with one or more therapeutically active agents.

13. A compound that is 6-((R)-sec-Butoxy)-4-(4-chlorophenyl)-3-(4-dimethylamino-phenyl)-7-methoxy-3,4-dihydro-1H-quinazolin-2-one, or a pharmaceutically acceptable salt thereof.

14. A pharmaceutical composition comprising a therapeutically effective amount of a compound of formula (I) as defined in claim 1, and one or more pharmaceutically acceptable carriers.

* * * * *